(12) United States Patent
Kang et al.

(10) Patent No.: US 9,324,948 B2
(45) Date of Patent: Apr. 26, 2016

(54) COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

(71) Applicant: SAMSUNG SDI CO., LTD., Yongin-si, Gyeonggi-do (KR)

(72) Inventors: Dong-Min Kang, Suwon-si (KR); Hyun-Jung Kim, Suwon-si (KR); Chang-Ju Shin, Suwon-si (KR); Jong-Woo Won, Suwon-si (KR); Nam-Heon Lee, Suwon-si (KR); Soo-Young Jeong, Suwon-si (KR); Ho-Kuk Jung, Suwon-si (KR); Mi-Young Chae, Suwon-si (KR)

(73) Assignee: SAMSUNG SDI CO., LTD., Yongin-si, Gyeonggi-do (KR)

( * ) Notice: Subject to any disclaimer, the term of this patent is extended or adjusted under 35 U.S.C. 154(b) by 27 days.

(21) Appl. No.: 14/484,872

(22) Filed: Sep. 12, 2014

(65) Prior Publication Data

US 2015/0034938 A1 Feb. 5, 2015

Related U.S. Application Data

(63) Continuation-in-part of application No. PCT/KR2012/011061, filed on Dec. 18, 2012.

(30) Foreign Application Priority Data

Apr. 24, 2012 (KR) .......................... 10-2012-0042769

(51) Int. Cl.
*H01L 51/00* (2006.01)
*C07D 401/14* (2006.01)
(Continued)

(52) U.S. Cl.
CPC .......... *H01L 51/0058* (2013.01); *C07D 239/74* (2013.01); *C07D 401/14* (2013.01);
(Continued)

(58) Field of Classification Search
CPC ............ H01L 51/0058; H01L 51/0067; H01L 51/0071; H01L 51/0072; H01L 51/5012; H01L 51/5056; H01L 51/5072; H01L 51/5088; H01L 51/5092; H01L 51/5096; H01L 51/5203
See application file for complete search history.

(56) References Cited

U.S. PATENT DOCUMENTS

2007/0122655 A1 5/2007 Deaton et al.
2012/0043531 A1* 2/2012 Jung ...................... H01L 51/006
257/40

FOREIGN PATENT DOCUMENTS

JP 2000-208261 A 7/2000
JP 2007-015993 A 1/2007
(Continued)

OTHER PUBLICATIONS

Deng, et al., "Direct, Metal-Free Amination of Heterocyclic Amides/Ureas with NH-Heterocycles and N-Substituted Anilines in $POCl_3$", J. Org. Chem, 2011, 76, 8262-8269.
(Continued)

*Primary Examiner* — Kyoung Lee
(74) *Attorney, Agent, or Firm* — Lee & Morse, P.C.

(57) ABSTRACT

A compound for an organic optoelectronic device, an organic light emitting diode including the same, and a display device including the organic light emitting diode are disclosed and the compound for an organic optoelectronic device represented by the following Chemical Formula 1 or 2 provides an organic light emitting diode having life-span characteristics due to excellent electrochemical and thermal stability, and high luminous efficiency at a low driving voltage.

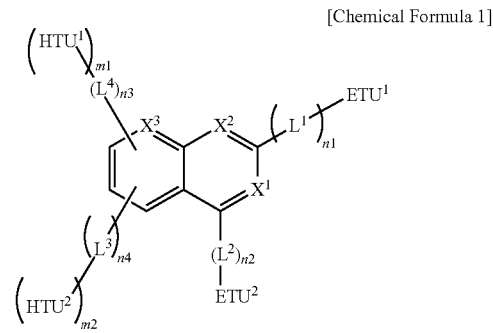

[Chemical Formula 1]

20 Claims, 3 Drawing Sheets

(51) Int. Cl.
*C07D 413/14* (2006.01)
*C07D 403/14* (2006.01)
*C07D 239/74* (2006.01)
*H01L 51/50* (2006.01)
*H01L 51/52* (2006.01)

(52) U.S. Cl.
CPC ............ *C07D403/14* (2013.01); *C07D 413/14* (2013.01); *H01L 51/0067* (2013.01); *H01L 51/0071* (2013.01); *H01L 51/0072* (2013.01); *H01L 51/5012* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5203* (2013.01)

(56) References Cited

FOREIGN PATENT DOCUMENTS

| JP | 2007-223928 A | 9/2007 |
|---|---|---|
| KR | 10-2011-0005666 A | 1/2011 |
| KR | 10-2011-0013220 A | 2/2011 |
| KR | 10-2011-0076488 A | 7/2011 |
| KR | 10-2011-0096453 A | 8/2011 |
| WO | WO 2004/096783 A1 | 11/2004 |
| WO | WO 2006/104118 A1 | 10/2006 |
| WO | WO-2008/015949 A1 | 2/2008 |
| WO | WO 2008/066358 A1 | 6/2008 |
| WO | WO 2011/014039 A1 | 2/2011 |
| WO | WO 2012/024132 A2 | 2/2012 |

OTHER PUBLICATIONS

Chihaya Adachi, et al., "Electroluminescence in Organic Films with Three-Layer Structure", Japanese Journal of Applied Physics, vol. 27, No. 2, Feb. 1988, pp. L269-L271.

Sebastian Scholz, et al., "Photochemical reactions in organic semiconductor thin films", Organic Electronics 8 (2007), pp. 709-717.

Extended European Search Report dated Nov. 18, 2015 in Corresponding European Patent Application No. 12875420.7.

* cited by examiner

COMPOUND FOR ORGANIC OPTOELECTRONIC DEVICE, ORGANIC LIGHT EMITTING DIODE INCLUDING THE SAME AND DISPLAY INCLUDING THE ORGANIC LIGHT EMITTING DIODE

CROSS-REFERENCE TO RELATED APPLICATION

This application is a continuation-in-part of pending International Application No. PCT/KR2012/011061, entitled "Compound tor Organic Optoelectronic Device, Organic Light Emitting Diode Including the Same and Display Including the Organic Light Emitting Diode," which was filed on Dec. 18, 2012, the entire contents of which are hereby incorporated by reference.

Korean Patent Application No. 10-2012-0042769 filed on Apr. 24, 2012 in the Korean Intellectual Properly Office, and entitled: "Compound for Organic Optoelectronic Device, Organic Light Emitting Diode Including the Same and Display Including the Organic Light Emitting Diode," is incorporated by reference herein in its entirety.

BACKGROUND

1. Field

A compound for an organic optoelectronic device being capable of providing an organic optoelectronic device having excellent life-span, efficiency, electrochemical stability, and thermal stability, an organic light emitting diode including the compound, and a display device including the organic light emitting diode are disclosed.

2. Description of the Related Art

An organic optoelectronic device is a device requiring a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light emitting diode, an organic solar cell, an organic photo conductor drum, an organic transistor, and the like, which require a hole injecting or transport material, an electron injecting or transport material, or a light emitting material.

Particularly, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a fractional organic material layer is interposed between an anode and a cathode. Herein, the organic material layer includes a multi-layer including different materials, for example a hole injection layer, a hole transport layer, an emission layer, an electron transport layer, and an electron injection layer, in order to improve efficiency and stability of an organic light emitting diode.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

Recently, it has became known that a phosphorescent light emitting material may be used for a light emitting material of an organic light emitting diode in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, and the like.

The light emitting material is classified as blue, green, and red light emitting materials according to emitted colors, and yellow and orange light emitting materials to emit colors approaching natural colors.

When one material is used as a light emitting material, a maximum light emitting wavelength is shifted to a long wavelength or color purity decreases because of interactions between molecules, or device efficiency decreases because of a light emitting quenching effect. Therefore, a host/dopant system is included as a light emitting material in order to improve color purity and increase luminous efficiency and stability through energy transfer.

In order to implement excellent performance of an organic light emitting diode, a material constituting an organic material layer, for example a hole injection material, a hole transport material, a light emitting material, an electron transport material, an electron injection material, and a light emitting material such as a host and/or a dopant, should be stable and have good efficiency. However, development of an organic material layer forming material for an organic light emitting diode has thus far not been satisfactory and thus there is a need for a novel material. This material development is also required for other organic optoelectronic devices.

The low molecular organic light emitting diode is manufactured as a thin film in a vacuum deposition method and can have good efficiency and life-span performance. A polymer organic light emitting diode is manufactured in an inkjet or spin coating method has an advantage of low initial cost and being large-sized.

Both low molecular organic light emitting and polymer organic light emitting diodes have an advantage of self-light emitting, high speed response, wide viewing angle, ultra-thin, high image quality, durability, large driving temperature range, and the like. In particular, they have good visibility due to self-light emitting characteristics compared with a conventional LCD (liquid crystal display) and have an advantage of decreasing thickness and weight of LCD up to a third, because they do not need a backlight.

In addition, since they have a response speed 1000 time faster microsecond unit than LCD, they can realize a perfect motion picture without after-image. Accordingly, based on these advantages, they have been remarkably developed to have 80 times efficiency and more than 100 times life-span since they come out for the first time in the late 1980s.

Recently, they keep being rapidly larger such as a 40-inch organic light emitting diode panel.

They are simultaneously required to have improved luminous efficiency and life-span in order to be larger. Herein, their luminous efficiency need smooth combination between holes and electrons in an emission layer. However, since an organic material in general has slower electron mobility than hole mobility, it has a drawback of inefficient combination between holes and electrons, and therefore, while increasing electron injection and mobility from a cathode and simultaneously preventing movement of holes is required.

In order to improve life-span, a material crystallization caused by Joule heats generated during device operating is required to be prevented. Accordingly, there has been a strong need for an organic compound having excellent electron injection and mobility, and high electrochemical stability.

SUMMARY

A compound for an organic optoelectronic device that may act as a hole injection and transport material or an electron injection and transport material, and also act as a light emitting host along with an appropriate dopant is provided.

An organic light emitting diode having excellent life-span, efficiency, driving voltage, electrochemical stability, and thermal stability and a display device including the same are provided.

In one embodiment of the present invention, a compound for an organic optoelectronic device represented by the following Chemical Formula 1 is provided.

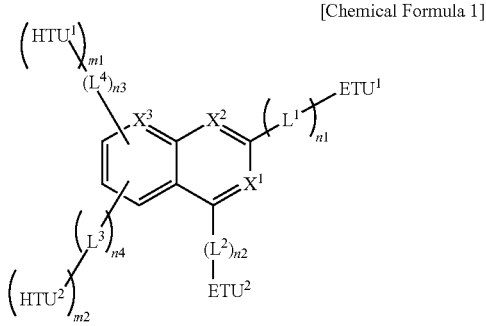

[Chemical Formula 1]

In the above Chemical Formula 1, at least one of $X^1$ to $X^3$ is N, $X^3$ is N or —CR'— wherein the R' is hydrogen, a substituted or unsubstituted C1 to C10 alkyl group or is linked to $L^4$, $L^1$ to $L^4$ are independently a single bond, a substituted or unsubstituted C6 to C30 arylene group or a substituted or unsubstituted C2 to C30 heteroarylene group, n1 to n4 are independently integers of 0 to 3, $ETU^1$ and $ETU^2$ are independently a substituted or unsubstituted C2 to C30 heteroaryl group having electron characteristics, $HTU^1$ and $HTU^2$ are independently a substituted or unsubstituted C6 to C30 aryl group having hole characteristics, and m1 and m2 are 0 or 1.

The compound for an organic optoelectronic device may be represented by the following Chemical Formula 2.

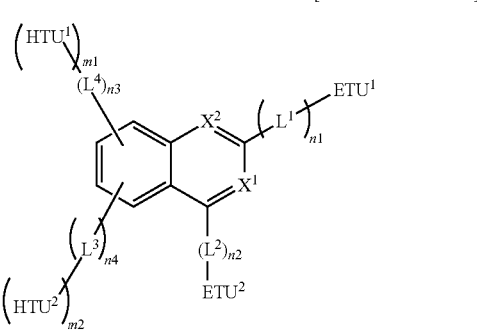

[Chemical Formula 2]

In the above Chemical Formula 2, at least one of $X^1$ and $X^2$ is N, $L^1$ to $L^4$ are independently a single bond, a substituted or unsubstituted C6 to C30 arylene group or a substituted or unsubstituted C2 to C30 heteroarylene group, n1 to n4 are independently integers of 0 to 3, $ETU^1$ and $ETU^2$ are independently a substituted or unsubstituted C2 to C30 heteroaryl group having electron characteristics, $HTU^1$ and $HTU^2$ are independently a substituted or unsubstituted C6 to C30 aryl group having hole characteristics, and m1 and m2 are 0 or 1.

The compound for an organic optoelectronic device may be represented by the following Chemical Formula 3.

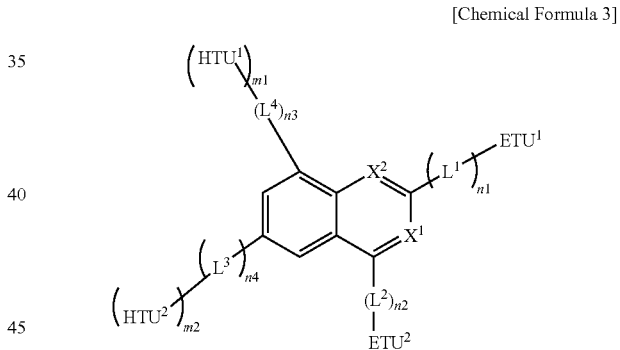

[Chemical Formula 3]

In the above Chemical Formula 3, at least one of $X^1$ and $X^2$ is N, $L^1$ to $L^4$ are independently a single bond, a substituted or unsubstituted C6 to C30 arylene group or a substituted or unsubstituted C2 to C30 heteroarylene group, n1 to n4 are independently integers of 0 to 3, $ETU^1$ and $ETU^2$ are independently a substituted or unsubstituted C2 to C30 heteroaryl group having electron characteristics, $HTU^1$ and $HTU^2$ are independently a substituted or unsubstituted C6 to C30 aryl group having hole characteristics, and m1 and m2 are 0 or 1.

The $X^2$ may be —CH—, and $X^1$ may be N.
The $X^1$ may be —CH—, and $X^2$ may be N.
The $X^1$ and $X^2$ may be N.
The n3 and m1 may be 0.
The m1 and m2 may not be 0.
The substituted or unsubstituted C2 to C30 heteroaryl group having electron characteristics may be a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

The substituted or unsubstituted C6 to C30 aryl group having hole characteristics may be a substituted or unsubstituted phenyl group, a substituted or unsubstituted naphthyl group, a substituted or unsubstituted phenanthrenyl group, a substituted or unsubstituted anthracenyl group, a substituted or unsubstituted fluorenyl group, a substituted or unsubstituted triphenylenyl group, a substituted or unsubstituted spiro-fluorenyl group, a substituted or unsubstituted terphenyl group, a substituted or unsubstituted pyrenyl group, a substituted or unsubstituted perylenyl group, or a combination thereof.

The compound for an organic optoelectronic device may be one of compounds represented by the following Chemical Formulae A-1 to A-393.

[Chemical Formula A-1]

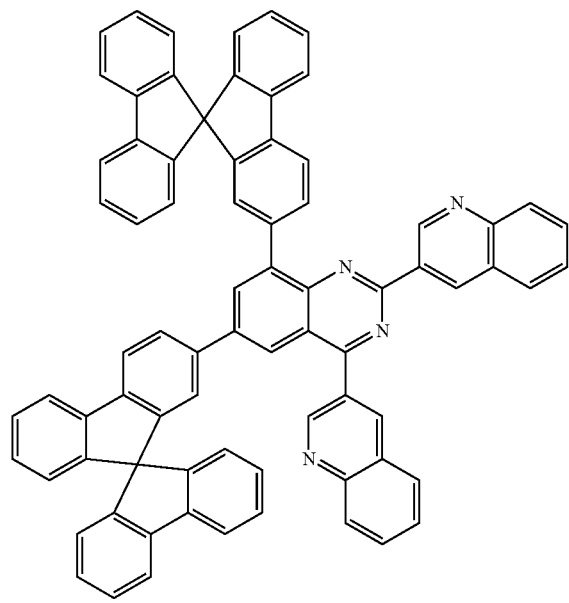

[Chemical Formula A-2]

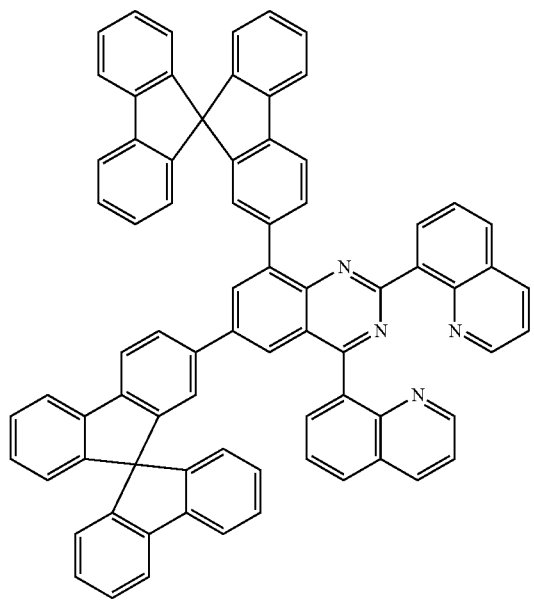

[Chemical Formula A-3]

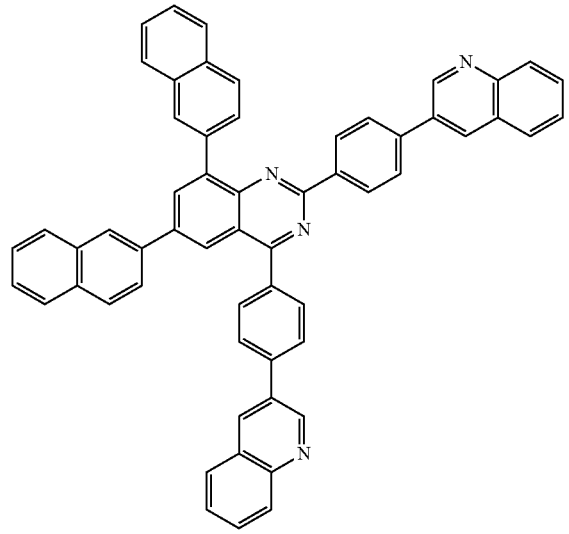

[Chemical Formula A-4]

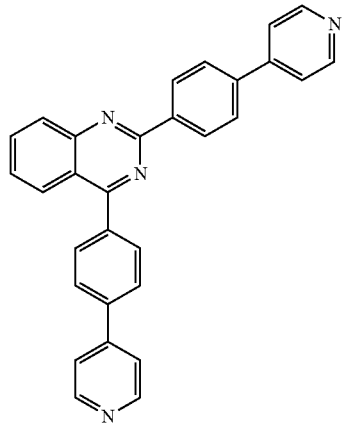

[Chemical Formula A-5]
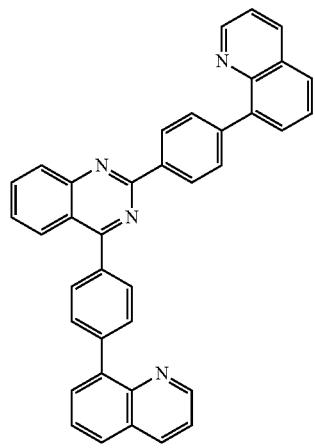
[Chemical Formula A-6]
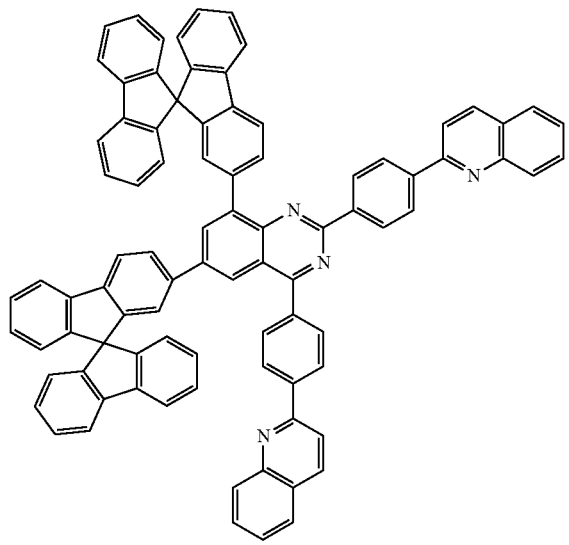
[Chemical Formula A-7]
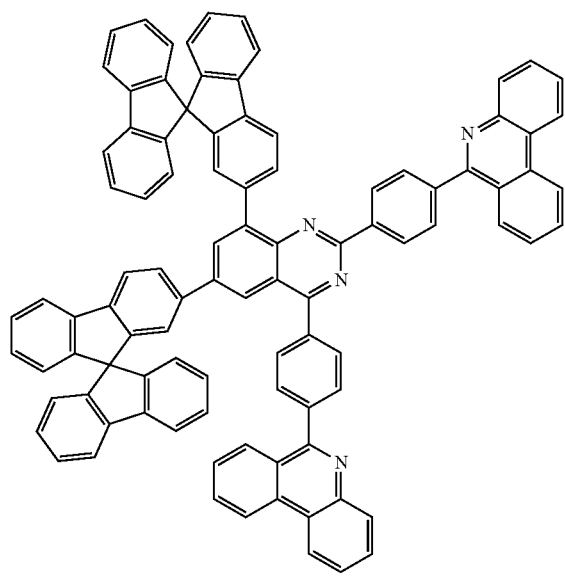
[Chemical Formula A-8]
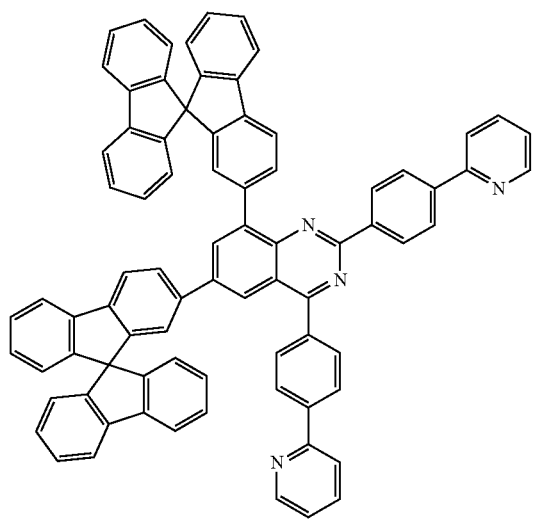

-continued
[Chemical Formula A-9]
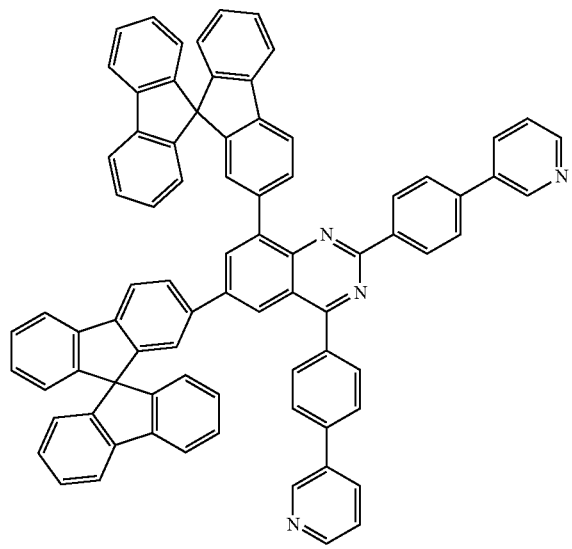
[Chemical Formula A-10]
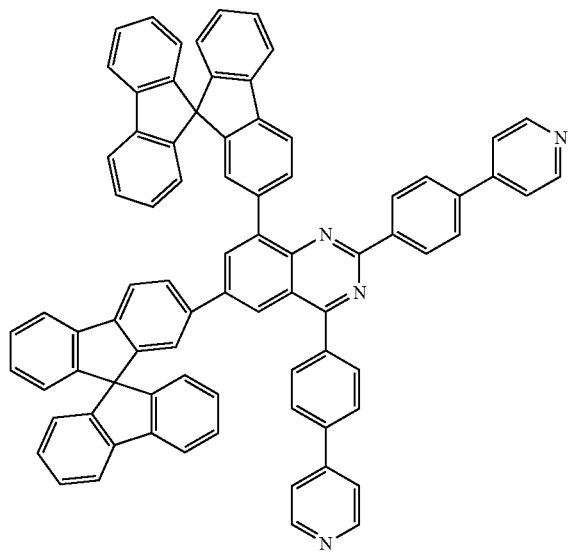
[Chemical Formula A-11]
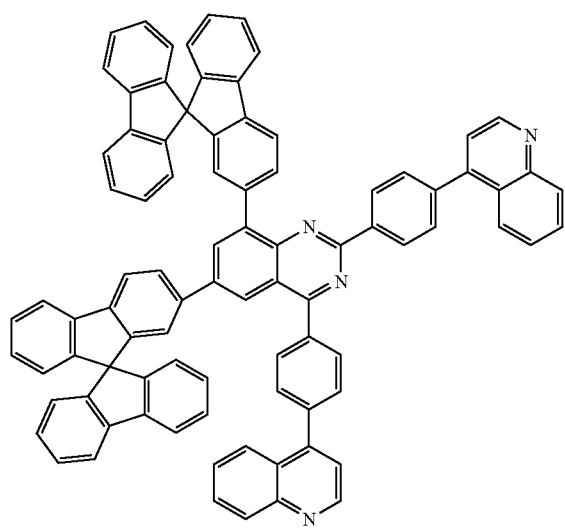
[Chemical Formula A-12]
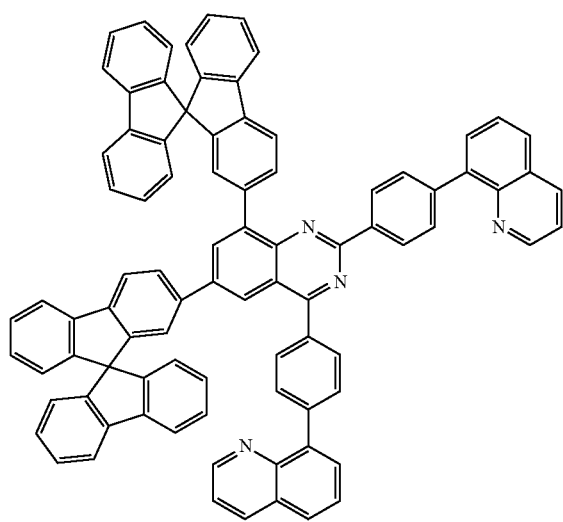

[Chemical Formula A-13]
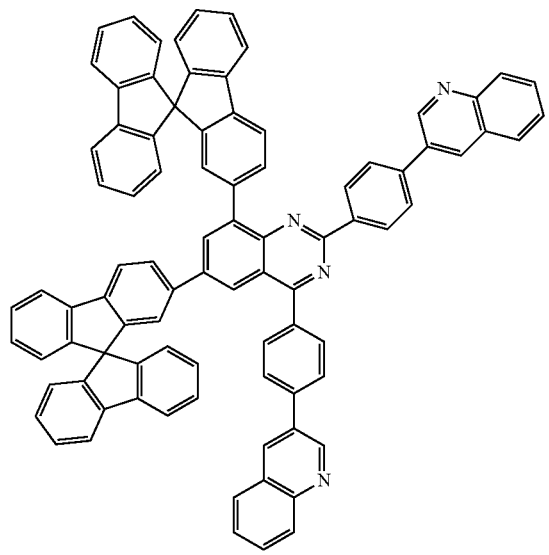
[Chemical Formula A-14]
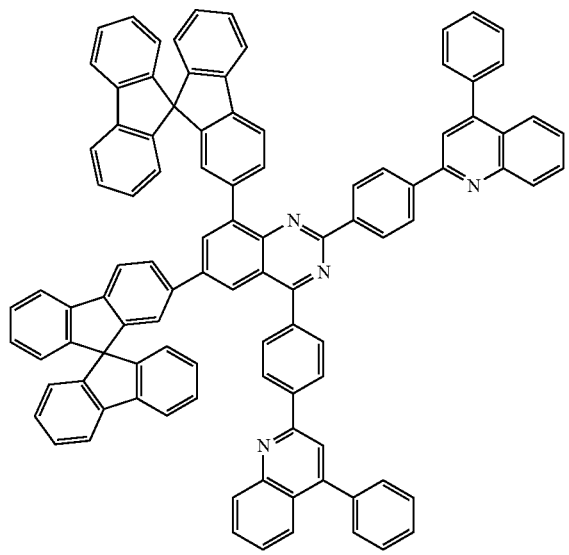
[Chemical Formula A-15]
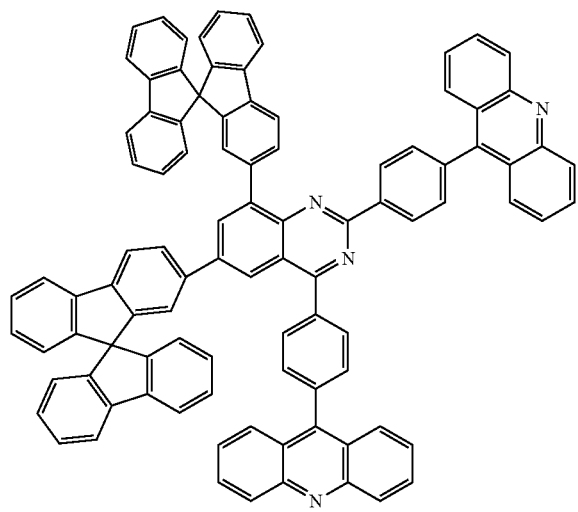
[Chemical Formula A-16]
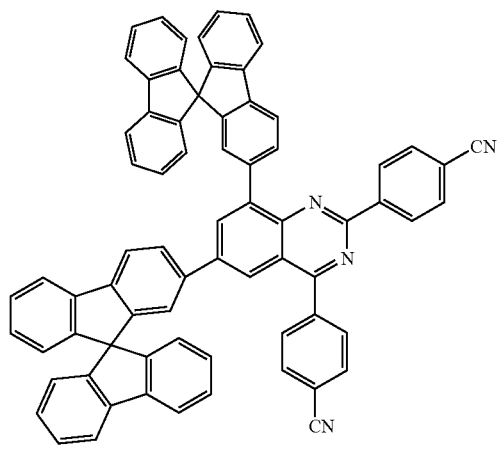
[Chemical Formula A-17]
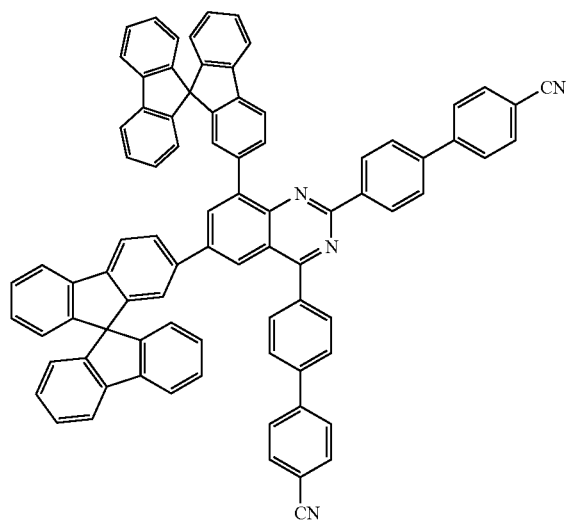
[Chemical Formula A-18]
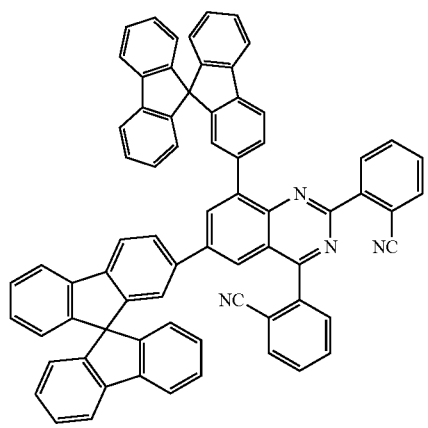

-continued
[Chemical Formula A-19]
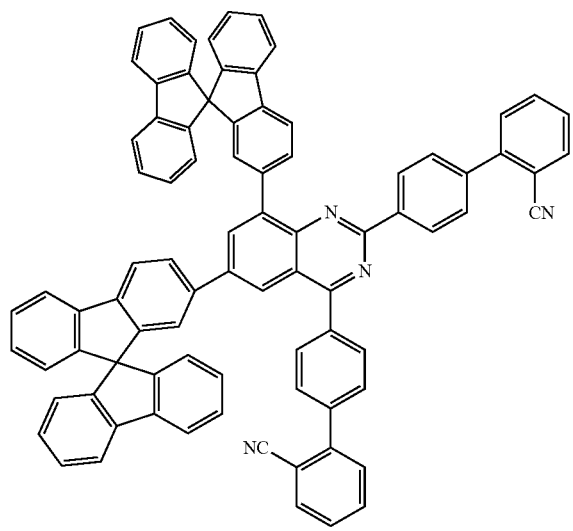
[Chemical Formula A-20]
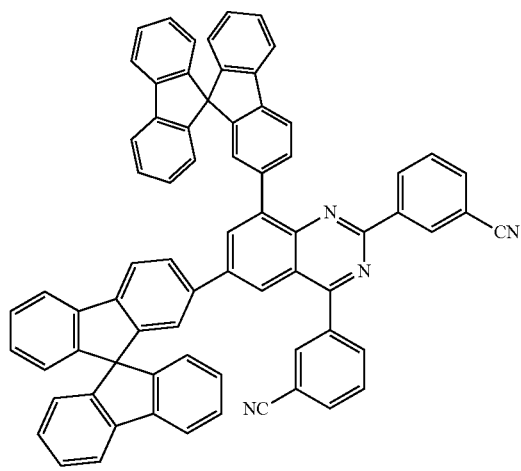
[Chemical Formula A-21]
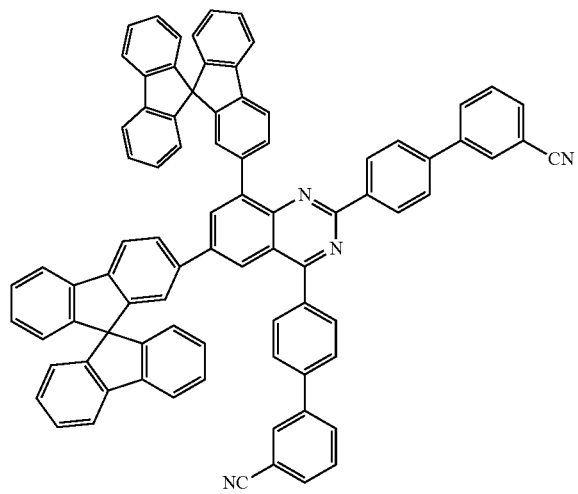
[Chemical Formula A-22]
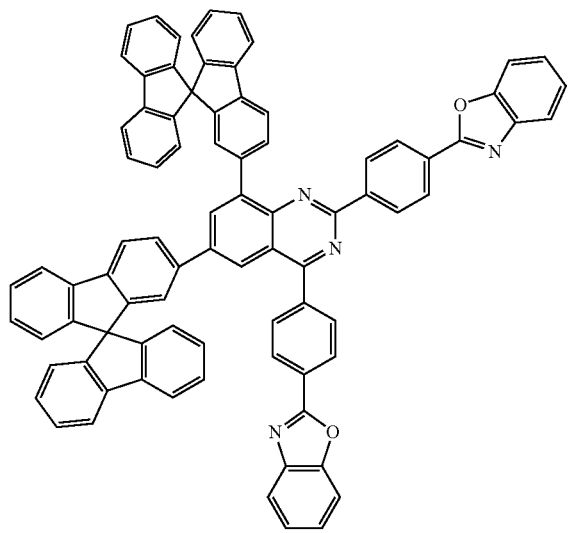
[Chemical Formula A-23]
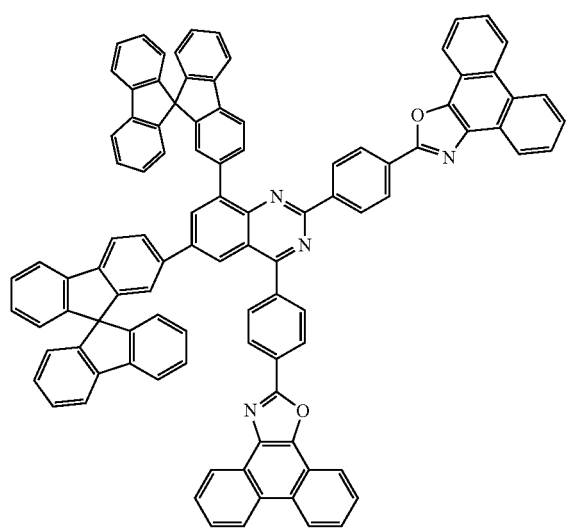
[Chemical Formula A-24]
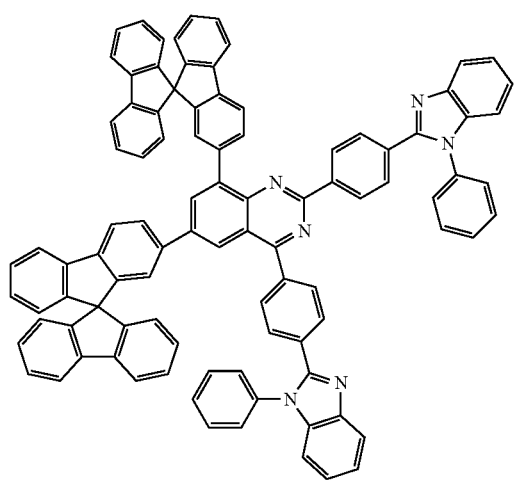

[Chemical Formula A-25]
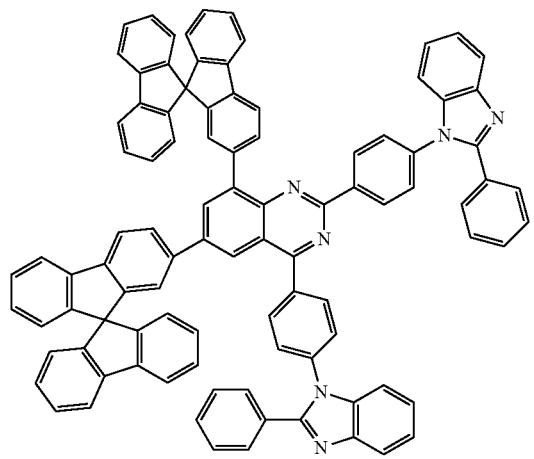
[Chemical Formula A-26]
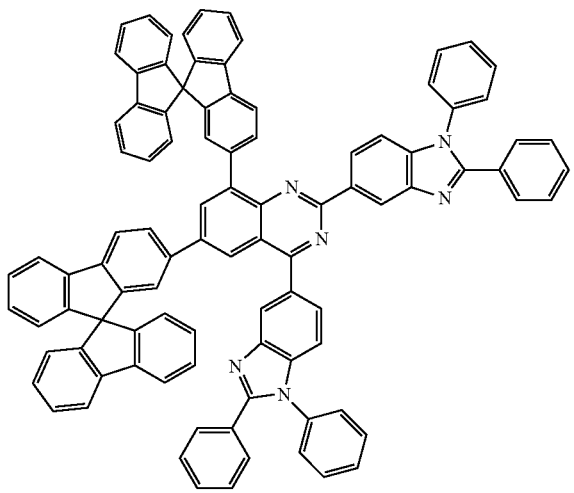
[Chemical Formula A-27]
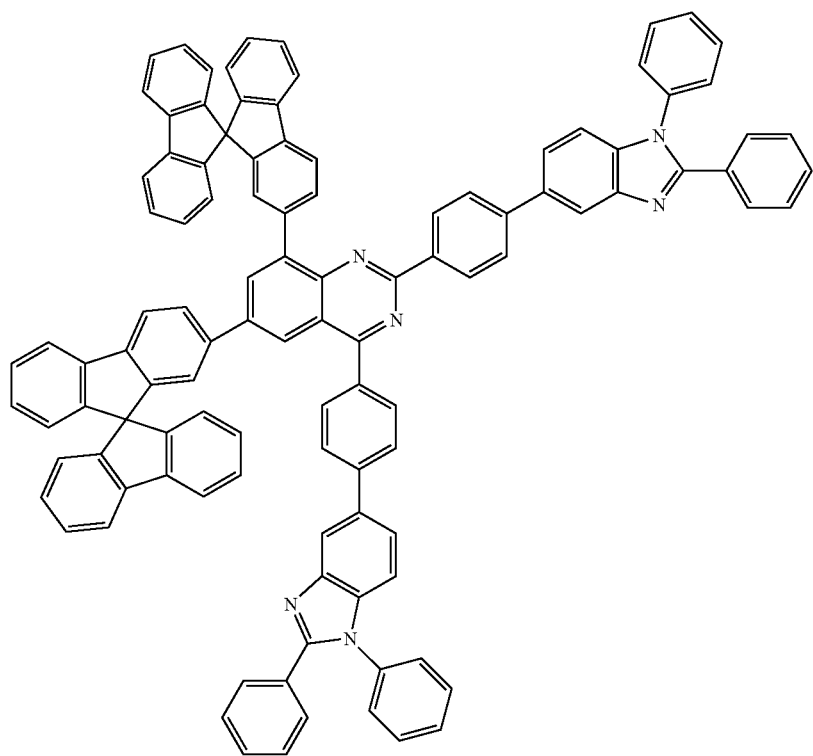

-continued
[Chemical Formula A-28]
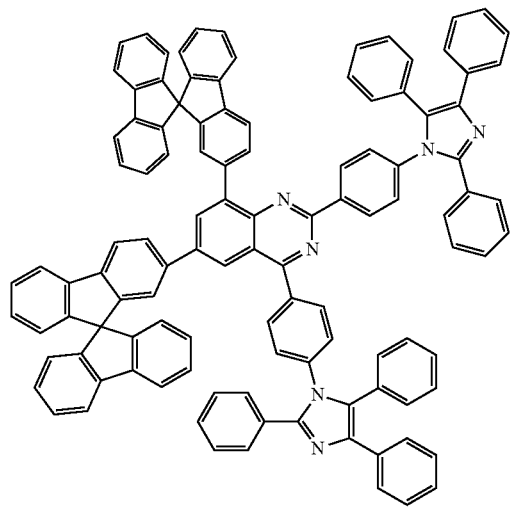
[Chemical Formula A-29]
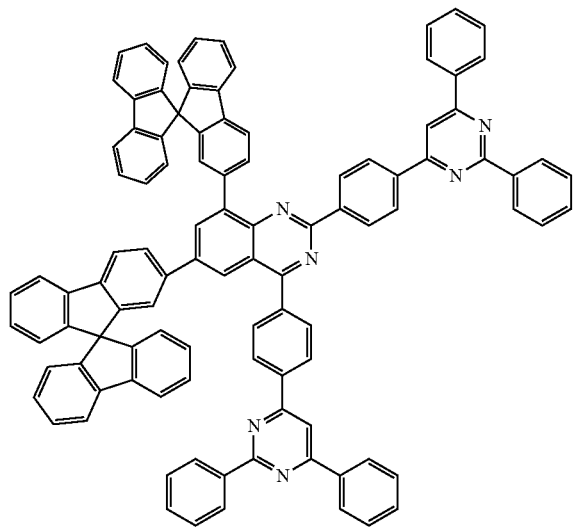
[Chemical Formula A-30]
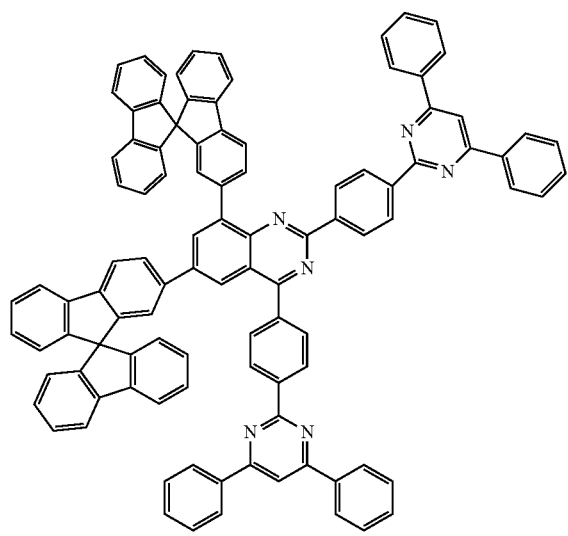
[Chemical Formula A-31]
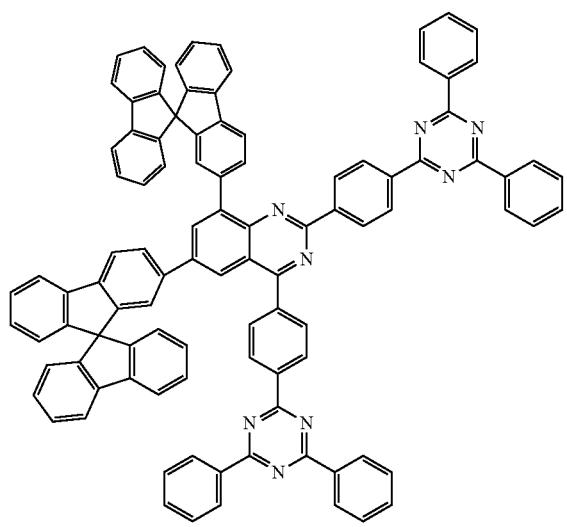
[Chemical Formula A-32]
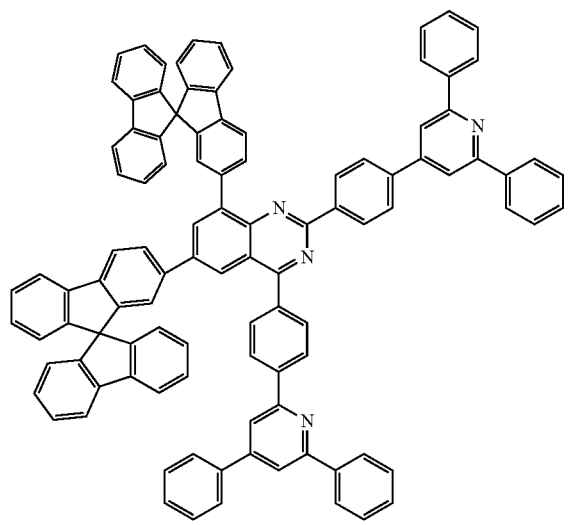
[Chemical Formula A-33]
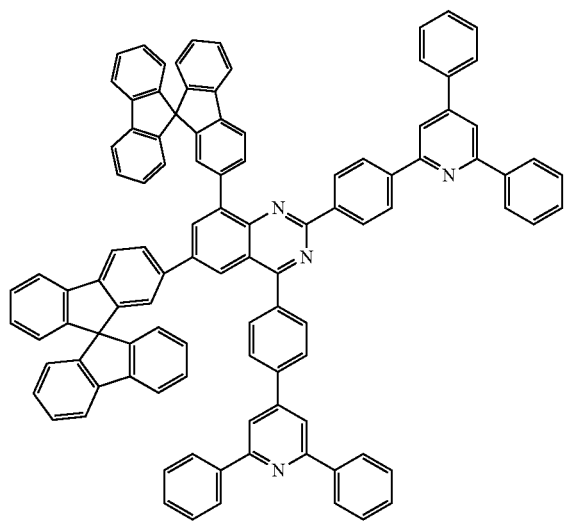

[Chemical Formula A-34]
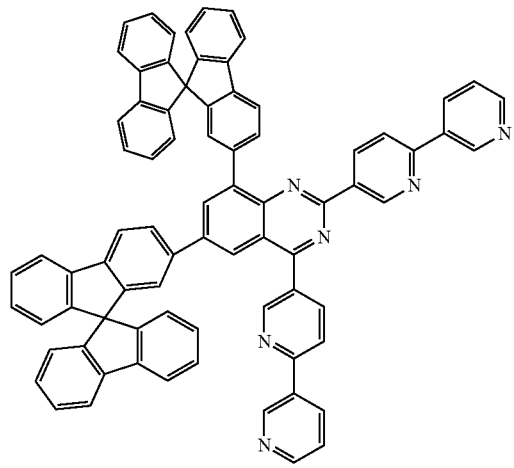
[Chemical Formula A-35]
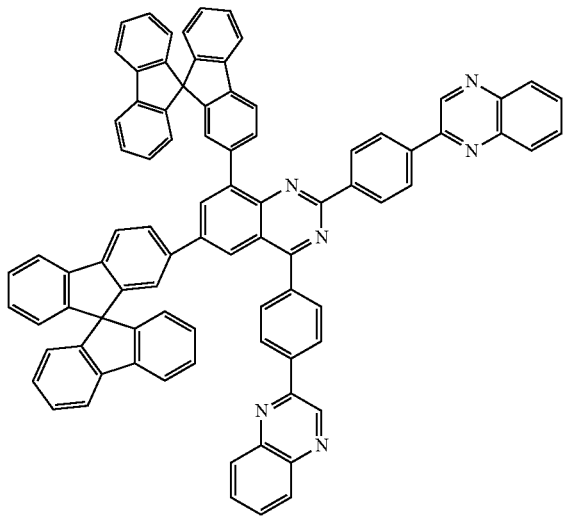
[Chemical Formula A-36]
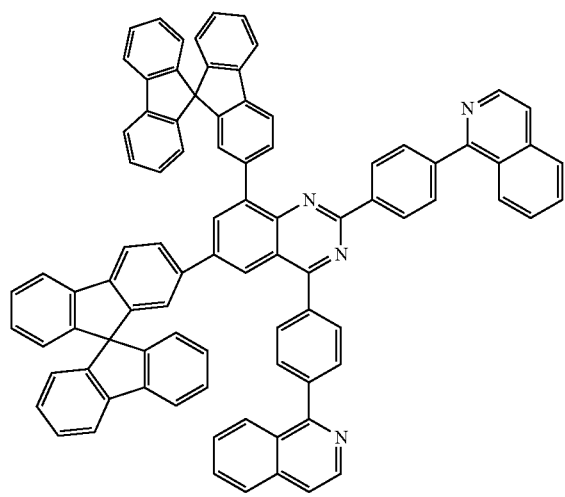
[Chemical Formula A-37]
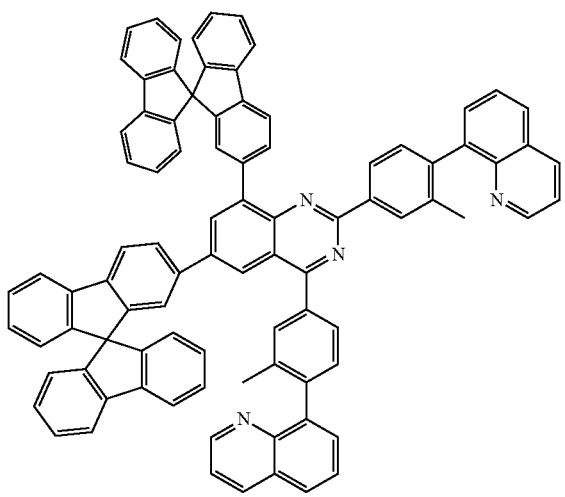
[Chemical Formula A-38]
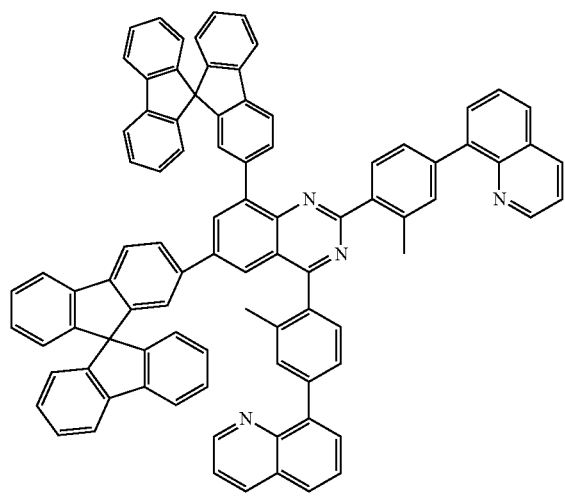
[Chemical Formula A-39]
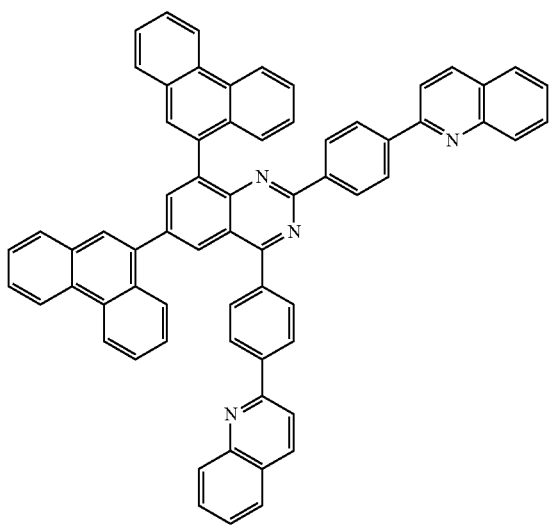

-continued
[Chemical Formula A-40]
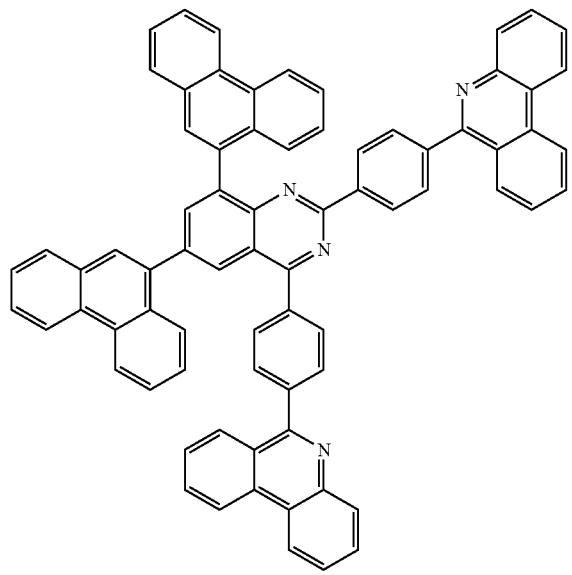
[Chemical Formula A-41]
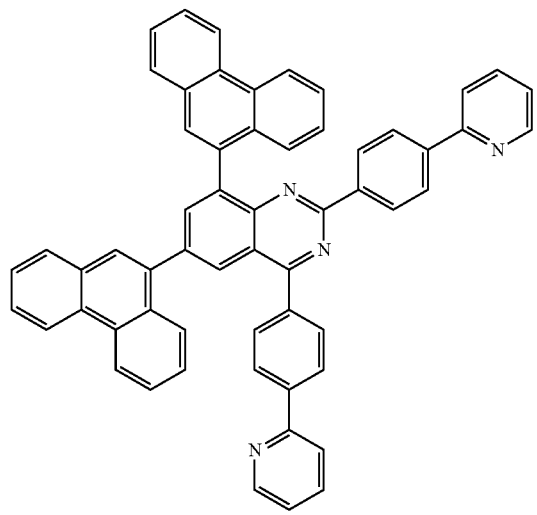
[Chemical Formula A-42]
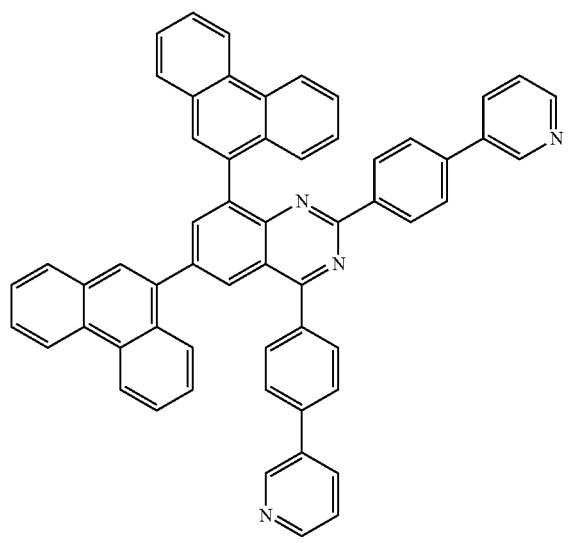
[Chemical Formula A-43]
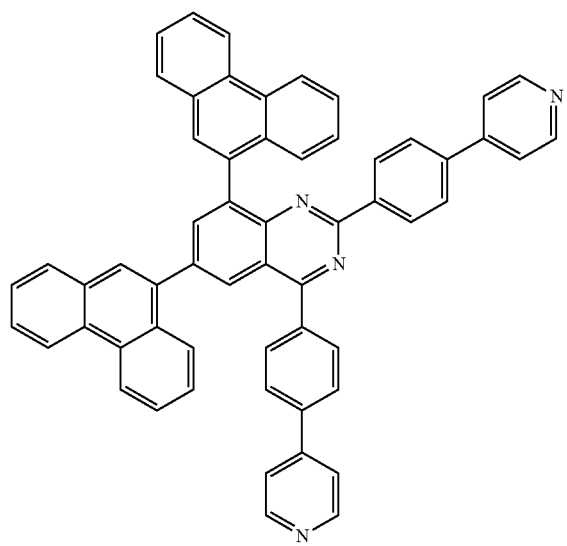

[Chemical Formula A-44]
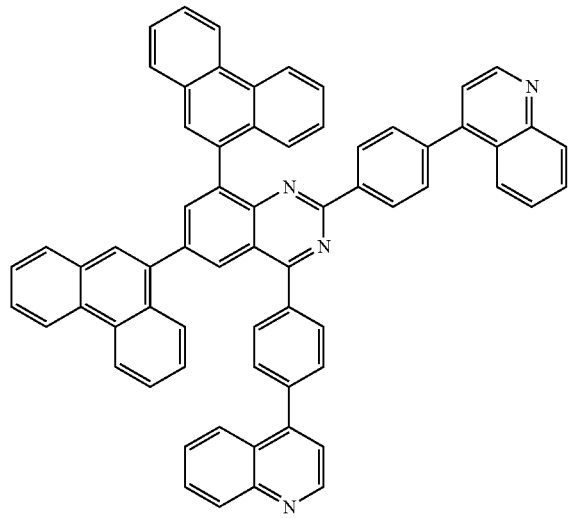
[Chemical Formula A-45]
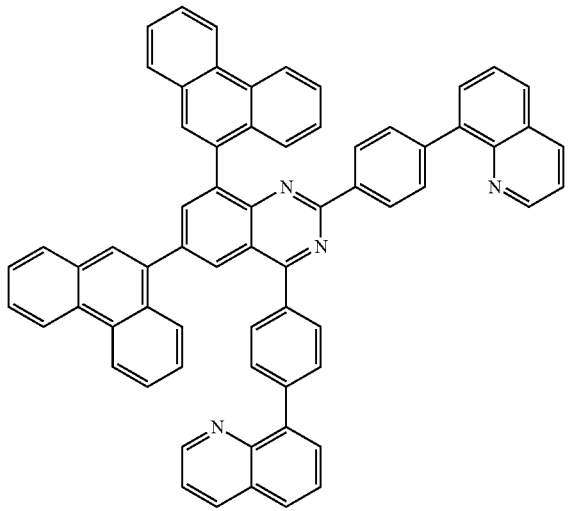
[Chemical Formula A-46]
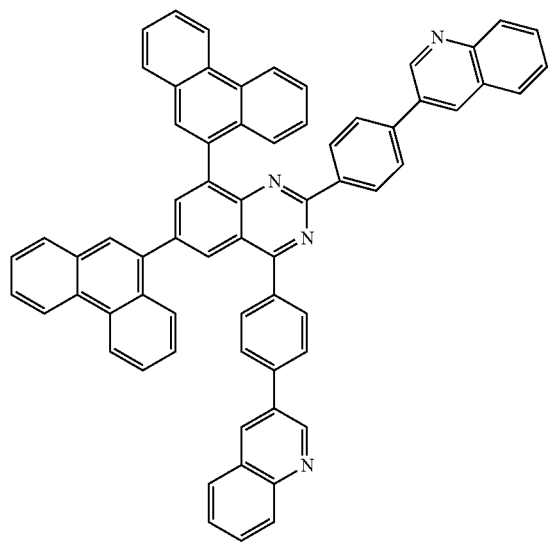
[Chemical Formula A-47]
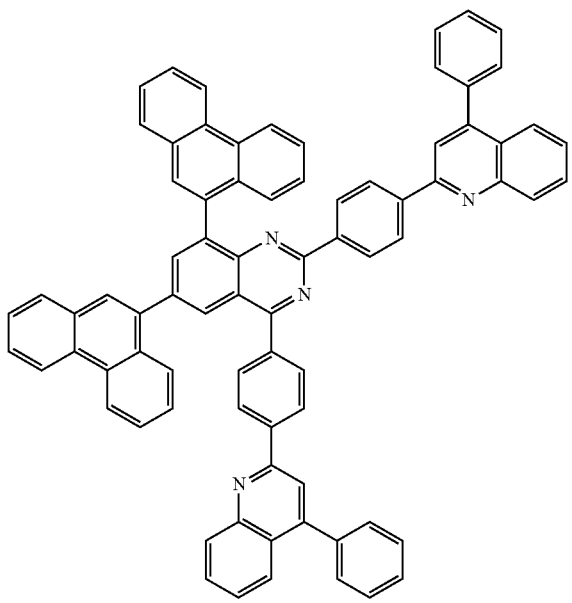

[Chemical Formula A-48]
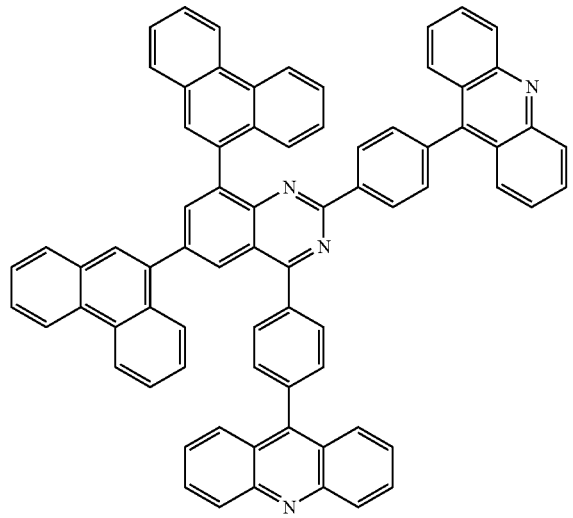
[Chemical Formula A-49]
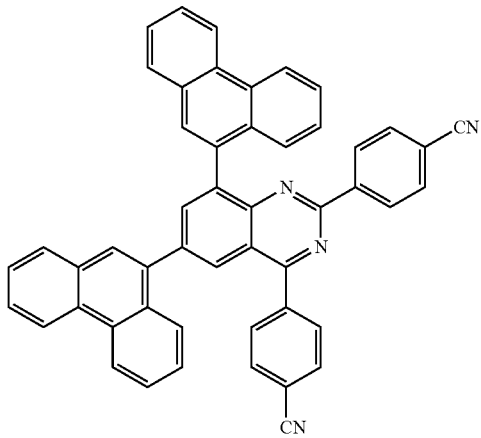
[Chemical Formula A-50]
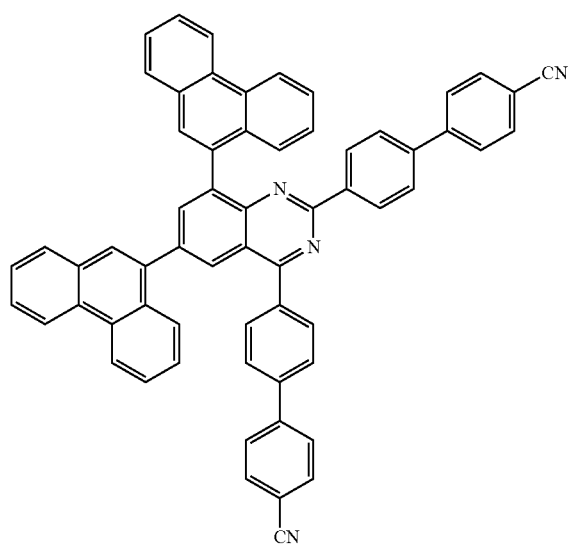
[Chemical Formula A-51]
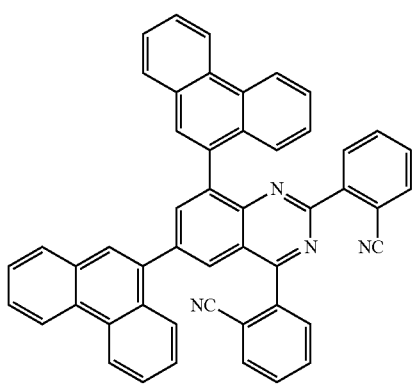
[Chemical Formula A-52]
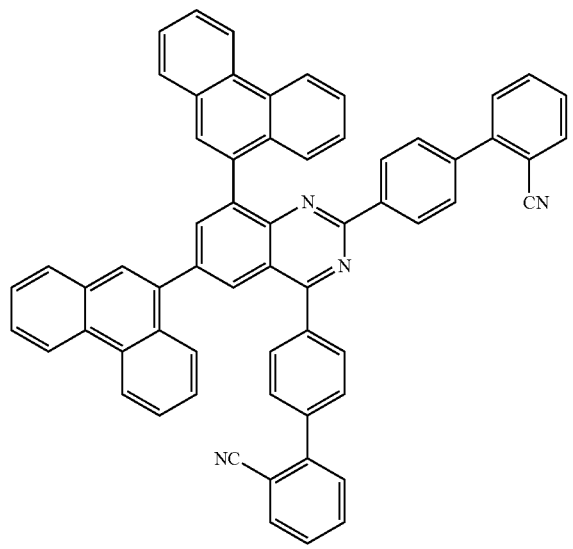
[Chemical Formula A-53]
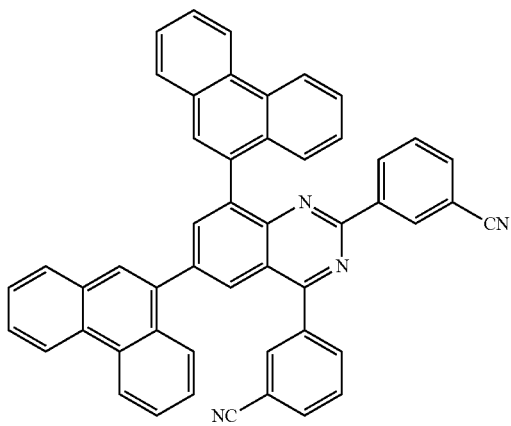

-continued
[Chemical Formula A-54]
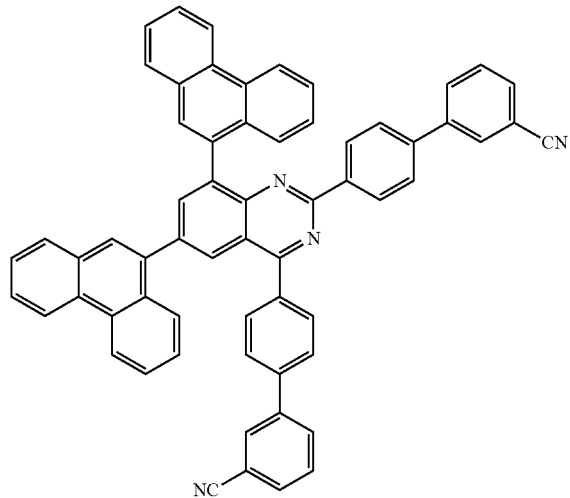
[Chemical Formula A-55]
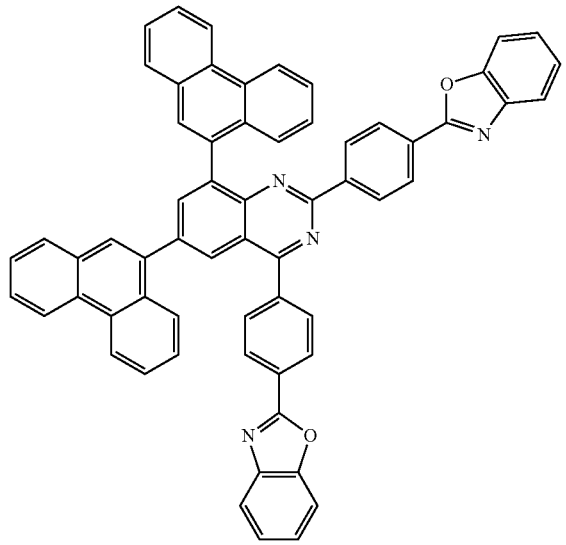
[Chemical Formula A-56]
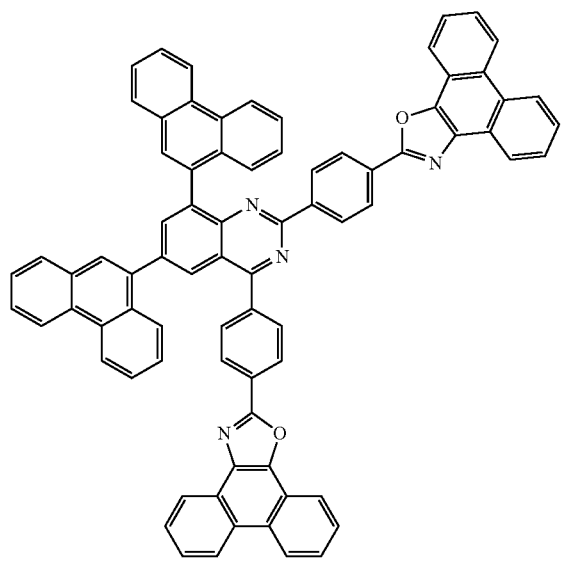
[Chemical Formula A-57]
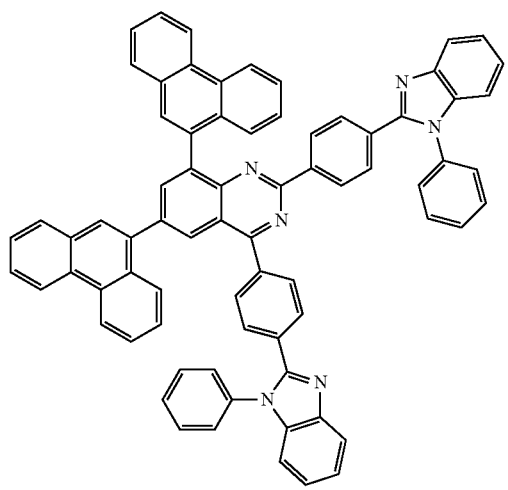
[Chemical Formula A-58]
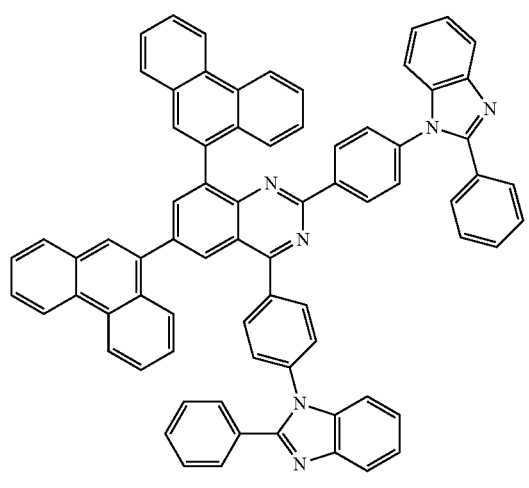
[Chemical Formula A-59]
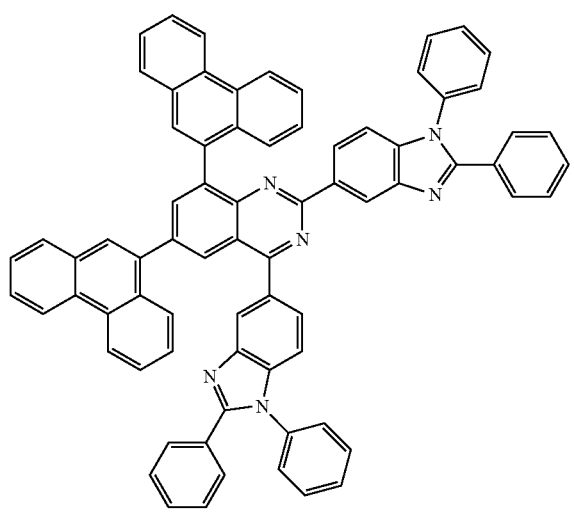

[Chemical Formula A-60]
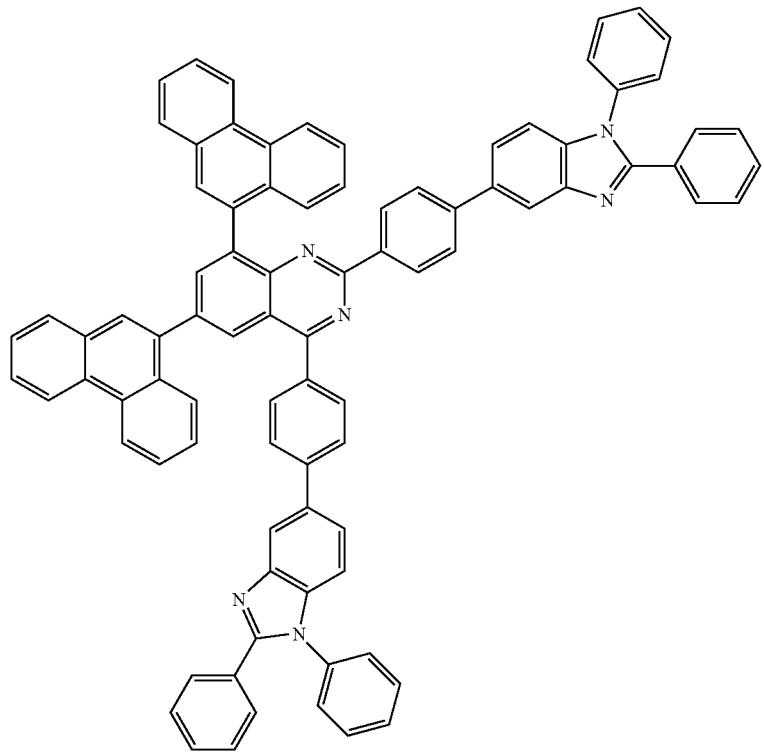
[Chemical Formula A-61]
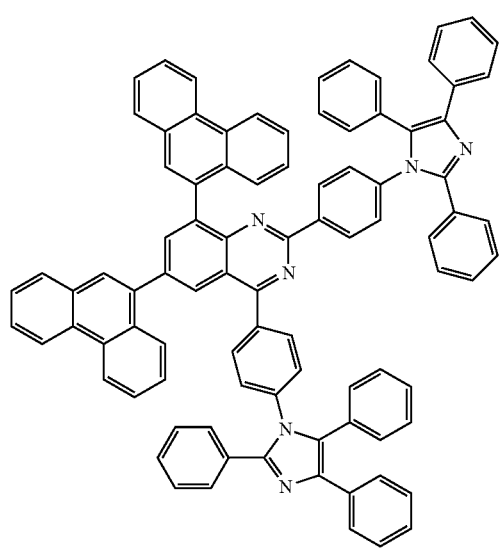
[Chemical Formula A-62]
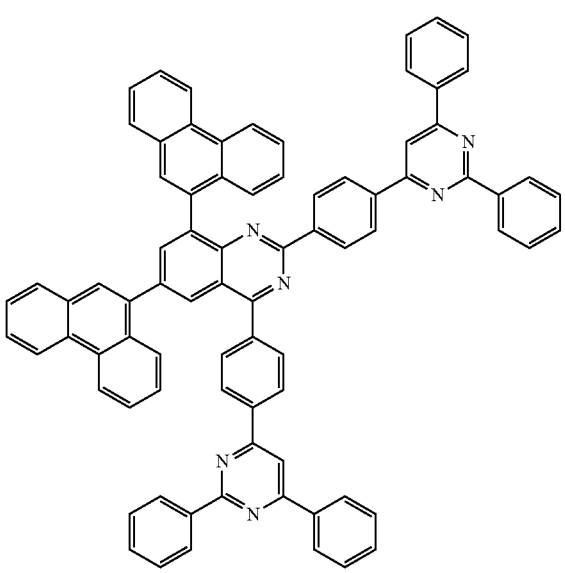

-continued
[Chemical Formula A-63]
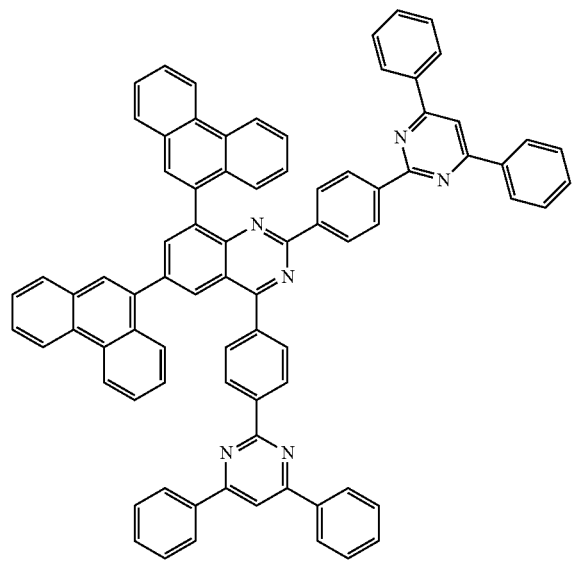
[Chemical Formula A-64]
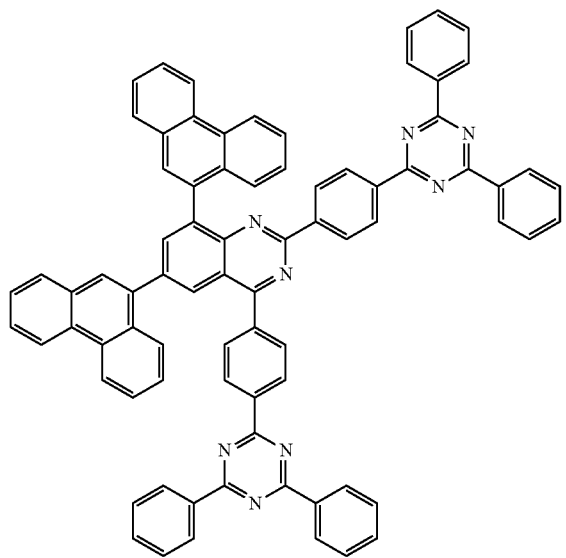
[Chemical Formula A-65]
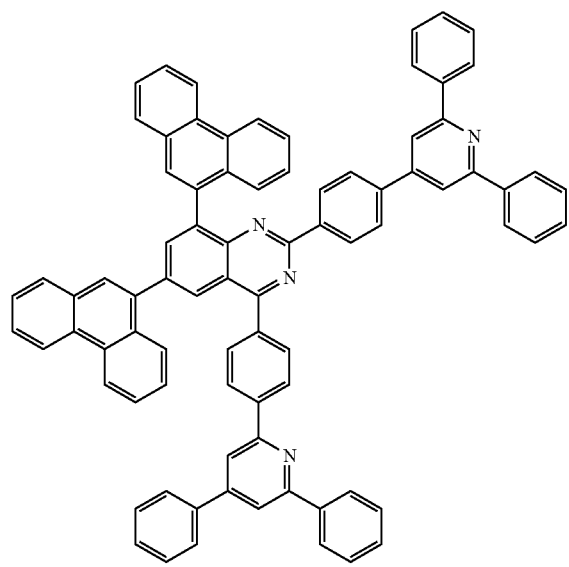
[Chemical Formula A-66]
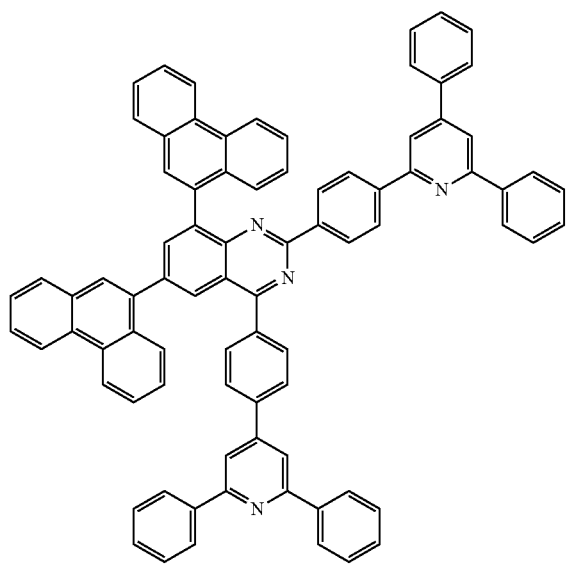

-continued
[Chemical Formula A-67]
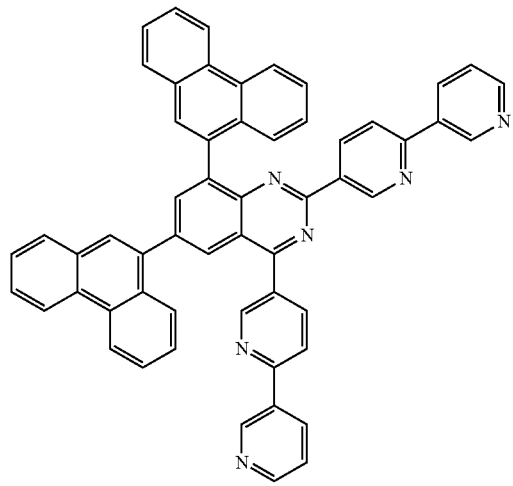
[Chemical Formula A-68]
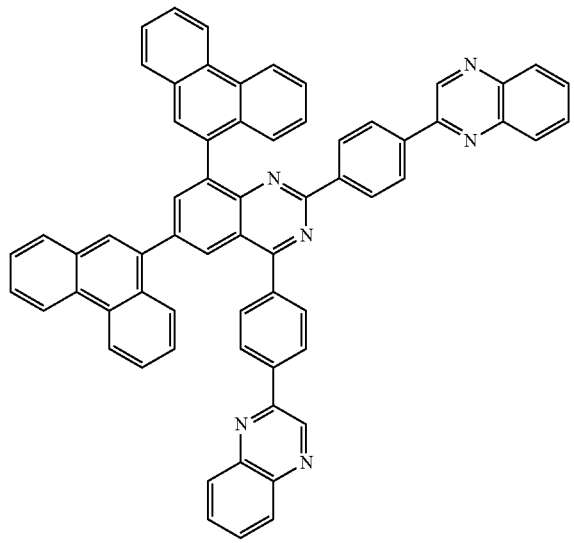
[Chemical Formula A-69]
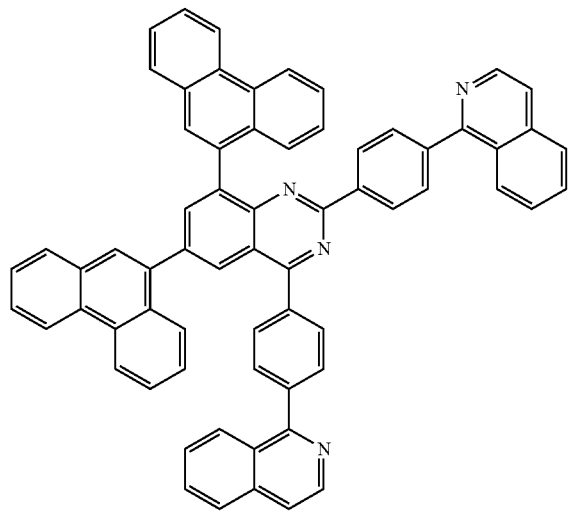
[Chemical Formula A-70]
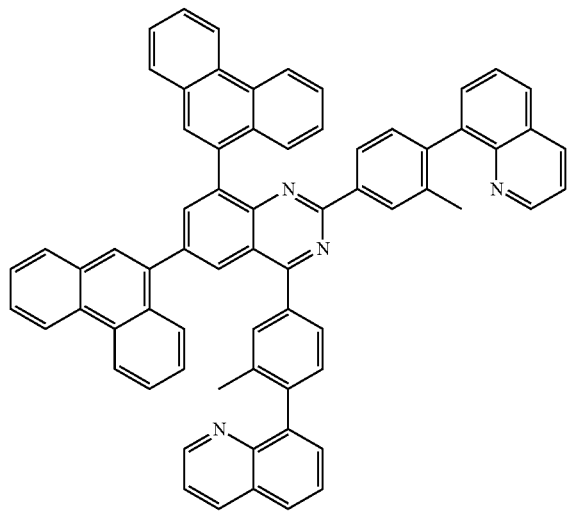
[Chemical Formula A-71]
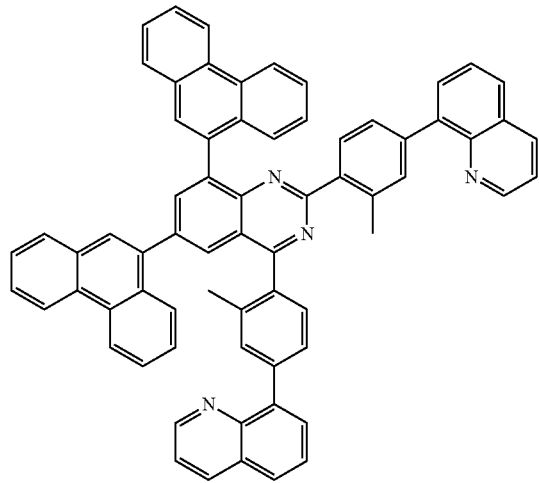
[Chemical Formula A-72]
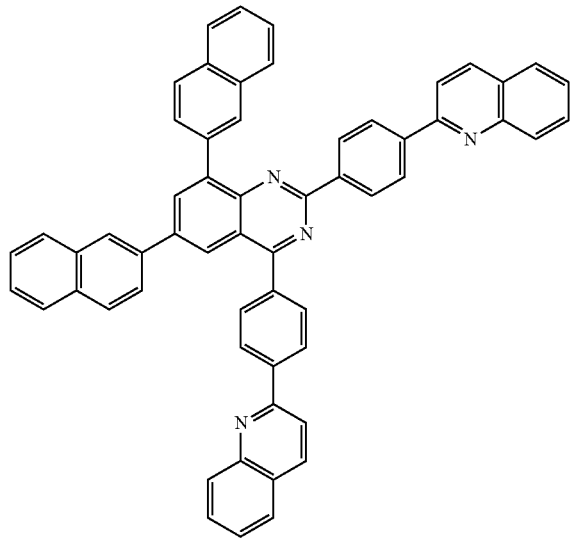

[Chemical Formula A-73]
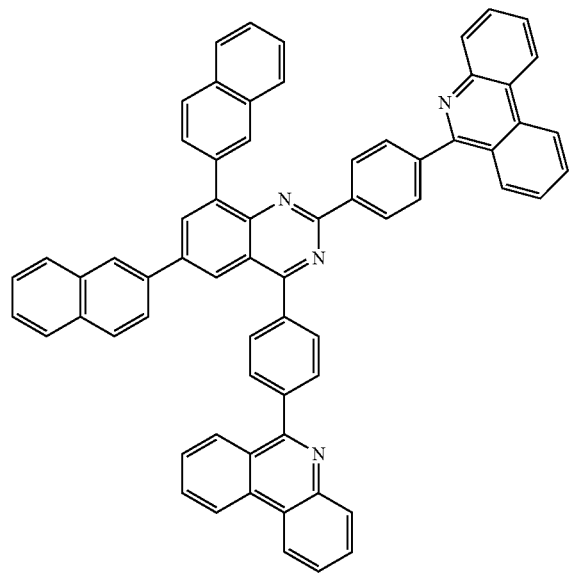
[Chemical Formula A-74]
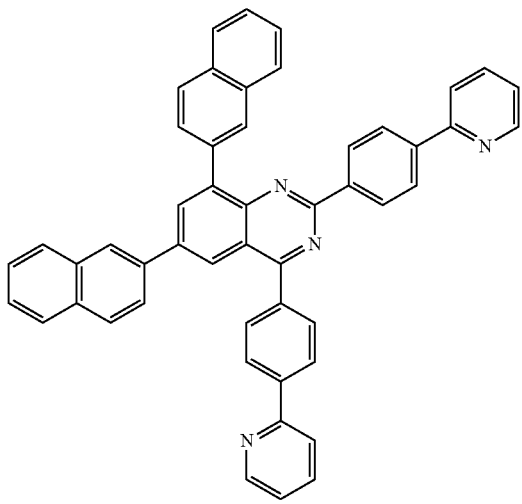
[Chemical Formula A-75]
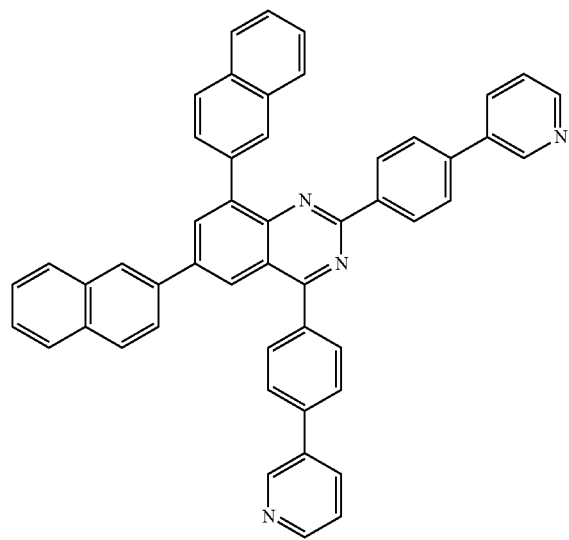
[Chemical Formula A-76]
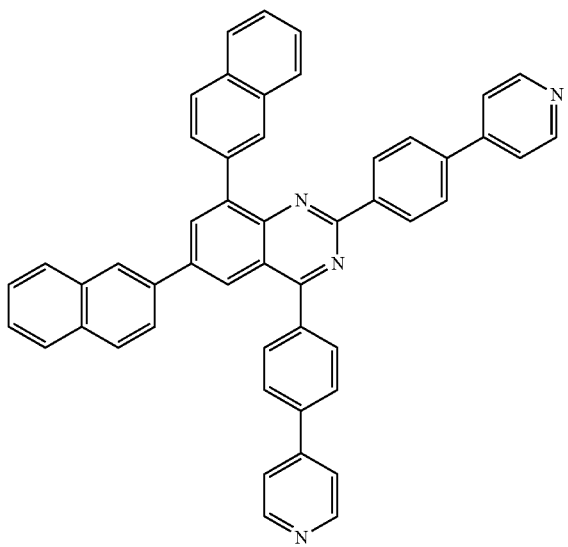

[Chemical Formula A-77]
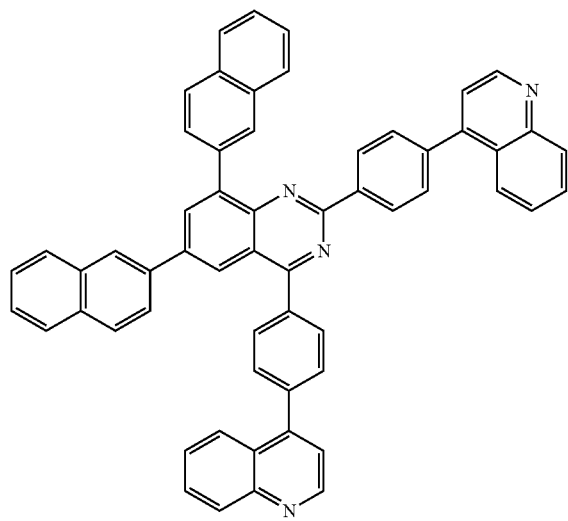
[Chemical Formula A-78]
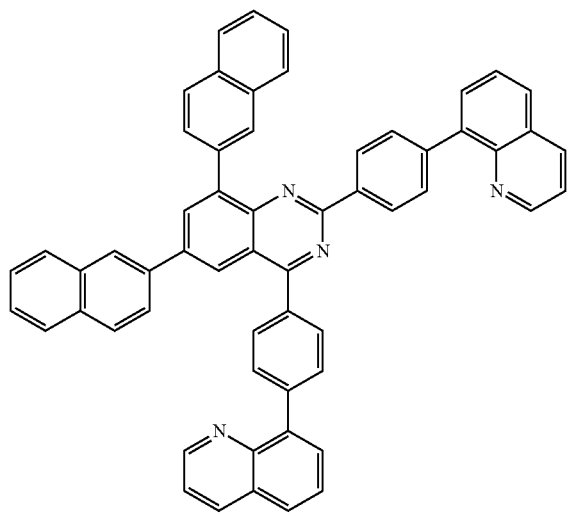
[Chemical Formula A-79]
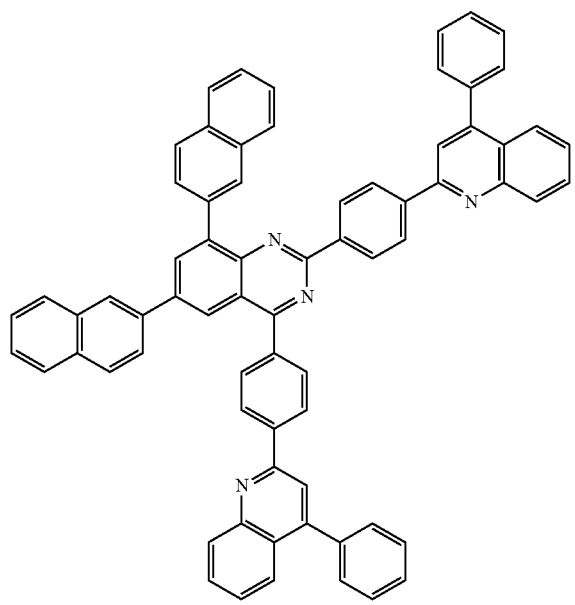
[Chemical Formula A-80]
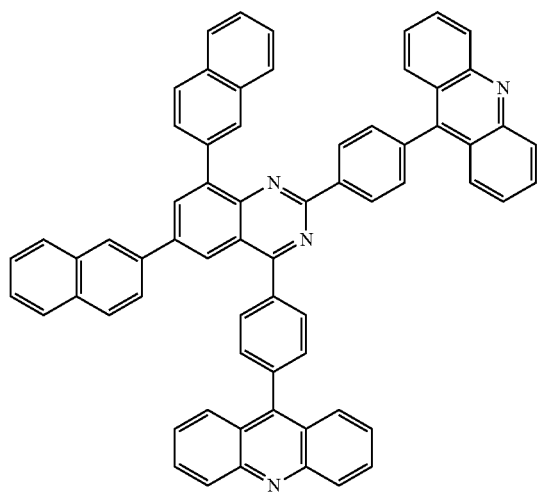

-continued
[Chemical Formula A-81]
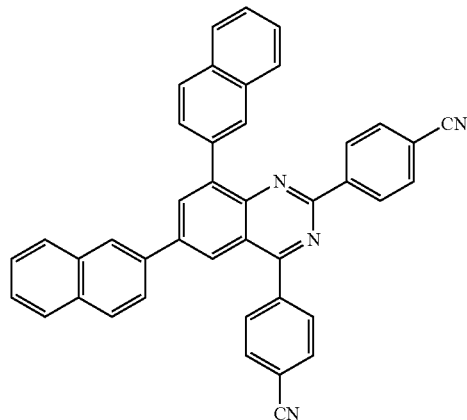
[Chemical Formula A-82]
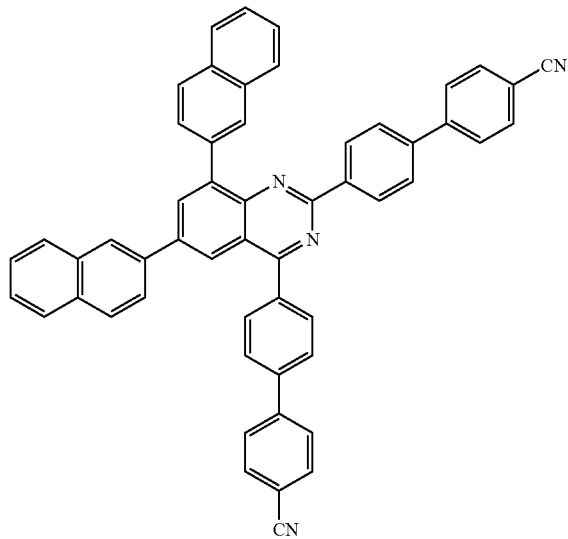
[Chemical Formula A-83]
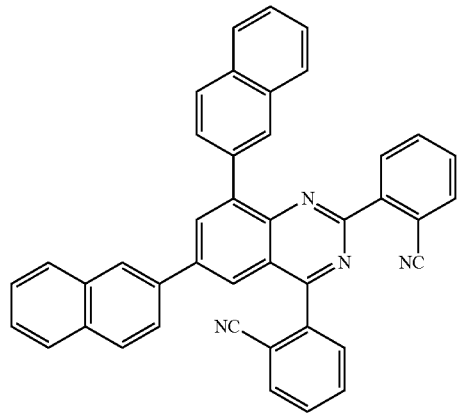
[Chemical Formula A-84]
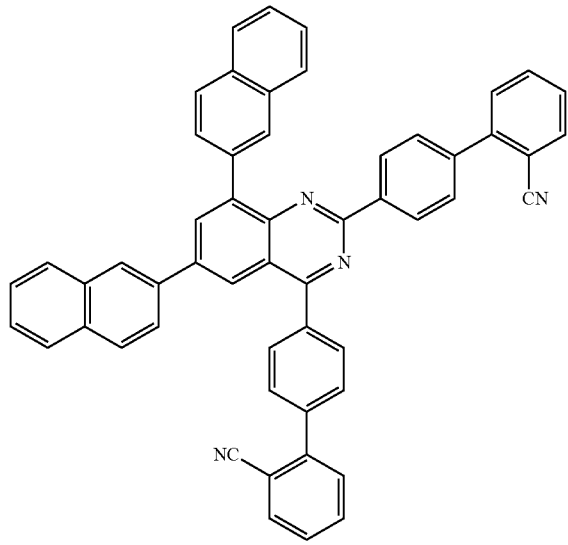
[Chemical Formula A-85]
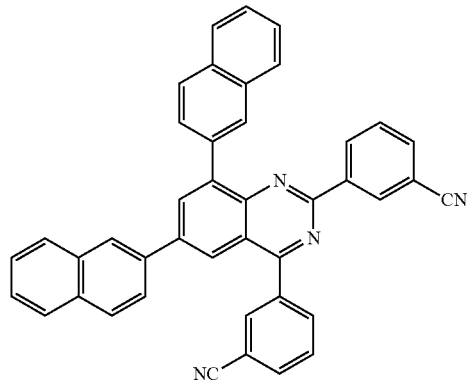
[Chemical Formula A-86]
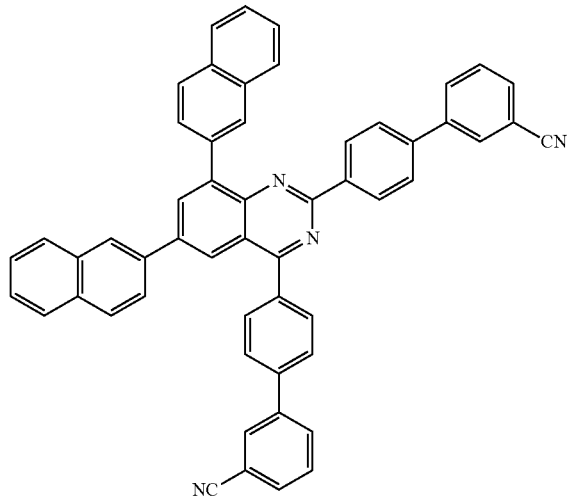

-continued
[Chemical Formula A-87]
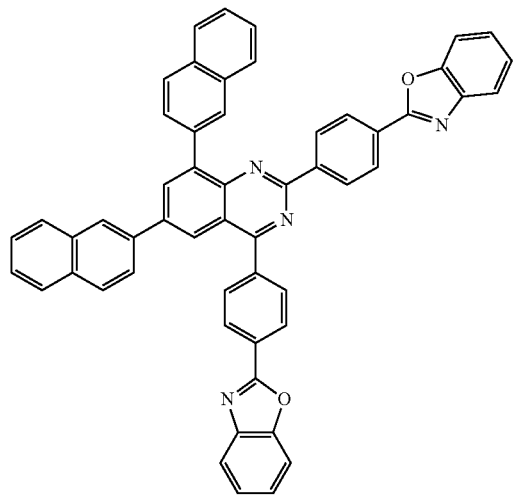
[Chemical Formula A-88]
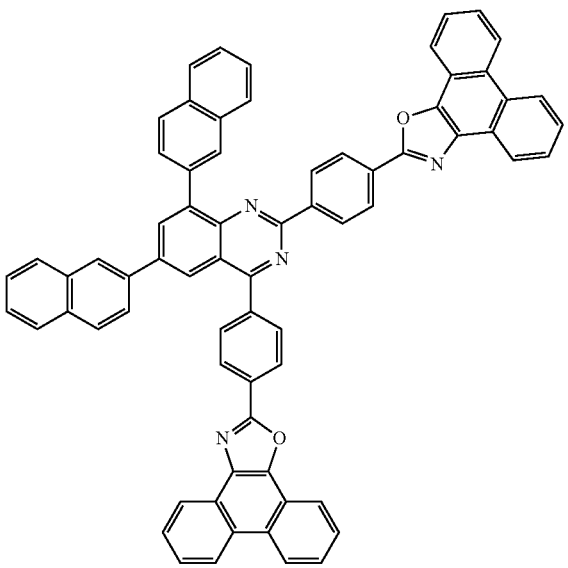
[Chemical Formula A-89]
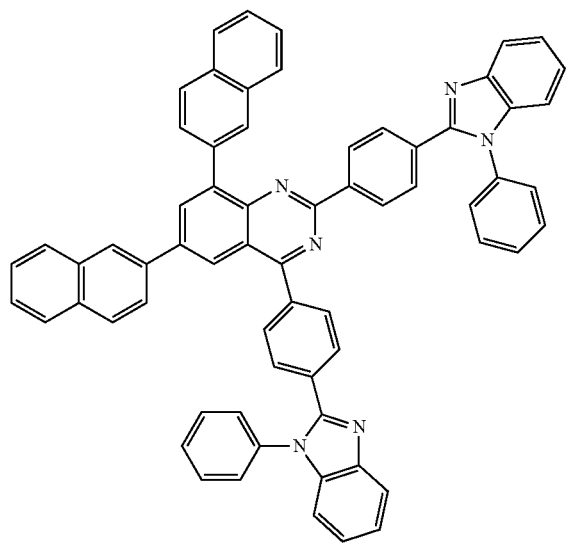
[Chemical Formula A-90]
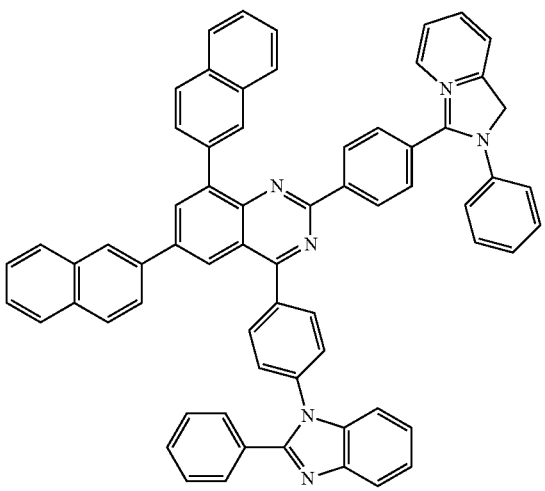

-continued
[Chemical Formula A91]
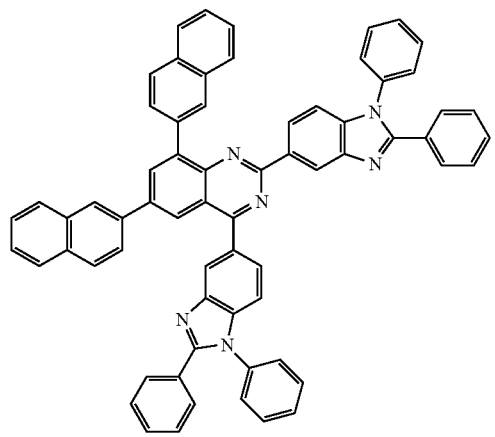
[Chemical Formula A-92]
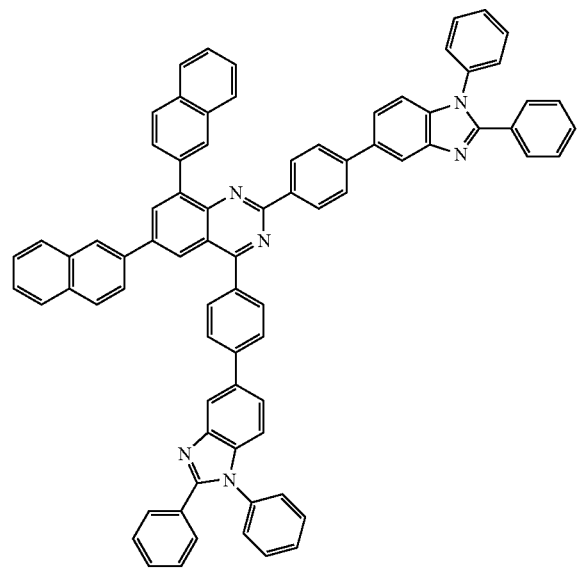
[Chemical Formula A-93]
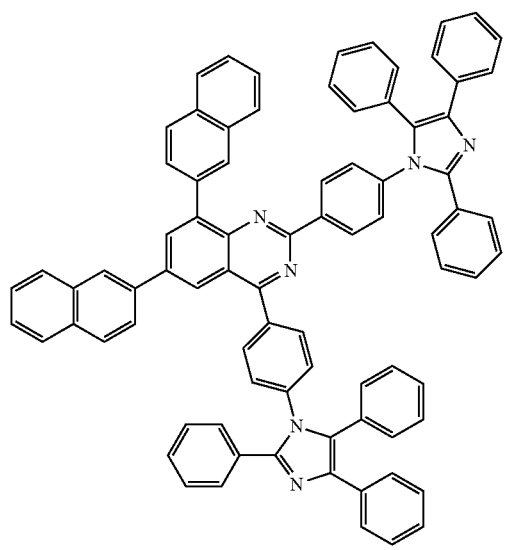
[Chemical Formula A-94]
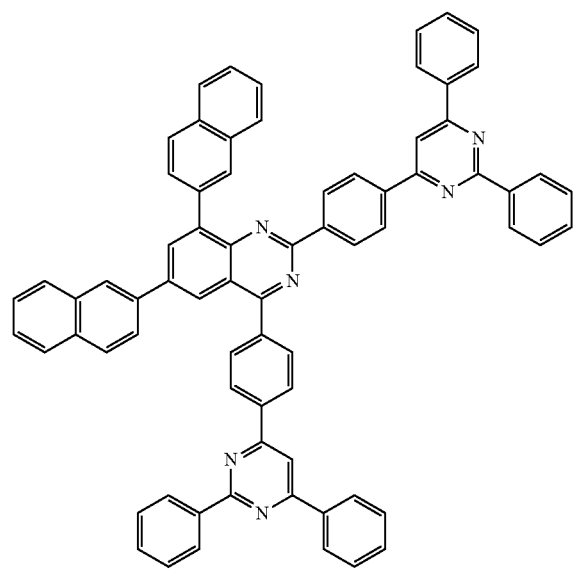

[Chemical Formula A-95]
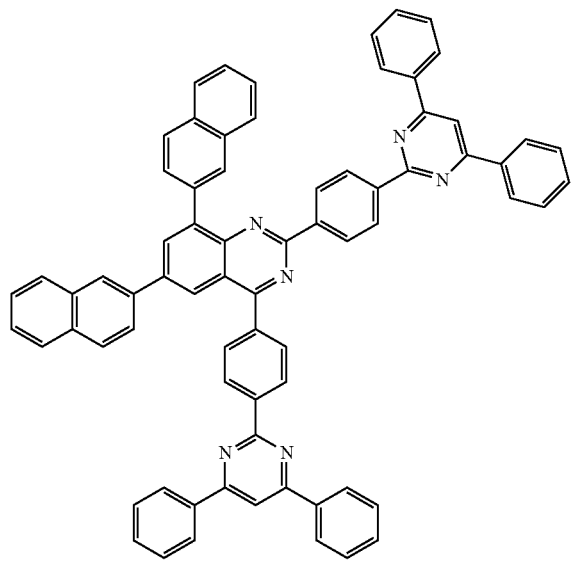
[Chemical Formula A-96]
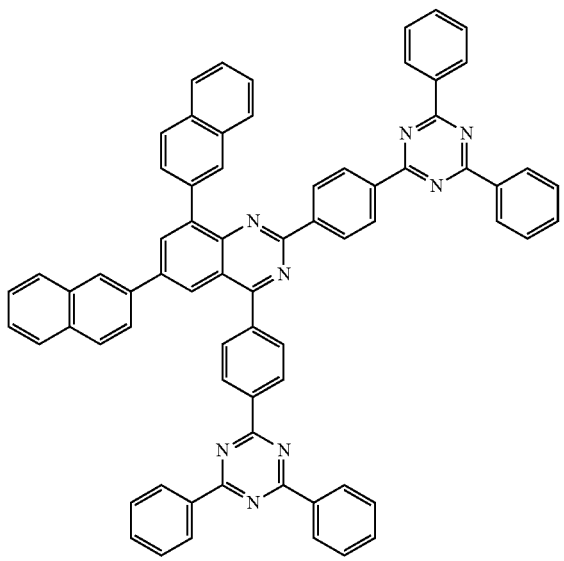
[Chemical Formula A-97]
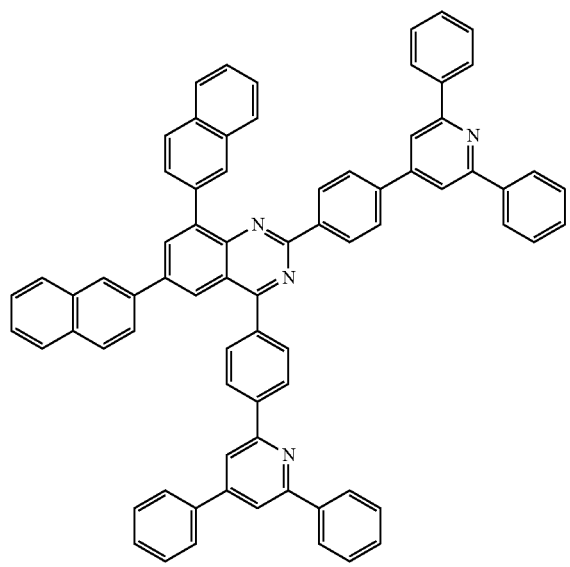
[Chemical Formula A-98]
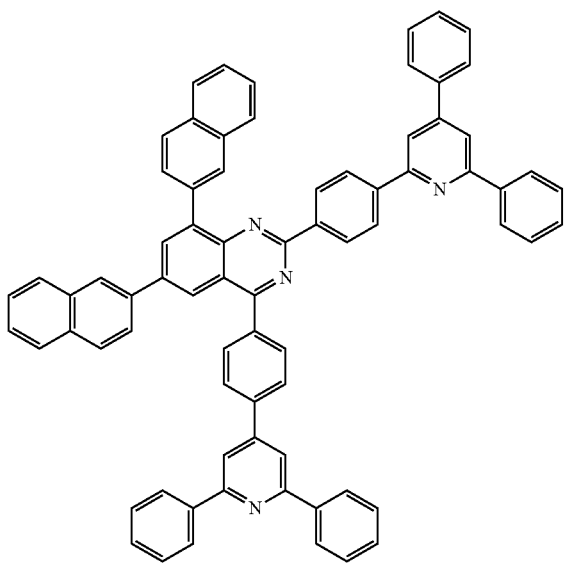

-continued
[Chemical Formula A-99]
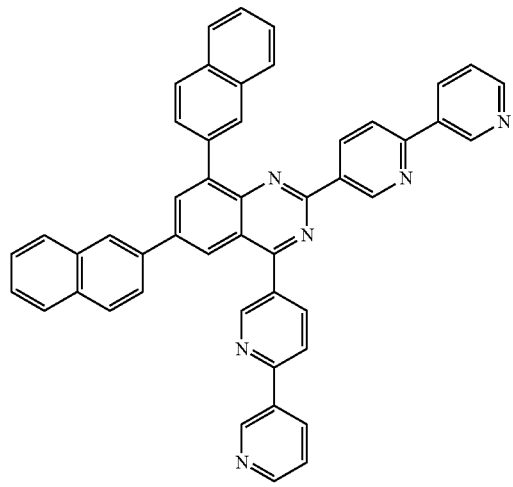
[Chemical Formula A-100]
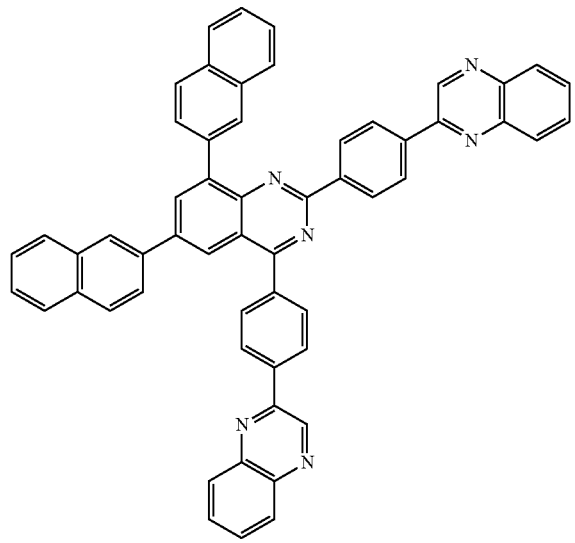
[Chemical Formula A-101]
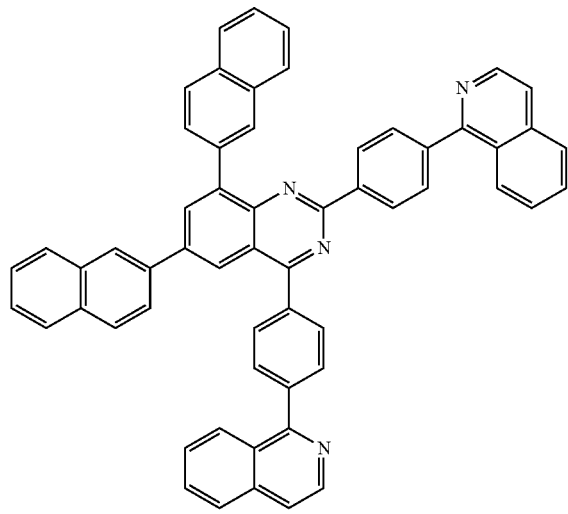
[Chemical Formula A-102]
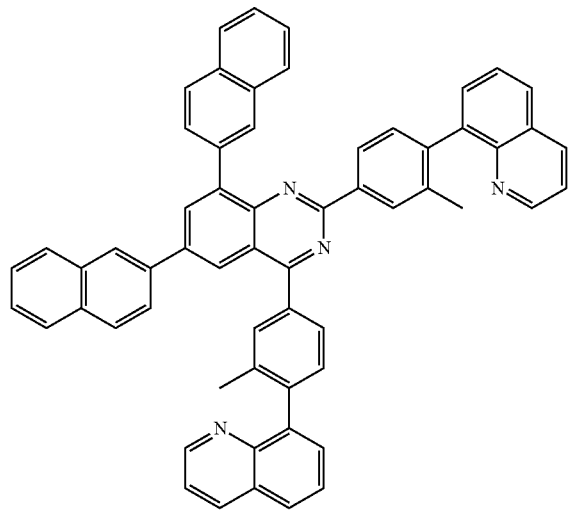
[Chemical Formula A-103]
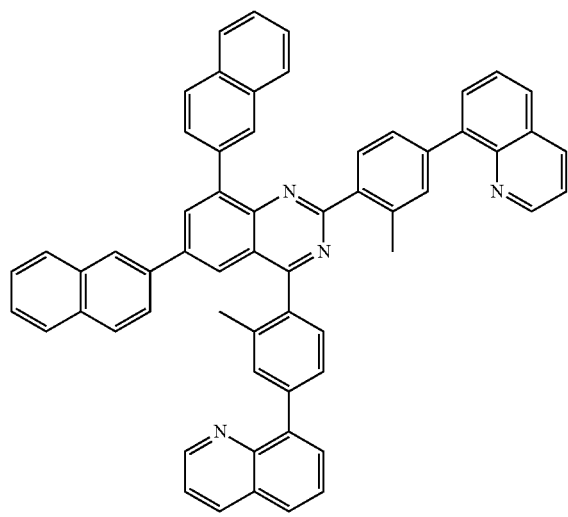
[Chemical Formula A-104]
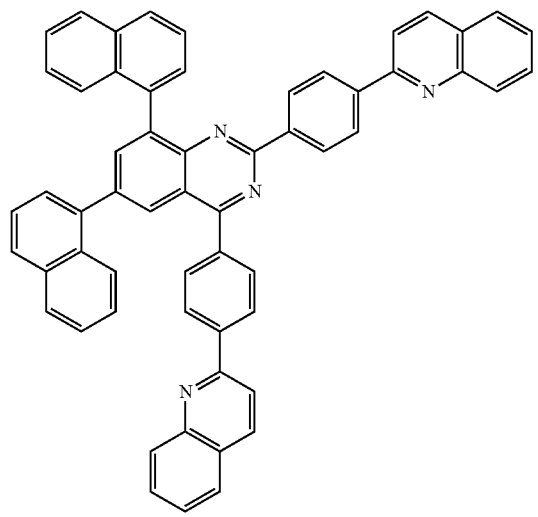

-continued
[Chemical Formula A-105]
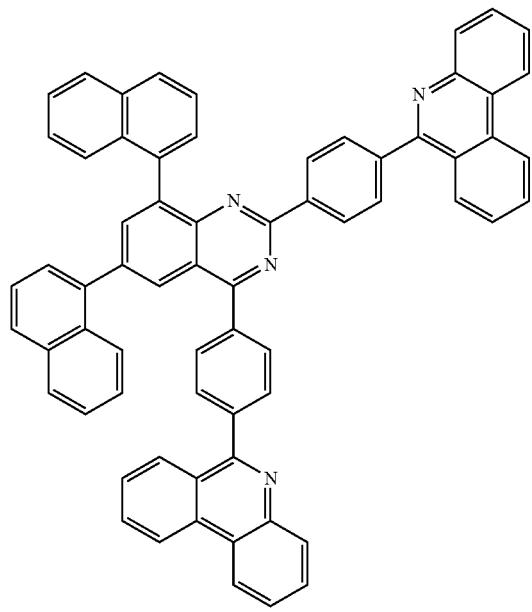
[Chemical Formula A-106]
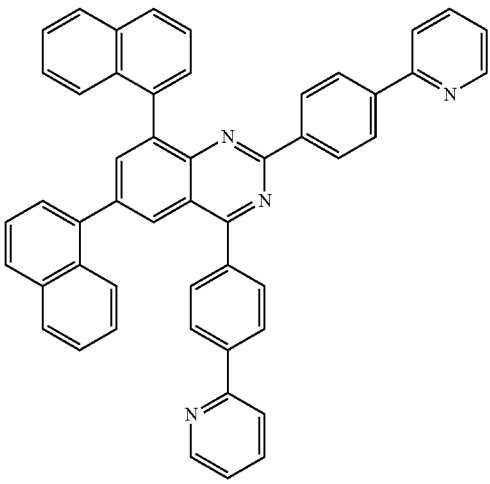
[Chemical Formula A-107]
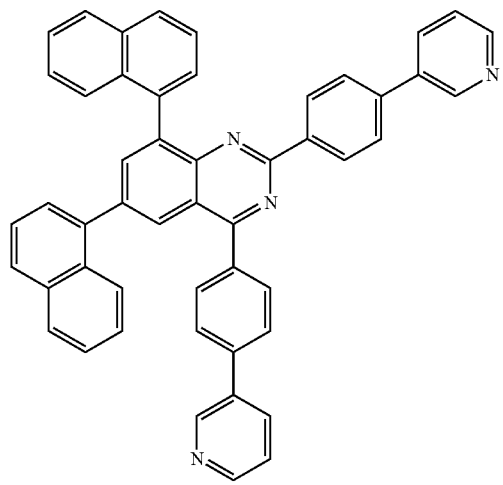
[Chemical Formula A-108]
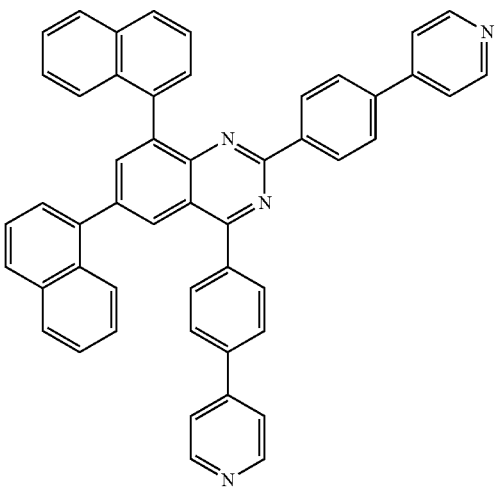
[Chemical Formula A-109]
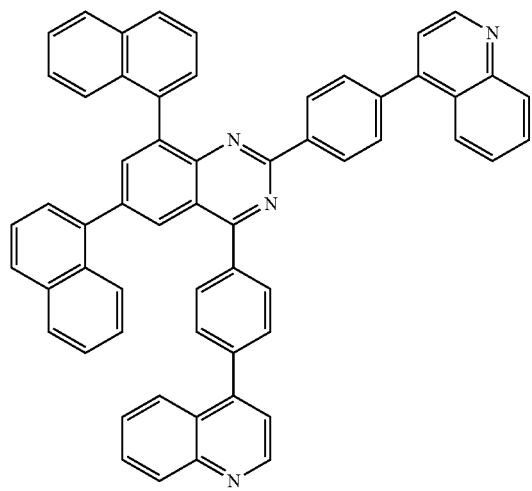
[Chemical Formula A-110]
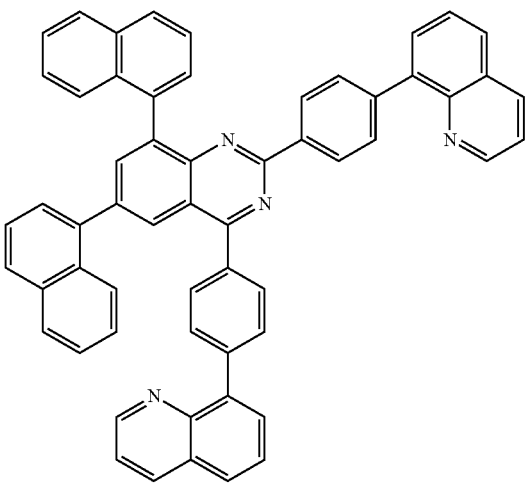

[Chemical Formula A-111]
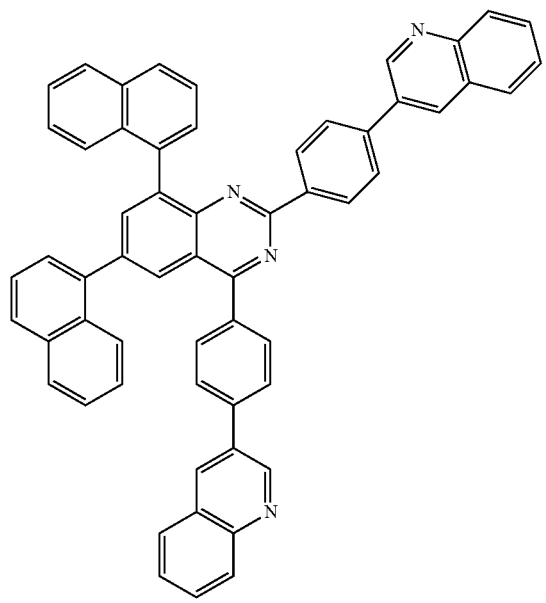
[Chemical Formula A-112]
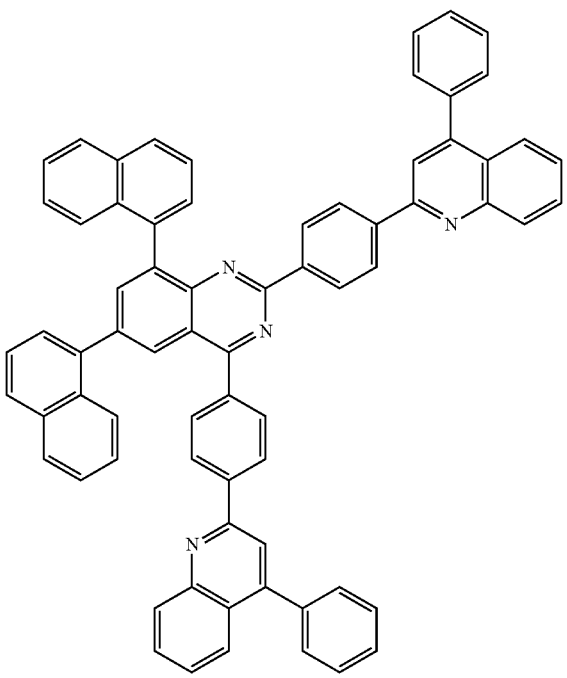
[Chemical Formula A-113]
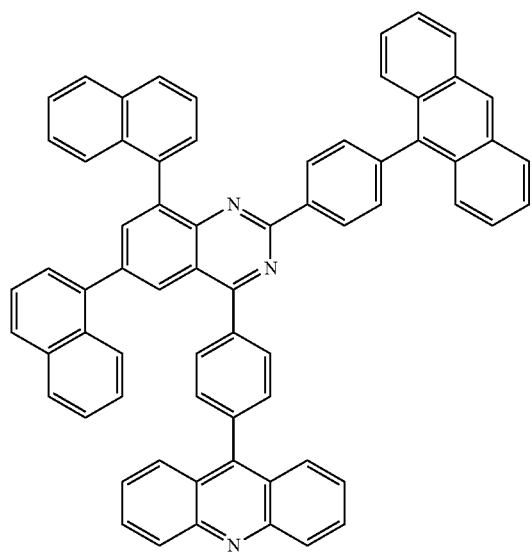
[Chemical Formula A-114]
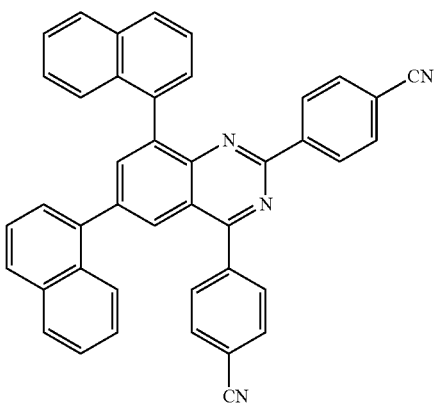

-continued
[Chemical Formula A-115]
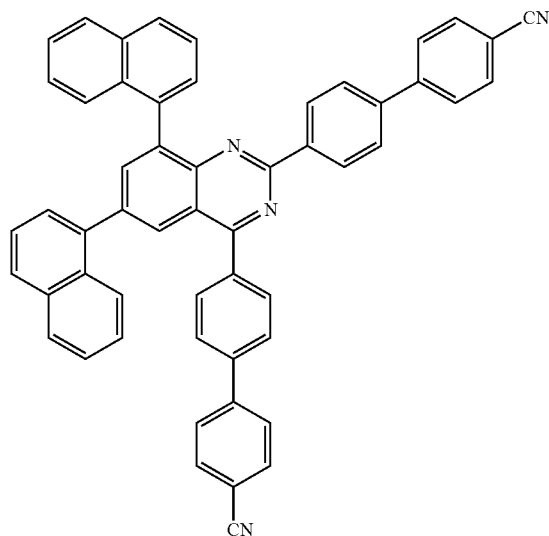
[Chemical Formula A-116]
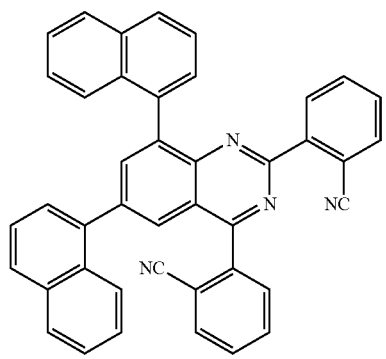
[Chemical Formula A-117]
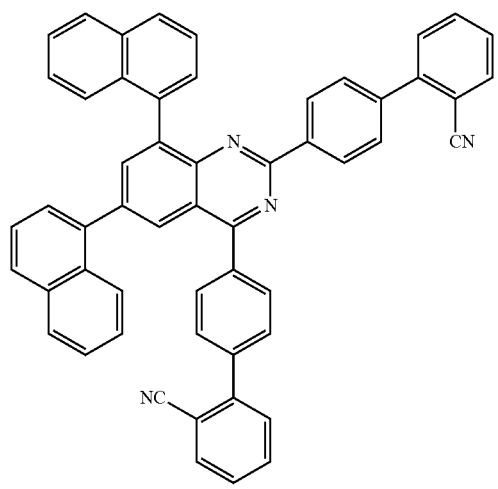
[Chemical Formula A-118]
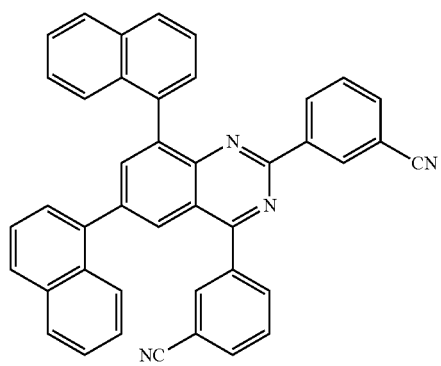
[Chemical Formula A-119]
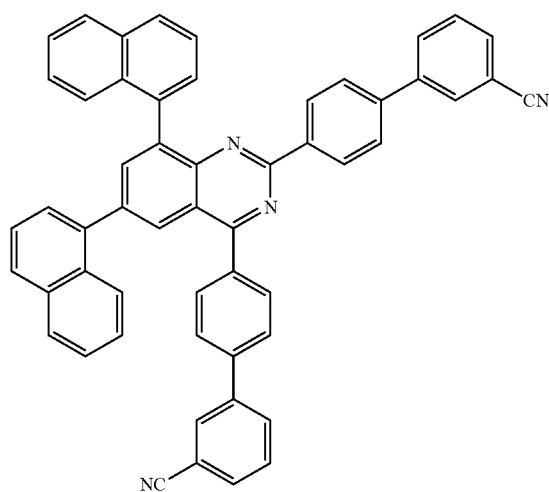
[Chemical Formula A-120]
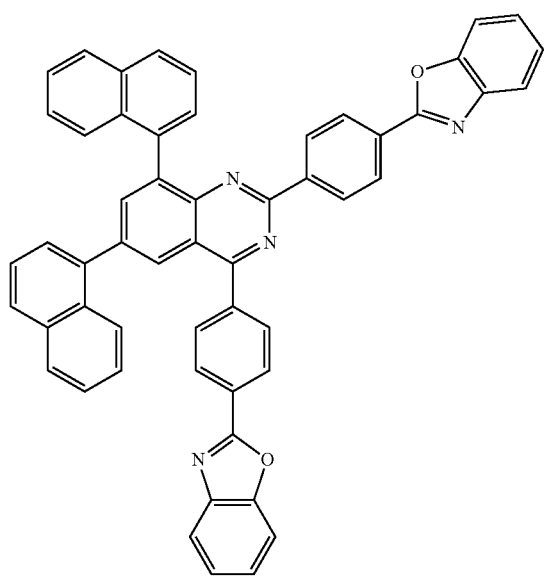

[Chemical Formula A-121]
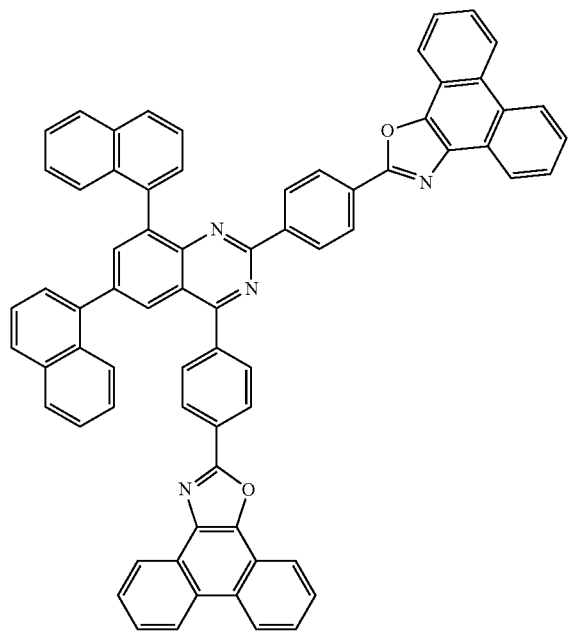
[Chemical Formula A-122]
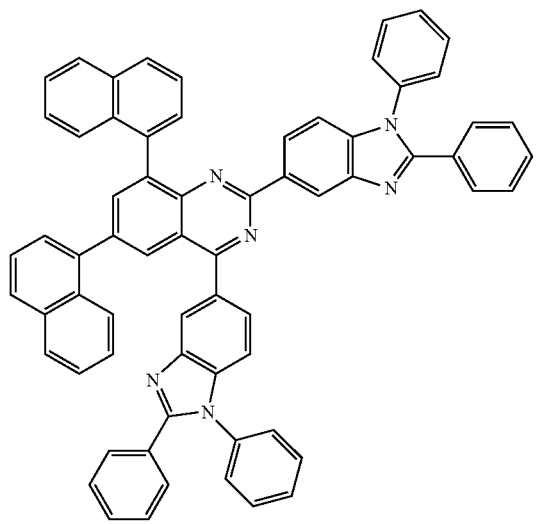
[Chemical Formula A-123]
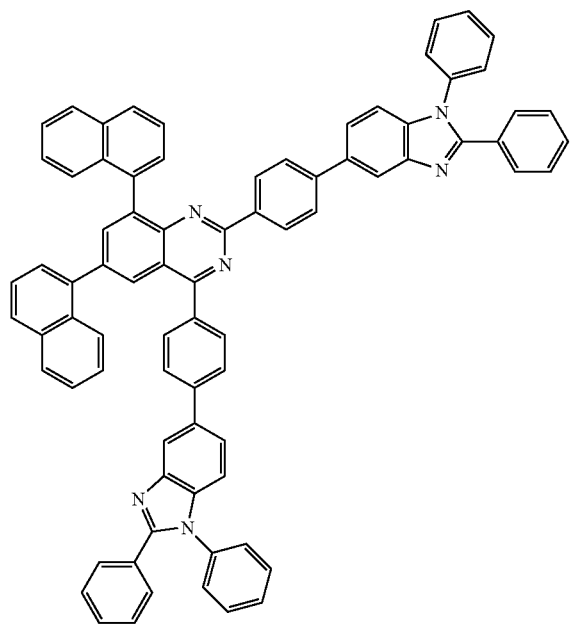
[Chemical Formula A-124]
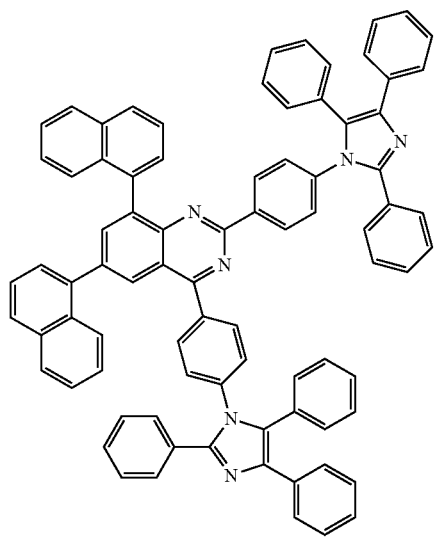

-continued
[Chemical Formula A-125]
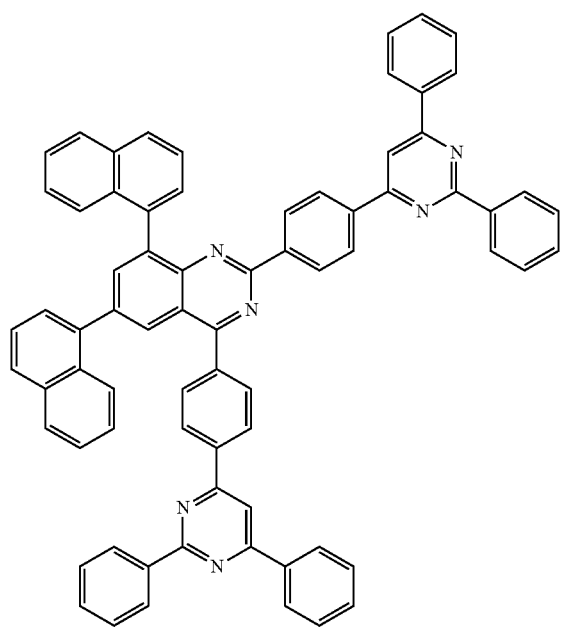
[Chemical Formula A-126]
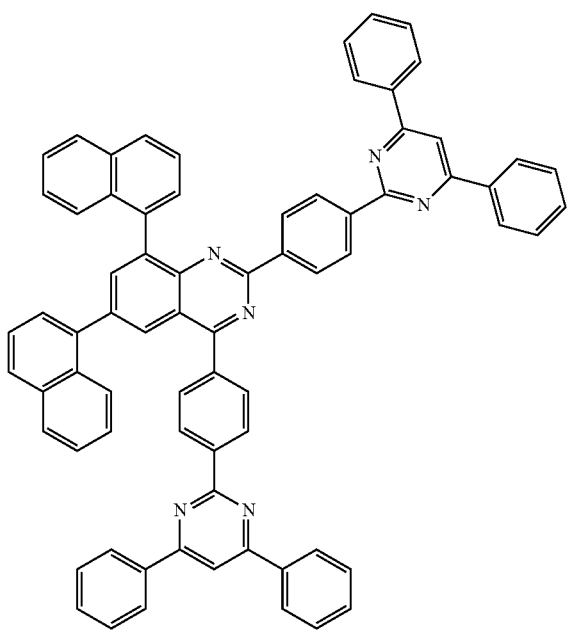
[Chemical Formula A-127]
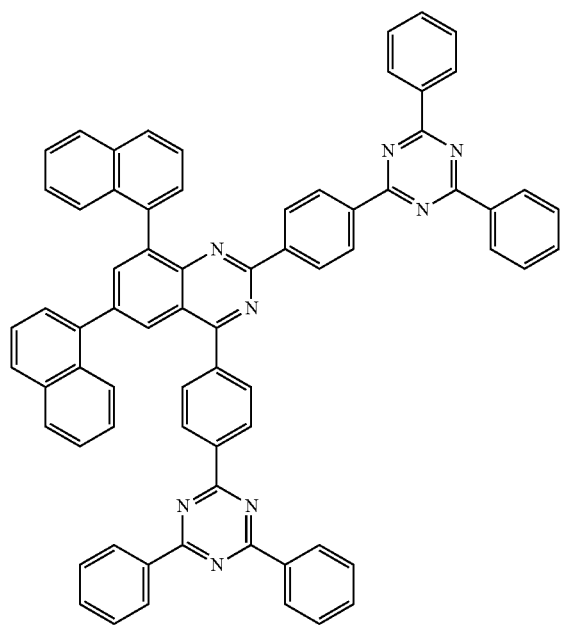
[Chemical Formula A-128]
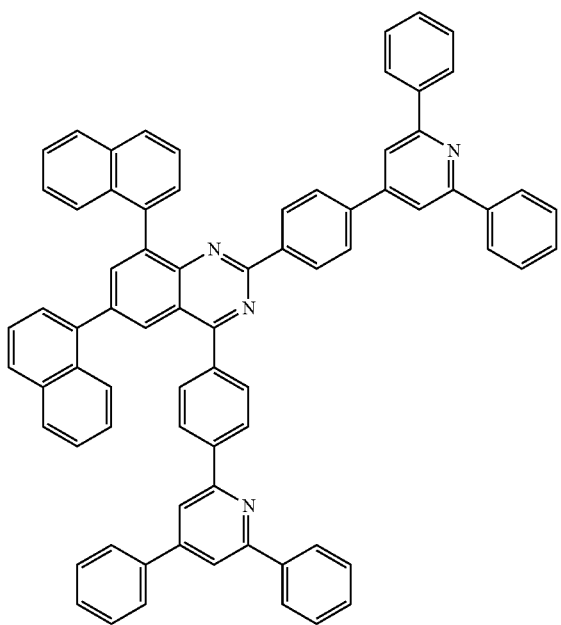

[Chemical Formula A-129]
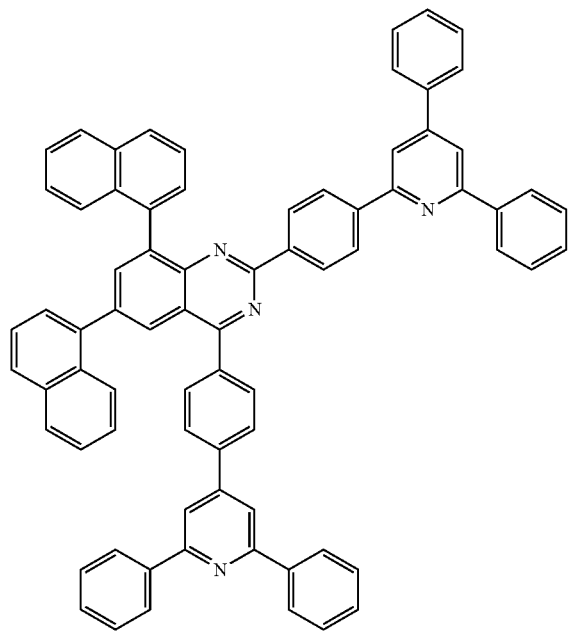
[Chemical Formula A-130]
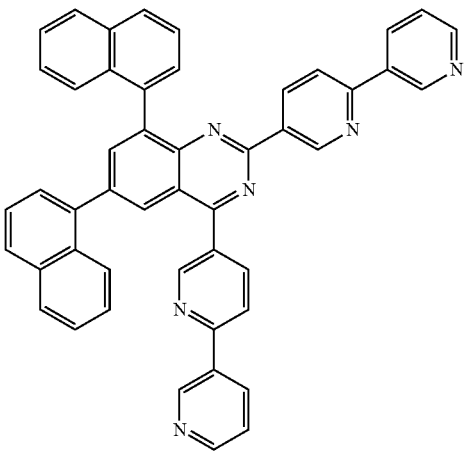
[Chemical Formula A-131]
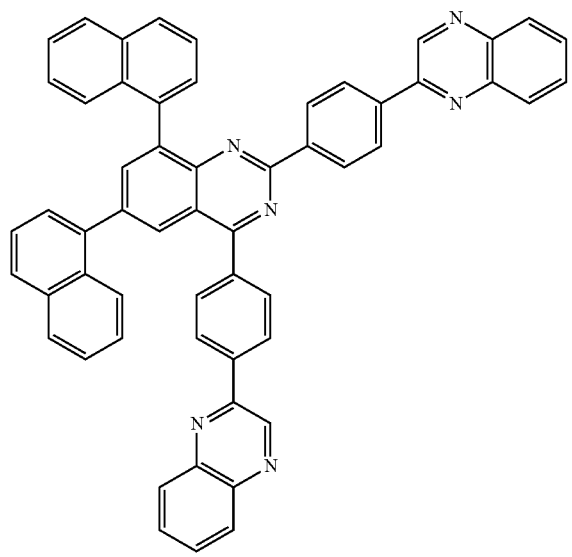
[Chemical Formula A-132]
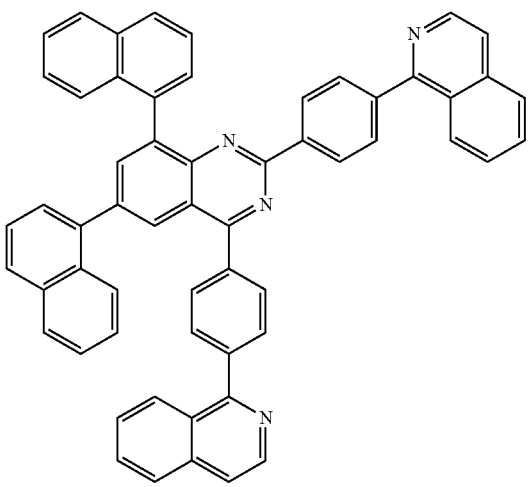

[Chemical Formula A-133]
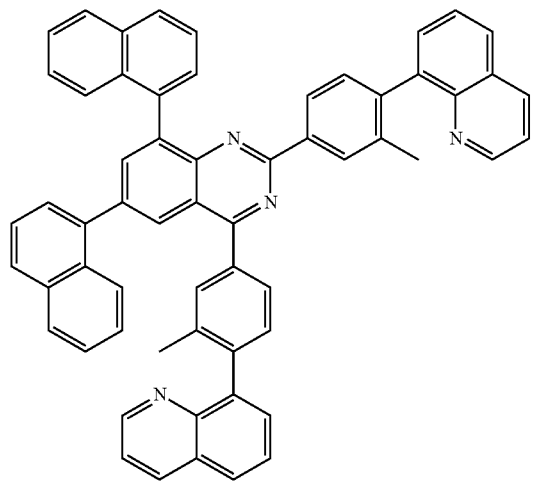
[Chemical Formula A-134]
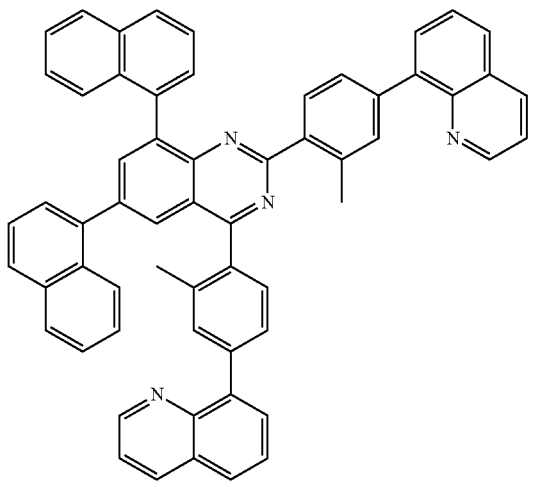
[Chemical Formula A-135]
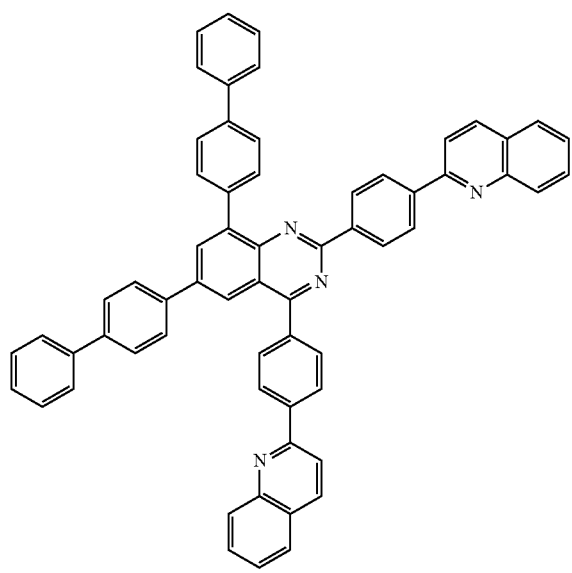
[Chemical Formula A-136]
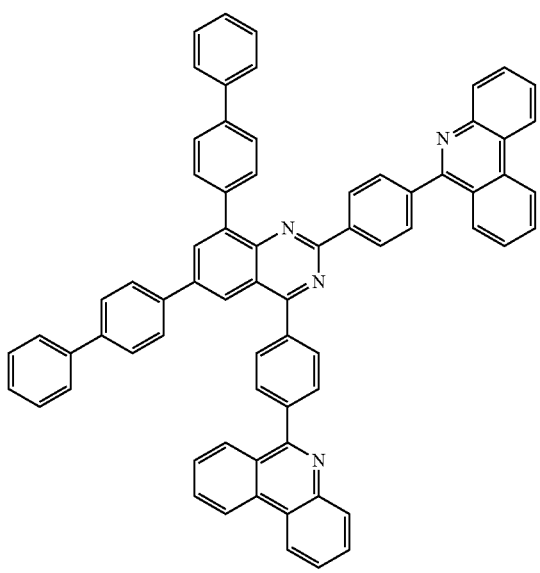
[Chemical Formula A-137]
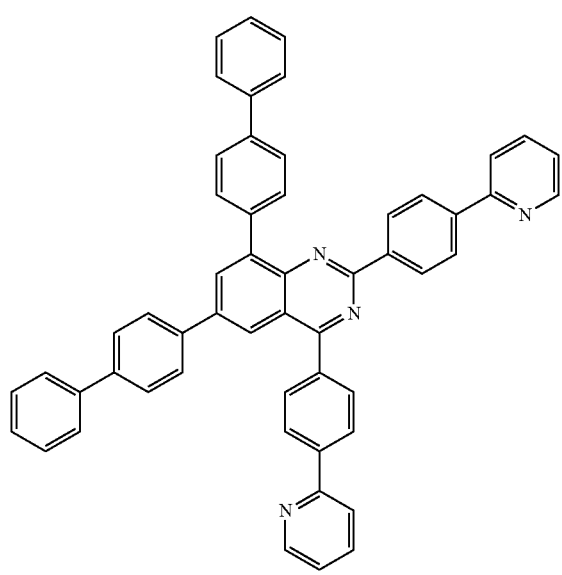
[Chemical Formula A-138]
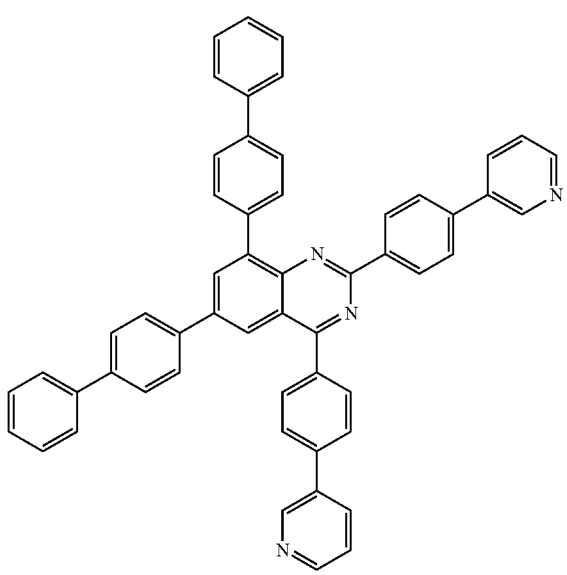

[Chemical Formula A-139]
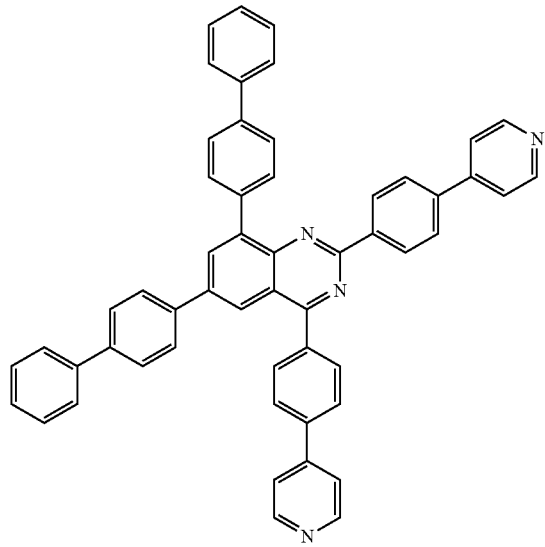
[Chemical Formula A-140]
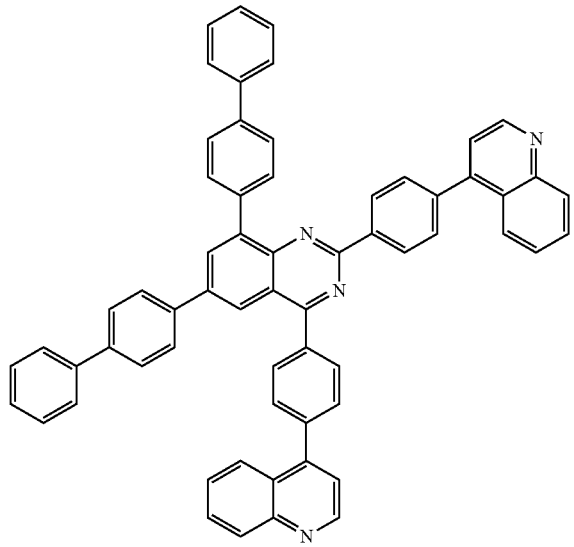
[Chemical Formula A-141]
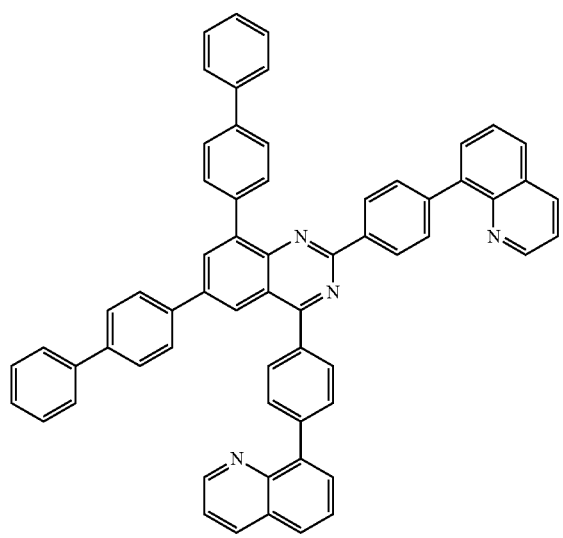
[Chemical Formula A-142]
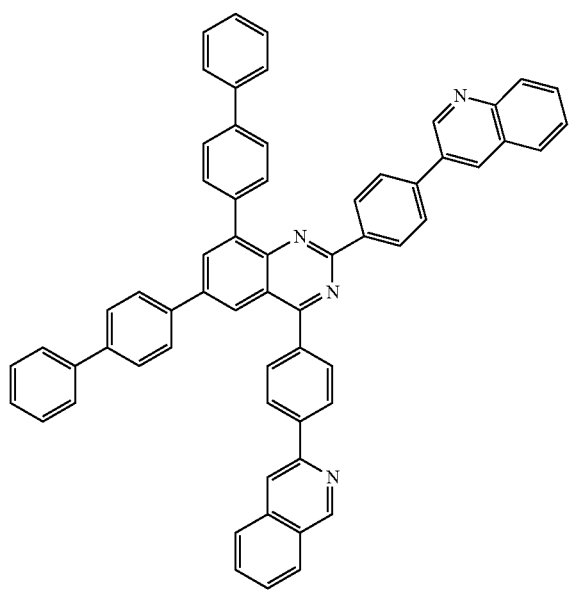

-continued
[Chemical Formula A-143]
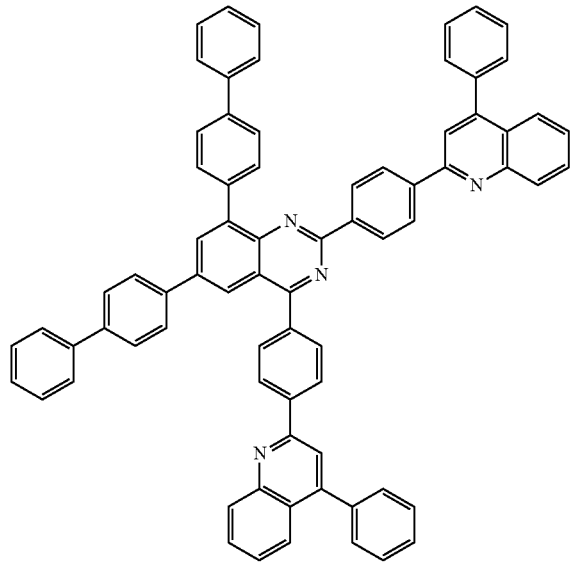
[Chemical Formula A-144]
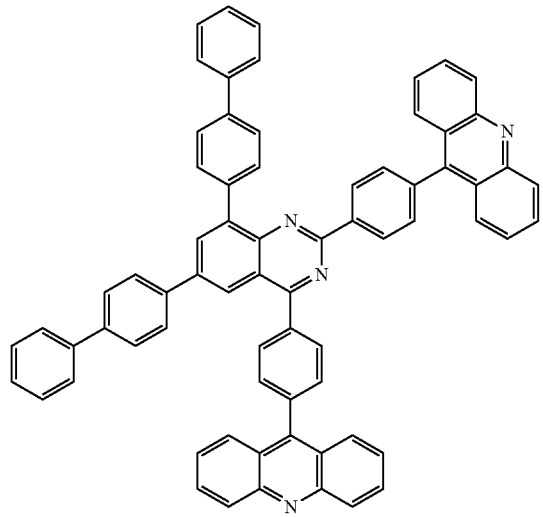
[Chemical Formula A-145]
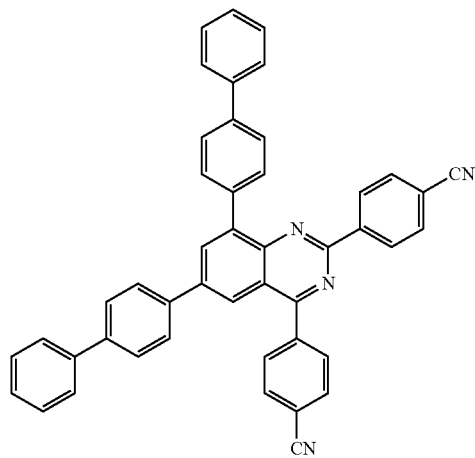
[Chemical Formula A-146]
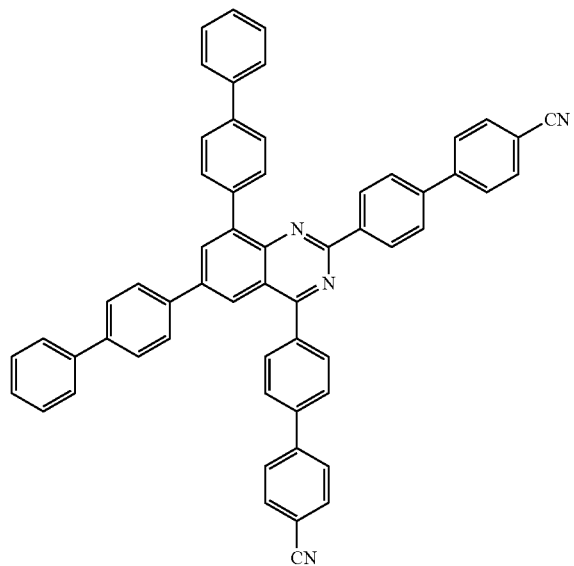

[Chemical Formula A-147]
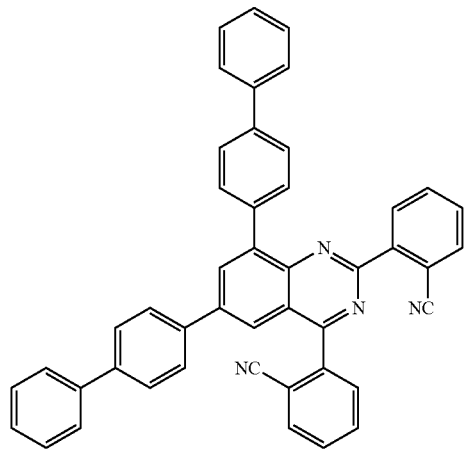
[Chemical Formula A-148]
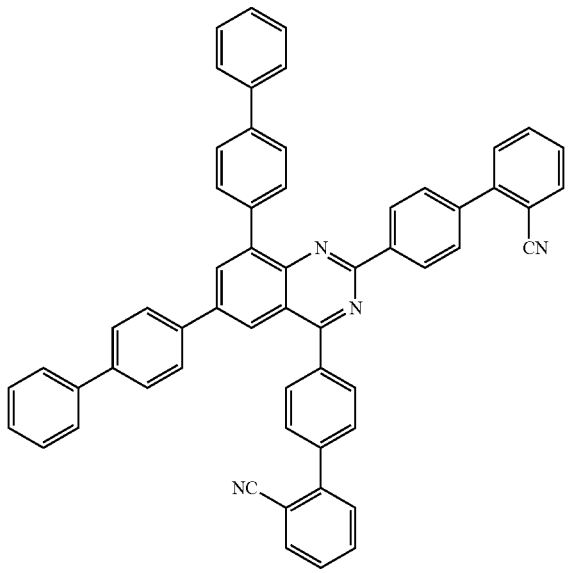
[Chemical Formula A-149]
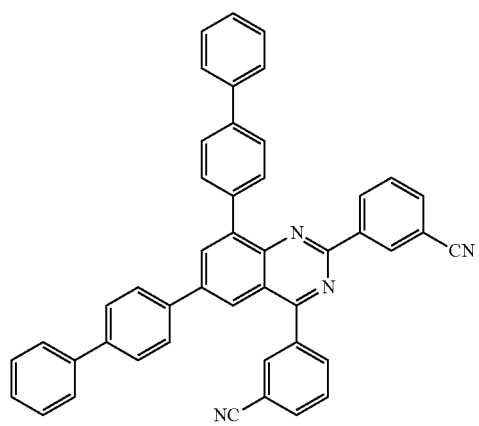
[Chemical Formula A-150]
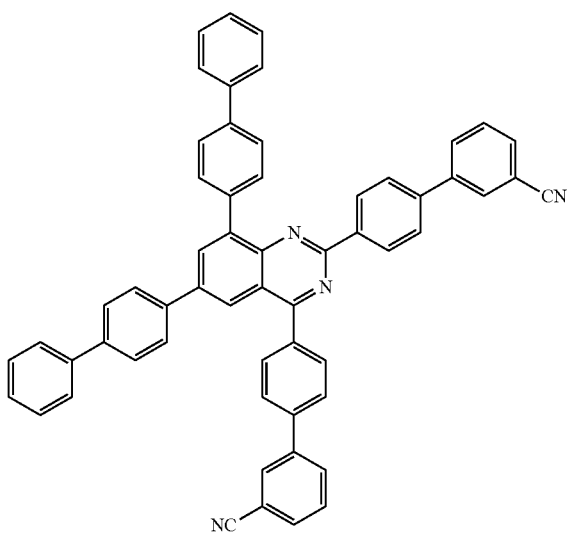

-continued
[Chemical Formula A-151]
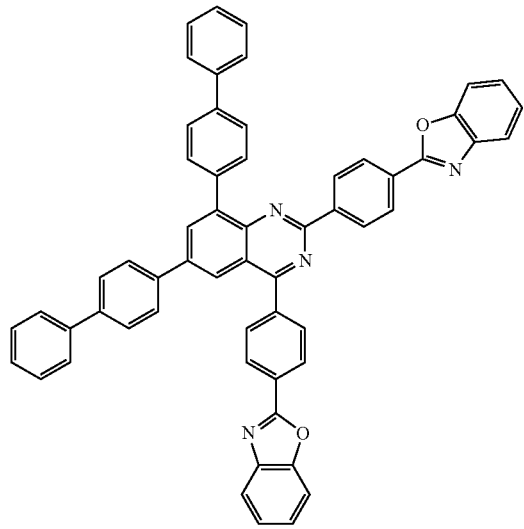
[Chemical Formula A-152]
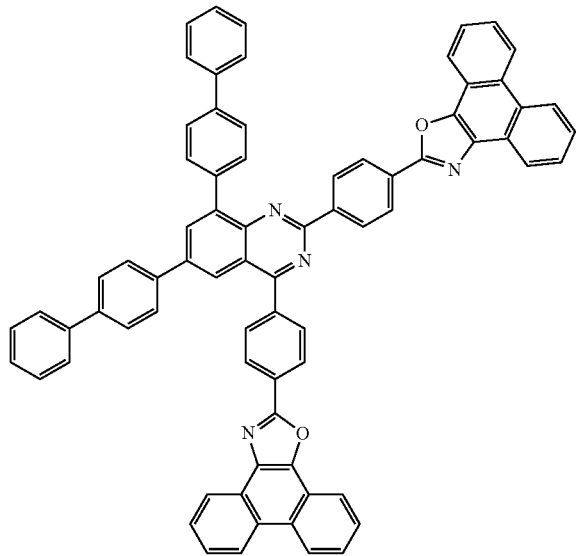
[Chemical Formula A-153]
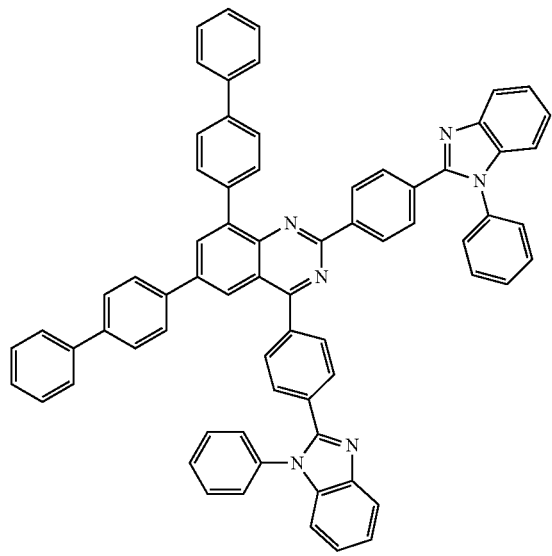
[Chemical Formula A154]
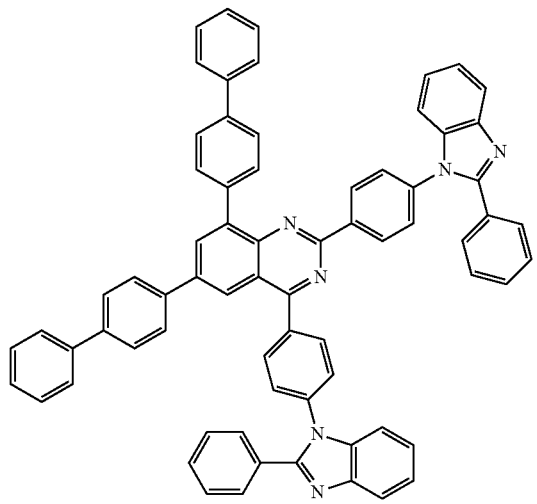

[Chemical Formula A-155]
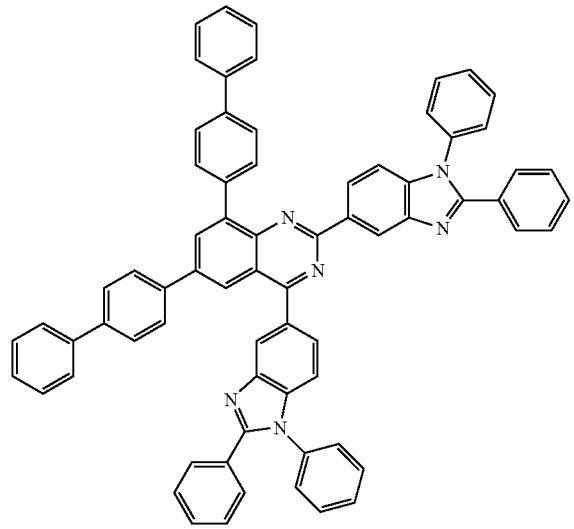
[Chemical Formula A-156]
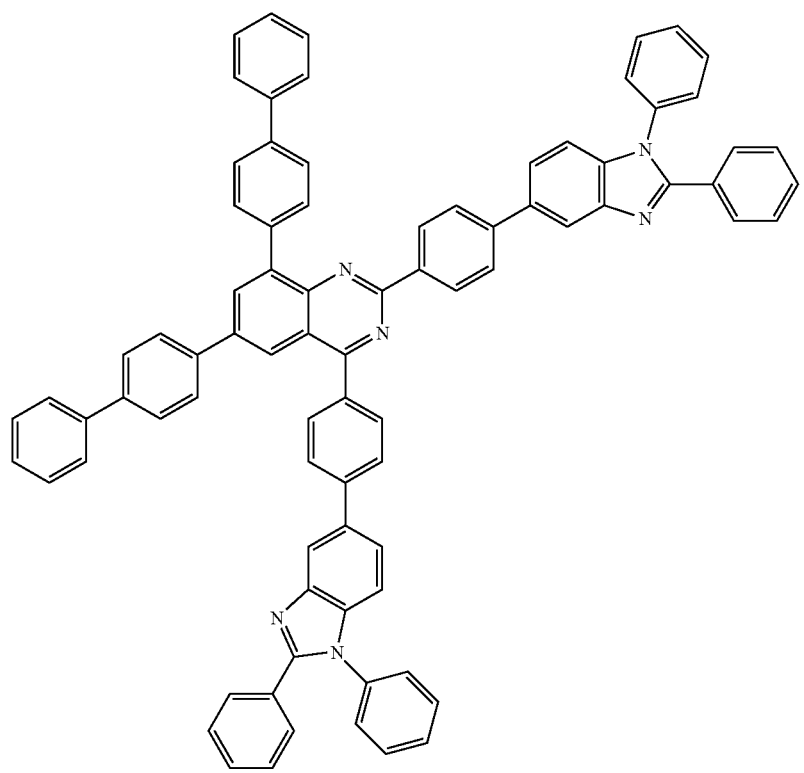

-continued
[Chemical Formula A-157]
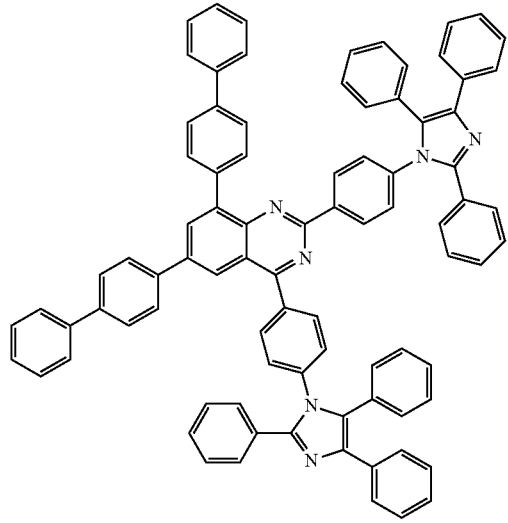
[Chemical Formula A-158]
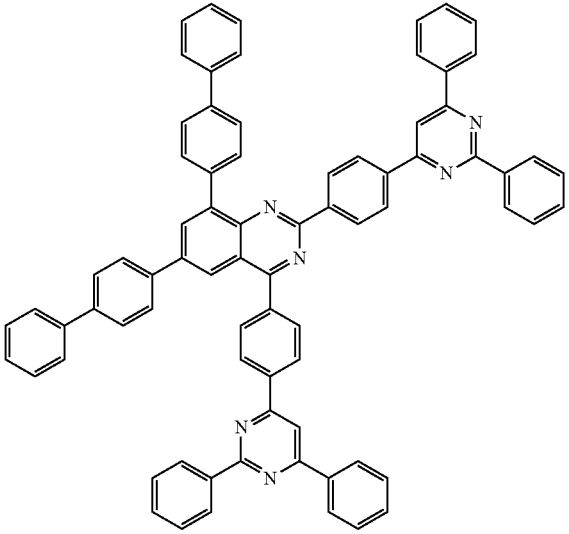
[Chemical Formula A-159]
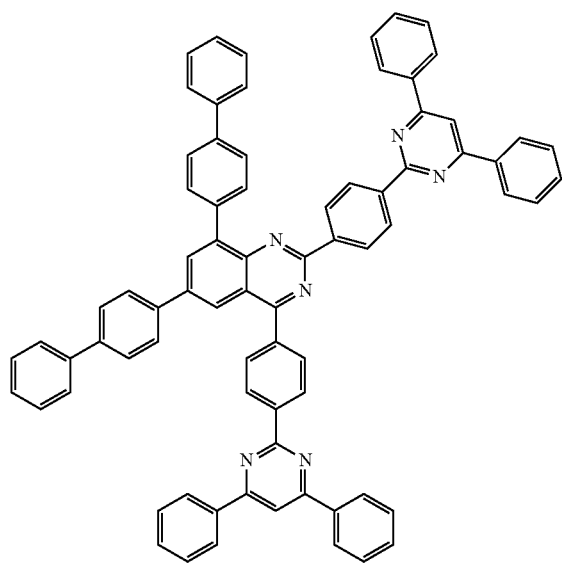
[Chemical Formula A-160]
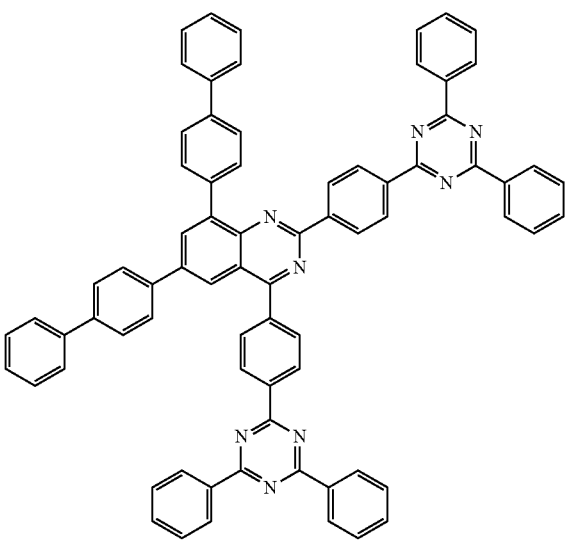

[Chemical Formula A-161]
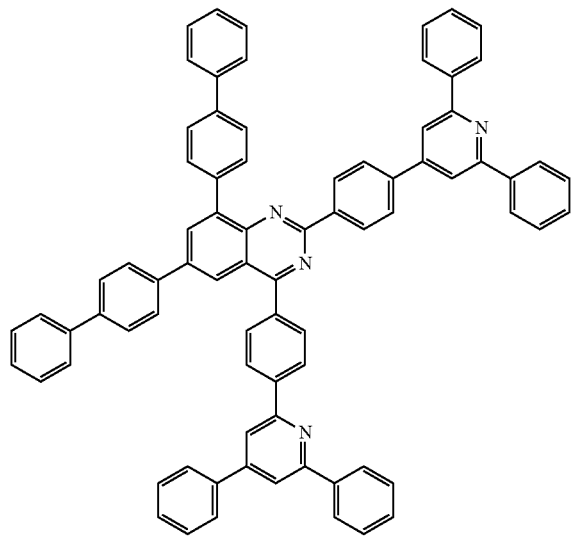
[Chemical Formula A-162]
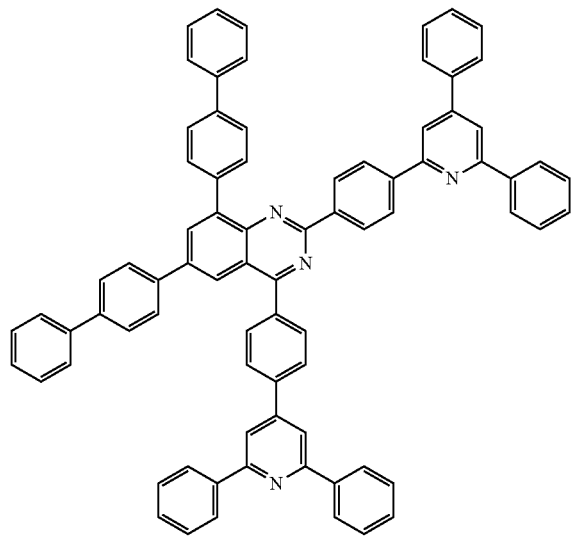
[Chemical Formula A-163]
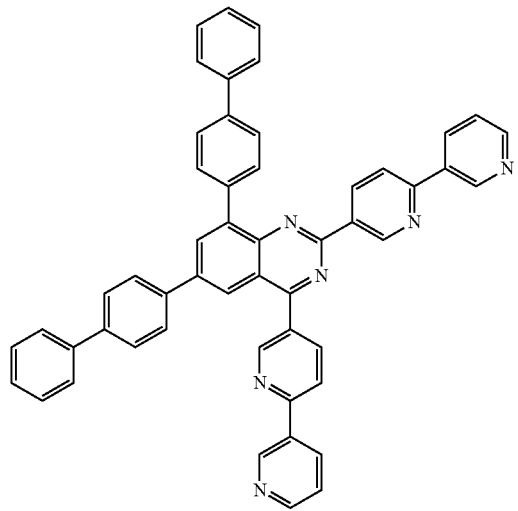
[Chemical Formula A-164]
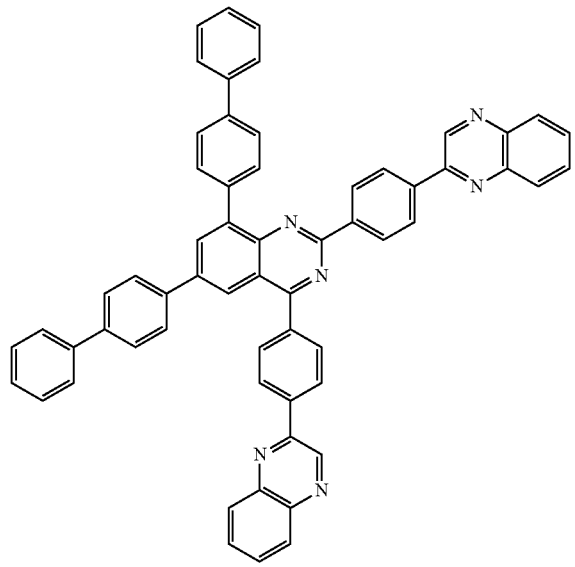

-continued
[Chmical Formula A-165]
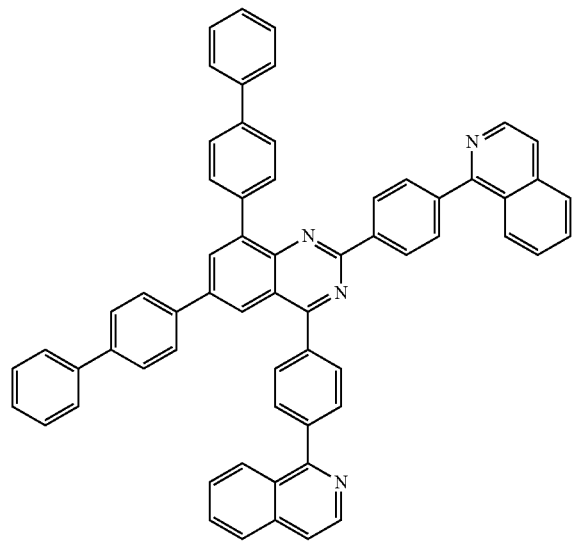
[Chemical Formula A-166]
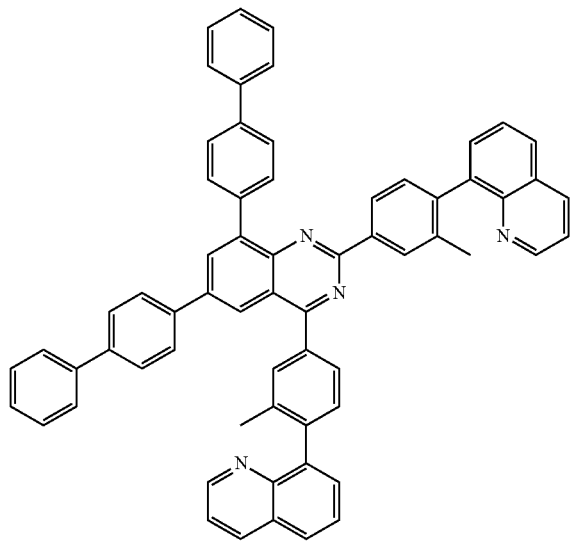
[Chemical Formula A-167]
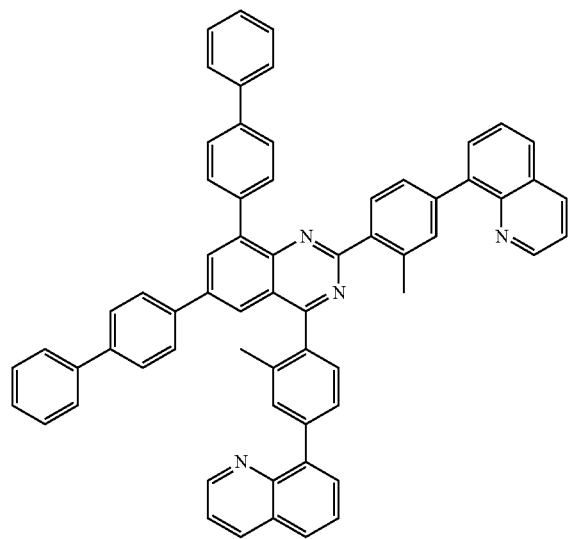
[Chemical Formula A-168]
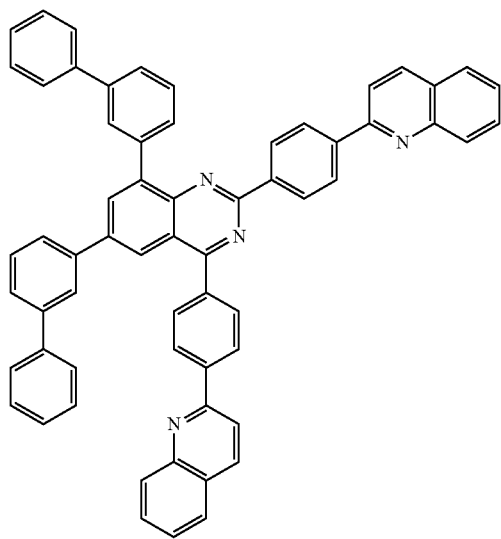

[Chemical Formula A-169]
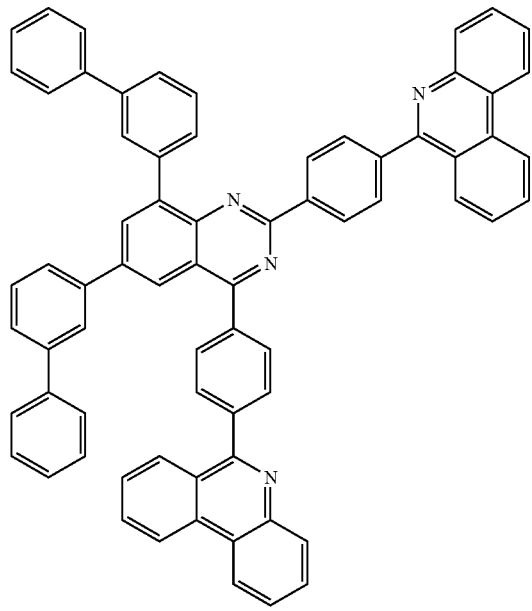
[Chemical Formula A-170]
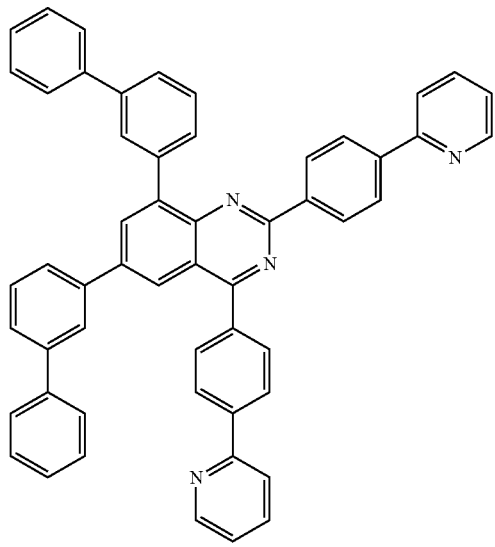
[Chemical Formula A-171]
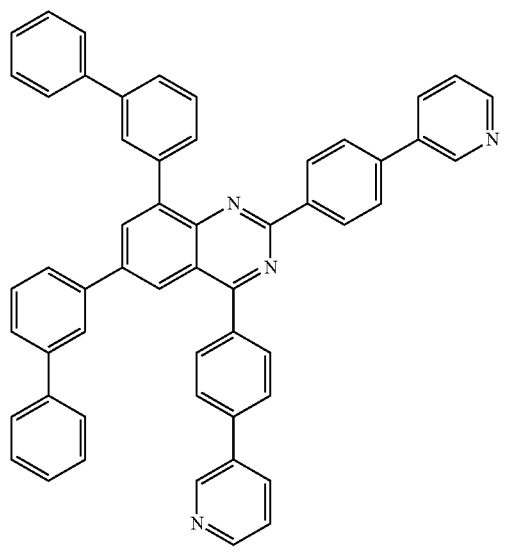
[Chemical Formula A-172]
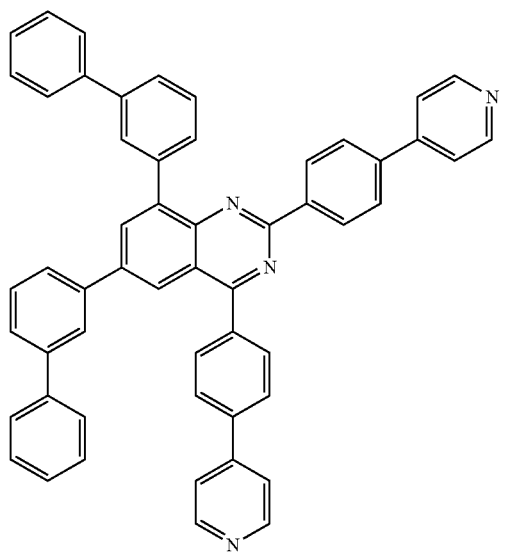

[Chemical Formula A-173]
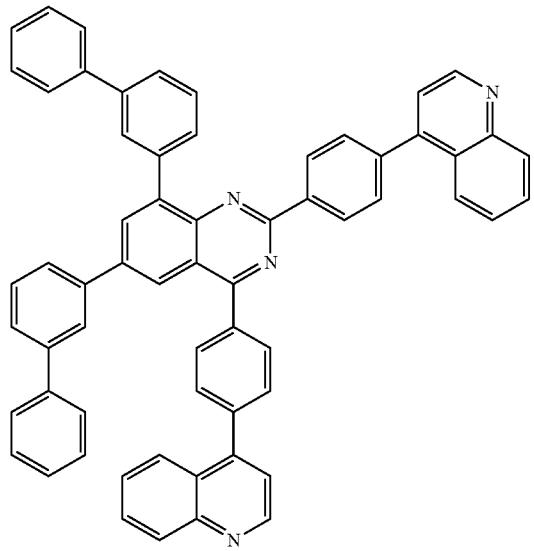
[Chemical Formula A-174]
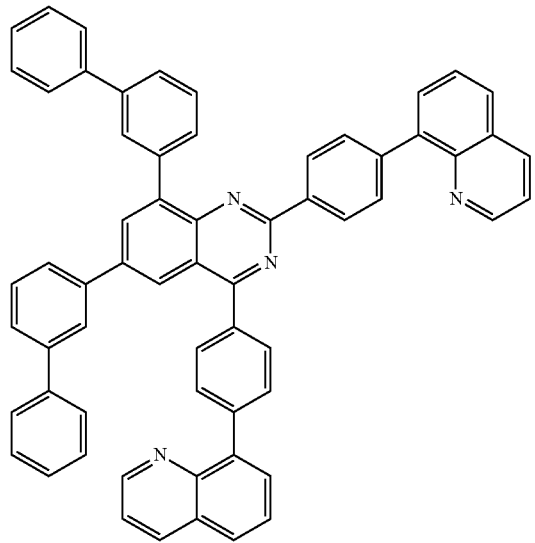
[Chemical Formula A-175]
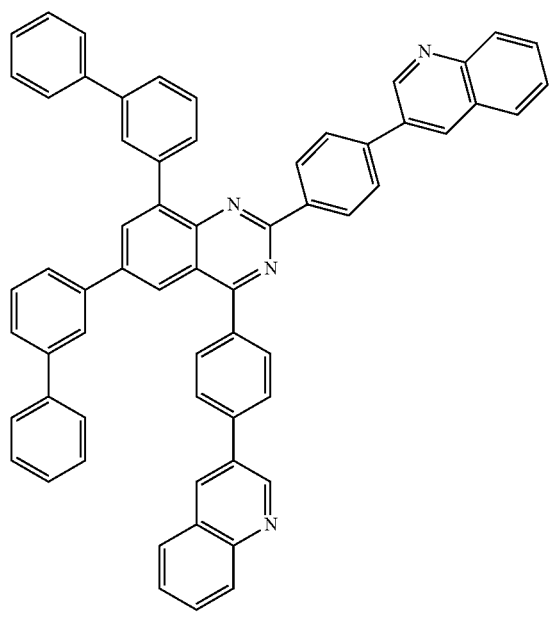
[Chemical Formula A-176]
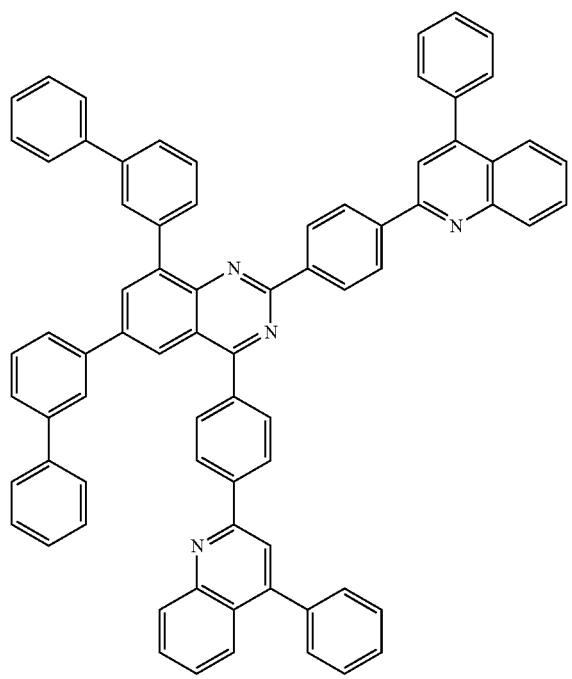

[Chemical Formula A-177]
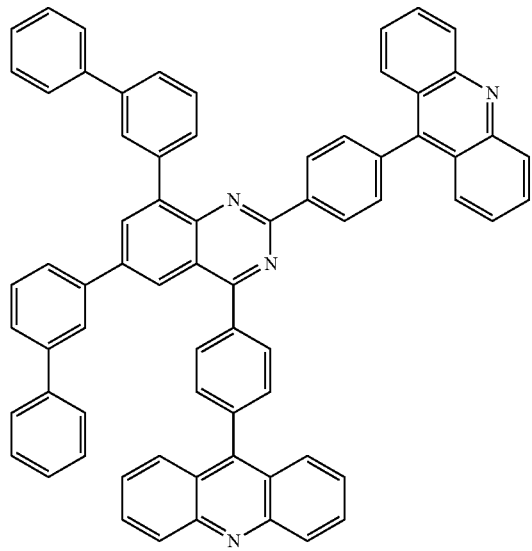
[Chemical Formula A-178]
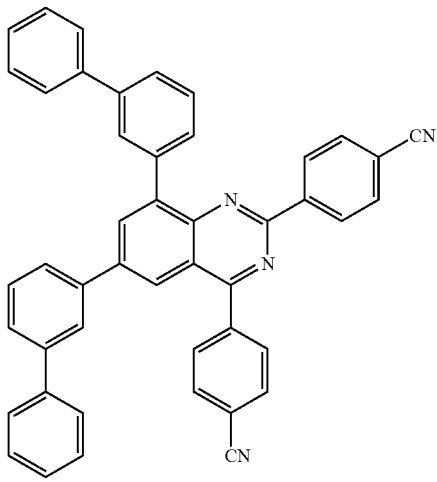
[Chemical Formula A-179]
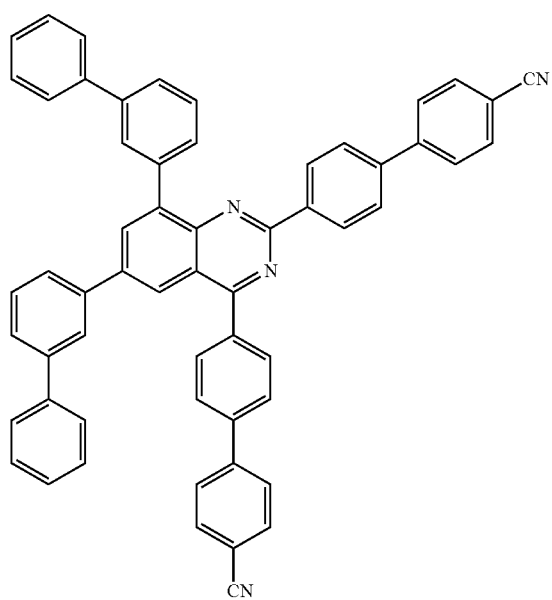
[Chemical Formula A-180]
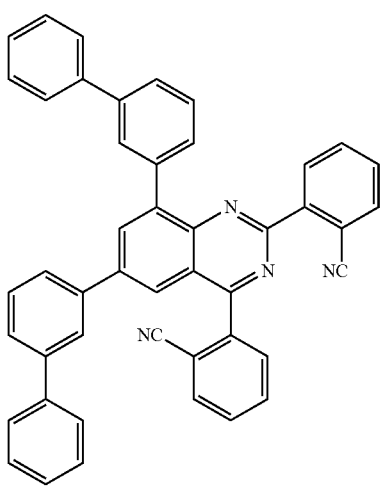

[Chemical Formula A-181]
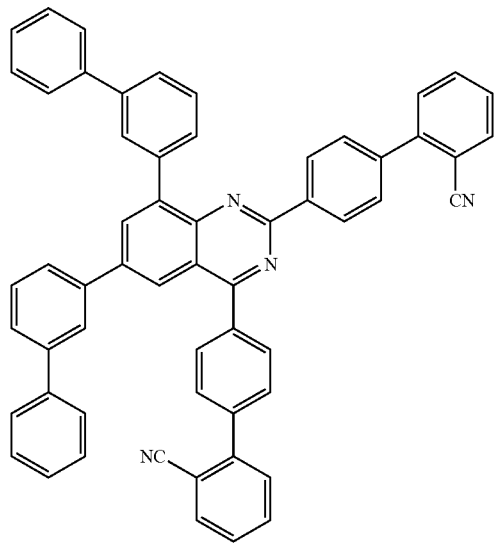
[Chemical Formula A-182]
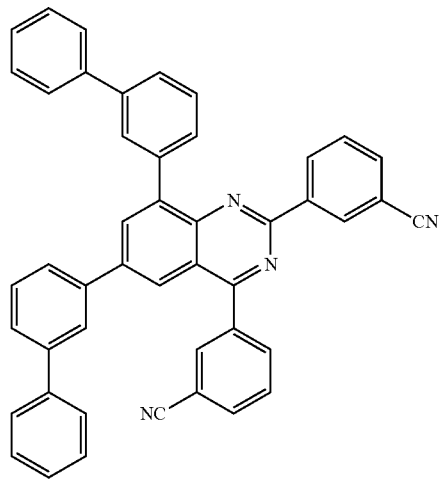
[Chemical Formula A-183]
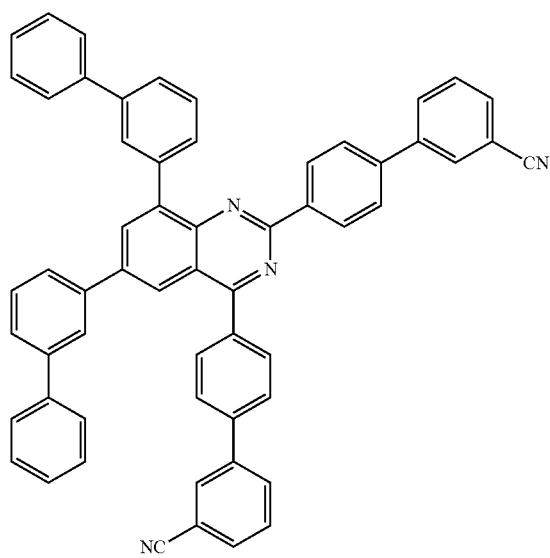
[Chemical Formula A-184]
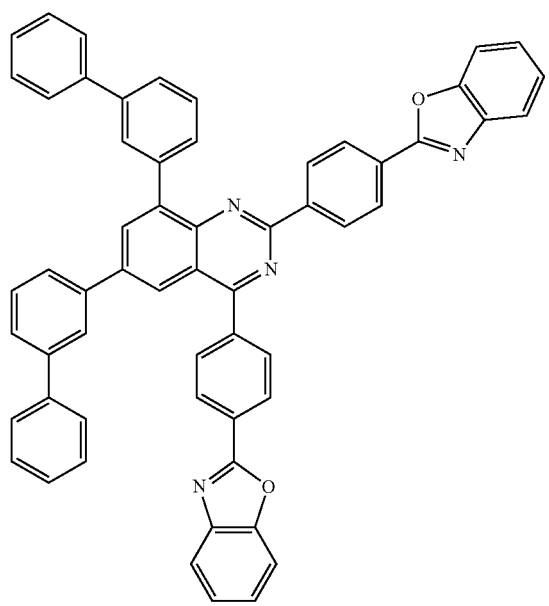

[Chemical Formula A-185]
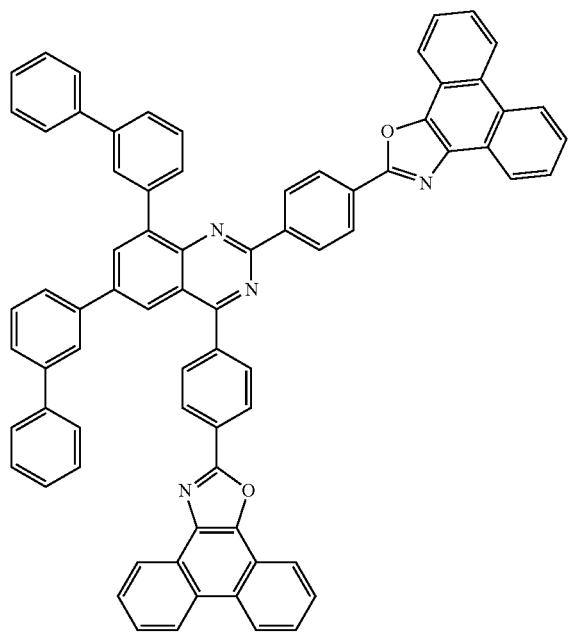
[Chemical Formula A-186]
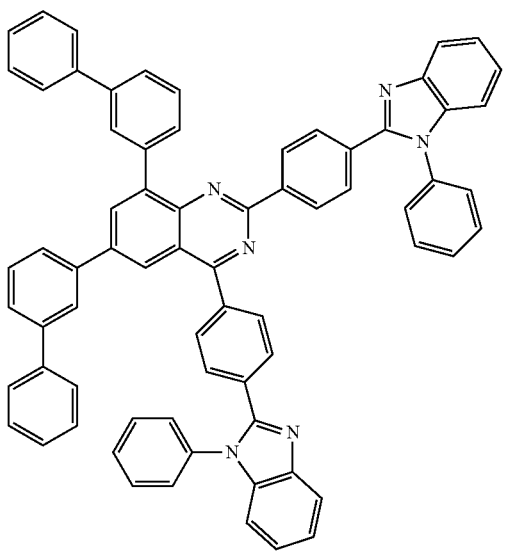
[Chemical Formula A-187]
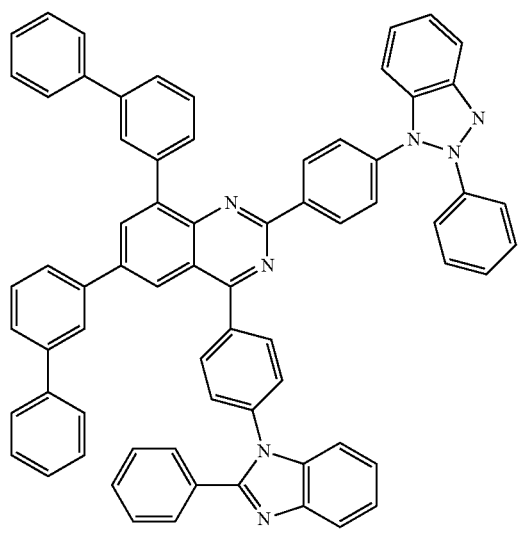
[Chemical Formula A-188]
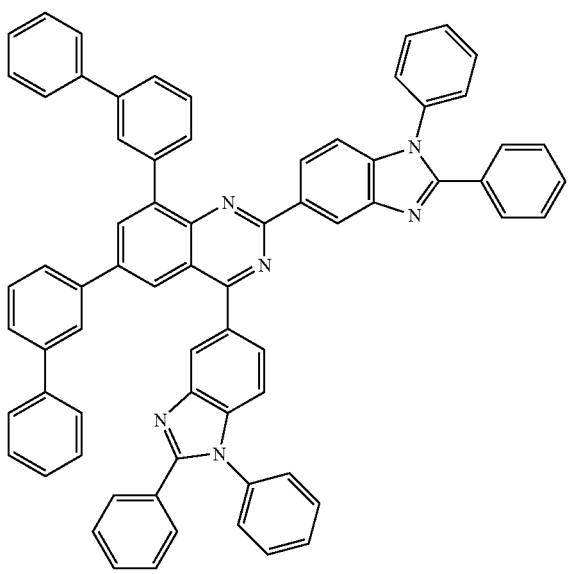

-continued
[Chemical Formula A-189]
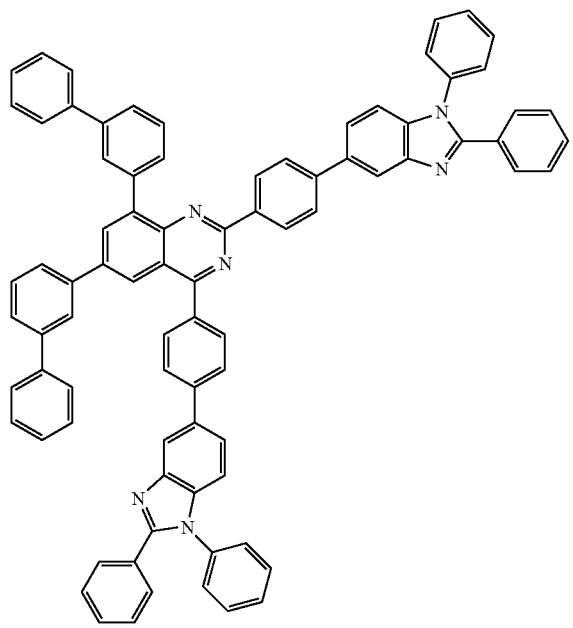
[Chemical Formula A-190]
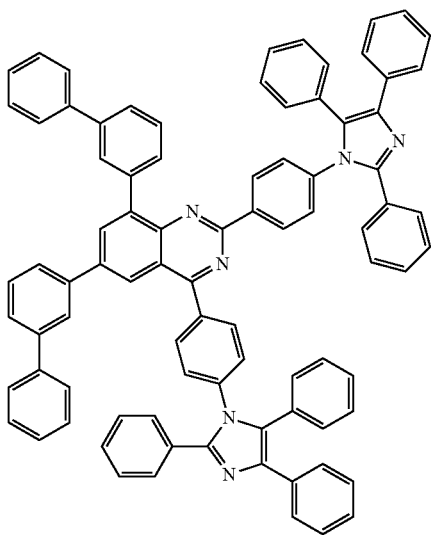
[Chemical Formula A-191]
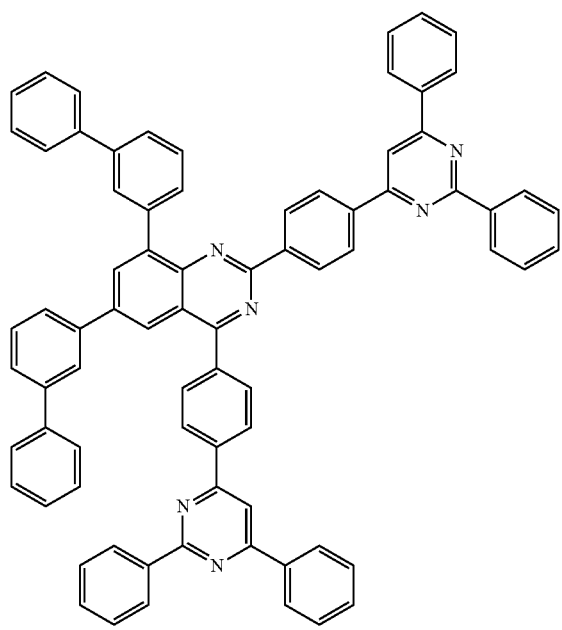
[Chemical Formula A-192]
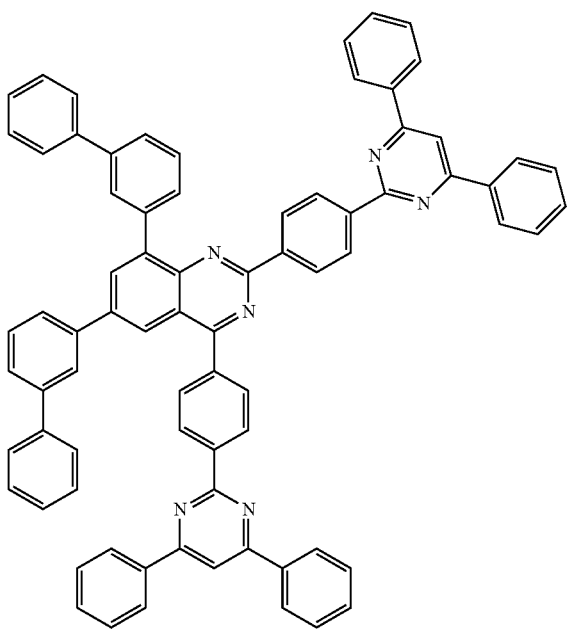

[Chemical Formula A-193]
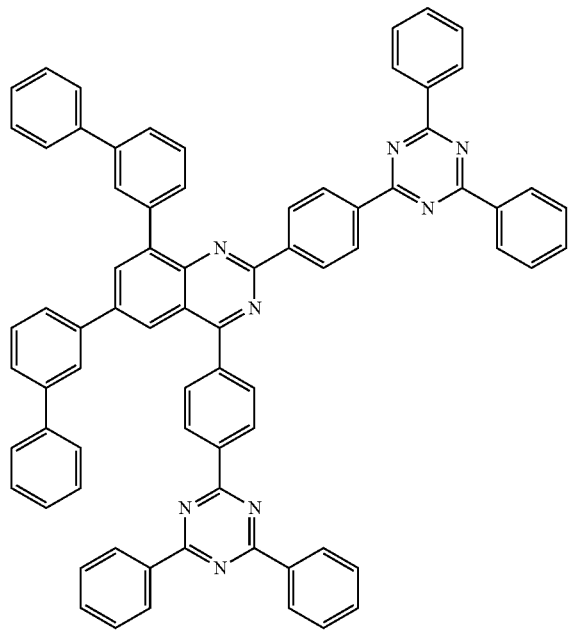
[Chemical Formula A-194]
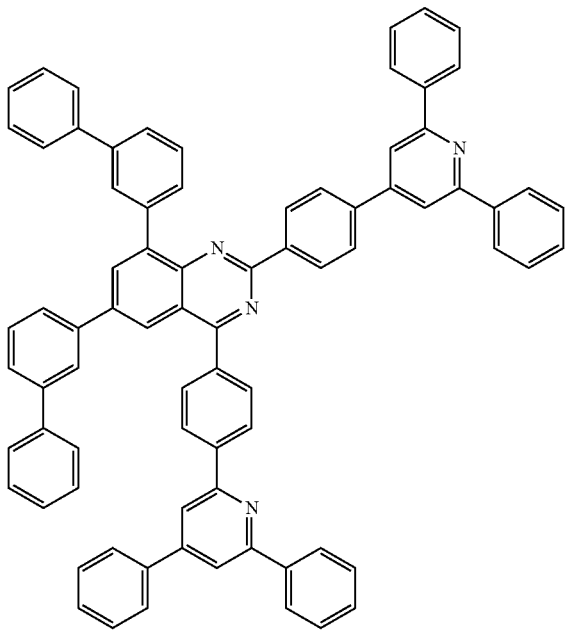
[Chemical Formula A-195]
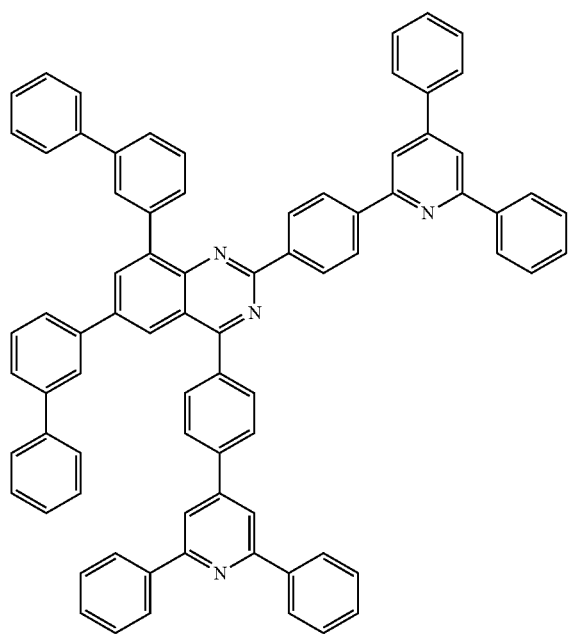
[Chemical Formula A-196]
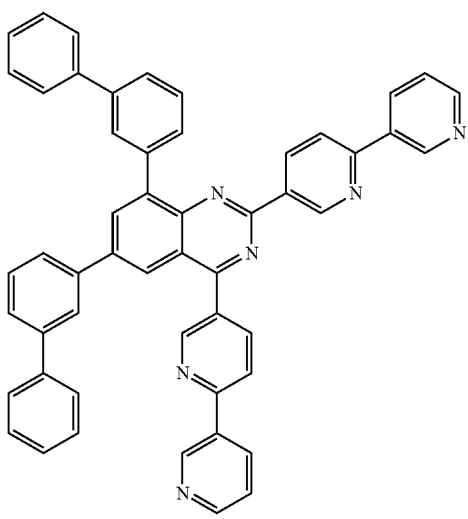

[Chemical Formula A-197]
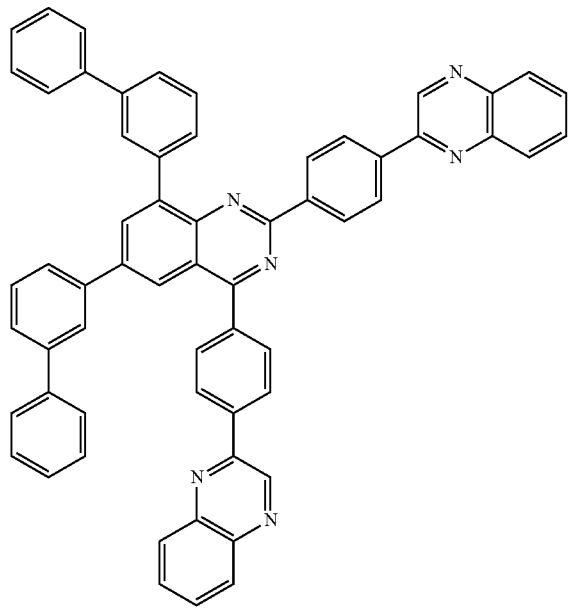
[Chemical Formula A-198]
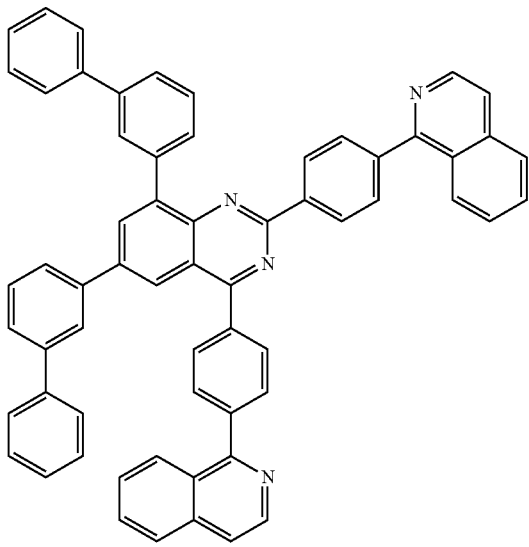
[Chemical Formula A-199]
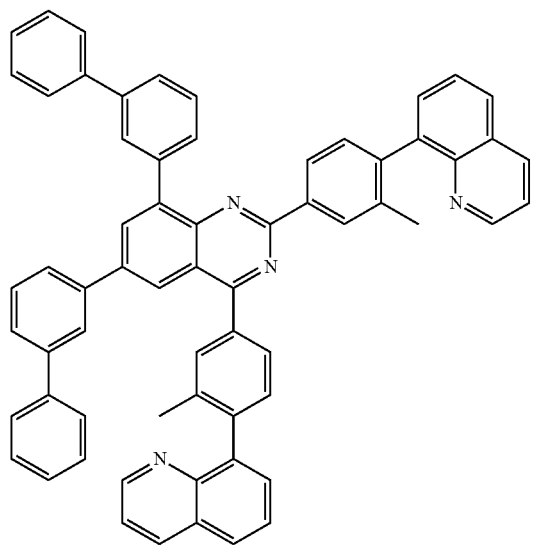
[Chemical Formula A-200]
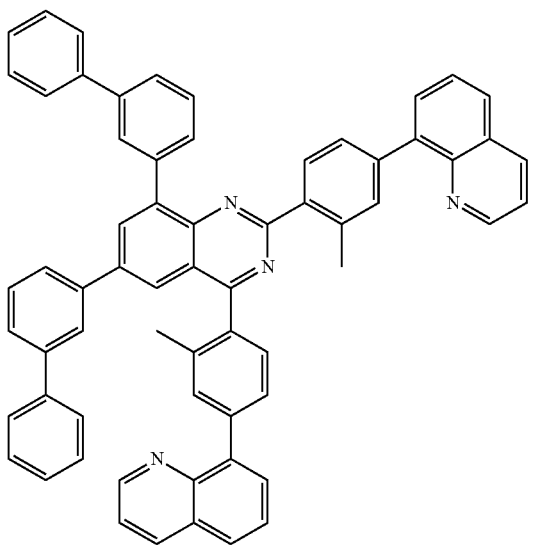

[Chemical Formula A-201]
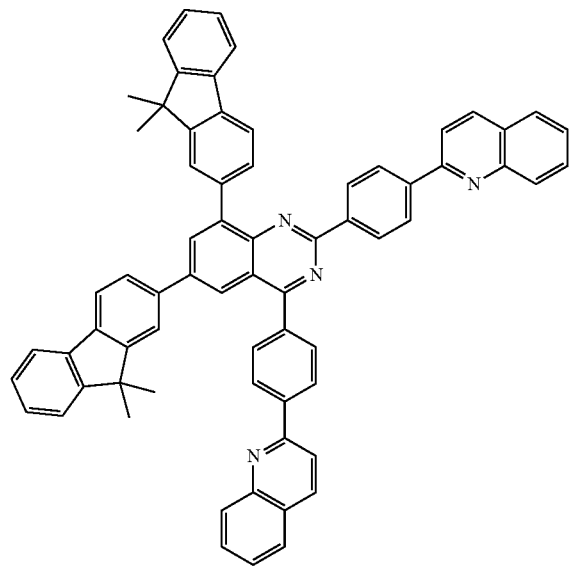
[Chemical Formula A-202]
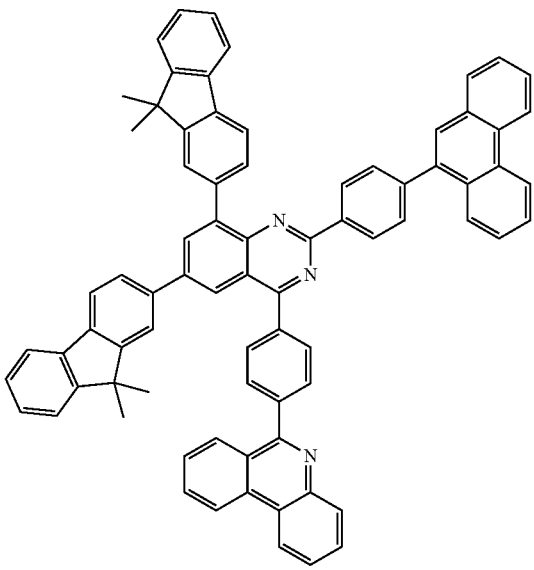
[Chemical Formula A-203]
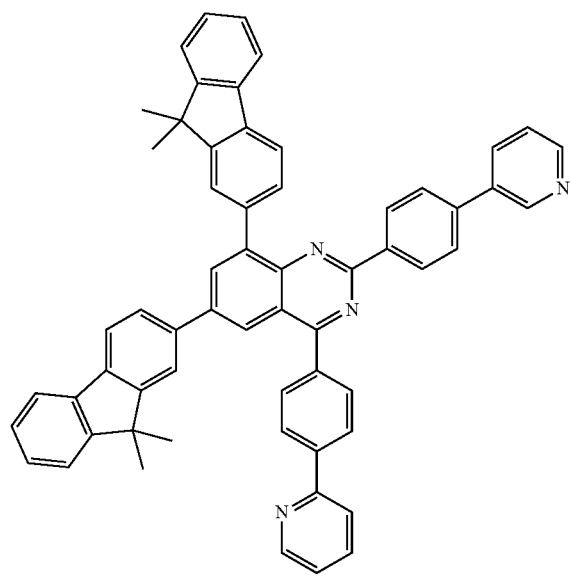
[Chemical Formula A-204]
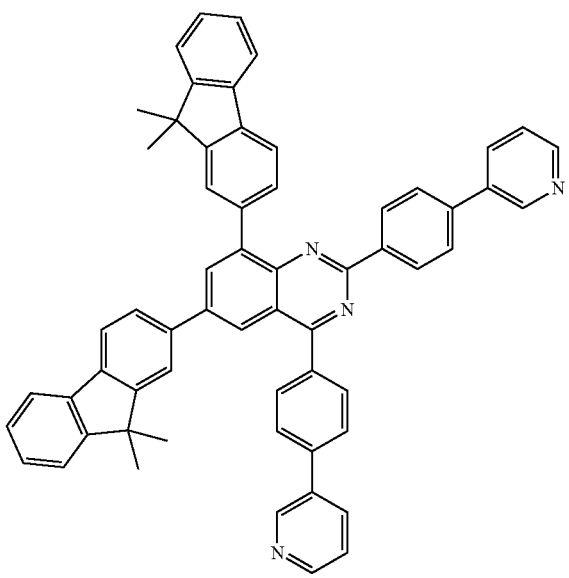

[Chemical Formula A-205]
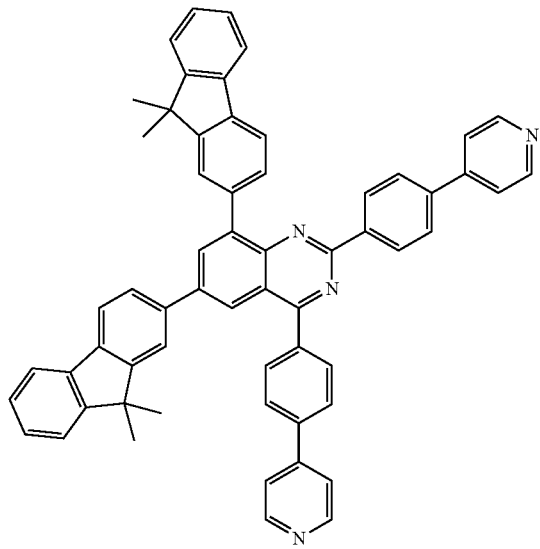
[Chemical Formula A-206]
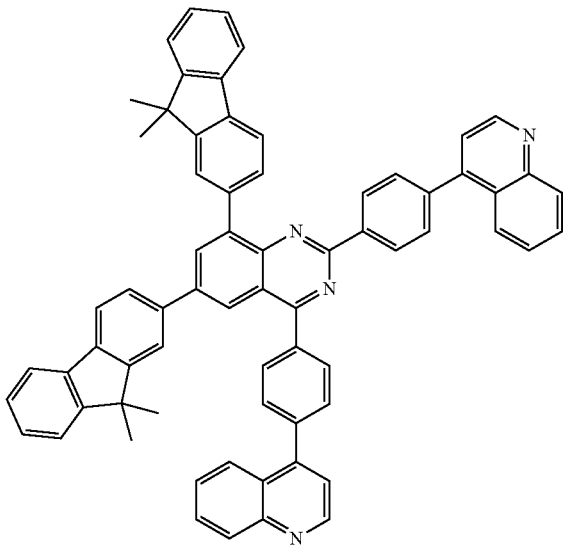
[Chemical Formula A-207]
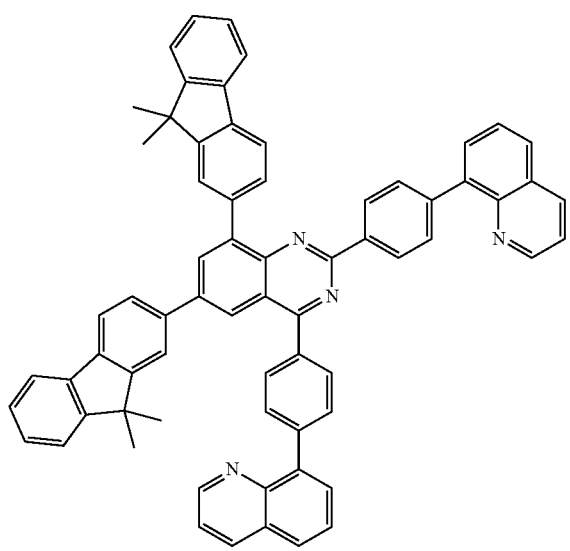
[Chemical Formula A-208]
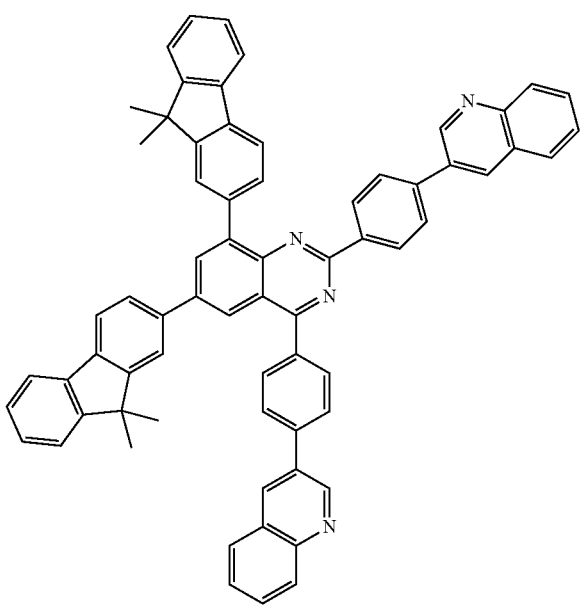

[Chemical Formula A-209]
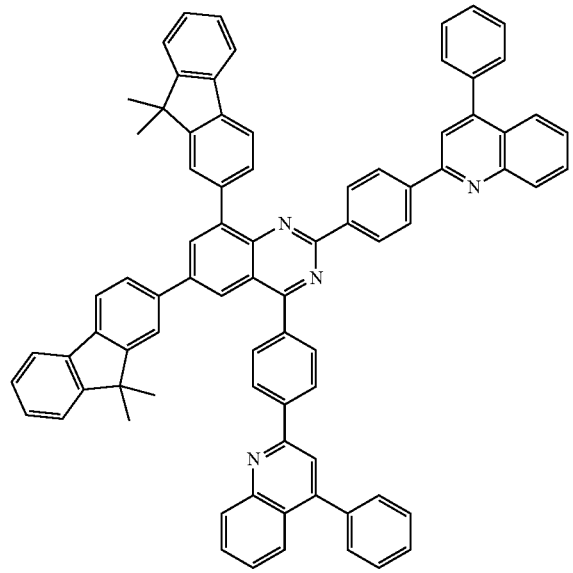
[Chemical Formula A-210]
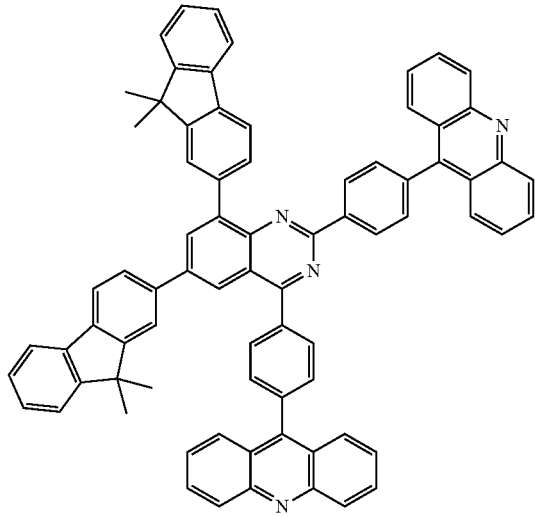
[Chemical Formula A-211]
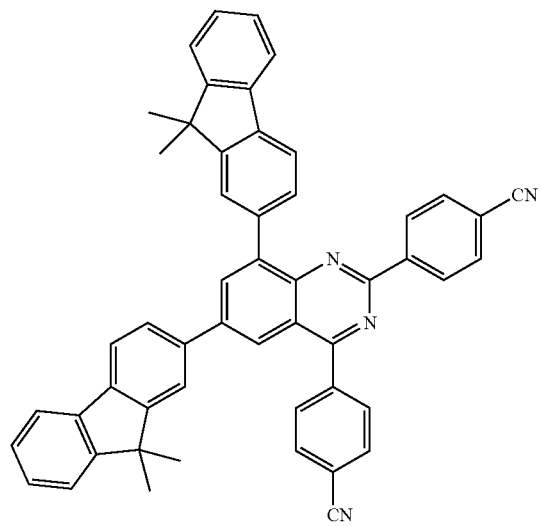
[Chemical Formula A-212]
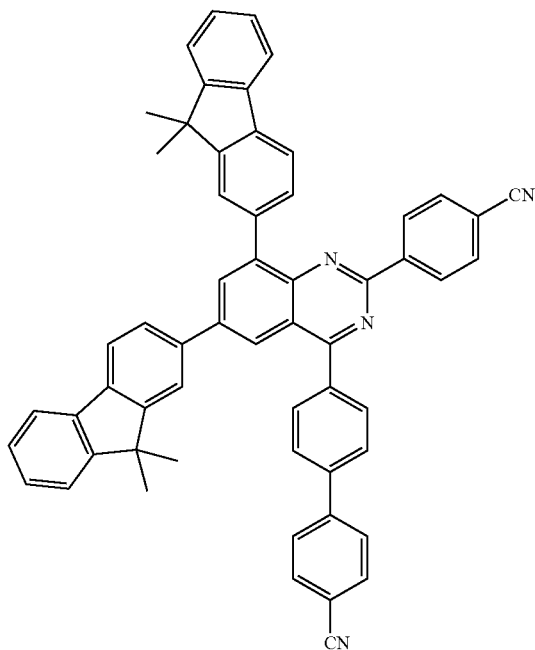

-continued
[Chemical Formula A-213]
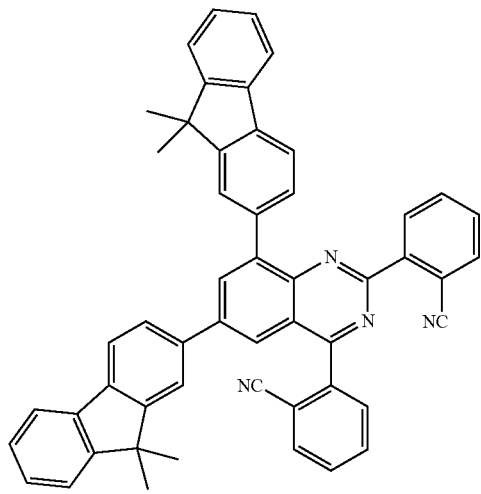
[Chemical Formula A-214]
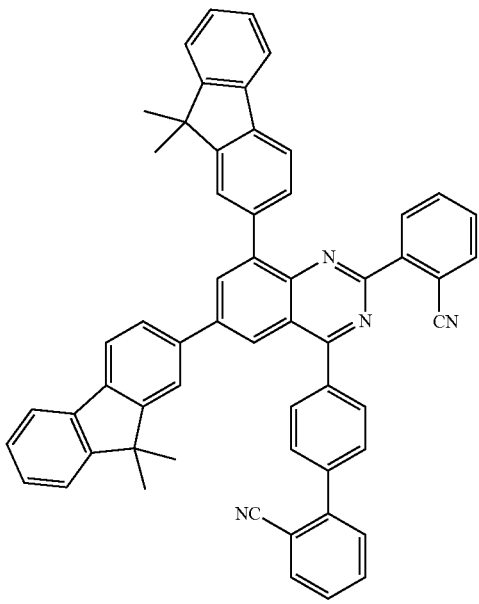
[Chemical Formula A-215]
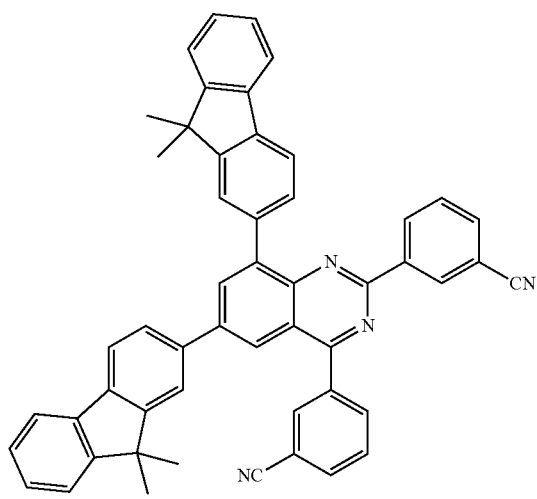
[Chemical Formula A-216]
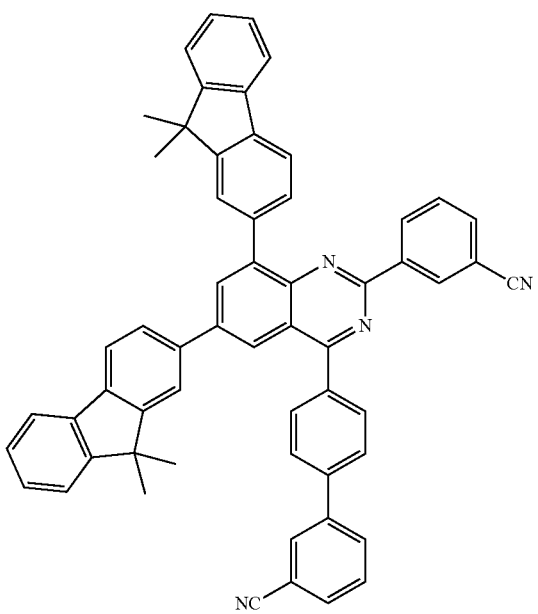

[Chemical Formula A-217]
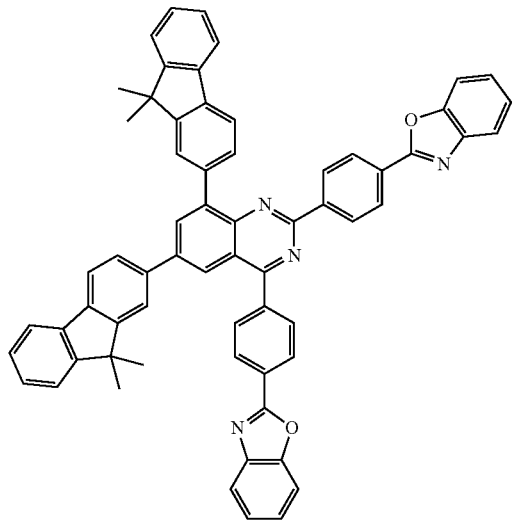
[Chemical Formula A-218]
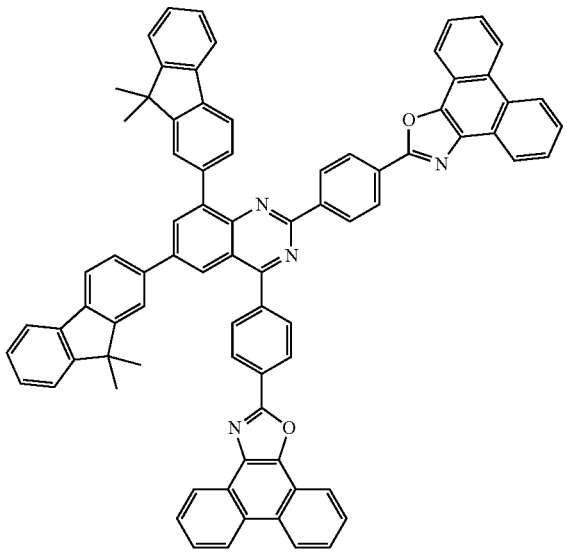
[Chemical Formula A-219]
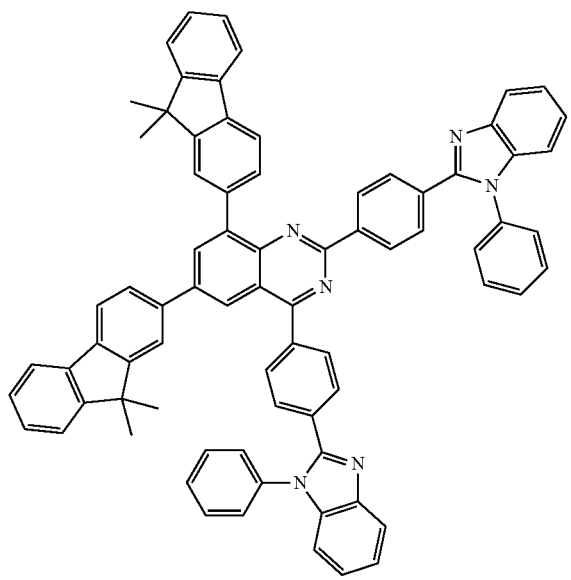
[Chemical Formula A-220]
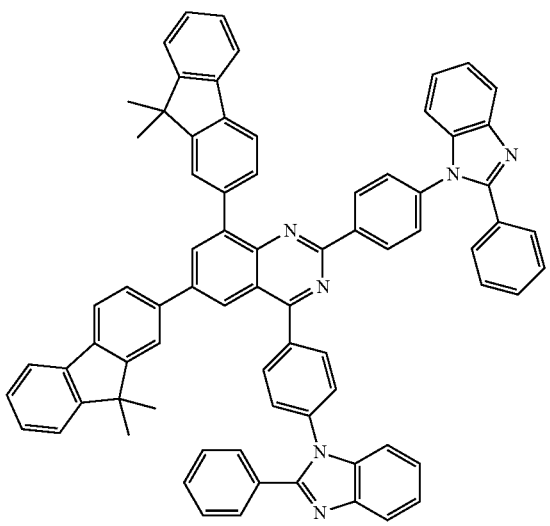

[Chemical Formula A-221]
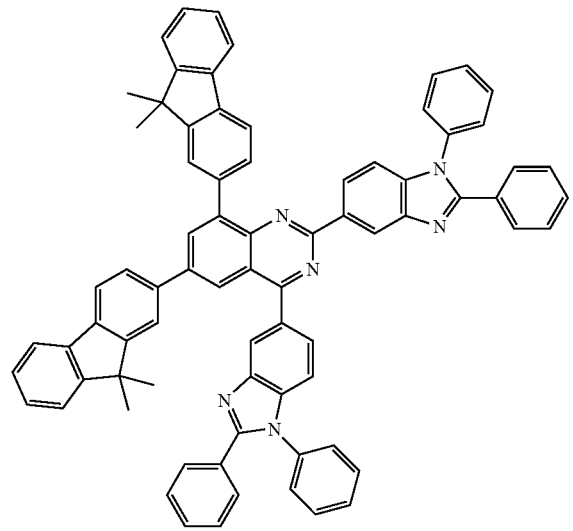
[Chemical Formula A-222]
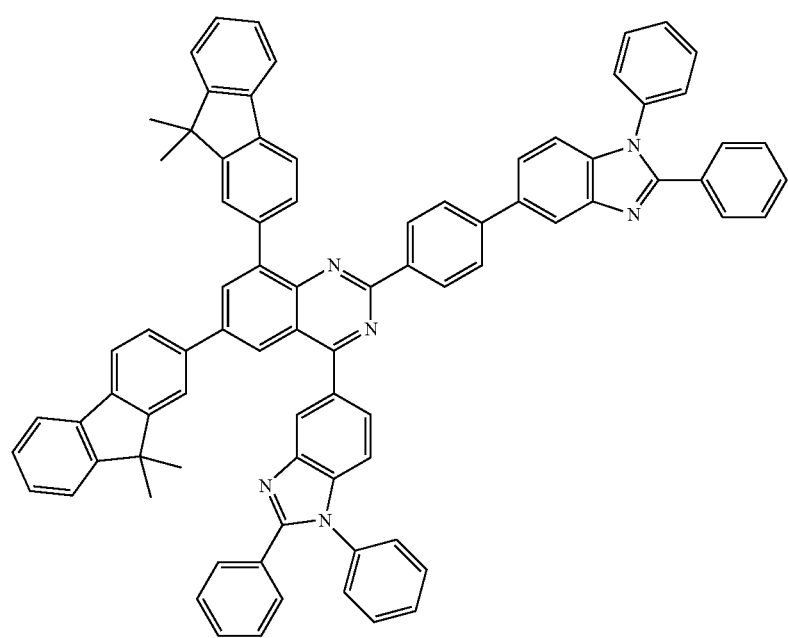

-continued
[Chemical Formula A-223]
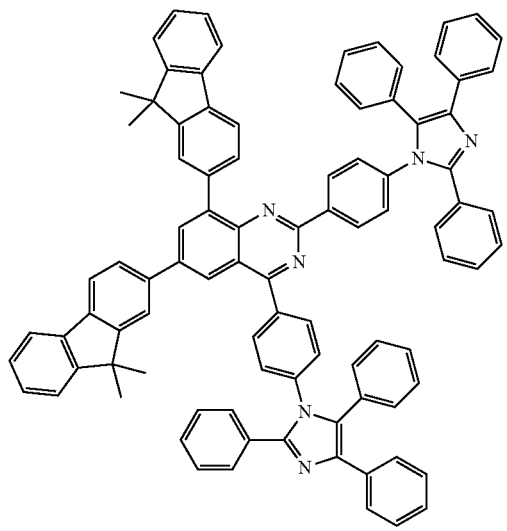
[Chemical Formula A-224]
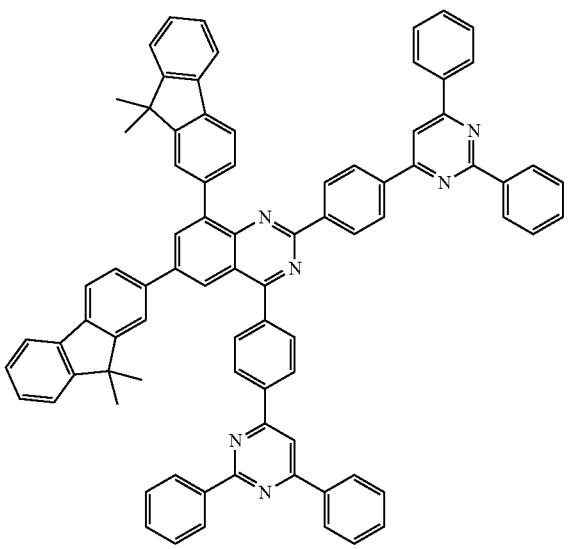
[Chemical Formula A-225]
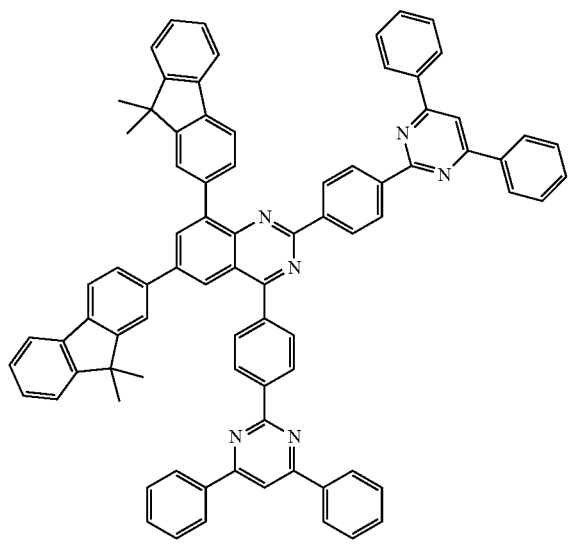
[Chemical Formula A-226]
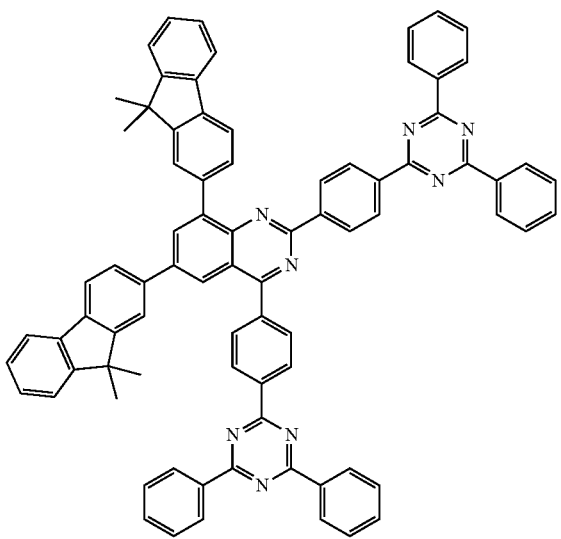

[Chemical Formula A-227]
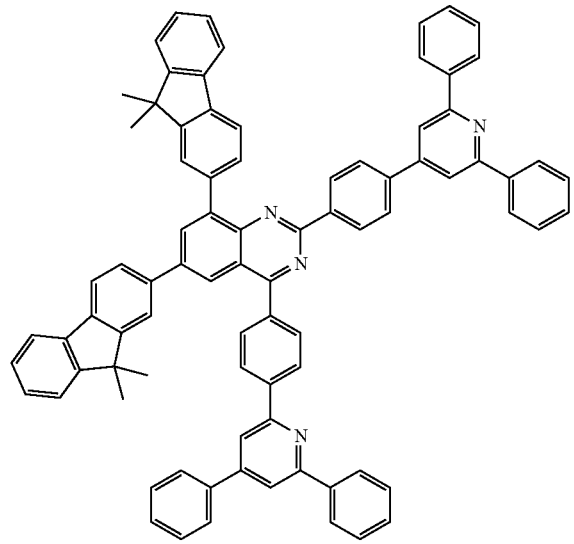
[Chemical Formula A-228]
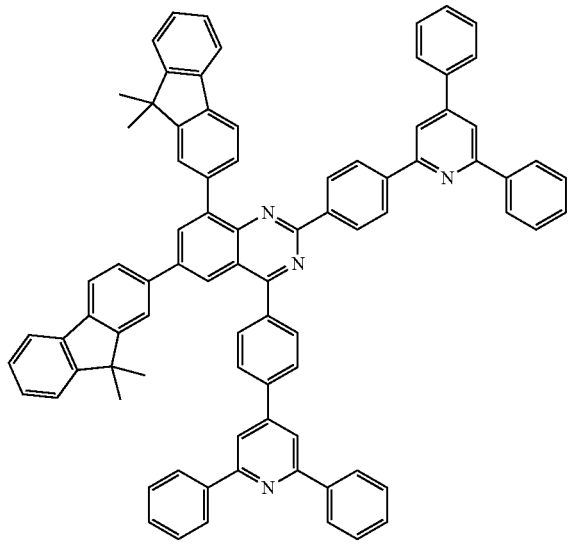
[Chemical Formula A-229]
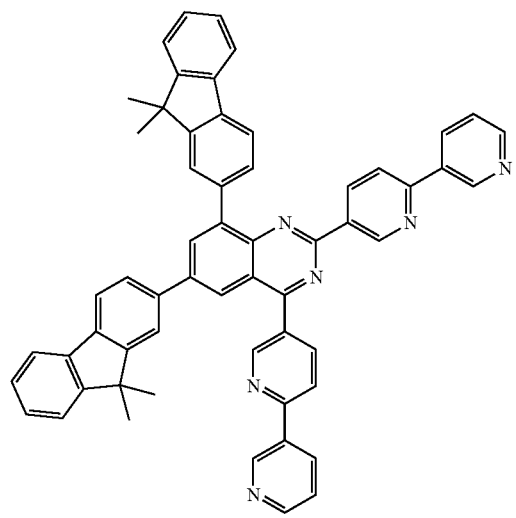
[Chemical Formula A-230]
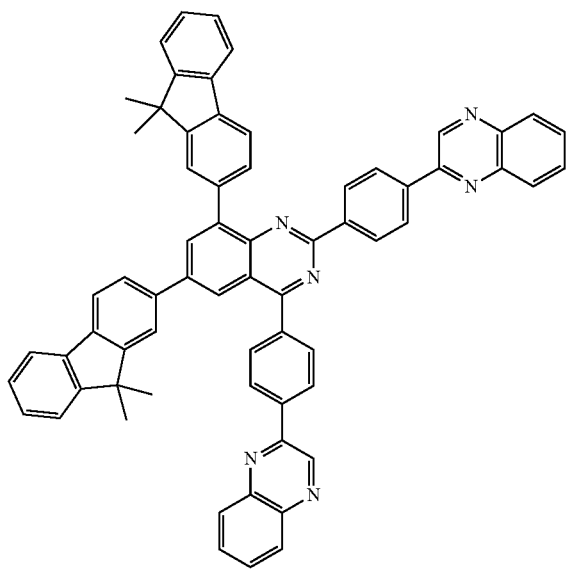

[Chemical Formula A-231]
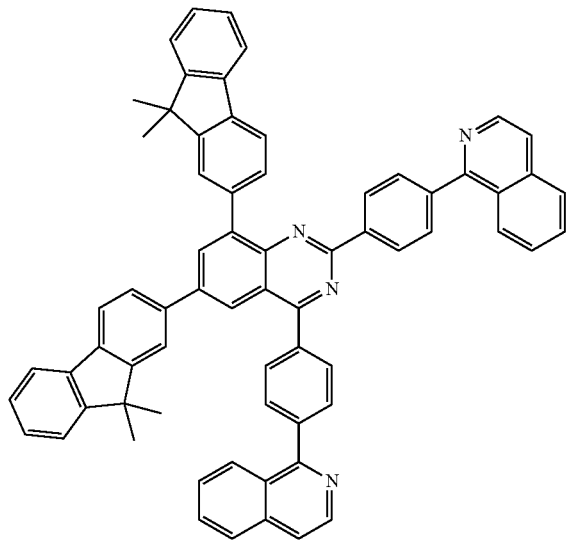
[Chemical Formula A-232]
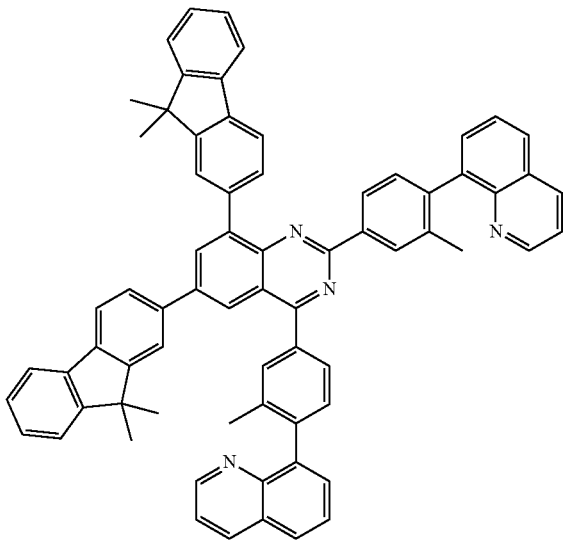
[Chemical Formula A-233]
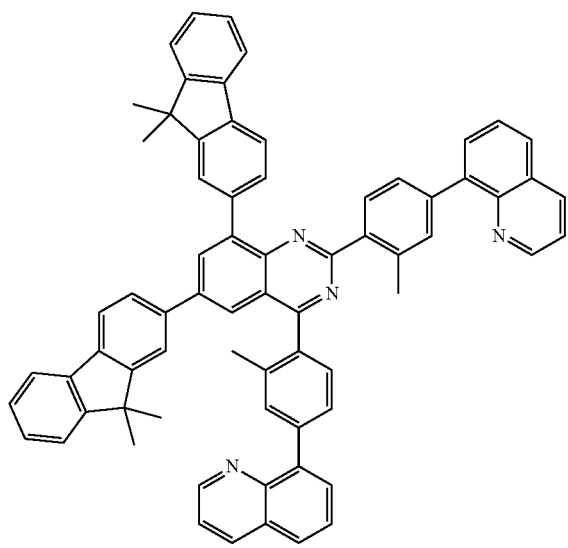
[Chemical Formula A-234]
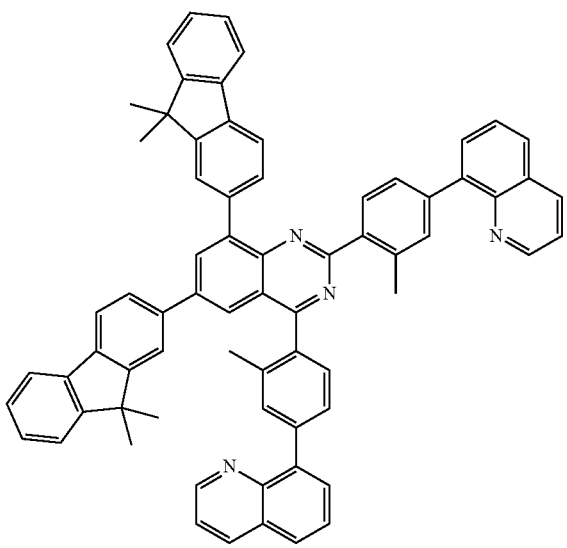

[Chemical Formula A-235]
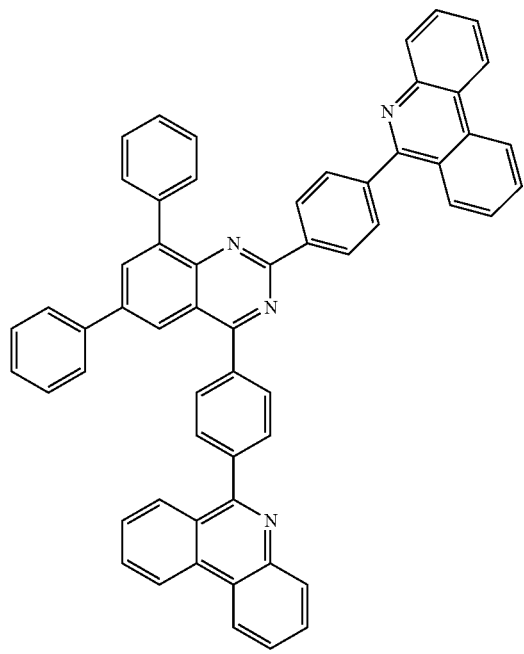
[Chemical Formula A-236]
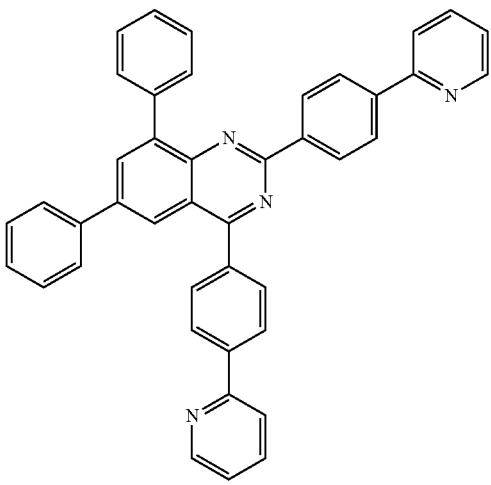
[Chemical Formula A-237]
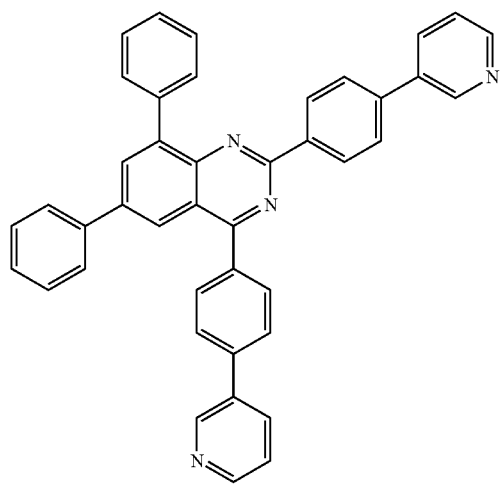
[Chemical Formula A-238]
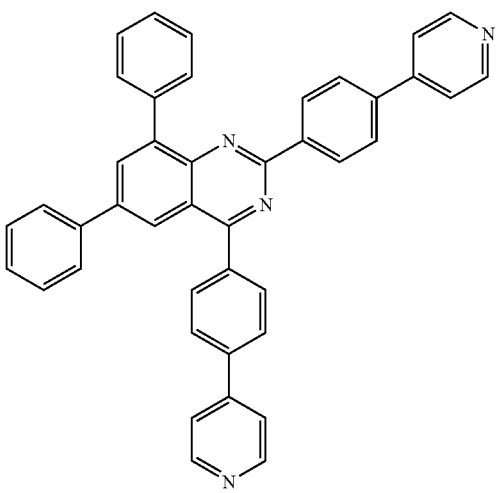

[Chemical Formula A-239]
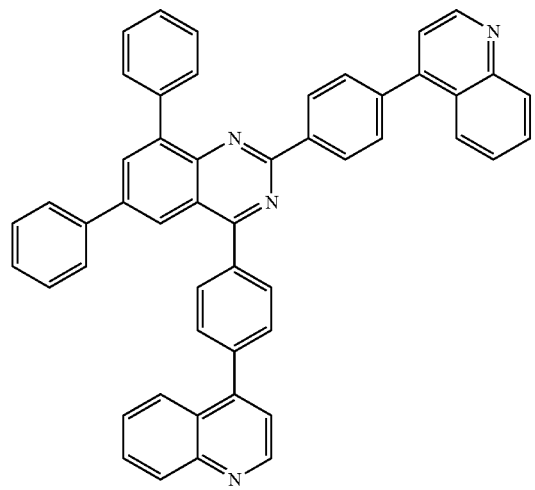
[Chemical Formula A-240]
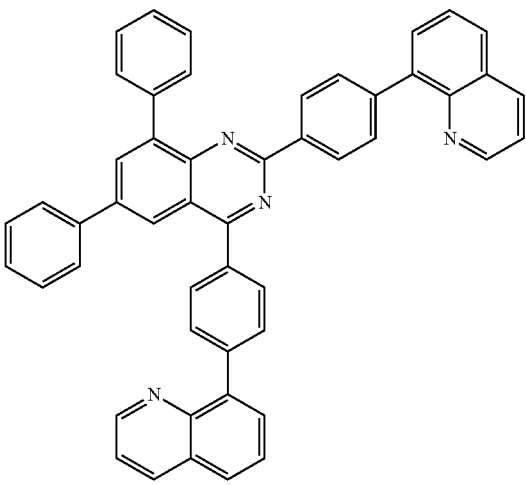
[Chemical Formula A-241]
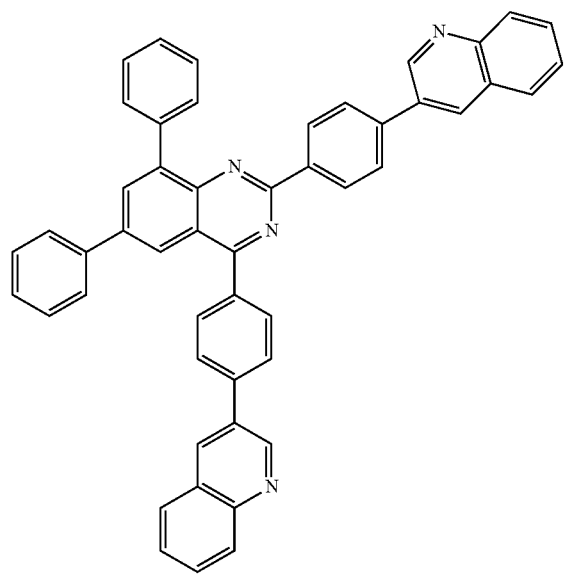
[Chemical Formula A-242]
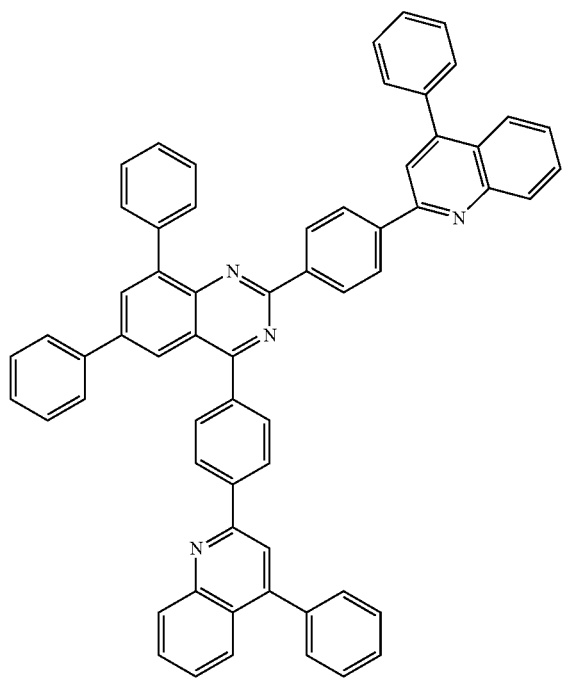

-continued
[Chemical Formula A-243]
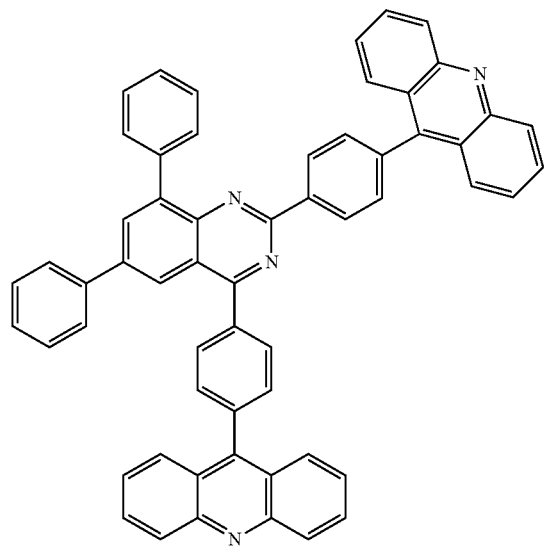
[Chemical Formula A-244]
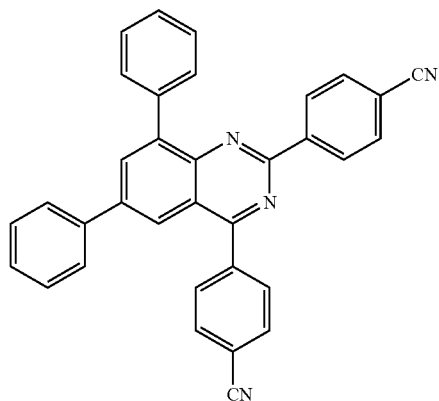
[Chemical Formula A-245]
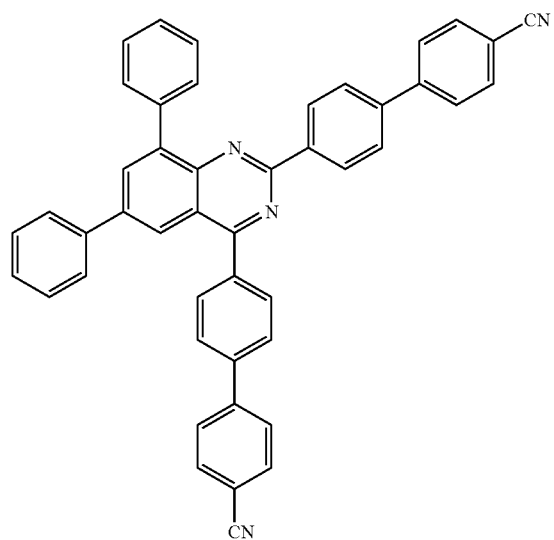
[Chemical Formula A-246]
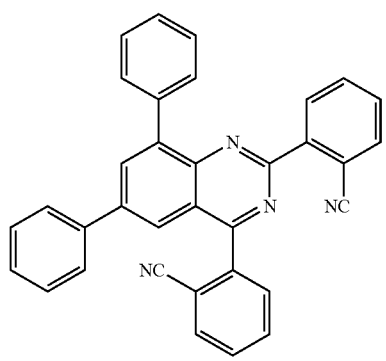
[Chemical Formula A-247]
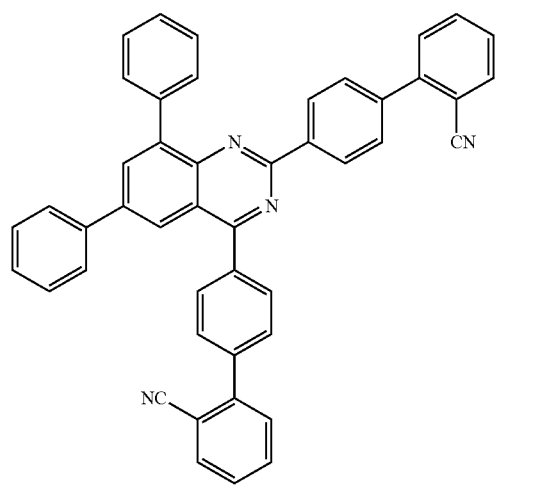
[Chemical Formula A-248]
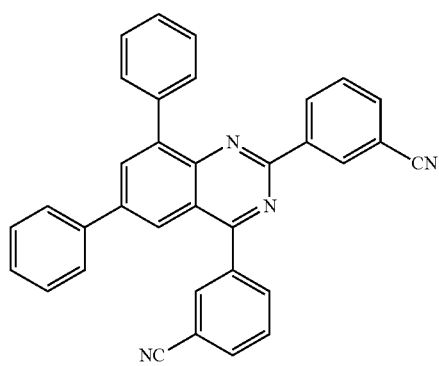

[Chemical Formula A-249]
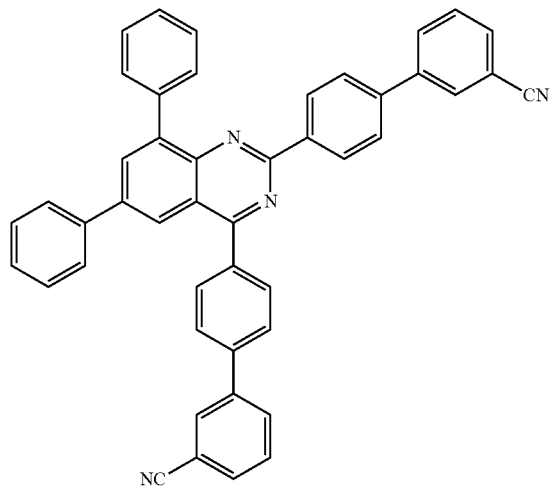
[Chemical Formula A-250]
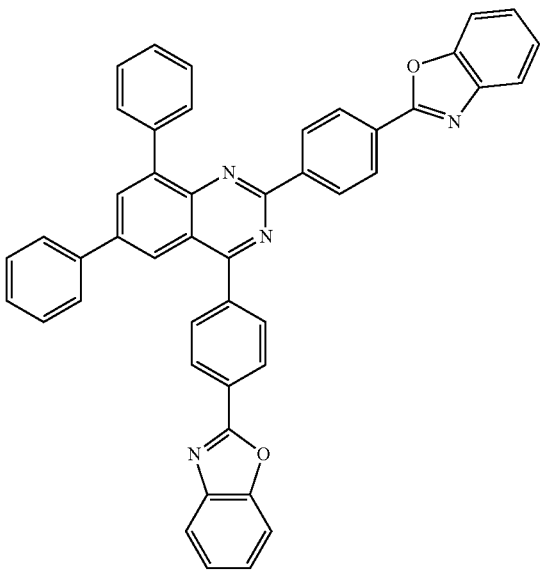
[Chemical Formula A-251]
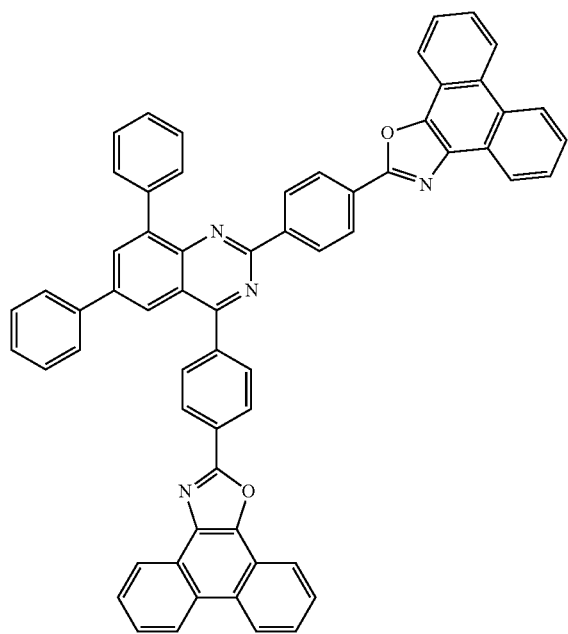
[Chemical Formula A-252]
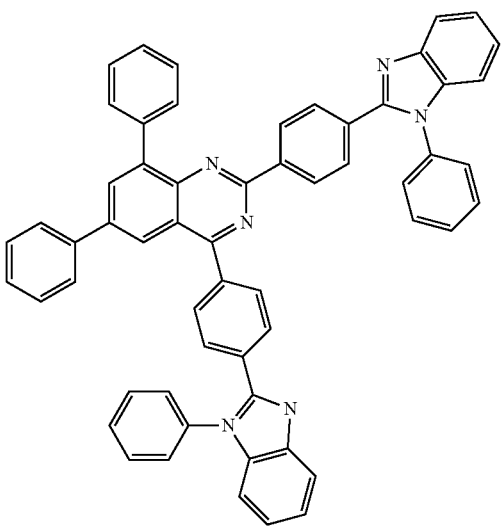

[Chemical Formula A-253]
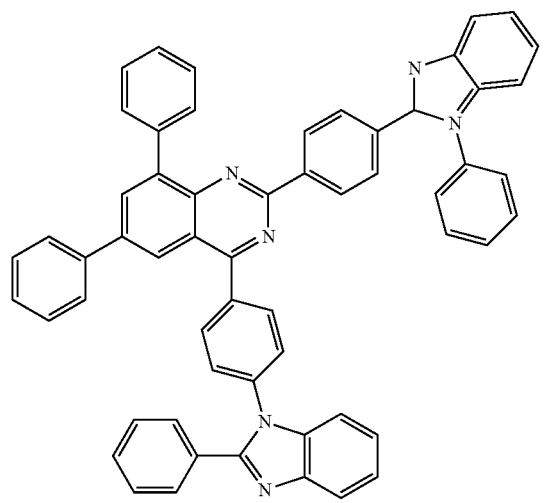
[Chemical Formula A-254]
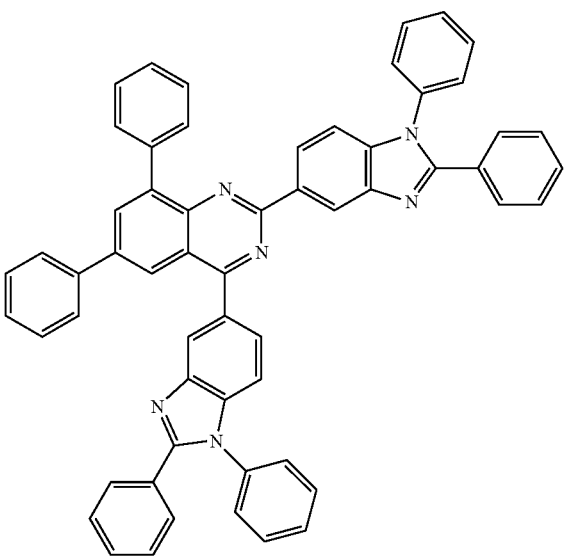
[Chemical Formula A-255]
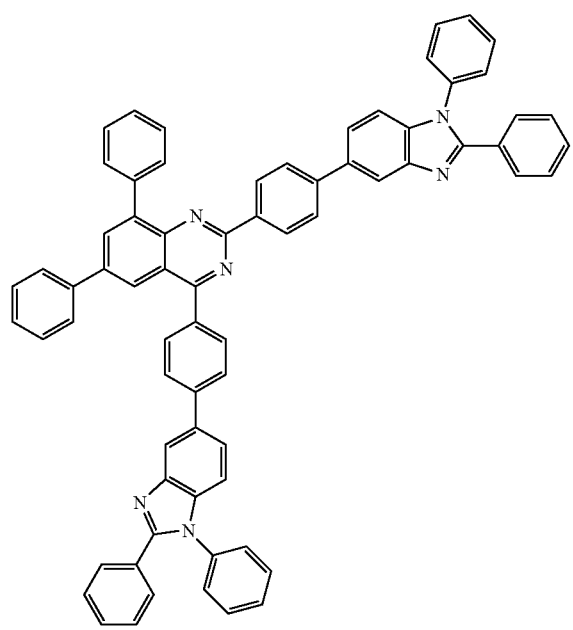
[Chemical Formula A-256]
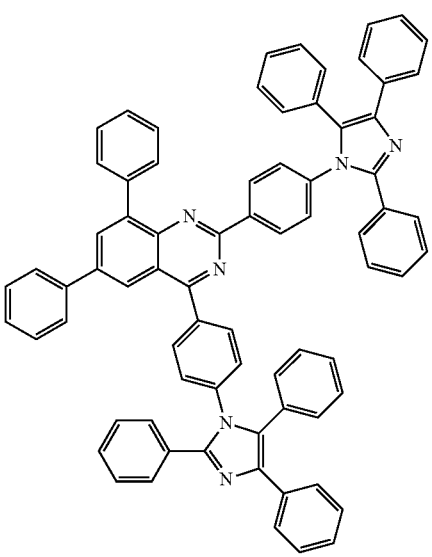

[Chemical Formula A-257]
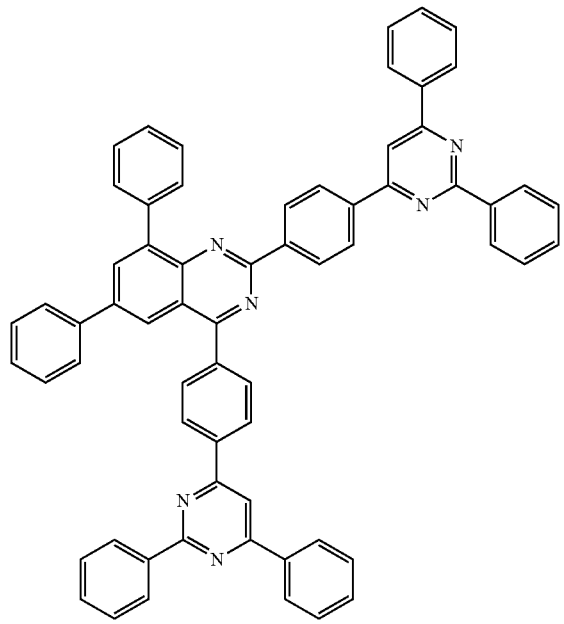
[Chemical Formula A-258]
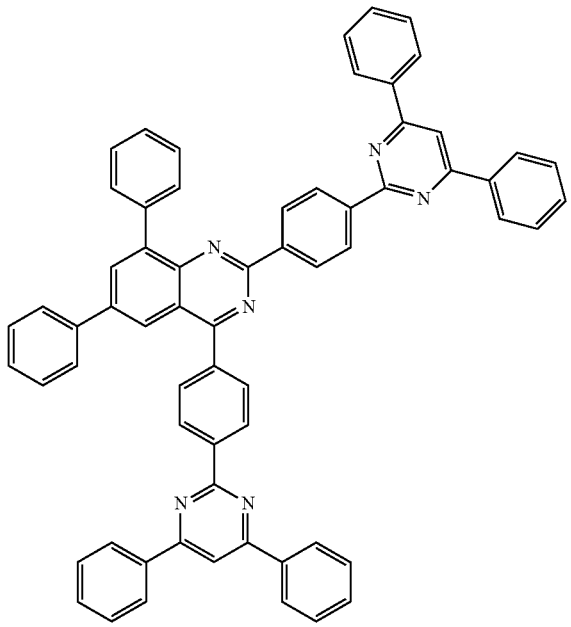
[Chemical Formula A-259]
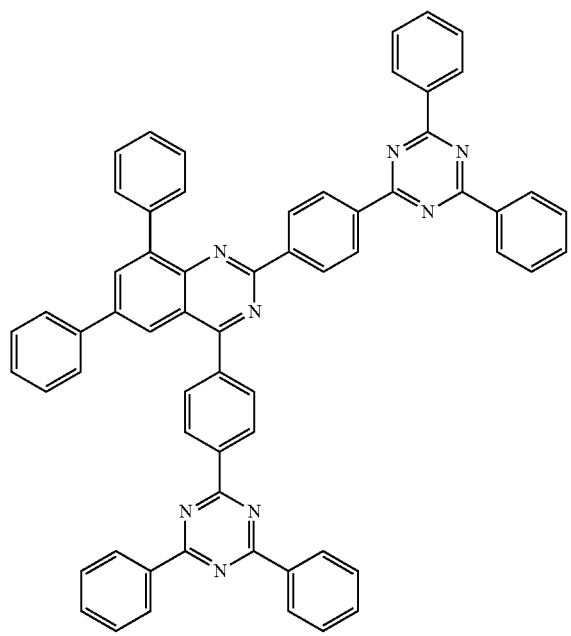
[Chemical Formula A-260]
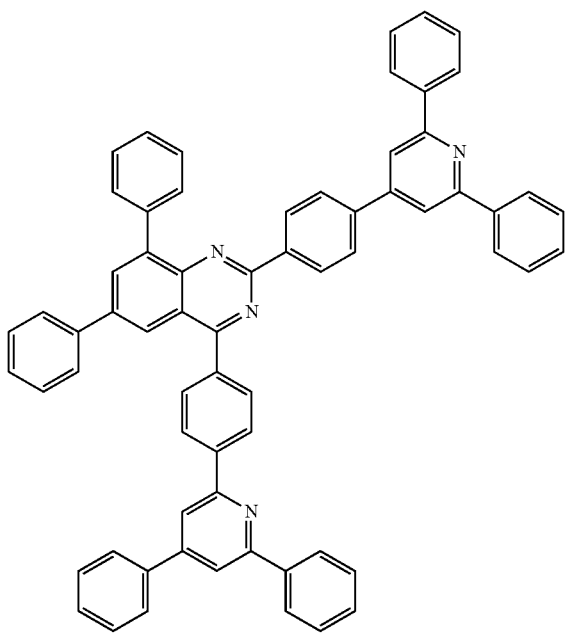

[Chemical Formula A-261]
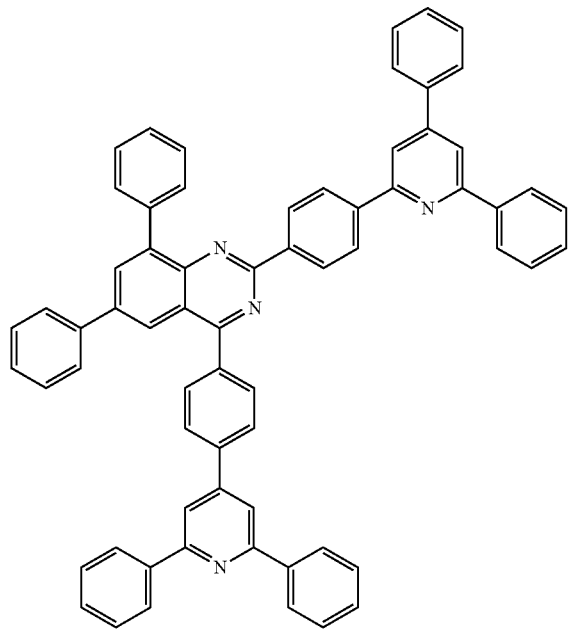
[Chemical Formula A-262]
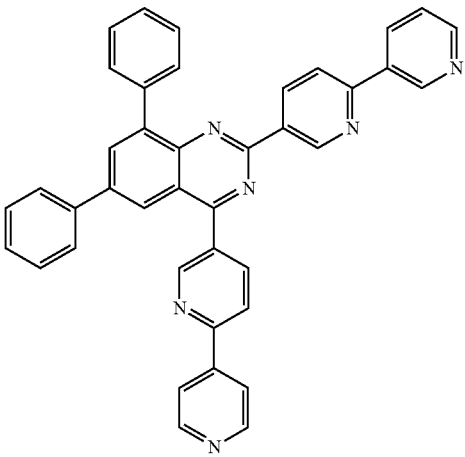
[Chemical Formula A-263]
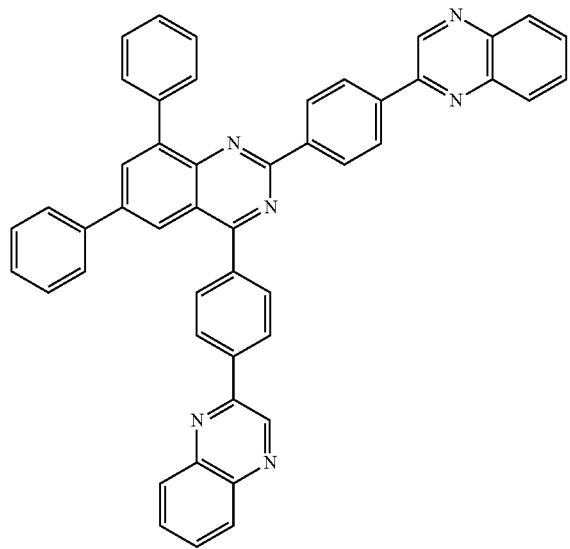
[Chemical Formula A-264]
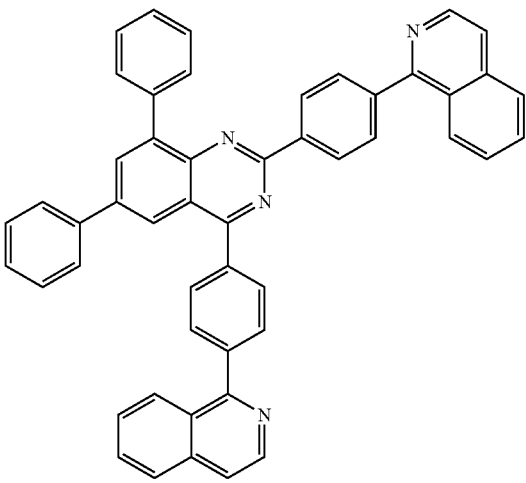

[Chemical Formula A-265]
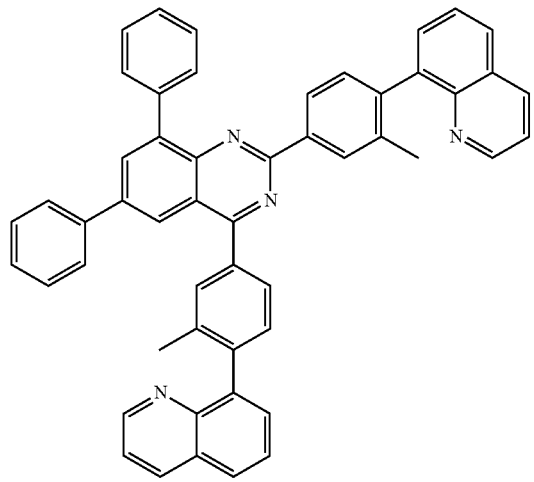
[Chemical Formula A-266]
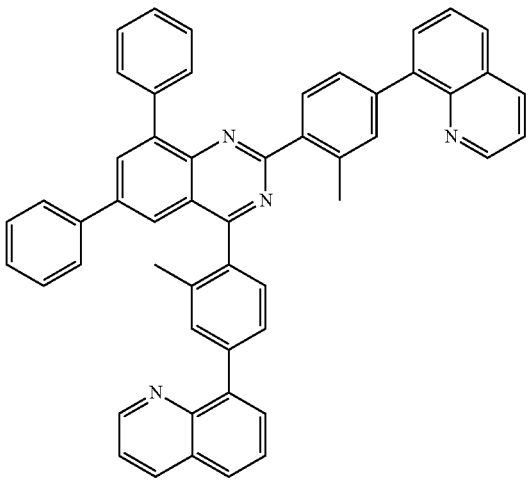
[Chemical Formula A-267]
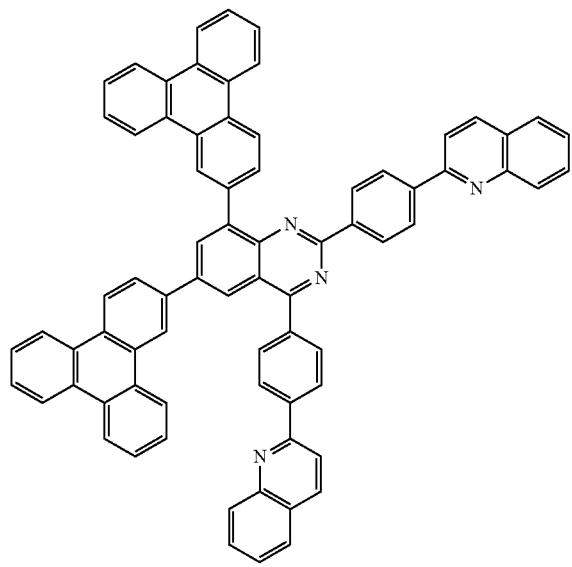
[Chemical Formula A-268]
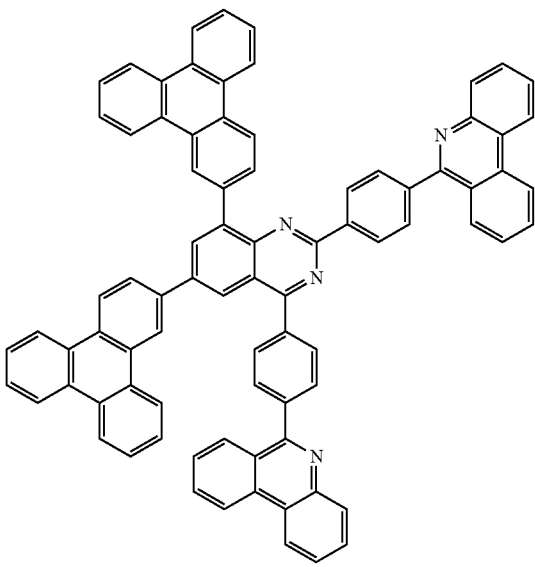
[Chemical Formula A-269]
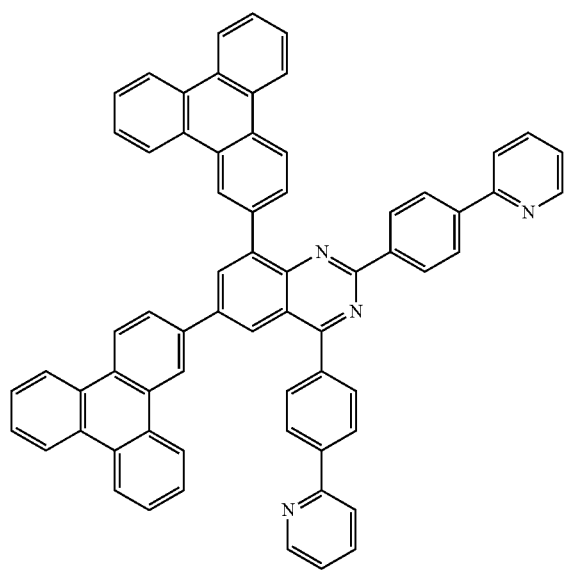
[Chemical Formula A-270]
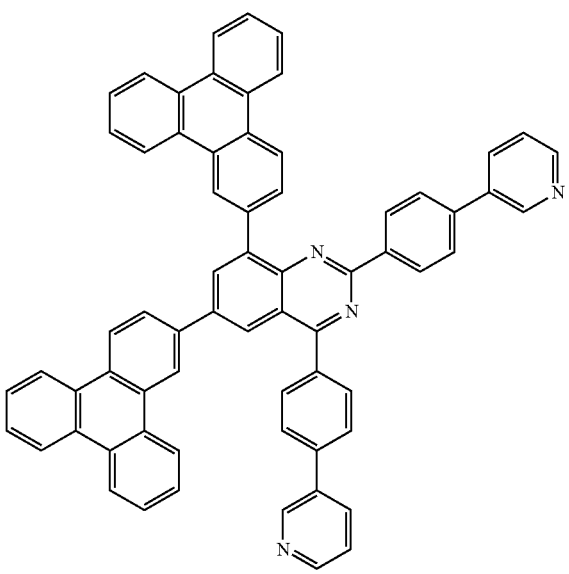

[Chemical Formula A-271]
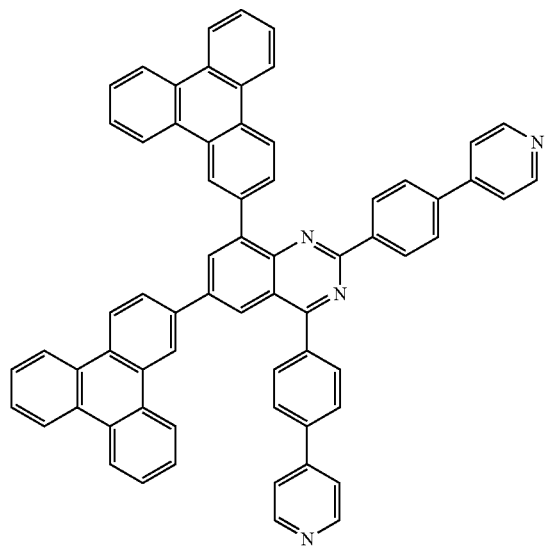
[Chemical Formula A-272]
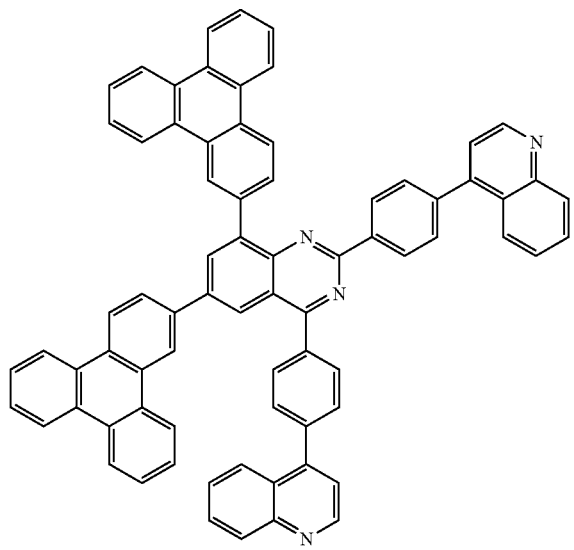
[Chemical Formula A-273]
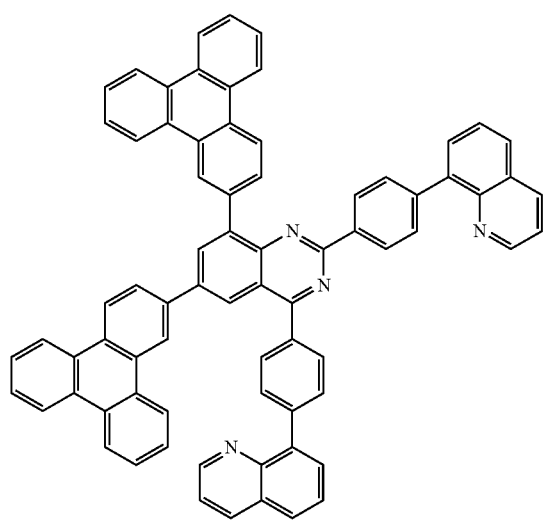
[Chemical Formula A-274]
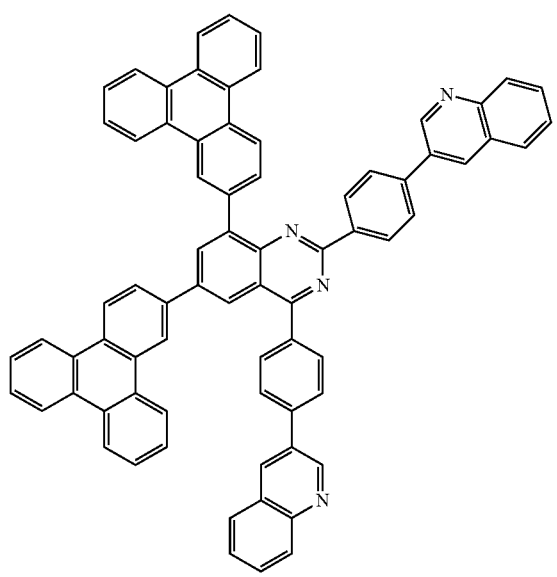

[Chemical Formula A-275]
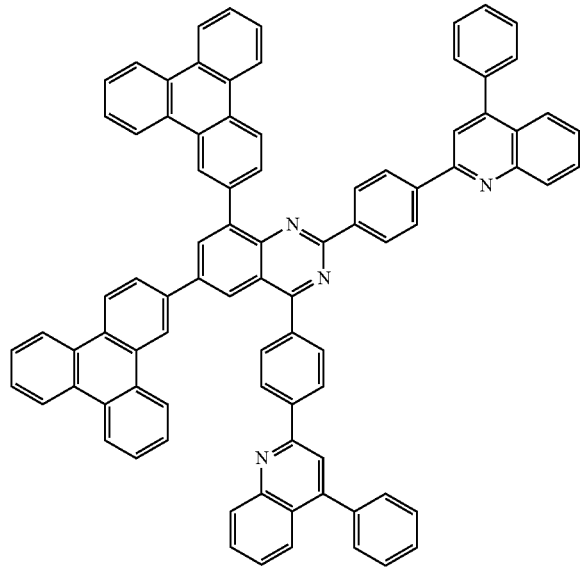
[Chemical Formula A-276]
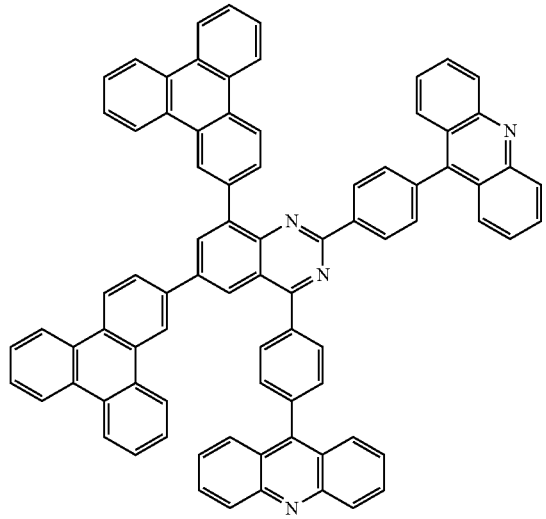
[Chemical Formula A-277]
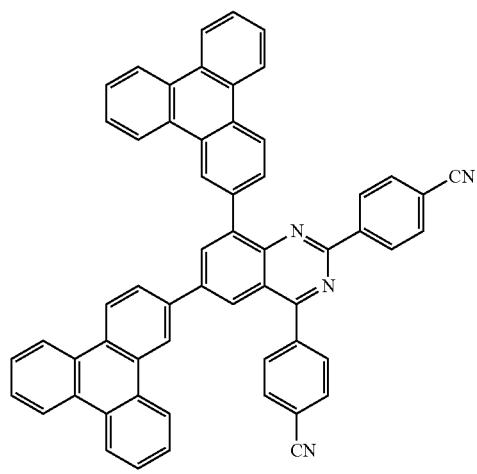
[Chemical Formula A-278]
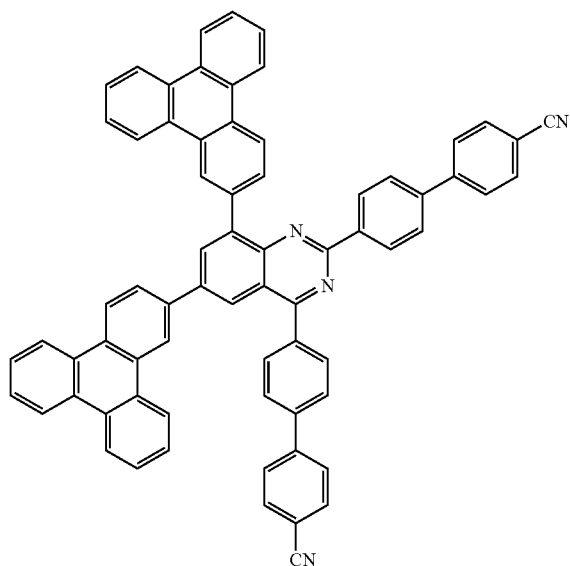

-continued
[Chemical Formula A-279]
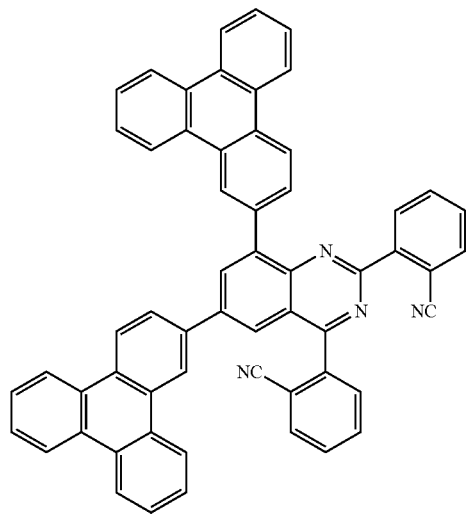
[Chemical Formula A-280]
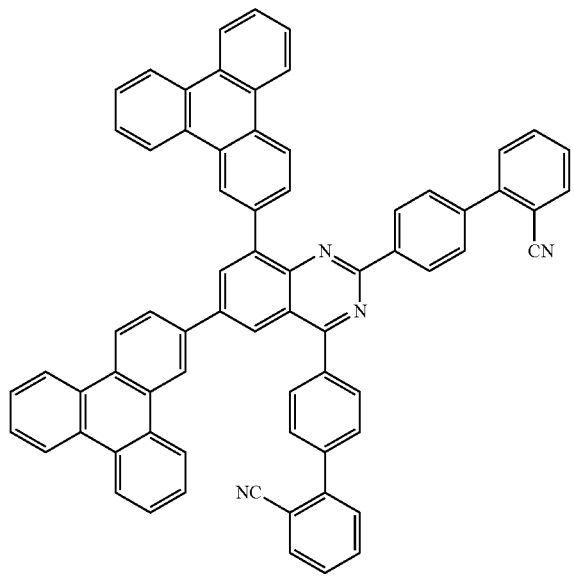
[Chemical Formula A-281]
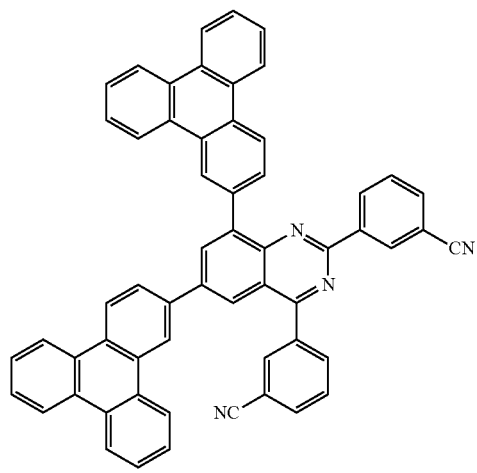
[Chemical Formula A-282]
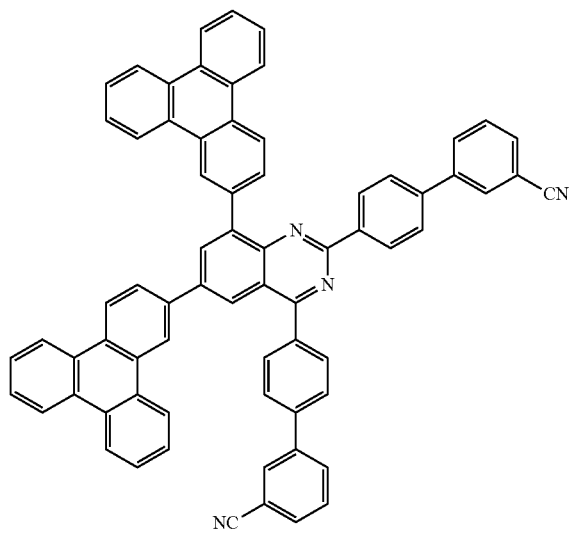

[Chemical Formula A-283]
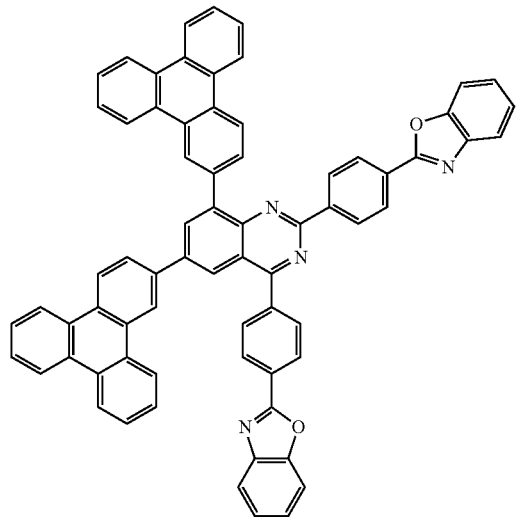
[Chemical Formula A-284]
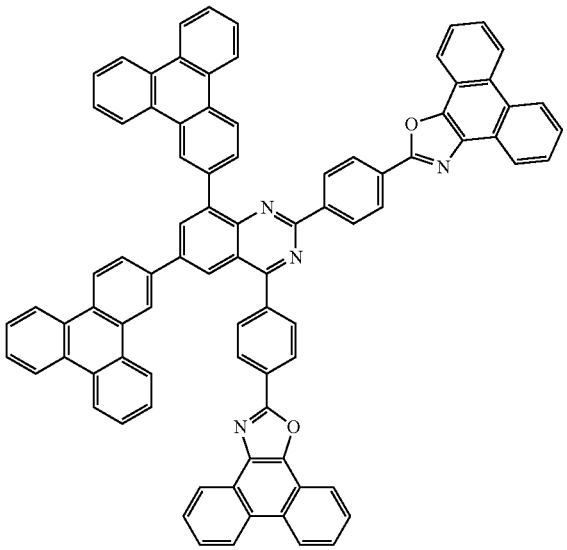
[Chemical Formula A-285]
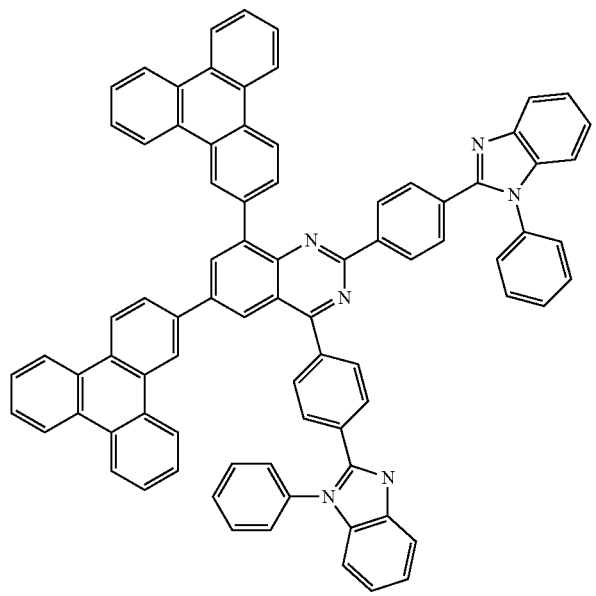
[Chemical Formula A-286]
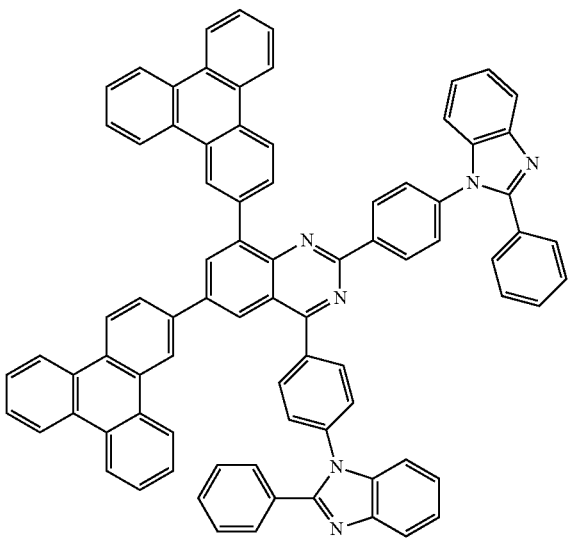

-continued
[Chemical Formula A-287]
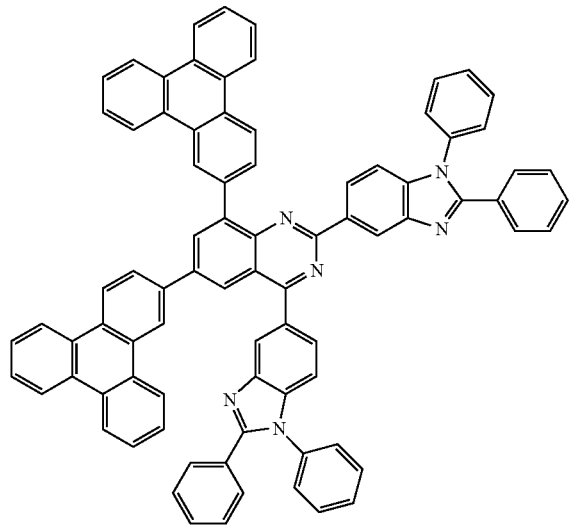
[Chemical Formula A-288]
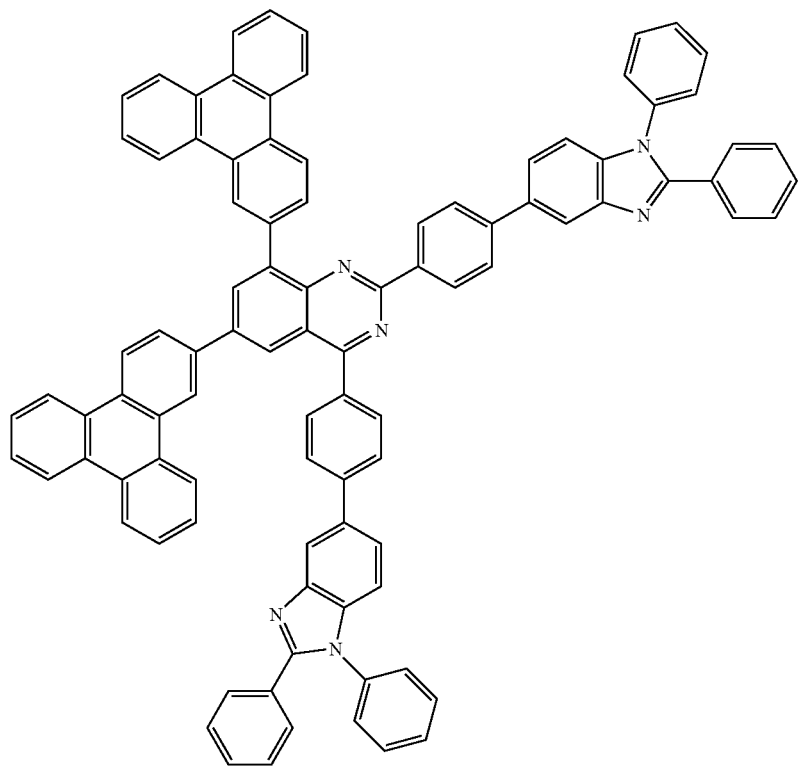

[Chemical Formula A-289]
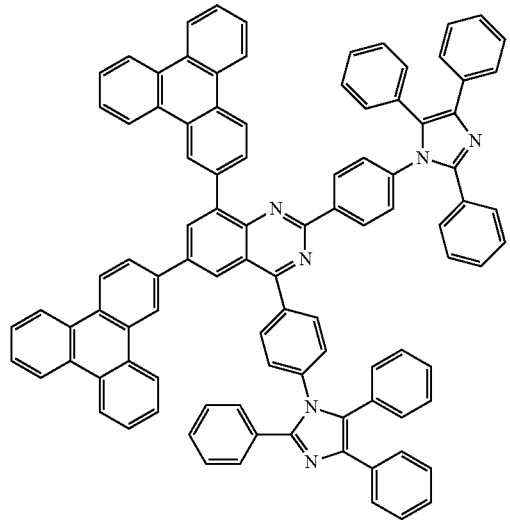
[Chemical Formula A-290]
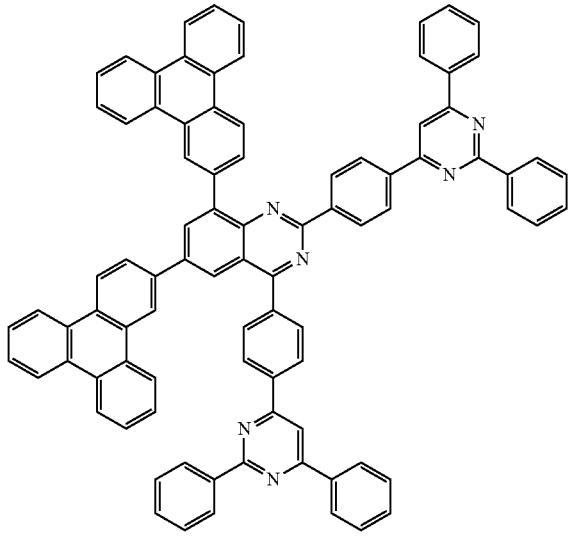
[Chemical Formula A-291]
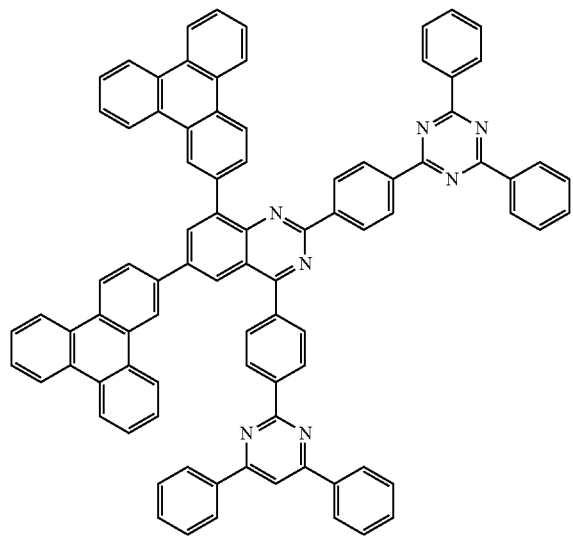
[Chemical Formula A-292]
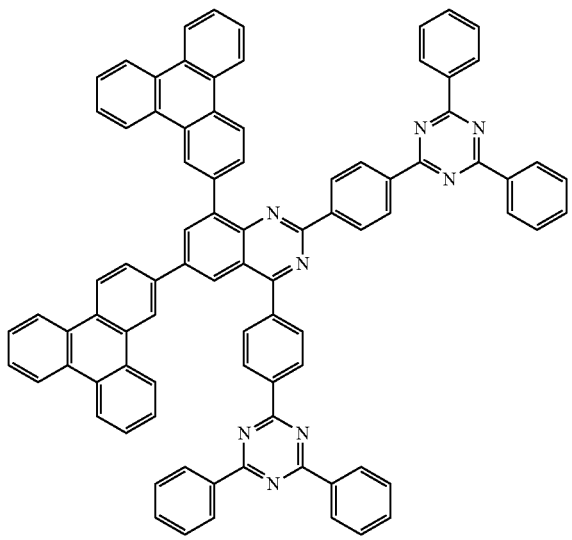
[Chemical Formula A-293]
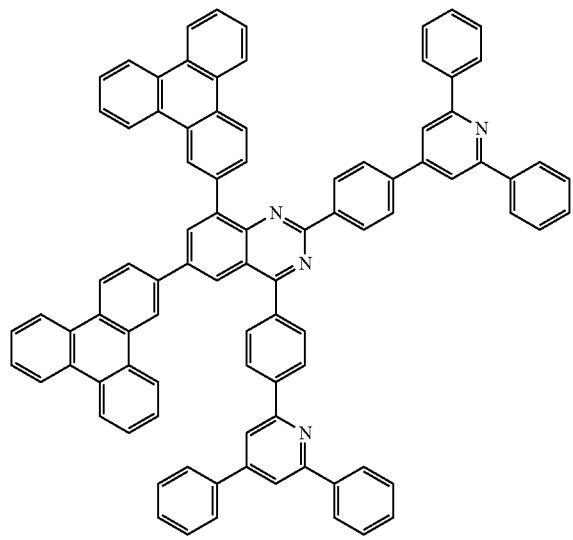
[Chemical Formula A-294]
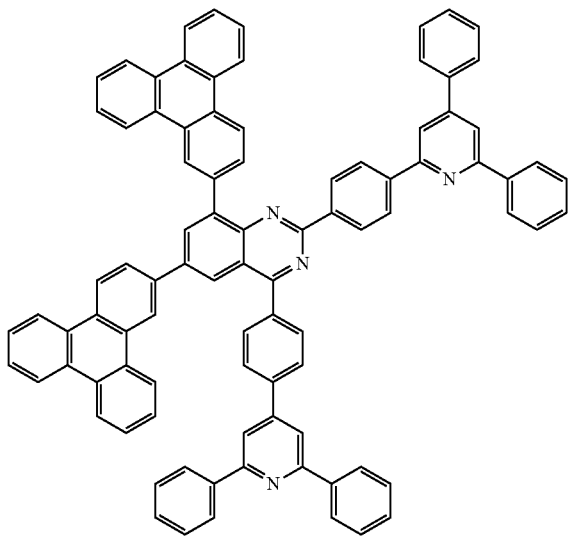

[Chemical Formula A-295]
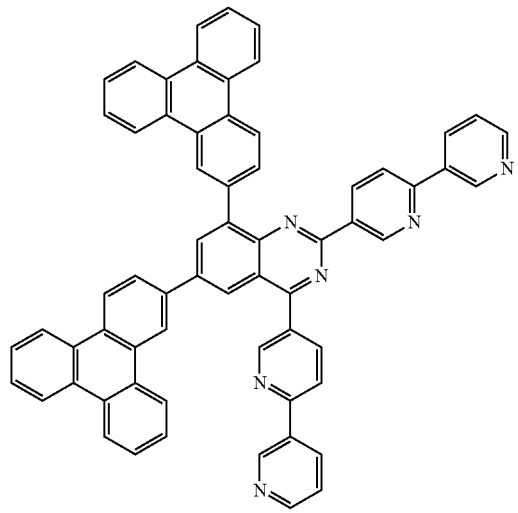
[Chemical Formula A-296]
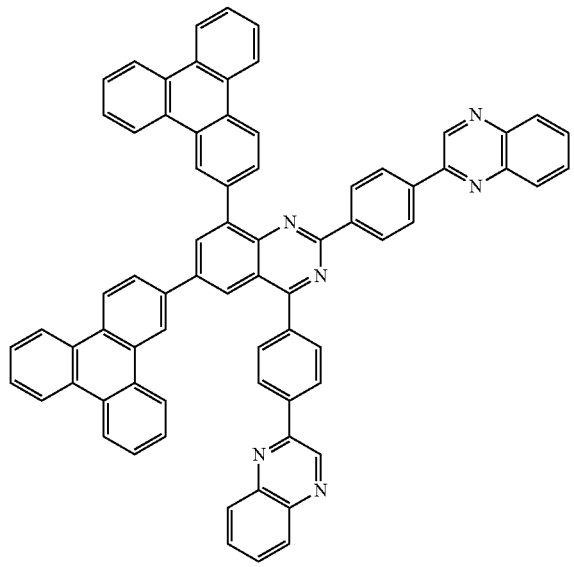
[Chemical Formula A-297]
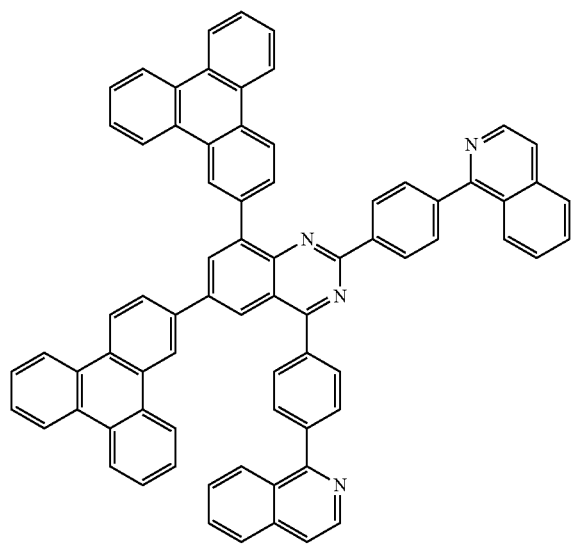
[Chemical Formula A-298]
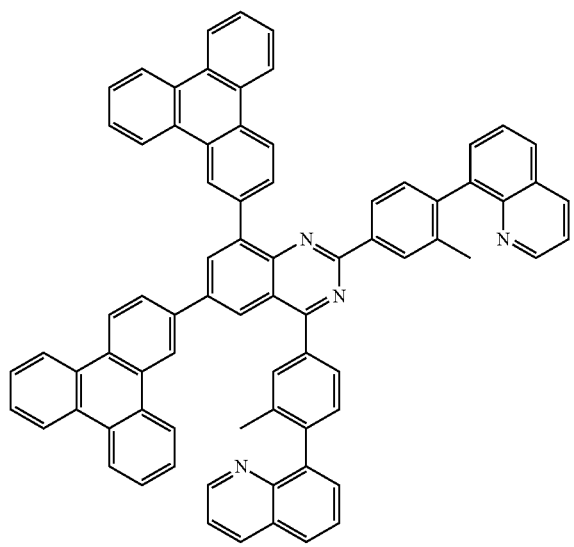

[Chemical Formula A-299]
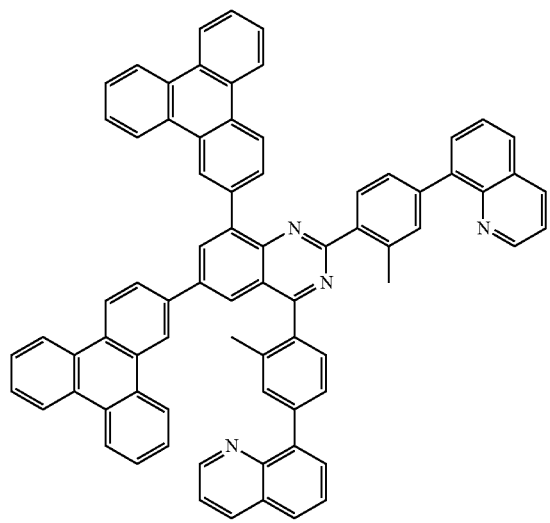
[Chemical Formula A-300]
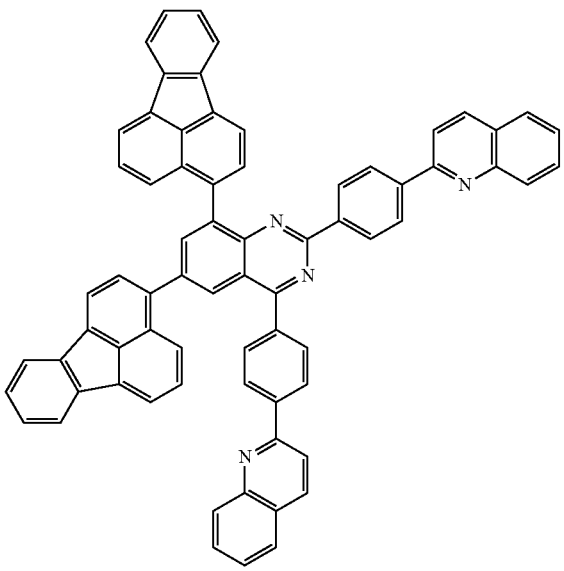
[Chemical Formula A-301]
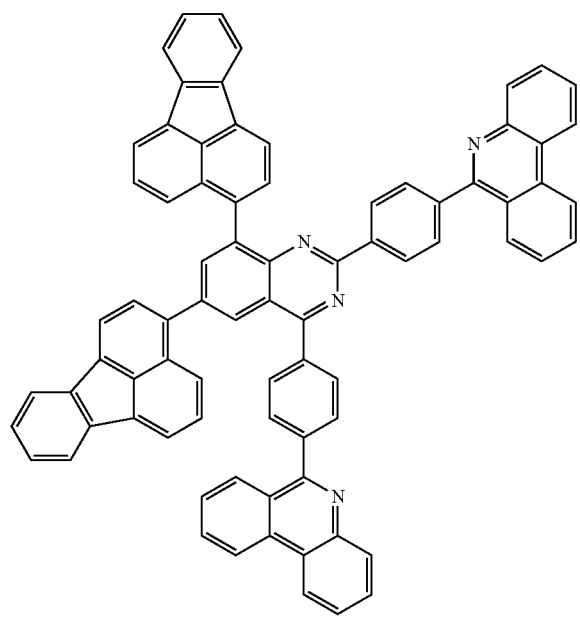
[Chemical Formula A-302]
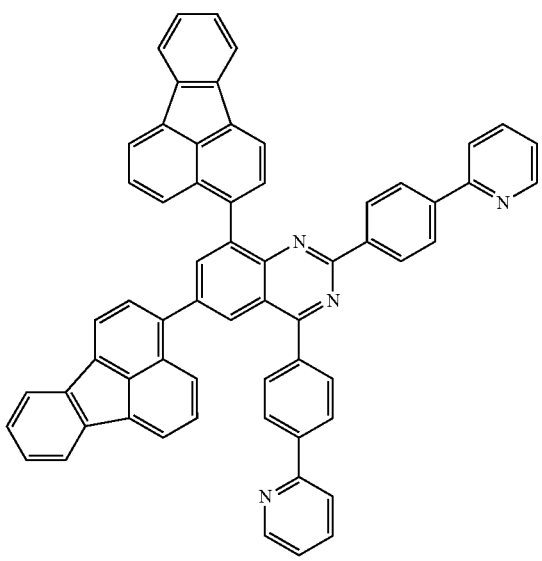

[Chemical Formula A-303]
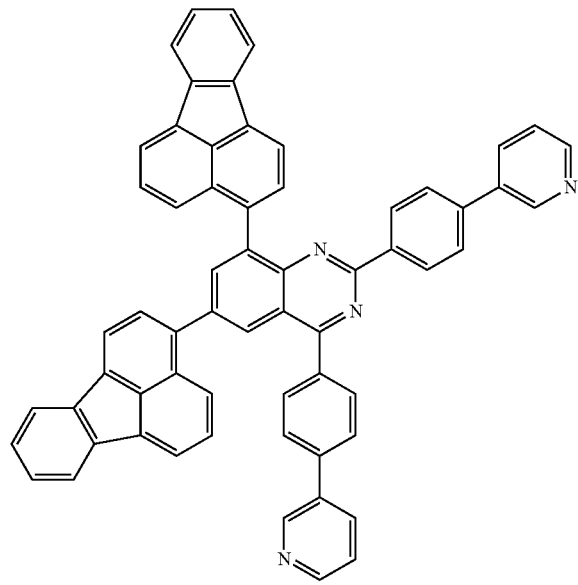
[Chemical Formula A-304]
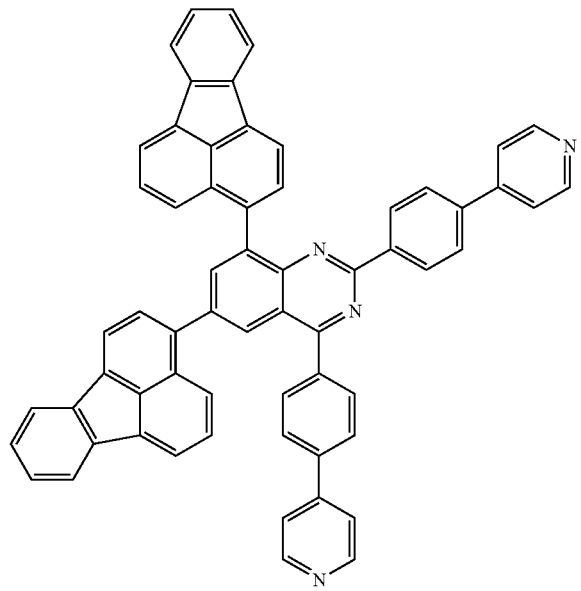
[Chemical Formula A-305]
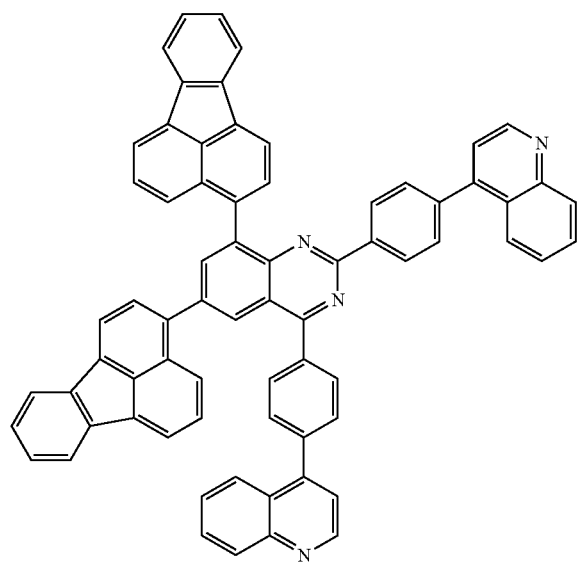
[Chemical Formula A-306]
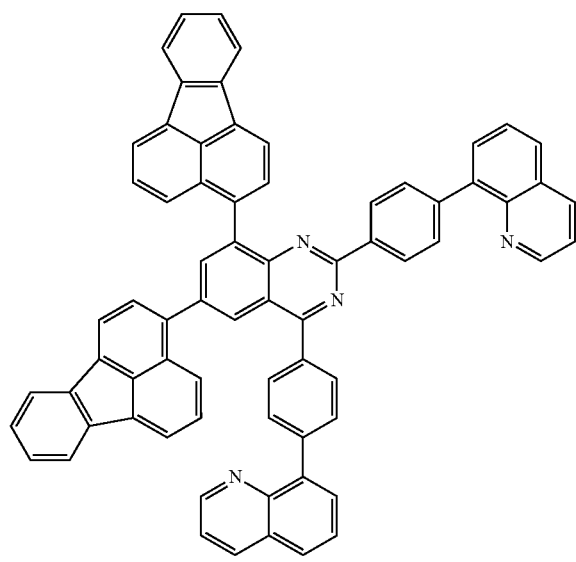

[Chemical Formula A-307]
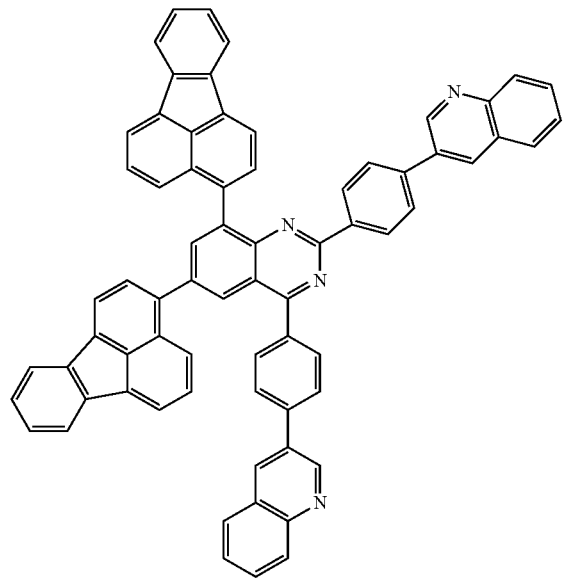
[Chemical Formula A-308]
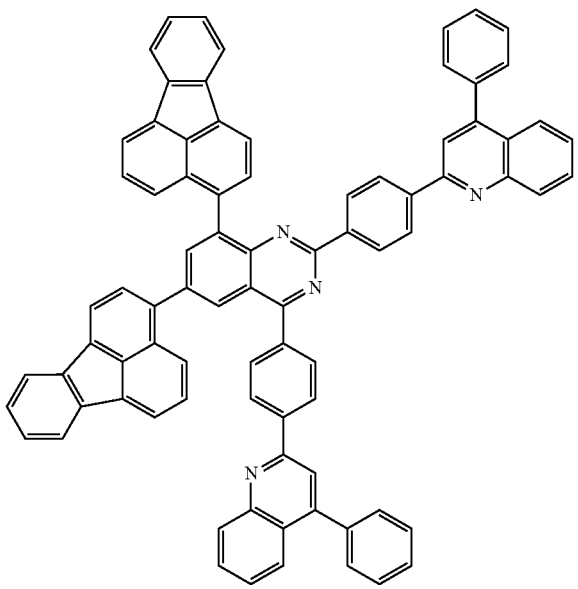
[Chemical Formula A-309]
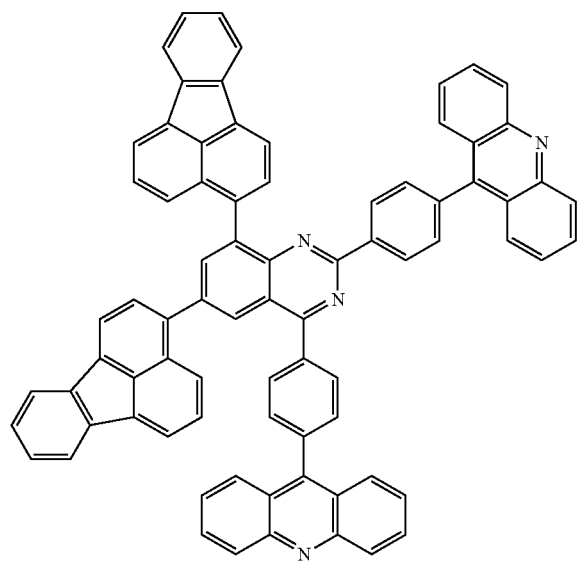
[Chemical Formula A-310]
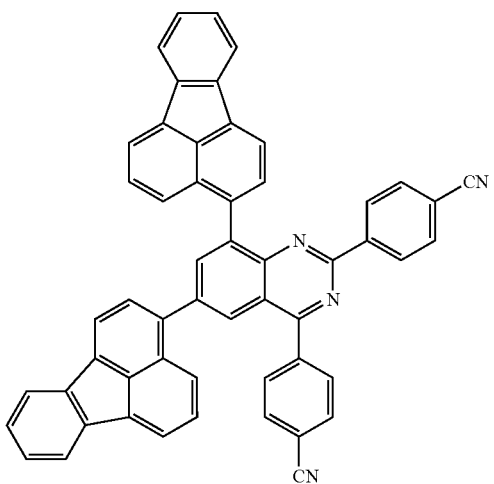

[Chemical Formula A-311]
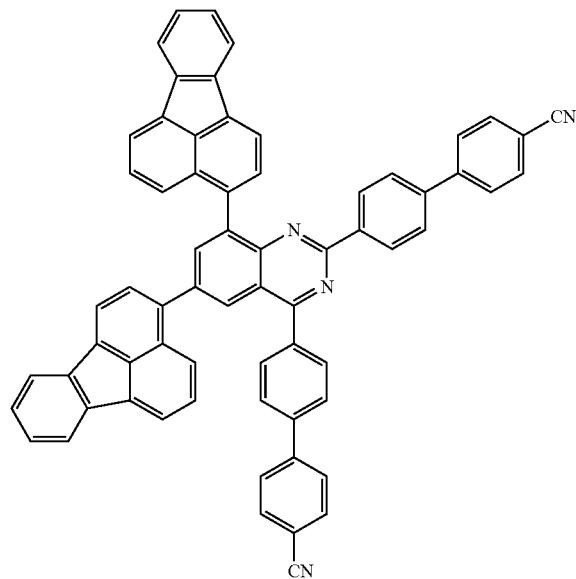
[Chemical Formula A-312]
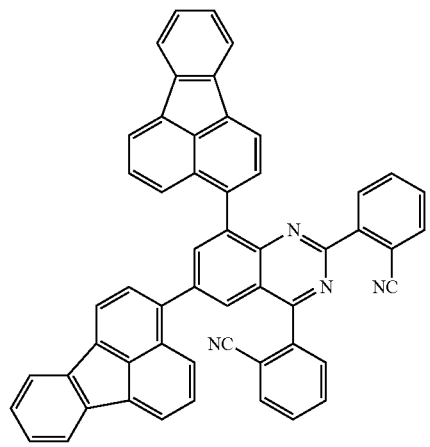
[Chemical Formula A-313]
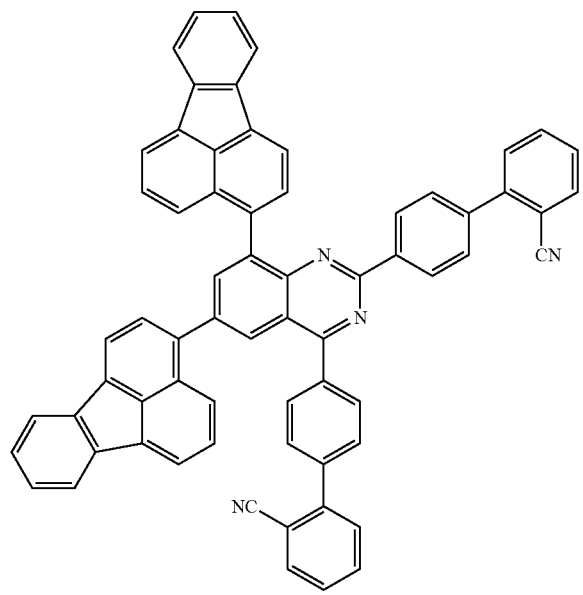
[Chemical Formula A-314]
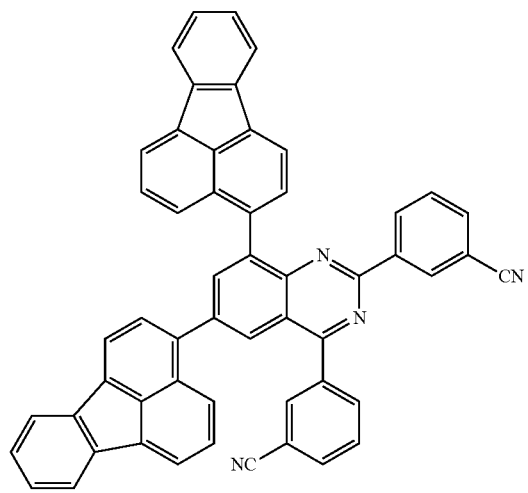

[Chemical Formula A-315]
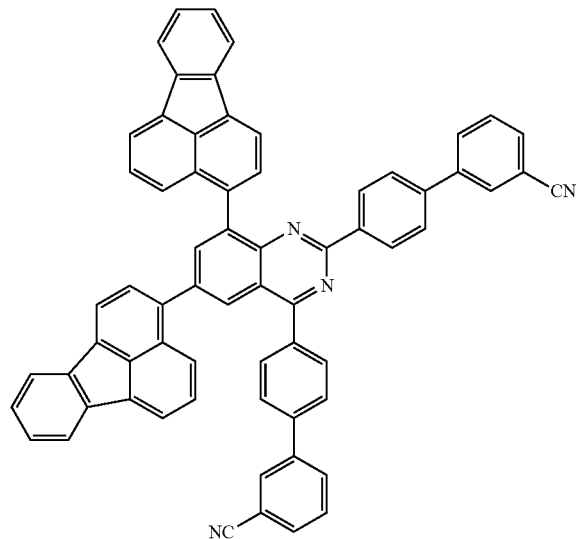
[Chemical Formula A-316]
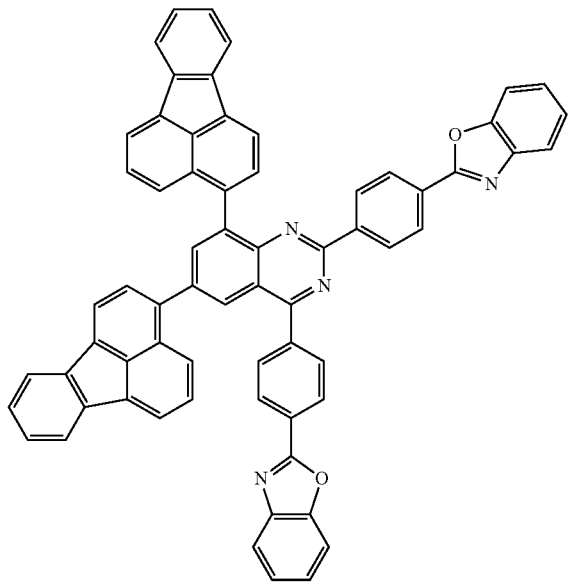
[Chemical Formula A-317]
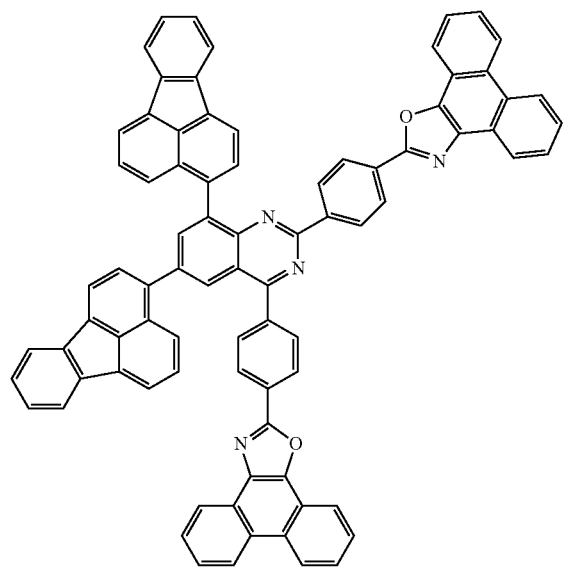
[Chemical Formula A-318]
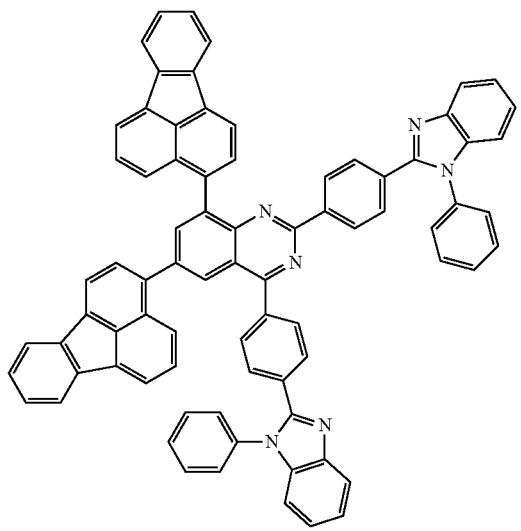

[Chemical Formula A-319]
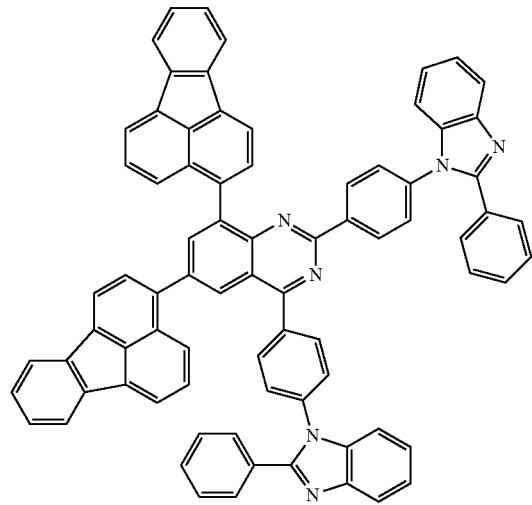
[Chemical Formula A-320]
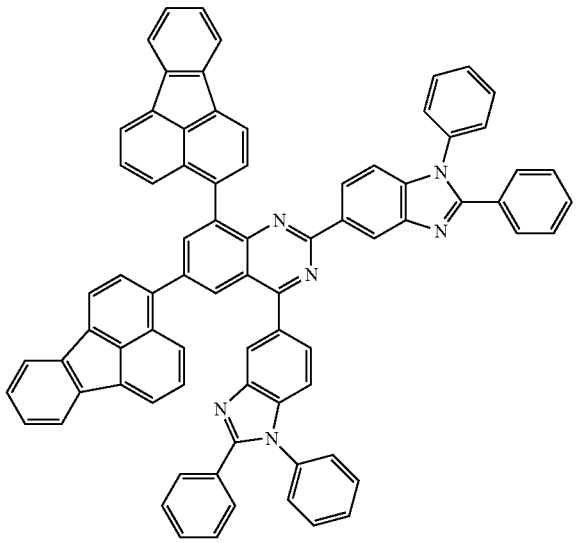
[Chemical Formula A-321]
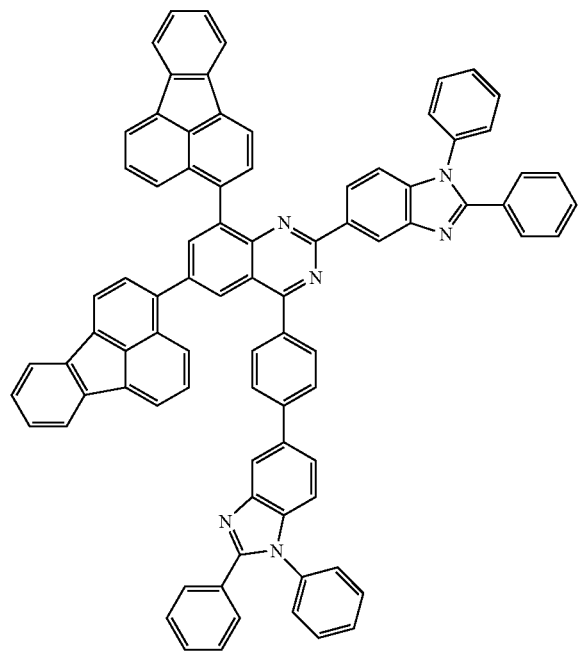
[Chemical Formula A-322]
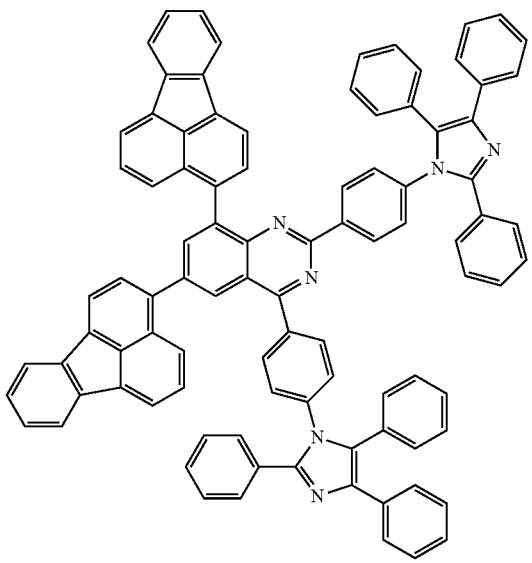

[Chemical Formula A-323]
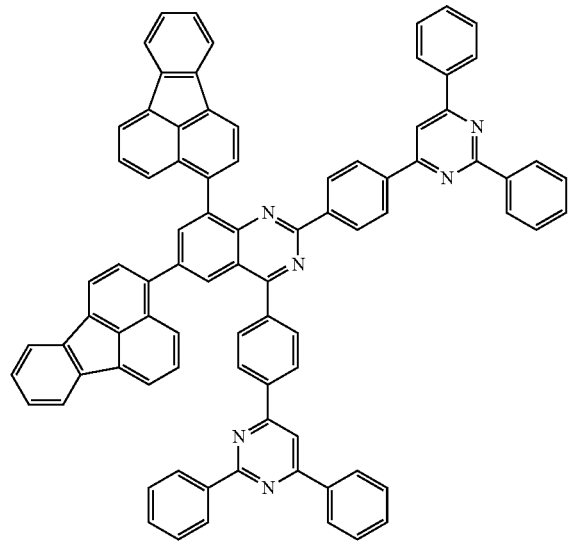
[Chemical Formula A-324]
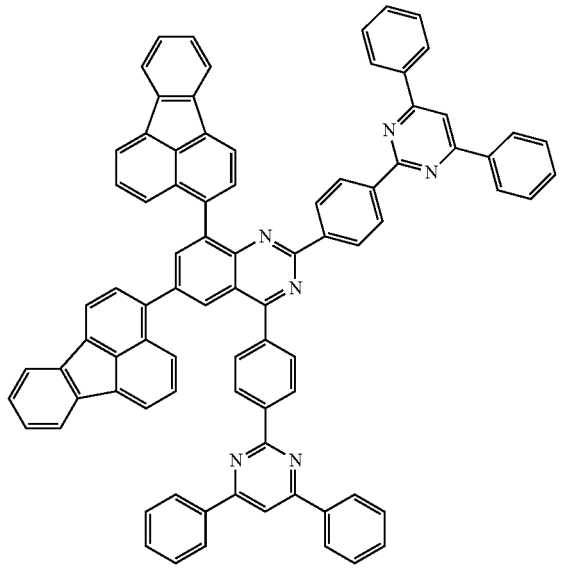
[Chemical Formula A-325]
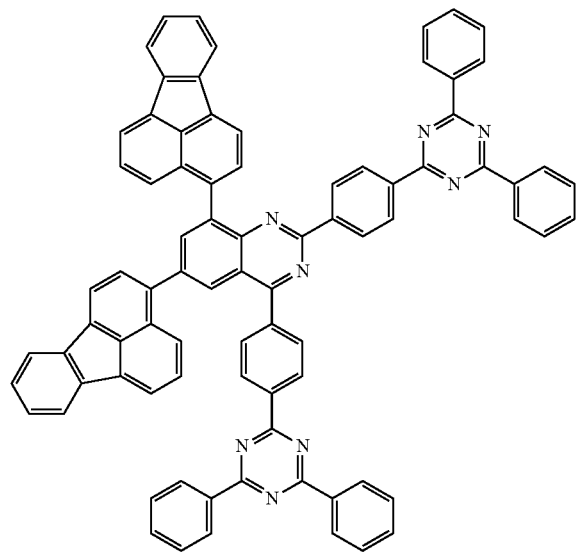
[Chemical Formula A-326]
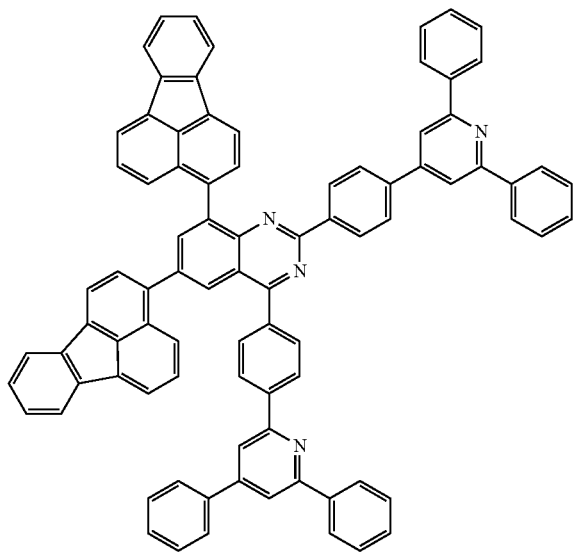

-continued
[Chemical Formula A-327]
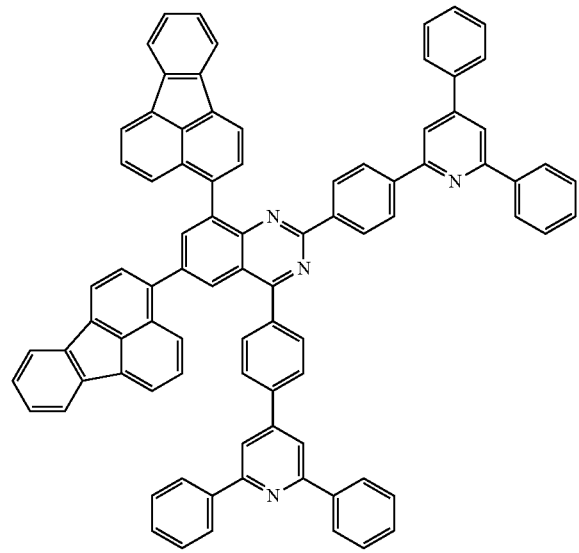
[Chemical Formula A-328]
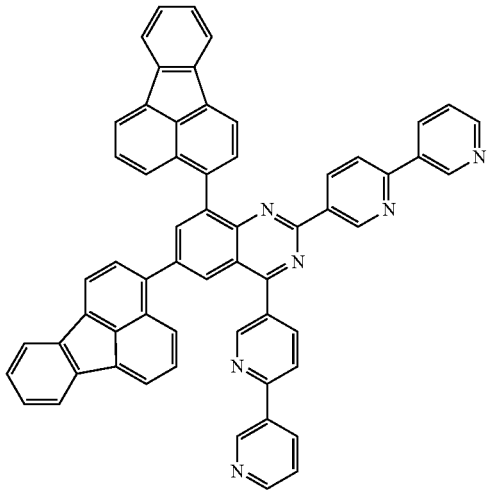
[Chemical Formula A-329]
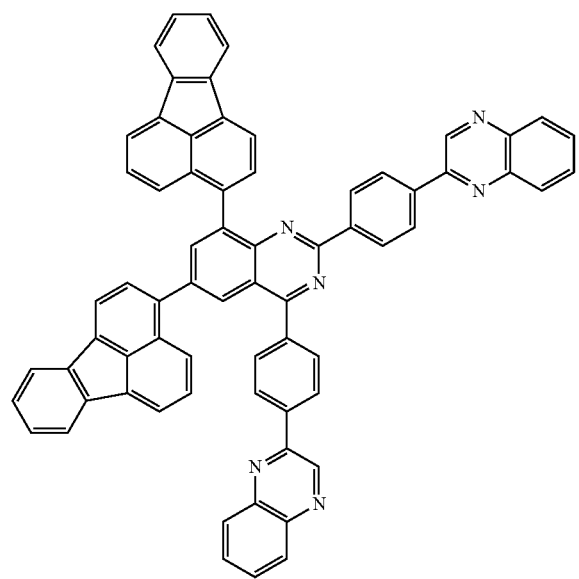
[Chemical Formula A-330]
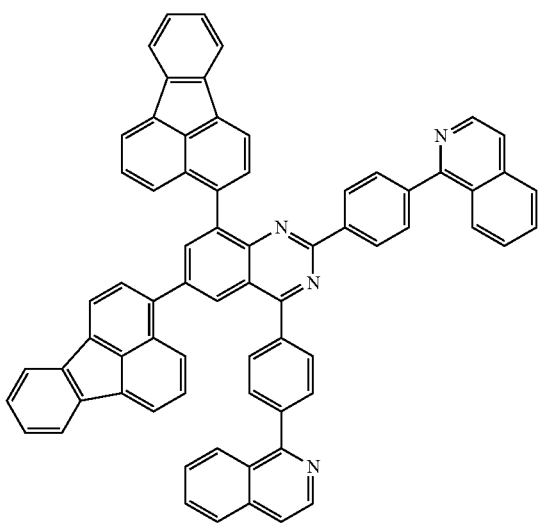

-continued
[Chemical Formula A-331]
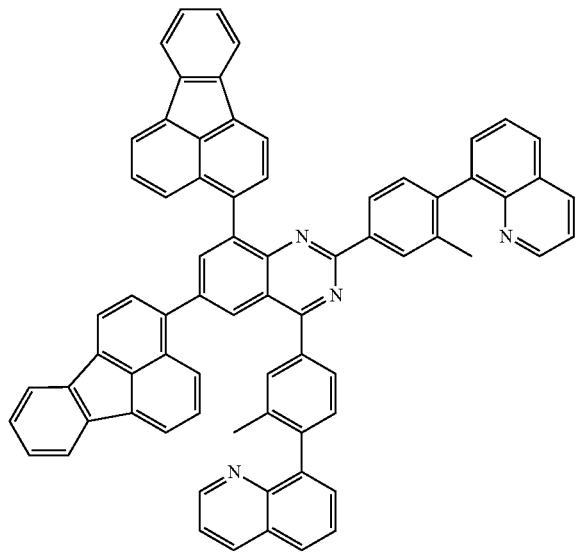
[Chemical Formula A-332]
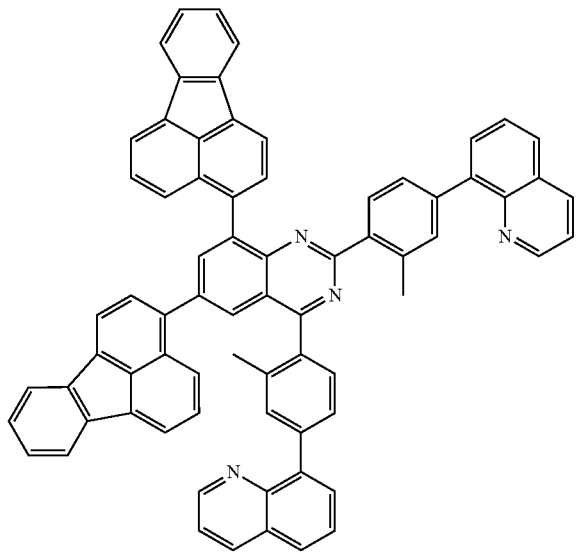
[Chemical Formula A-333]
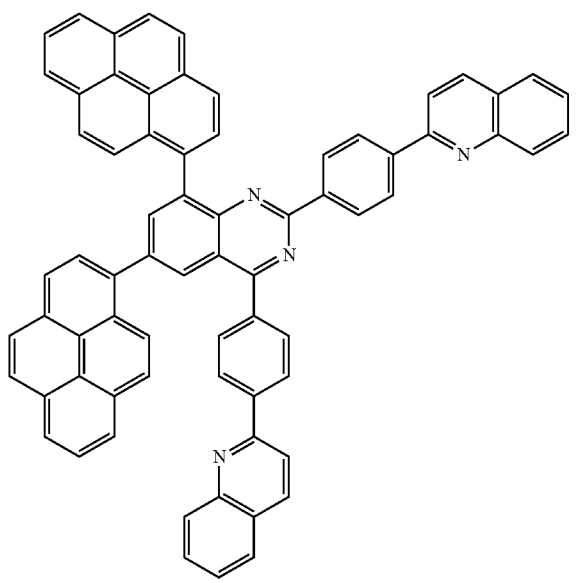
[Chemical Formula A-334]
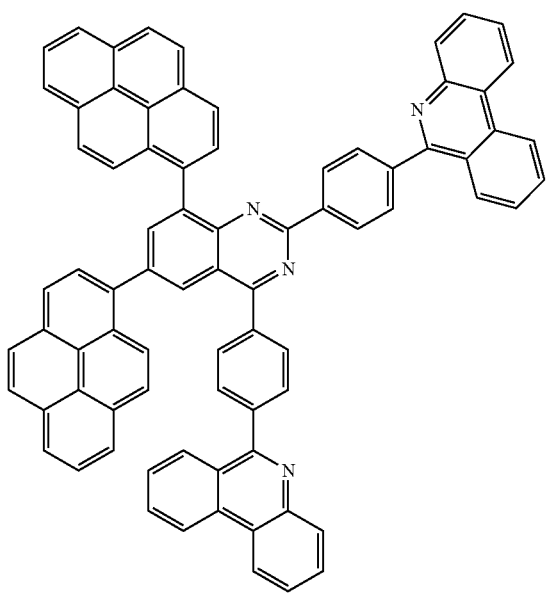

[Chemical Formula A-335]
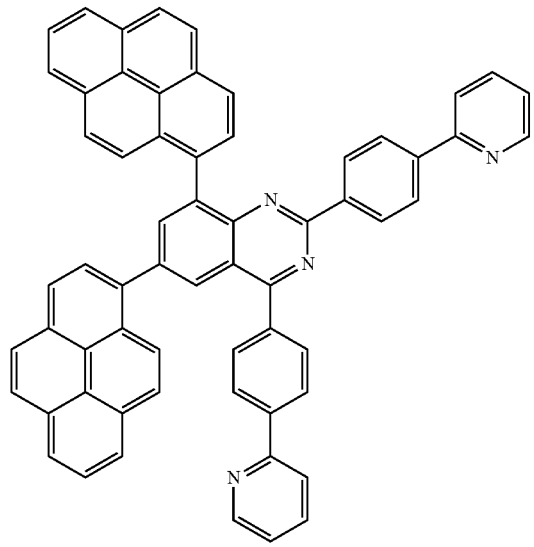
[Chemical Formula A-336]
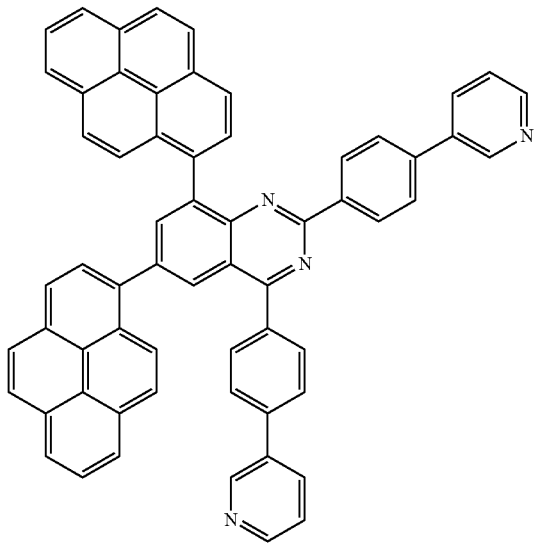
[Chemical Formula A-337]
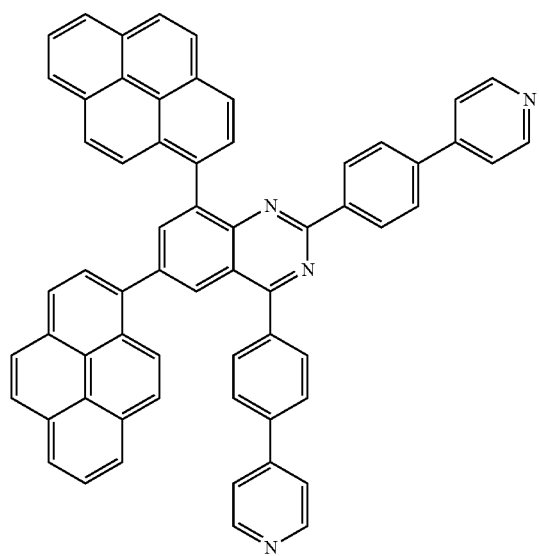
[Chemical Formula A-338]
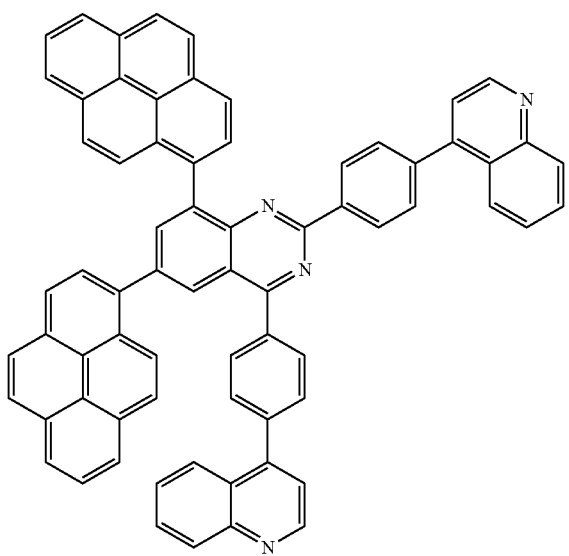

[Chemical Formula A-339]
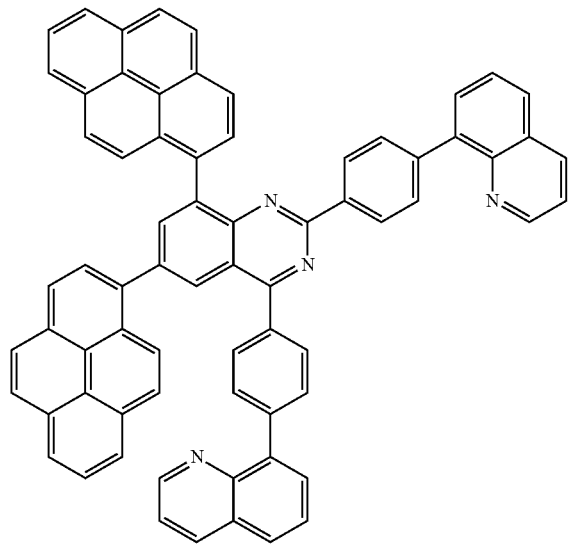
[Chemical Formula A-340]
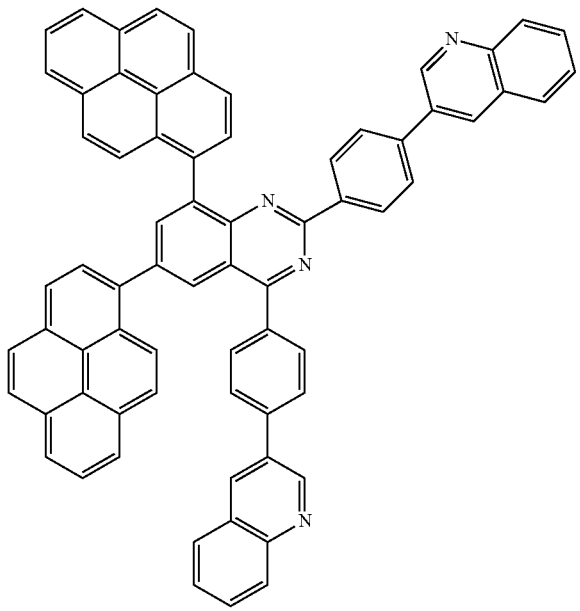
[Chemical Formula A-341]
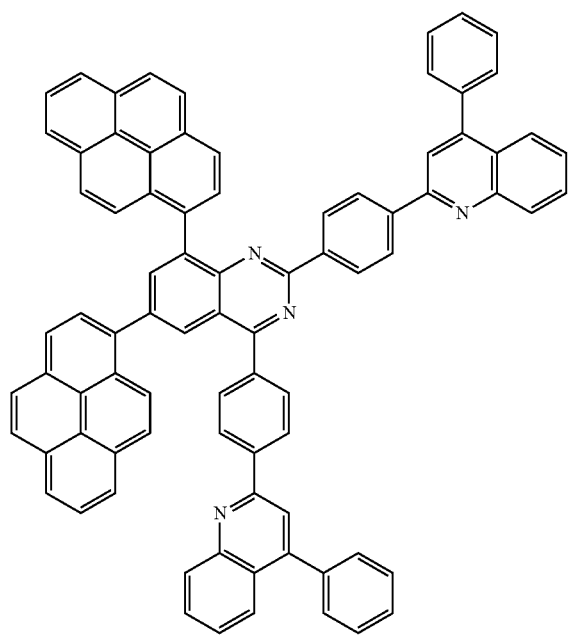
[Chemical Formula A-342]
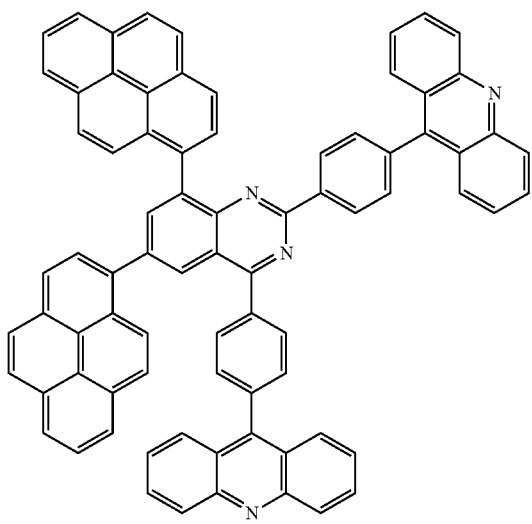

[Chemical Formula A-343]
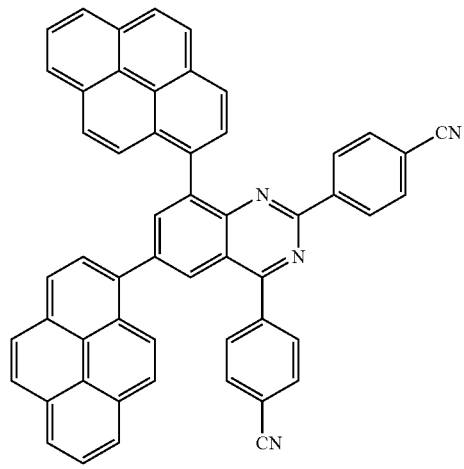
[Chemical Formula A-344]
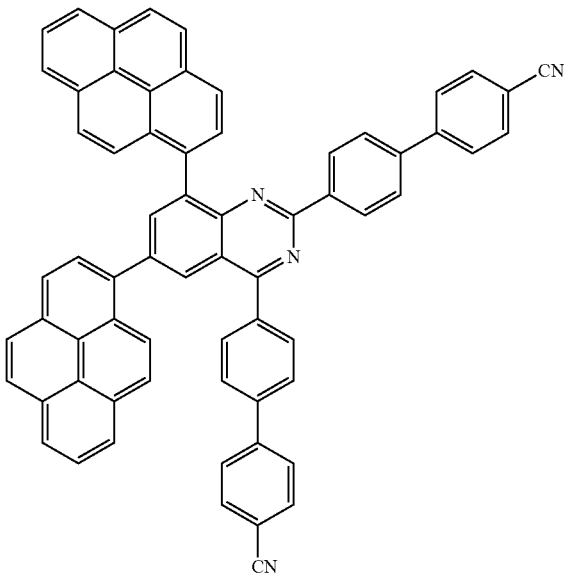
[Chemical Formula A-345]
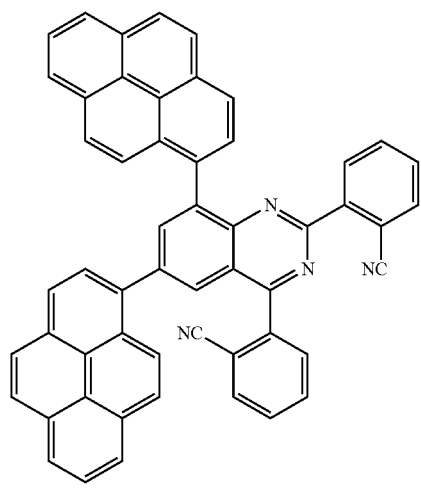
[Chemical Formula A-346]
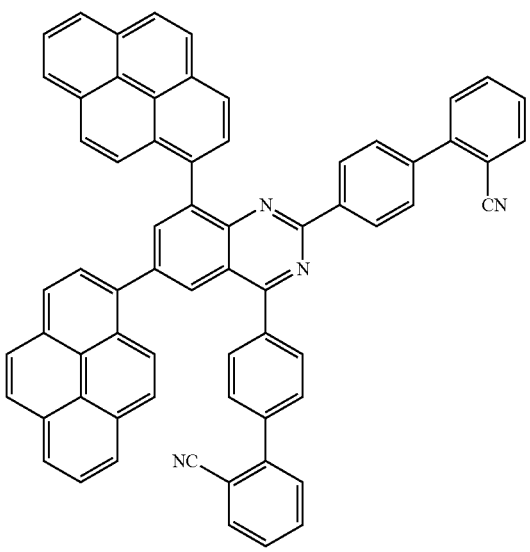

-continued
[Chemical Formula A-347]
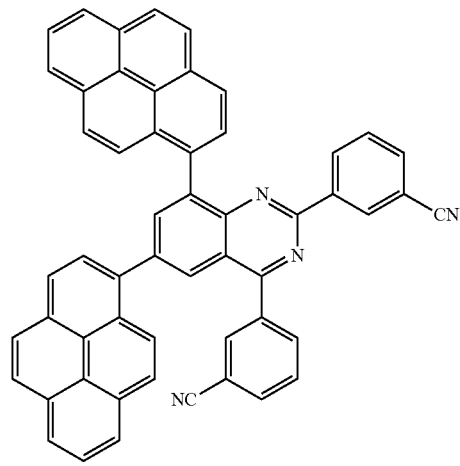
[Chemical Formula A-348]
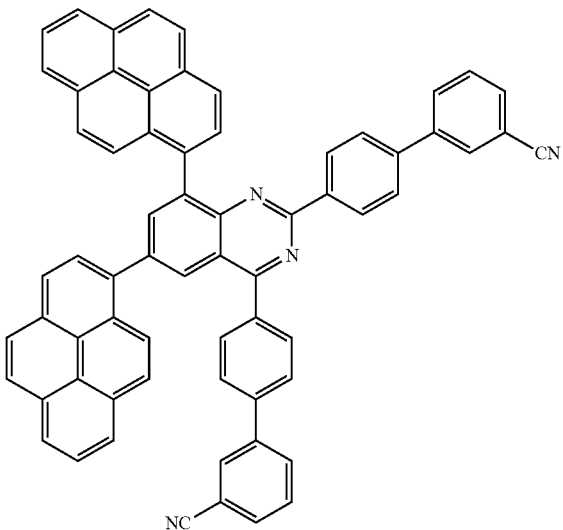
[Chemical Formula A-349]
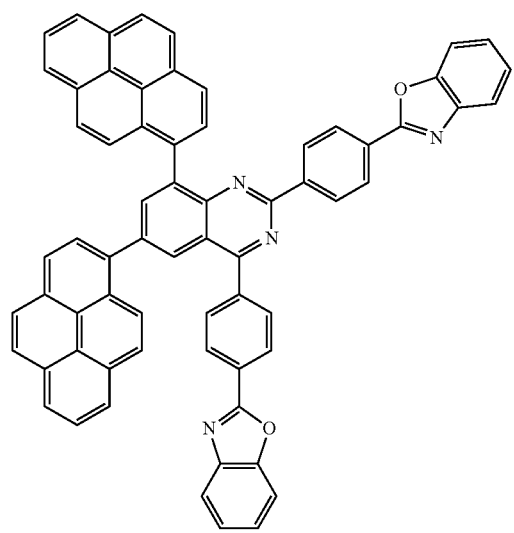
[Chemical Formula A-350]
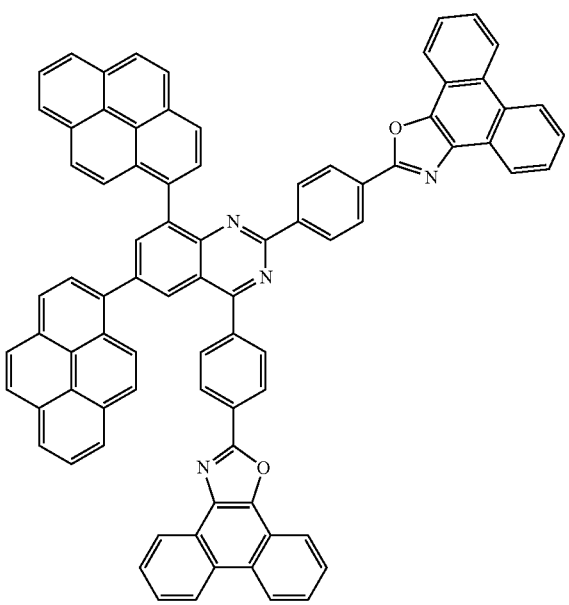

-continued
[Chemical Formula A-351]
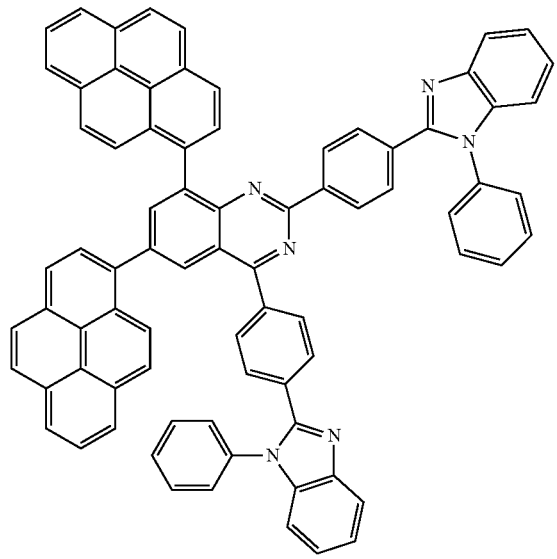
[Chemical Formula A-352]
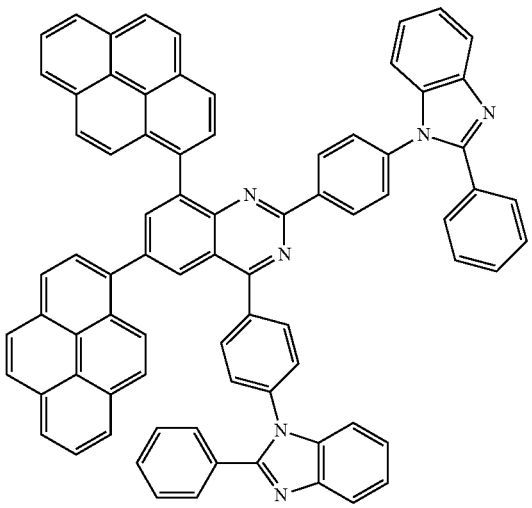
[Chemical Formula A-353]
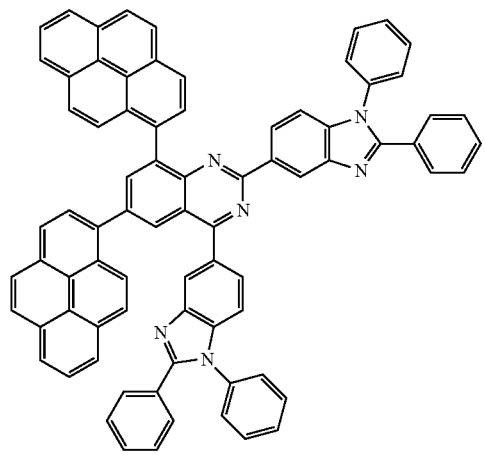
[Chemical Formula A-354]
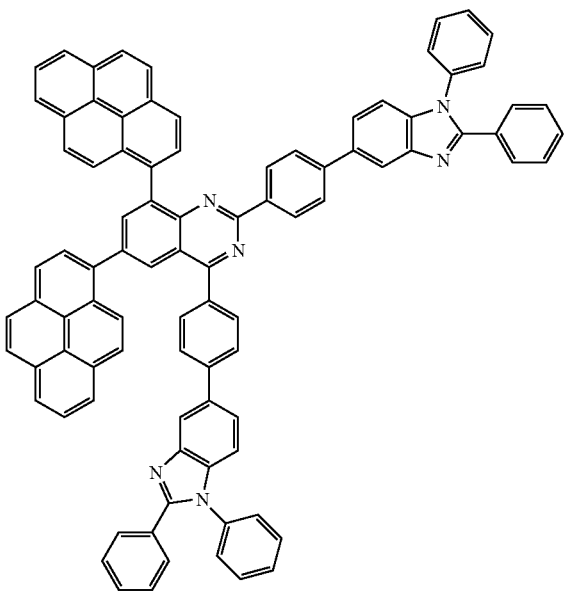

[Chemical Formula A-355]
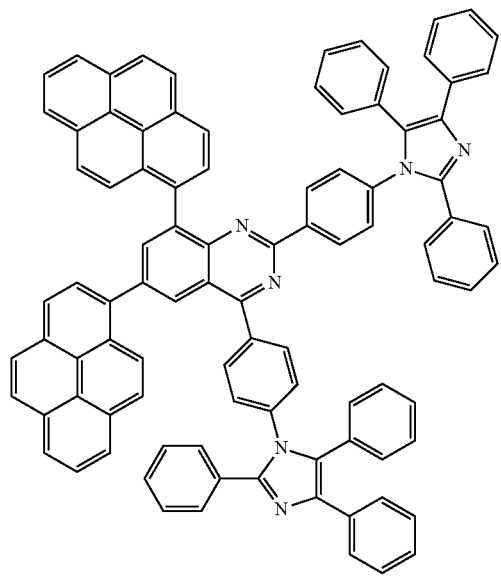
[Chemical Formula A-356]
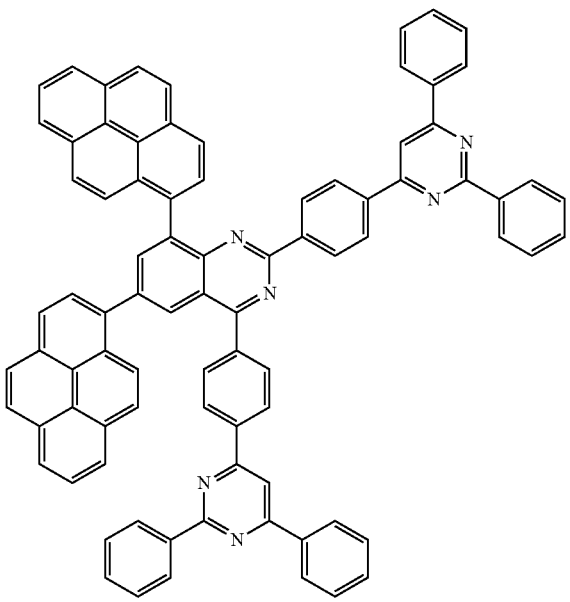
[Chemical Formula A-357]
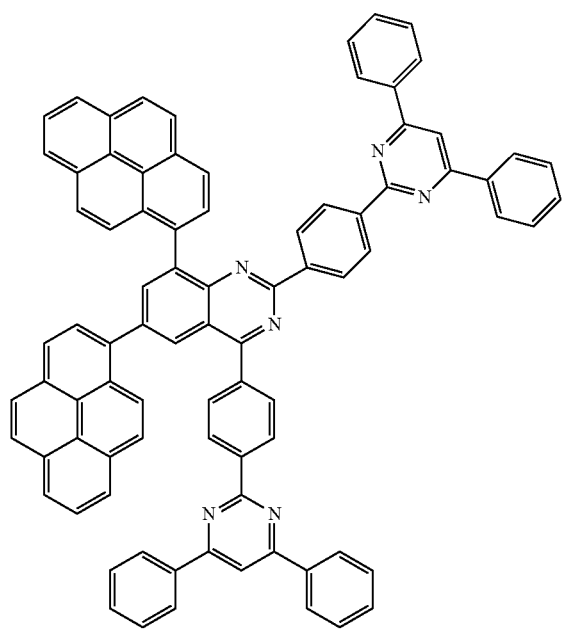
[Chemical Formula A-358]
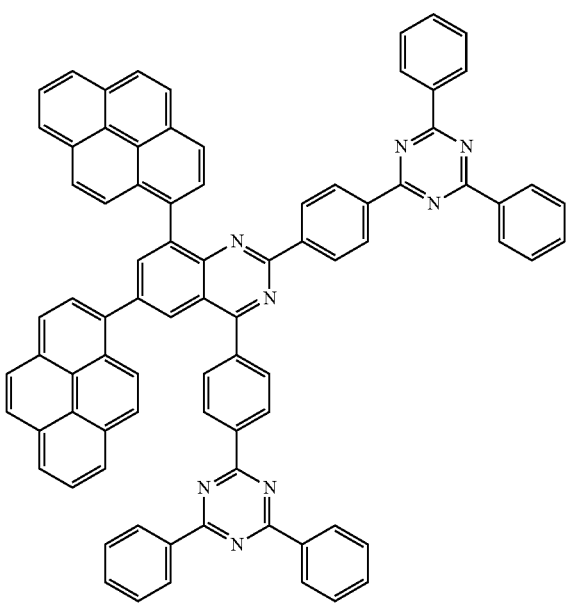

[Chemical Formula A-359]
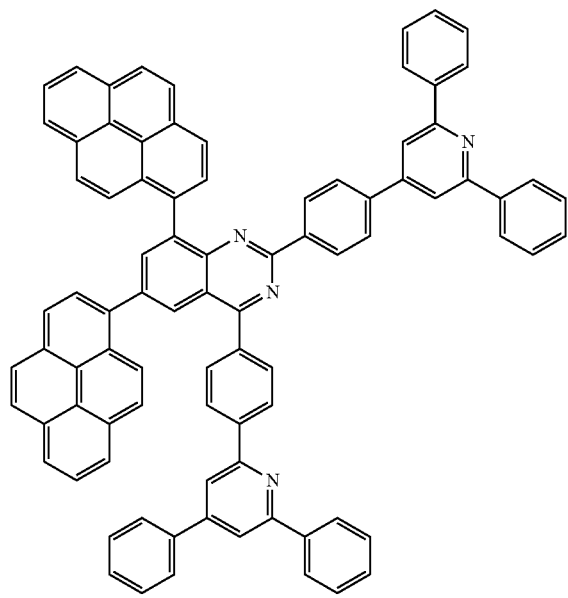
[Chemical Formula A-360]
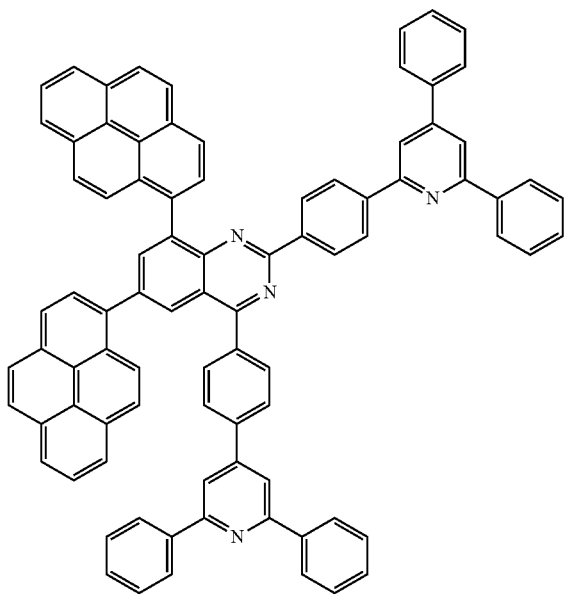
[Chemical Formula A-361]
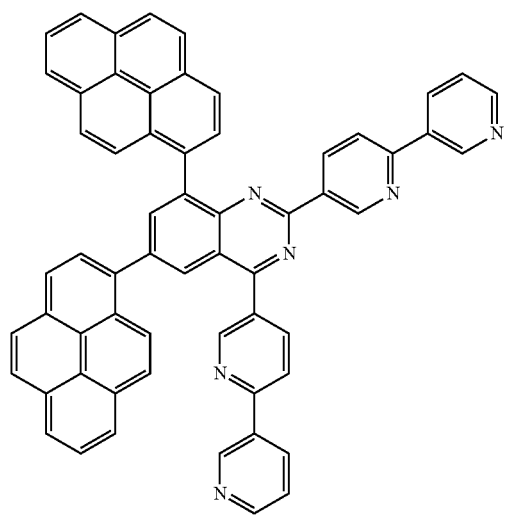
[Chemical Formula A-362]
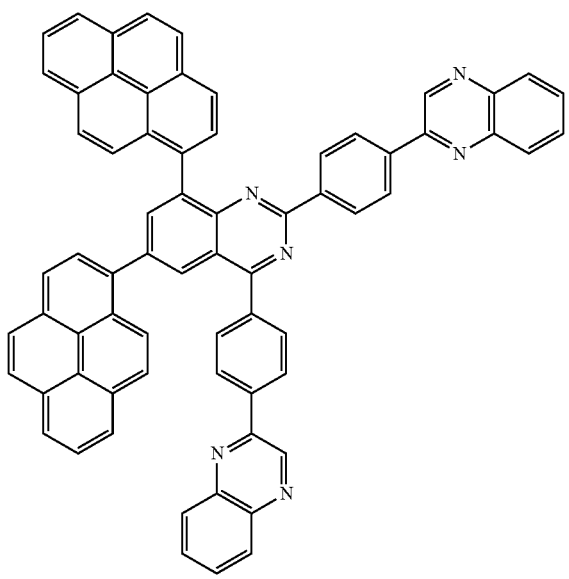

[Chemical Formula A-363]
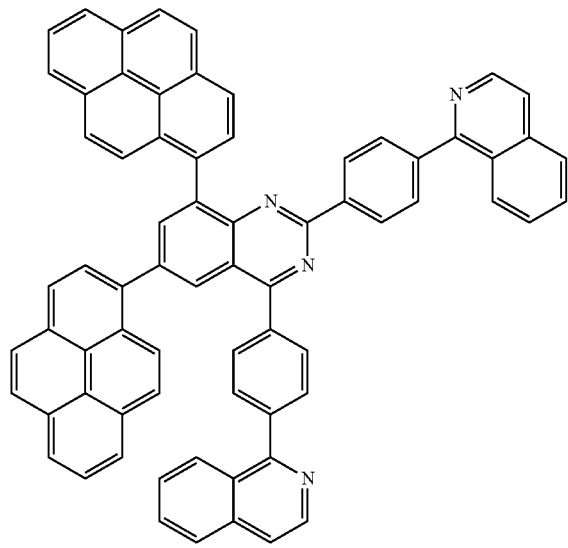
[Chemical Formula A-364]
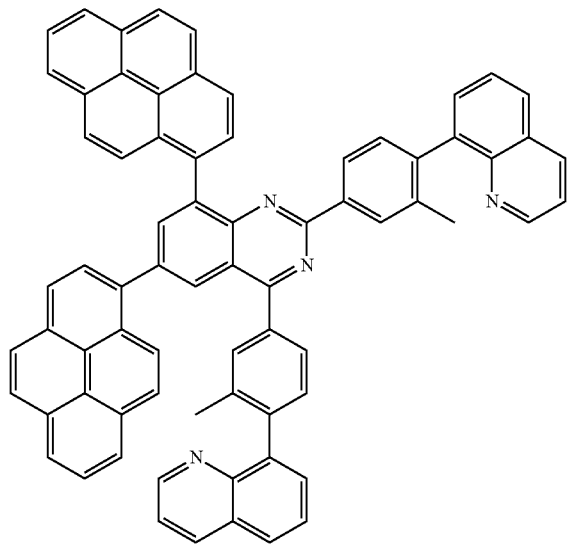
[Chemical Formula A-365]
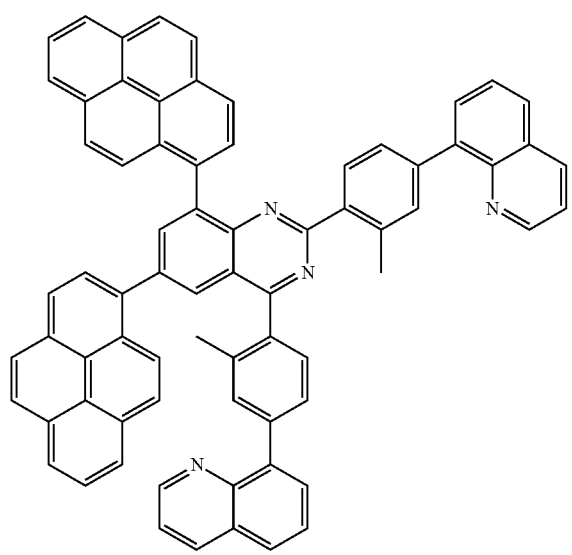
[Chemical Formula A-366]
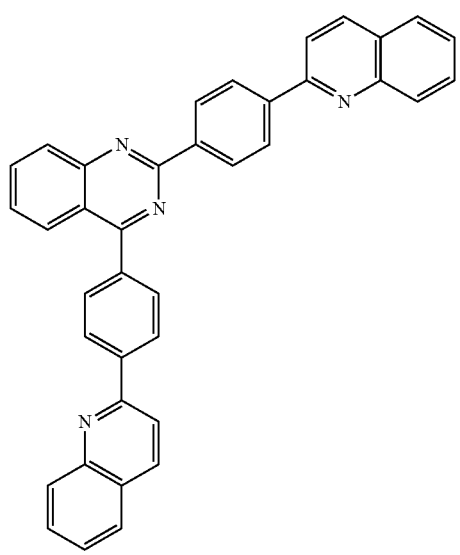

[Chemical Formula A-367]
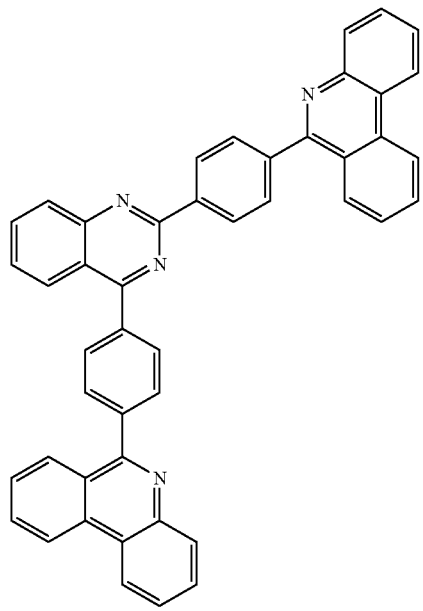
[Chemical Formula A-368]
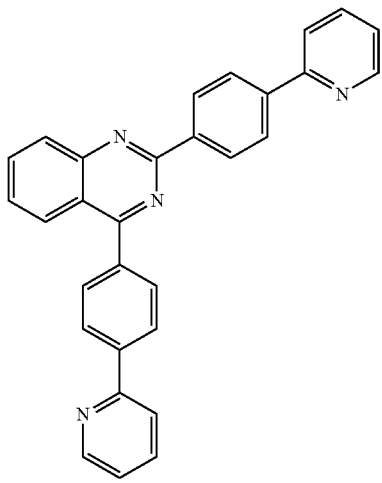
[Chemical Formula A-369]
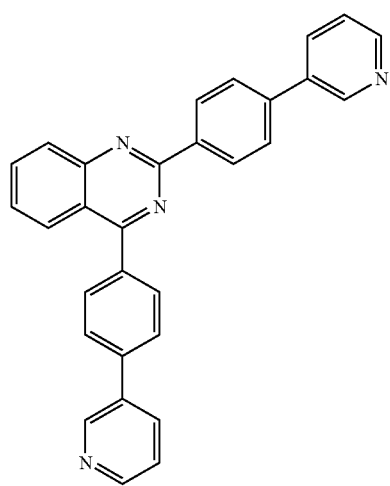
[Chemical Formula A-370]
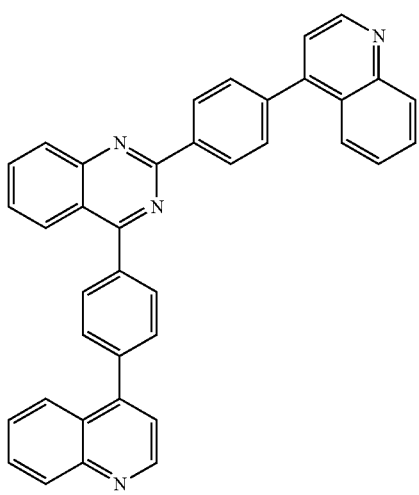

-continued
[Chemical Formula A-371]
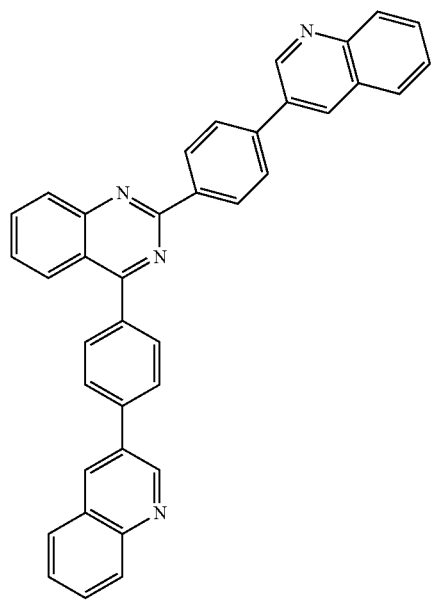
[Chemical Formula A-372]
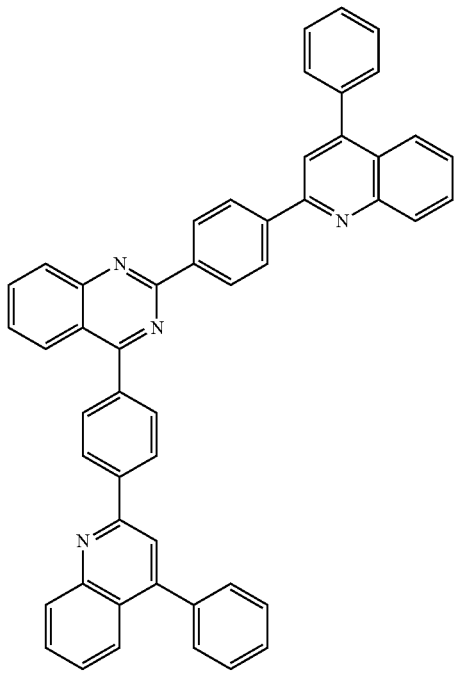
[Chemical Formula A-373]
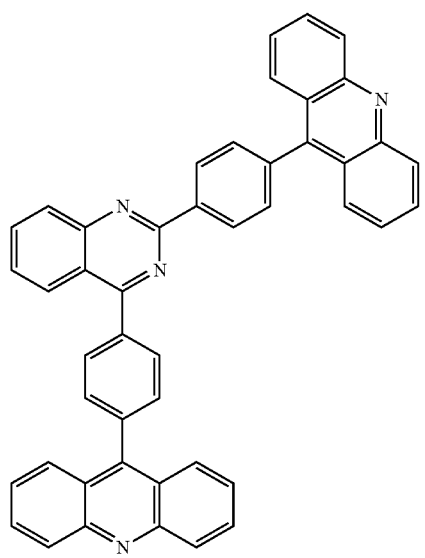
[Chemical Formula A-374]
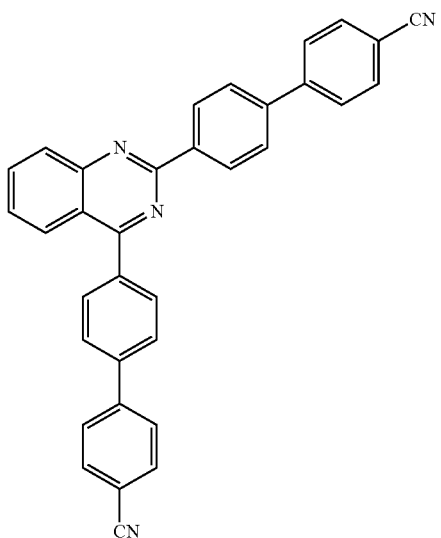

[Chemical Formula A-375]
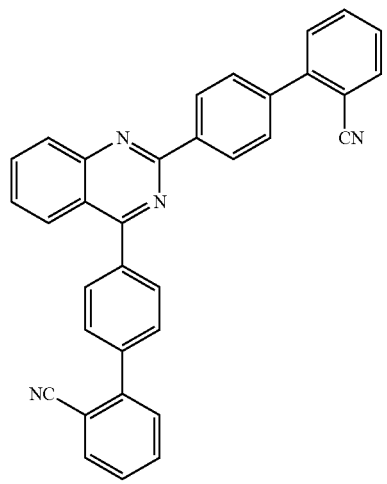
[Chemical Formula A-376]
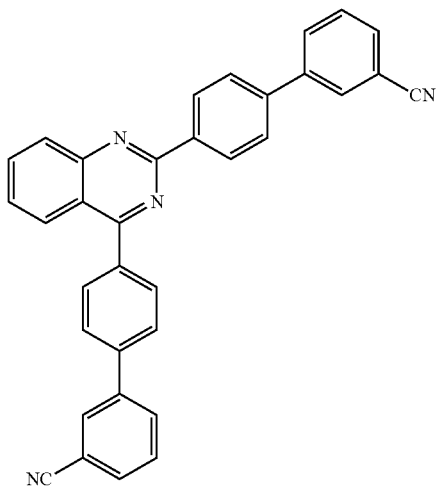
[Chemical Formula A-377]
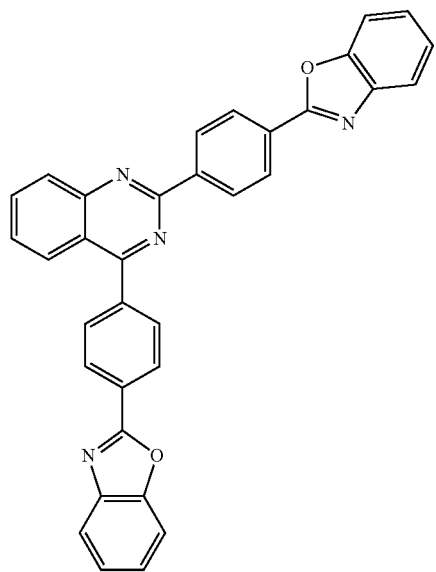
[Chemical Formula A-378]
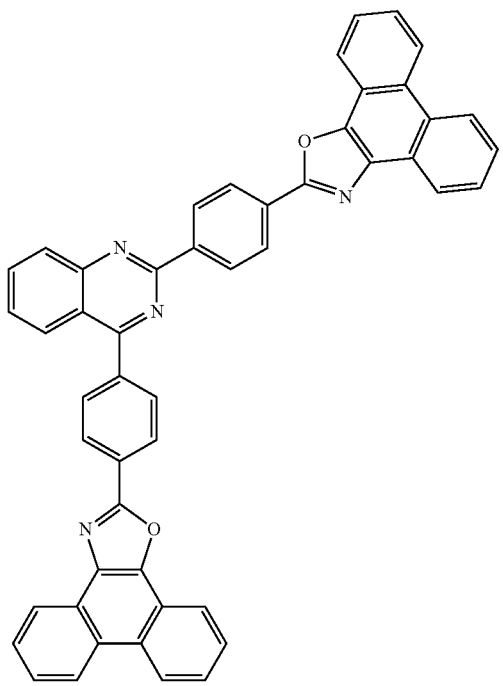

[Chemical Formula A-379]
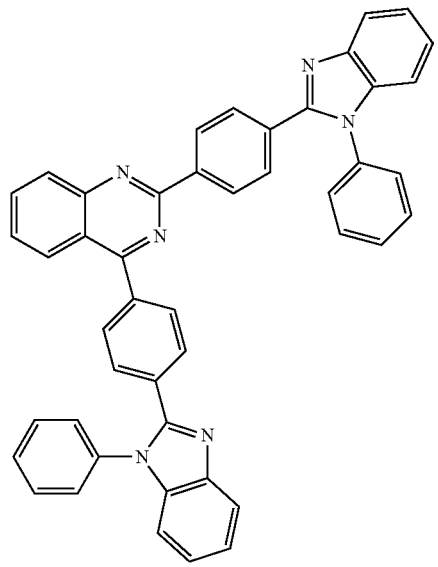
[Chemical Formula A-380]
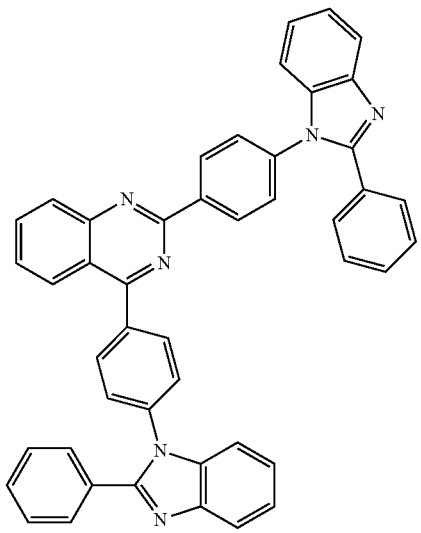
[Chemical Formula A-381]
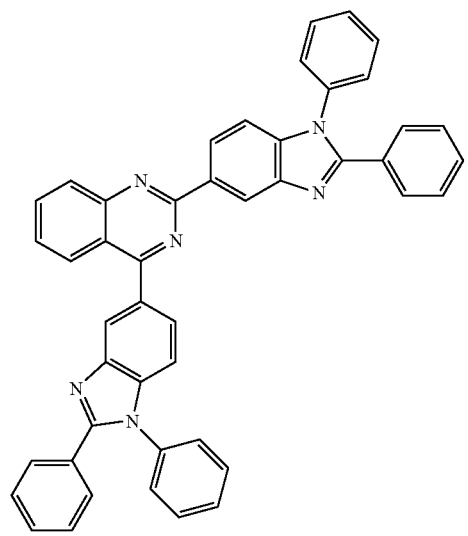
[Chemical Formula A-382]
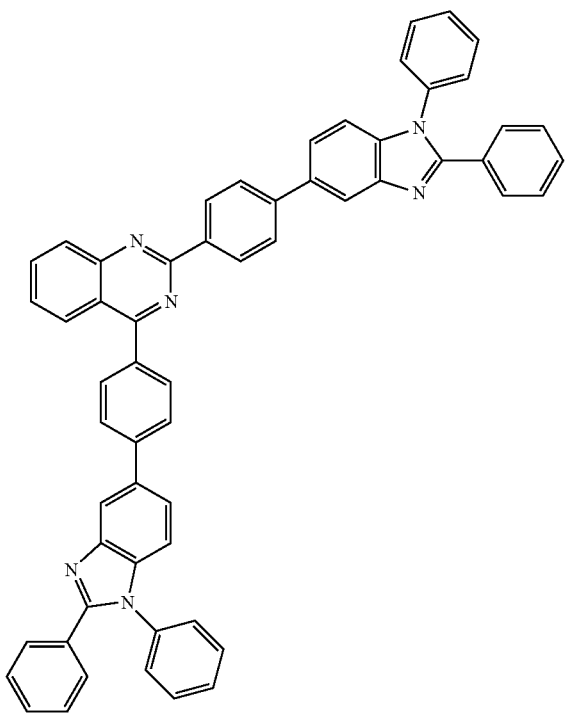

[Chemical Formula A-383]
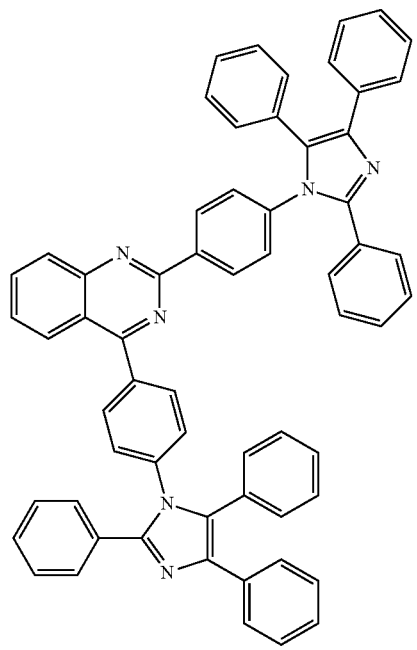
[Chemical Formula A-384]
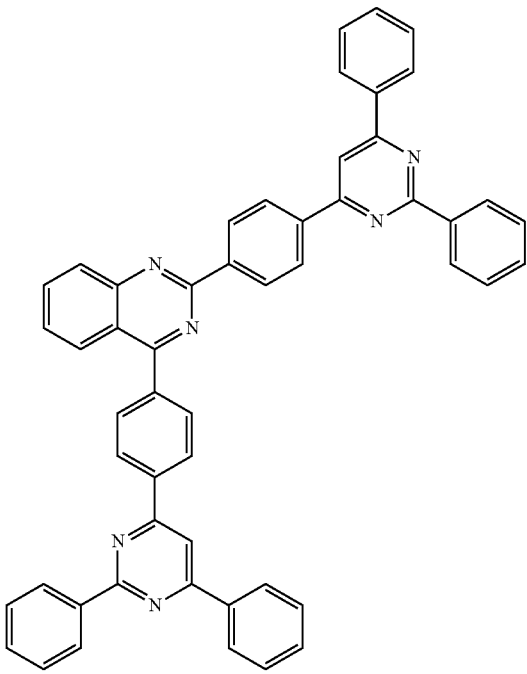
[Chemical Formula A-385]
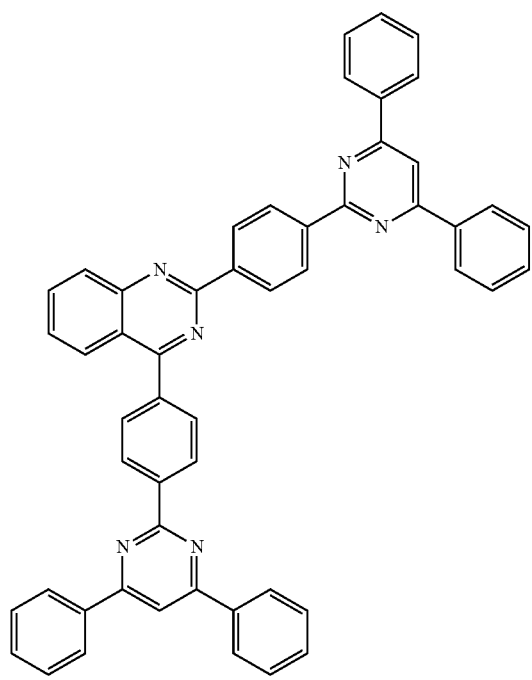
[Chemical Formula A-386]
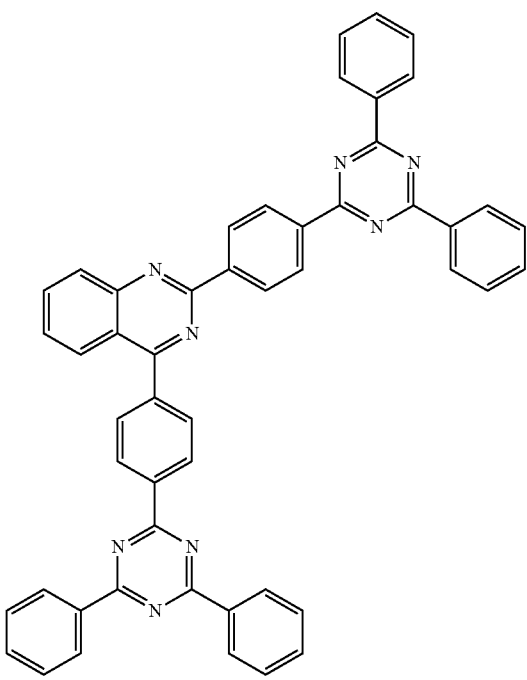

[Chemical Formula A-387]
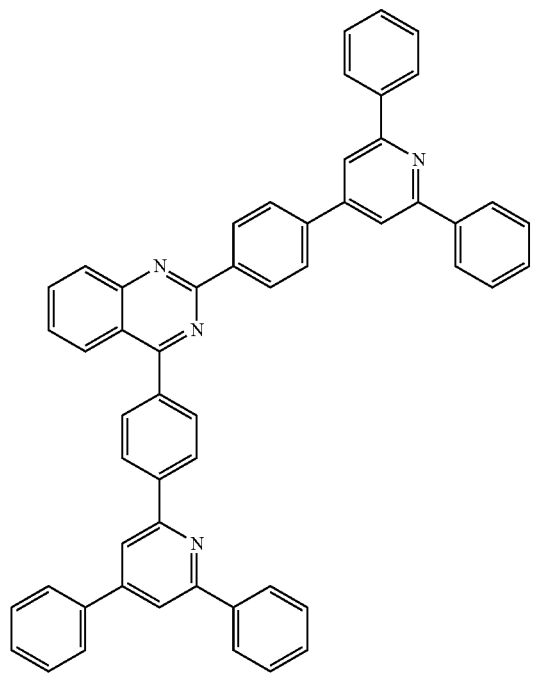
[Chemical Formula A-388]
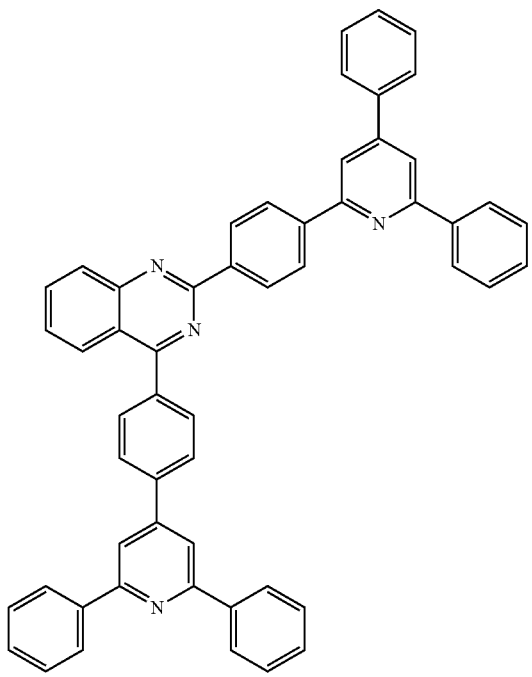
[Chemical Formula A-389]
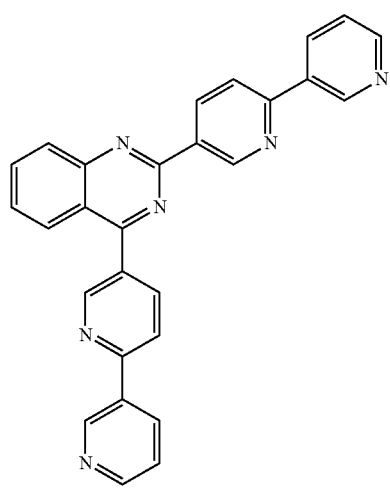
[Chemical Formula A-390]
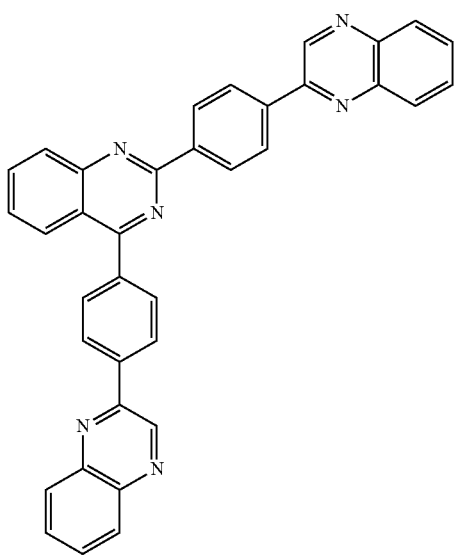

[Chemical Formula A-391]
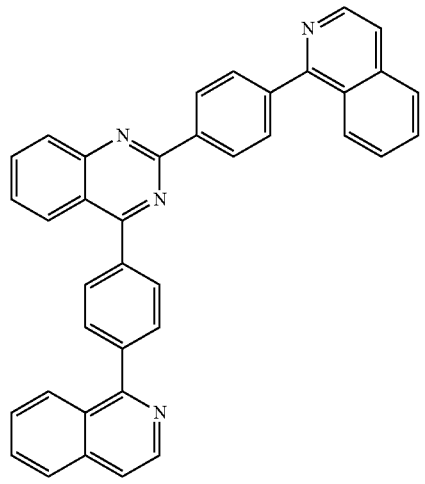
[Chemical Formula A-392]
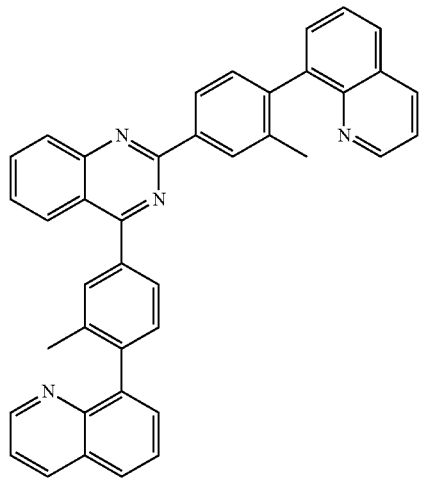
[Chemical Formula A-393]
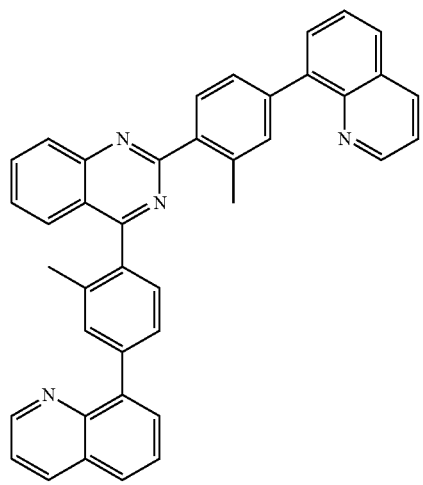
The compound for an organic optoelectronic device may be one of compounds represented by the following Chemical Formulae B-1 to B-30.
[Chemical Formula B-1]
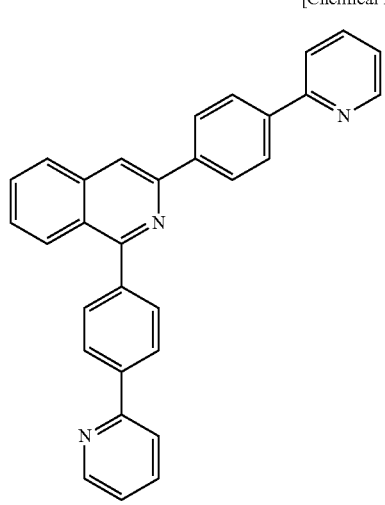
[Chemical Formula B-2]
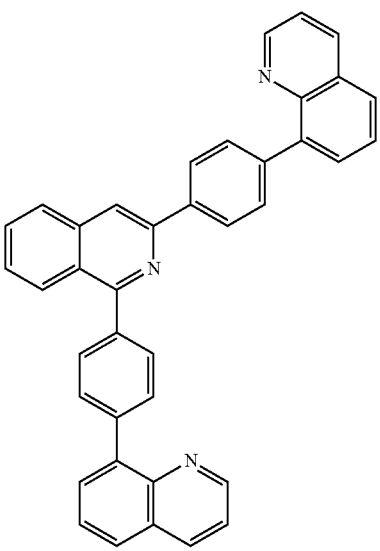

[Chemical Formula B-3]
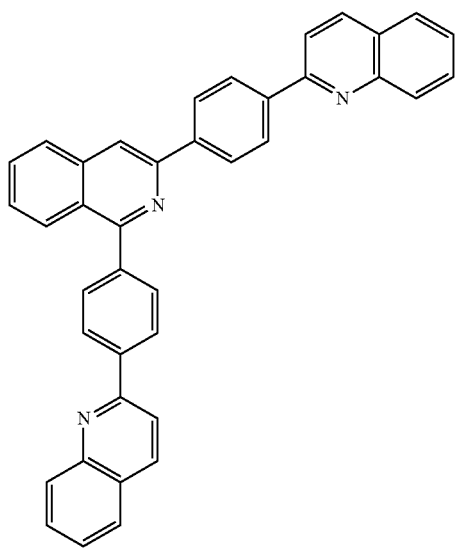
[Chemical Formula B-4]
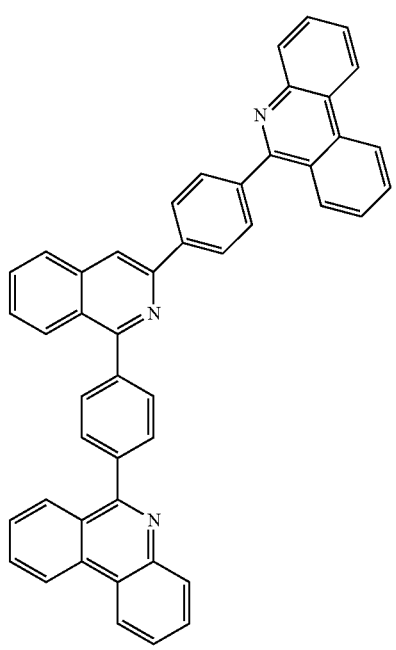
[Chemical Formula B-5]
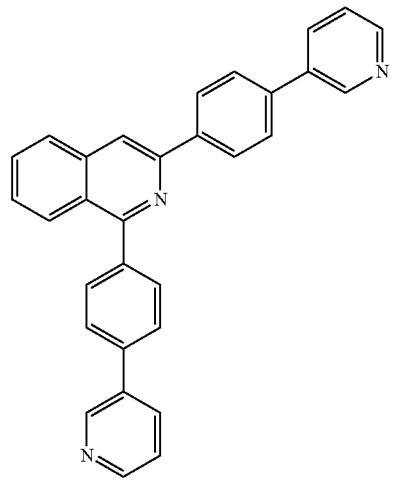
[Chemical Formula B-6]
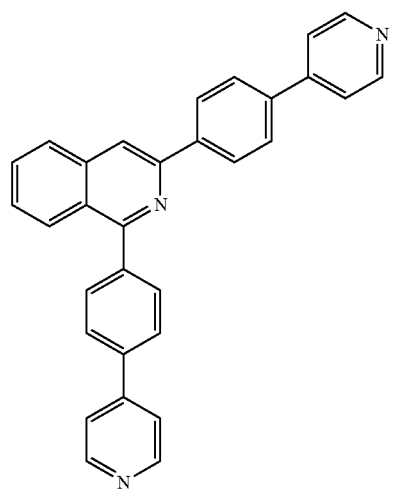
[Chemical Formula B-7]
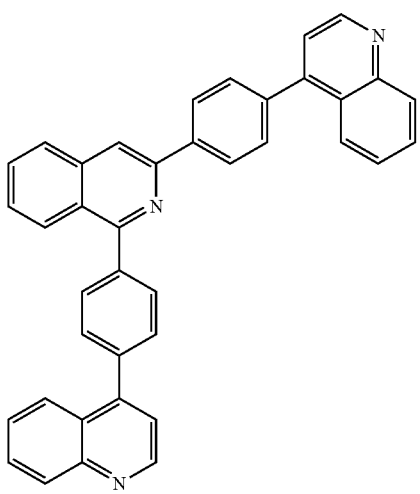

[Chemical Formula B-8]
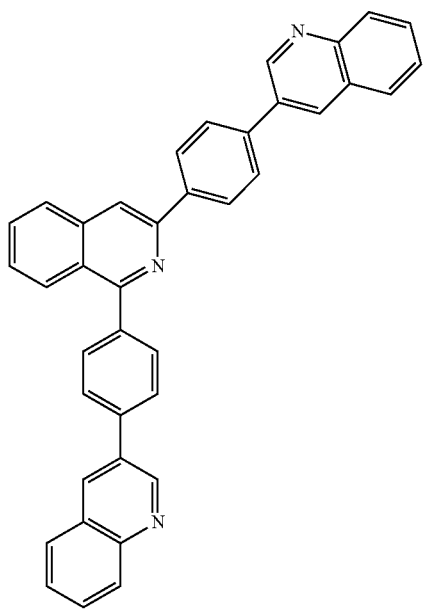
[Chemical Formula B-9]
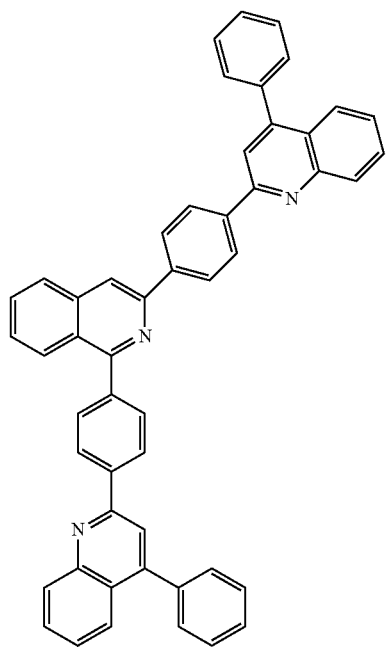
[Chemical Formula B-10]
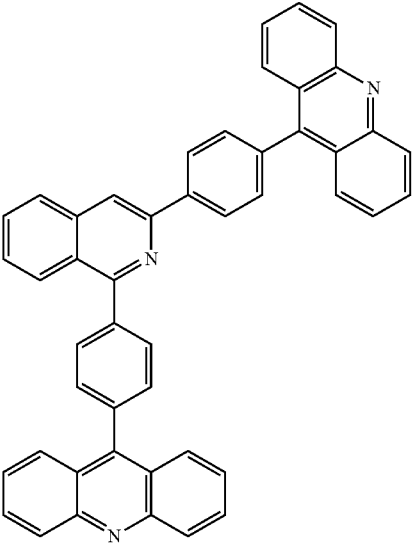
[Chemical Formula B-11]
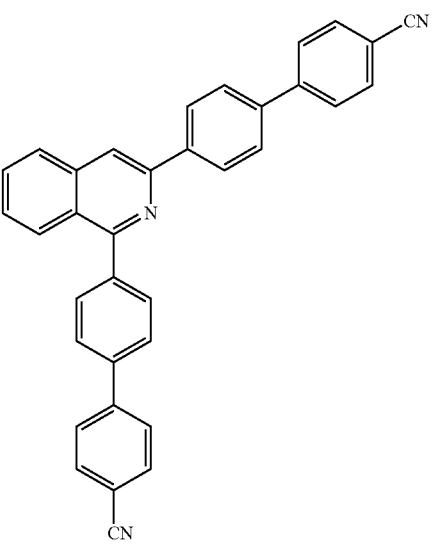
[Chemical Formula B-12]
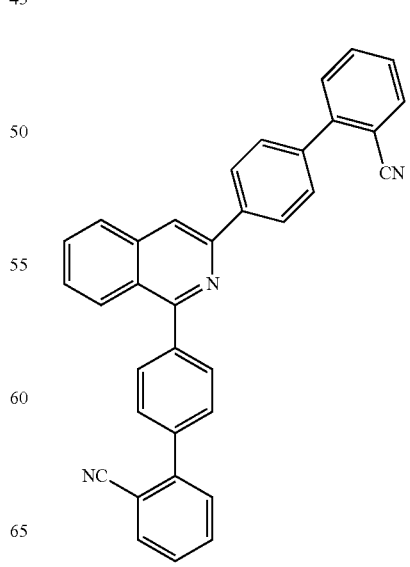

[Chemical Formula B-13]
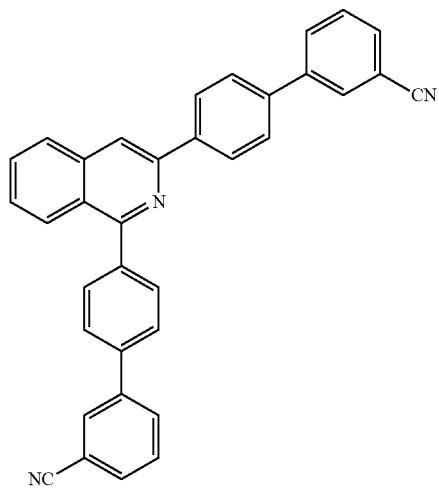
[Chemical Formula B-14]
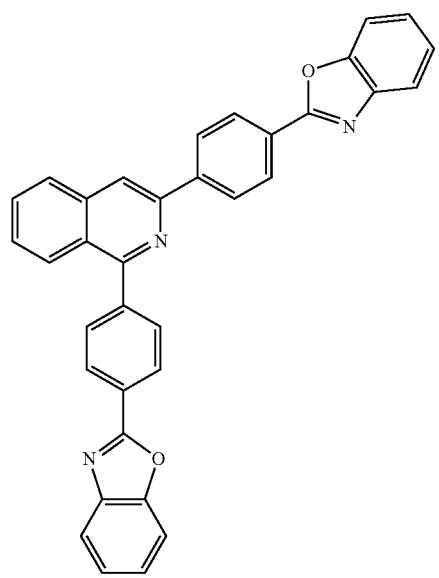
[Chemical Formula B-15]
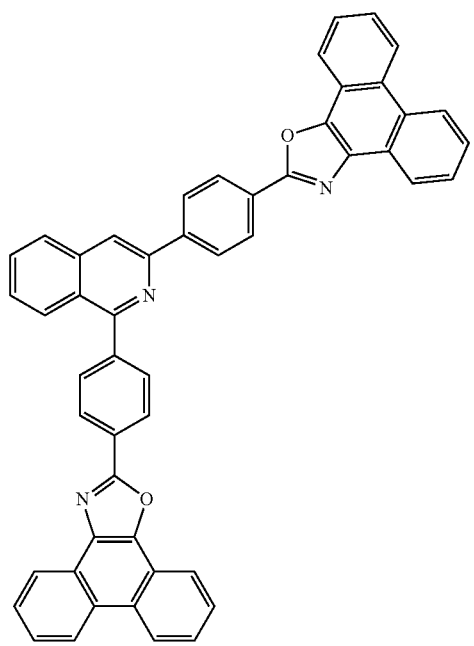
[Chemical Formula B-16]
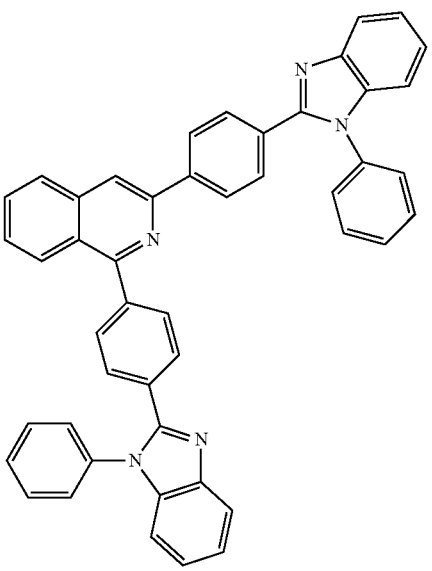

[Chemical Formula B-17]
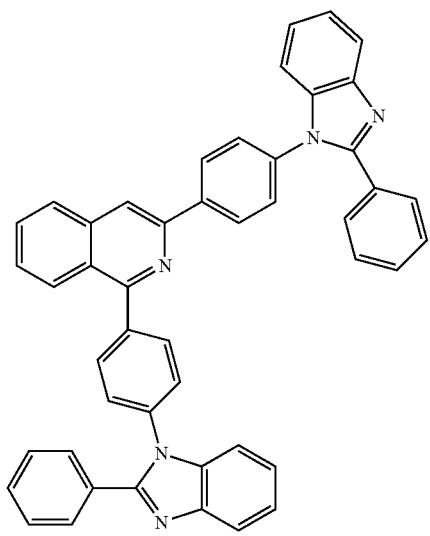
[Chemical Formula B-18]
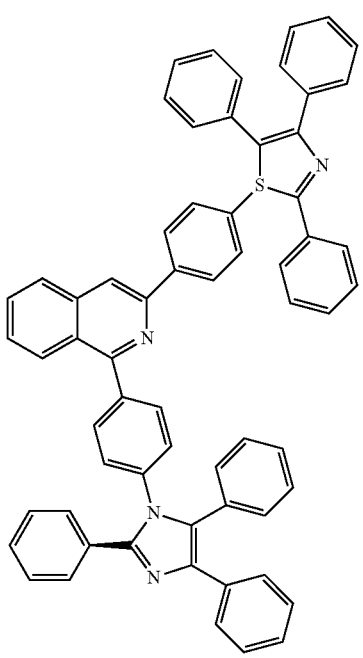
[Chemical Formula B-19]
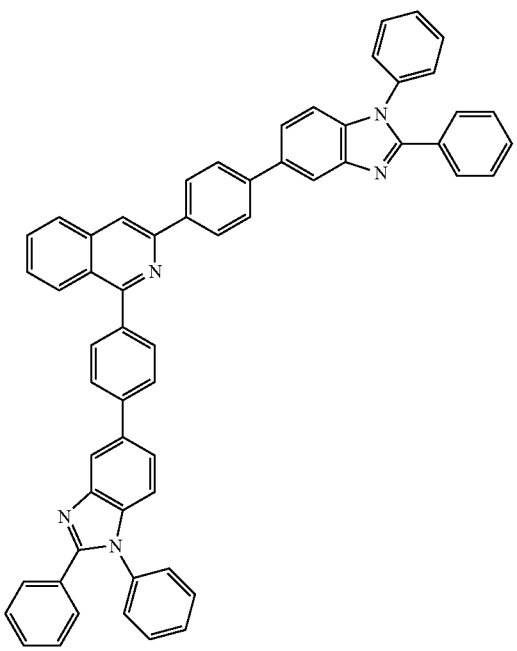
[Chemical Formula B-20]

[Chemical Formula B-21]
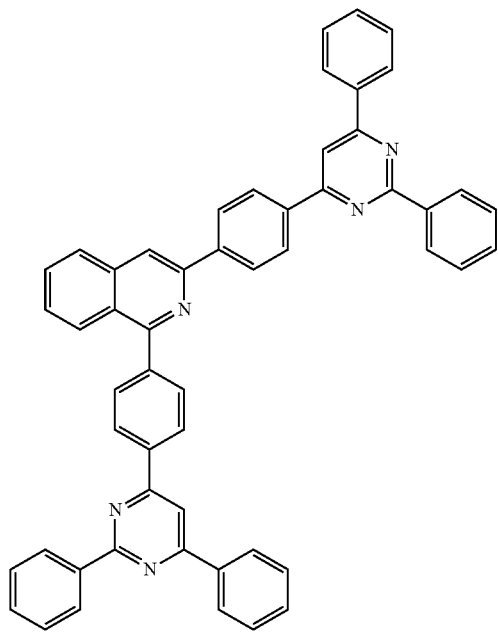
[Chemical Formula B-22]
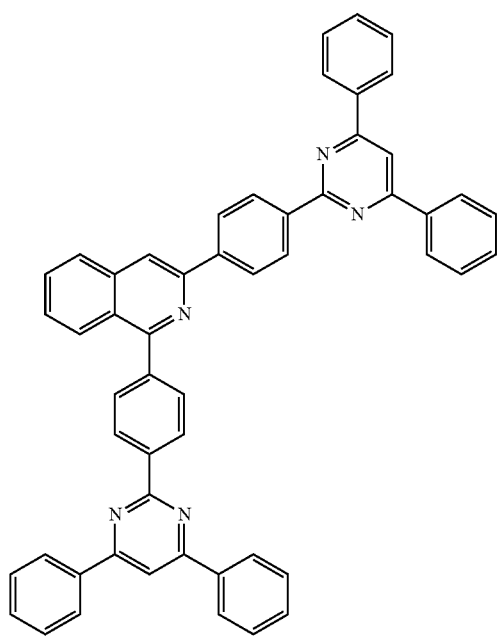
[Chemical Formula B-23]
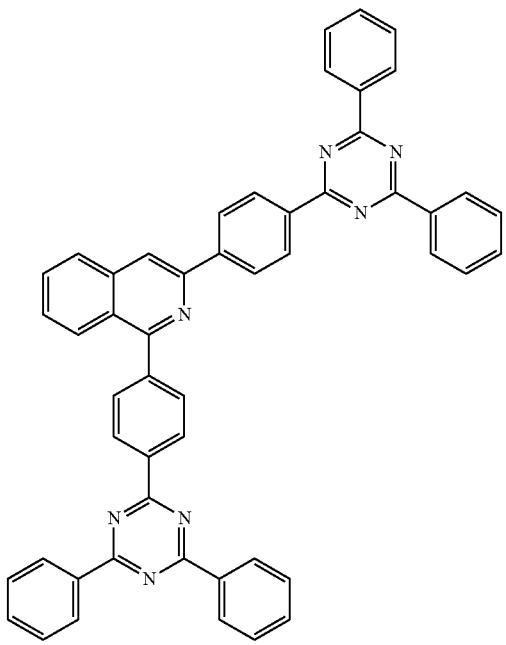
[Chemical Formula B-24]
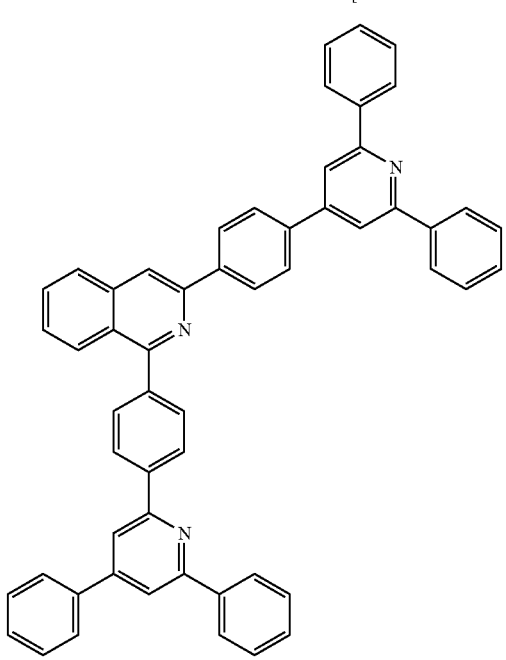

[Chemical Formula B-25]
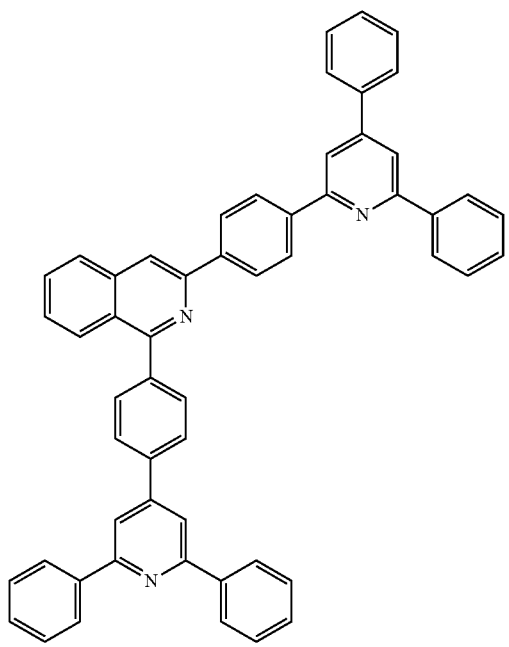
[Chemical Formula B-26]
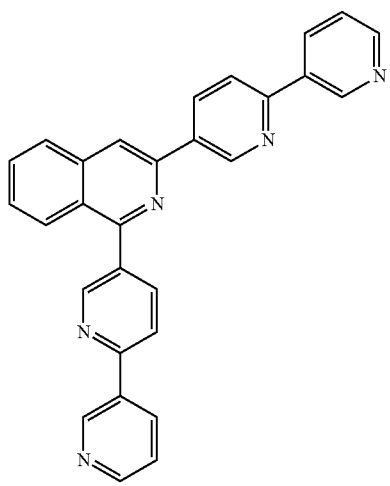
[Chemical Formula B-27]
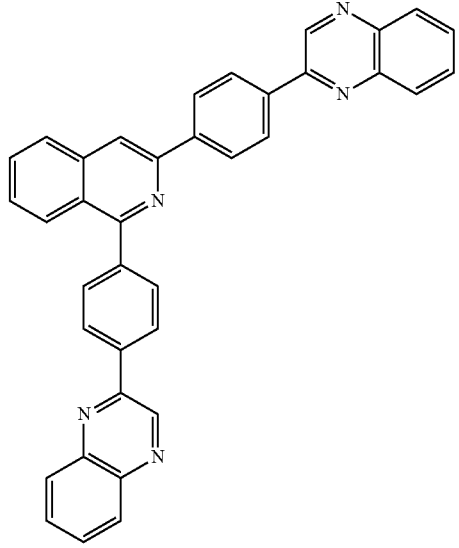
[Chemical Formula B-28]
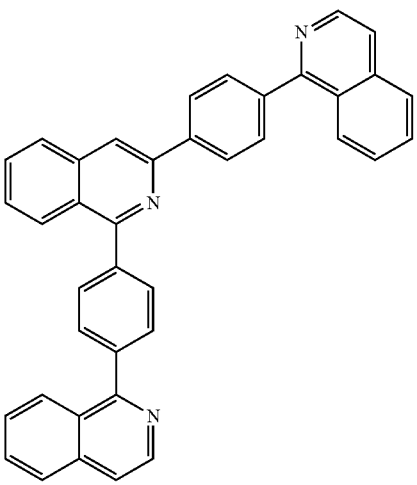
[Chemical Formula B-29]
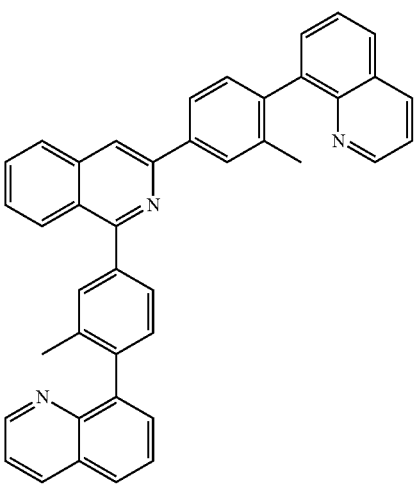

[Chemical Formula B-30]

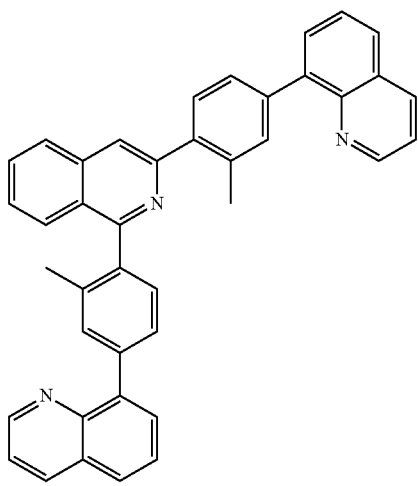

The compound for an organic optoelectronic device may have triplet exciton energy (T1) of greater than or equal to 2.0 eV.

The organic optoelectronic device may be selected from the group consisting of an organic photoelectric device, an organic light emitting diode, an organic solar cell, an organic transistor, an organic photo-conductor drum, and an organic memory device.

In another embodiment of the present invention, provided is an organic light emitting diode including an anode, a cathode, and at least one organic thin layer interposed between the anode and cathode, wherein at least one of the organic thin layers includes the above compound for an organic optoelectronic device.

The organic thin layer may be selected from the group consisting of an emission layer, a hole transport layer, a hole injection layer, an electron transport layer, an electron injection layer, a hole blocking layer, and a combination thereof.

The compound for an organic optoelectronic device may be included in a hole transport layer or a hole injection layer.

The compound for an organic optoelectronic device may be included in an emission layer.

The compound for an organic optoelectronic device may be used as a phosphorescent or fluorescent host material in an emission layer.

In yet another embodiment of the present invention, a display device including the above organic light emitting diode is provided.

A compound having high hole or electron transport properties, film stability, thermal stability, and high triplet exciton energy may be provided.

Such a compound may be used as a hole injection/transport material, host material, or electron injection/transport material of an emission layer. An organic optoelectronic device using the same has improved life-span characteristics and high luminous efficiency at a low driving voltage due to excellent electrochemical and thermal stability.

BRIEF DESCRIPTION OF THE DRAWINGS

Features will become apparent to those of ordinary skill in the art by describing in detail exemplary embodiments with reference to the attached drawings in which.

DETAILED DESCRIPTION

Figure 1:
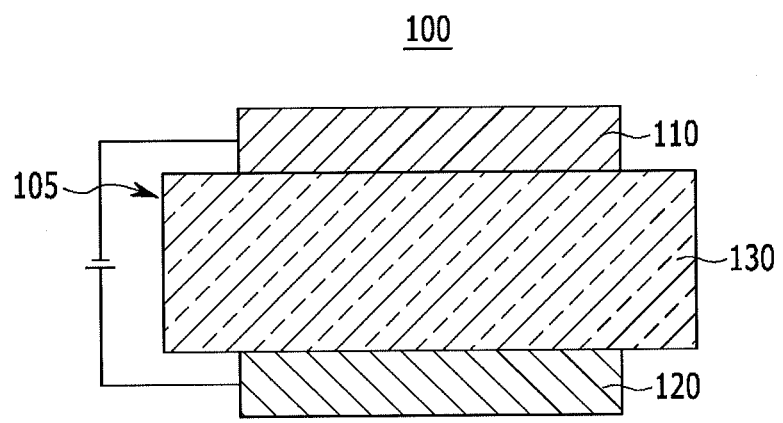
FIGS. 1 to 5 illustrate cross-sectional views showing organic light emitting diodes according to various embodiments of the present invention including the compound for an organic optoelectronic device according to one embodiment of the present invention.

Hereinafter, embodiments of the present invention are described in detail. However, these embodiments are exemplary, and tins disclosure is not limited thereto.

In the present specification, when a definition is not otherwise provided, "substituted" refers to one substituted with a substituent selected from the group consisting of deuterium, a halogen, hydroxy group, an amino group, a substituted or unsubstituted C1 to C30 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of at least one hydrogen of a substituent or a compound.

The two adjacent substituent selected from the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as trifluoromethyl group and the like, or cyano group may be fused to form a ring.

In the present specification, when specific definition is not otherwise provided, "hetero" refers to one including 1 to 3 hetero atoms selected from the group consisting of N, O, S, and P, and remaining carbons in one functional group.

In the present specification, when a definition is not otherwise provided, "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be "a saturated alkyl group" without any double bond or triple bond.

The "alkenylene group" refers to a functional group of at least one carbon-carbon double bond of at least two carbons, and the "alkynylene group" refers to a functional group of at least one carbon-carbon triple bond of at least two carbons. The alkyl group may be branched, linear or cyclic regardless of being saturated or unsaturated.

The alkyl group may be a C1 to C20 alkyl group. More specifically, the alkyl group may be a C1 to C10 alkyl group or a C1 to C6 alkyl group.

For example, a C1 to C4 alkyl group may have 1 to 4 carbon atoms in an alkyl chain which may be selected from the group consisting of methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, and the like.

"Aromatic group" refers to a cyclic functional group where all elements have p-orbitals, and these p-orbitals forms conjugation. Specific examples are aryl group and a heteroaryl group.

"Aryl groups" includes monocyclic or fused ring polycyclic (i.e., rings sharing adjacent pairs of carbon atoms) groups.

"Heteroaryl group" refers to aryl group including 1 to 3 hetero atoms selected from the group consisting of N, O, S, and P, and remaining carbons. When the heteroaryl group is a fused ring, each ring may include 1 to 3 hetero atoms.

In the present specification, the carbazole-based derivative may refer to a substituted structure where a nitrogen atom of a substituted or unsubstituted carbazolyl group is substituted with a hetero atom except nitrogen, or carbon. Specific examples may be dibenzofuran (dibenzofuranyl group), dibenzothiophene (dibenzothienyl group), fluorene (fluorenyl group), and the like.

In the present specification, hole characteristics refer to characteristics that holes formed in the anode is easily injected into the emission layer and transported in the emission layer due to conductive characteristics according to HOMO level.

Electron characteristics refer to characteristics that electron formed in the cathode is easily injected into the emission layer and transported in the emission layer due to conductive characteristics according to LUMO level.

The compound for an organic optoelectronic device according to one embodiment of the present invention has a structure that a naphthalene-derived core including at least one nitrogen has necessarily two substituents having electron characteristics.

In addition, the compound for an organic optoelectronic device according to one embodiment of the present invention may include one or two substituents having hole characteristics.

In the compound for an organic optoelectronic device, the substituent having electron characteristics is bonded in a direction that the nitrogen is included in the core including at least one nitrogen.

In addition, the substituent having hole characteristics may be included in opposition to the substituent having electron characteristics.

Accordingly, the compound for an organic optoelectronic device may selectively have bipolar characteristics.

When the substituent having hole characteristics is not included, the compound may have an appropriate HOMO/LUMO level used for an electron transport layer (ETL) or an electron injection layer (EIL) for an organic optoelectronic device.

In other words, the compound for an organic optoelectronic device may selectively include an appropriate substituent having hole characteristics if necessary.

In addition, the core structure may be bonded with various substituents to adjust the entire electron and hole characteristics of a compound.

Accordingly, the core structure may be used as a light emitting material, an electron injection material or an electron transport material for an organic optoelectronic device. In particular, the core structure may be appropriately used as an electron injection material and/or electron transport material.

The compound for an organic optoelectronic device includes a core moiety and various substituents for a substituent for substituting the core moiety and thus may have various energy bandgaps.

When the compound having an appropriate energy level depending on a substituent is used to manufacture an organic optoelectronic device, the compound reinforces hole transport capability or electron transport capability and thus, brings about excellent effects in terms of efficiency and a driving voltage, and also, has excellent electrochemical and thermal stability and thus, may improve life-span characteristics of the organic optoelectronic device.

According to one embodiment of the present invention, a compound for an organic optoelectronic device represented by the following Chemical Formula 1 is provided.

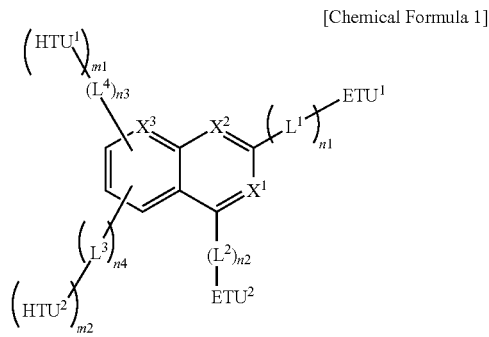

[Chemical Formula 1]

In the above Chemical Formula 1, at least one of $X^1$ to $X^3$ is N, X3 is N or —CR'—, wherein the R' is hydrogen, a substituted or unsubstituted C1 to C10 alkyl group or is linked to $L^4$, $L^1$ to $L^4$ are independently a single bond, a substituted or unsubstituted C6 to C30 arylene group or a substituted or unsubstituted C2 to C30 heteroarylene group, n1 to n4 are independently integers of 0 to 3, $ETU^1$ and $ETU^2$ are independently a substituted or unsubstituted C2 to C30 heteroaryl group having electron characteristics, $HTU^1$ and $HTU^2$ are independently a substituted or unsubstituted C6 to C30 aryl group having hole characteristics, and m1 and m2 are 0 or 1.

More specifically, the compound for an organic optoelectronic device may be represented by the following Chemical Formula 2.

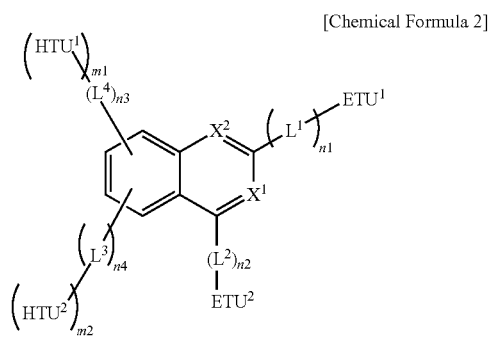

[Chemical Formula 2]

In the above Chemical Formula 2, at least one of $X^1$ and $X^2$ is N, $L^1$ to $L^4$ are independently a single bond, a substituted or unsubstituted C6 to C30 arylene group or a substituted or unsubstituted C2 to C30 heteroarylene group, n1 to b4 are independently integers of 0 to 3, $ETU^1$ and $ETU^2$ are independently a substituted or unsubstituted C2 to C30 heteroaryl group having electron characteristics, $HTU^1$ and $HTU^2$ are independently a substituted or unsubstituted C6 to C30 aryl group having hole characteristics, and m1 and m2 are 0 or 1.

More specifically, the compound for an organic optoelectronic device may be represented by the following Chemical Formula 3.

[Chemical Formula 3]

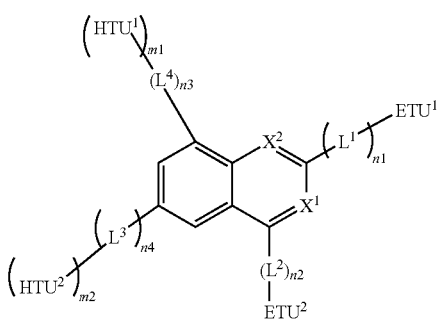

In the above Chemical Formula 3, at least one of $X^1$ and $X^2$ is N, $L^1$ to $L^4$ are independently a single bond, a substituted or unsubstituted C6 to C30 arylene group or a substituted or unsubstituted C2 to C30 heteroarylene group, n1 to n4 are independently integers of 0 to 3, $ETU^1$ and $ETU^2$ are independently a substituted or unsubstituted C2 to C30 heteroaryl group having electron characteristics, $HTU^1$ and $HTU^1$ are independently a substituted or unsubstituted C6 to C30 aryl group having hole characteristics, and m1 and m2 are 0 or 1.

The $X^2$ may be —CH—, and $X^1$ may be N. The $X^1$ may be —CH—, and $X^2$ may be N. In this way, when the core structure has a quinoline shape, thermal stability and charge mobility may be improved compared with a pyridine core structure.

The $X^1$ and $X^2$ may be N. In this way, when the core structure has a quinazoline shape, thermal stability and charge mobility may be improved compared with a pyrimidine or triazine core structure.

The n3 and m1 may be 0. Or, the m1 and m2 may not be 0.

In this way, one or two substituents having hole characteristics may be selectively included.

The $L^1$ to $L^4$ may be independently a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted pyrenylene group, a substituted or unsubstituted fluroenylene group, a substituted or unsubstituted fluoranthenyl group, a substituted or unsubstituted triphenylene group, a substituted or unsubstituted pyridinyl group, a substituted or unsubstituted pyrimidinyl group, a substituted or unsubstituted triazinyl group, and the like.

The substituted or unsubstituted C2 to C30 heteroaryl group having electron characteristics may be a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted banzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof, but is not limited thereto.

More specifically the substituted or unsubstituted C2 to C30 heteroaryl group having electron characteristics may be selected from the following Chemical Formulae S-1 to S-5.

[Chemical Formula S-1]

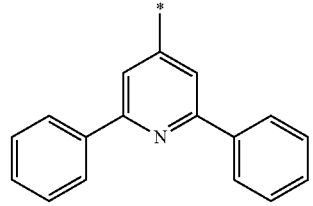

[Chemical Formula S-2]

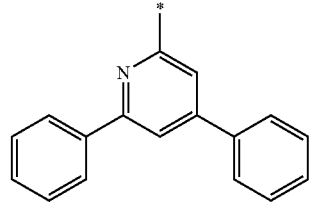

[Chemical Formula S-3]

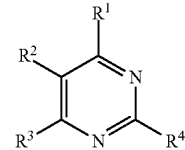

[Chemical Formula S-4]

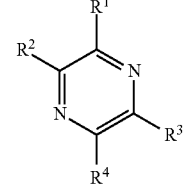

[Chemical Formula S-5]

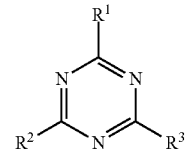

In the S-1 and S-2, * indicates a bonding position. In the above Chemical Formulae S-3 to S-5, $R^1$ to $R^4$ independently indicates hydrogen, deuterium, a C1 to C30 alkyl group, a C6 to C30 aryl group, or a combination thereof, in the above Chemical Formulae S-3 and S-4, one of $R^1$ to $R^4$ indicates a bonding position, and in the above Chemical Formula S-5, one of $R^1$ to $R^3$ indicates a bonding position.

The substituted or unsubstituted C6 to C30 aryl group having hole characteristics may be a substituted or unsubstituted phenyl group, a substituted or unsubstituted naphthyl group, a substituted or unsubstituted phenanthrenyl group, a substituted or unsubstituted anthracenyl group, a substituted or unsubstituted fluorenyl group, a substituted or unsubstituted triphenylenyl group, a substituted or unsubstituted spiro-fluoreuyl group, a substituted or unsubstituted terphenyl group, a substituted or unsubstituted pyrenyl group, a substituted or unsubstituted perylenyl group, or a combination thereof, but is not limited thereto.

More specifically, the compound for an organic optoelectronic device may be represented by the following Chemical Formulae A-1 to A-393, but is not limited thereto.

[Chemical Formula A-1]
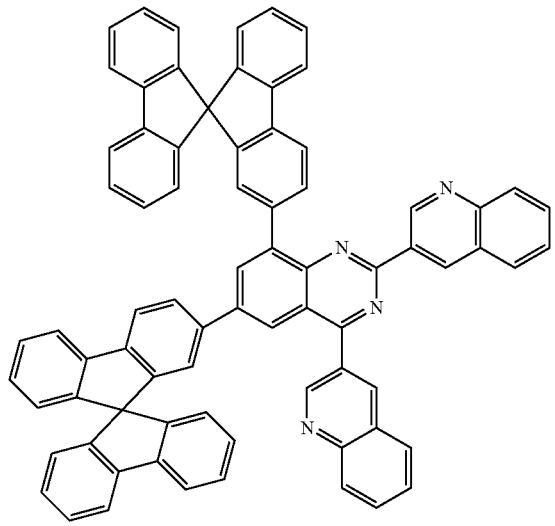
[Chemical Formula A-2]
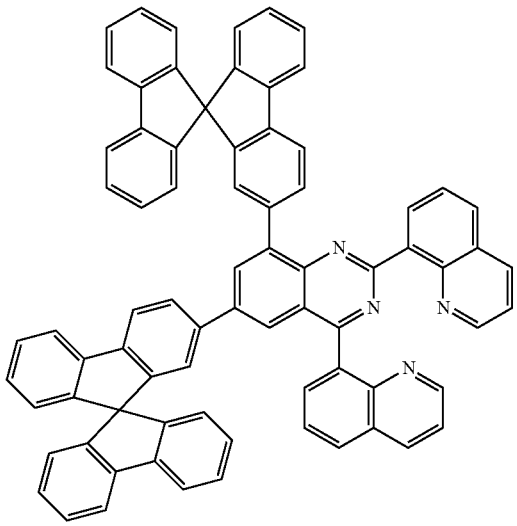
[Chemical Formula A-3]
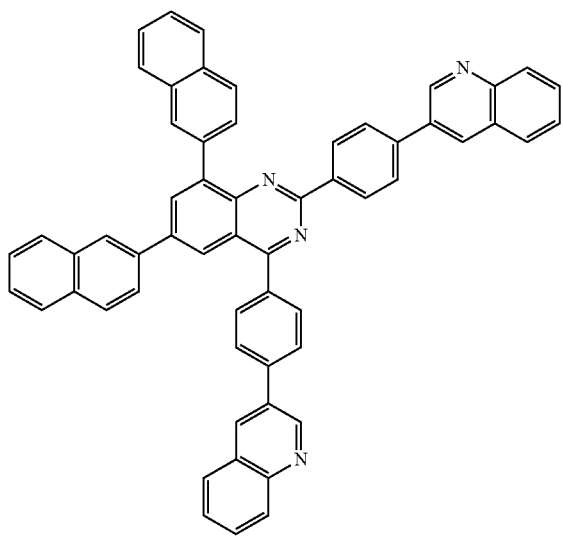 [SMILES: c1ccc2cc(-c3cc(-c4ccc5ccccc5c4)c4nc(-c5ccc(-c6cnc7ccccc7c6)cc5)nc(-c5ccc(-c6cnc7ccccc7c6)cc5)c4c3)ccc2c1]
[Chemical Formula A-4]
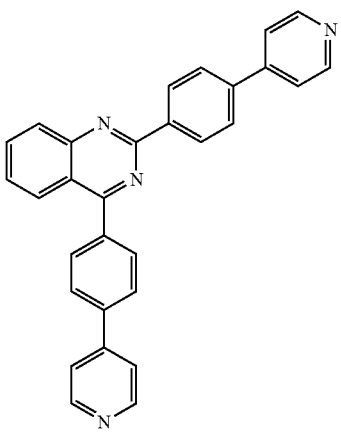
[Chemical Formula A-5]
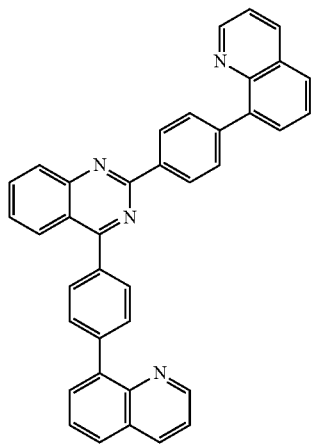
[Chemical Formula A-6]
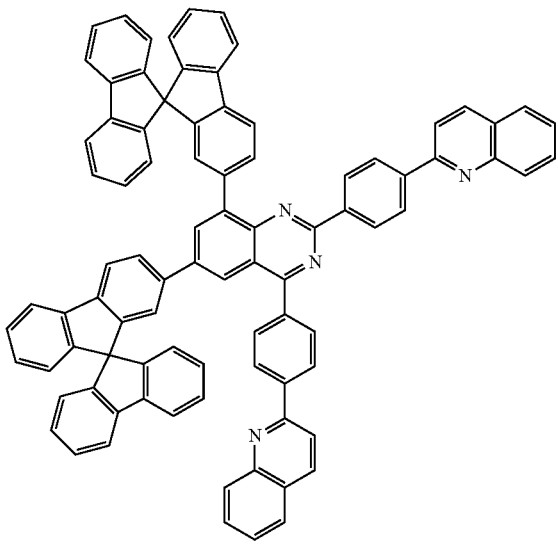

-continued
[Chemical Formula A-7]
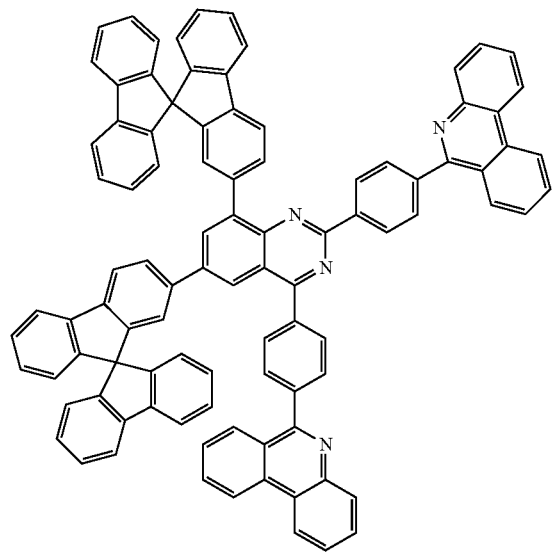
[Chemical Formula A-8]
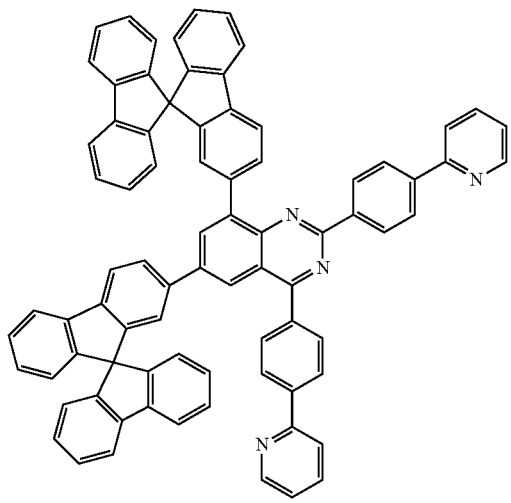
[Chemical Formula A-9]
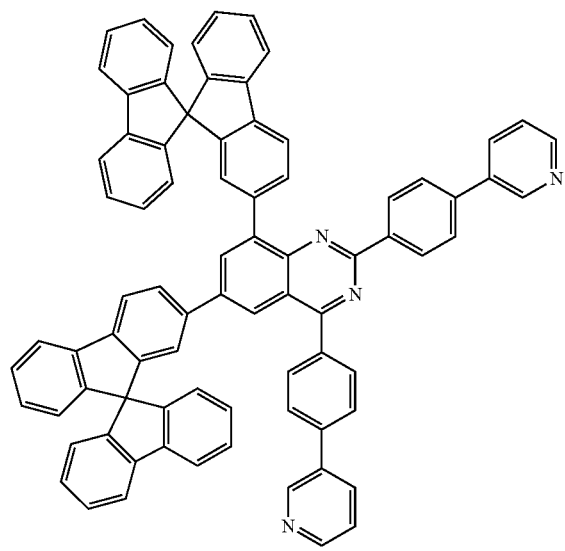
[Chemical Formula A-10]
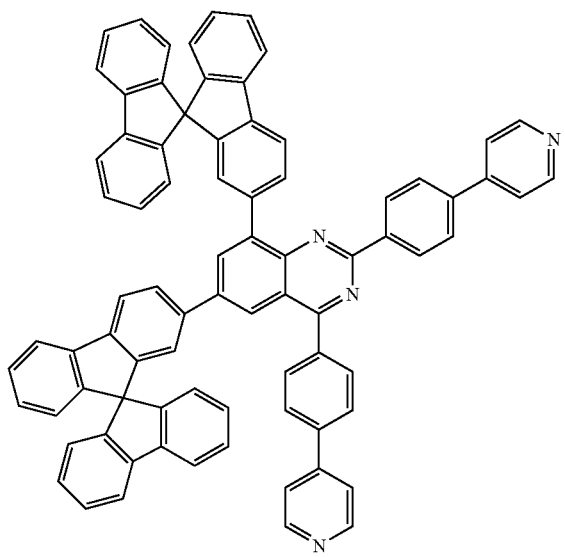

[Chemical Formula A-11]
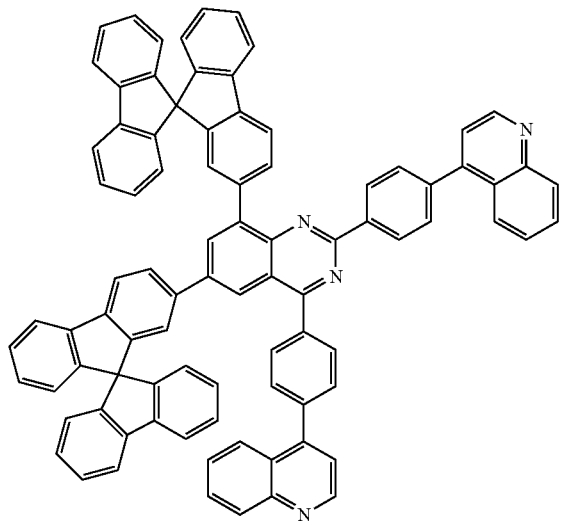
[Chemical Formula A-12]
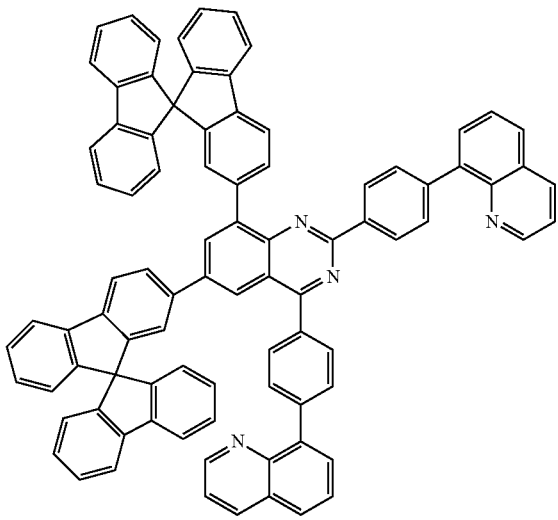
[Chemical Formula A-13]
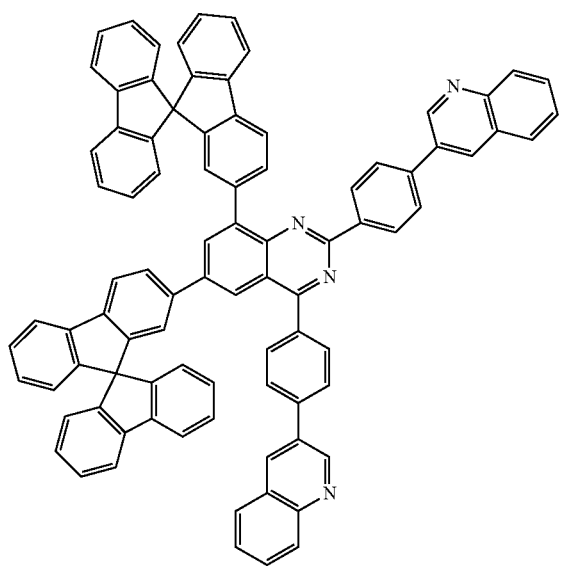
[Chemical Formula A-14]
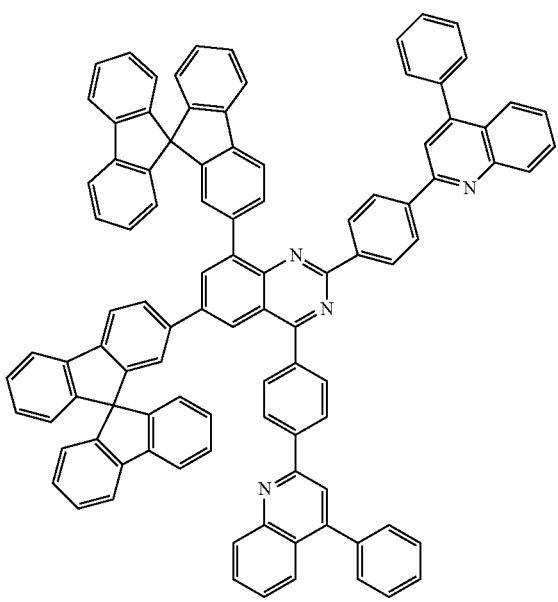

-continued
[Chemical Formula A-15]
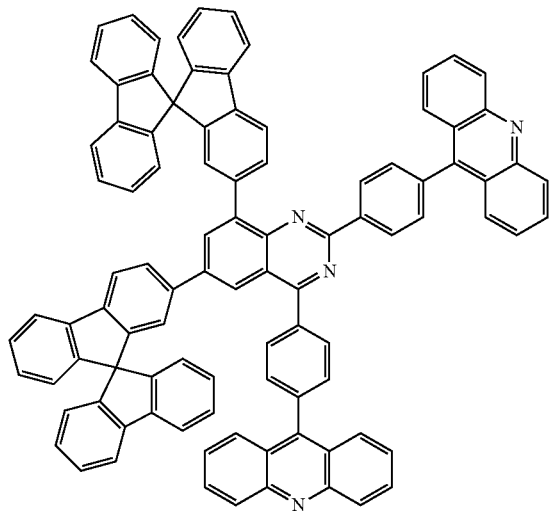
[Chemical Formula A-16]
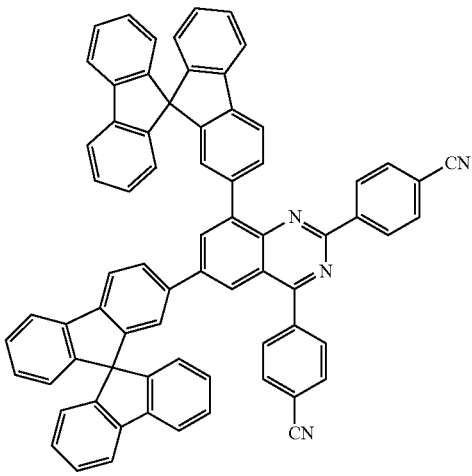
[Chemical Formula A-17]
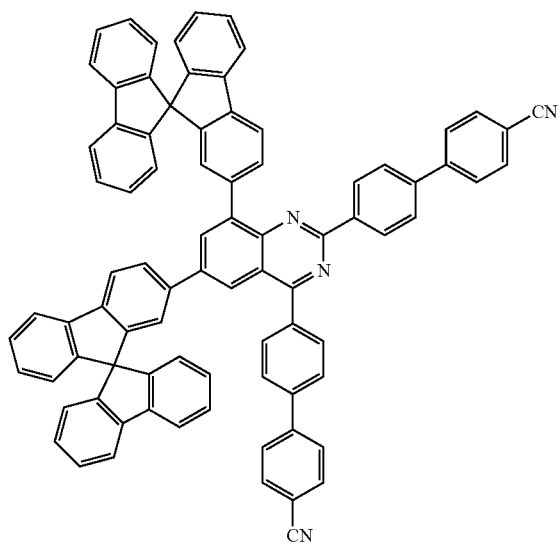
[Chemical Formula A-18]
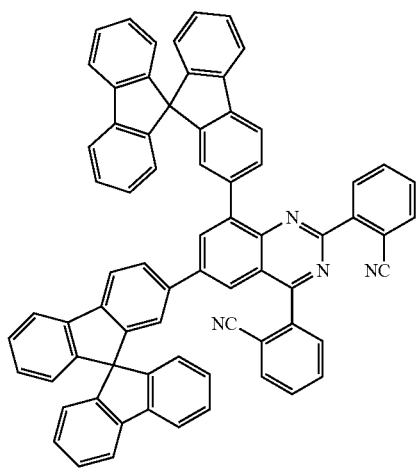
[Chemical Formula A-19]
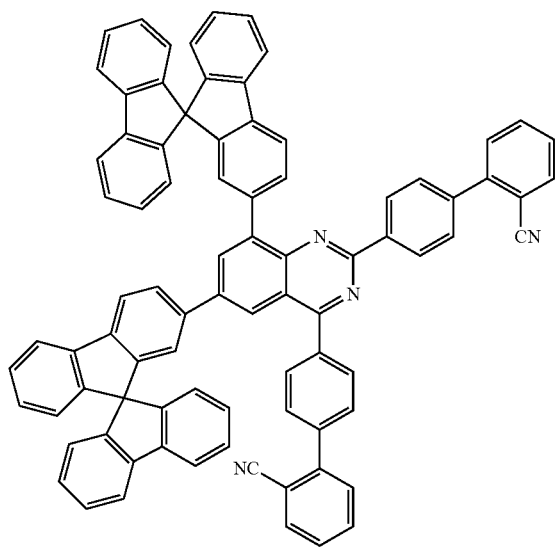
[Chemical Formula A-20]
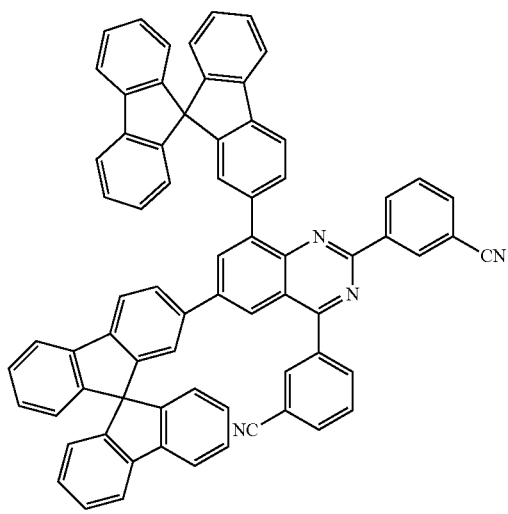

-continued
[Chemical Formula A-21]
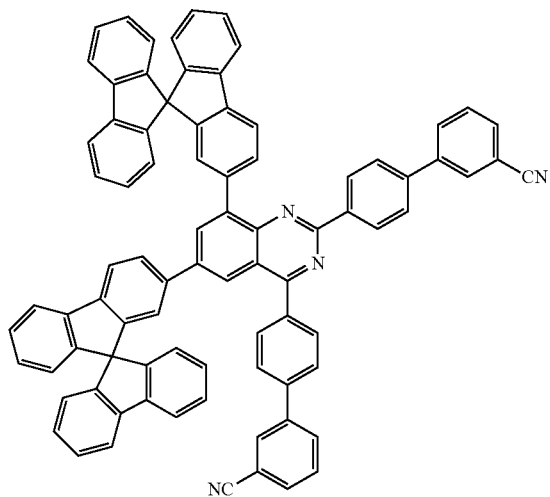
[Chemical Formula A-22]
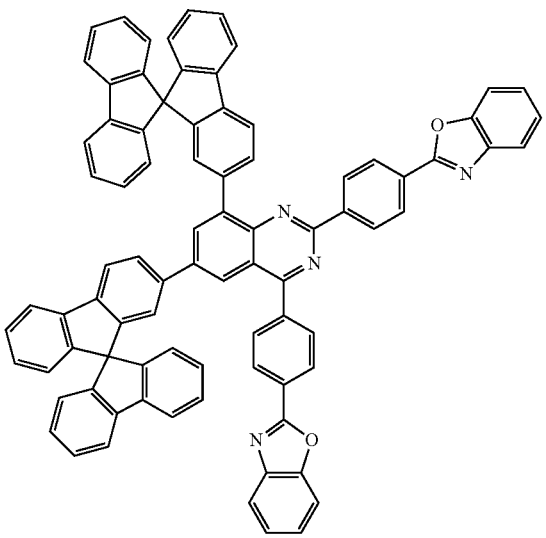
[Chemical Formula A-23]
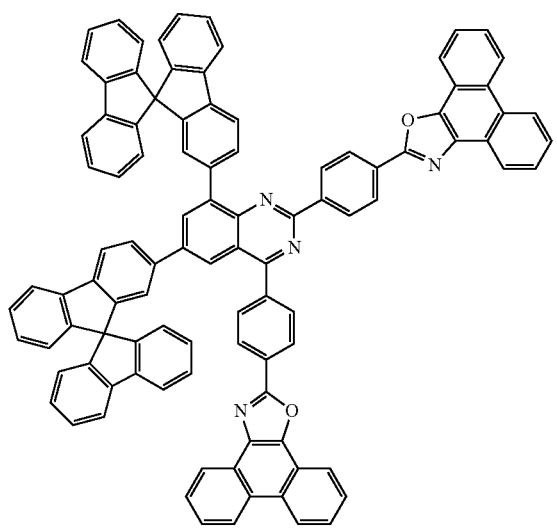
[Chemical Formula A-24]
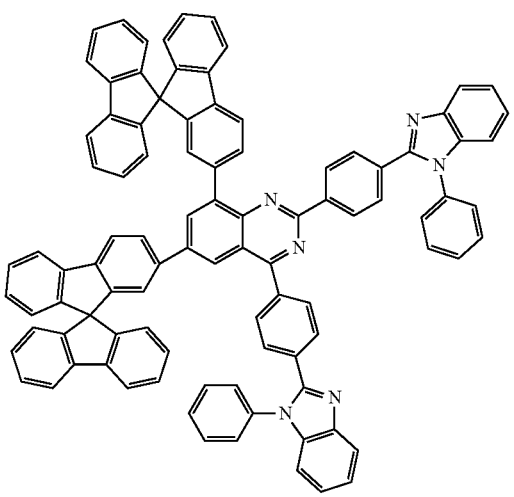
[Chemical Formula A-25]
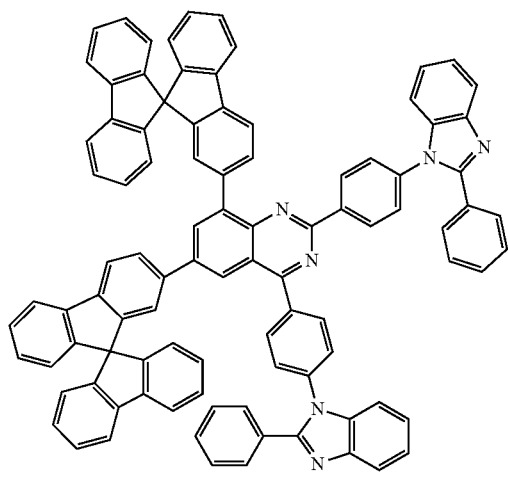
[Chemical Formula A-26]
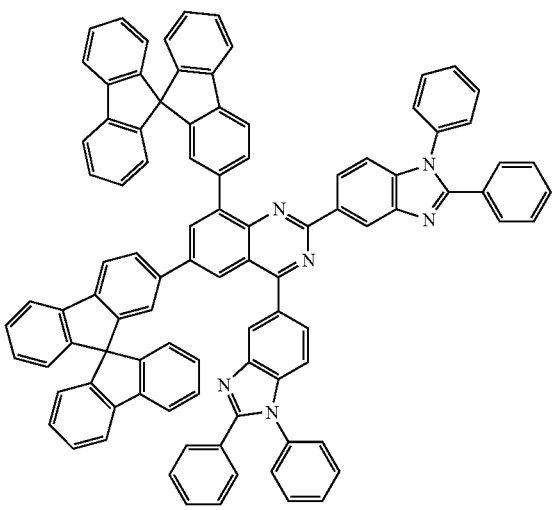

[Chemical Formula A-27]
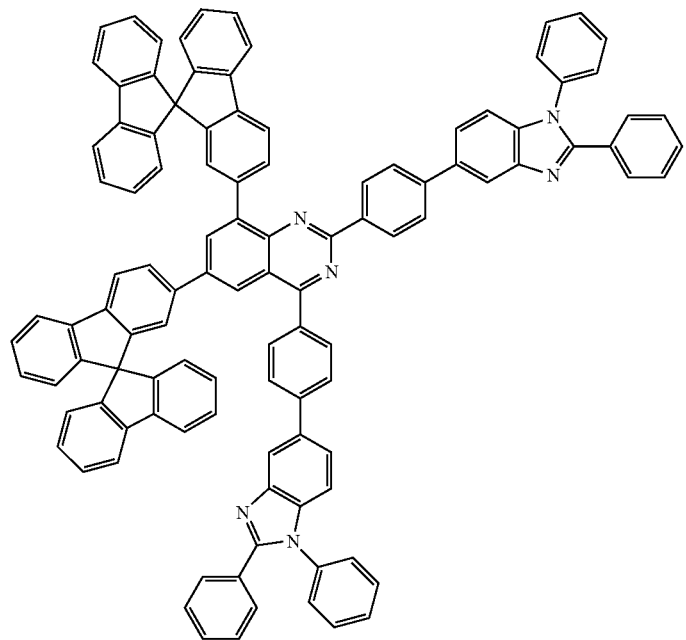
[Chemical Formula A-28]
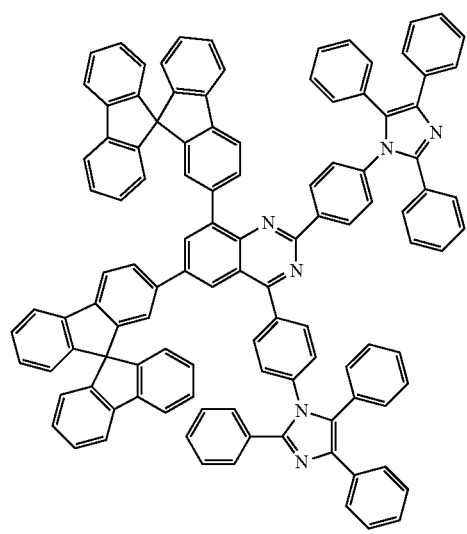
[Chemical Formula A-29]
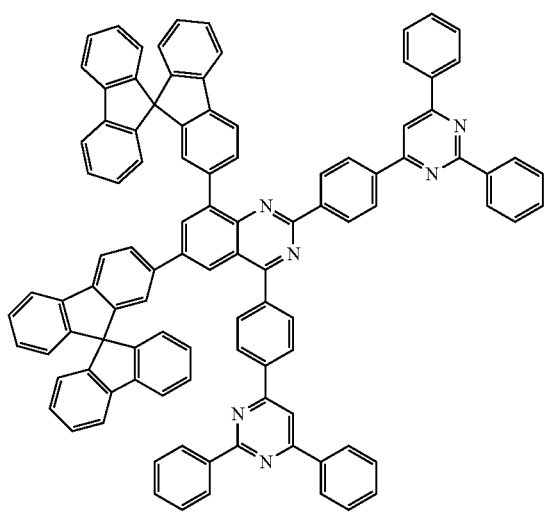

[Chemical Formula A-30]
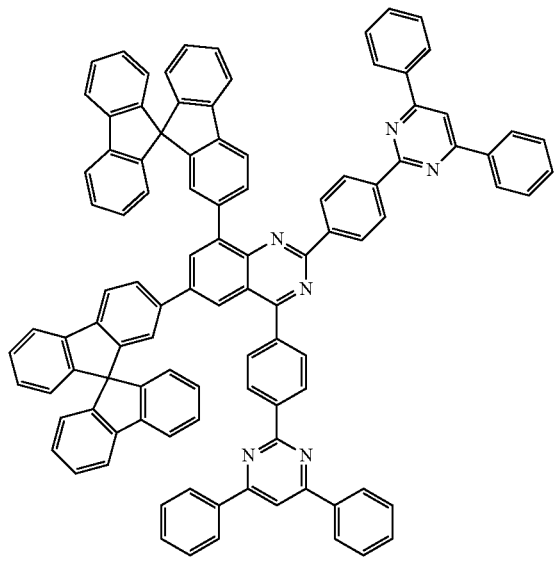
[Chemical Formula A-31]
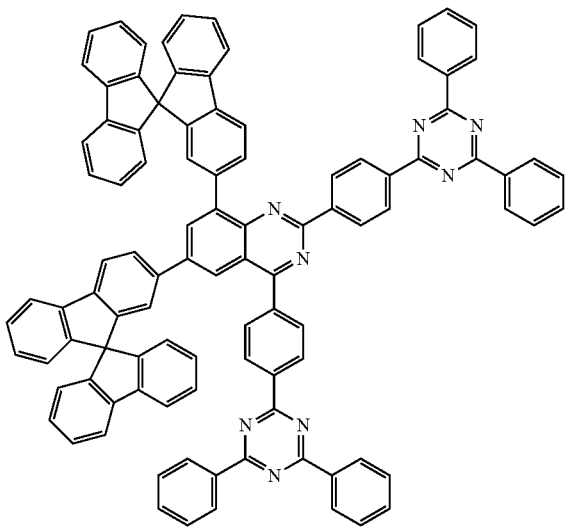
[Chemical Formula A-32]
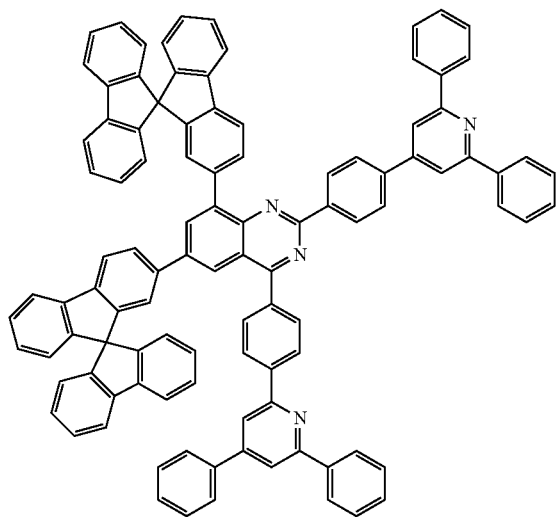
[Chemical Formula A-33]
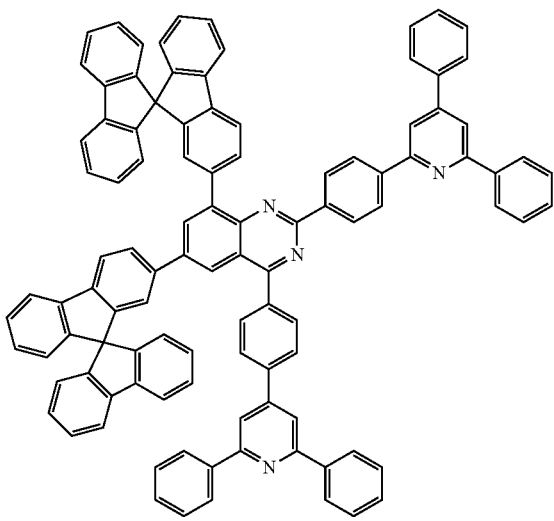

-continued
[Chemical Formula A-34]
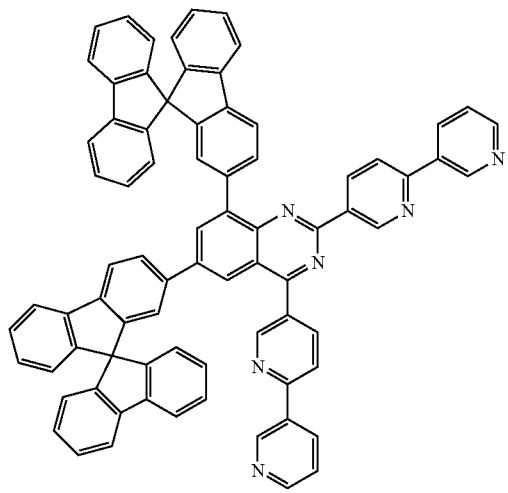
[Chemical Formula A-35]
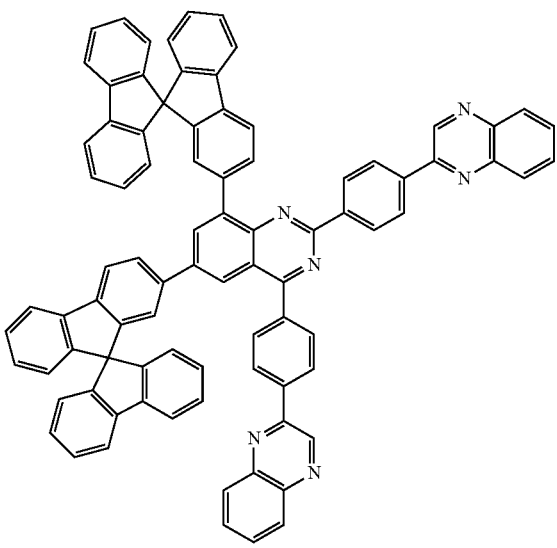
[Chemical Formula A-36]
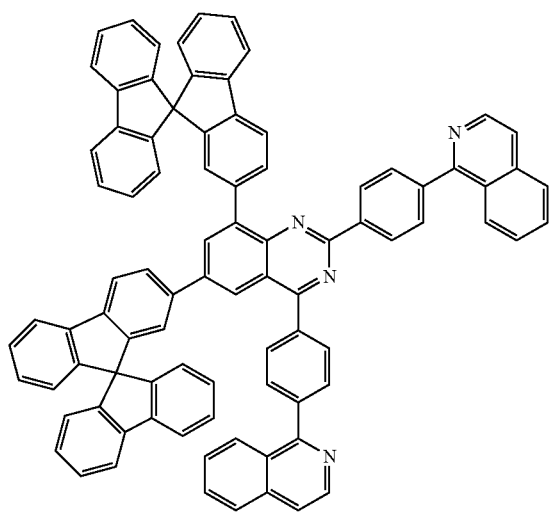
[Chemical Formula A-37]
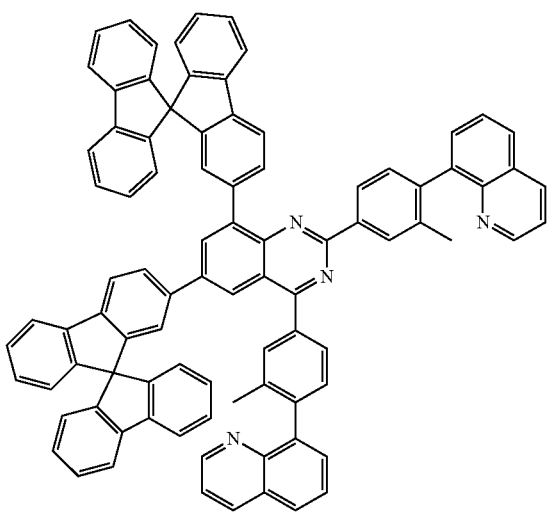
[Chemical Formula A-38]
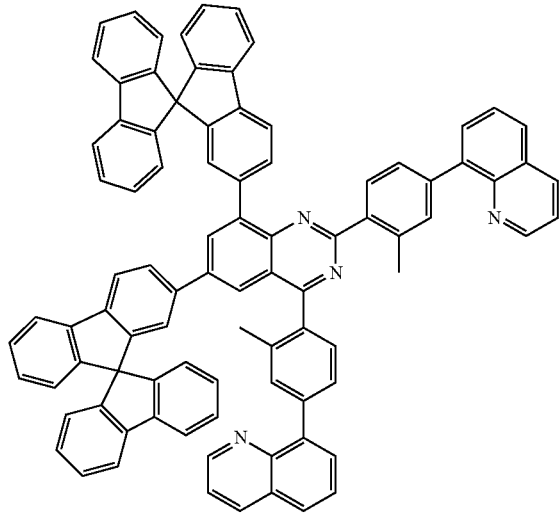
[Chemical Formula A-39]
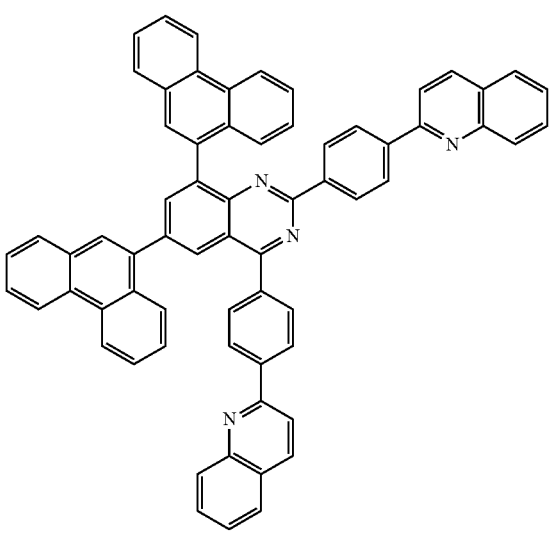

[Chemical Formula A-40]
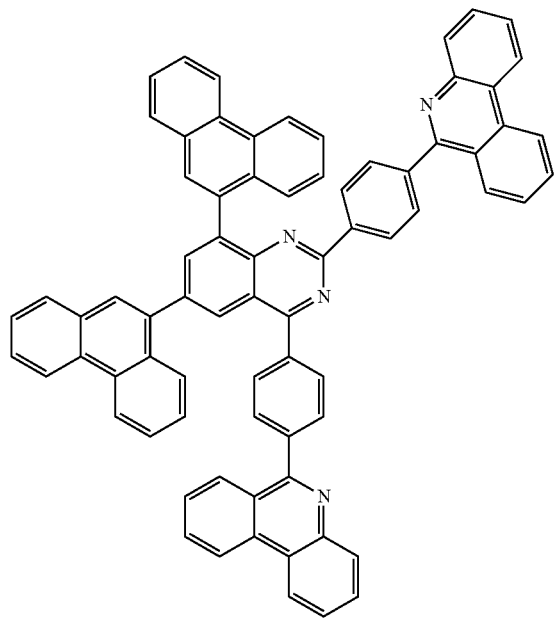
[Chemical Formula A-41]
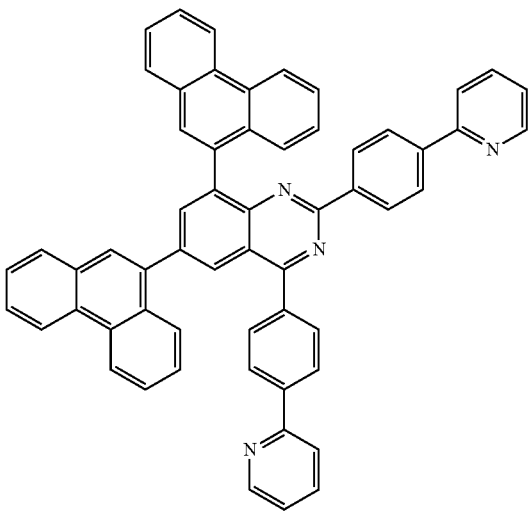
[Chemical Formula A-42]
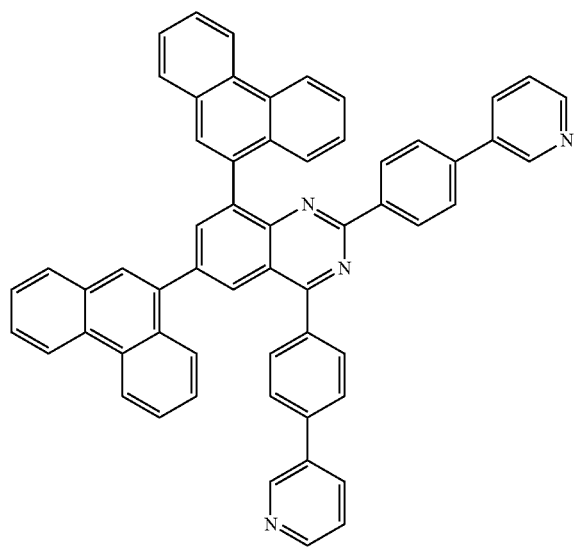
[Chemical Formula A-43]
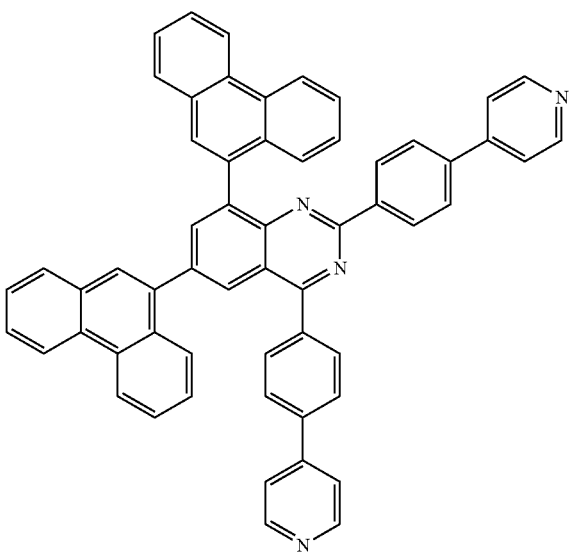

[Chemical Formula A-44]
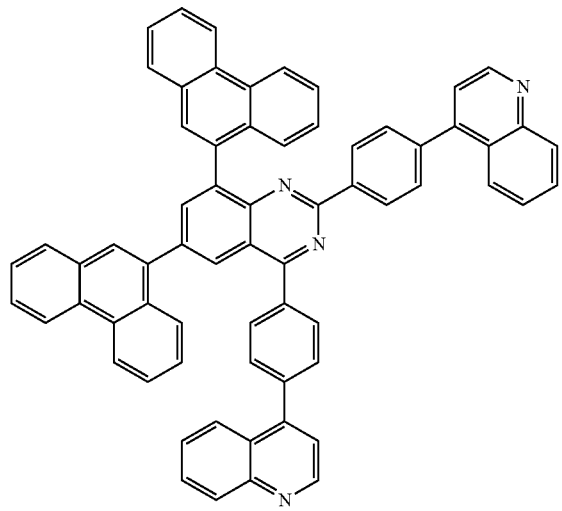
[Chemical Formula A-45]
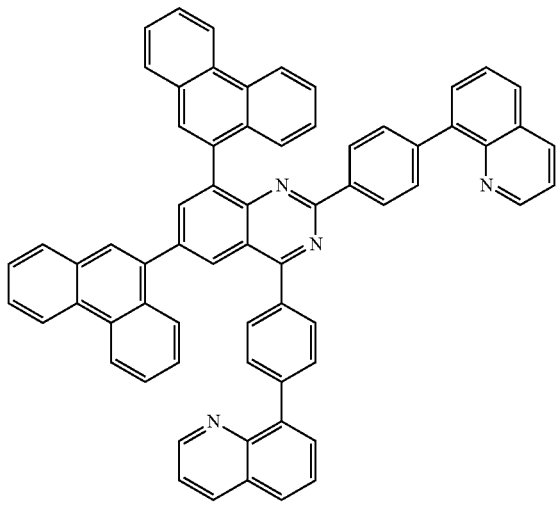
[Chemical Formula A-46]
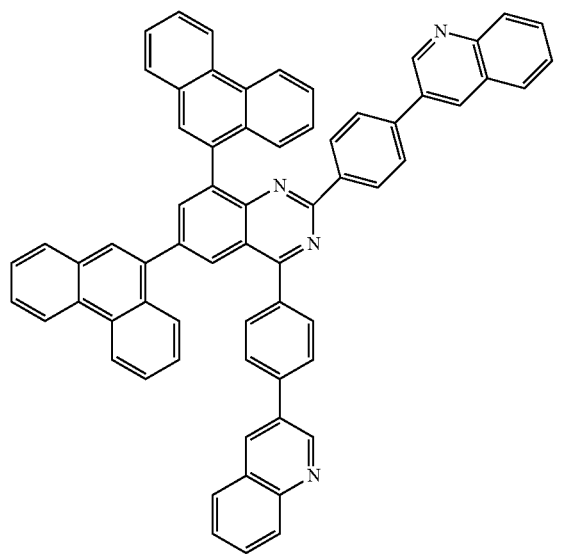
[Chemical Formula A-47]
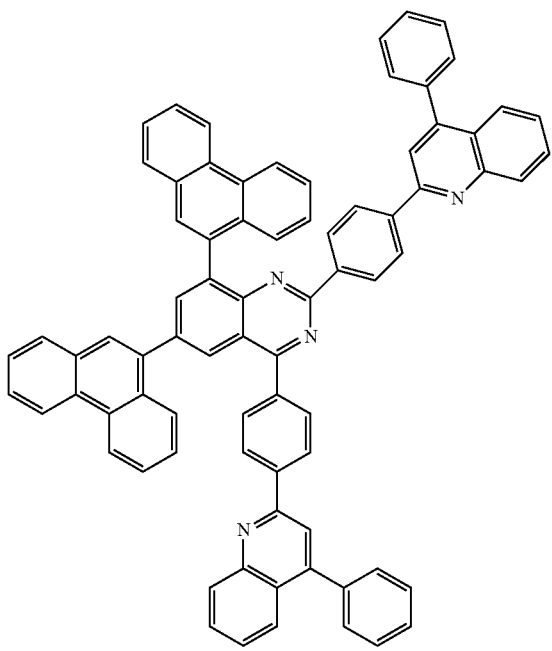

-continued
[Chemical Formula A-48]
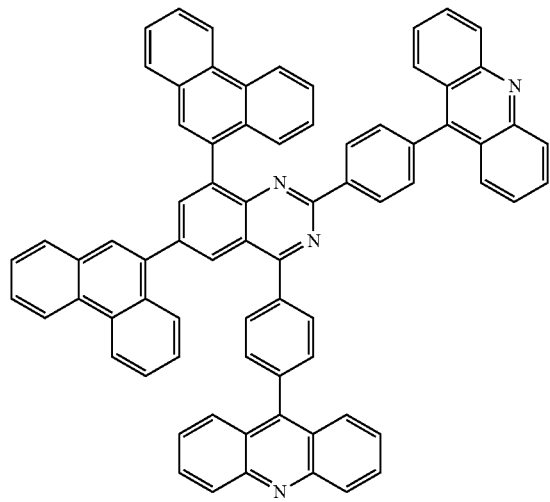
[Chemical Formula A-49]
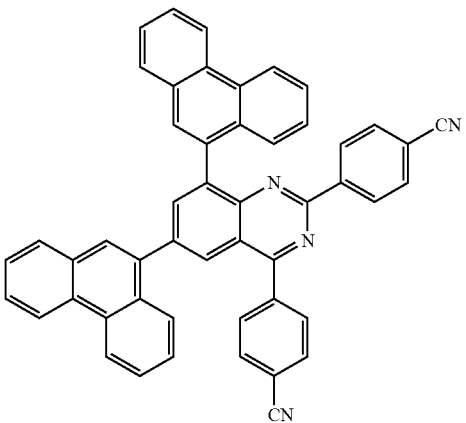
[Chemical Formula A-50]
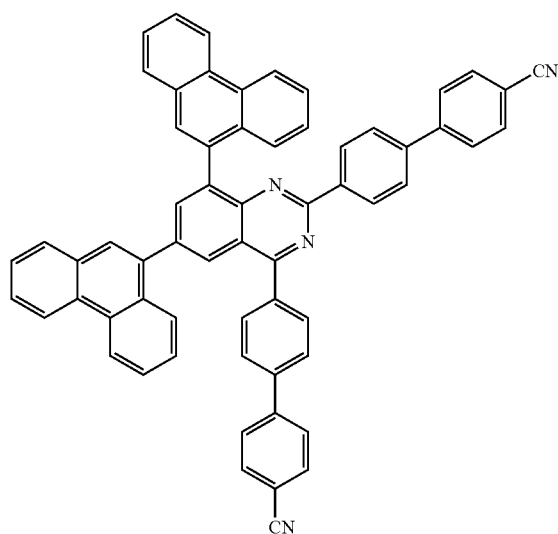
[Chemical Formula A-51]
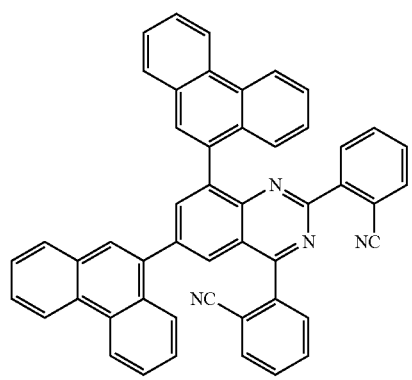
[Chemical Formula A-52]
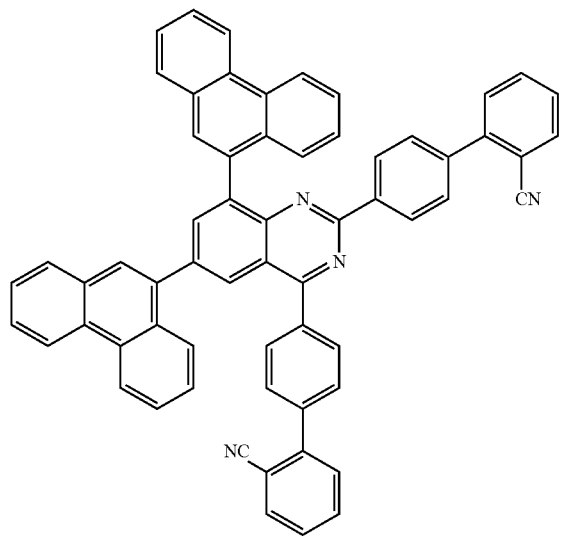
[Chemical Formula A-53]
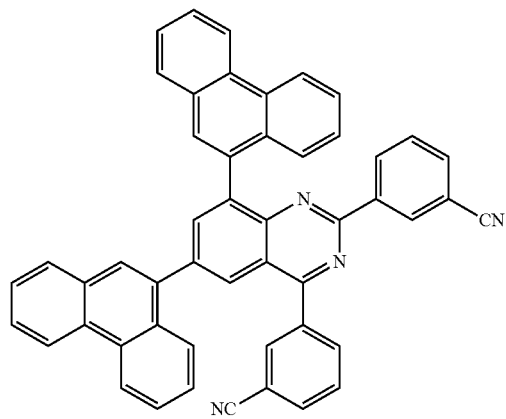

-continued
[Chemical Formula A-54]
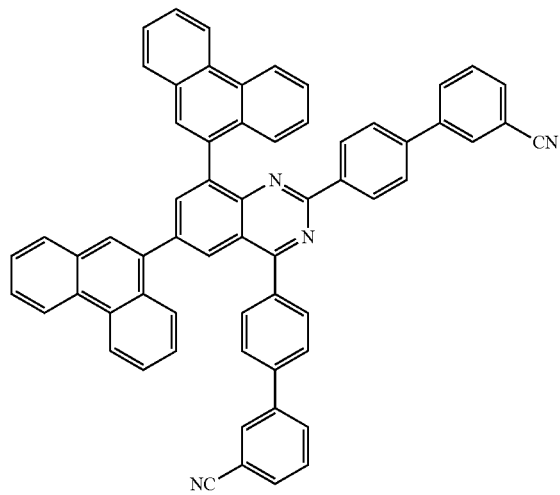
[Chemical Formula A-55]
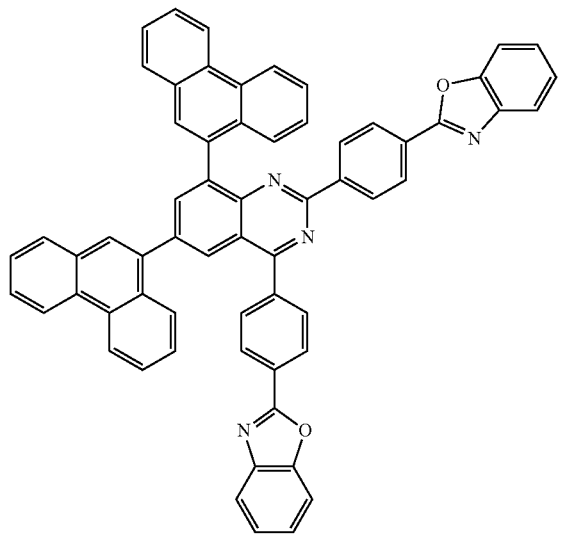
[Chemical Formula A-56]
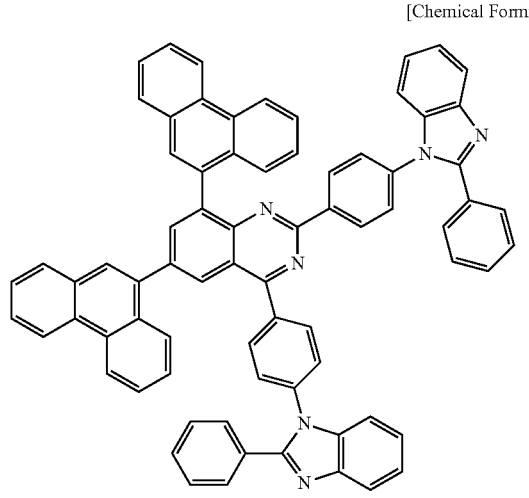
[Chemical Formula A-57]
[Chemical Formula A-58]
[Chemical Formula A-59]
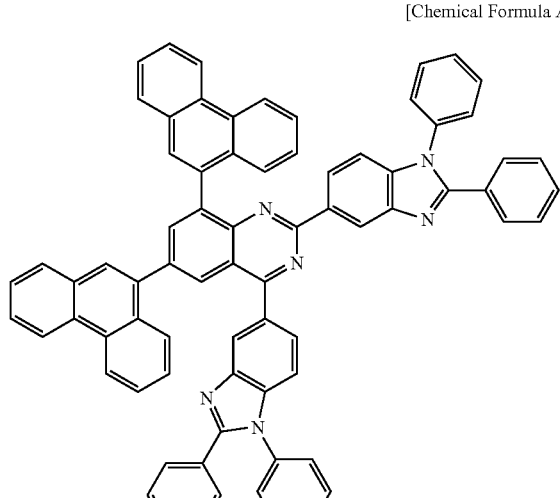

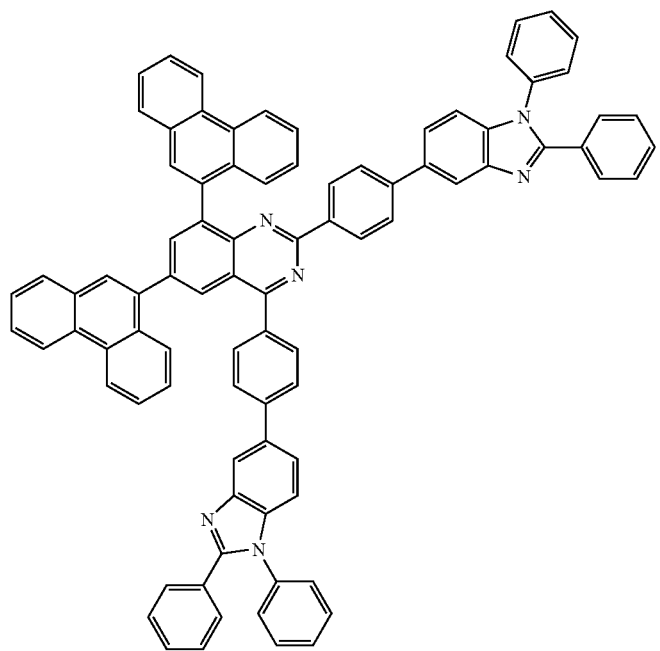
[Chemical Formula A-60]
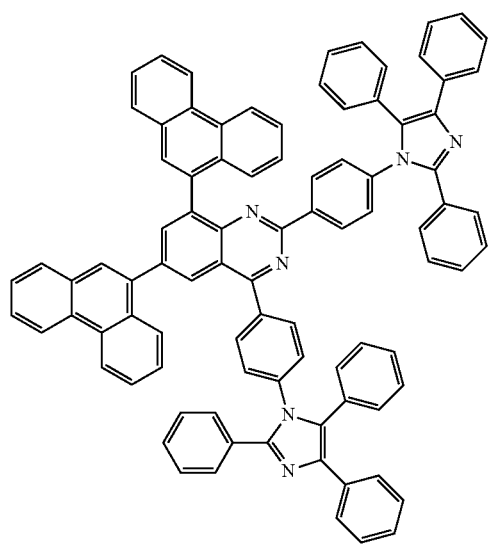
[Chemical Formula A-61]
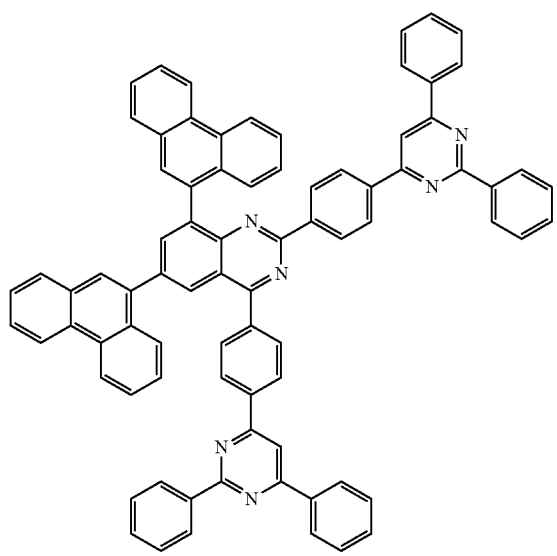
[Chemical Formula A-62]

[Chemical Formula A-63]
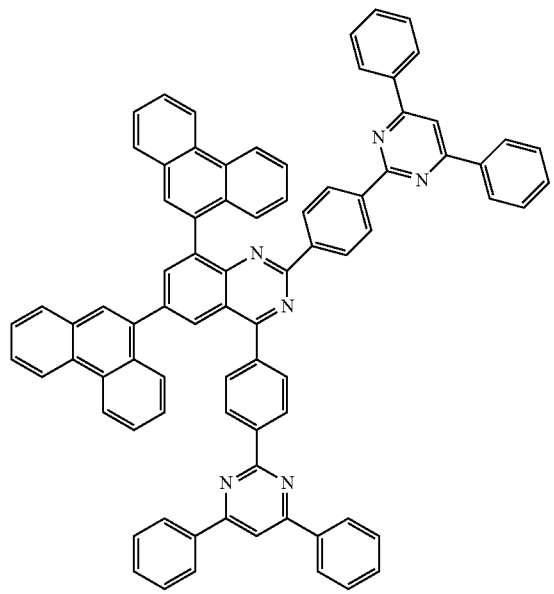
[Chemical Formula A-64]
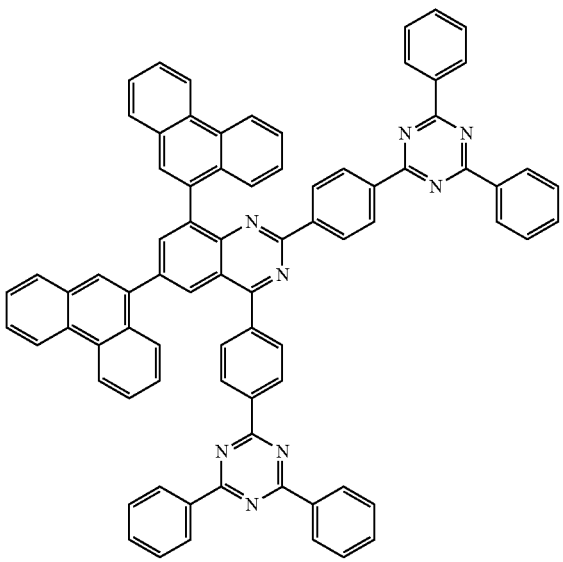
[Chemical Formula A-65]
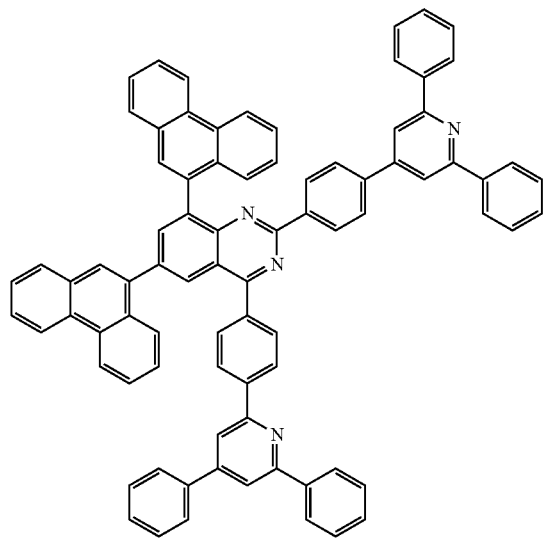
[Chemical Formula A-66]
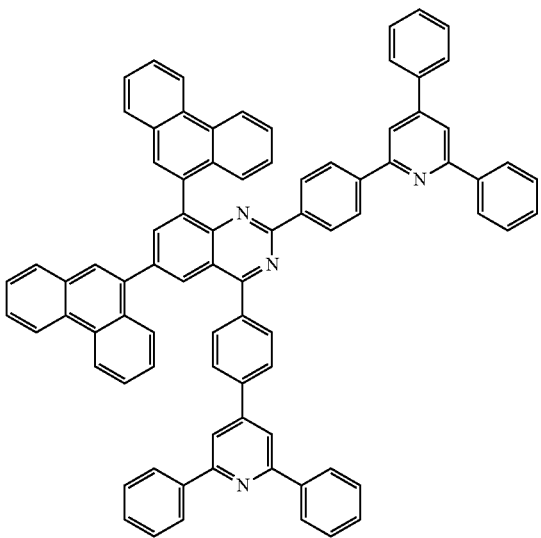

[Chemical Formula A-67]
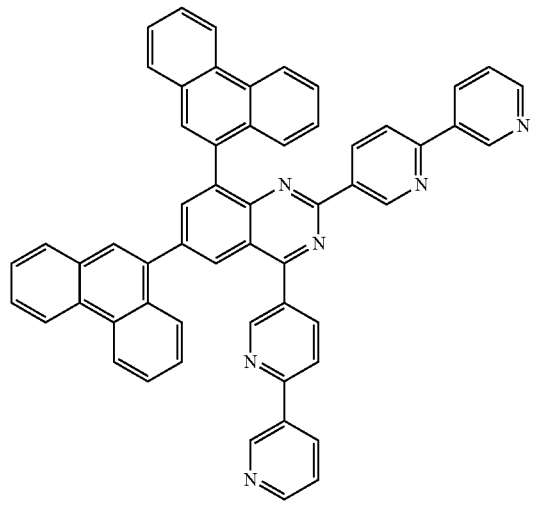
[Chemical Formula A-68]
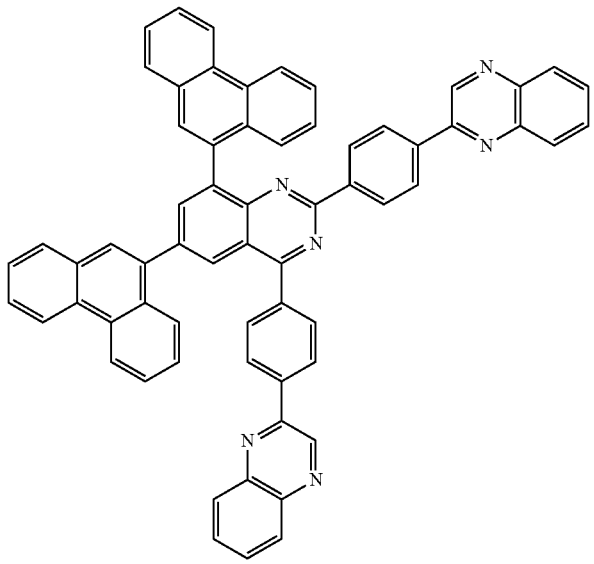
[Chemical Formula A-69]
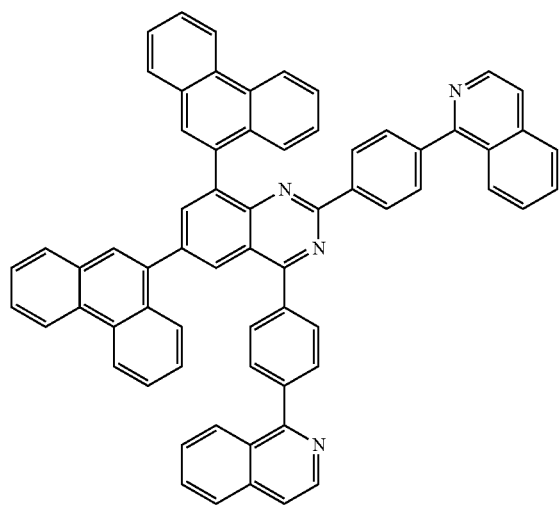
[Chemical Formula A-70]
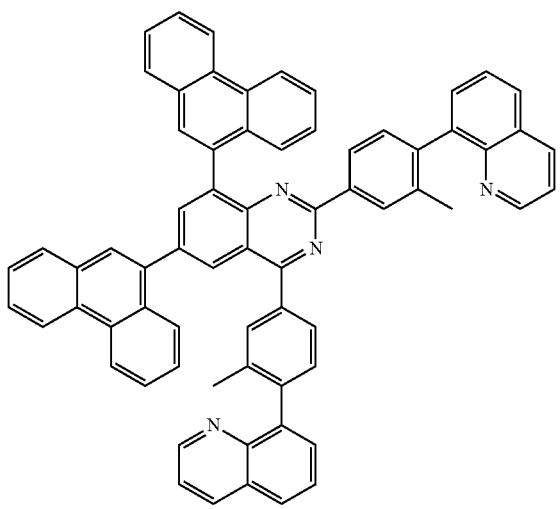

[Chemical Formula A-71]
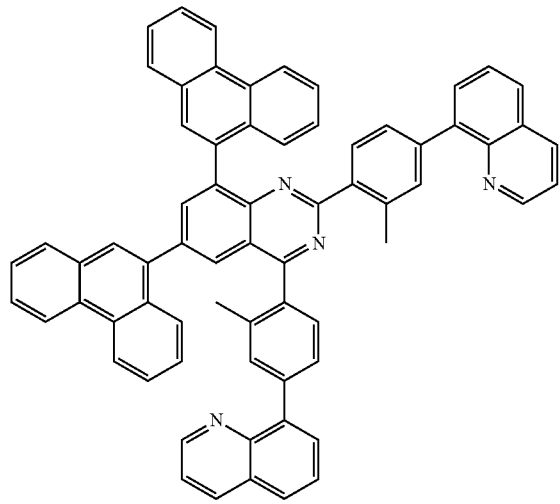
[Chemical Formula A-72]
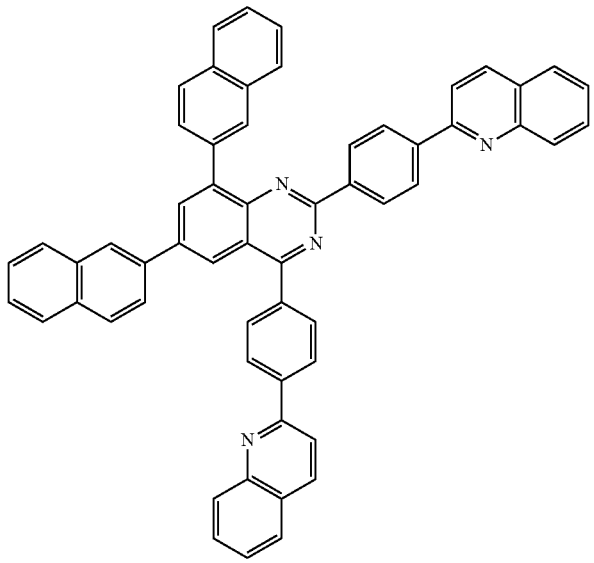
[Chemical Formula A-73]
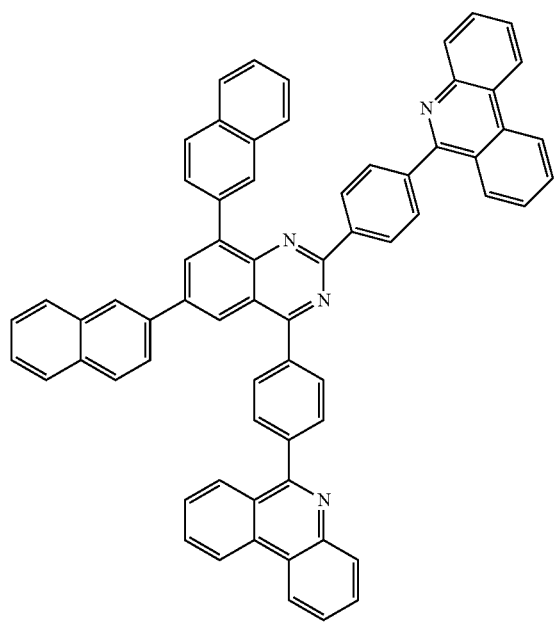
[Chemical Formula A-74]
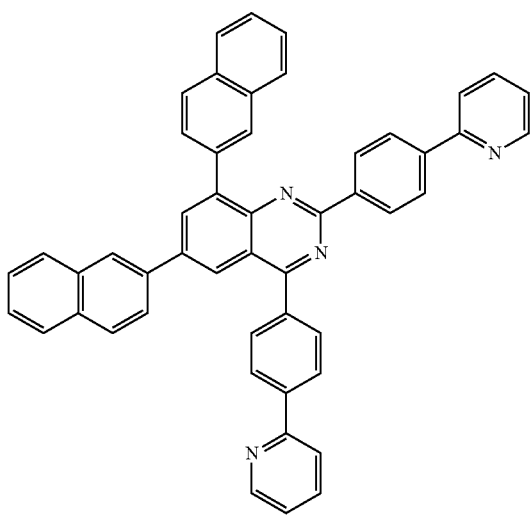

[Chemical Formula A-75]
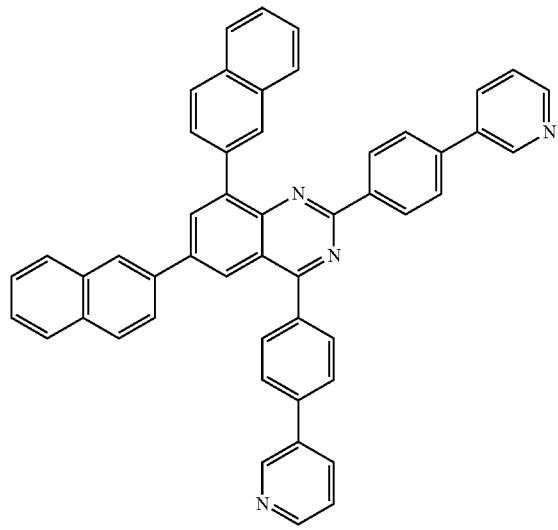
[Chemical Formula A-76]
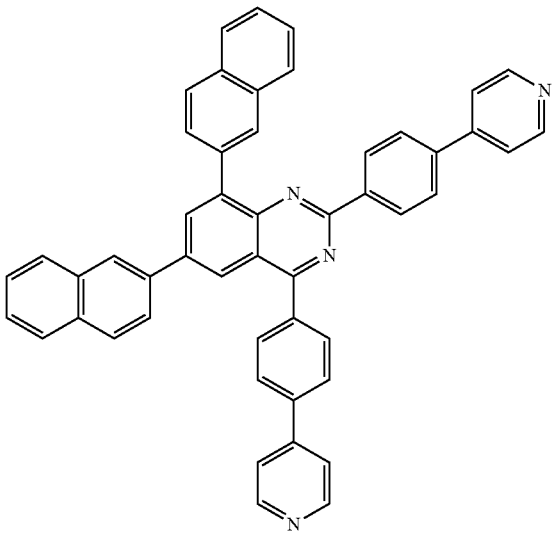
[Chemical Formula A-77]
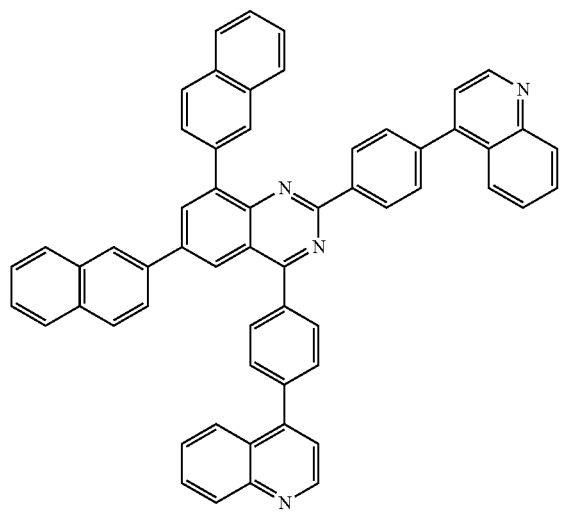
[Chemical Formula A-78]
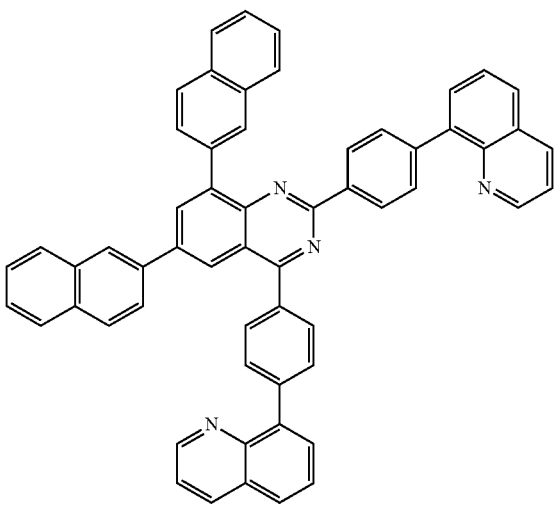

[Chemical Formula A-79]
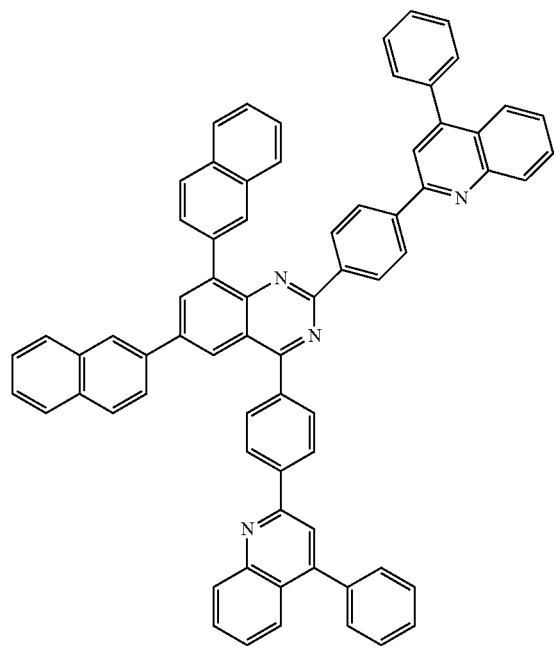
[Chemical Formula A-80]
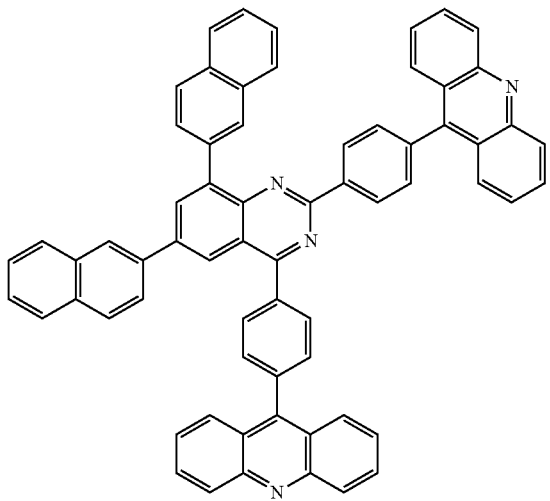
[Chemical Formula A-81]
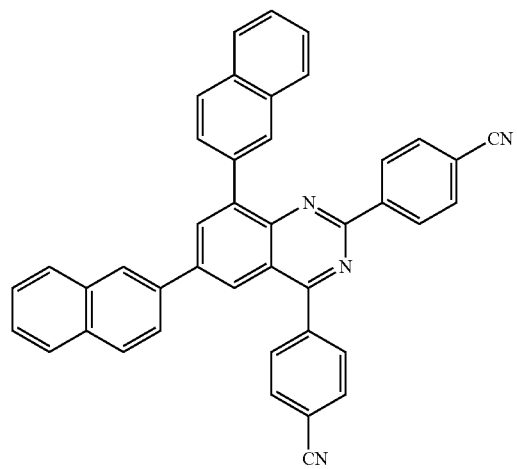
[Chemical Formula A-82]
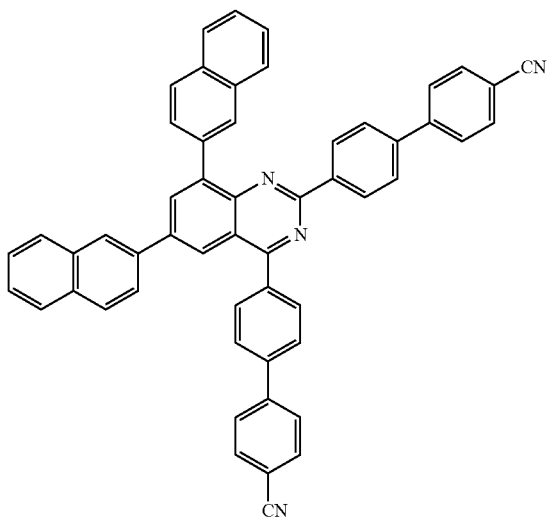

[Chemical Formula A-83]
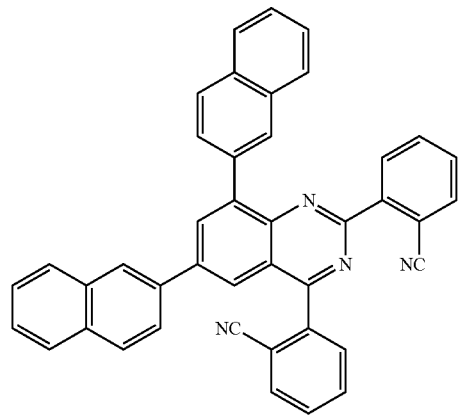
[Chemical Formula A-84]
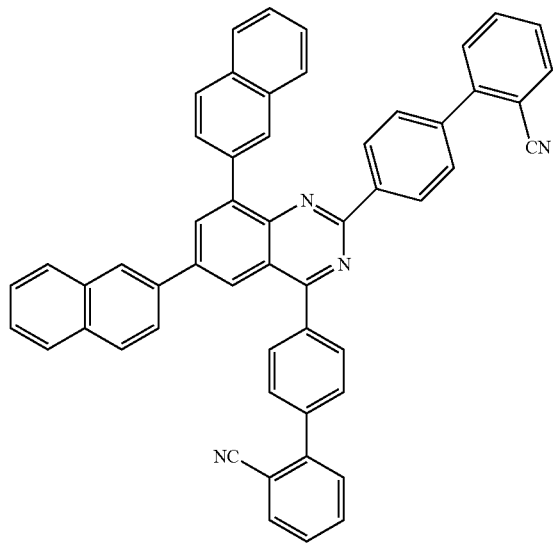
[Chemical Formula A-85]
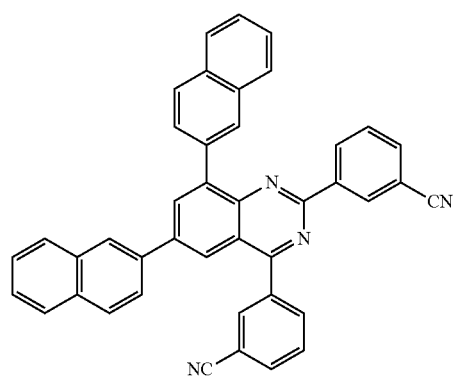
[Chemical Formula A-86]
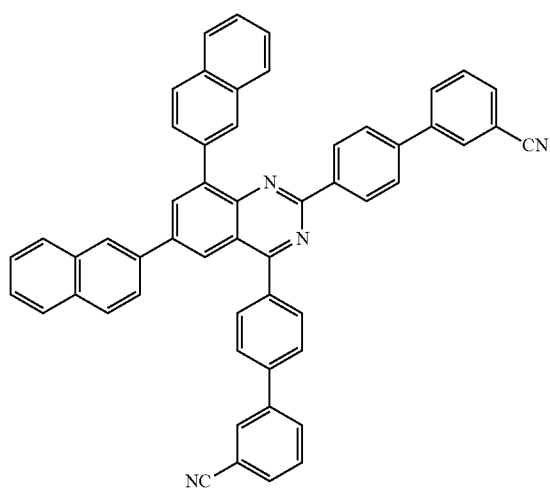

-continued
[Chemical Formula A-87]
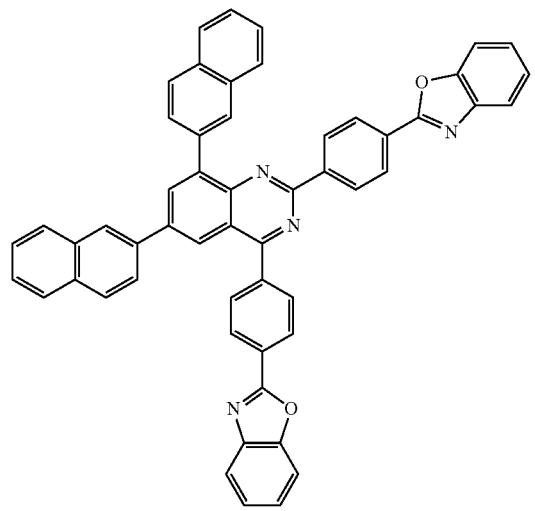
[Chemical Formula A-88]
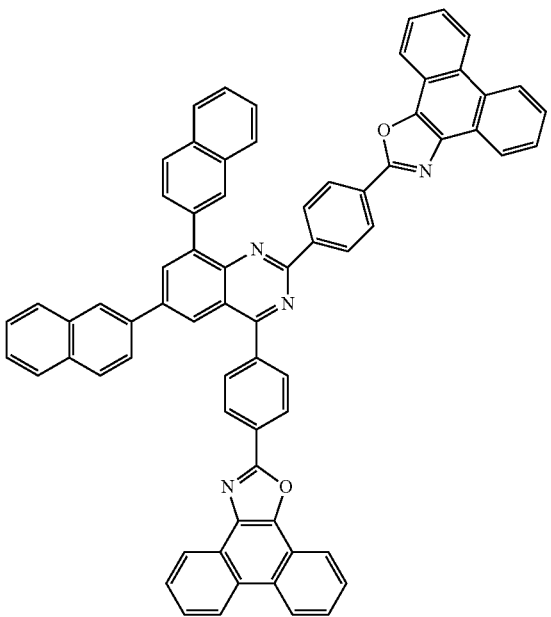
[Chemical Formula A-89]
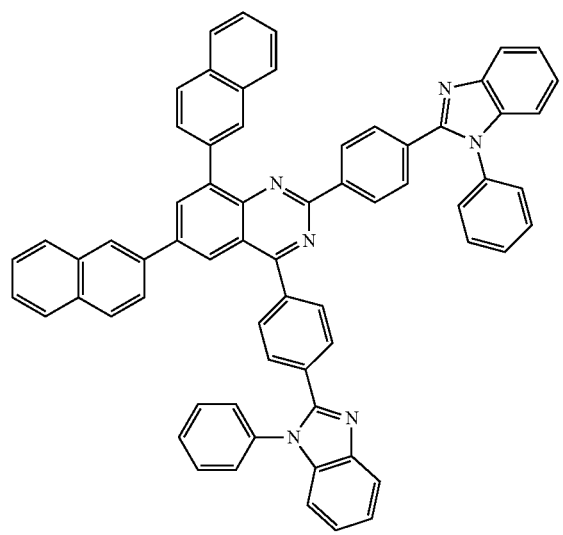
[Chemical Formula A-90]
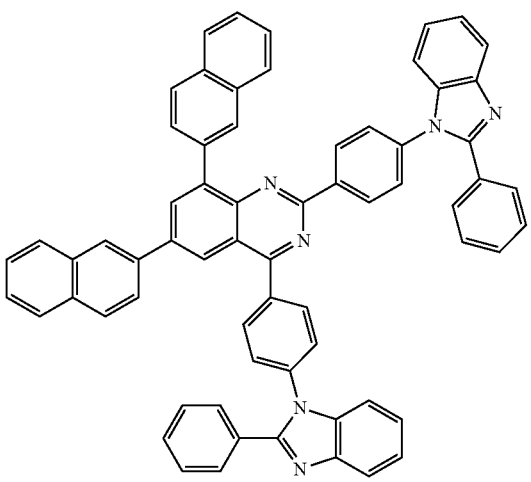

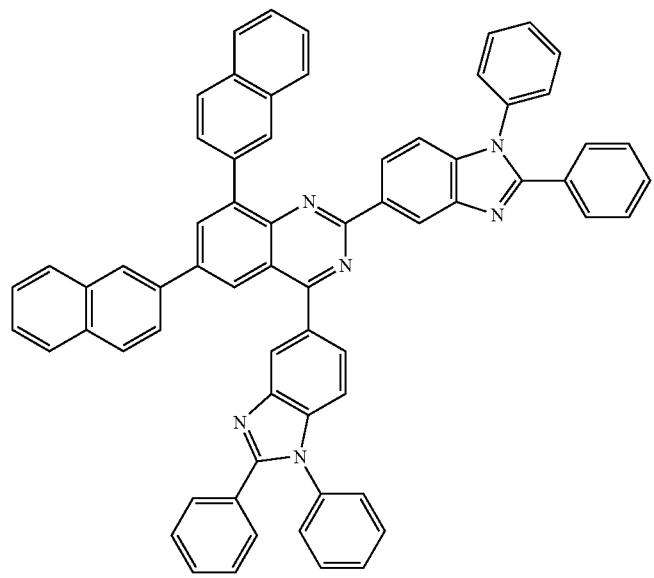
[Chemical Formula A-91]
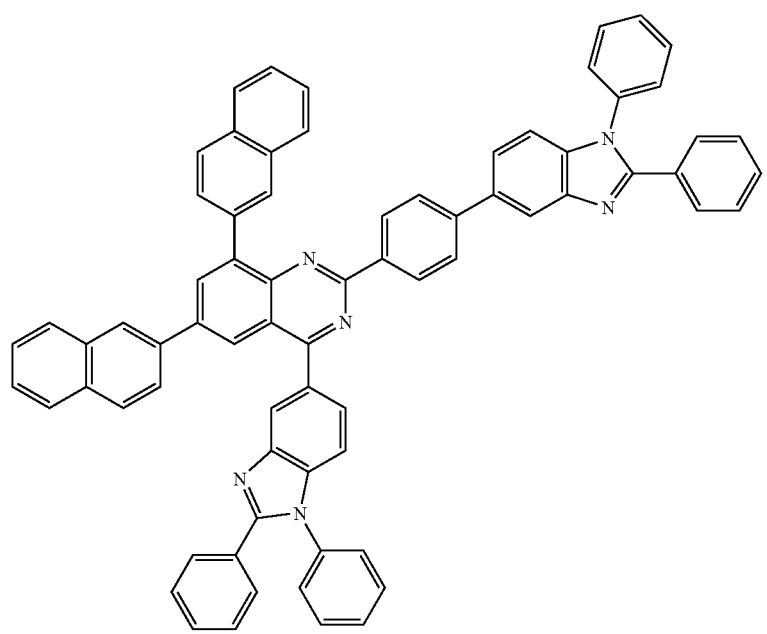
[Chemical Formula A-92]

-continued
[Chemical Formula A-93]
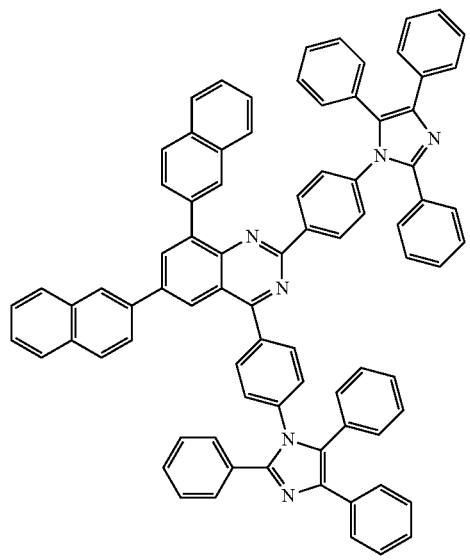
[Chemical Formula A-94]
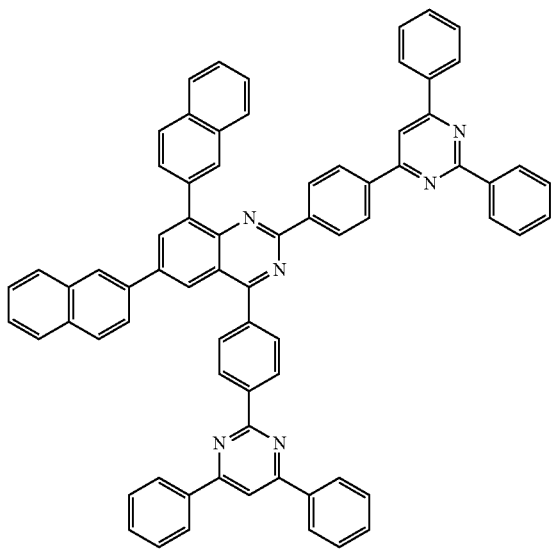
[Chemical Formula A-95]
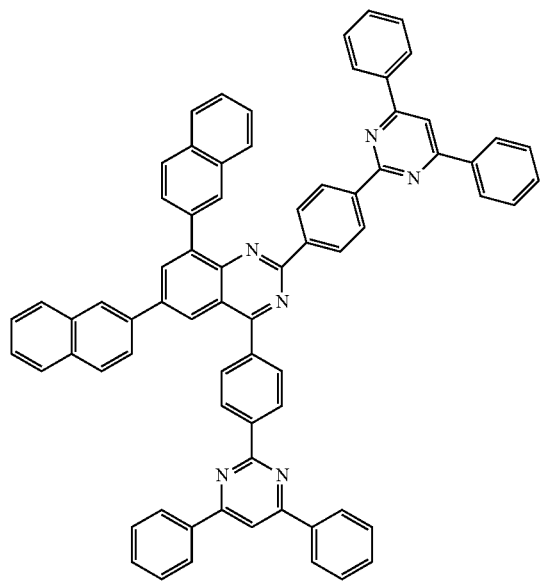
[Chemical Formula A-96]
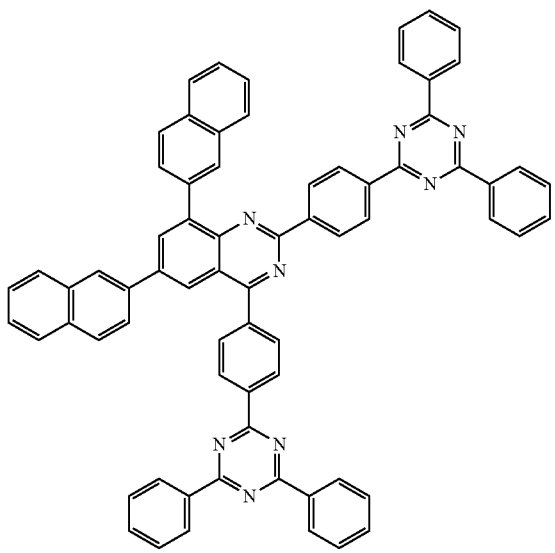

-continued
[Chemical Formula A-97]
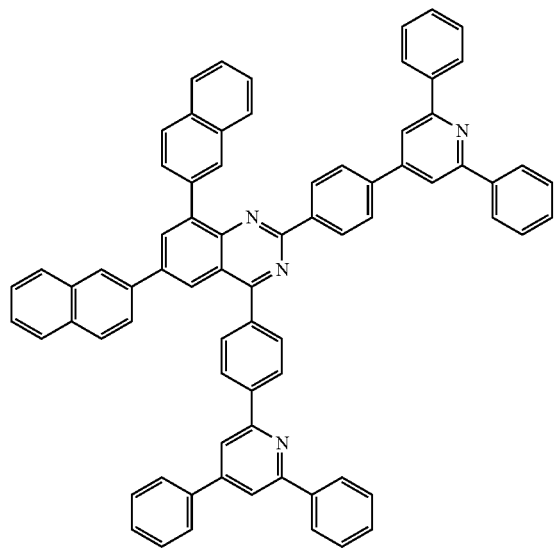
[Chemical Formula A-98]
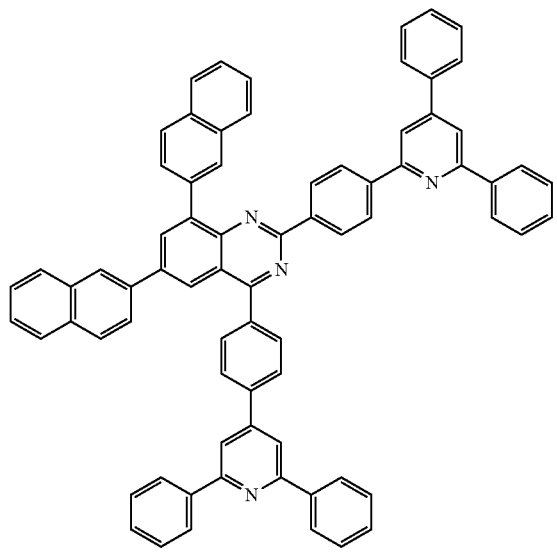
[Chemical Formula A-99]
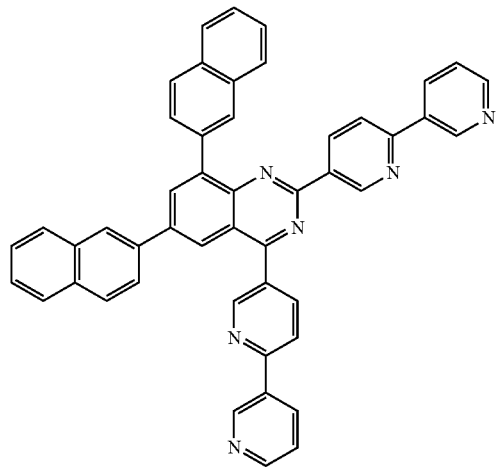
[Chemical Formula A-100]
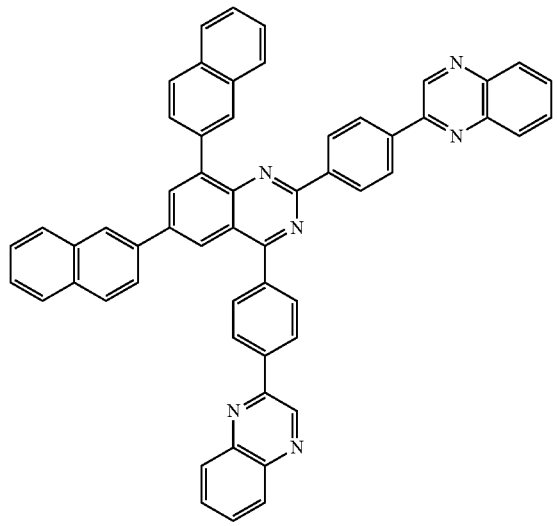
[Chemical Formula A-101]
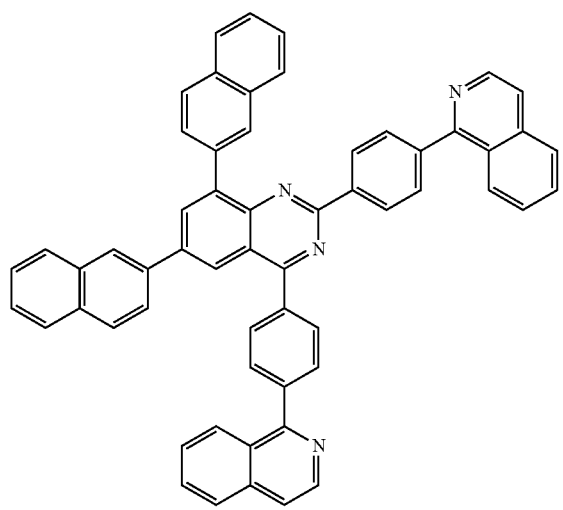
[Chemical Formula A-102]
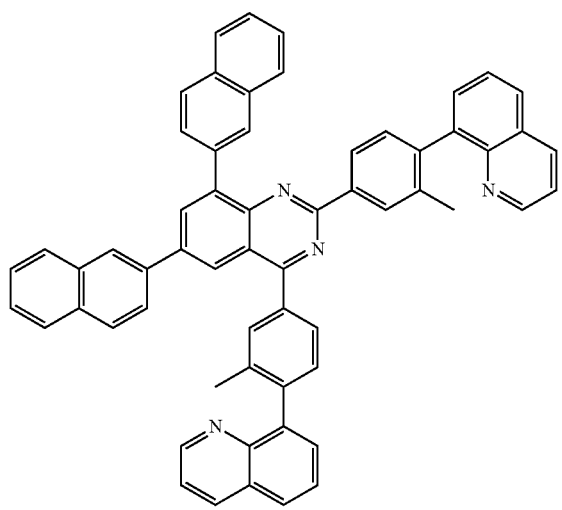

-continued
[Chemical Formula A-103]
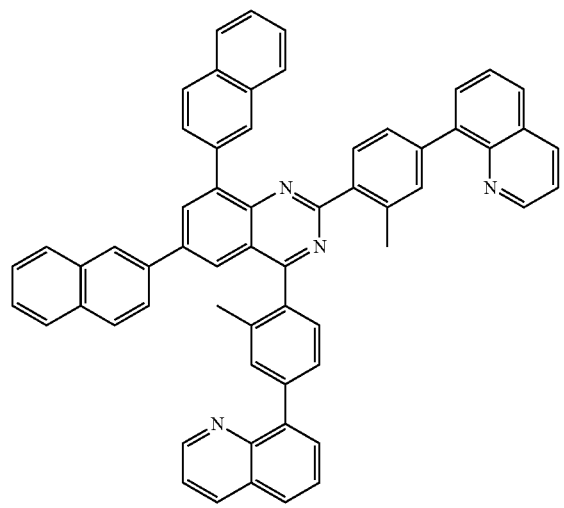
[Chemical Formula A-104]
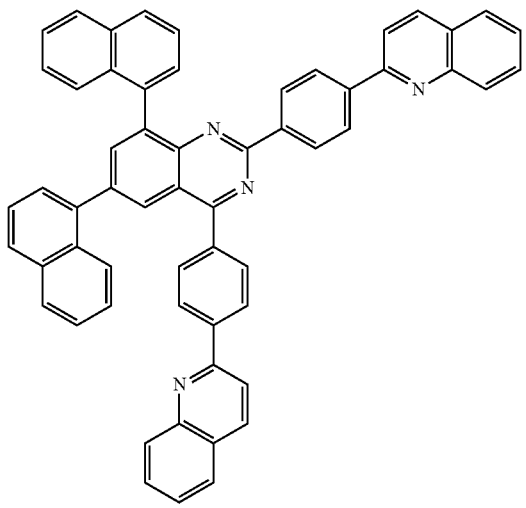
[Chemical Formula A-105]
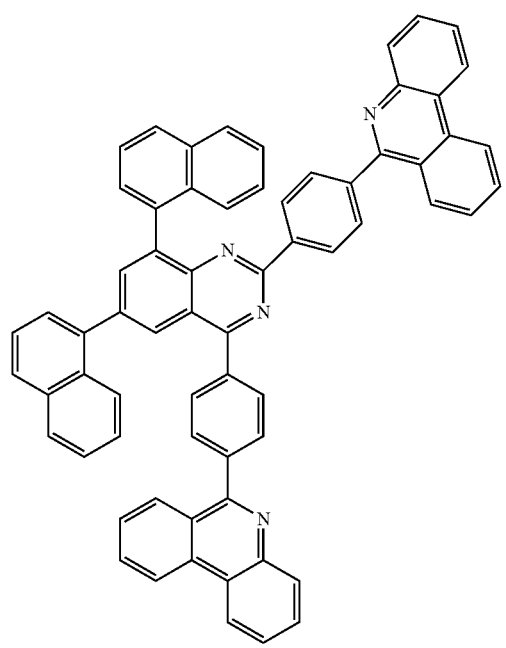
[Chemical Formula A-106]
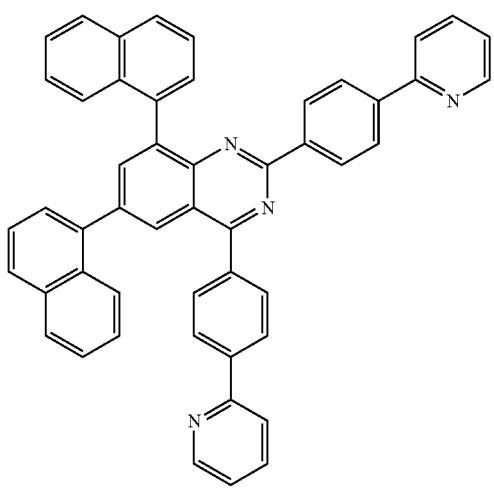

-continued
[Chemical Formula A-107]
[Chemical Formula A-108]
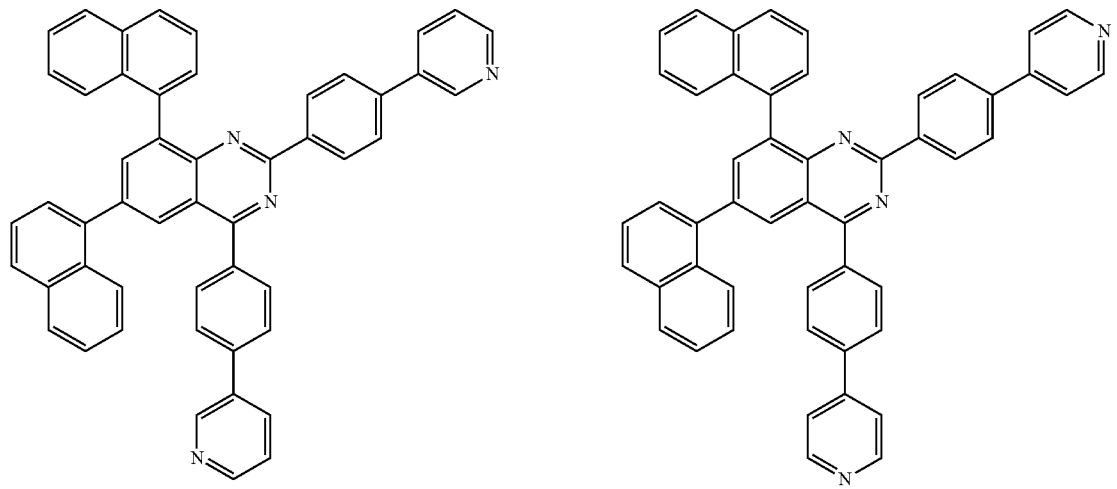
[Chemical Formula A-109]
[Chemical Formula A-110]
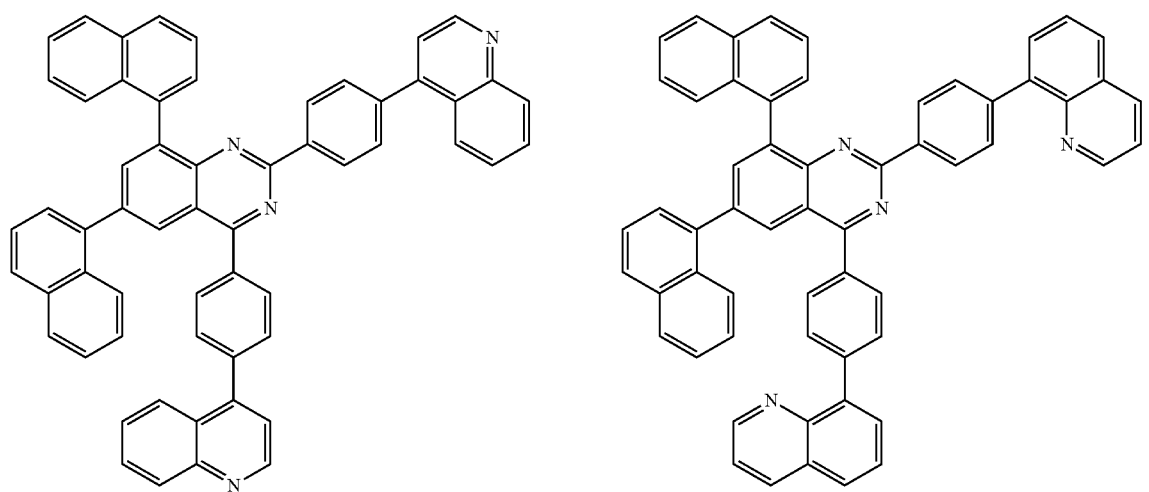

-continued
[Chemical Formula A-111]
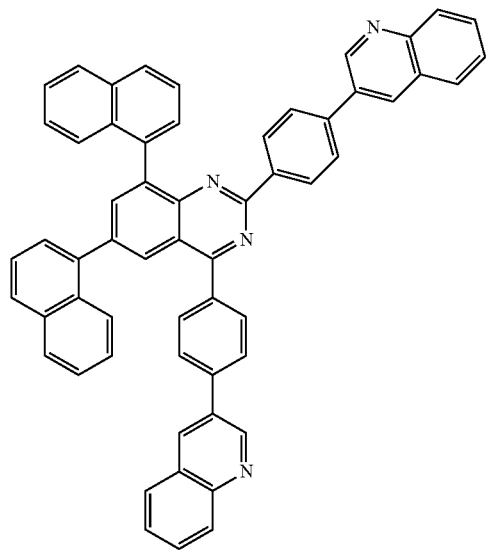
[Chemical Formula A-112]
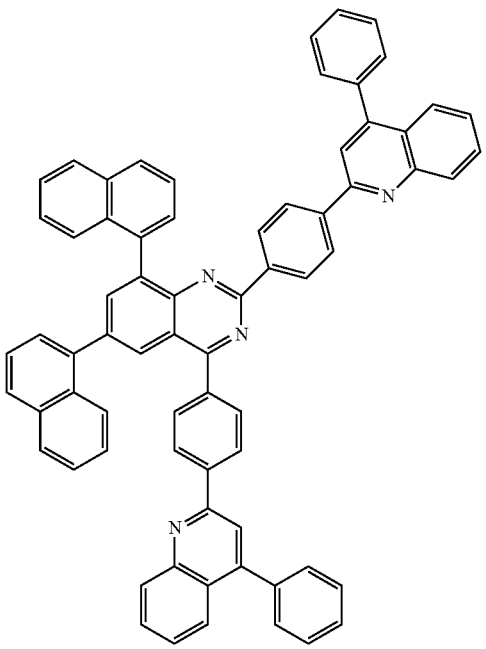
[Chemical Formula A-113]
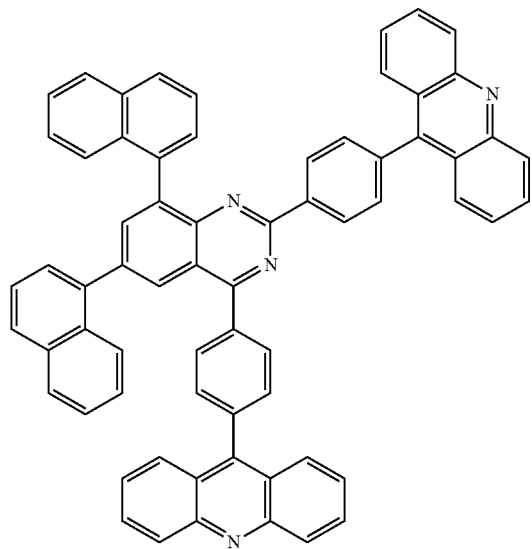
[Chemical Formula A-114]
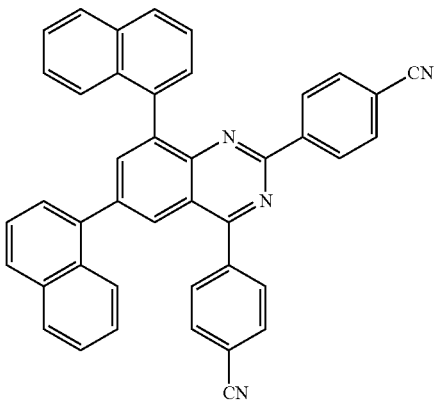

-continued
[Chemical Formula A-115]
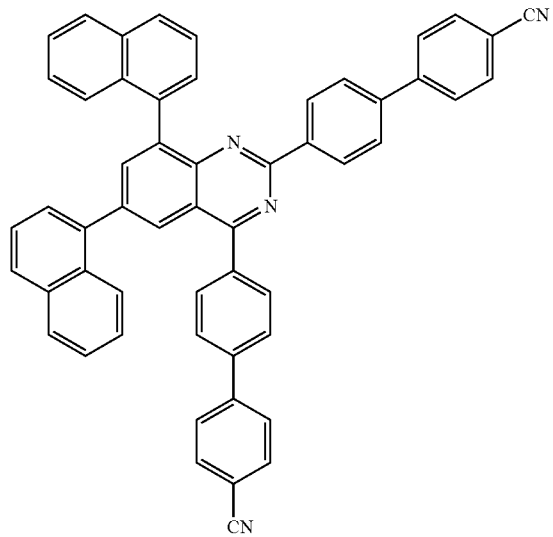
[Chemical Formula A-116]
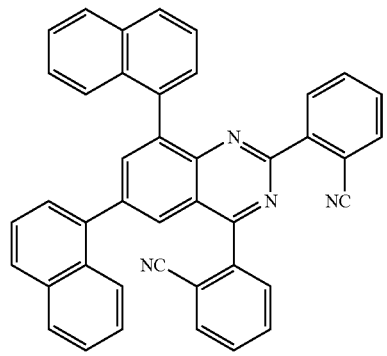
[Chemical Formula A-117]
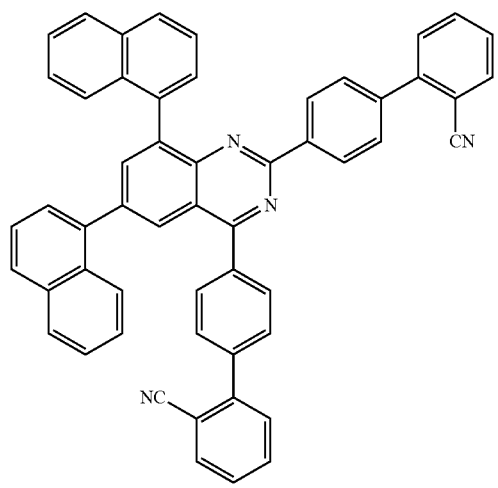
[Chemical Formula A-118]
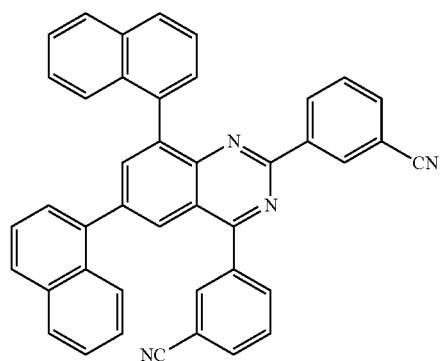
[Chemical Formula A-119]
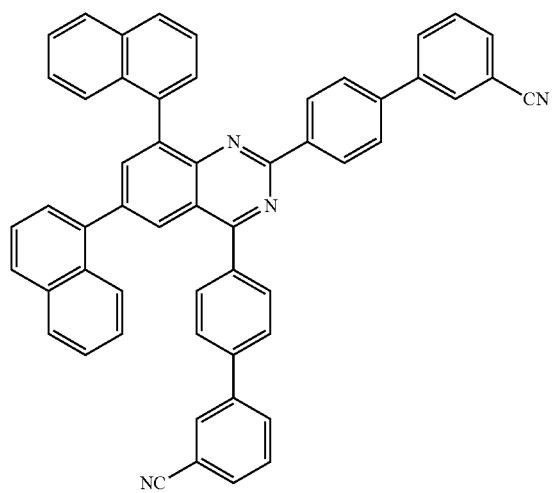
[Chemical Formula A-120]
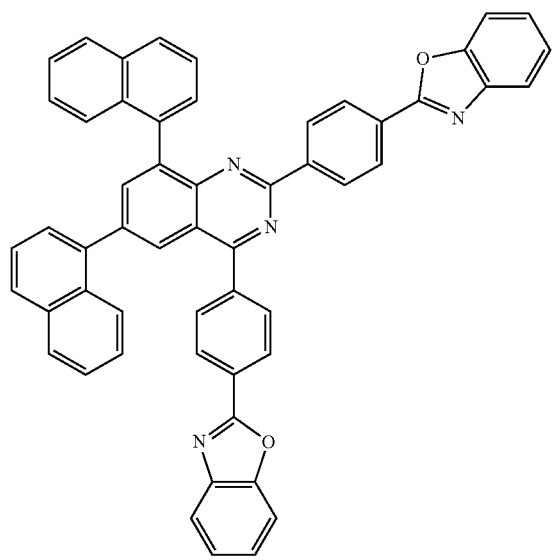

-continued
[Chemical Formula A-121]
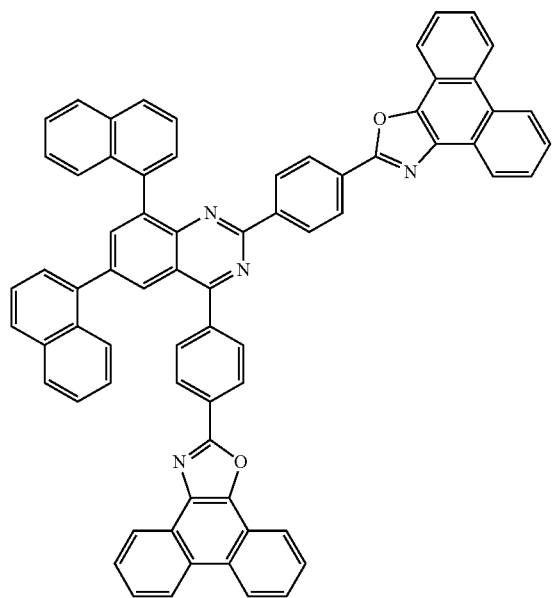
[Chemical Formula A-122]
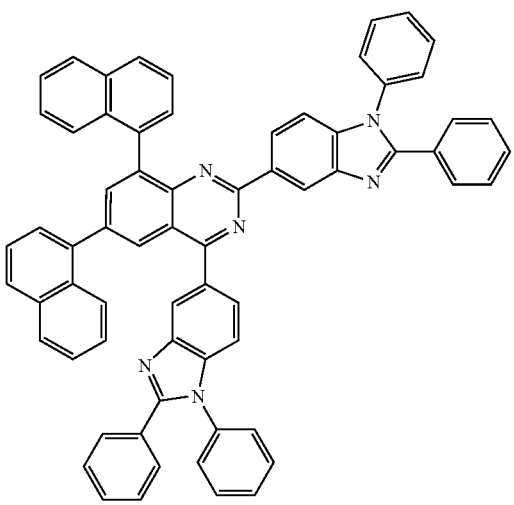
[Chemical Formula A-123]
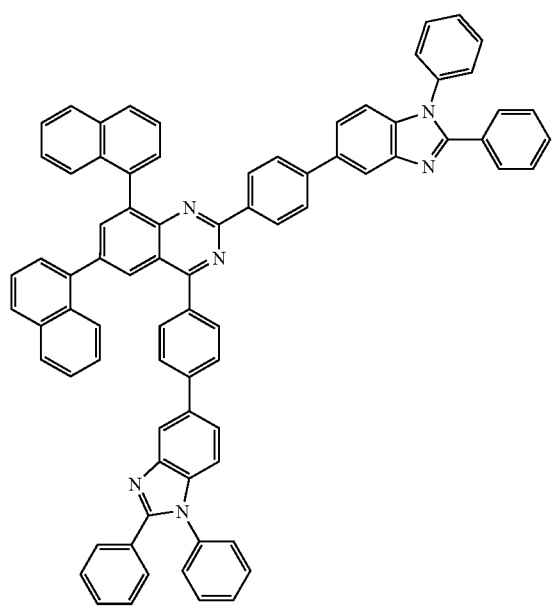
[Chemical Formula A-124]
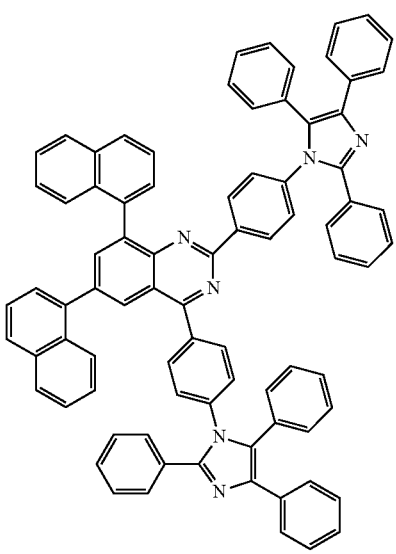

-continued
[Chemical Formula A-125]
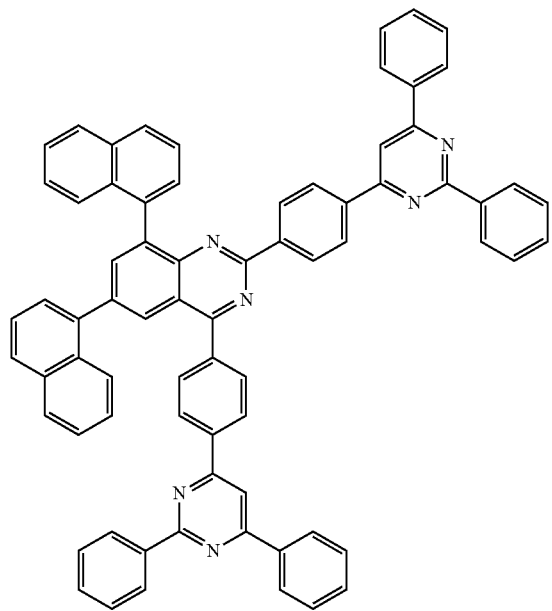
[Chemical Formula A-126]
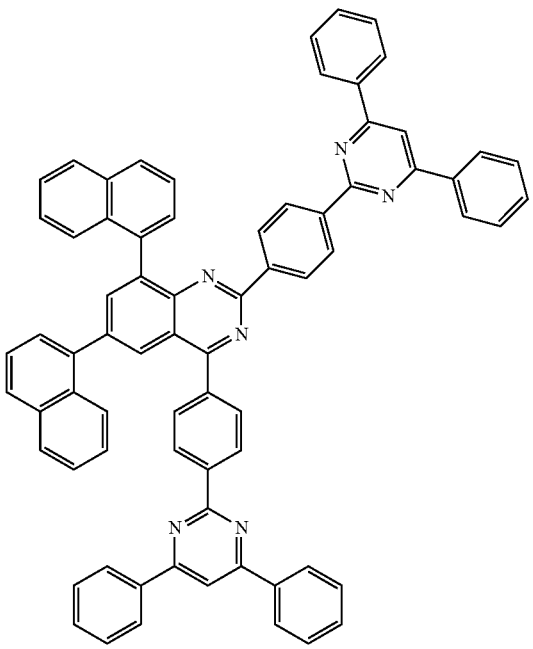
[Chemical Formula A-127]
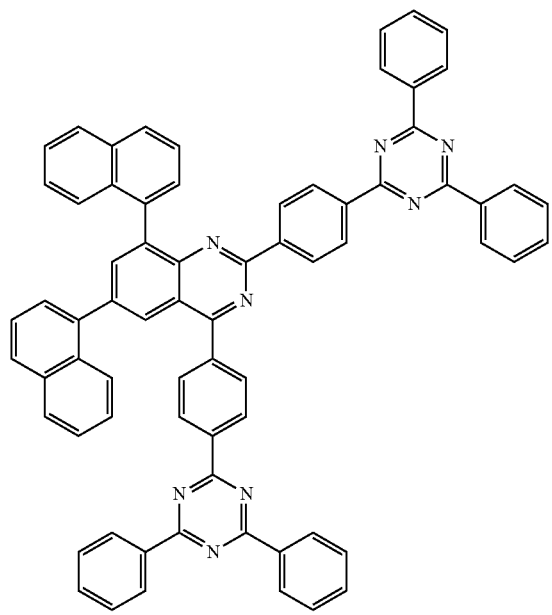
[Chemical Formula A-128]
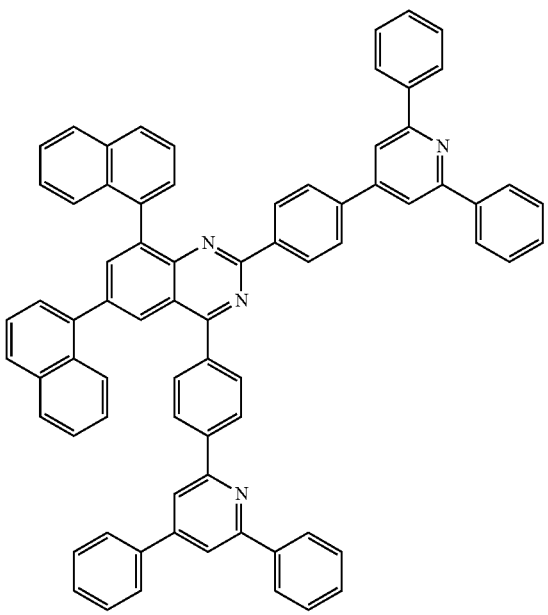

[Chemical Formula A-129]
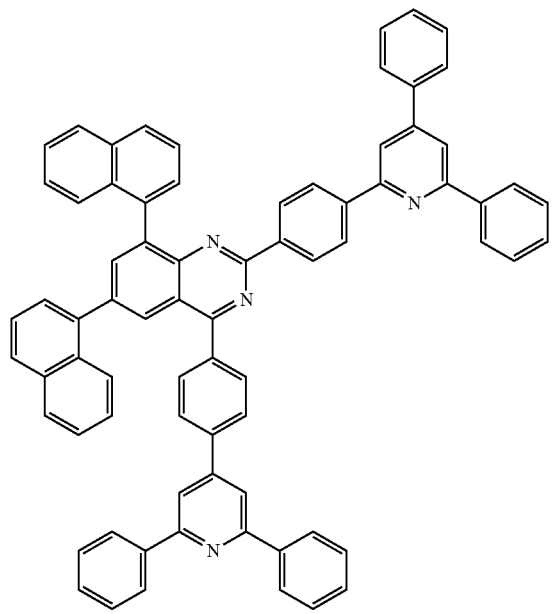
[Chemical Formula A-130]
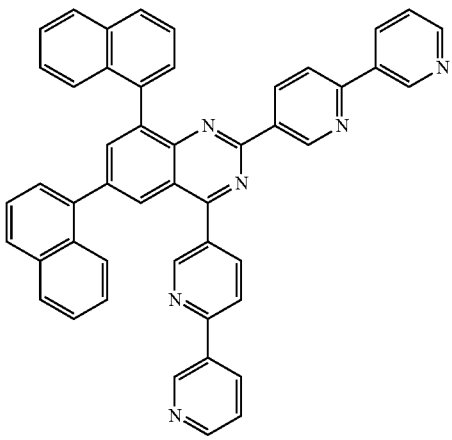
[Chemical Formula A-131]
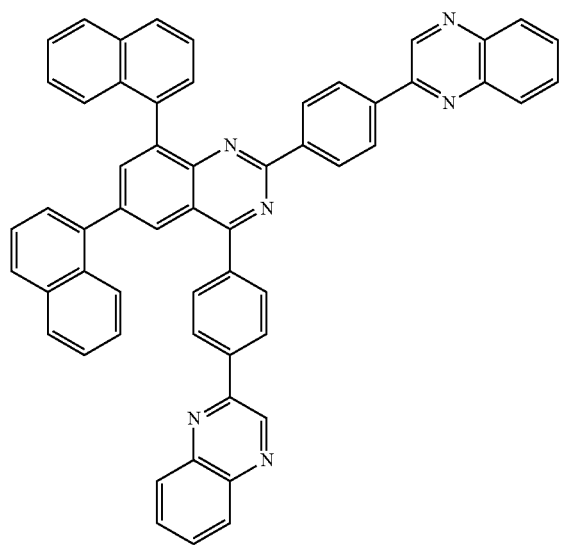
[Chemical Formula A-132]
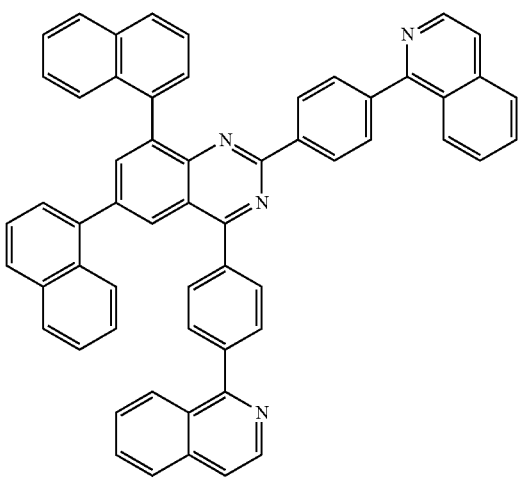

[Chemical Formula A-133]
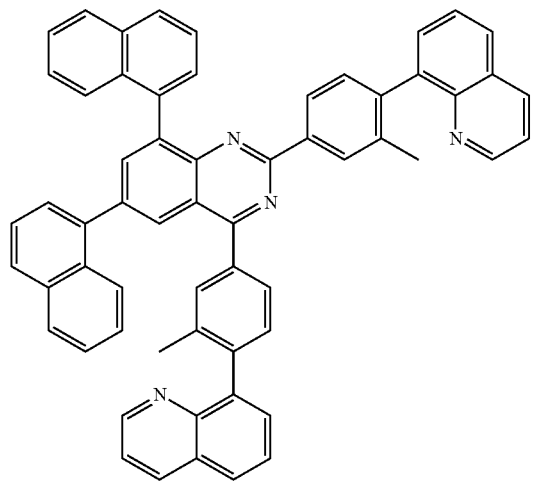
[Chemical Formula A-134]
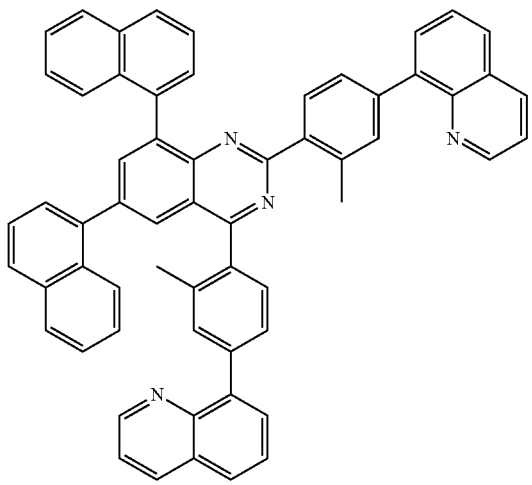
[Chemical Formula A-135]
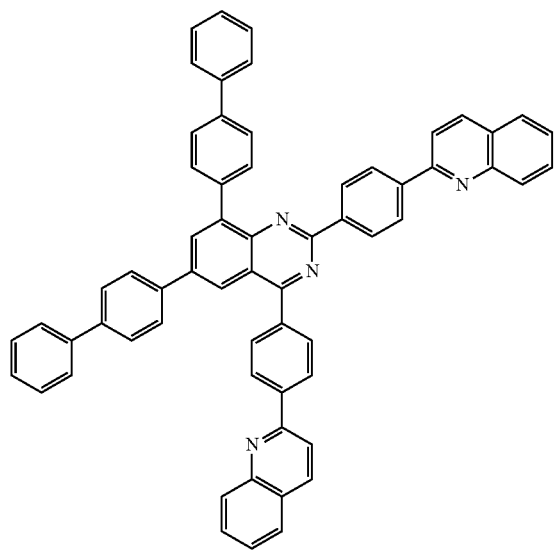
[Chemical Formula A-136]
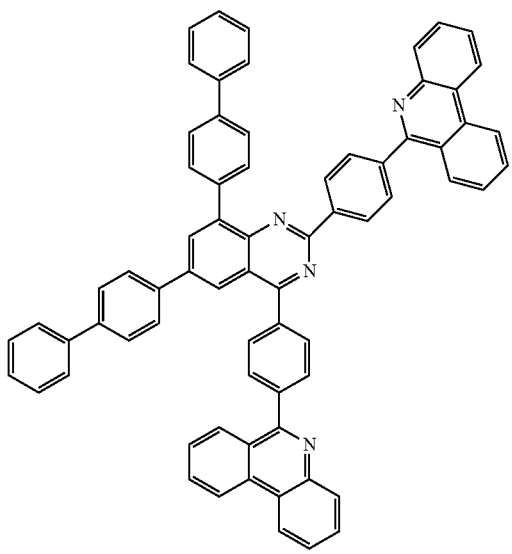
[Chemical Formula A-137]
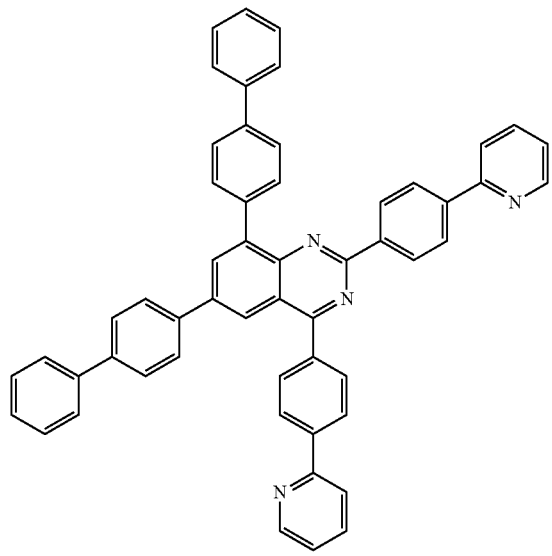
[Chemical Formula A-138]
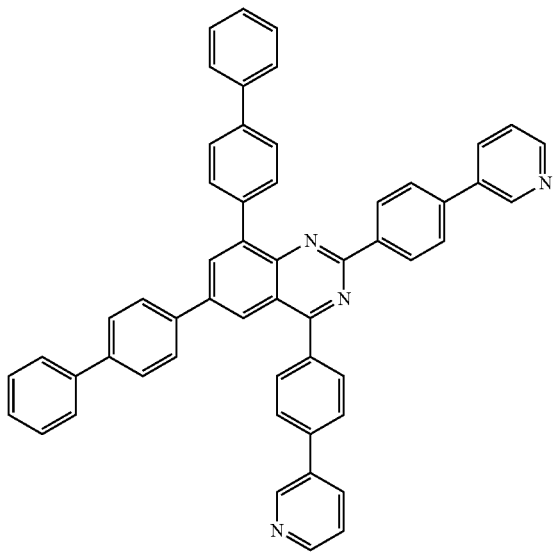

[Chemical Formula A-139]
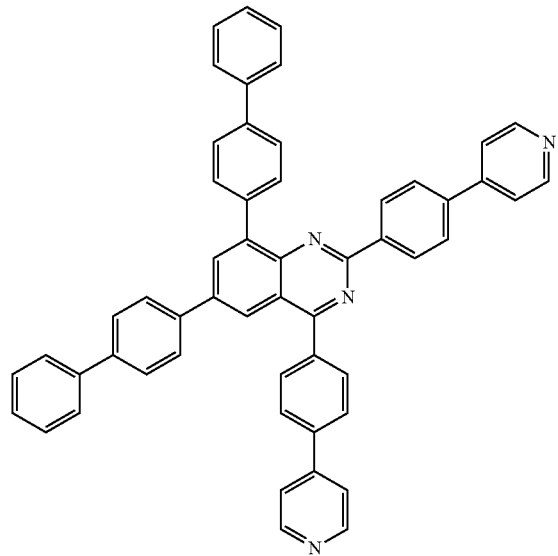
[Chemical Formula A-140]
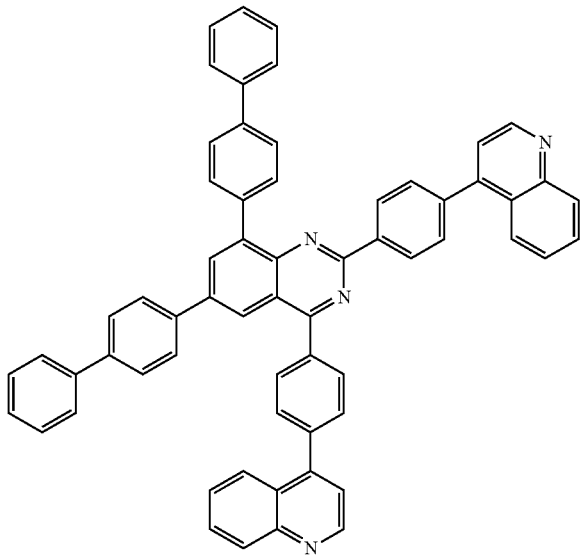
[Chemical Formula A-141]
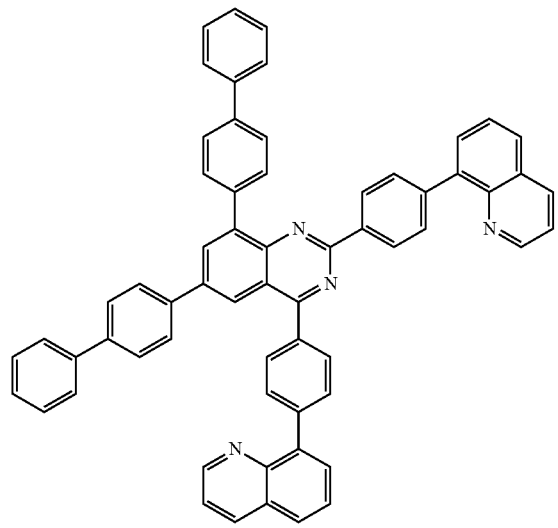
[Chemical Formula A-142]
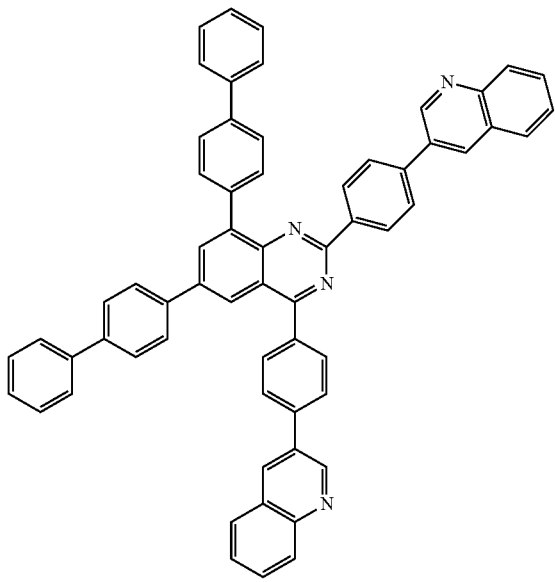

[Chemical Formula A-143]
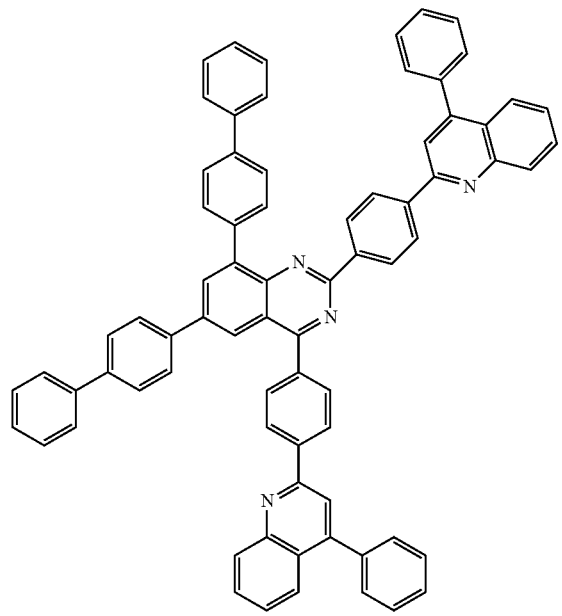
[Chemical Formula A-144]
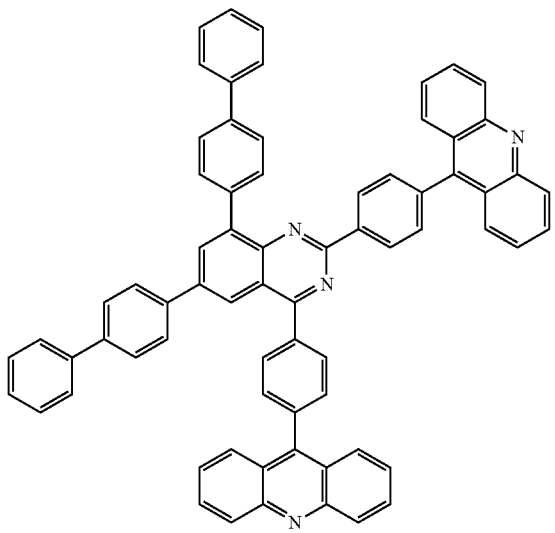
[Chemical Formula A-145]
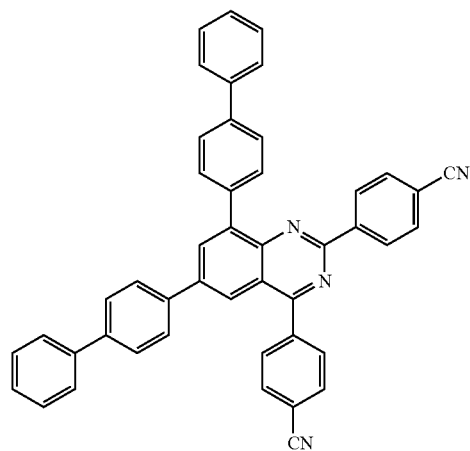
[Chemical Formula A-146]
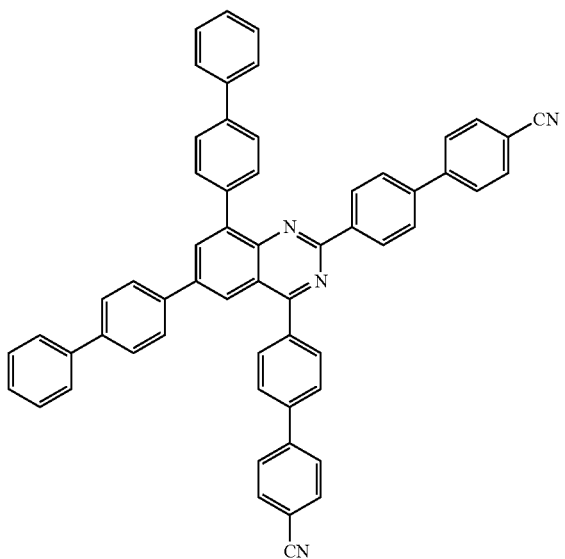

[Chemical Formula A-147]
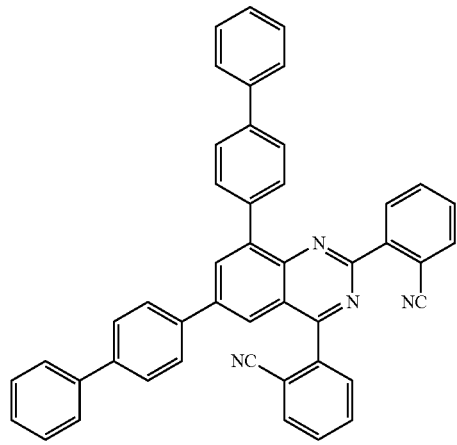
[Chemical Formula A-148]
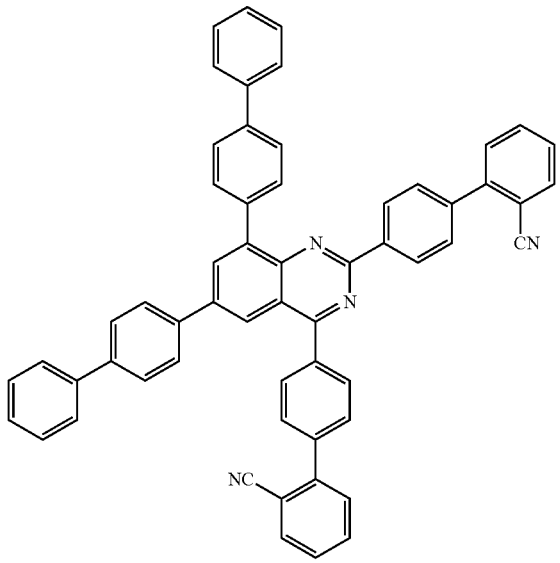
[Chemical Formula A-149]
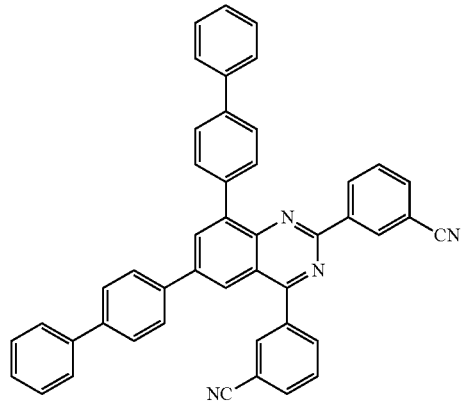
[Chemical Formula A-150]
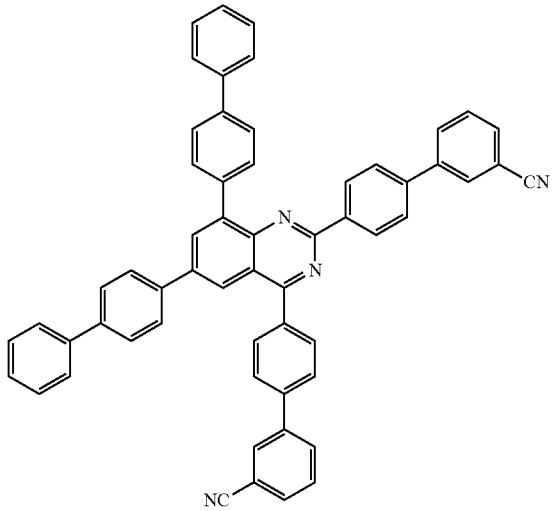
[Chemical Formula A-151]
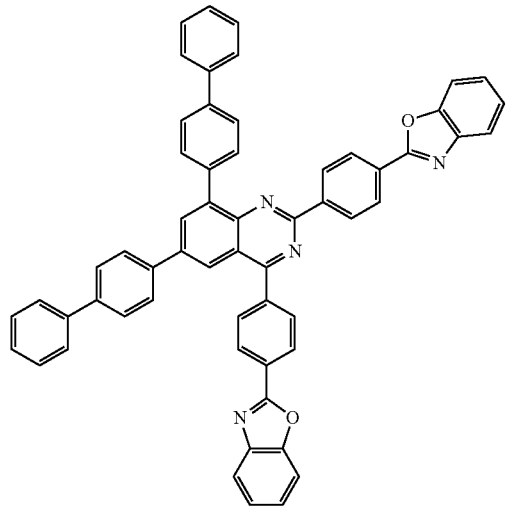
[Chemical Formula A-152]
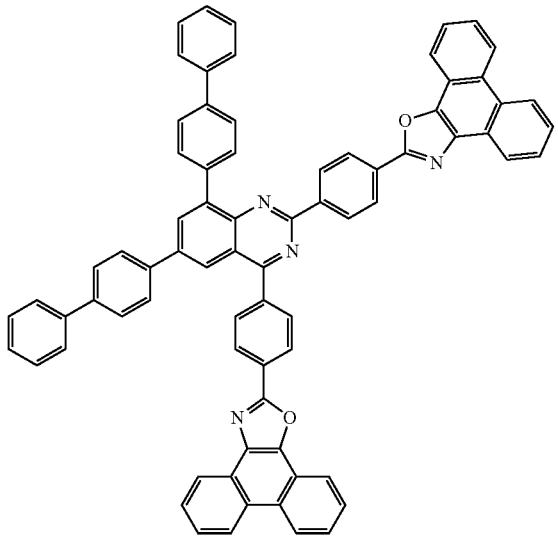

-continued
[Chemical Formula A-153]
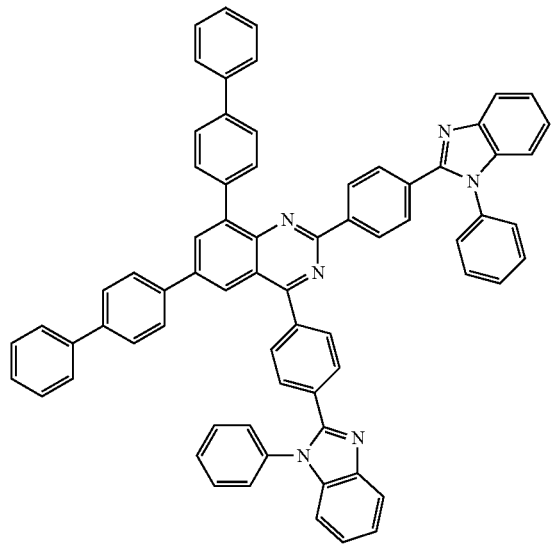
[Chemical Formula A-154]
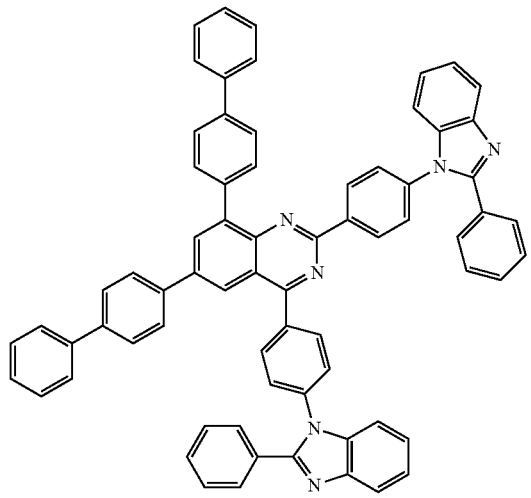
[Chemical Formula A-155]
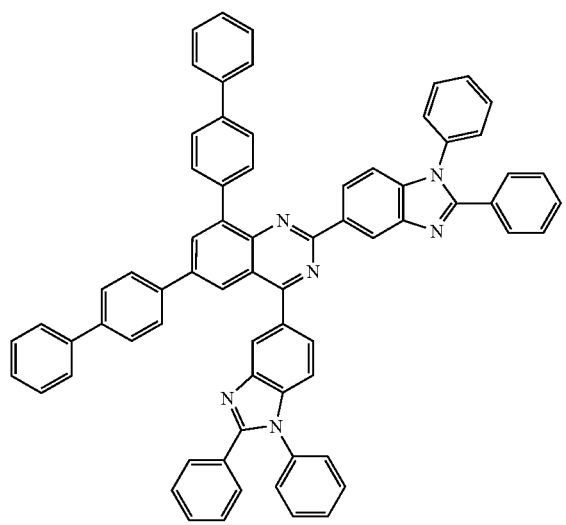
[Chemical Formula A-156]
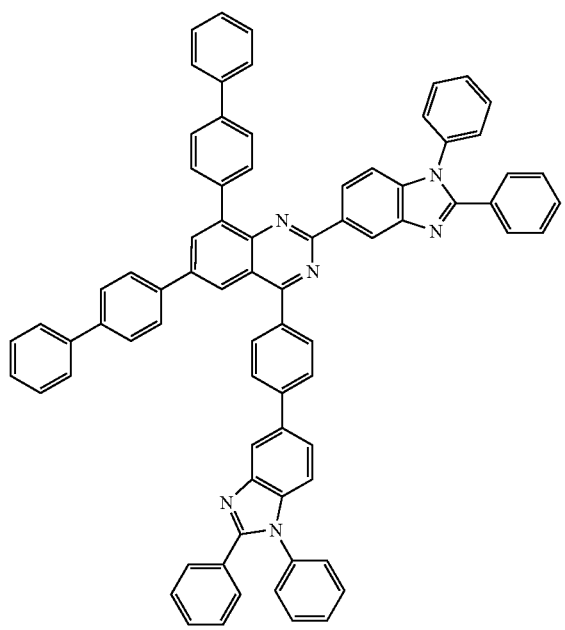

-continued
[Chemical Formula A-157]
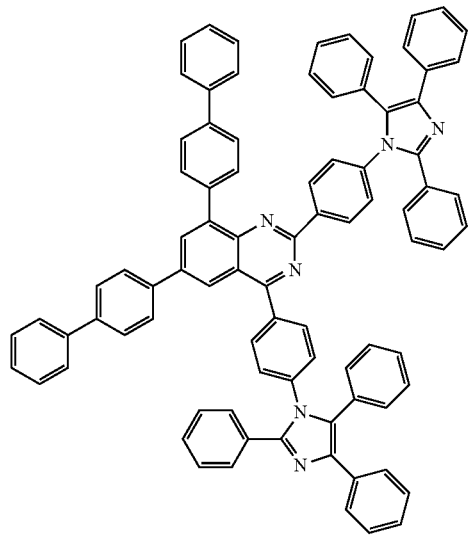
[Chemical Formula A-158]
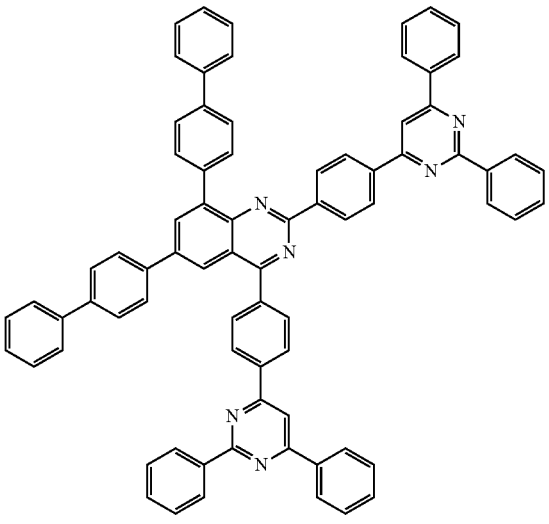
[Chemical Formula A-159]
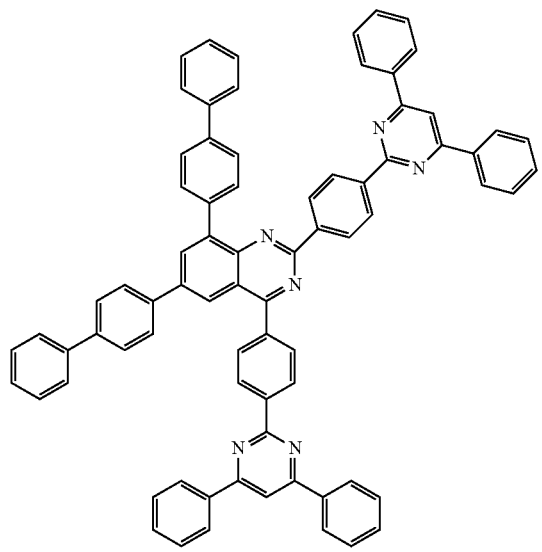
[Chemical Formula A-160]
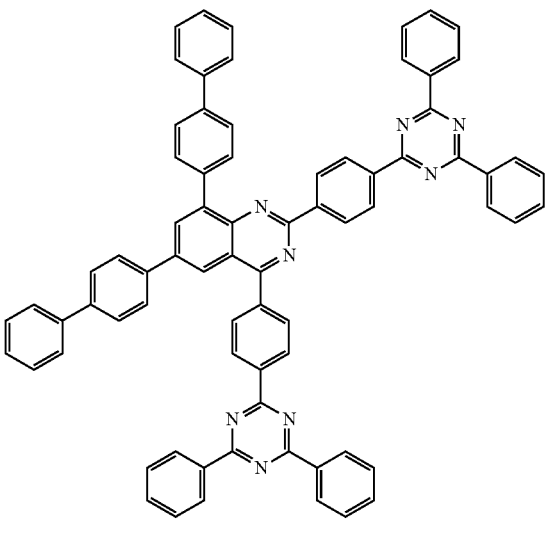
[Chemical Formula A-161]
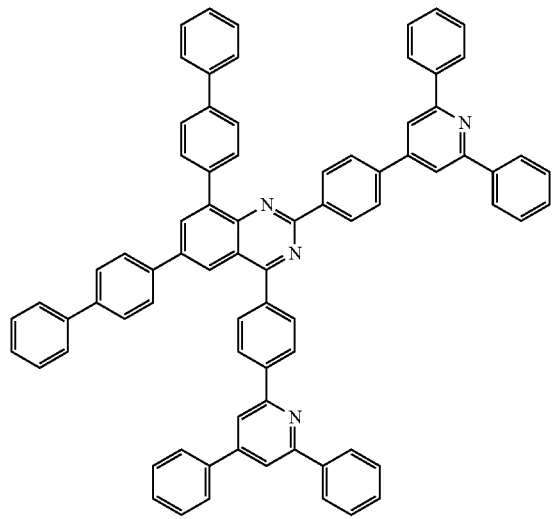
[Chemical Formula A-162]
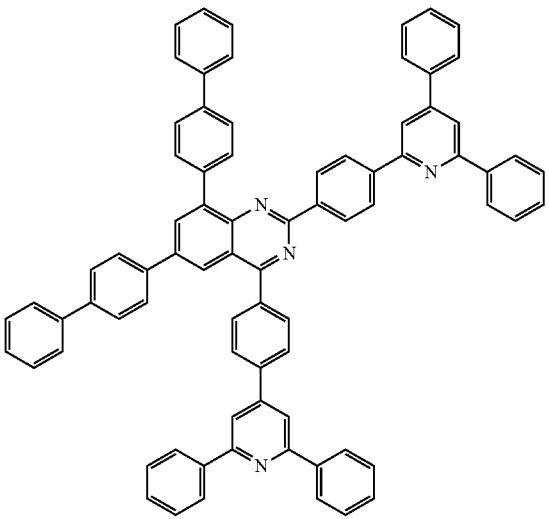

-continued
[Chemical Formula A-163]
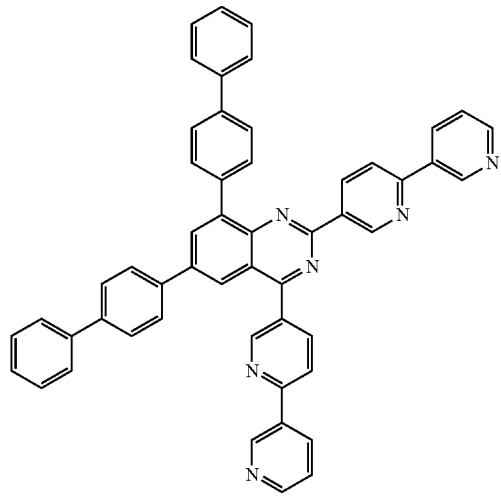
[Chemical Formula A-164]
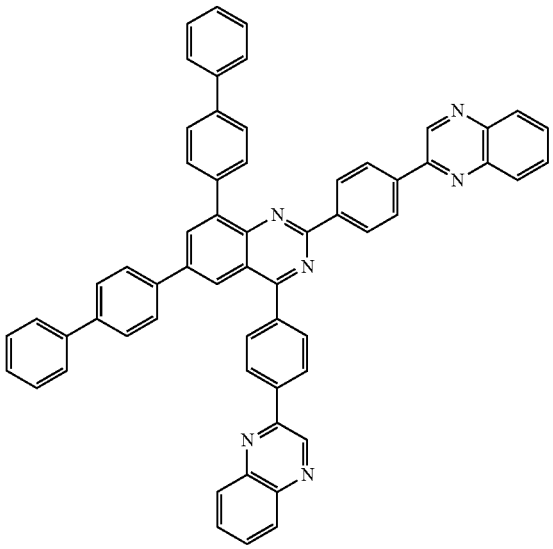
[Chemical Formula A-165]
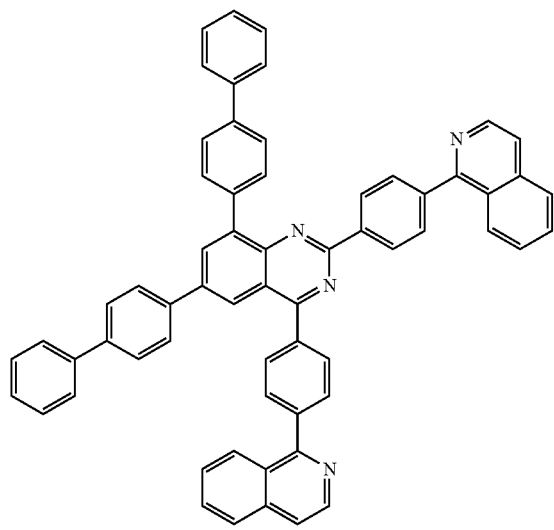
[Chemical Formula A-166]
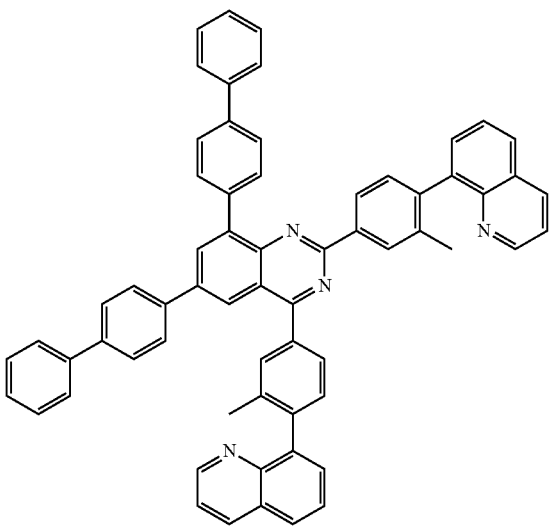
[Chemical Formula A-167]
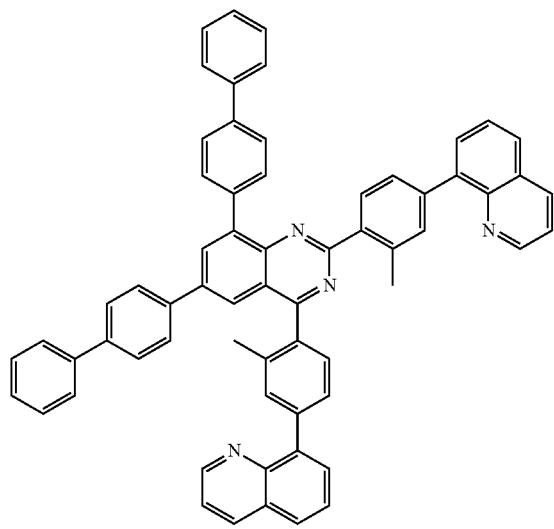
[Chemical Formula A-168]
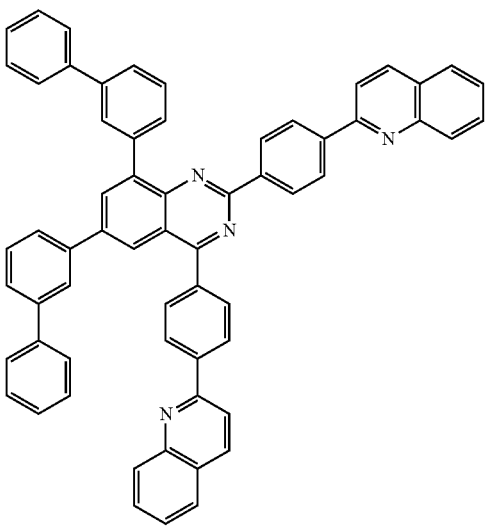

[Chemical Formula A-169]
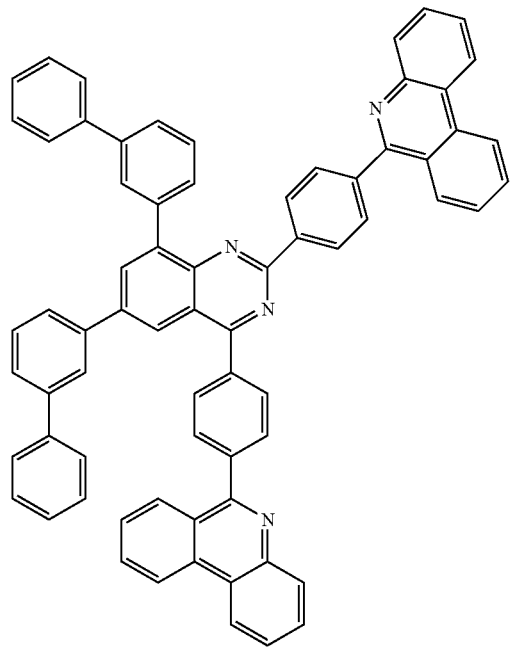
[Chemical Formula A-170]
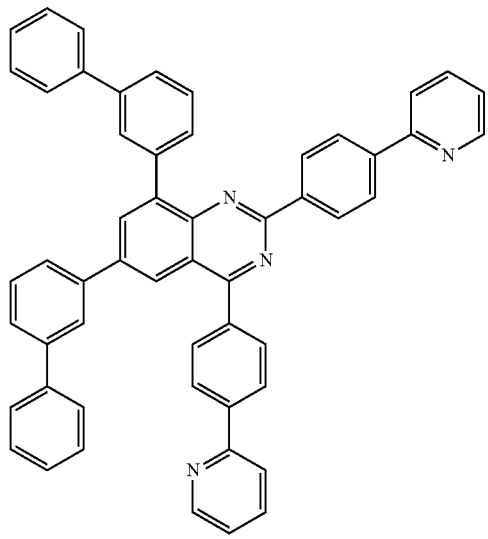
[Chemical Formula A-171]
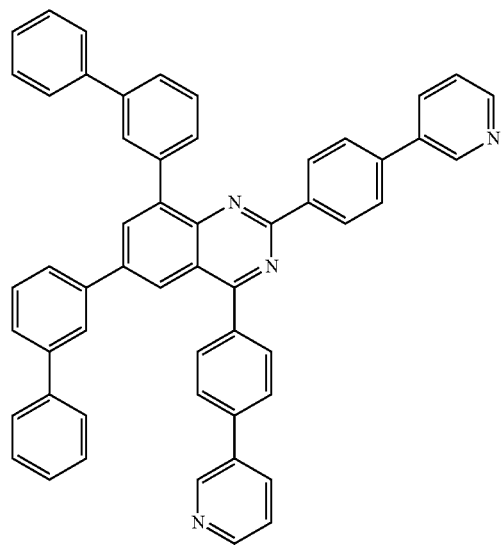
[Chemical Formula A-172]
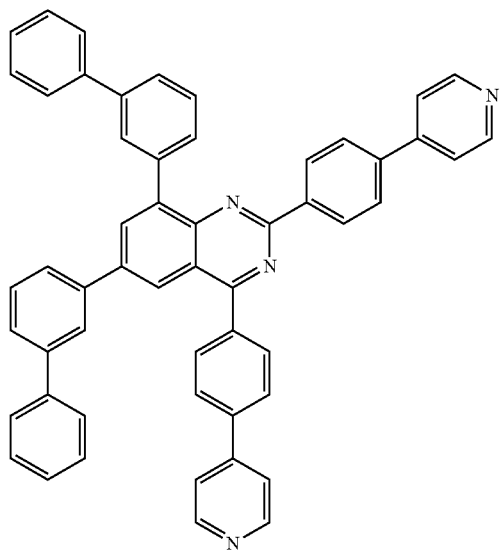

-continued
[Chemical Formula A-173]
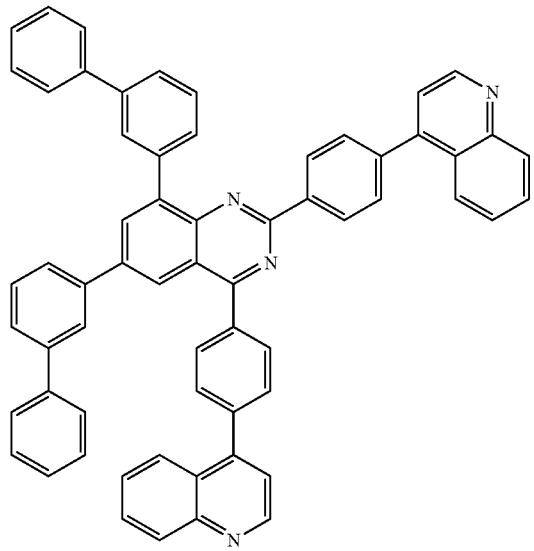
[Chemical Formula A-174]
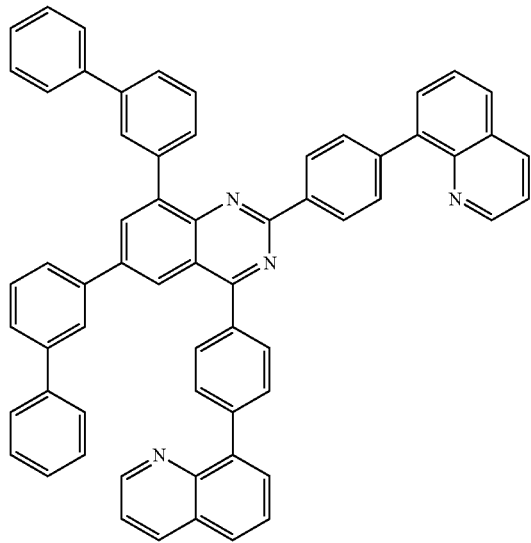
[Chemical Formula A-175]
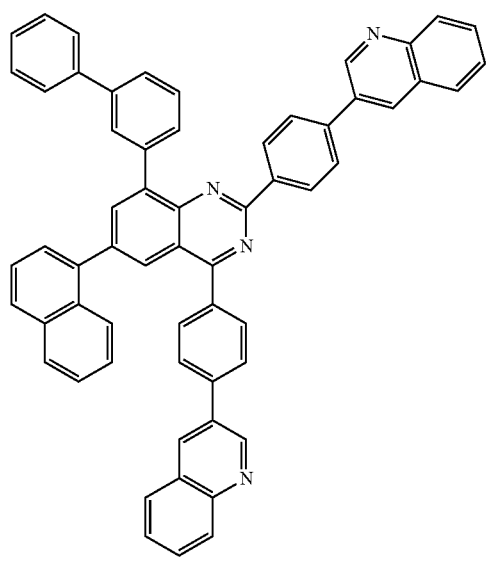
[Chemical Formula A-176]
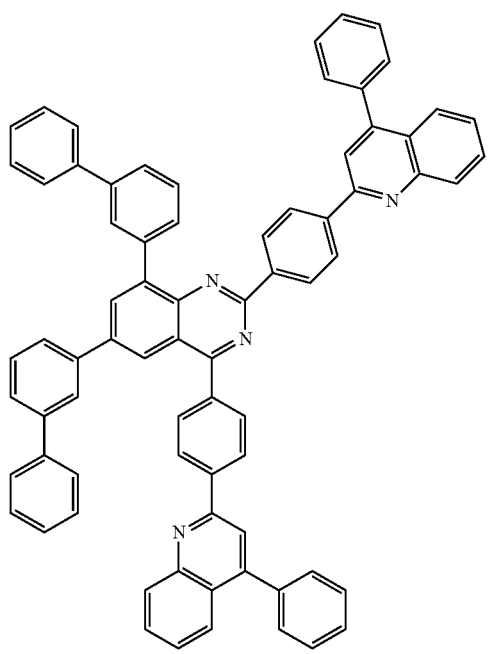

[Chemical Formula A-177]
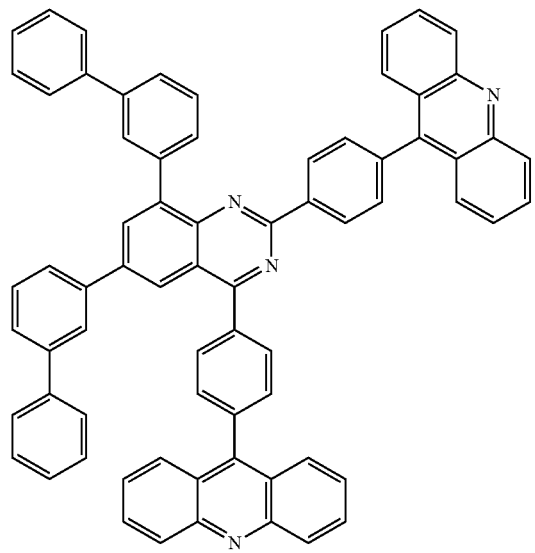
[Chemical Formula A-178]
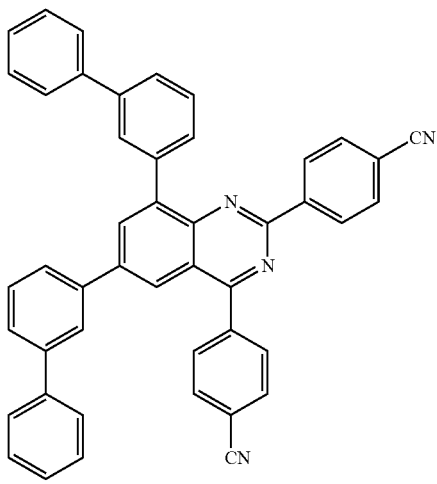
[Chemical Formula A-179]
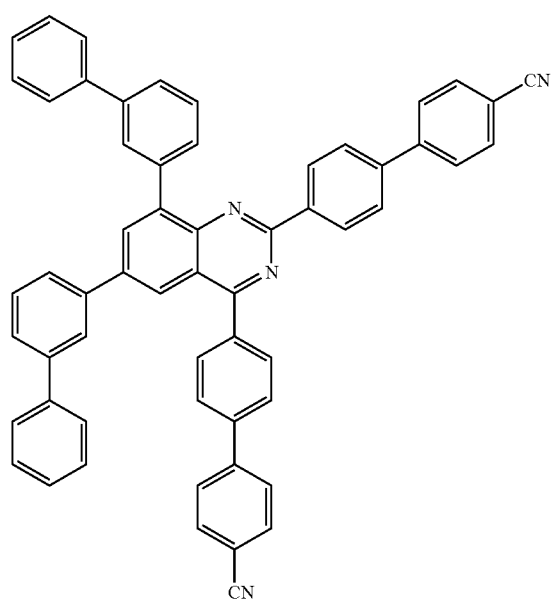
[Chemical Formula A-180]
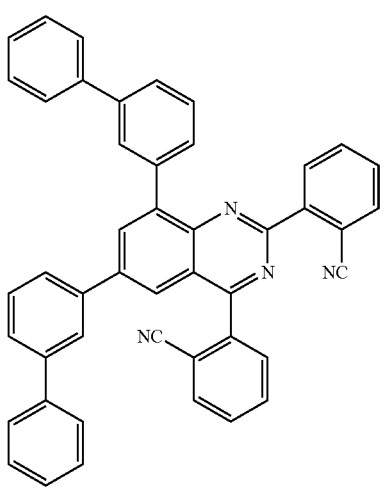

[Chemical Formula 181]
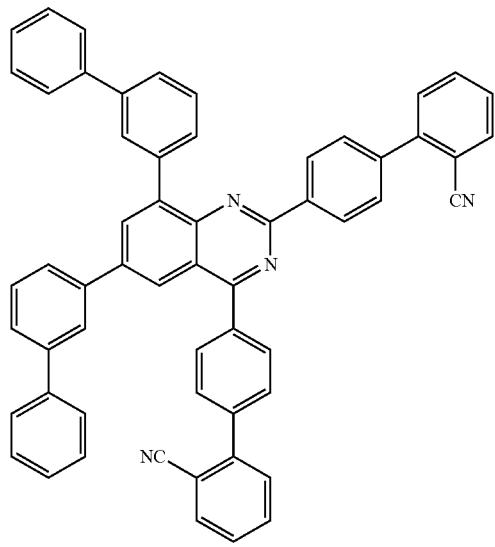
[Chemical Formula A-182]
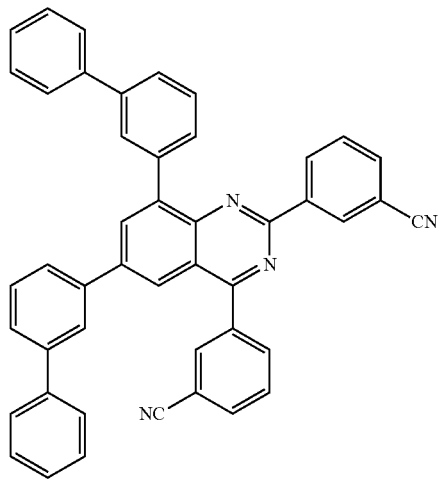
[Chemical Formula A-183]
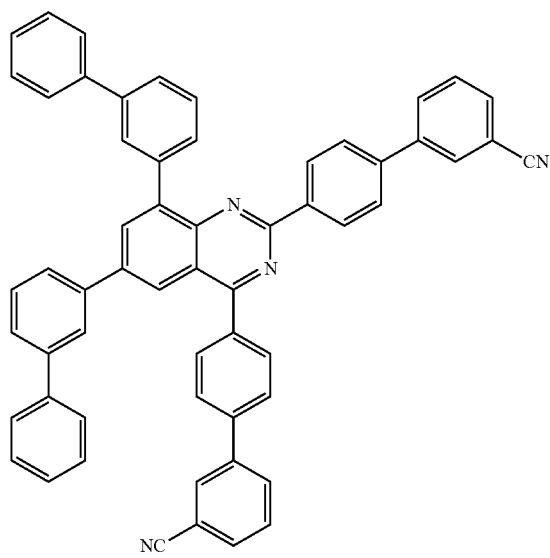
[Chemical Formula A-184]
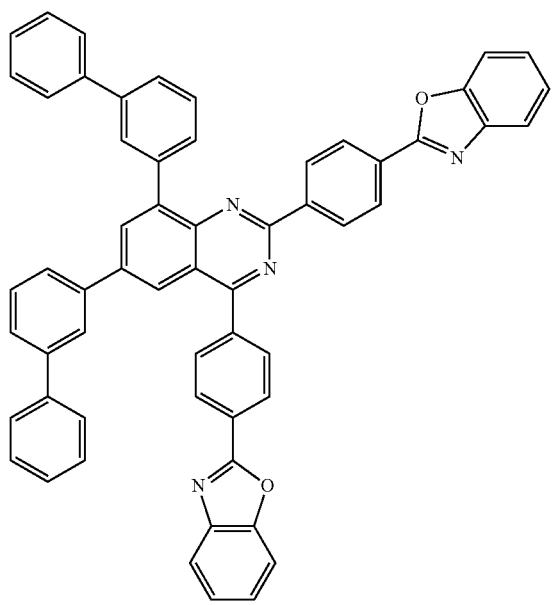

-continued
[Chmeical Formula A-185]
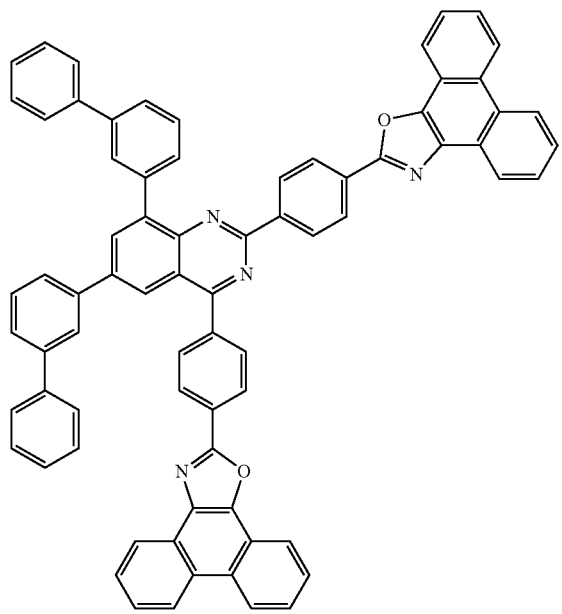
[Chemical Formula A-186]
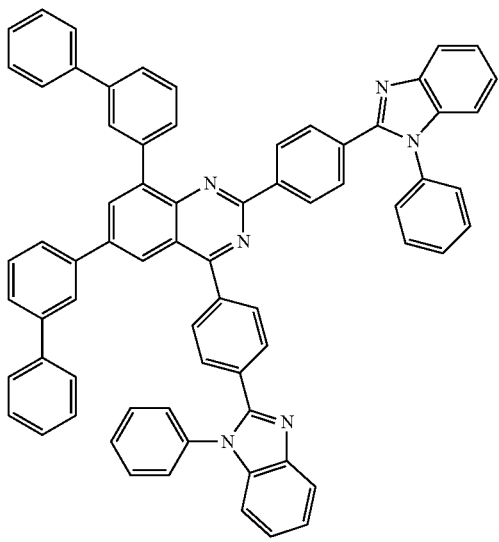
[Chemical Formula A-187]
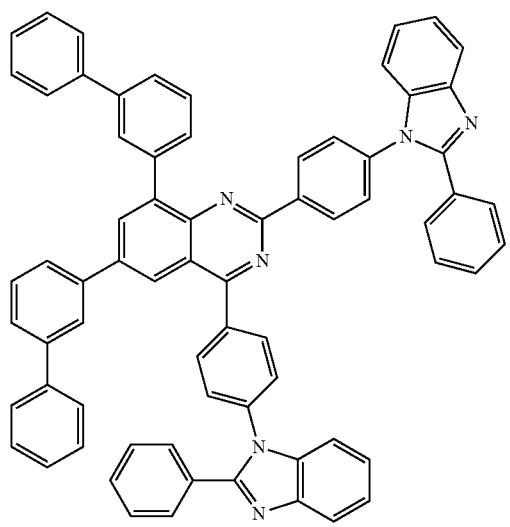
[Chemical Formula A-188]
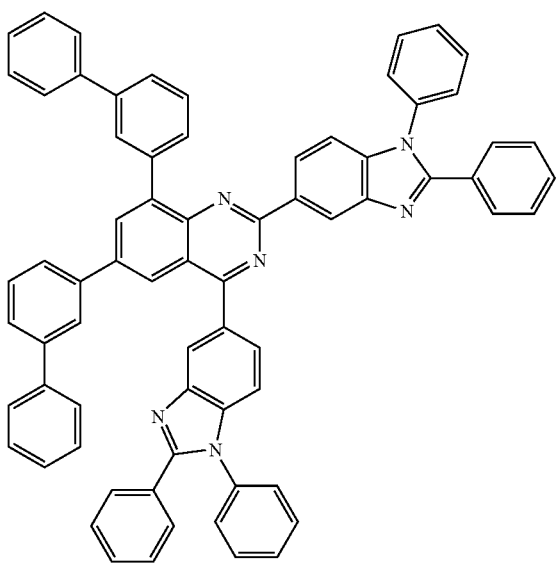

[Chemical Formula A-189]
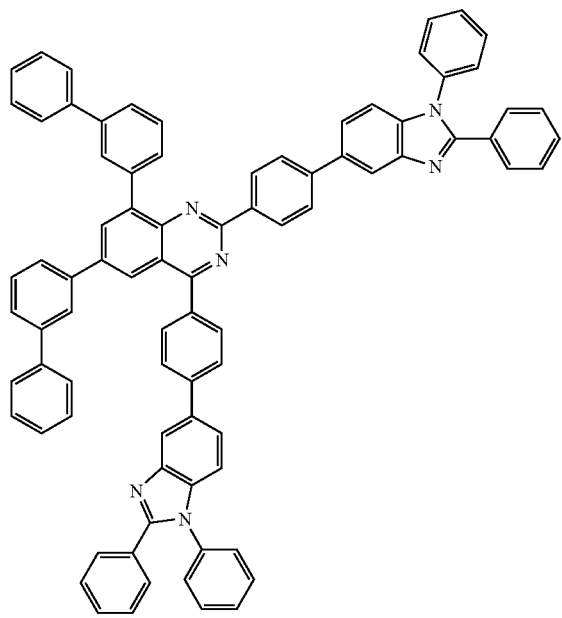
[Chemical Formula A-190]
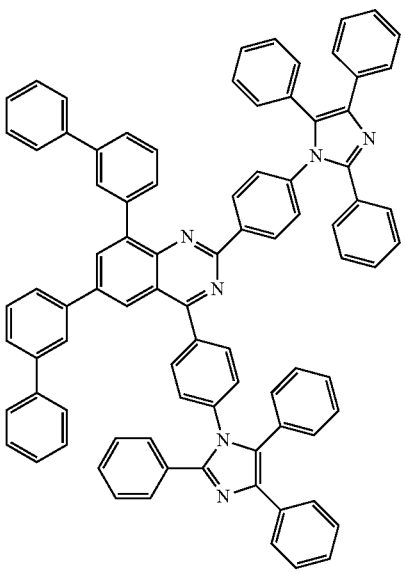
[Chemical Formula A-191]
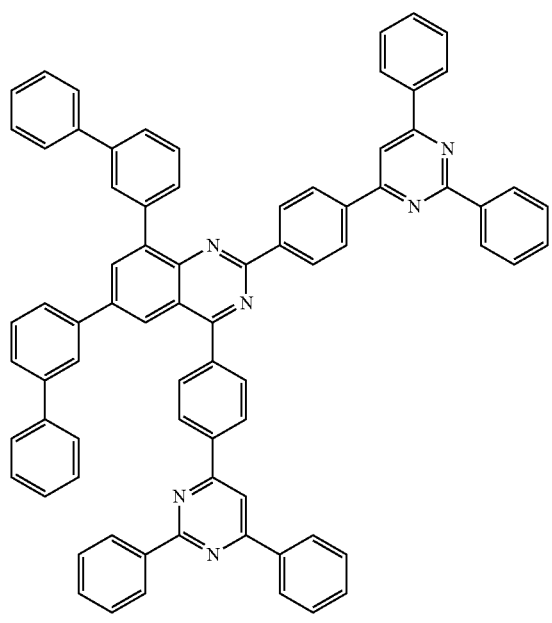
[Chemical Formula A-192]
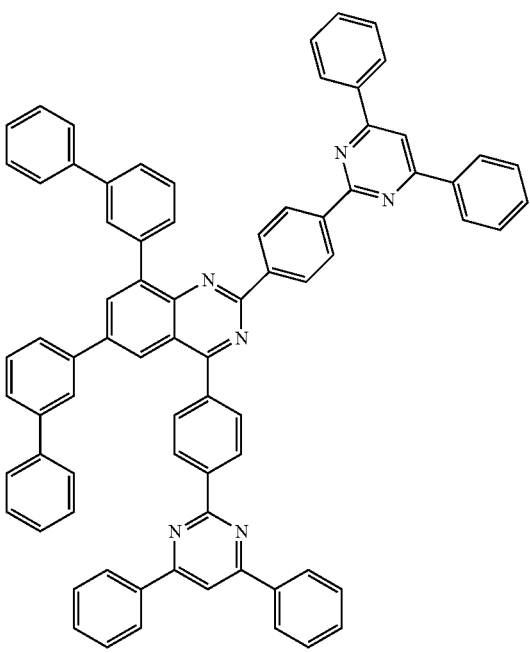

-continued
[Chemical Formula A-193]
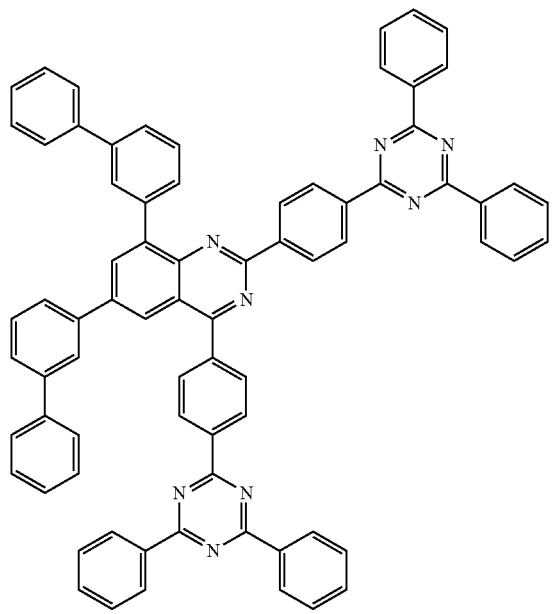
[Chemical Formula A-194]
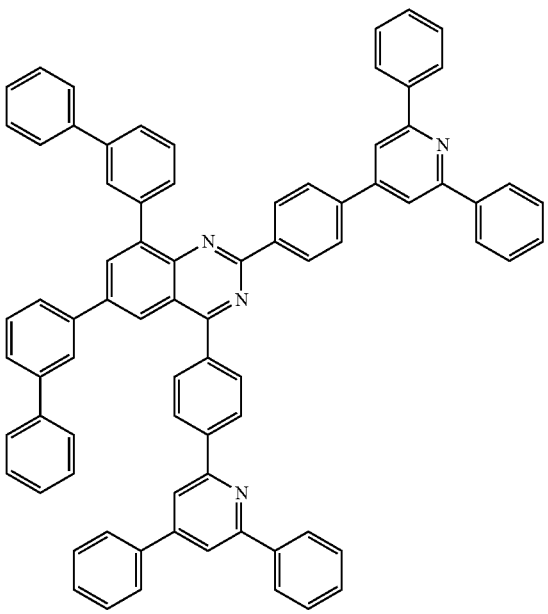
[Chemical Formula A-195]
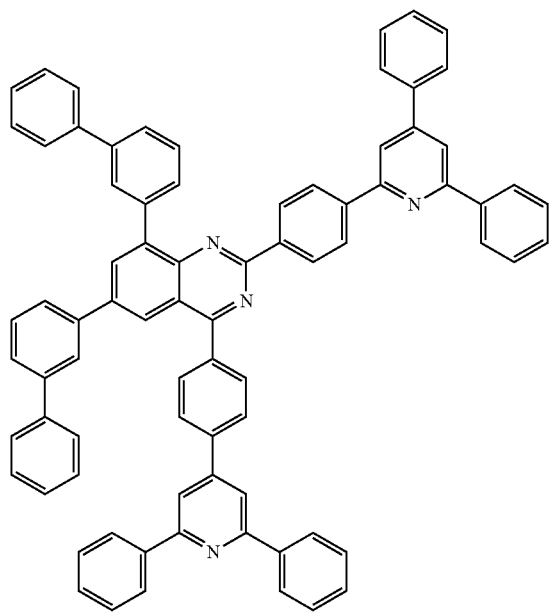
[Chemical Formula A-196]
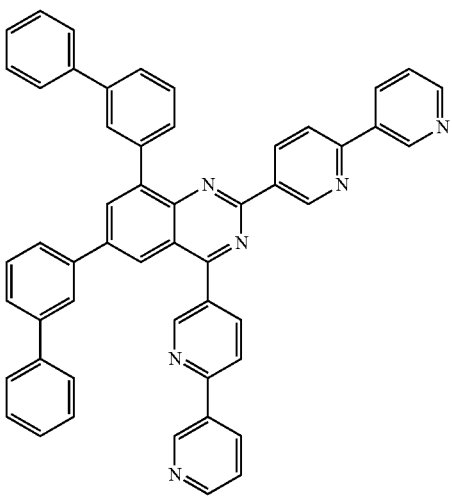

[Chemical Formula A-197]
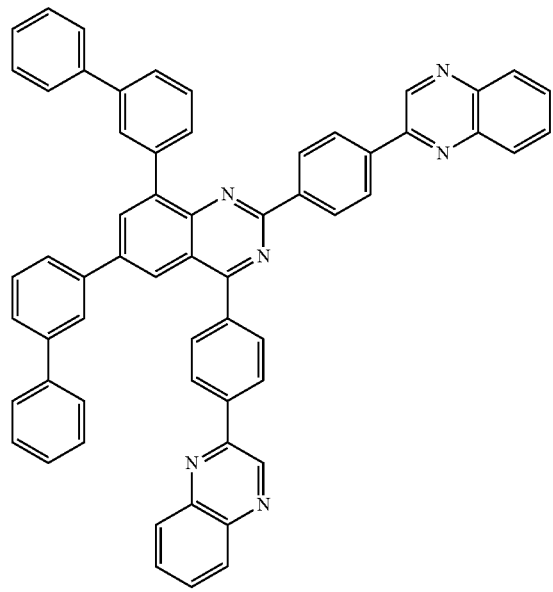
[Chemical Formula A-198]
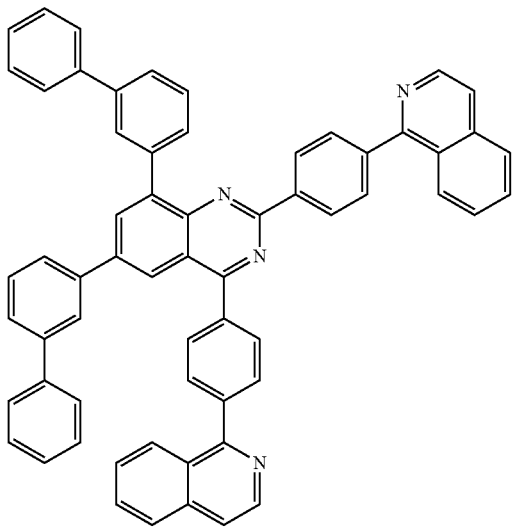
[Chemical Formula A-199]
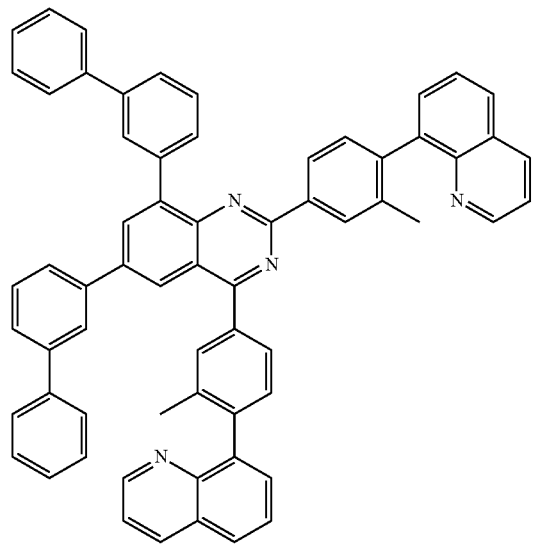
[Chemical Formula A-200]
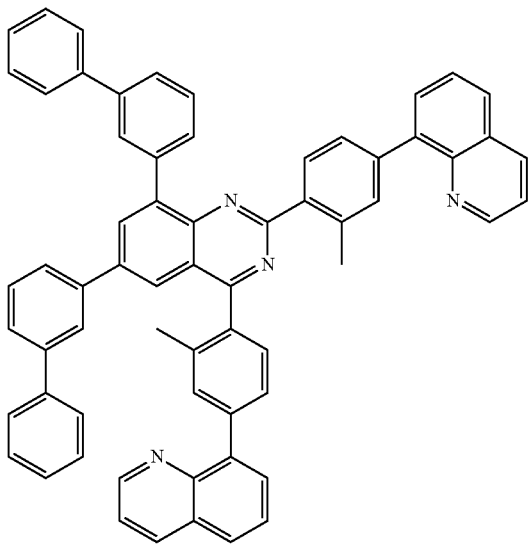

[Chemical Formula A-201]
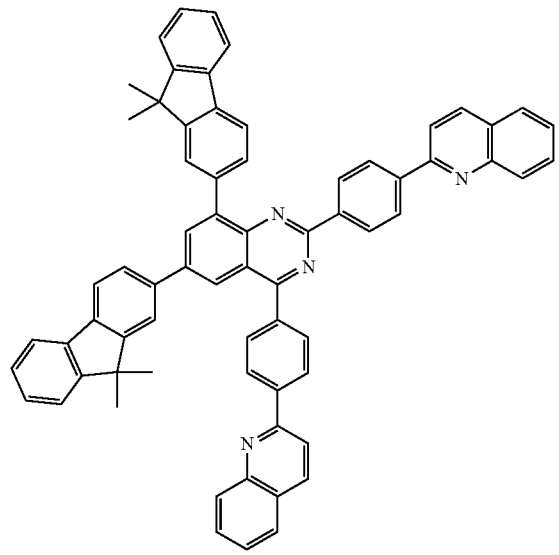
[Chemical Formula A-202]
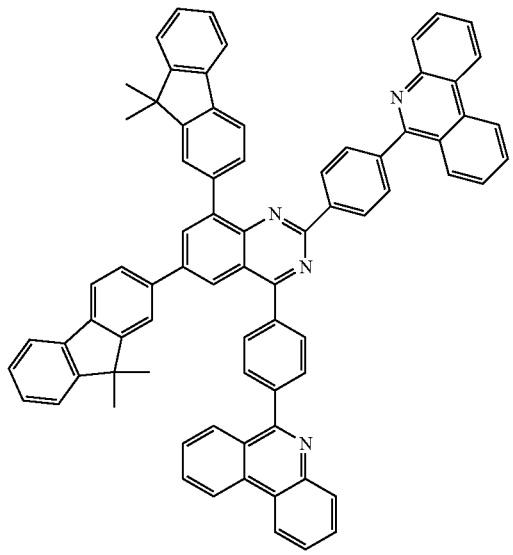
[Chemical Formula A-203]
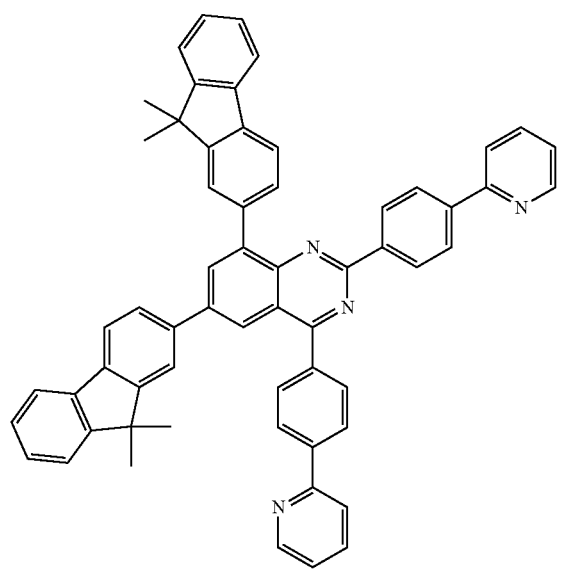
[Chemical Formula A-204]
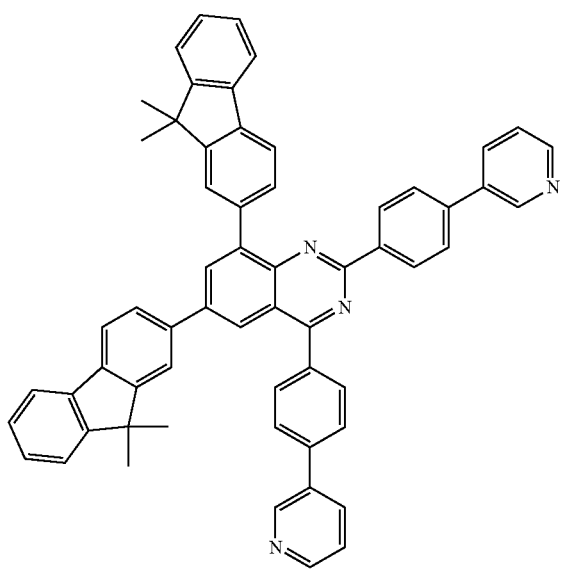

[Chemical Formula A-205]
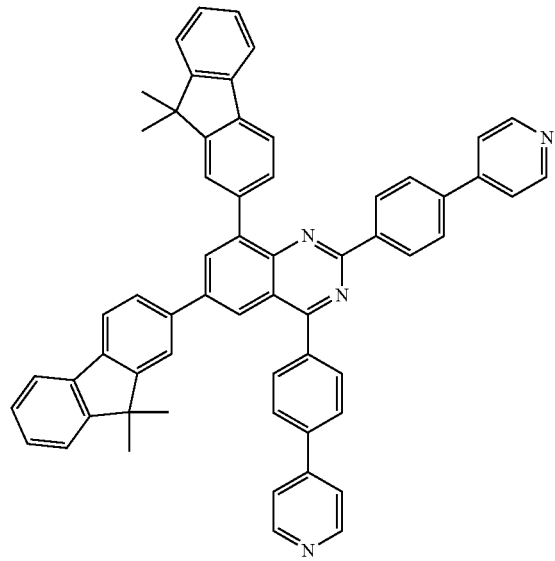
[Chemical Formula A-206]
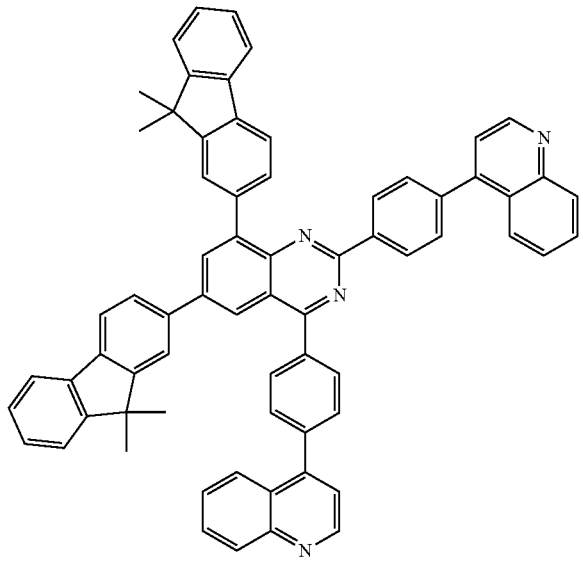
[Chemical Formula A-207]
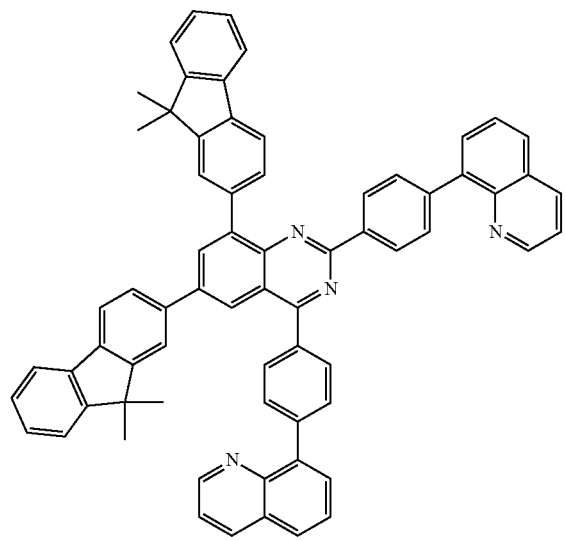
[Chemical Formula A-208]
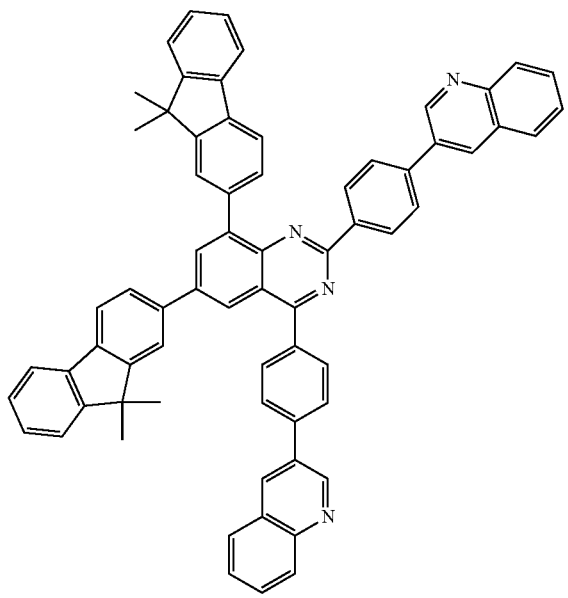

[Chemical Formula A-209]
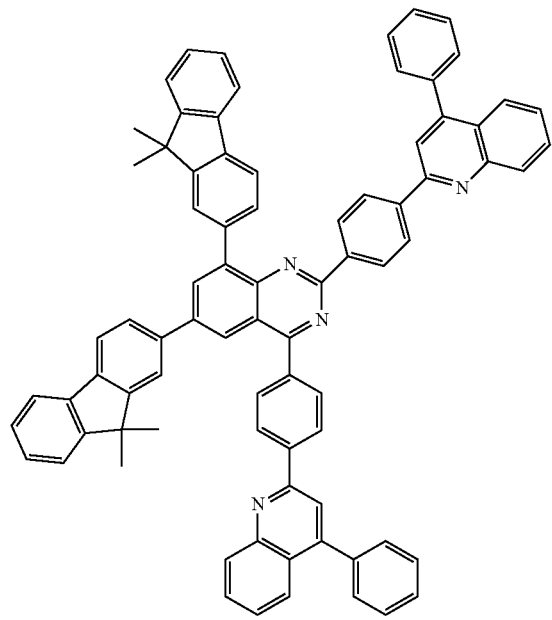
[Chemical Formula A-210]
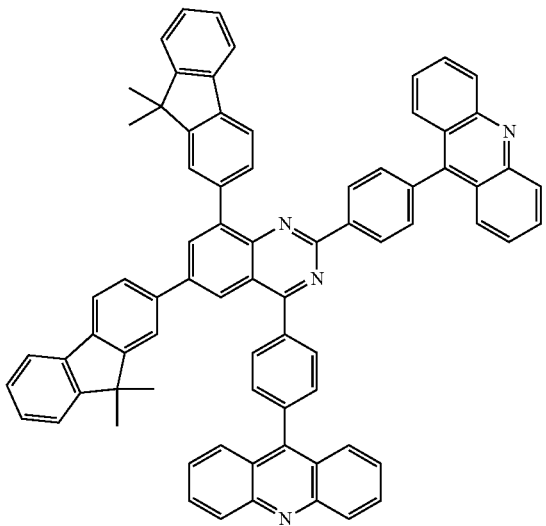
[Chemical Formula A-211]
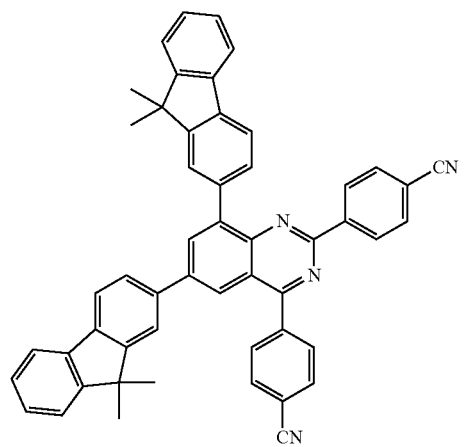
[ChemICal Formula A-212]
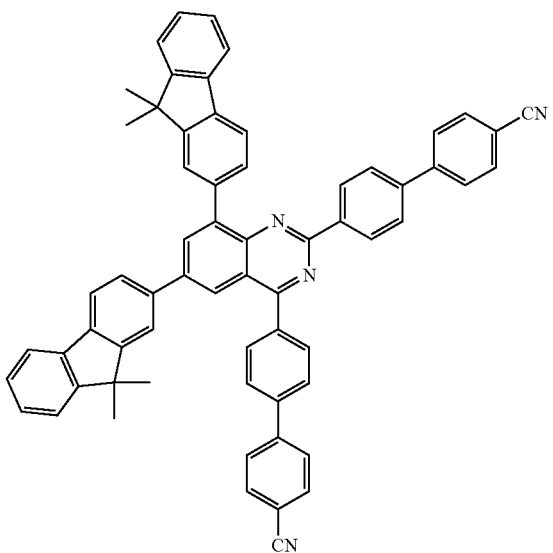

[Chemical Formula A-213]
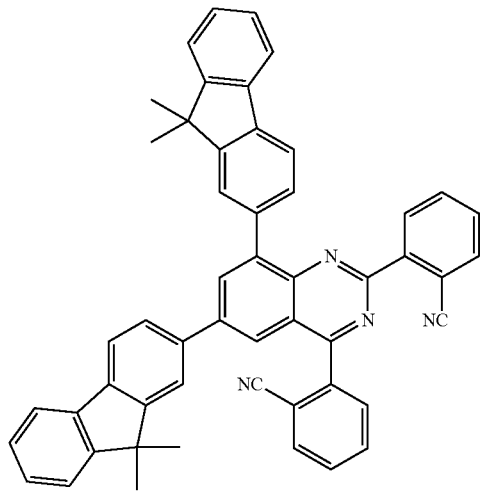
[Chemical Formula A-214]
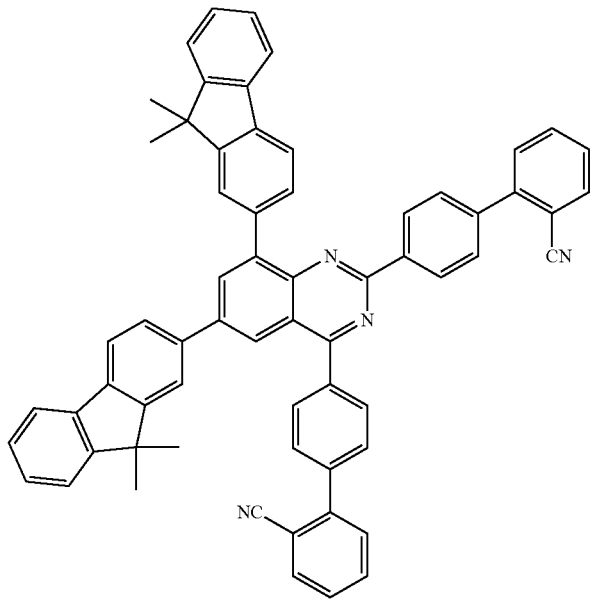
[Chemical Formula A-215]
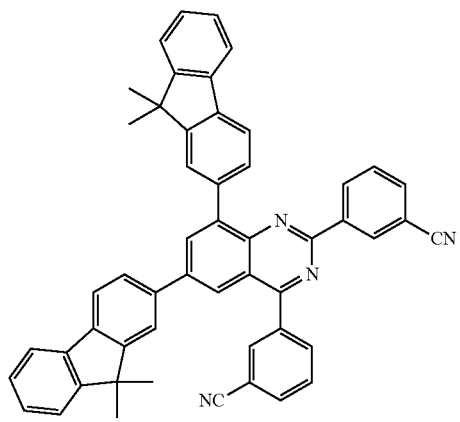
[Chemical Formula A-216]
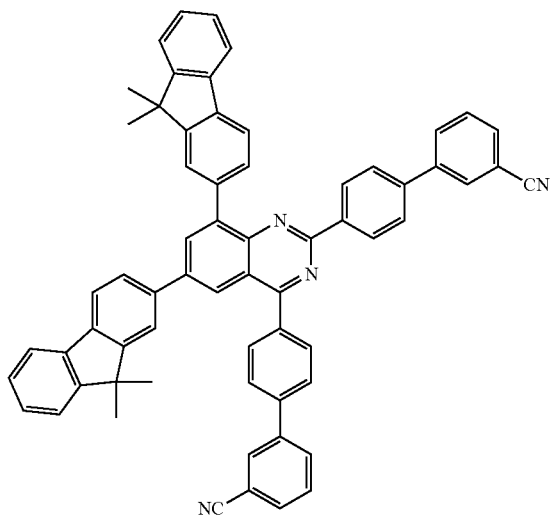

-continued
[Chemical Formula A-217]
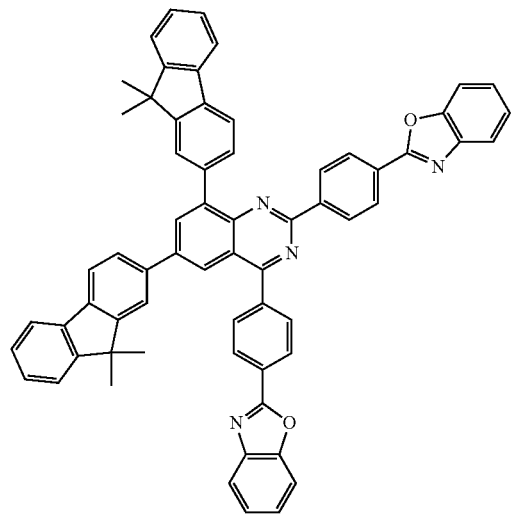
[Chemical Formula A-218]
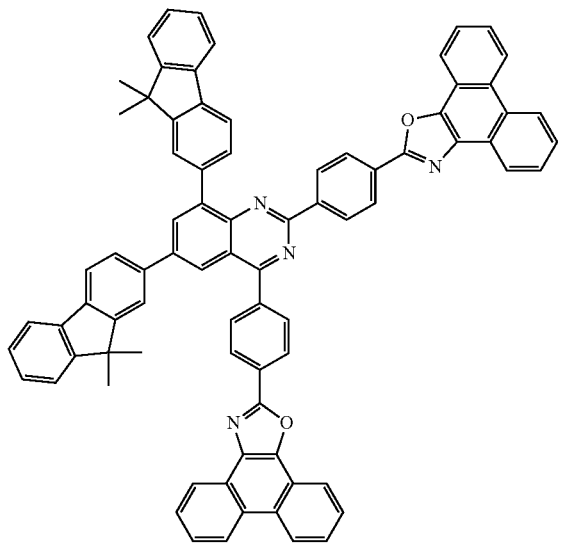
[Chemical Formula A-219]
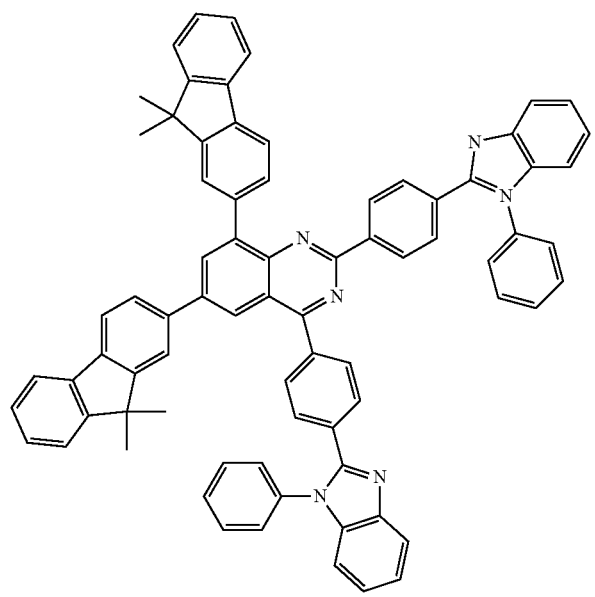
[Chemical Formula A-220]
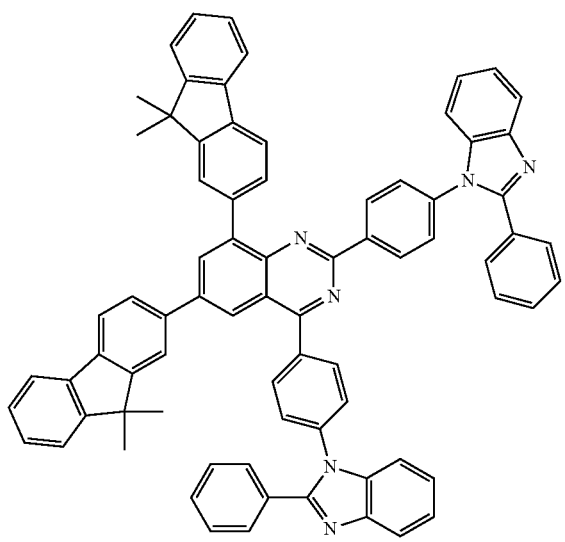

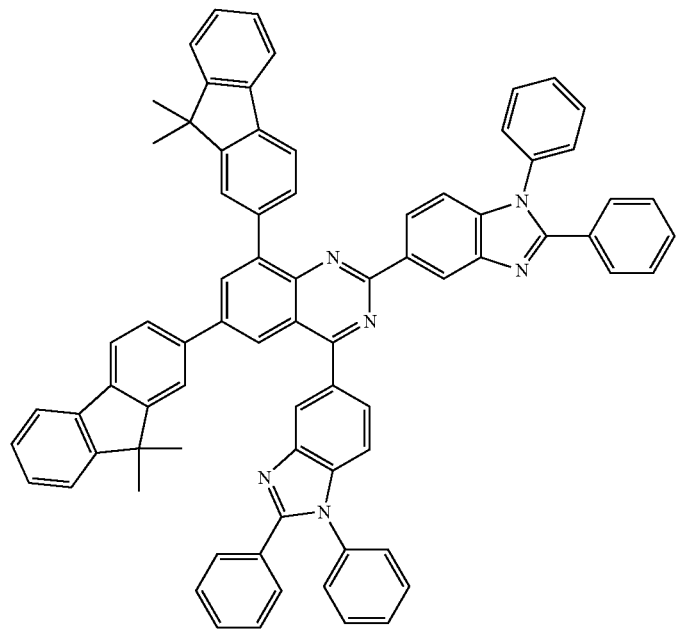
[Chemical Formula A-221]
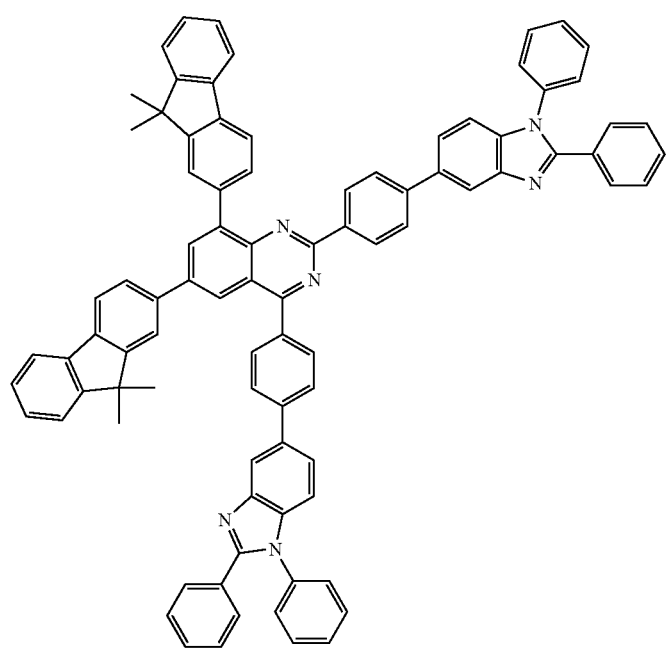
[Chemical Formula A-222]

[Chemical Formula A-223]
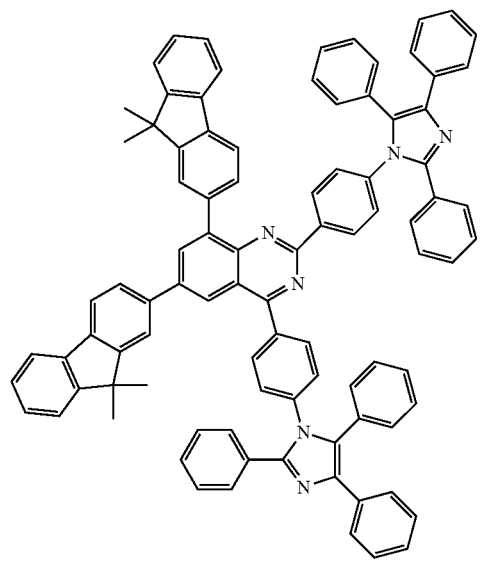
[Chemical Formula A-224]
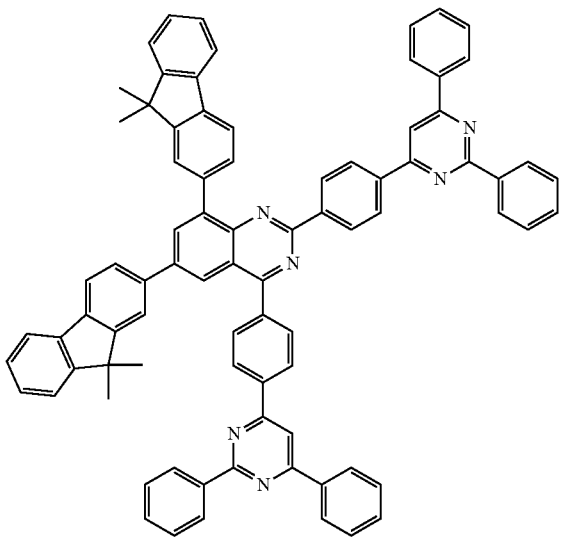
[Chemical Formula A-225]
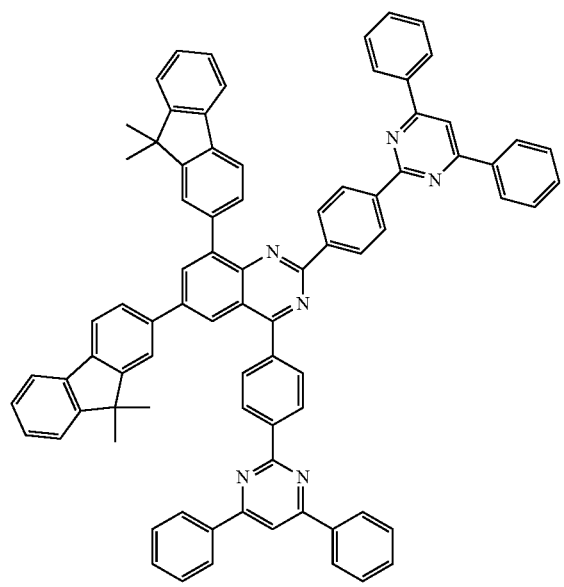
[Chemical Formula A-226]
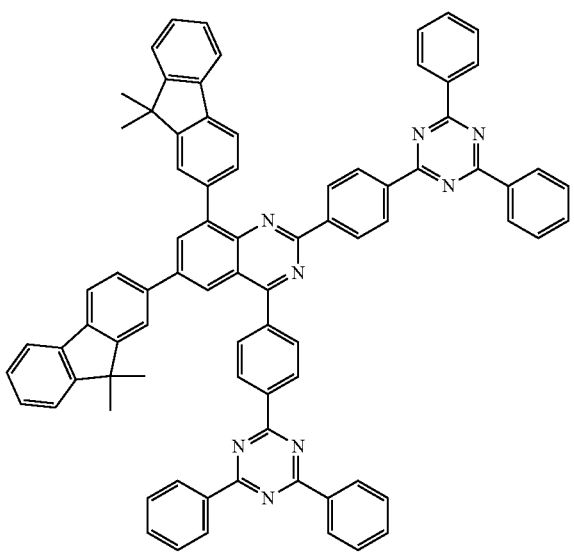

-continued
[Chemical Formula A-227]
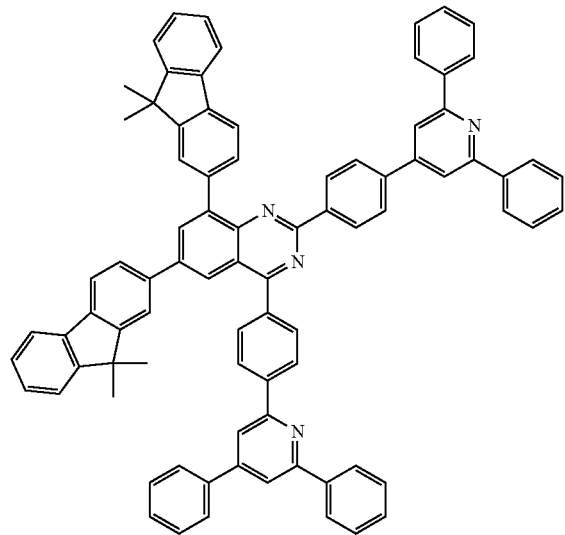
[Chemical Formula A-228]
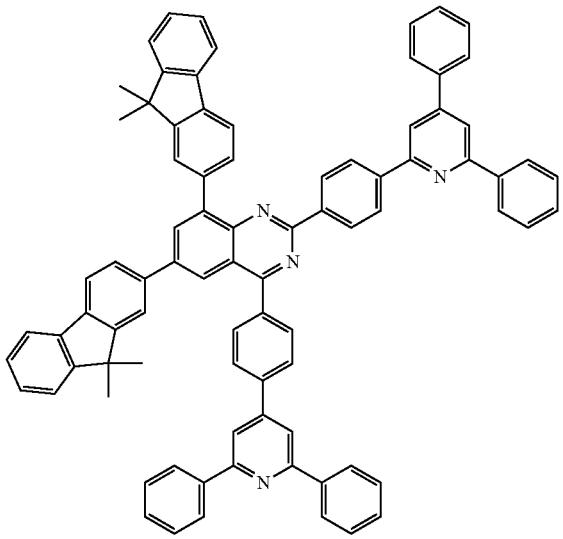
[Chemical Formula A-229]
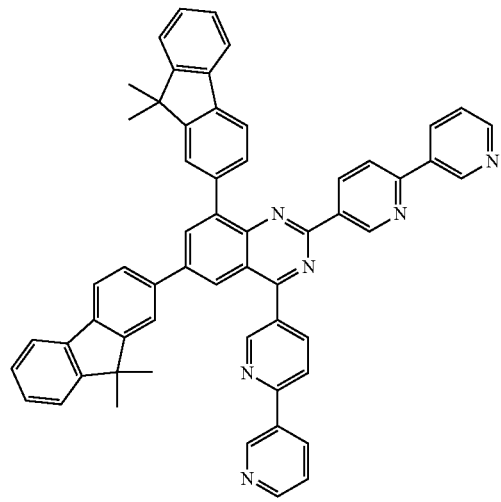
[Chemical Formula A-230]
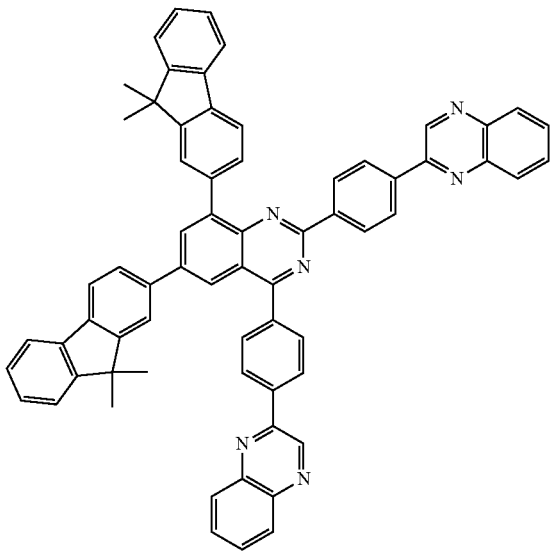

[Chemical Formula A-231]
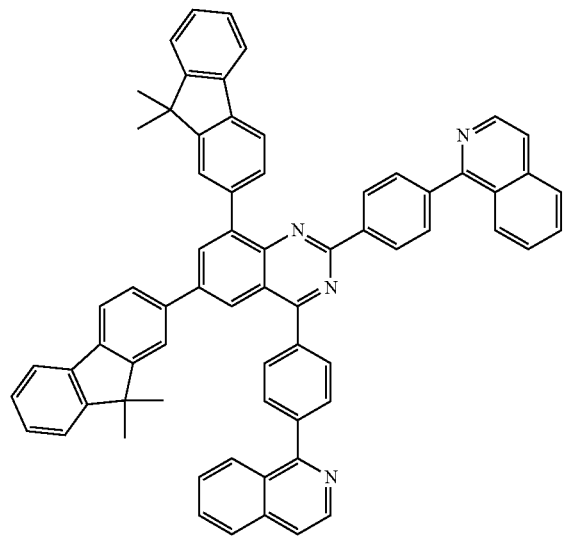
[Chemical Formula A-232]
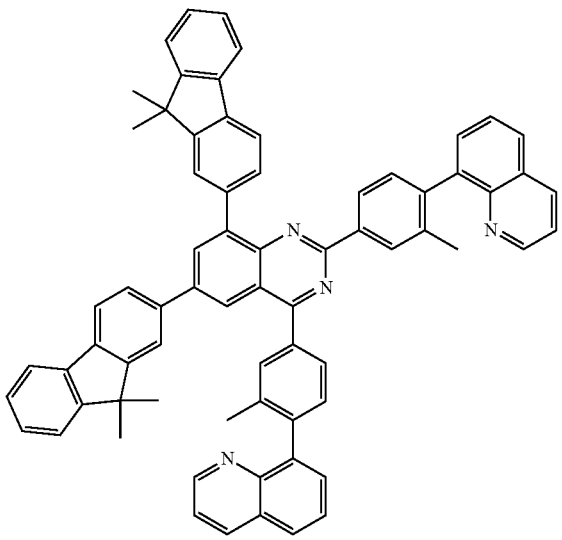
[Chemical Formula A-233]
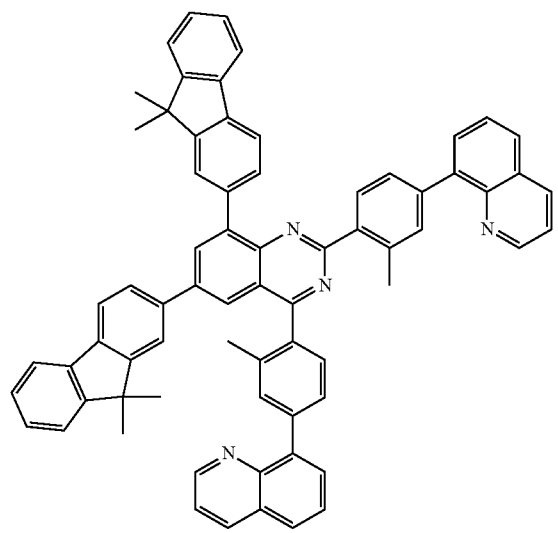
[Chemical Formula A-234]
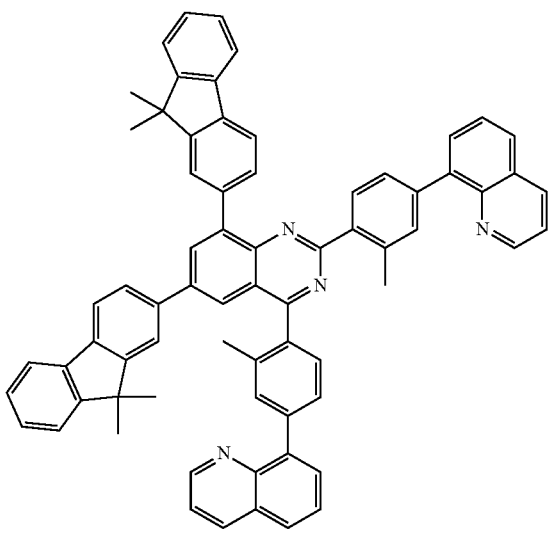

[Chemical Formula A-235]
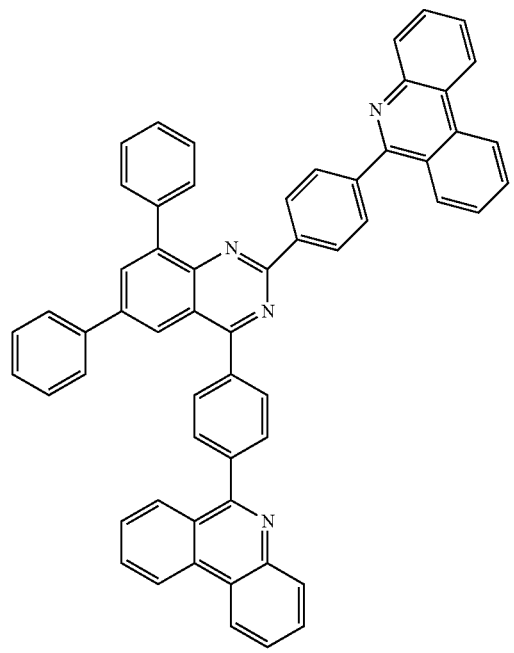
[Chemical Formula A-236]
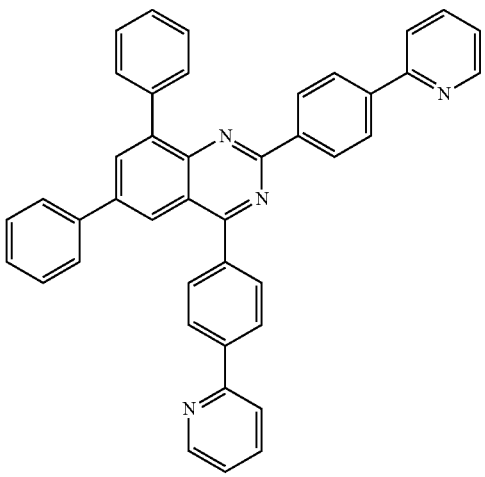
[Chemical Formula A-237]
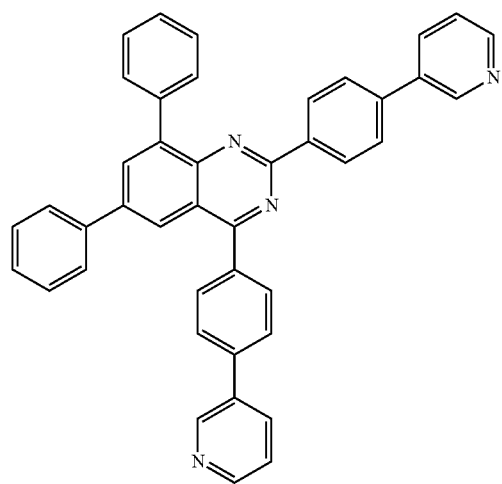
[Chemical Formula A-238]
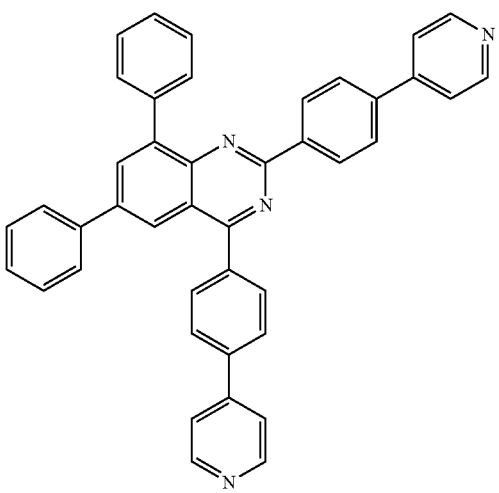

[Chemical Formula A-239]
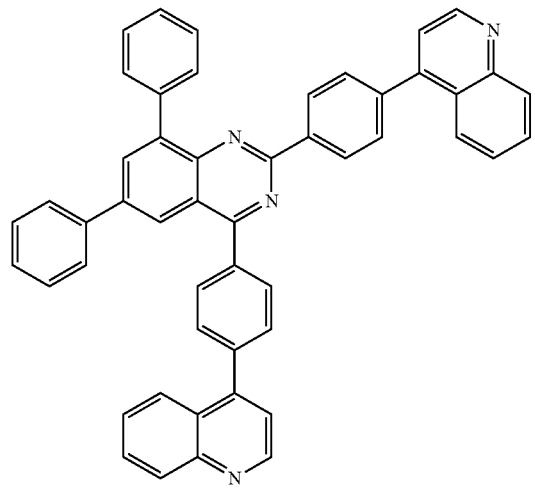
[Chemical Formula A-240]
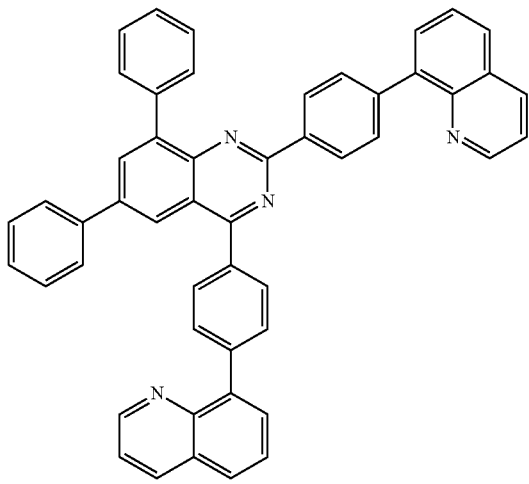
[Chemical Formula A-241]
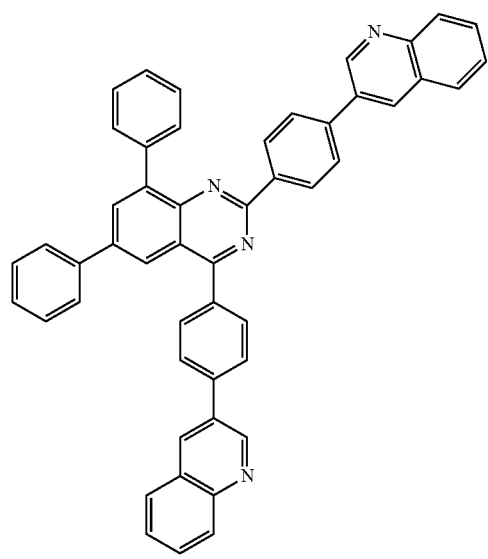
[Chemical Formula A-242]
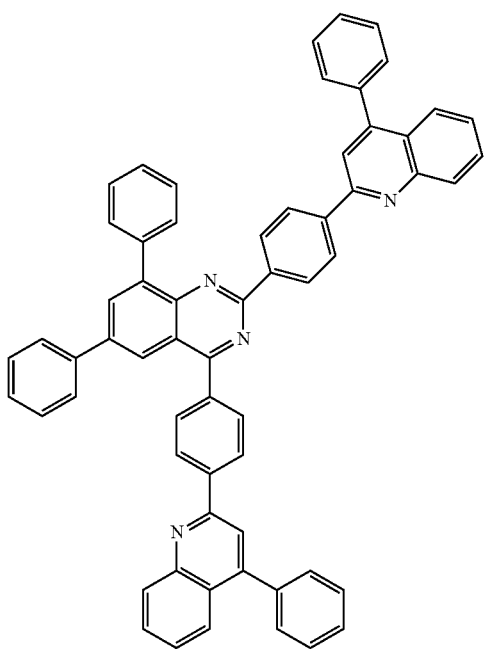

-continued
[Chemical Formula A-243]
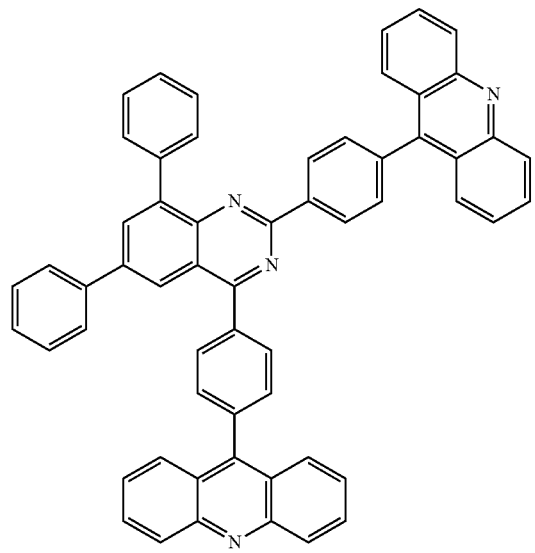
[Chemical Formula A-244]
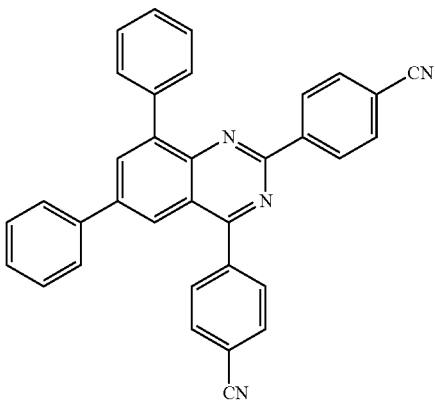
[Chemical Formula A-245]
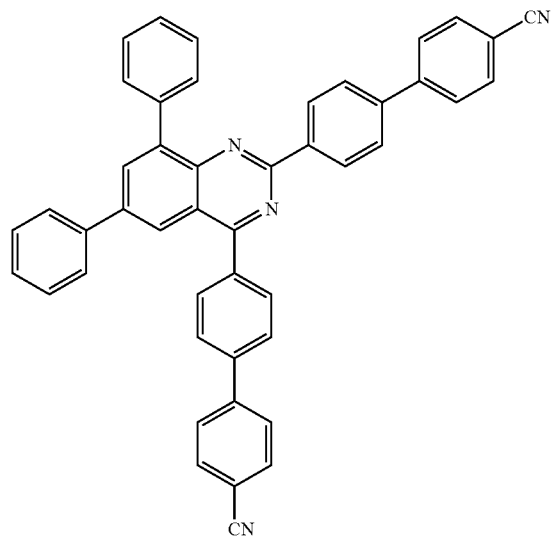
[Chemical Formula A-246]
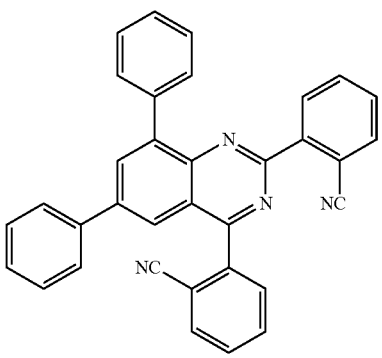
[Chemical Formula A-247]
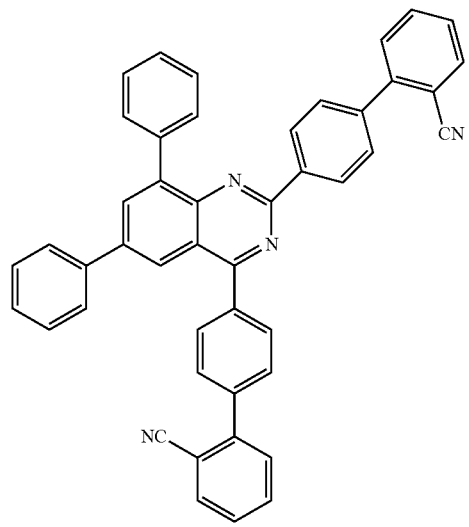
[Chemical Formula A-248]
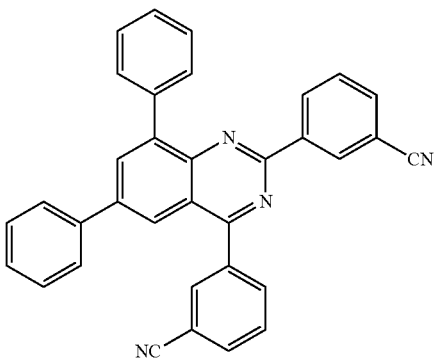

[Chemical Formula A-249]
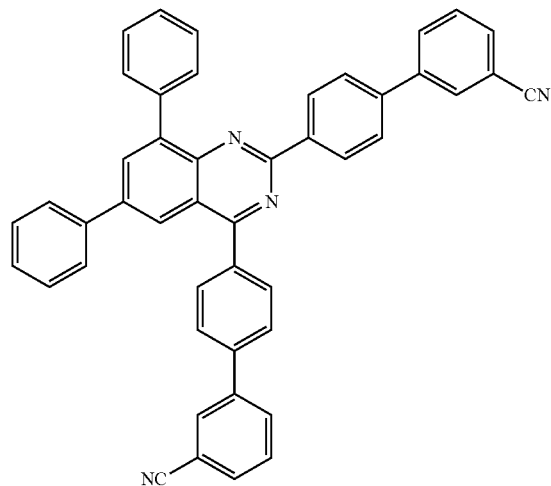
[Chemical Formula A-250]
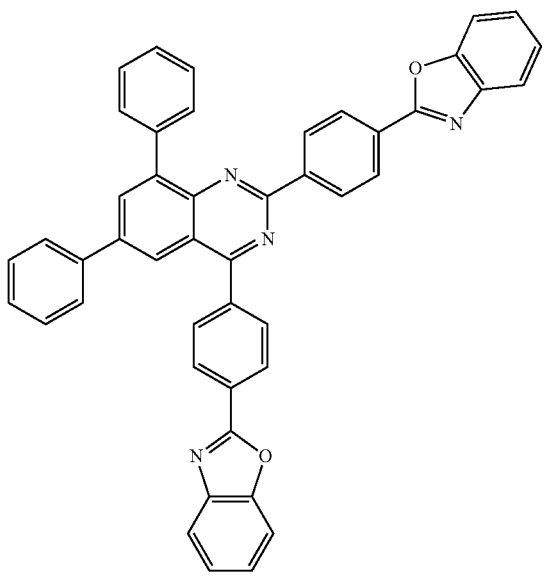
[Chemical Formula A-251]
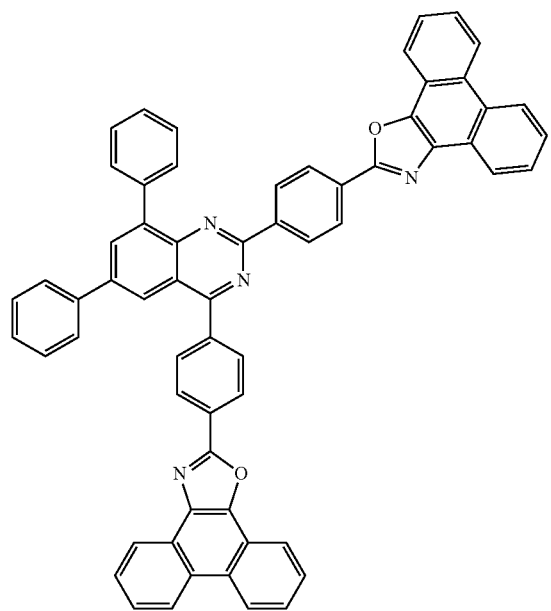
[Chemical Formula A-252]
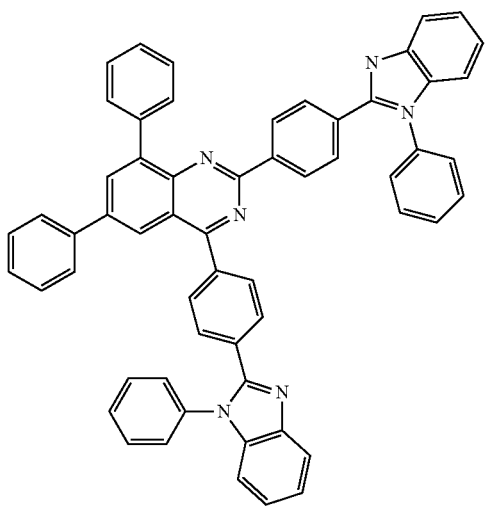

[Chemical Formula A-253]
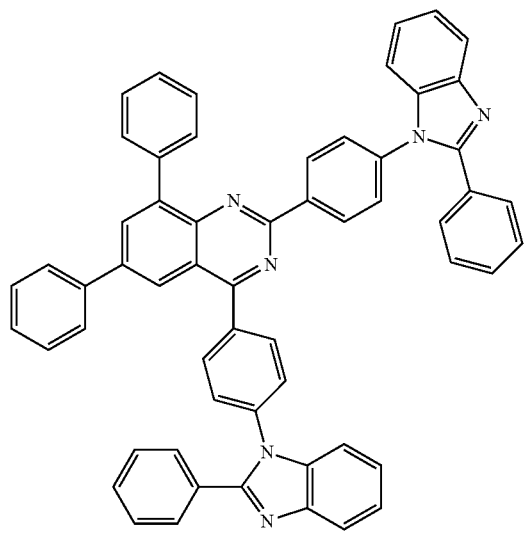
[Chemical Formula A-254]
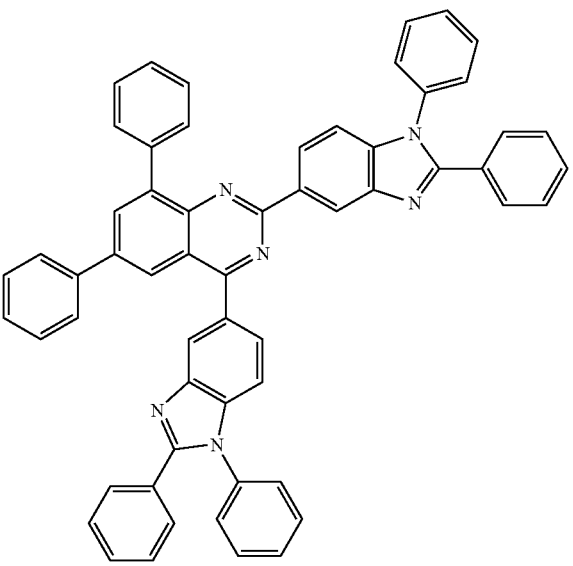
[Chemical Formula A-255]
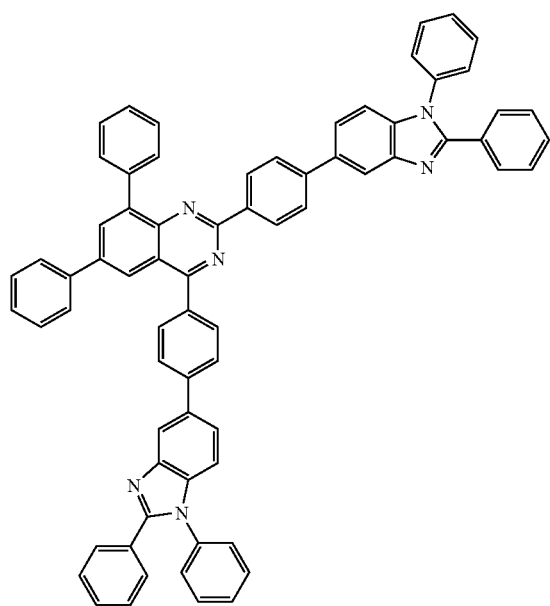
[Chemical Formula A-256]
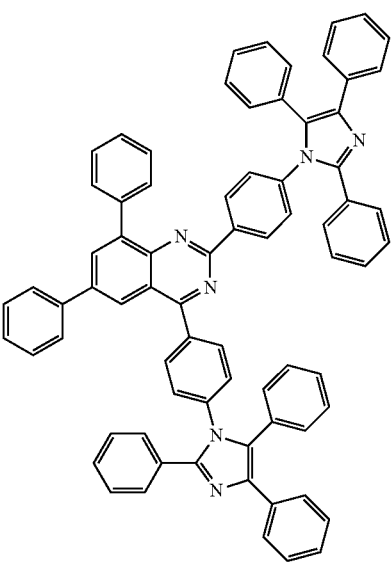

[Chemical Formula A-257]
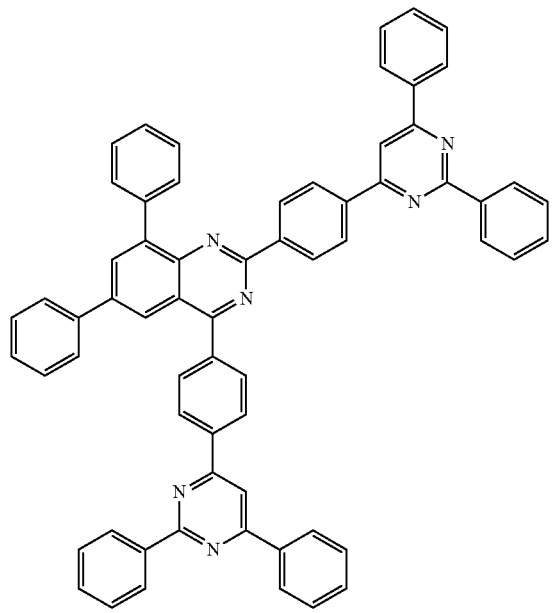
[Chemical Formula A-258]
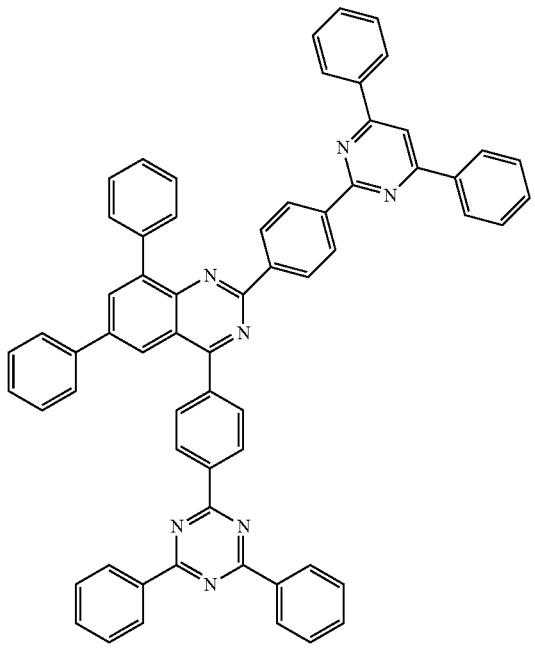
[Chemical Formula A-259]
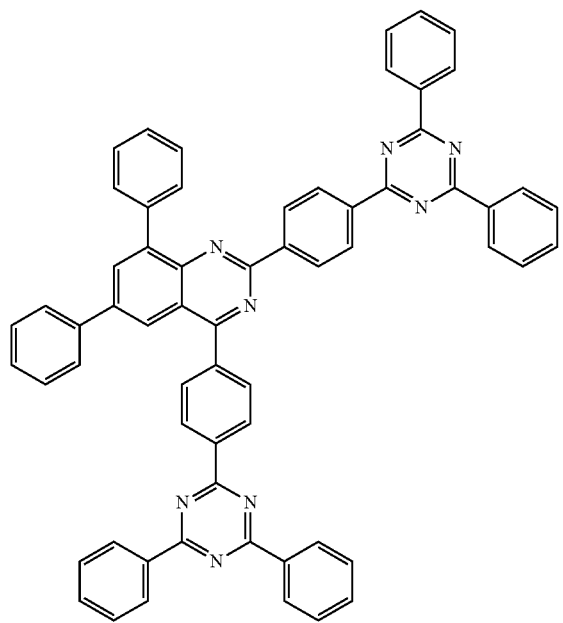
[Chemical Formula A-260]
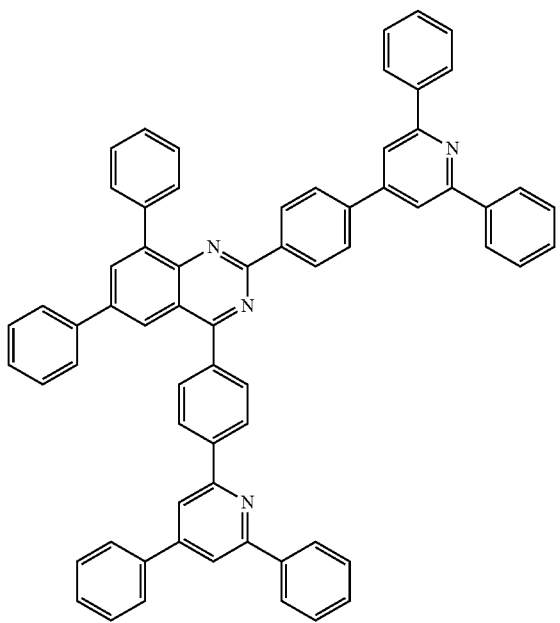

[Chemical Formula A-261]
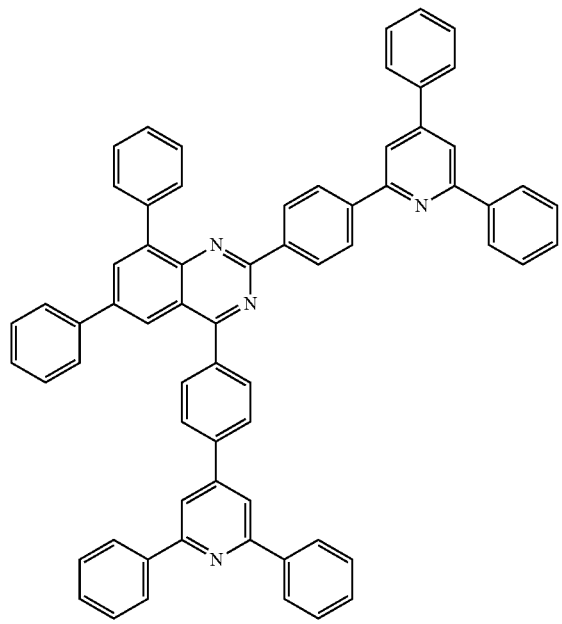
[Chemical Formula A-262]
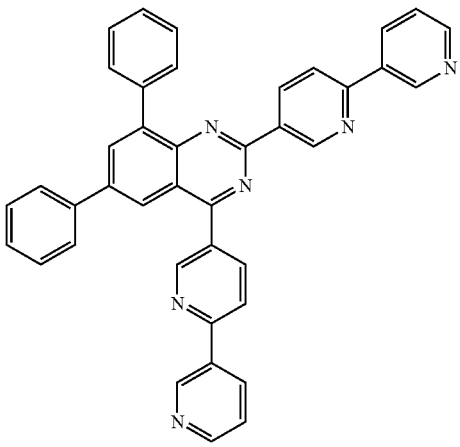
[Chemical Formula A-263]
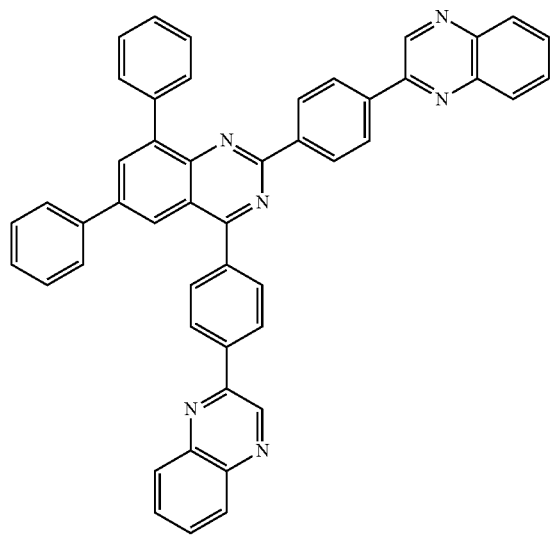
[Chemical Formula A-264]
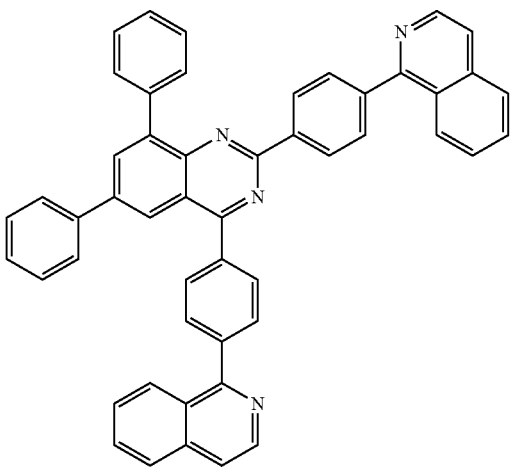

-continued
[Chemical Formula A-265]
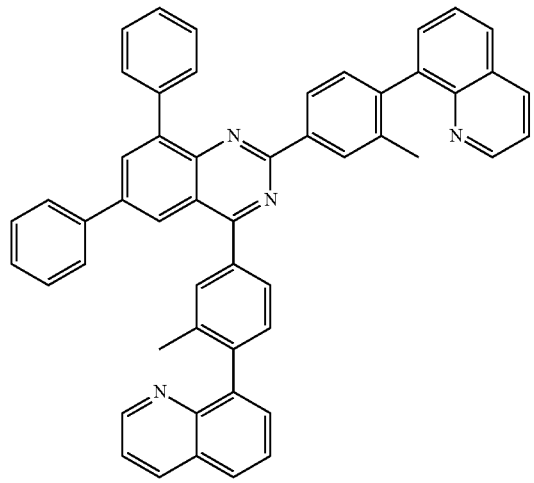
[Chemical Formula A-266]
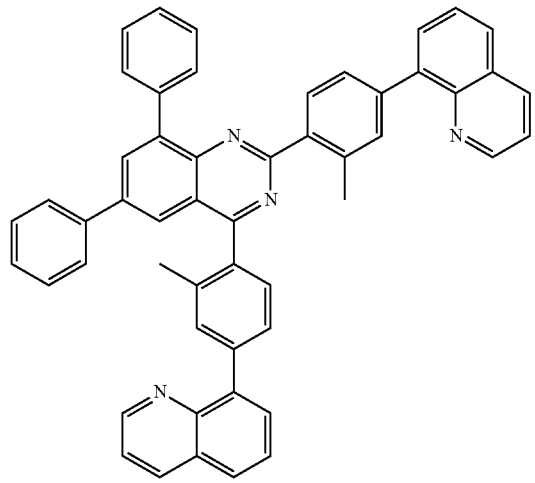
[Chemical Formula A-267]
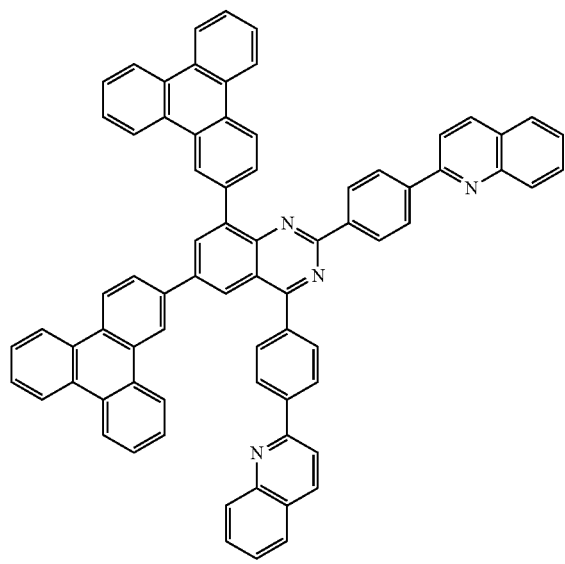
[Chemical Formula A-268]
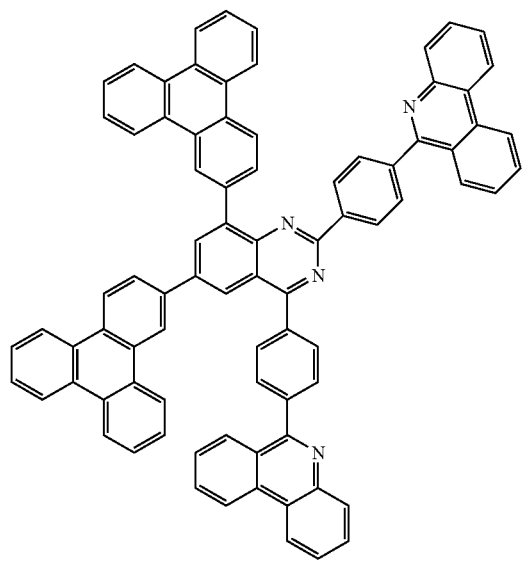
[Chemical Formula A-269]
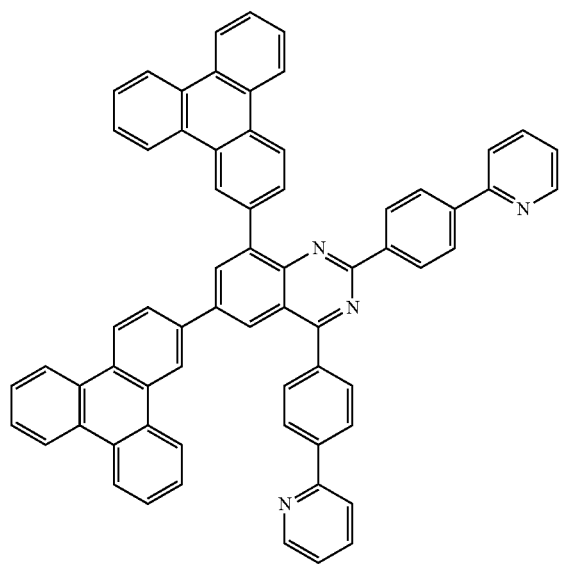
[Chemical Formula A-270]
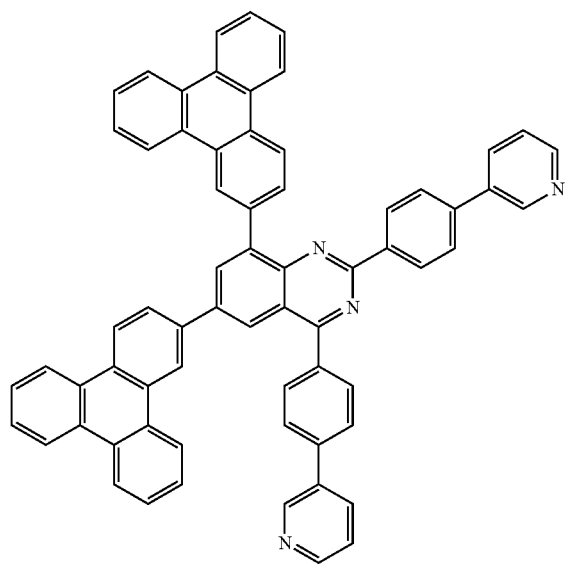

[Chemical Formula A-271]
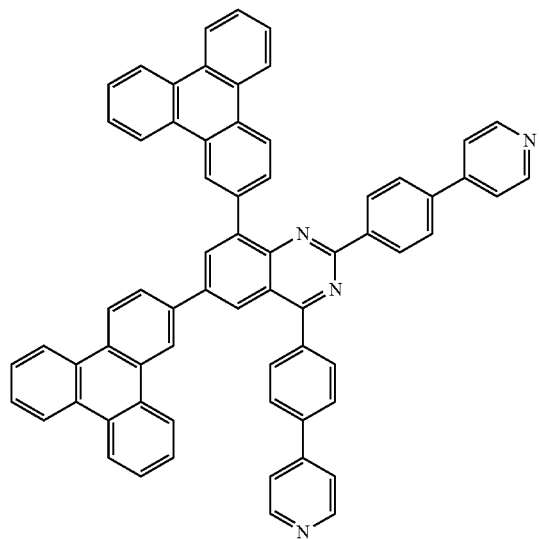
[Chemical Formula A-272]
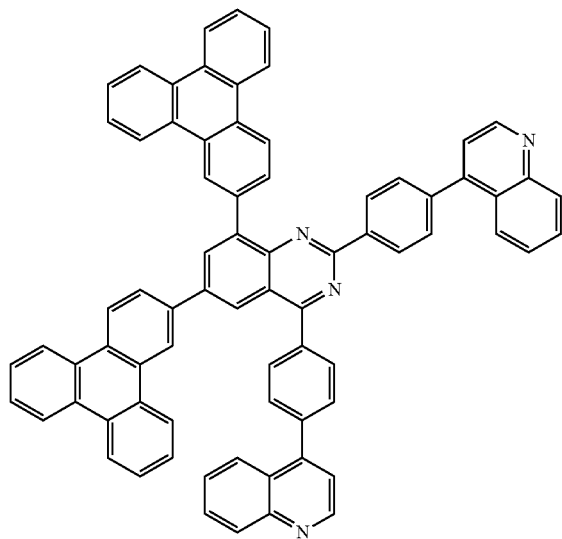
[Chemical Formula A-273]
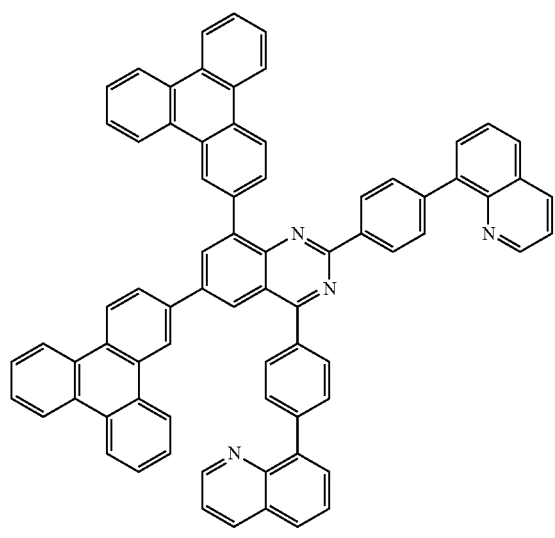
[Chemical Formula A-274]
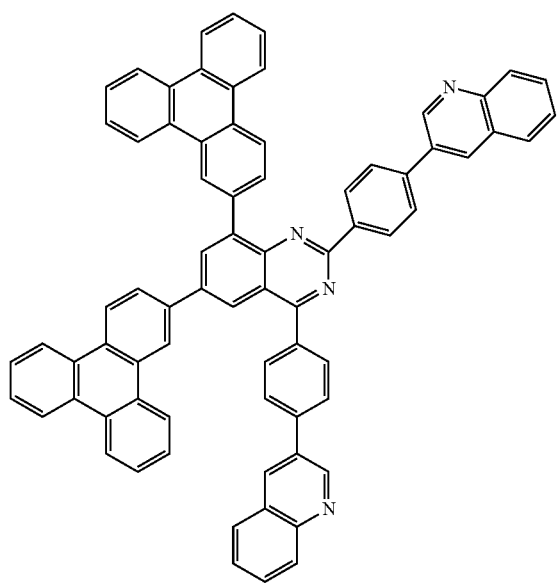

[Chemical Formula A-275]
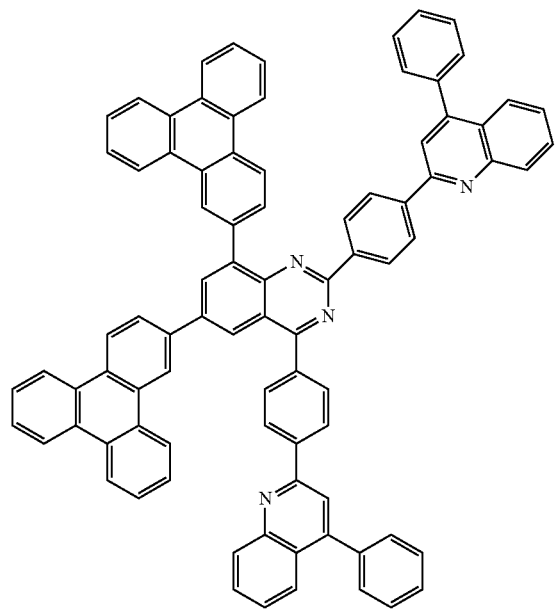
[Chemical Formula A-276]
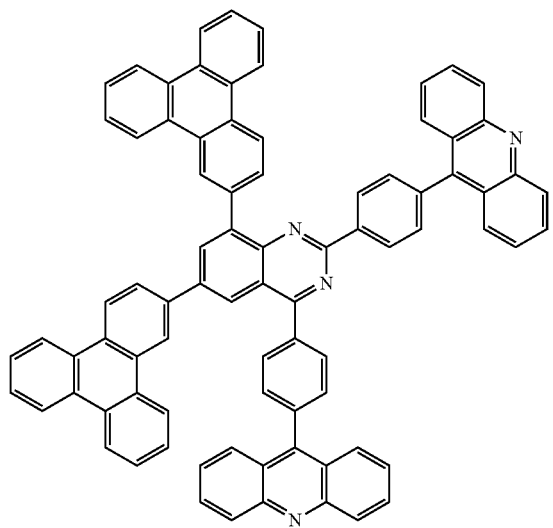
[Chemical Formula A-277]
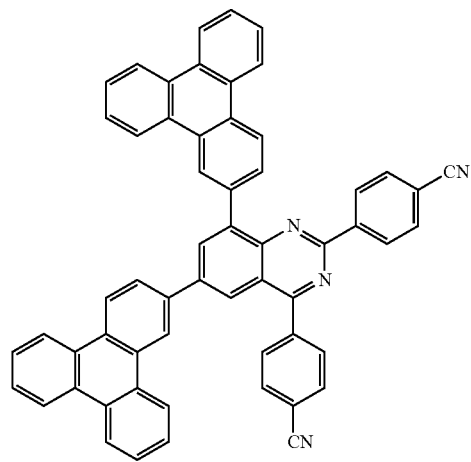
[Chemical Formula A-278]
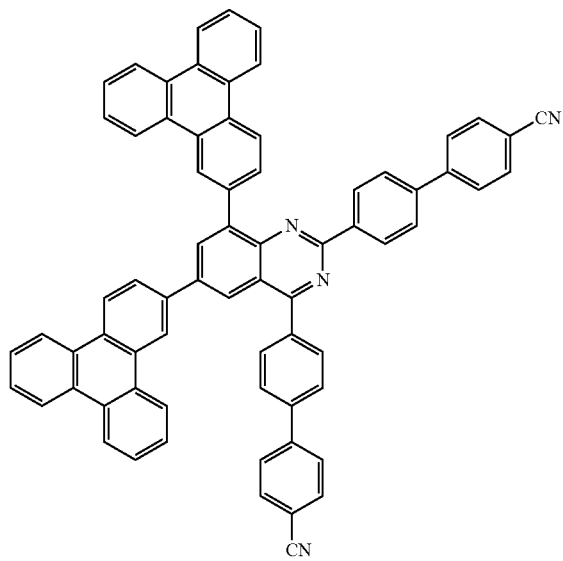

337
-continued
[Chemical Formula A-279]
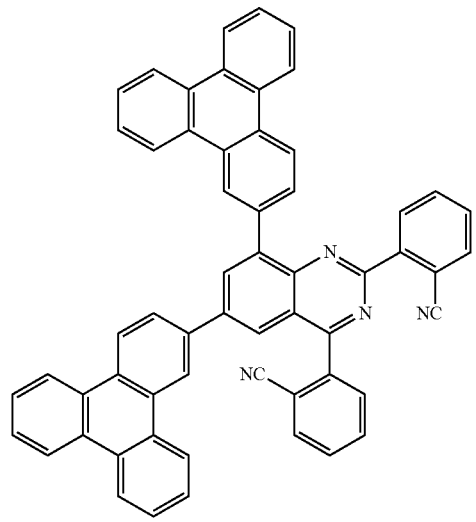
[Chemical Formula A-280]
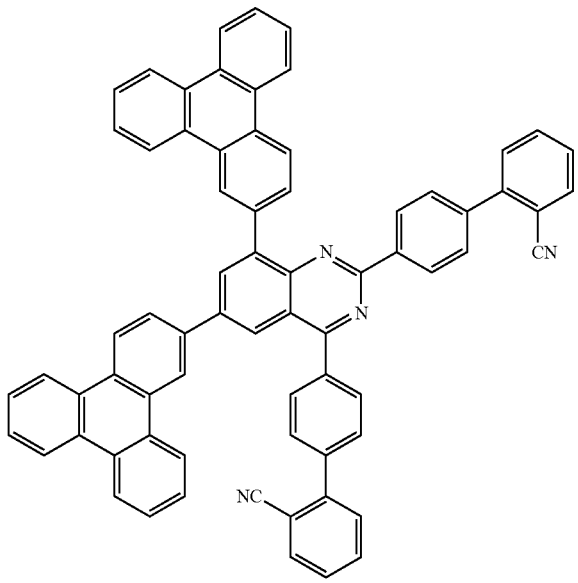
[Chemical Formula A-281]
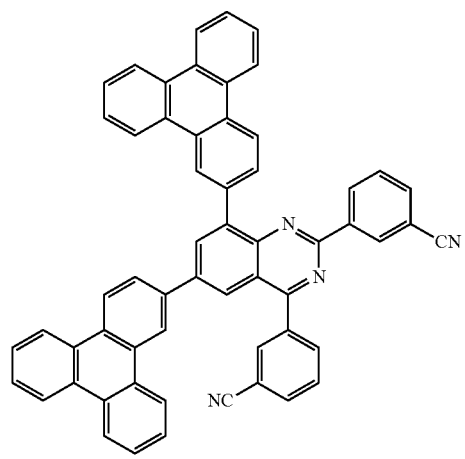
[Chemical Formula A-282]
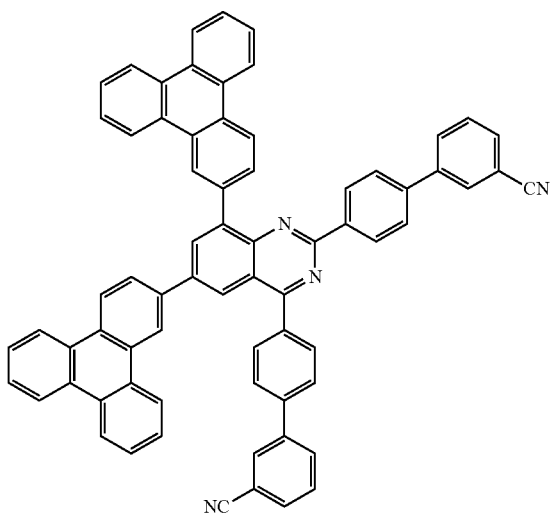

[Chemical Formula A-283]
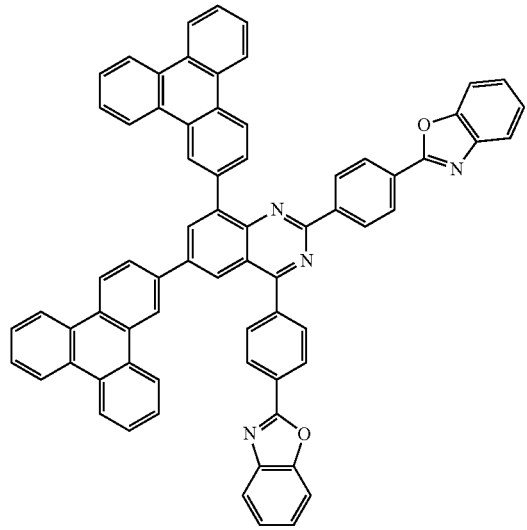
[Chemical Formula A-284]
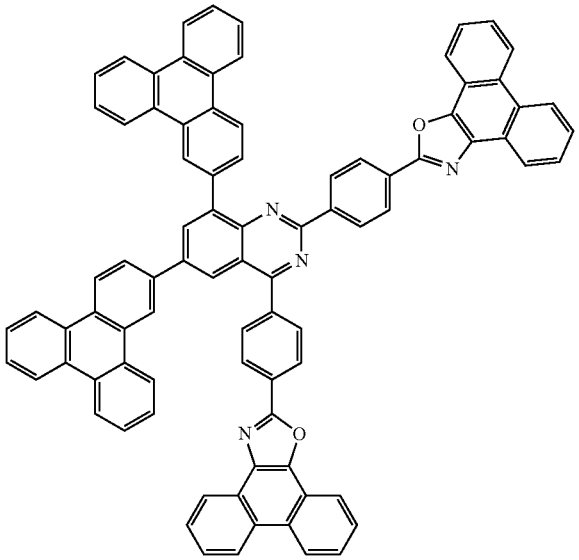
[Chemical Formula A-285]
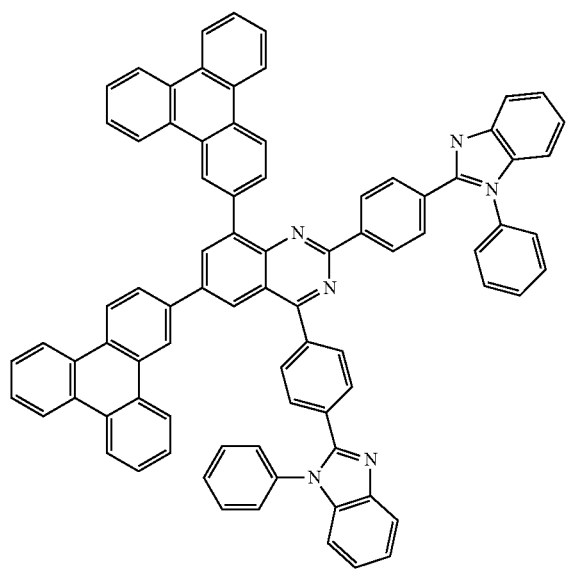
[Chemical Formula A-286]
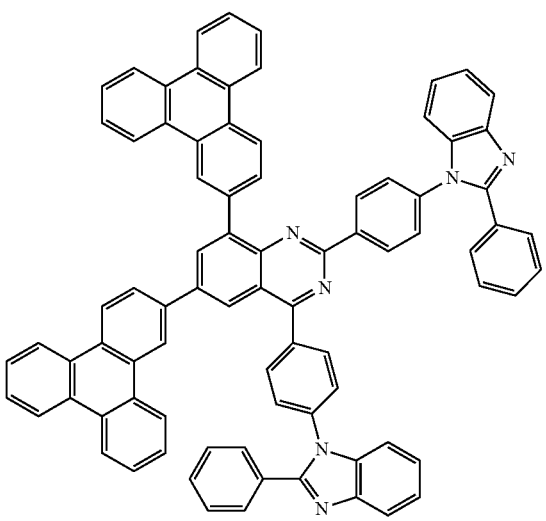

[Chemical Formula A-287]
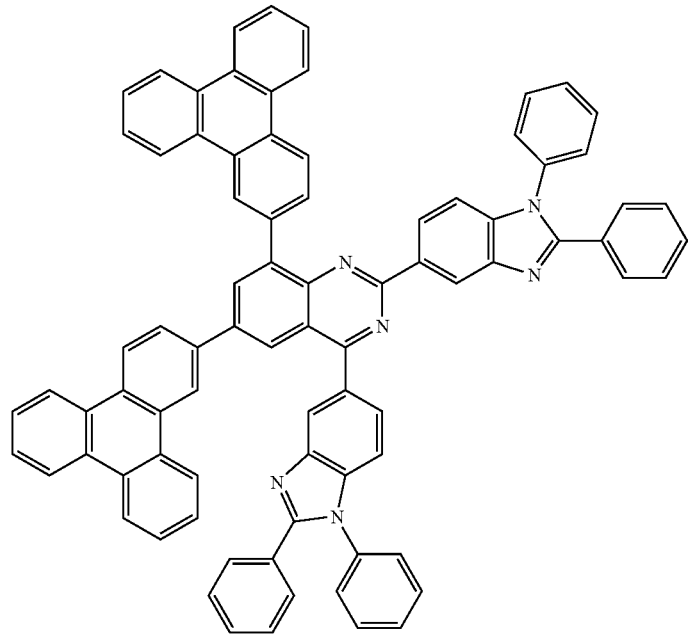
[Chemical Formula A-288]
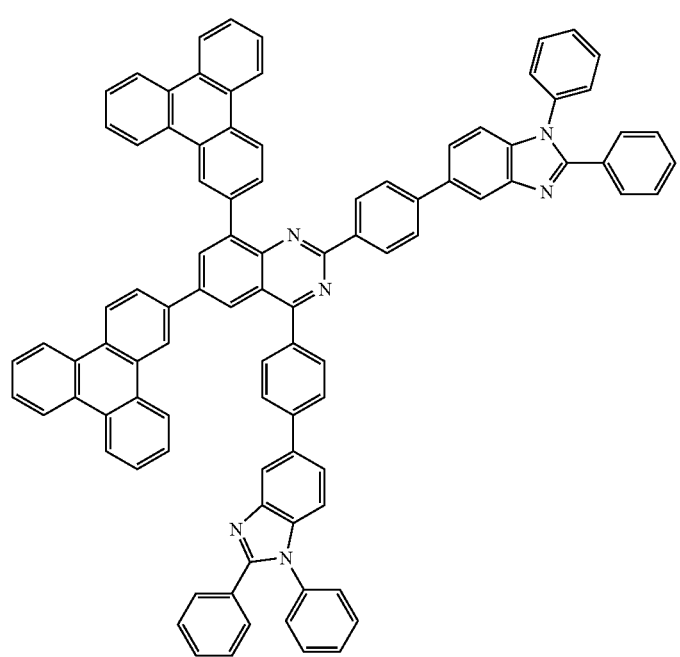

[Chemical Formula A-289]
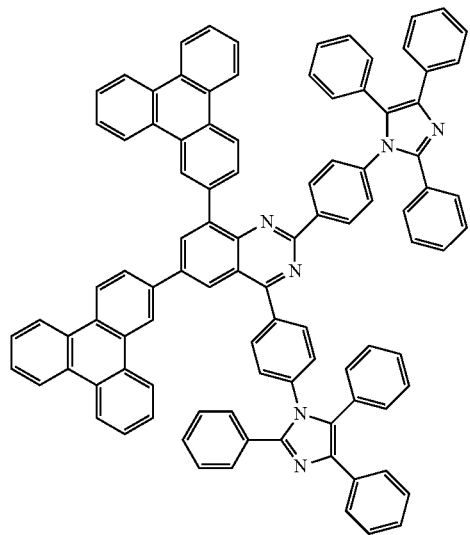
[Chemical Formula A-290]
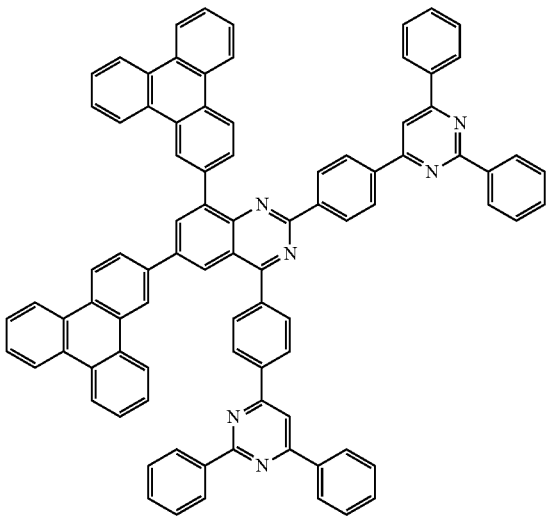
[Chemical Formula A-291]
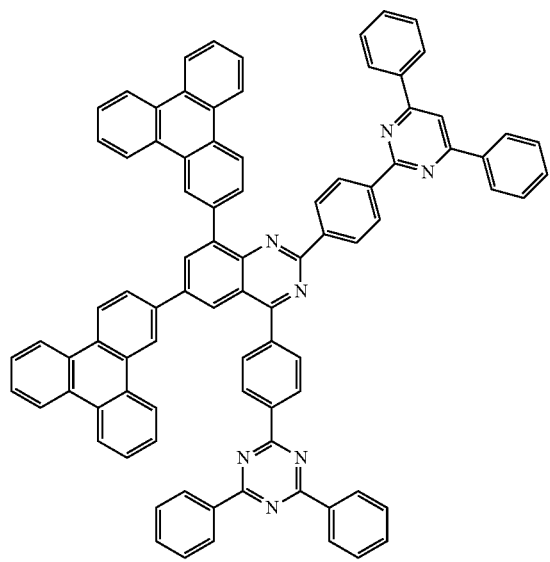
[Chemical Formula A-292]
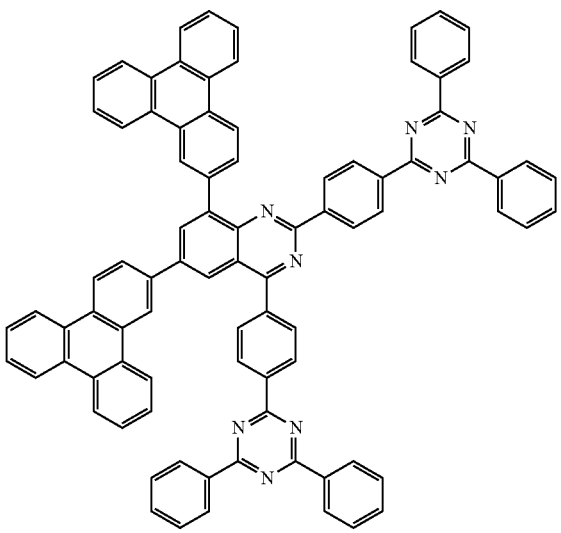

-continued
[Chemical Formula A-293]
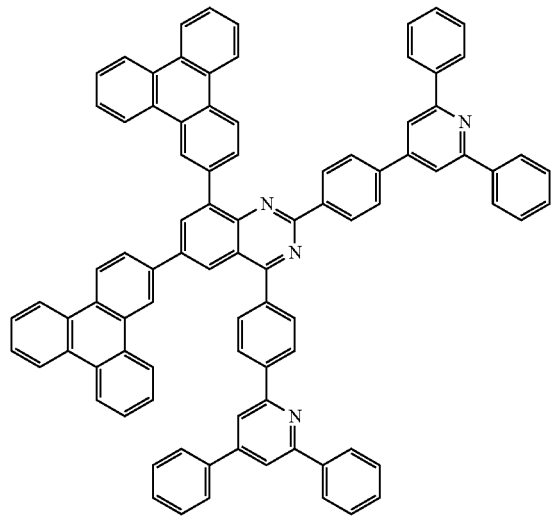
[Chemical Formula A-294]
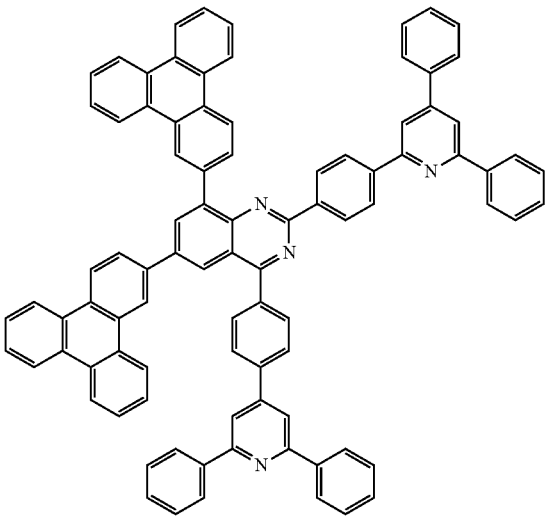
[Chemical Formula A-295]
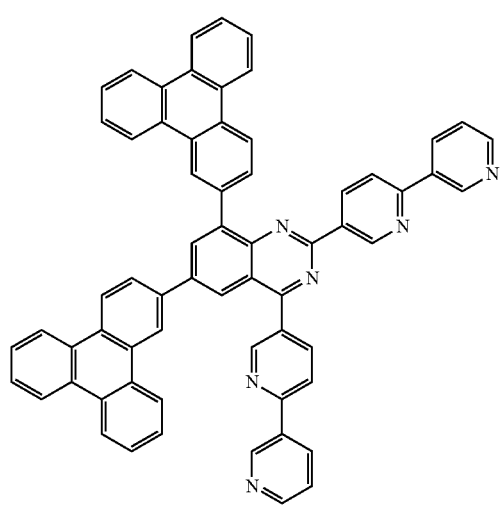
[Chemical Formula A-296]
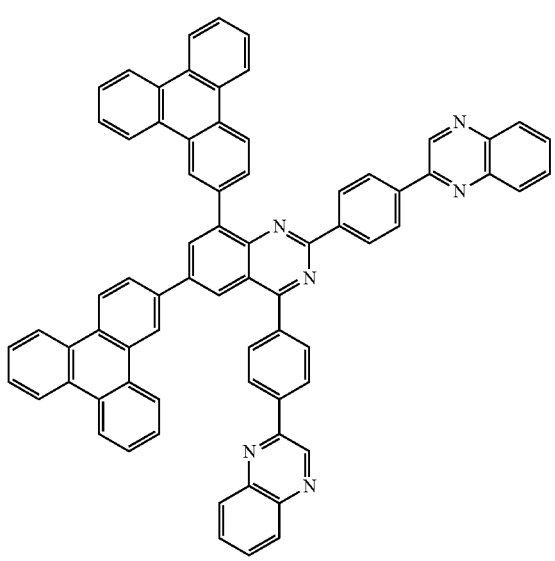
[Chemical Formula A-297]
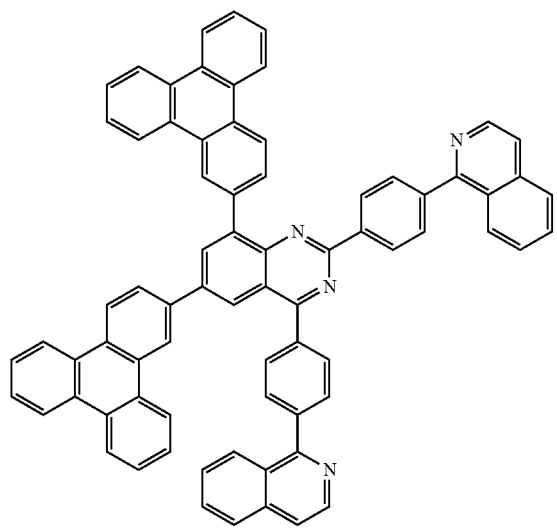
[Chemical Formula A-298]
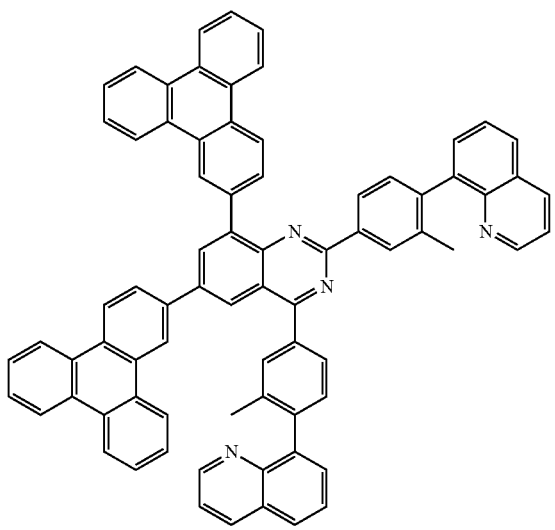

[Chemical Formula A-299]
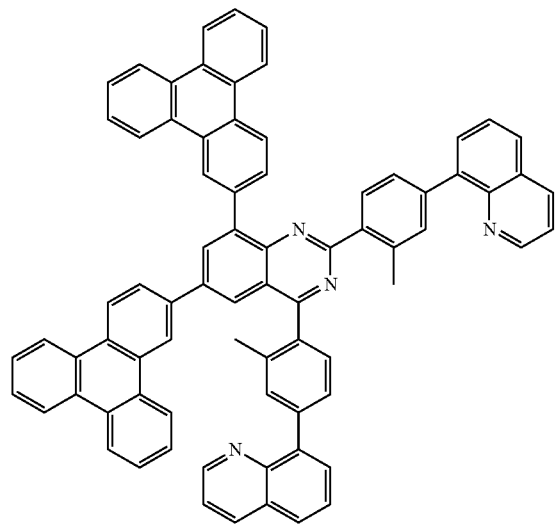
[Chemical Formula A-300]
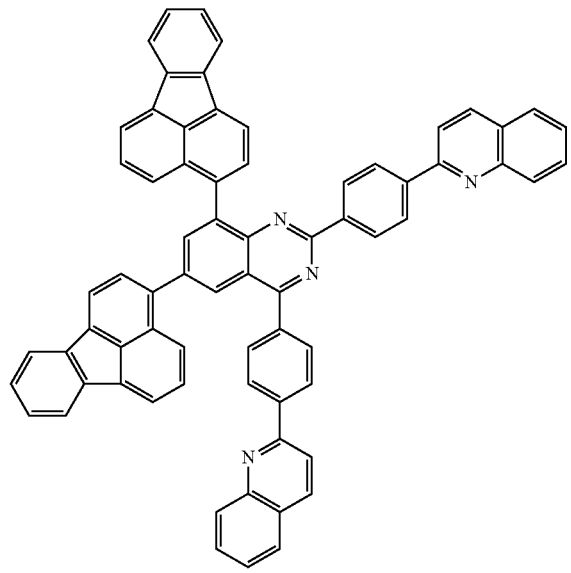
[Chemical Formula A-301]
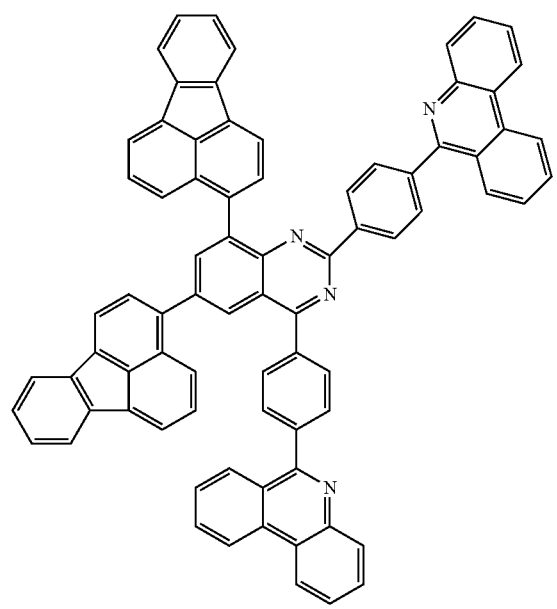
[Chemical Formula A-302]
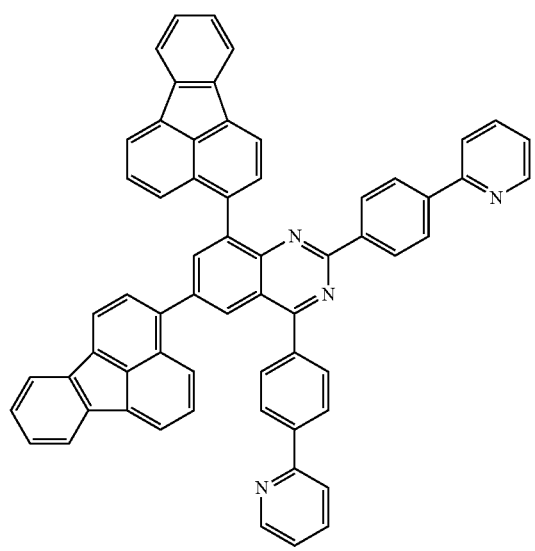

[Chemical Formula A-303]
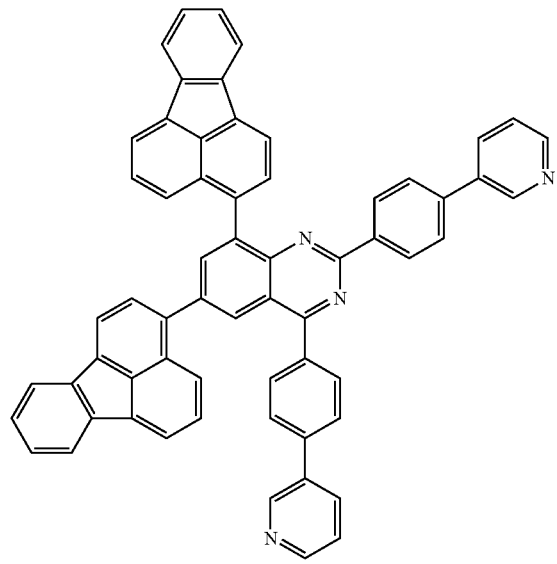
[Chemical Formula A-304]
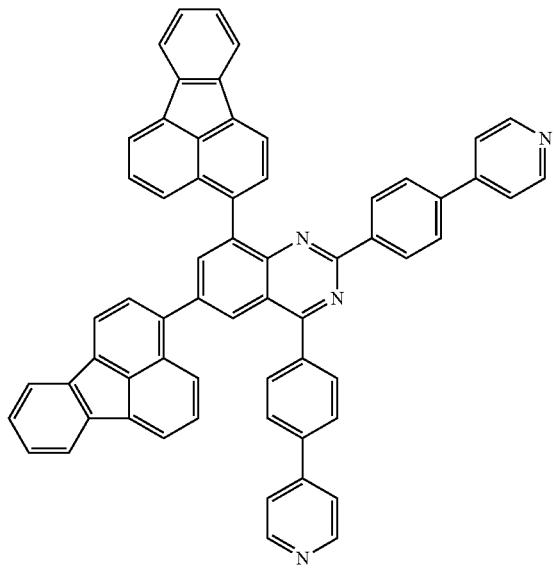
[Chemical Formula A-305]
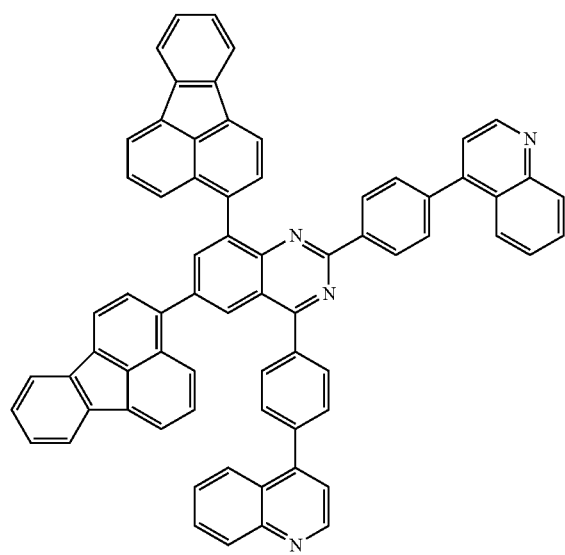
[Chemical Formula A-306]
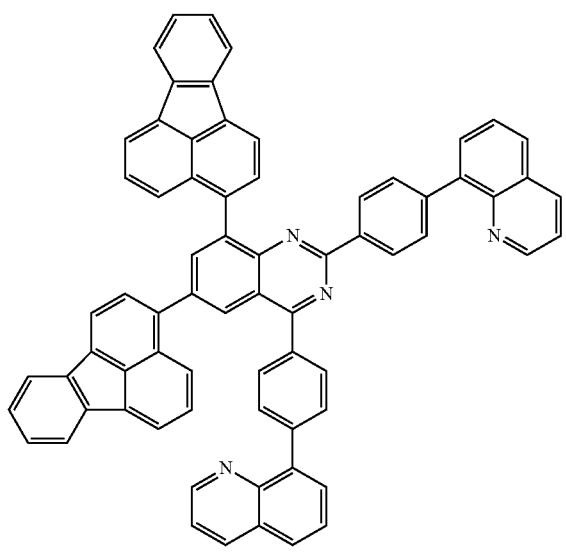

-continued
[Chemical Formula A-307]
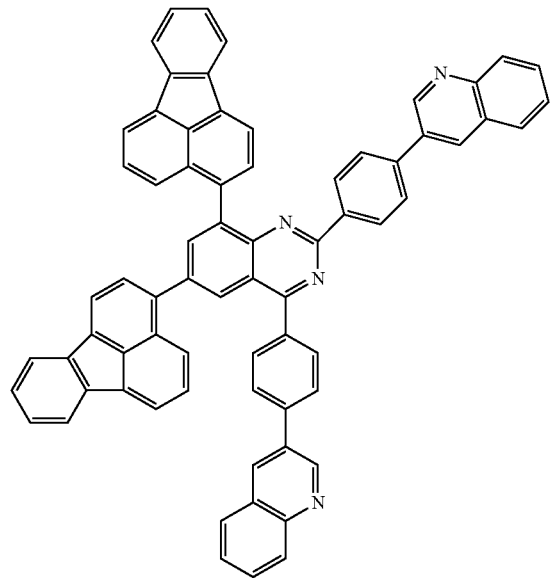
[Chemical Formula A-308]
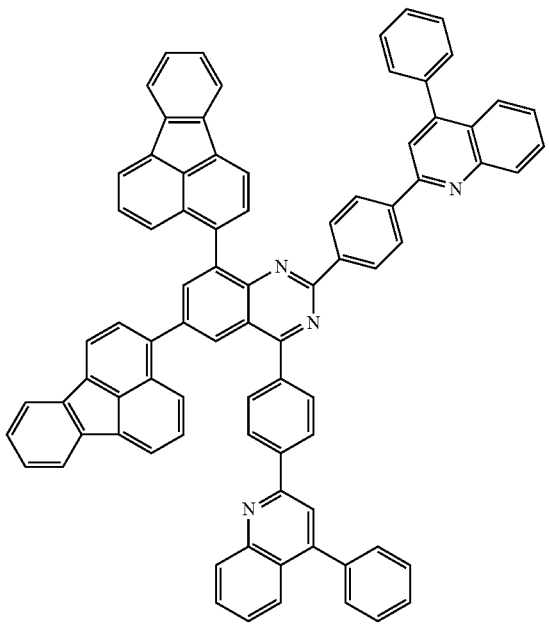
[Chemical Formula A-309]
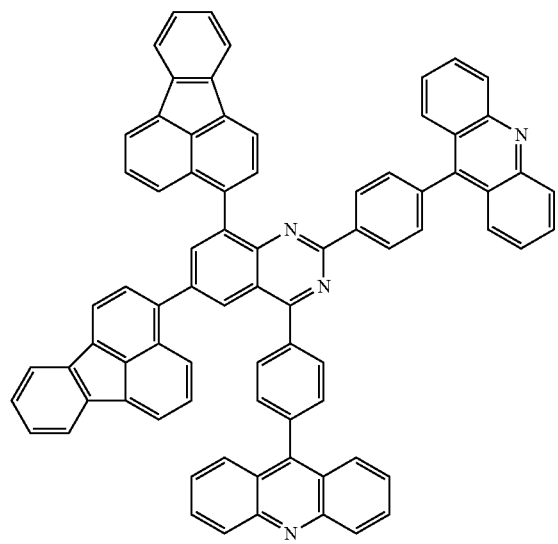
[Chemical Formula A-310]
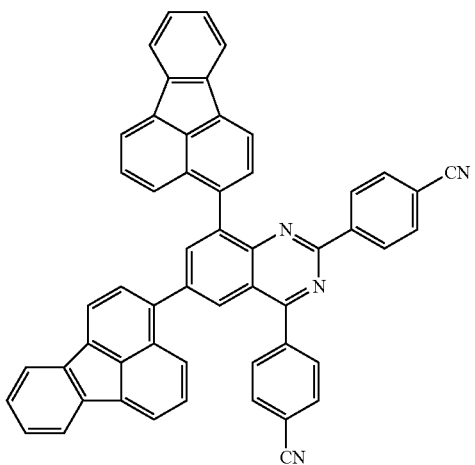

[Chemical Formula A-311]
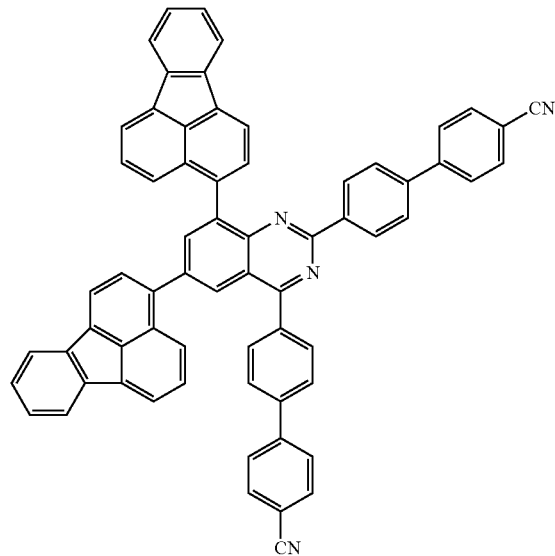
[Chemical Formula A-312]
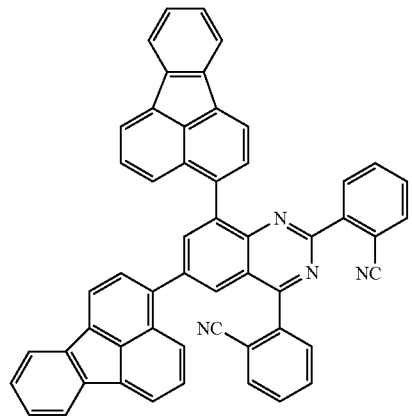
[Chemical Formula A-313]
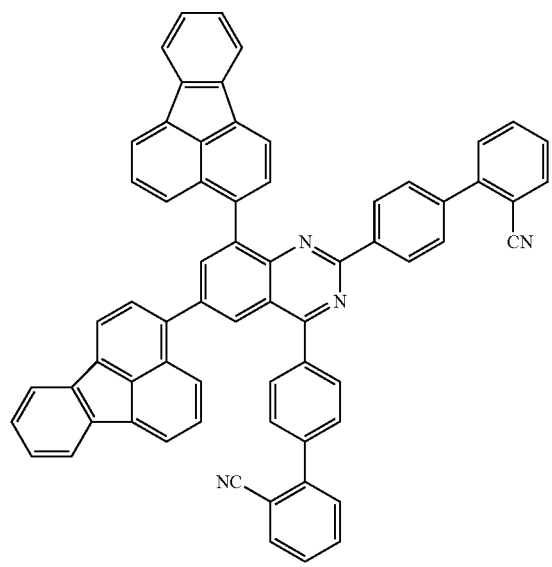
[Chemical Formula A-314]
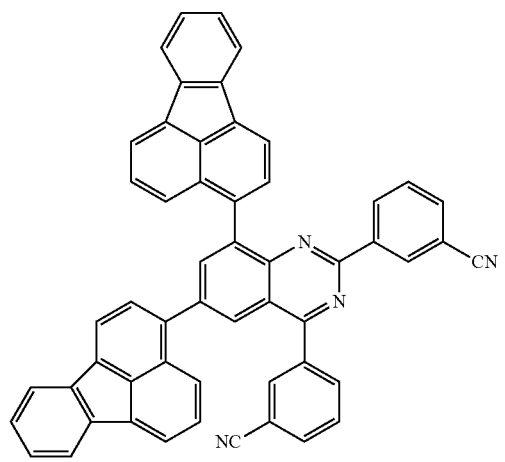

[Chemical Formula A-315]
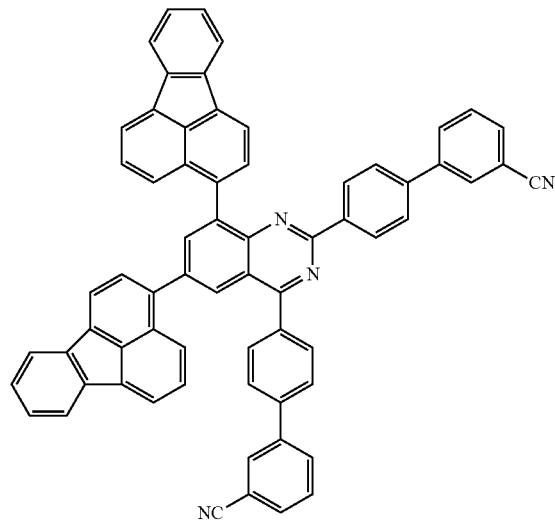
[Chemical Formula A-316]
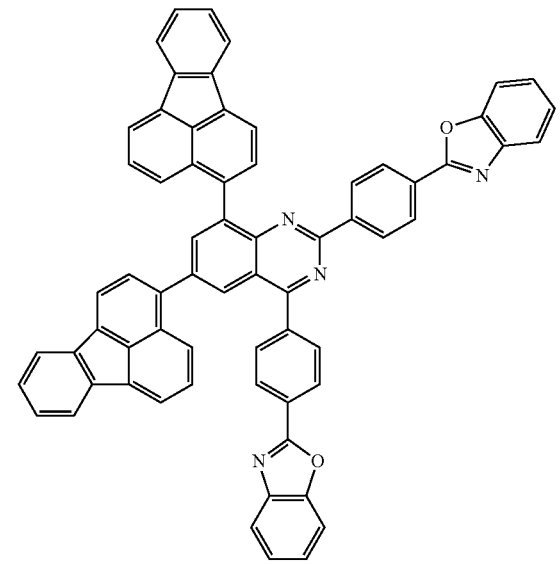
[Chemical Formula A-317]
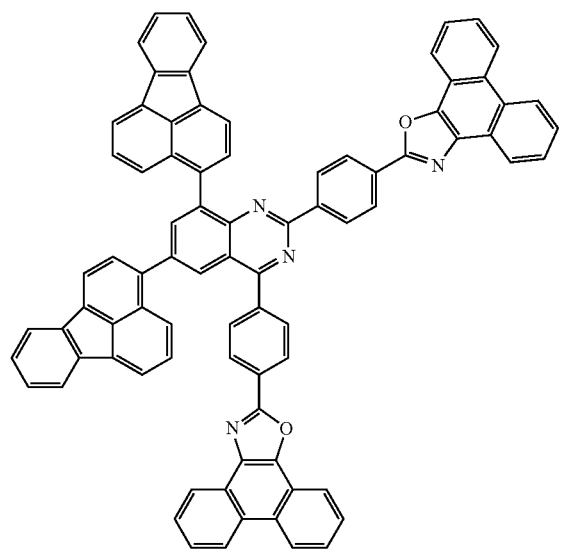
[Chemical Formula A-318]
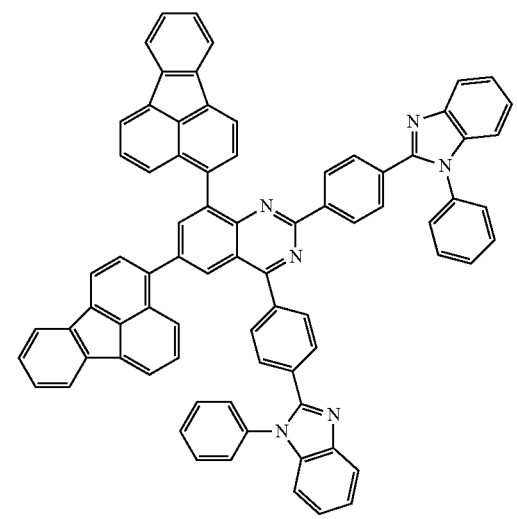

[Chemical Formula A-319]
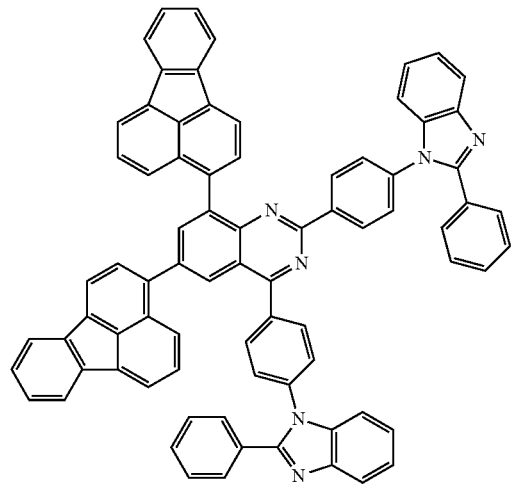
[Chemical Formula A-320]
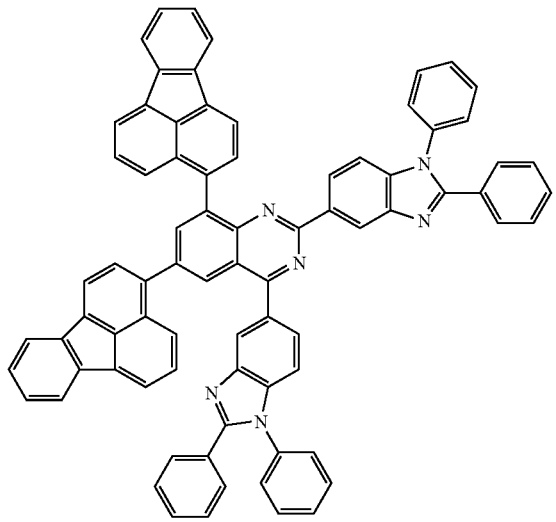
[Chemical Formula A-321]
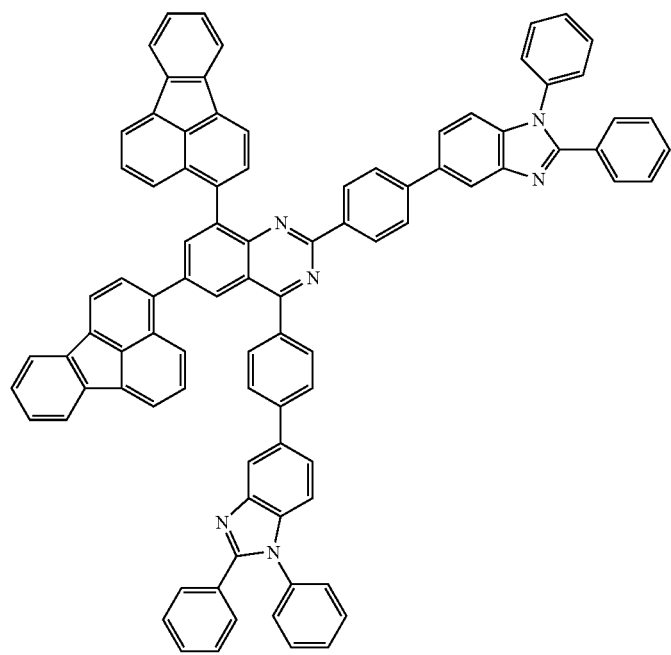

-continued
[Chemical Formula A-322]
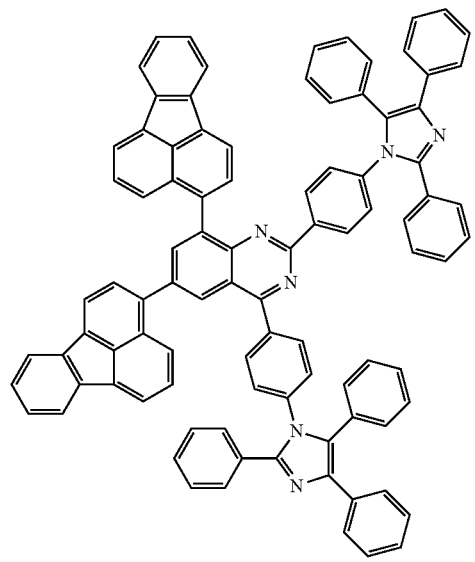
[Chemical Formula A-323]
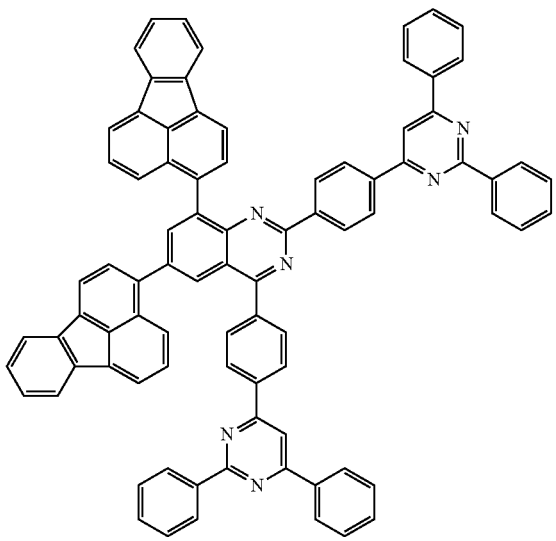
[Chemical Formula A-324]
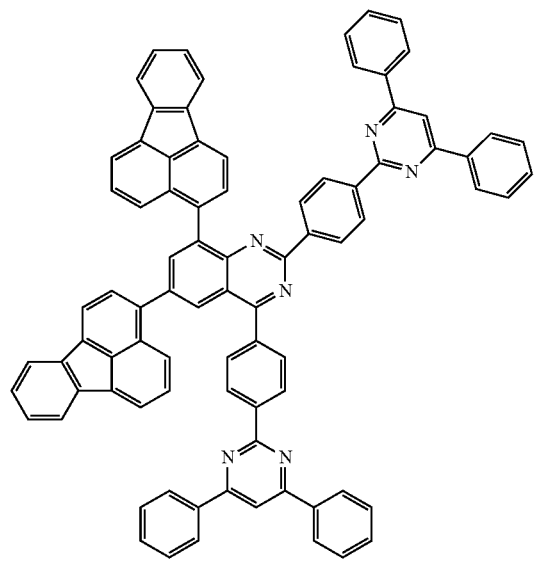
[Chemical Formula A-325]
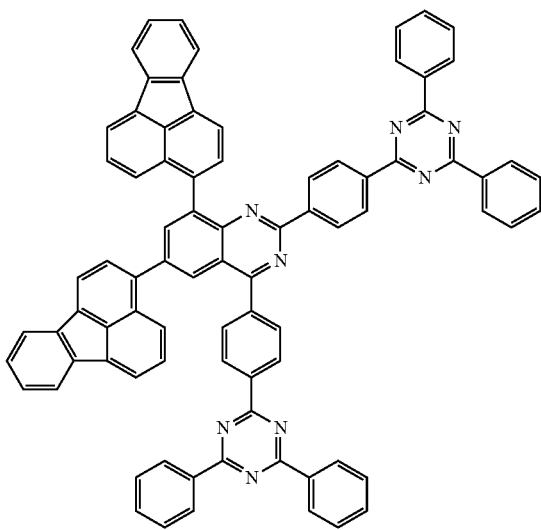

-continued
[Chemical Formula A-326]
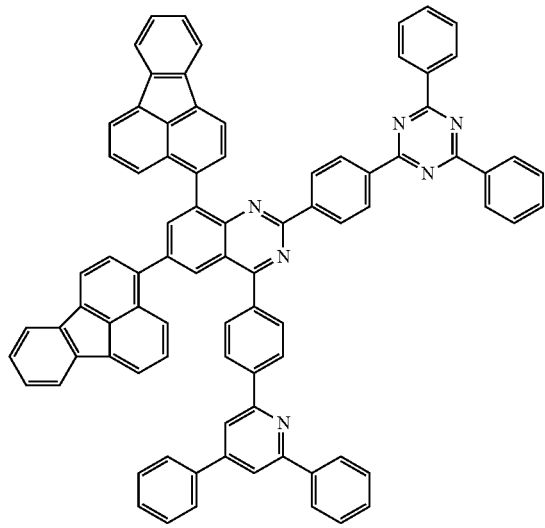
[Chemical Formula A-327]
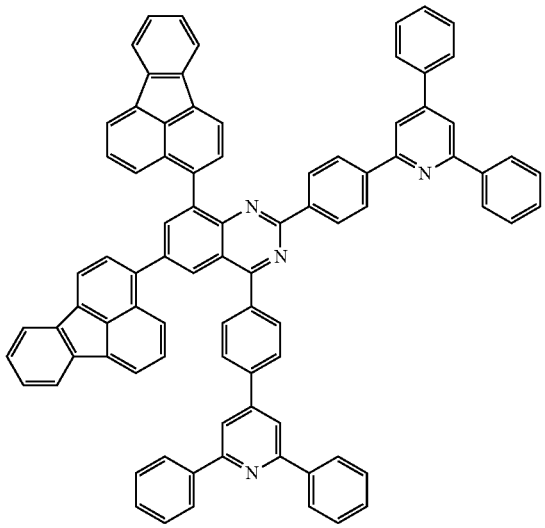
[Chemical Formula A-328]
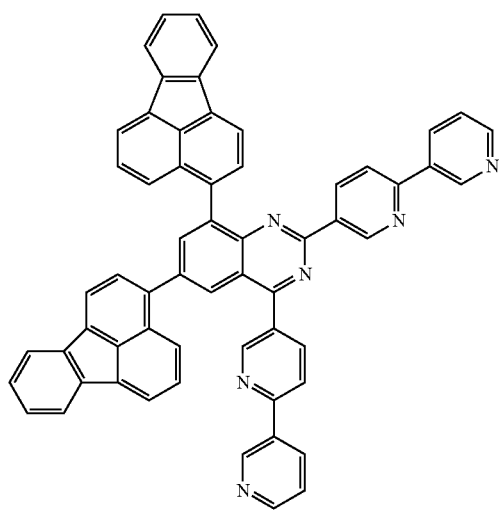
[Chemical Formula A-329]
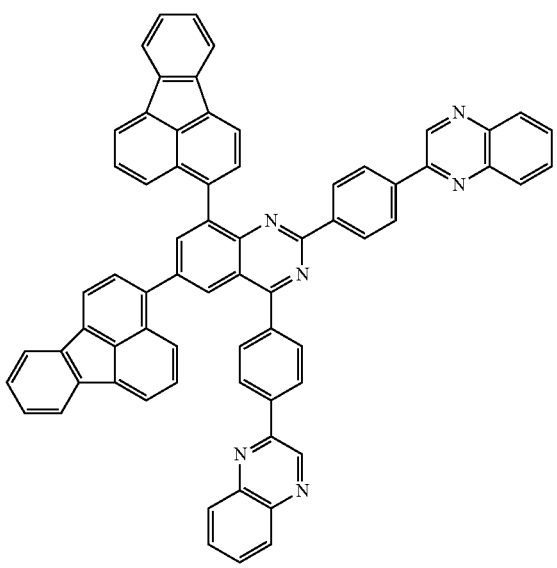
[Chemical Formula A-330]
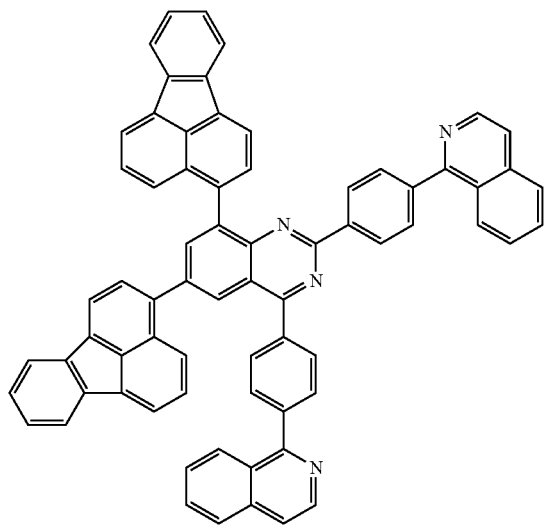
[Chemical Formula A-331]
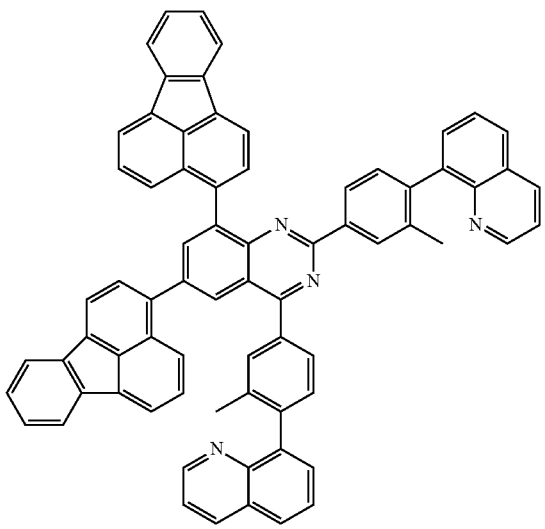

-continued
[Chemical Formula A-332]
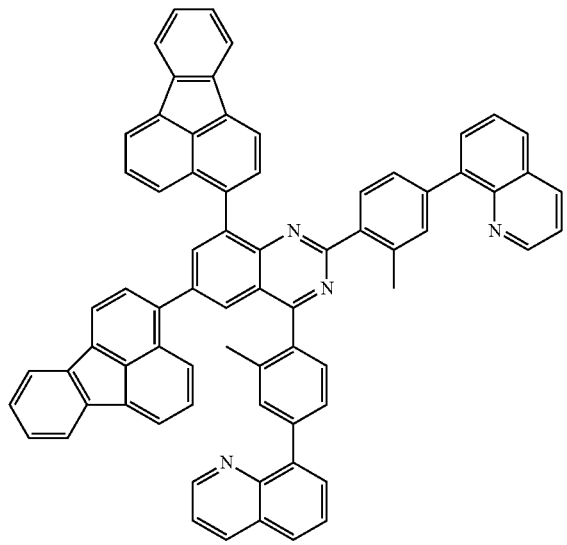
[Chemical Formula A-333]
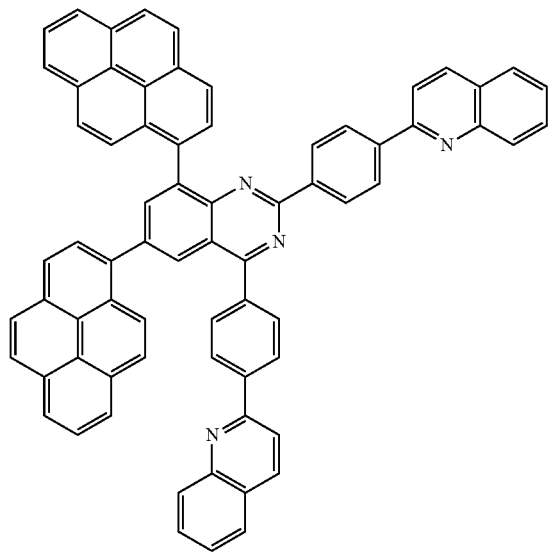
[Chemical Formula A-334]
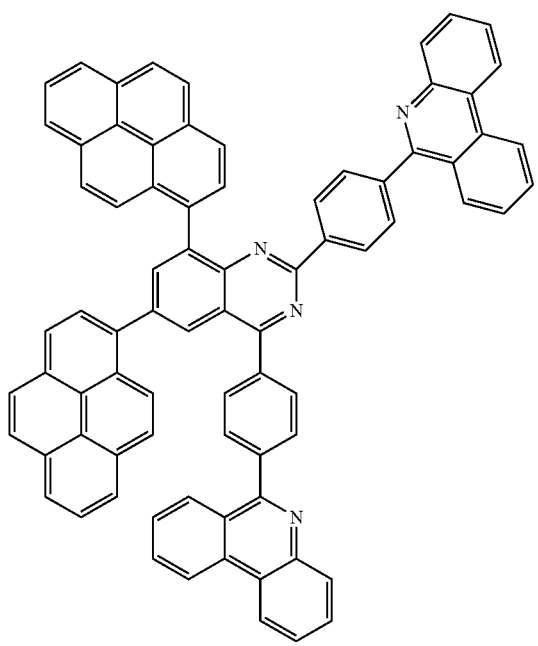
[Chemical Formula A-335]
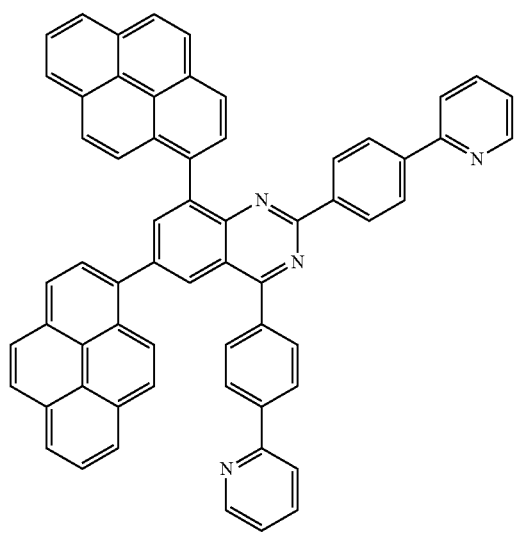

[Chemical Formula A-336]
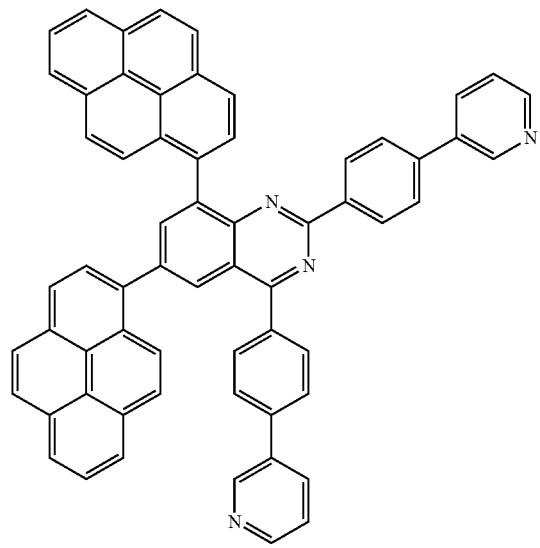
[Chemical Formula A-337]
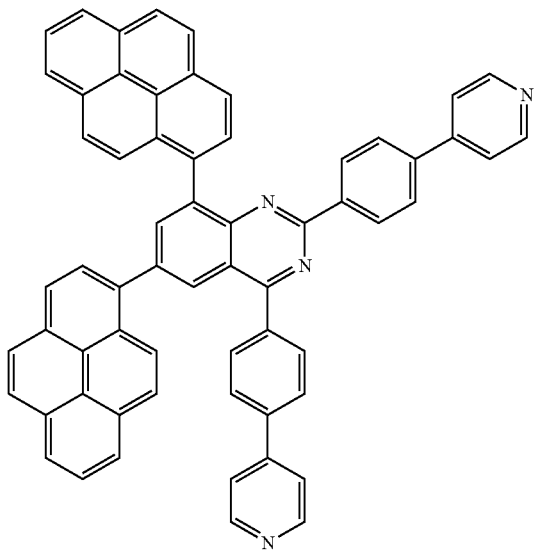
[Chemical Formula A-338]
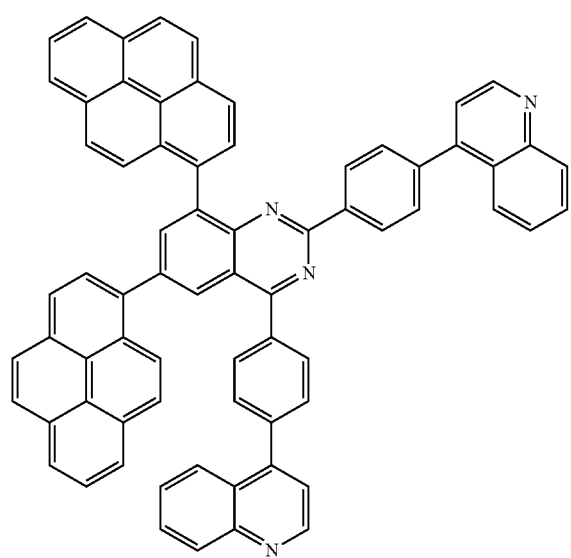
[Chemical Formula A-339]
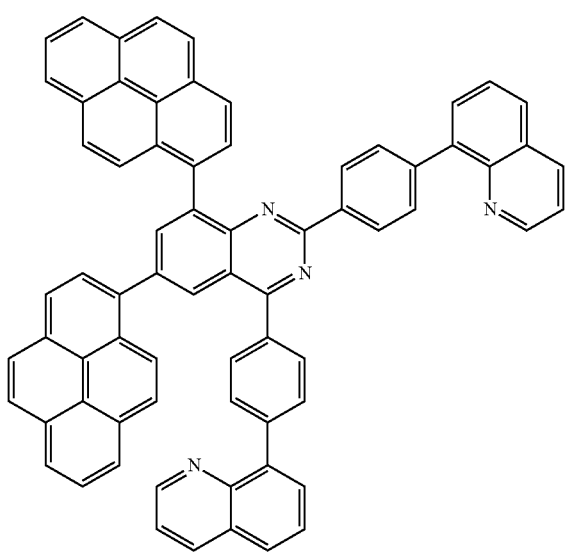

[Chemical Formula A-340]
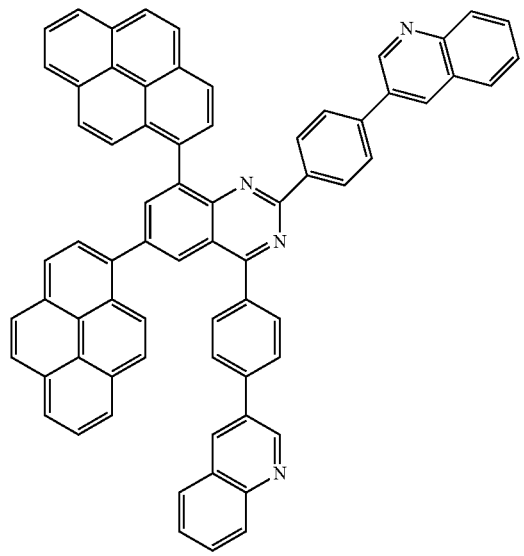
[Chemical Formula A-341]
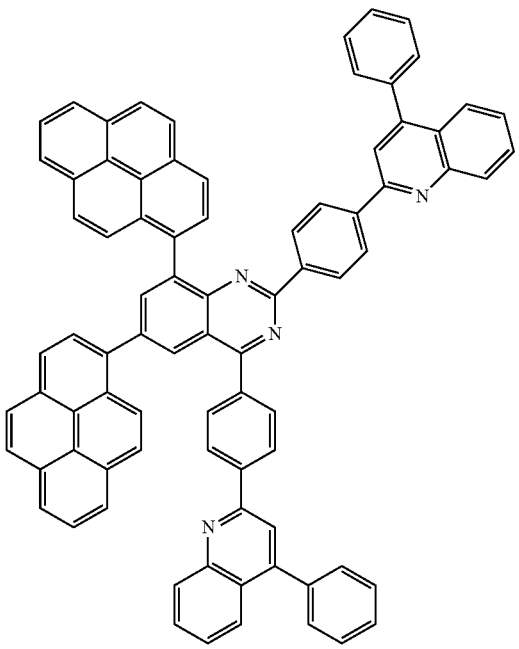
[Chemical Formula A-342]
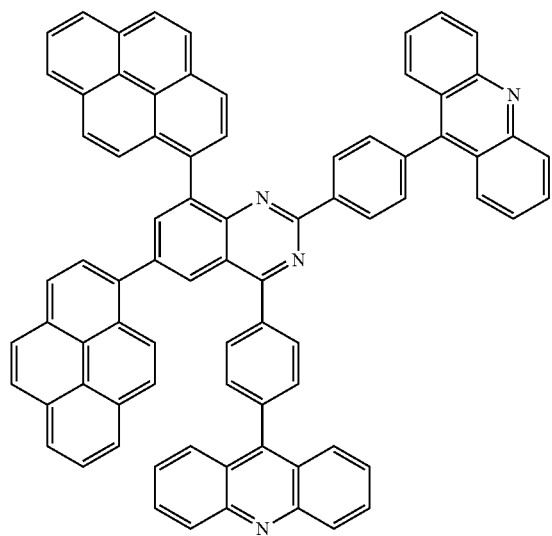
[Chemical Formula A-343]
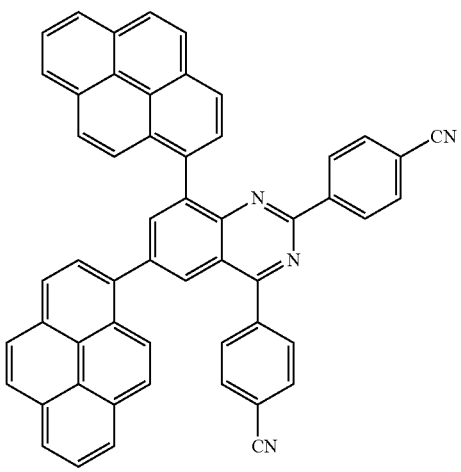

[Chemical Formula A-344]
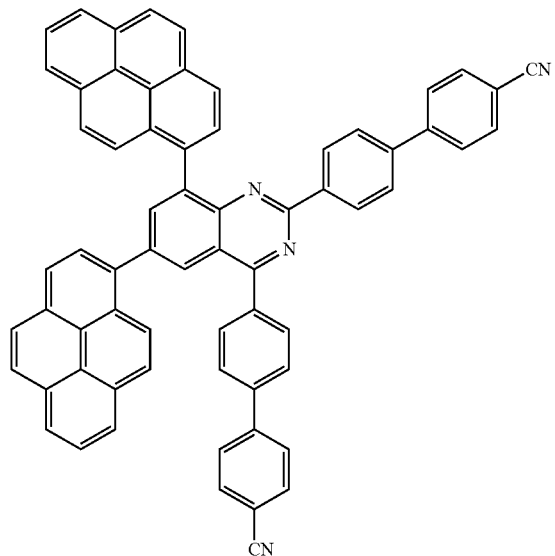
[Chemical Formula A-345]
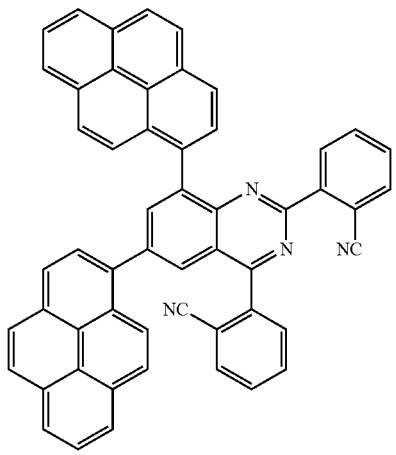
[Chemical Formula A-346]
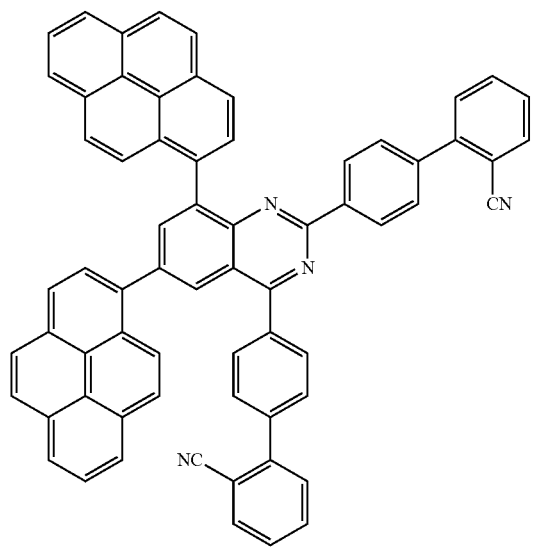
[Chemical Formula A-347]
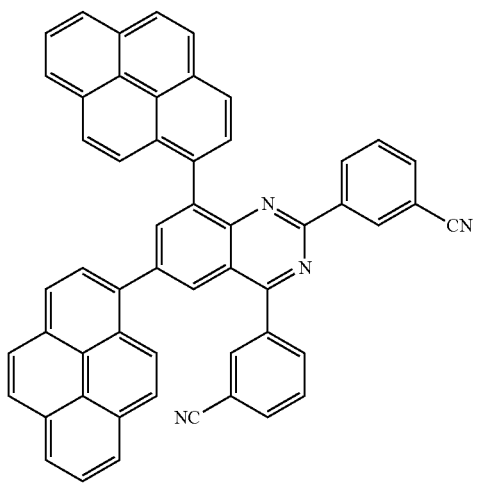

[Chemical Formula A-348]
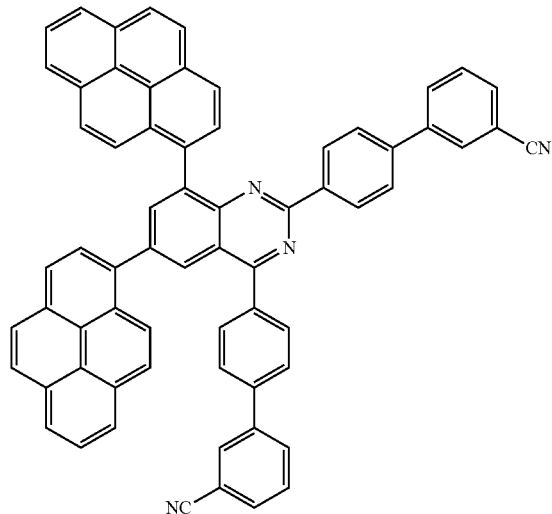
[Chemical Formula A-349]
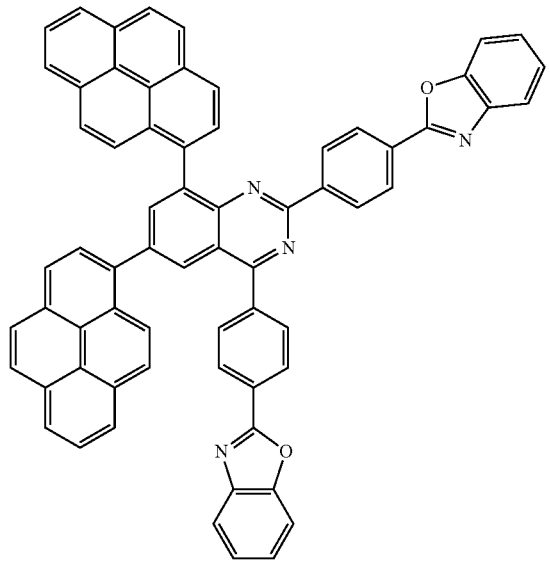
[Chemical Formula A-350]
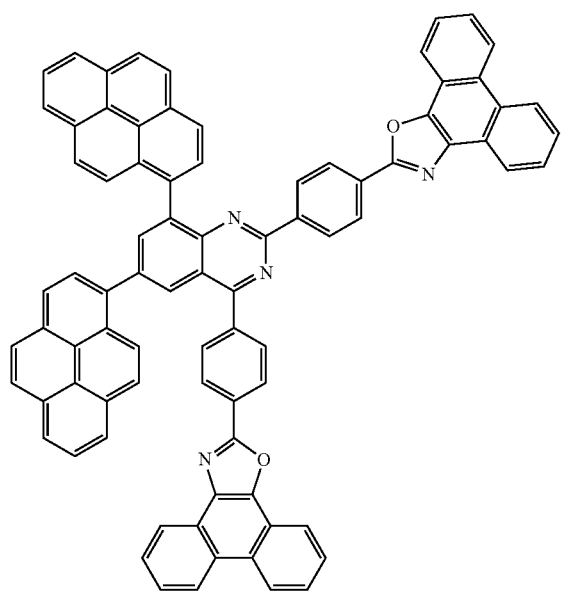
[Chemical Formula A-351]
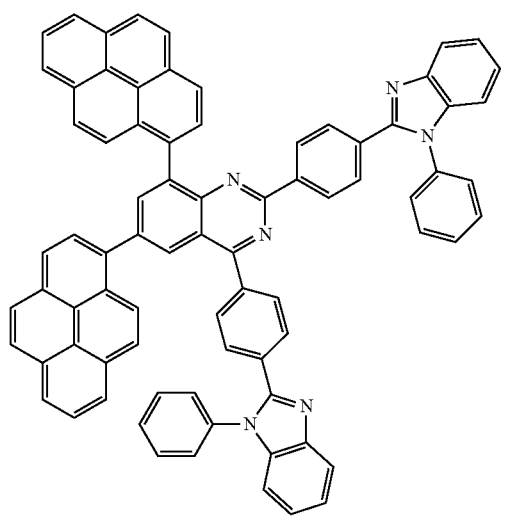

[Chemical Formula A-352]
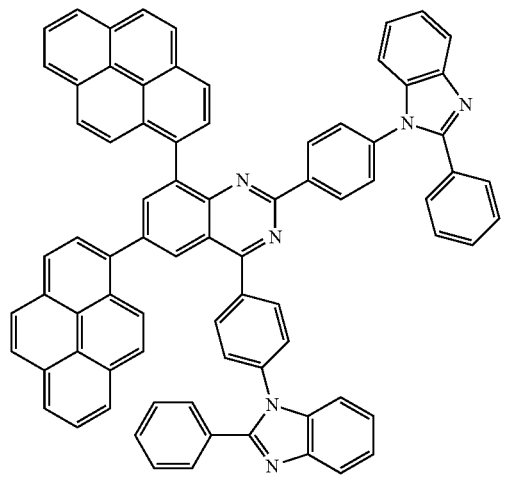
[Chemical Formula A-353]
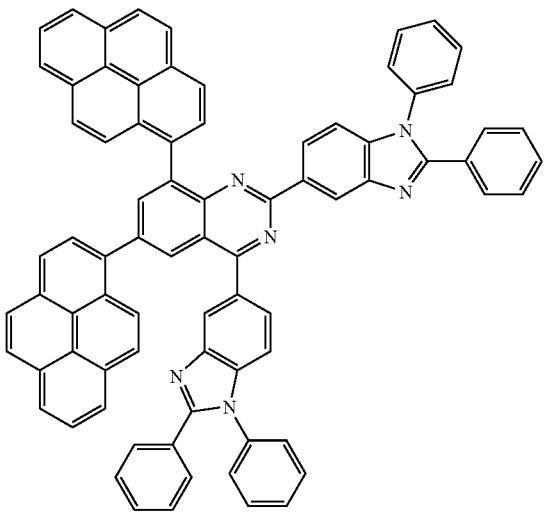
[Chemical Formula A-354]
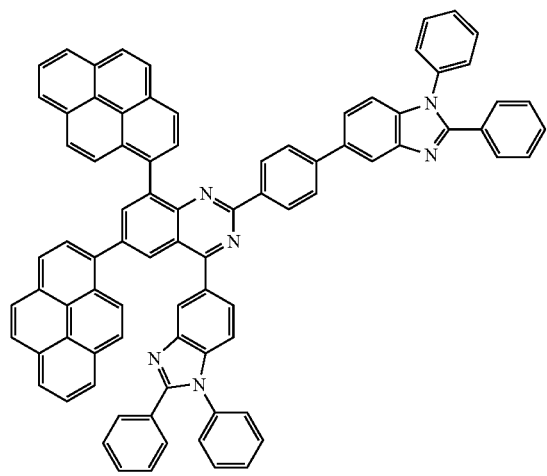
[Chemical Formula A-355]
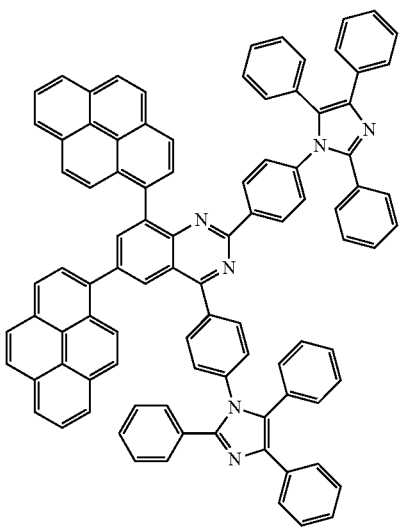

[Chemical Formula A-356]
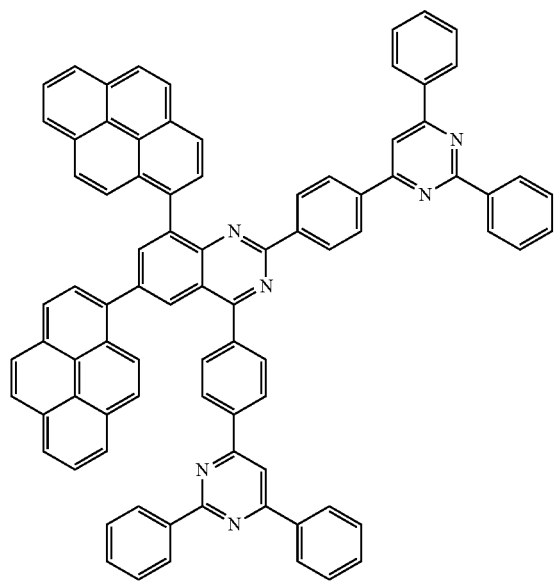
[Chemical Formula A-357]
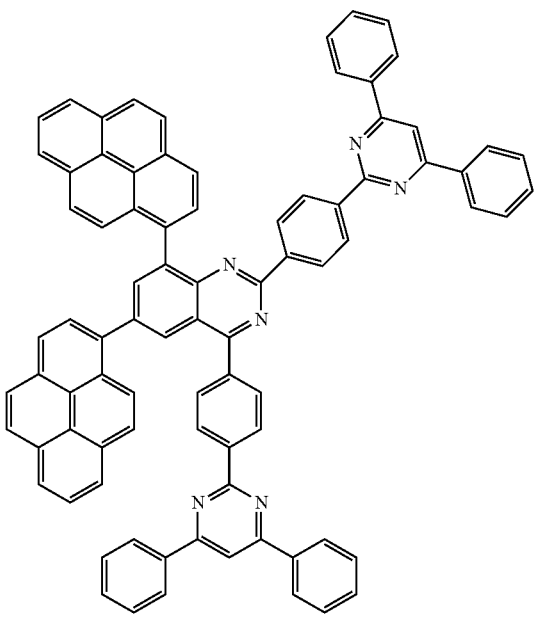
[Chemical Formula A-358]
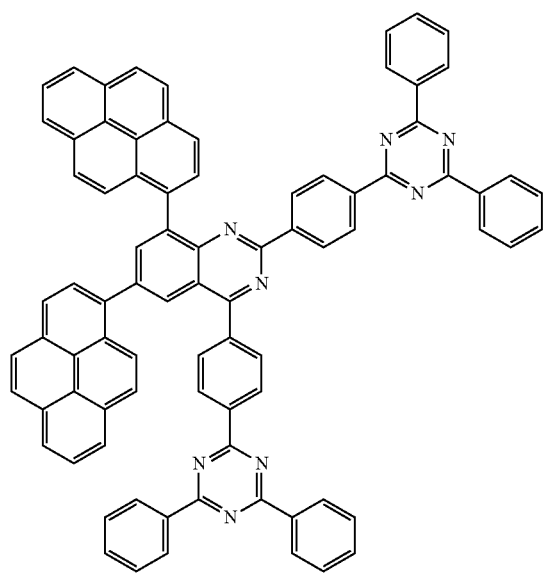
[Chemical Formula A-359]
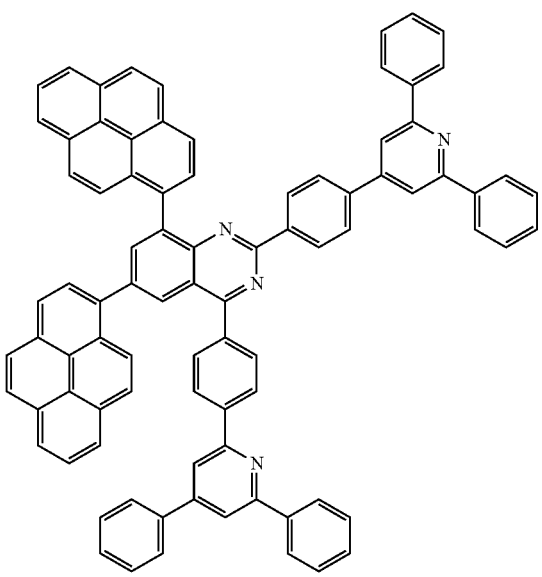

[Chemical Formula A-360]
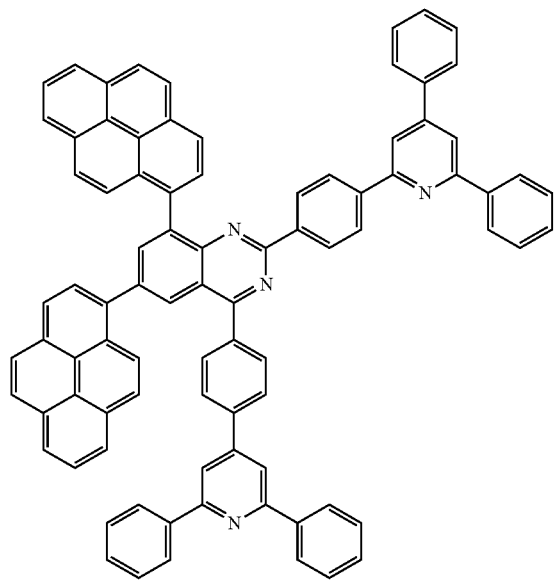
[Chemical Formula A-361]
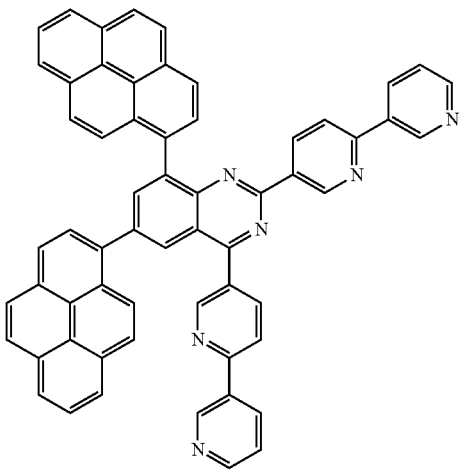
[Chemical Formula A-362]
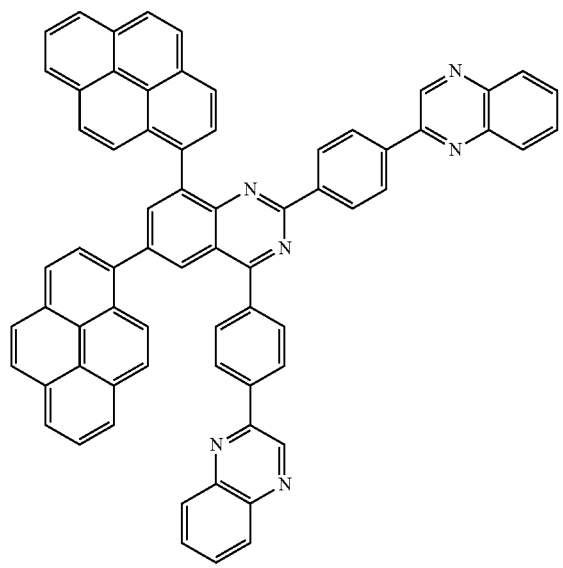
[Chemical Formula A-363]
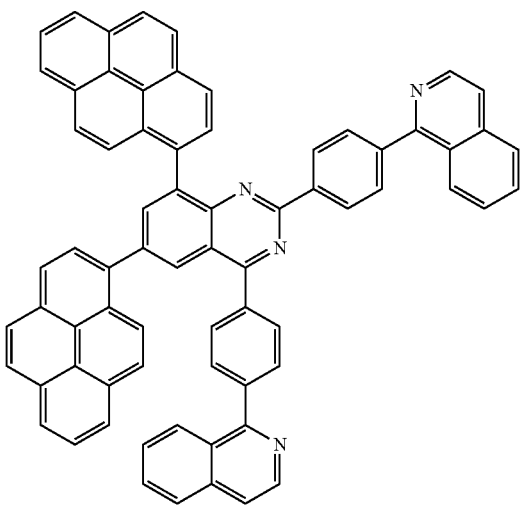

-continued
[Chemical Formula A-364]
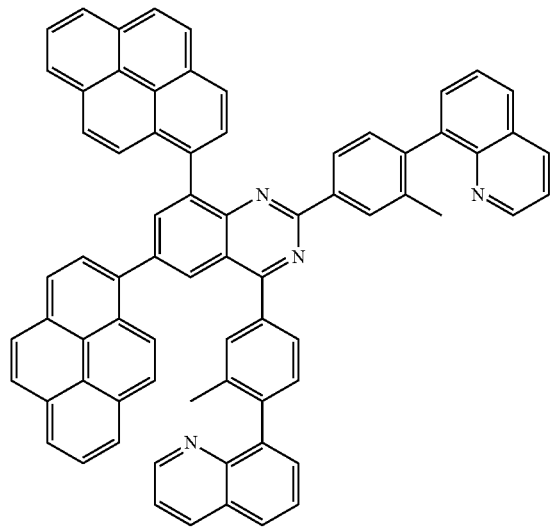
[Chemical Formula A-365]
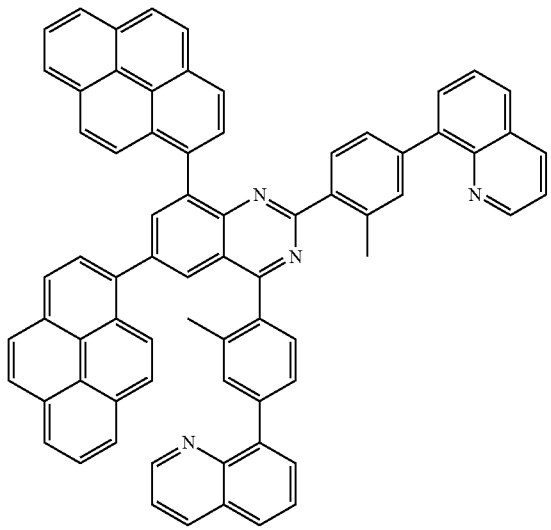
[Chemical Formula A-366]
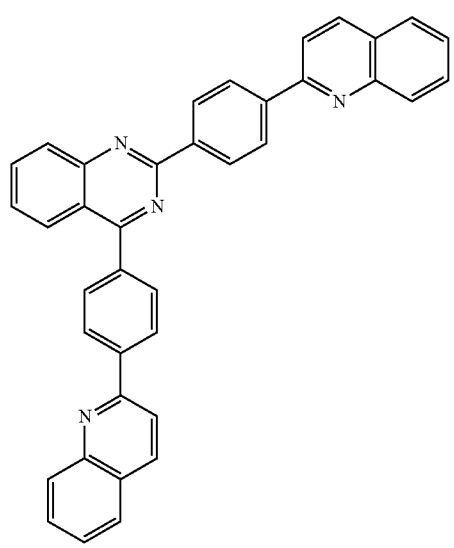
[Chemical Formula A-367]
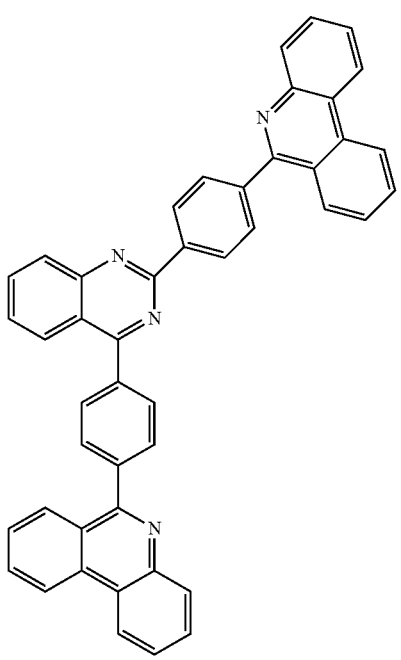

[Chemical Formula A-368]
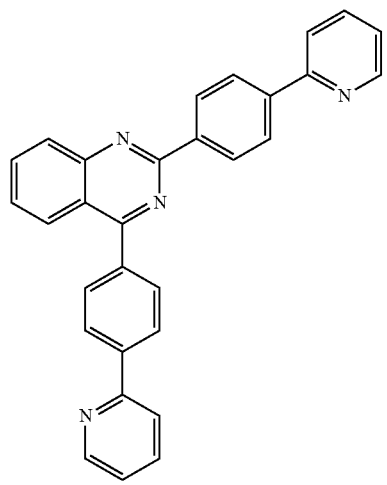
[Chemical Formula A-369]
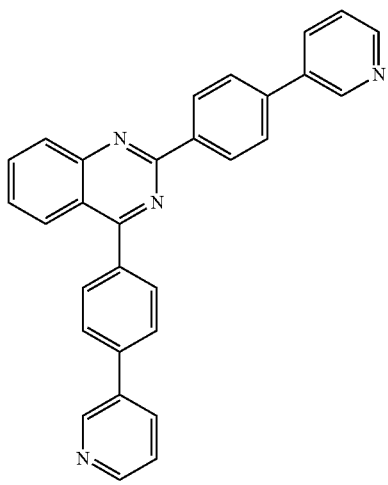
[Chemical Formula A-370]
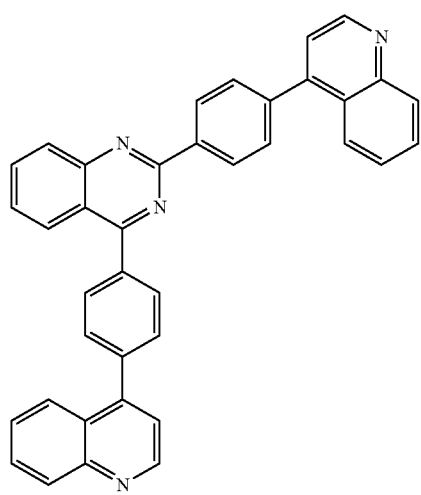
[Chemical Formula A-371]
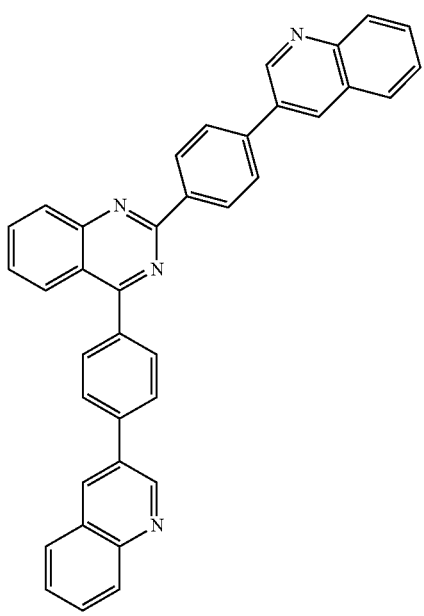

[Chemical Formula A-372]
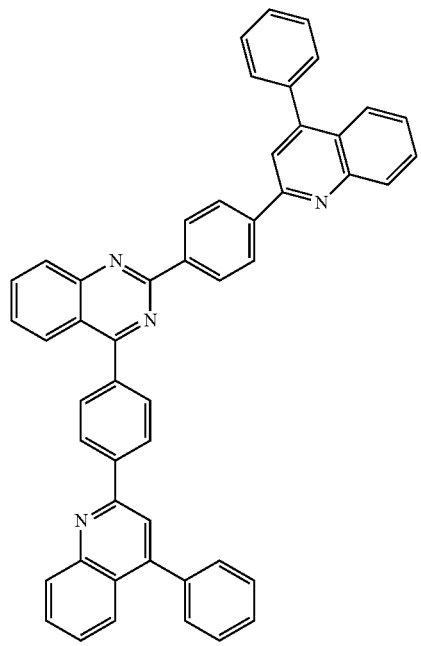
[Chemical Formula A-373]
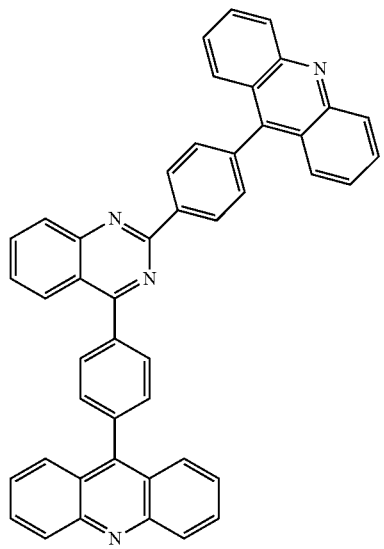
[Chemical Formula A-374]
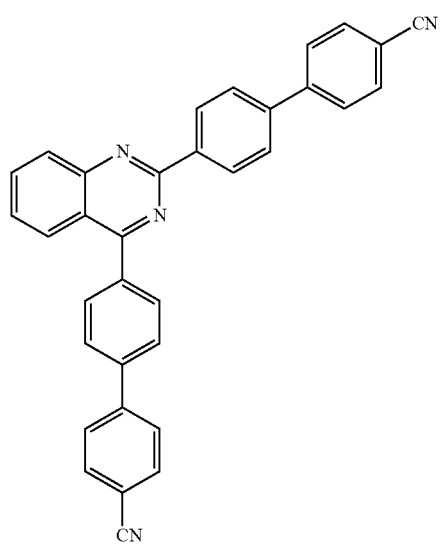
[Chemical Formula A-375]
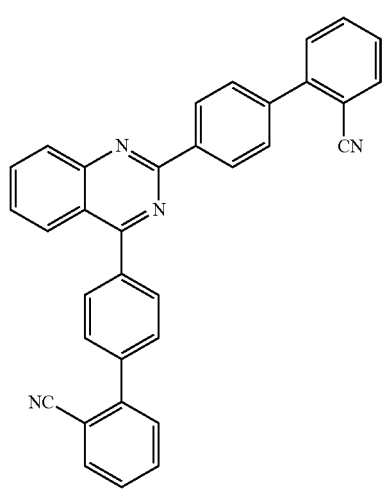

[Chemical Formula A-376]
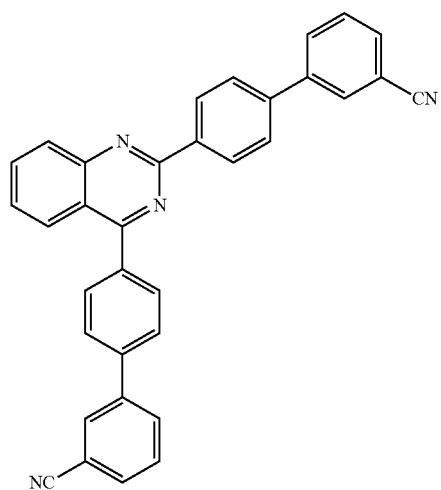
[Chemical Formula A-377]
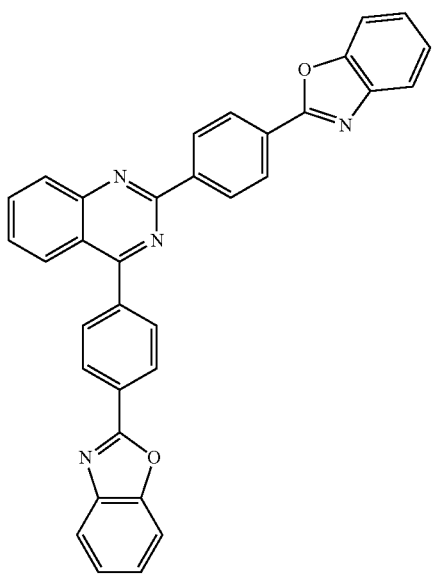
[Chemical Formula A-378]
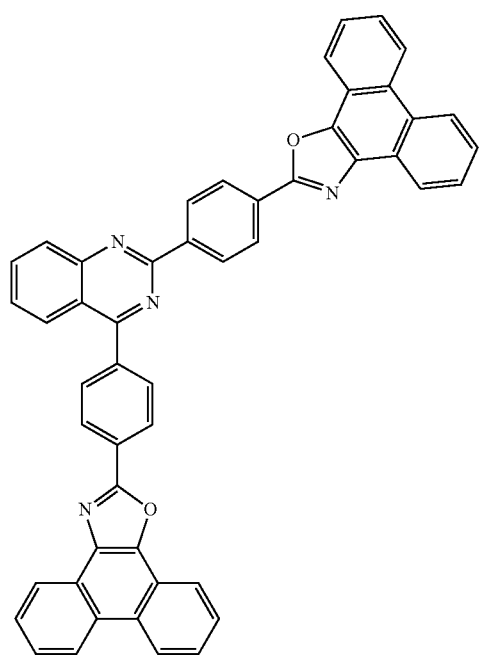
[Chemical Formula A-379]
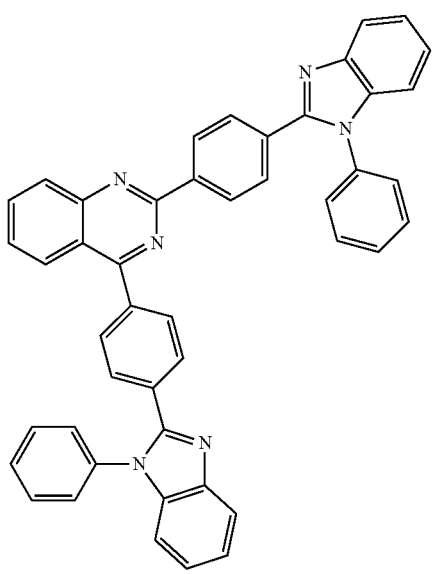

-continued
[Chemical Formula A-380]
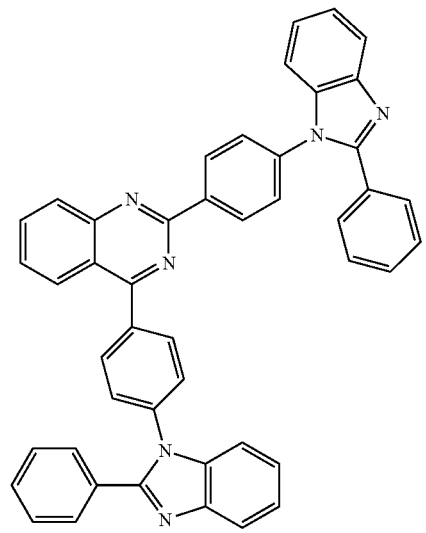
[Chemical Formula A-381]
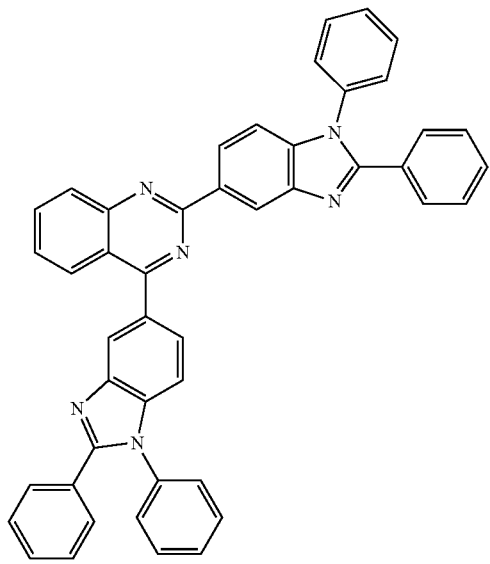
[Chemical Formula A-382]
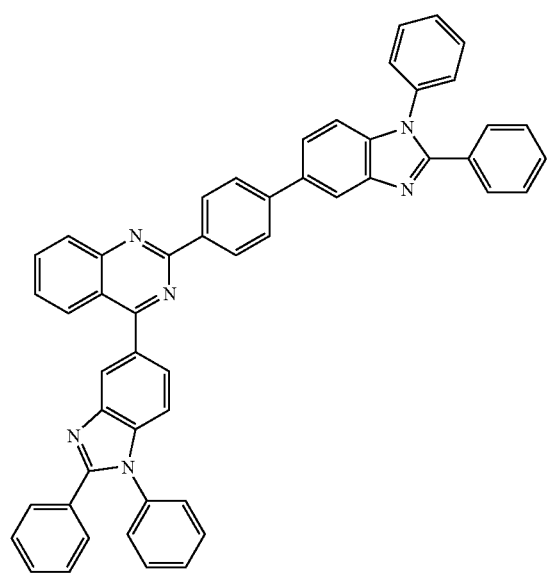
[Chemical Formula A-383]
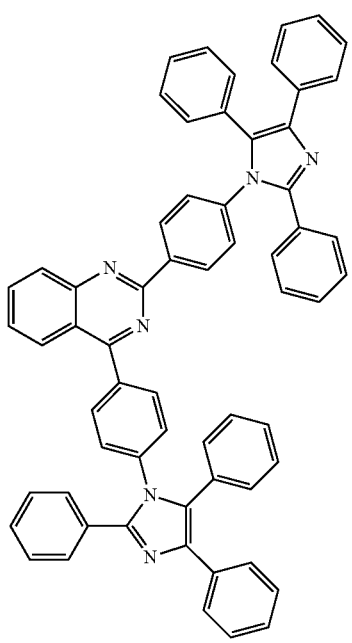

[Chemical Formula A-384]
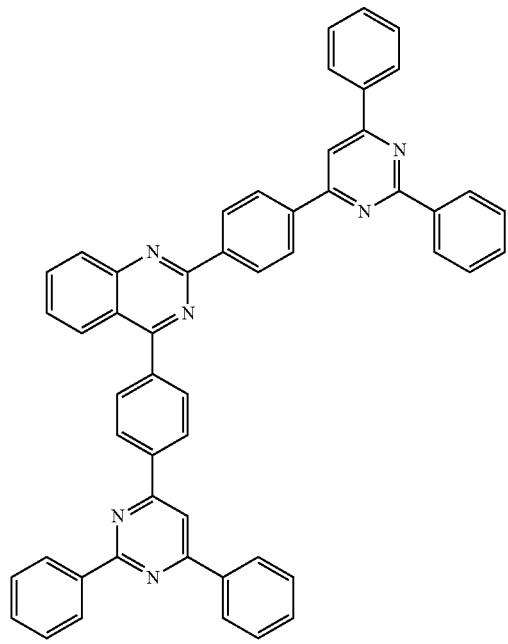
[Chemical Formula A-385]
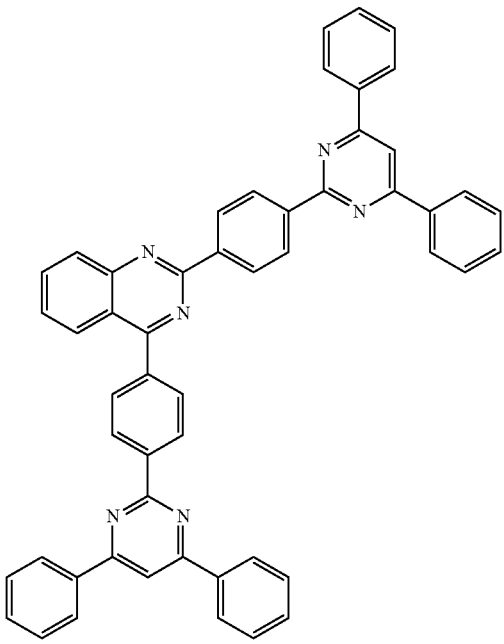
[Chemical Formula A-386]
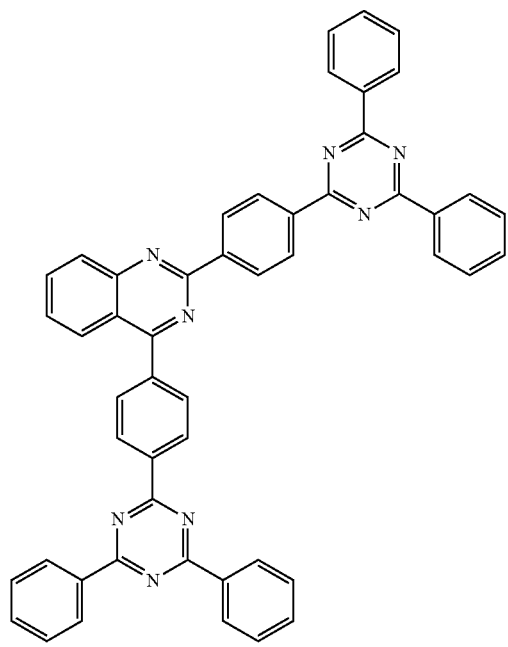
[Chemical Formula A-387]
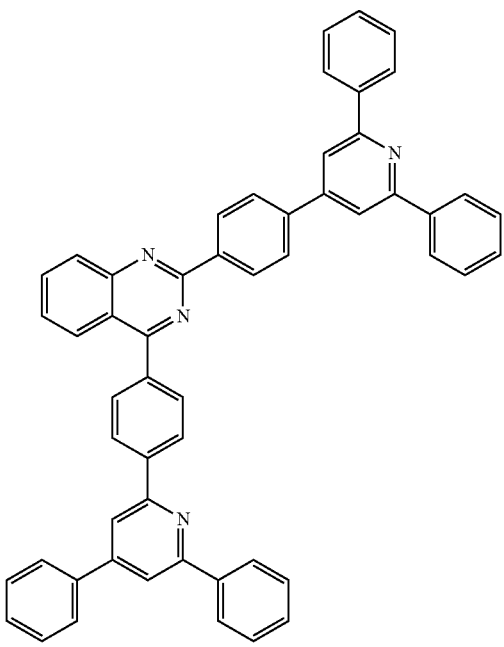

[Chemical Formula A-388]
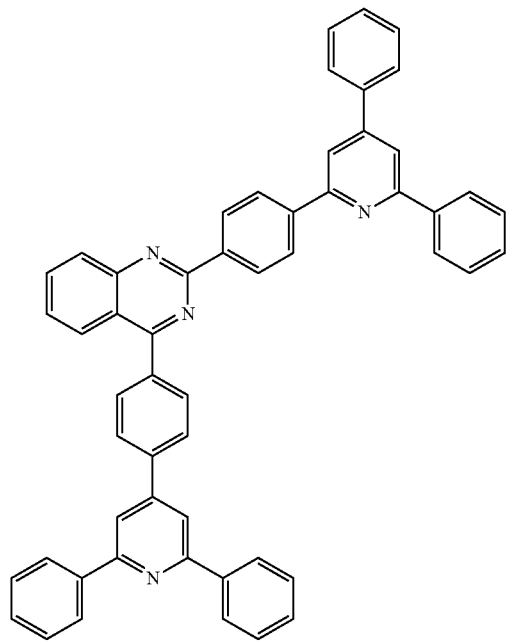
[Chemical Formula A-389]
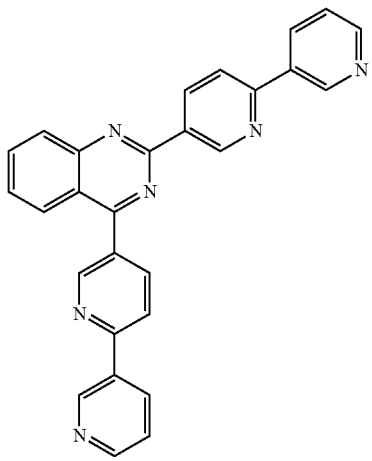
[Chemical Formula A-390]
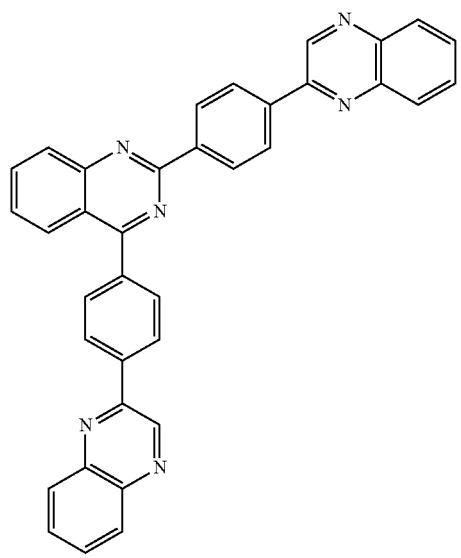
[Chemical Formula A-391]
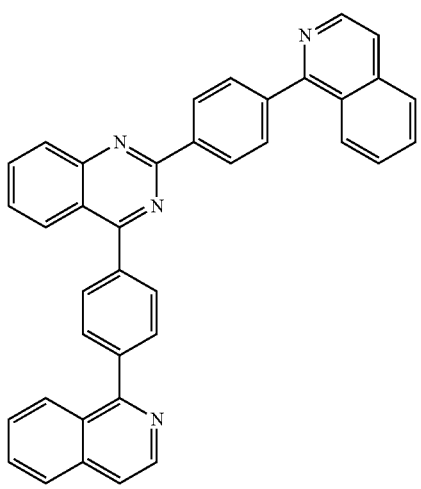

-continued
[Chemical Formula A-392]
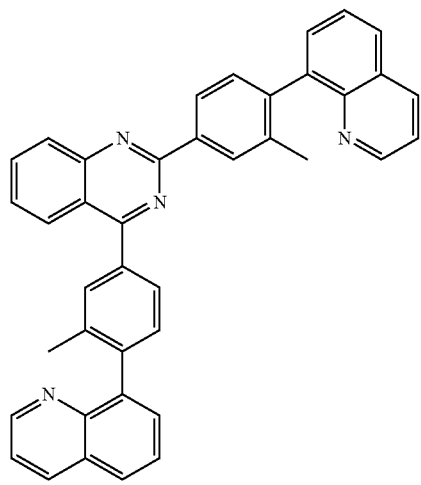
[Chemical Formula A-393]
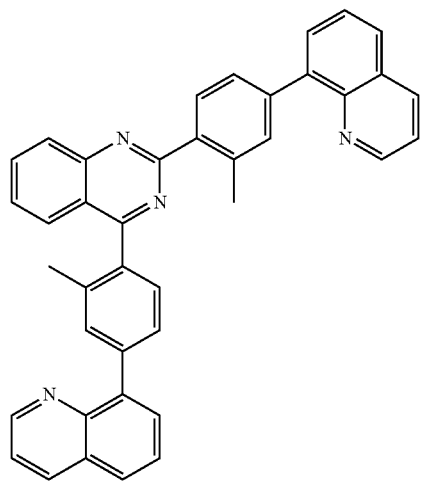
More specifically, the compound for an organic optoelectronic device may be represented by the following Chemical Formulae B-1 to B-30, but is not limited thereto.
[Chemical Formula B-1]
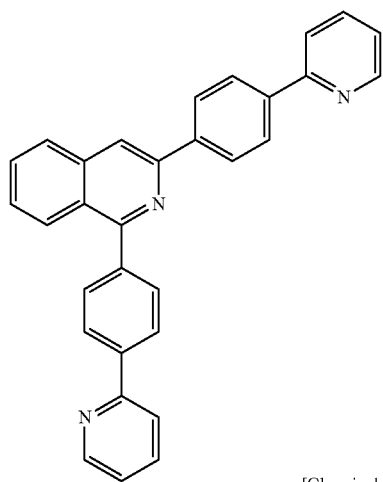
[Chemical Formula B-2]
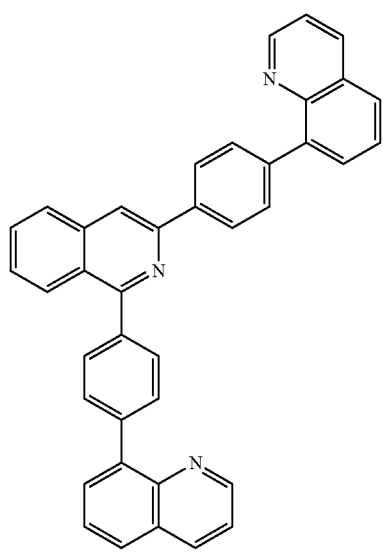
[Chemical Formula B-3]
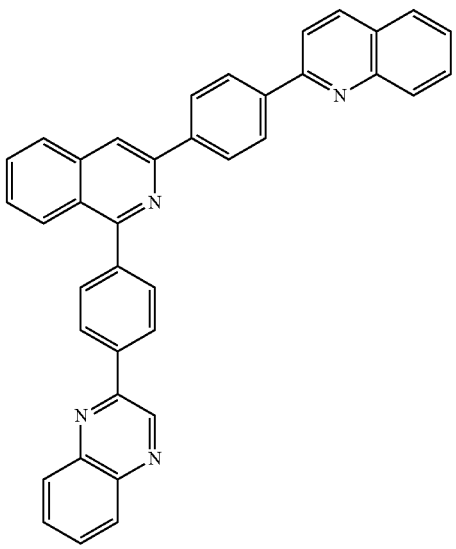

[Chemical Formula B-4]
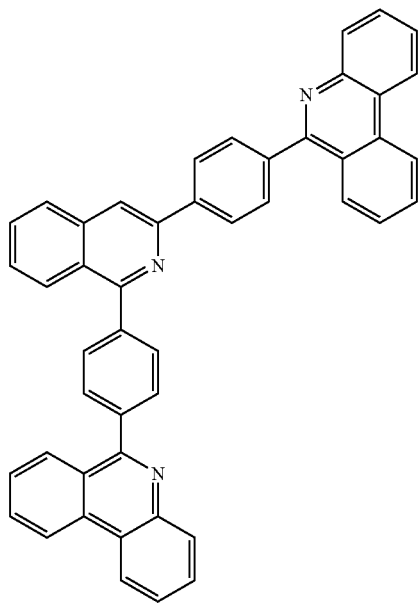
[Chemical Formula B-5]
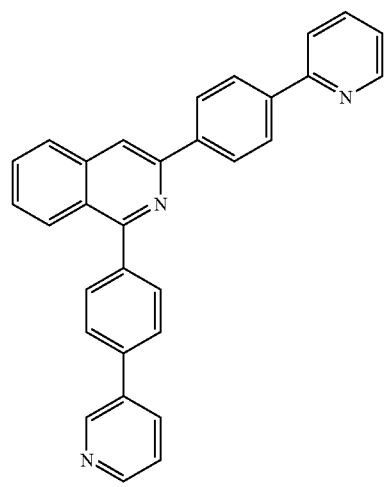
[Chemical Formula B-6]
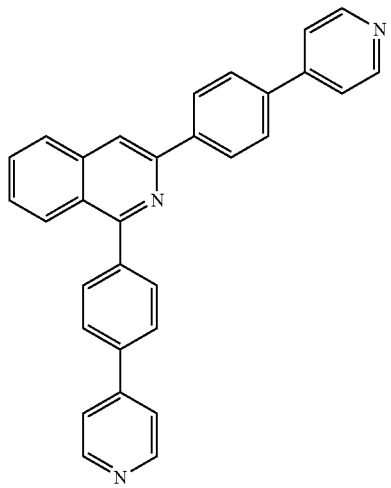
[Chemical Formula B-7]
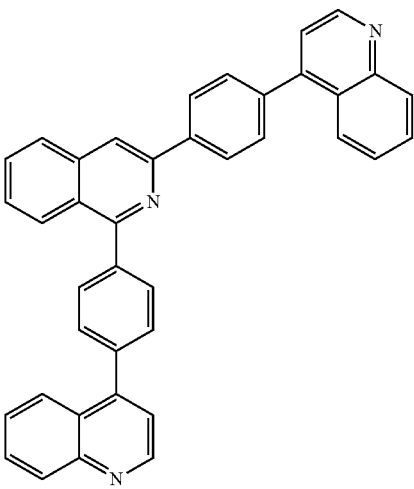
[Chemical Formula B-8]
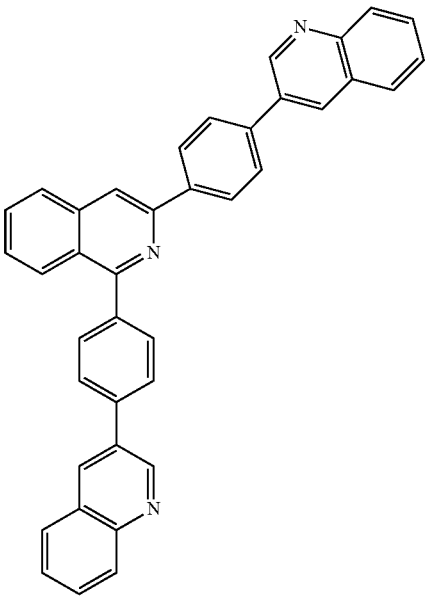

[Chemical Formula B-9]
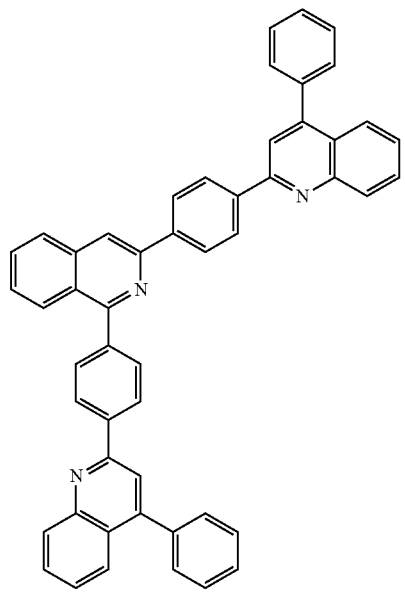
[Chemical Formula B-10]
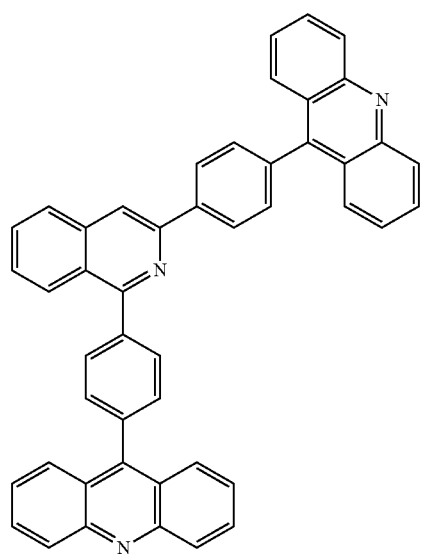
[Chemical Formula B-11]
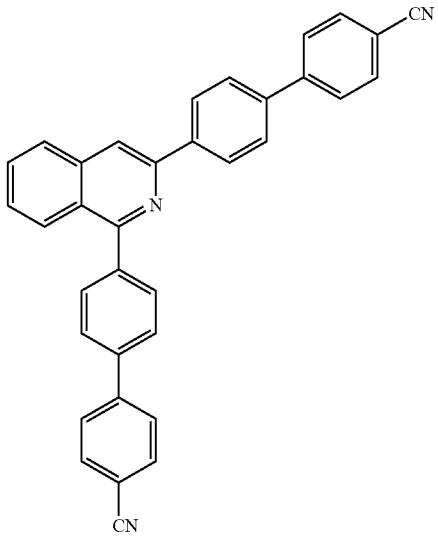
[Chemical Formula B-12]
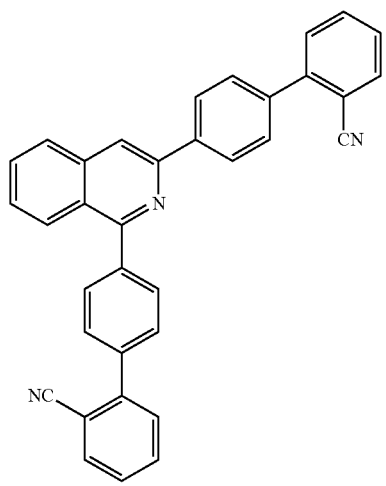
[Chemical Formula B-13]
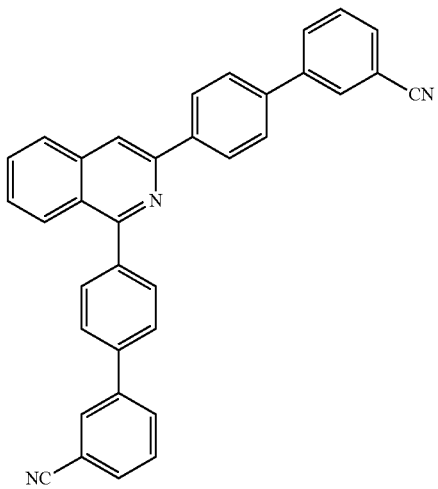

[Chemical Formula B-14]
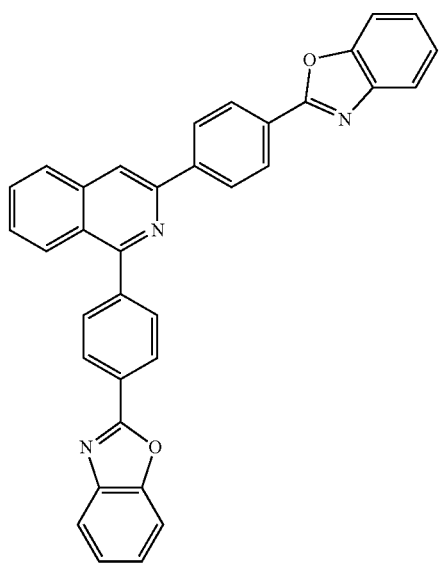
[Chemical Formula B-16]
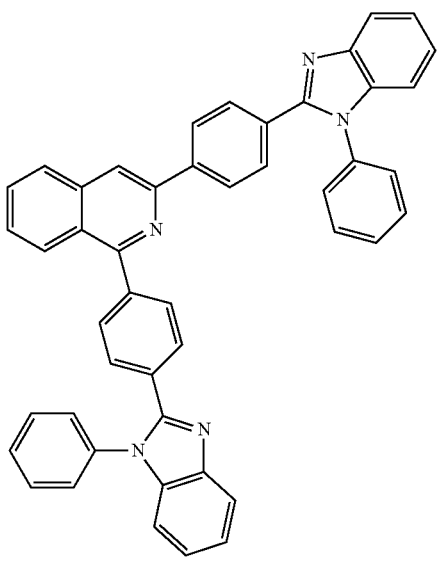
[Chemical Formula B-15]
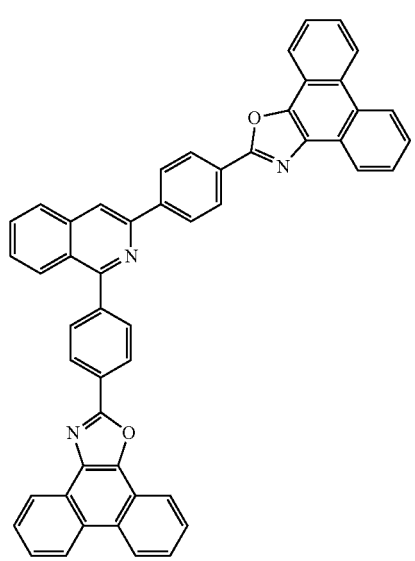
[Chemical Formula B-17]
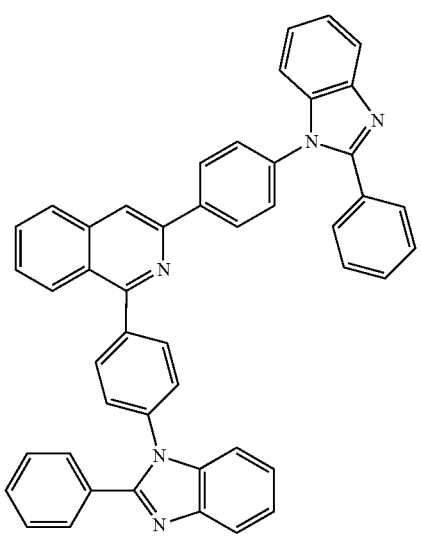

[Chemical Formula B-18]
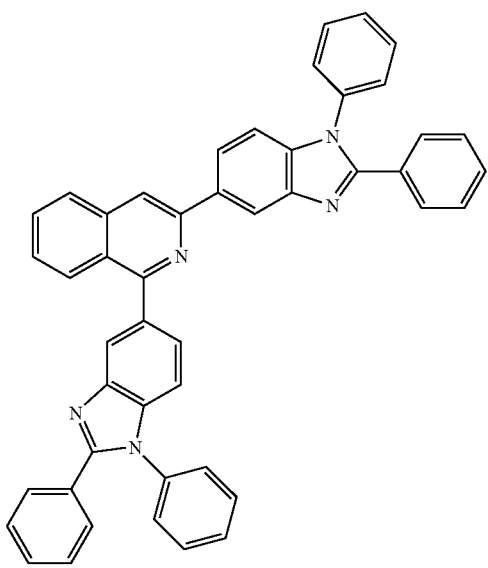
[Chemical Formula B-19]
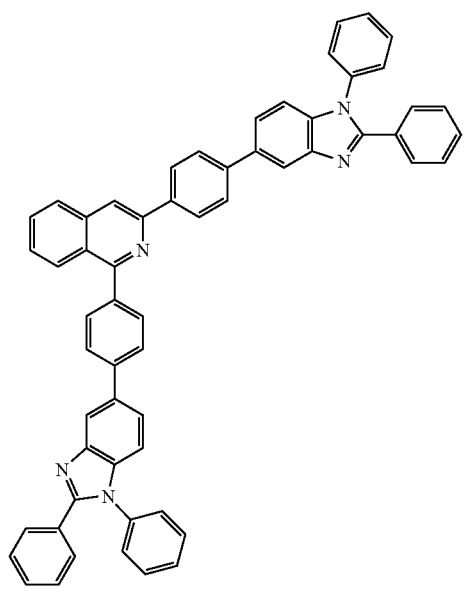
[Chemical Formula B-20]
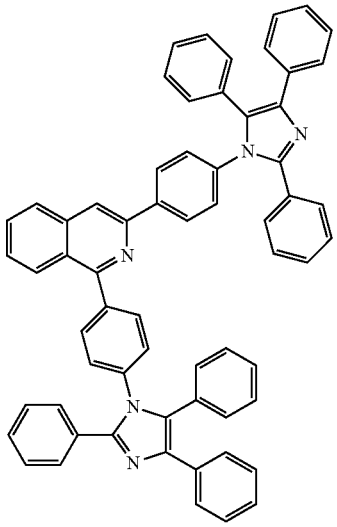
[Chemical Formula B-21]
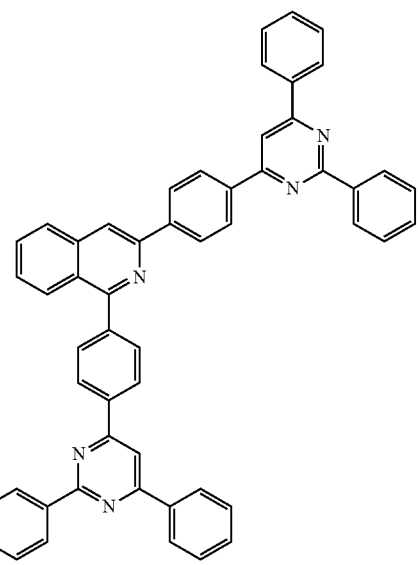

-continued
[Chemical Formula B-22]
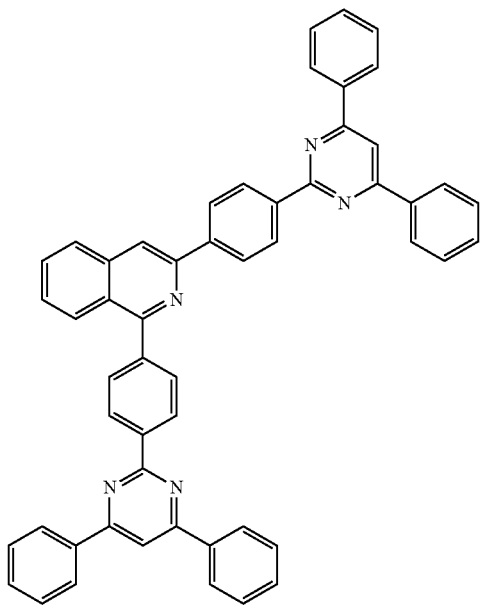
[Chemical Formula B-23]
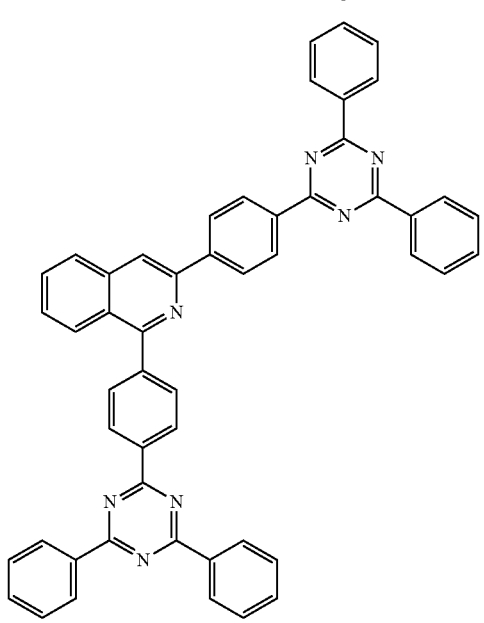
-continued
[Chemical Formula B-24]
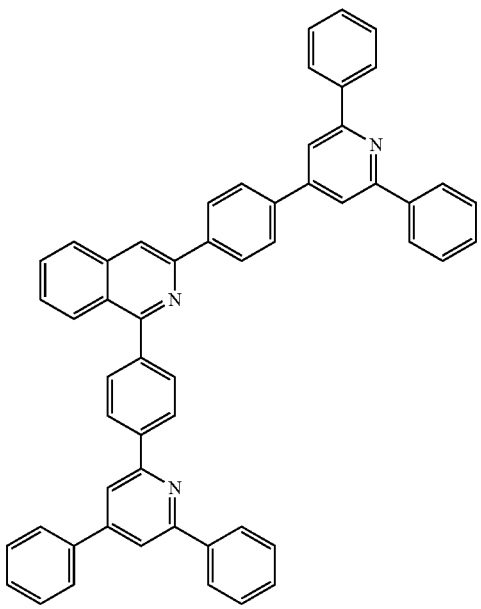
[Chemical Formula B-25]
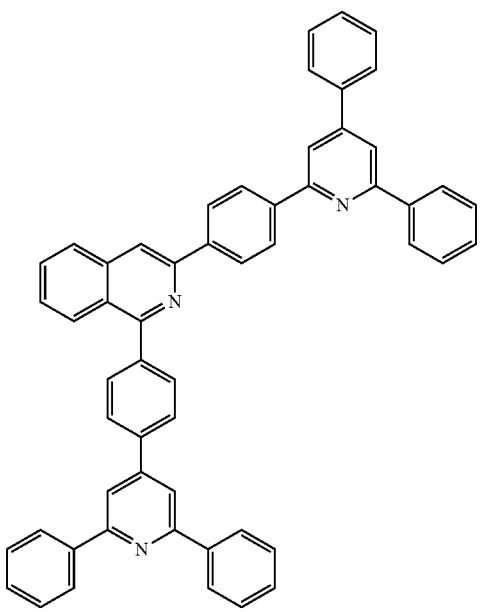

[Chemical Formula B-26]

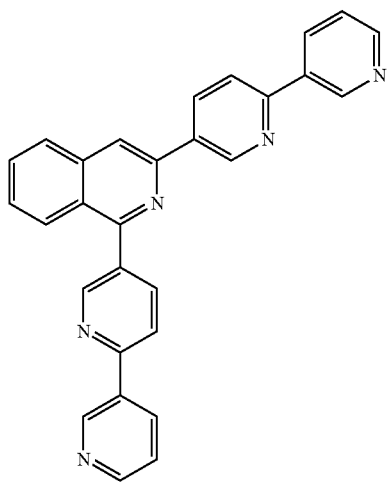

[Chemical Formula B-27]

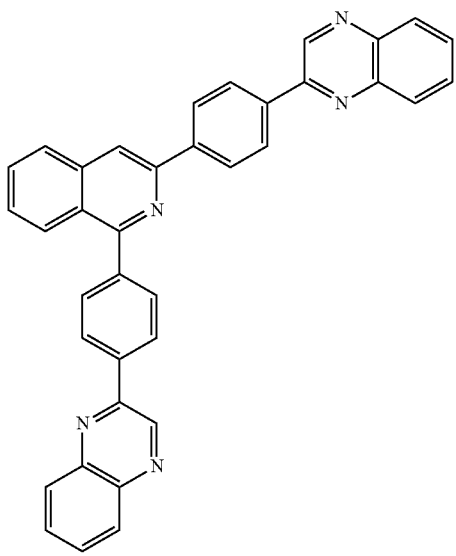

[Chemical Formula B-28]

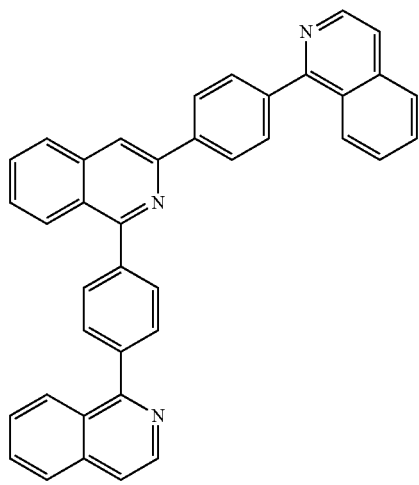

[Chemical Formula B-29]

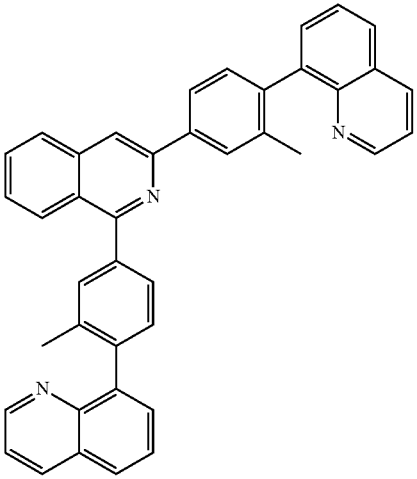

[Chemical Formula B-30]

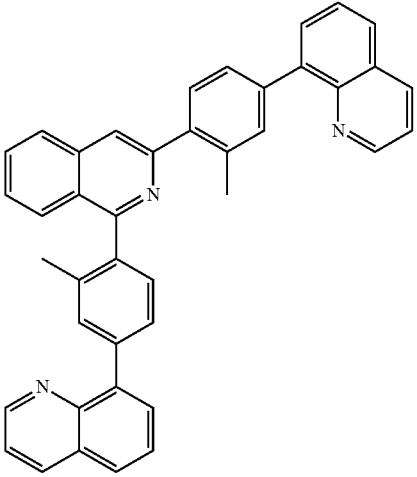

When the above compound according to one embodiment of the present invention requires both electron and hole characteristics, the functional group having electron characteristics may be introduced to effectively improve life-span of an organic light emitting diode and decreasing its driving voltage.

The above compound for an organic optoelectronic device according to one embodiment of the present invention shows a maximum light emitting wavelength in a range of about 320 to 500 nm, high triplet exciton energy (T1) of greater than equal to 2.0 eV and specifically, 2.0 to 4.0 eV and thus, has an advantage of increasing luminous efficiency of a dopant by well transporting charges of a host having high triplet exciton energy to the dopant and decreasing a driving voltage by freely adjusting HOMO and LUMO energy levels and accordingly, may be used as a host material or a charge transport material.

In addition, the compound for an organic optoelectronic device has optical and electrical activity and thus, may be used as a non-linear optical material, an electrode material, an electrochromic material, an optical switch, a sensor, a module, a wave guide, an organic transistor, a laser, an optical absorbing material, a dielectric material, and a material for a separation membrane and the like.

The compound for an organic optoelectronic device including the above compounds has a glass transition temperature of greater than or equal to 90° C. and a thermal decomposition temperature of greater than or equal to 400° C., indicating improved thermal stability. Thereby, it is possible to produce an organic optoelectronic device having a high efficiency.

The compound for an organic optoelectronic device including the above compounds may play a role for emitting light or injecting and/or transporting electrons, and also act as a light emitting host with an appropriate dopant. In other words, the compound for an organic optoelectronic device may be used as a phosphorescent or fluorescent host material, a blue light emitting dopant material, or an electron transport material.

The compound for an organic optoelectronic device according to one embodiment of the present invention is used for an organic thin layer, and it may improve the life-span characteristics, efficiency characteristics, electrochemical stability, and thermal stability of an organic optoelectronic device and decrease the driving voltage.

Therefore, according to another embodiment, an organic optoelectronic device that includes the compound for an organic optoelectronic device is provided. The organic optoelectronic device may include an organic photoelectric device, an organic light emitting diode, an organic solar cell, an organic transistor, an organic photo-conductor drum, an organic memory device, and the like. For example, the compound for an organic optoelectronic device according to one embodiment may be included in an electrode or an electrode buffer layer in the organic solar cell to improve the quantum efficiency, and it may be used as an electrode material for a gate, a source-drain electrode, or the like in the organic transistor.

Hereinafter, an organic light emitting diode is specifically described.

An organic light emitting diode according to another embodiment of the present invention includes an anode, a cathode, and at least one or more organic thin layer between the anode and the cathode, and at least one of the organic thin layers may include the compound for an organic optoelectronic device according to one embodiment of the present invention.

The organic thin layer including the compound for an organic optoelectronic device may include a layer selected from the group consisting of an emission layer, a hole transport layer, a hole injection layer, an electron transport layer, an electron injection layer, a hole blocking layer, and a combination thereof, and the at least one layer includes the compound for an organic optoelectronic device according to one embodiment. Particularly, the compound for an organic optoelectronic device according to one embodiment may be included in an electron transport layer or electron injection layer. In addition, when the compound for an organic optoelectronic device is included in the emission layer, the compound for an organic optoelectronic device may be included as a phosphorescent or fluorescent host, and particularly, as a fluorescent blue dopant material.

FIGS. 1 to 5 are cross-sectional views showing organic light emitting diodes including the compound for an organic optoelectronic device according to one embodiment of the present invention.

Referring to FIGS. 1 to 5, organic light emitting diodes 100, 200, 300, 400, and 500 according to one embodiment include at least one organic thin layer 105 interposed between an anode 120 and a cathode 110.

The anode 120 includes an anode material, which is preferably a material having a large work function to help hole injection into an organic thin layer. Specific examples of the anode material include: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or $SnO_2$:Sb; or a conductive polymer such as poly(3-methyhlthiophene), poly[3,4-(ethylene-1,2-dioxy)thiophene] (PEDT), polypyrrole, and polyaniline, but is not limited thereto. It is preferable to include a transparent electrode including indium tin oxide (ITO) as an anode.

The cathode 110 includes a cathode material, which is a material having a small work function to help electron injection into an organic thin layer. Specific examples of the cathode material include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca, but is not limited thereto. It is preferable to include a metal electrode including aluminum as a cathode.

First, referring to FIG. 1, the organic light emitting diode 100 includes the only emission layer 130 as an organic thin layer 105, and the organic thin layer 105 may be present as the only emission layer 130.

Figure 2:
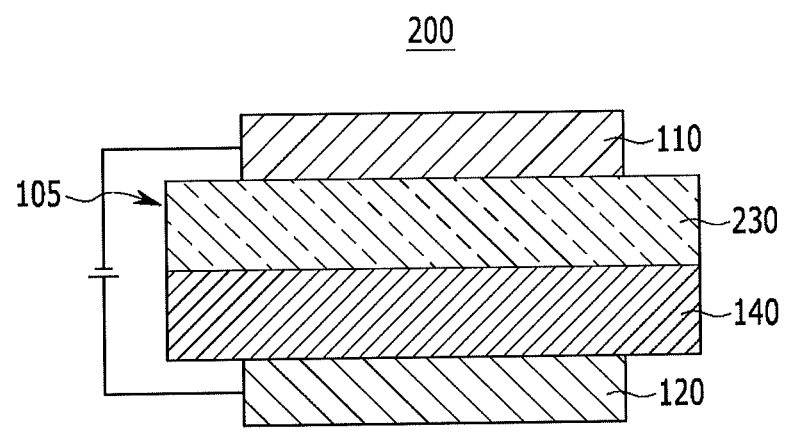

Referring to FIG. 2, a double-layered organic light emitting diode 200 includes an organic thin layer 105 including an emission layer 230 including an electron transport layer (ETL), and a hole transport layer (HTL) 140 and as shown in FIG. 2, the organic thin layer 105 includes a double layer of the emission layer 230 and hole transport layer (HTL) 140. The emission layer 130 also functions as an electron transport layer (ETL), and the hole transport layer (HTL) 140 layer has an excellent binding property with a transparent electrode such as ITO or an excellent hole transport capability.

Figure 3:
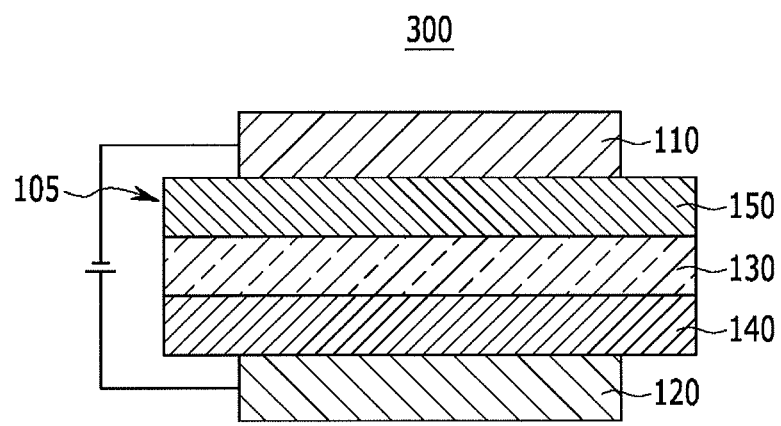

Referring to FIG. 3, a three-layered organic light emitting diode 300 includes an organic thin layer 105 including an electron transport layer (ETL) 150, an emission layer 130, and a hole transport layer (HTL) 140. The emission layer 130 is independently installed, and layers having an excellent electron transport capability or an excellent hole transport capability are separately stacked.

Figure 4:
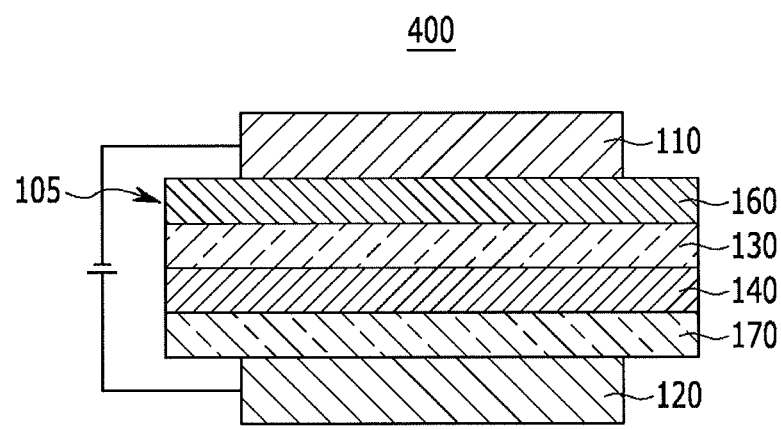

Referring to FIG. 4, a four-layered organic light emitting diode 400 includes an organic thin layer 105 including an electron injection layer (EIL) 160, an emission layer 130, a hole transport layer (HTL) 140, and a hole injection layer (HIL) 170 for adherence with the cathode of ITO.

Figure 5:
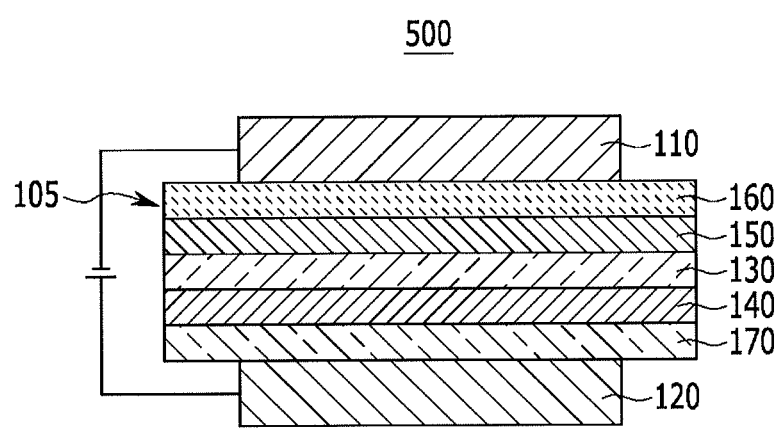

Referring to FIG. 5, a five-layered organic light emitting diode 500 includes an organic thin layer 105 including an electron transport layer (ETL) 150, an emission layer 130, a hole transport layer (HTL) 140, and a hole injection layer (HIL) 170, and further includes an electron injection layer (EIL) 160 to achieve a low voltage.

In FIGS. 1 to 5, the organic thin layer 105 including at least one selected from the group consisting of an electron transport layer (ETL) 150, an electron injection layer (EIL) 160, emission layers 130 and 230, a hole transport layer (HTL) 140, a hole injection layer (HIL) 170, and combinations thereof includes the compound for an organic optoelectronic device. Herein, the compound for an organic optoelectronic device may be used for an electron transport layer (ETL) 150 including the electron transport layer (ETL) 150 or electron injection layer (EIL) 160, and when it is used for the electron transport layer (ETL), it is possible to provide an organic light emitting diode having a more simple structure because it does not require an additional hole blocking layer (not shown).

Furthermore, when the compound for an organic optoelectronic device is included in the emission layers 130 and 230, the compound for an organic optoelectronic device may be included as a phosphorescent or fluorescent host or a fluorescent blue dopant.

The organic light emitting diode may be manufactured by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

According to one embodiment of the present invention, a display device including the organic light emitting diode is provided.

Hereinafter, the embodiments are illustrated in more detail with reference to examples. These examples, however, should not in any sense be interpreted as limiting the scope of the present invention.

(Preparation of Compound for Organic Optoelectronic Device)

Example 1

Preparation of Compound A-4

The compound A-4 was synthesized through the following Reaction Scheme 1 as specific examples of a compound for an organic optoelectronic device according to the present invention.

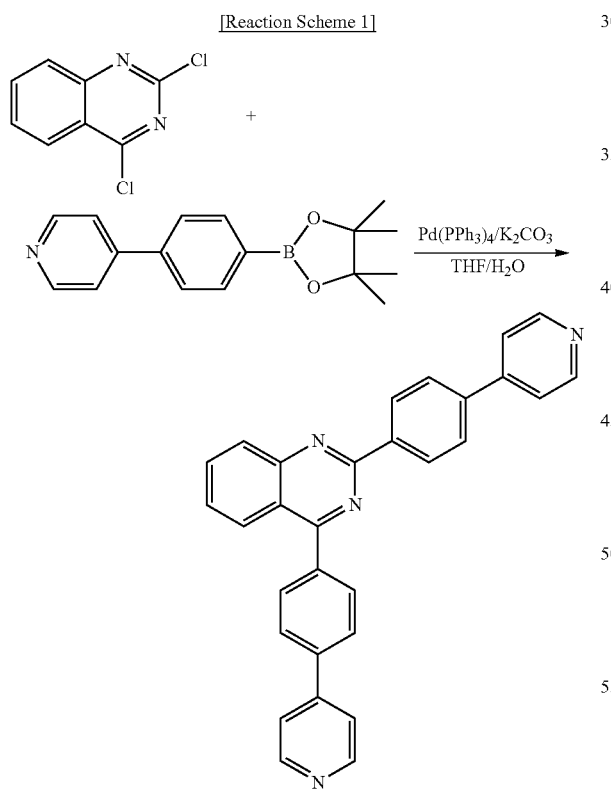

10.0 g (50.2 mmol) of 2,4-dichloroquinazoline, 3.11 g (110.5 mmol) of 4-(4-(4,4,5,5-tetramethyl-1,3,2-dioxaborolan-2-yl)phenyl)pyridine and 2.9 g (2.5 mmol) of tetrakis(triphenylphosphine)palladium [Pd(PPh$_3$)$_4$] were dissolved in 200 ml of tetrahydrofuran (THF) as a solvent, a solution obtained by dissolving 27.8 g (200.9 mmol) of potassium carbonate (K$_2$CO$_3$) in 100 ml of water was added thereto, and the mixture was reacted at 90° C. for 12 hours. After removing the solvent under a reduced pressure, the obtained reactant was washed with water and methanol. The residue was recrystallized with toluene, and the precipitated crystal was separated with a filter, washed with methanol and dried, obtaining 15.0 g of a white solid compound (a yield: 68%). (calculation value: 436.51, measurement value: MS[M+1] 436.86)

Example 2

Synthesis of Compound A-5

The compound A-5 was synthesized through the following Reaction Scheme 2 as specific examples of a compound for an organic optoelectronic device according to the present invention.

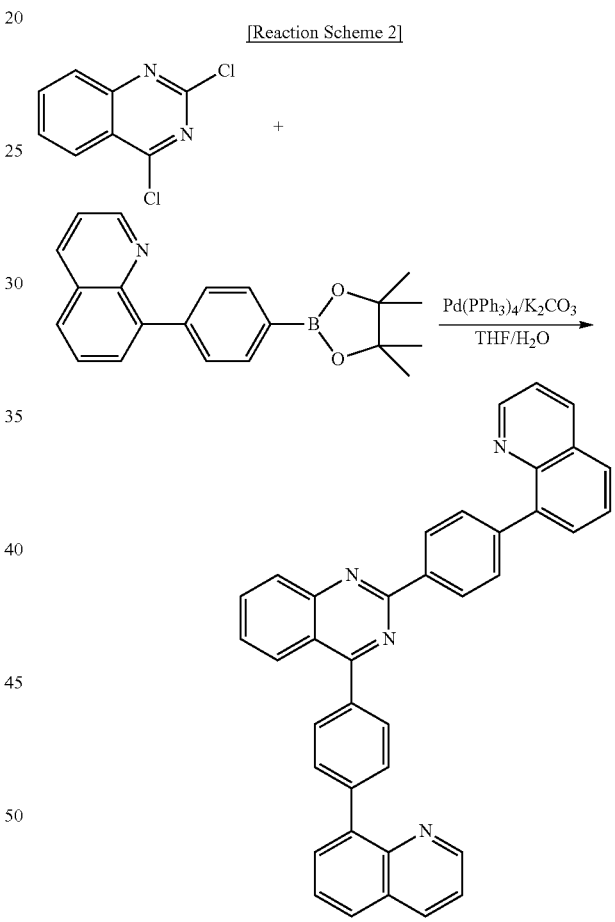

8.0 g (40.2 mmol) of 2,4-dichloroquinazoline, 20.1 g (88.4 mmol) of 8-(4-(4,4,5,5-tetramethyl-1,3,2-dioxaborolan-2-yl)phenyl)quinoline and 2.3 g (2.0 mmol) of tetrakis(triphenylphosphine)palladium [Pd(PPh$_3$)$_4$] were dissolved in 200 ml of tetrahydrofuran (THF) as a solvent, a solution obtained by dissolving 22.2 g (160.8 mmol) of potassium carbonate (K$_2$CO$_3$) in 100 ml of water was added thereto, and the mixture was reacted at 90° C. for 12 hours. After removing the solvent under a reduced pressure, the obtained reactant was washed with water and methanol. The residue was recrystallized with toluene, and the precipitated crystal was separated with a filter, washed with methanol and dried, obtaining 15.0 g of a white solid compound (a yield: 69%). (calculation value: 536, measurement value: MS[M+1] 536.97)

Example 3

Synthesis of Compound B-8

The compound B-8 was synthesized through the following Reaction Scheme 3 as specific examples of a compound for an organic optoelectronic device according to the present invention.

[Reaction Scheme 3]

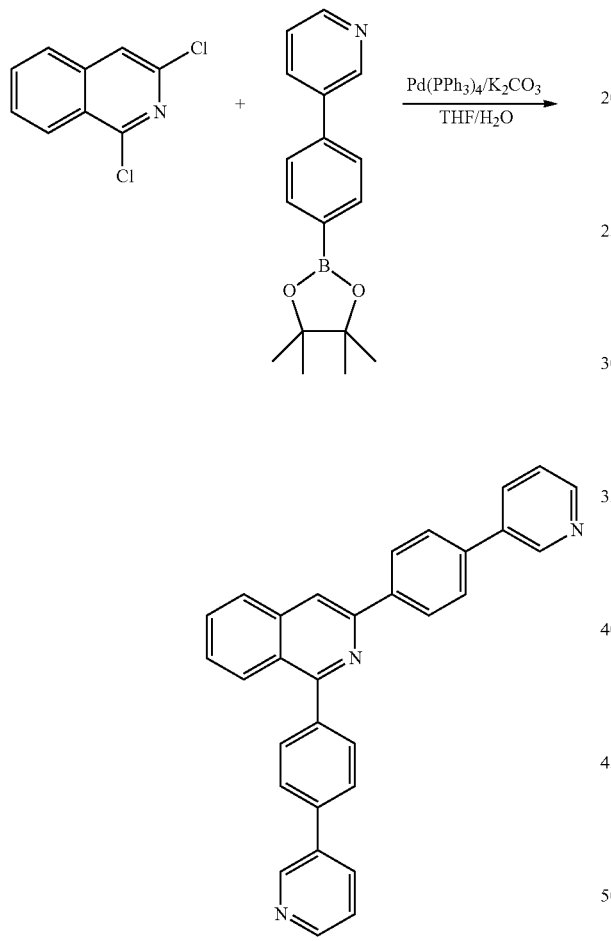

10.0 g (50.5 mmol) of 1,3-dichloroisoquinoline, 31.2 g (111.1 mmol) of 3-(4-(4,4,5,5-tetramethyl-1,3,2-dioxaborolan-2-yl)phenyl)pyridine and 2.9 g (2.5 mmol) of tetrakis(triphenylphosphine)palladium [Pd(PPh₃)₄] were dissolved in 200 ml of tetrahydrofuran (THF) as a solvent, a solution obtained by dissolving 27.9 g (201.9 mmol) of potassium carbonate (K₂CO₃) in 100 ml of water, and the mixture was reacted at 90° C. for 12 hours. After removing the solvent under a reduced pressure, the obtained reactant was washed with water and methanol. The residue was recrystallized with toluene, and the precipitated crystal was separated with a filter, washed with methanol and dried, obtaining 14.0 g of a white solid compound (a yield: 64%). calculation value: 435.52, measurement value: MS[M+1] 435.87)

Example 4

Synthesis of Compound B-2

The compound B-2 was synthesized through the following Reaction Scheme 4 as specific examples of a compound for an organic optoelectronic device according to the present invention.

[Reaction Scheme 4]

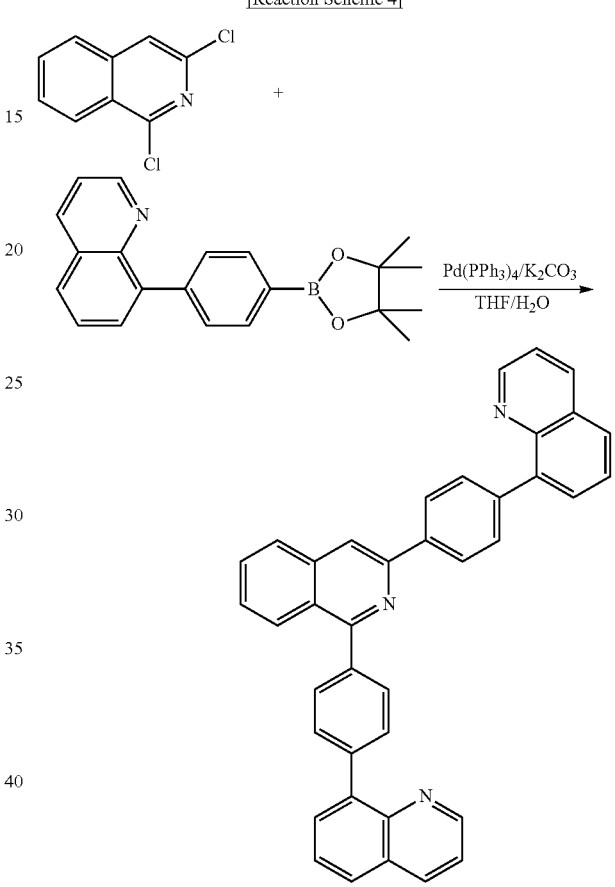

8.0 g (40.4 mmol) of 1,3-dichloroisoquinoline, 29.4 g (88.9 mmol) of 8-(4-(4,4,5,5-tetramethyl-1,3,2-dioxaborolan-2-yl)phenyl)quinoline and 2.3 g (2.0 mmol) of tetrakis(triphenylphosphine)palladium [Pd(PPh₃)₄] were dissolved in 200 ml of tetrahydrofuran (THF) as a solvent, a solution obtained by dissolving 22.3 g (161.6 mmol) of potassium carbonate (K₂CO₃) in 100 ml of water was added thereto, and the mixture was reacted at 90° C. for 12 hours. After removing the solvent under a reduced pressure, the obtained reactant was washed with water and methanol. The residue was recrystallized with toluene, and the precipitated crystal was separated with a filter, washed with methanol and dried, obtaining 15.0 g of a white solid compound (a yield: 69%). (calculation value: 535.64, measurement value: MS[M+1] 535.99)

Example 5

Synthesis of Compound A-1

The compound A-1 was synthesized through four steps in the following Reaction Scheme 5 as specific examples of a compound for an organic optoelectronic device according to the present invention.

[Reaction Scheme 5]

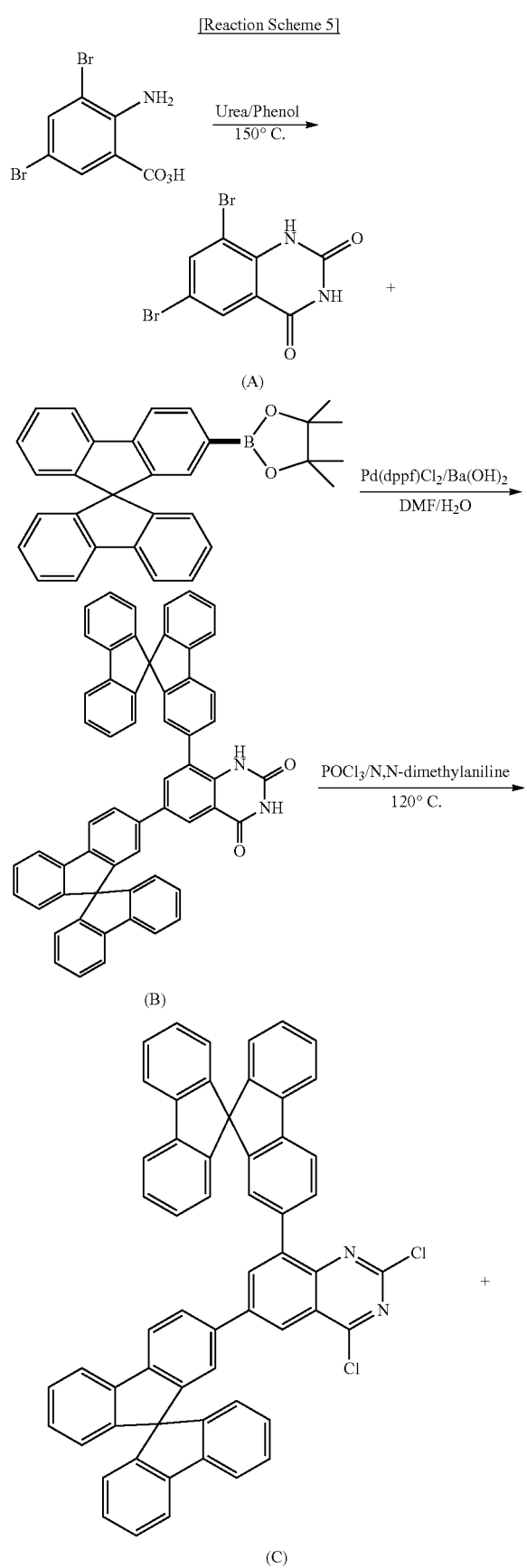

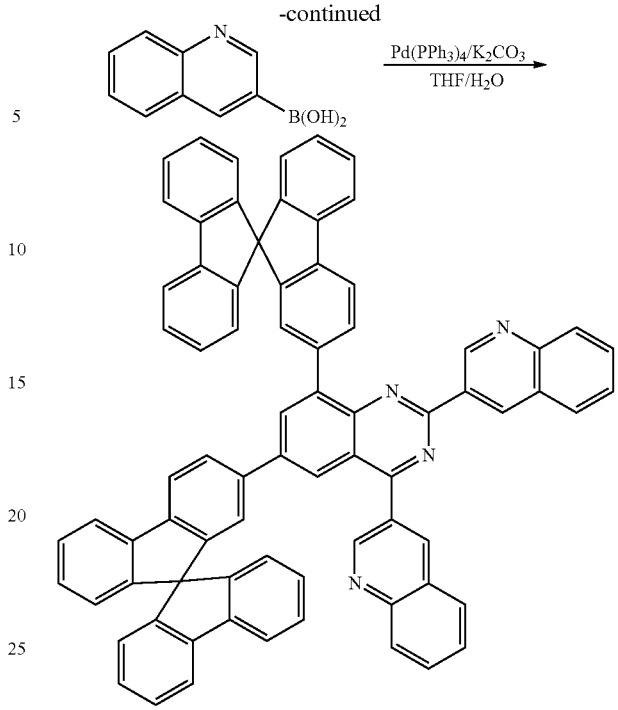

First Step; Synthesis of Intermediate Product (A)

20.0 g (67.8 mmol) of 3,5-dibromoanthranilic acid, 21.2 g (352.6 mmol) of urea and 28.1 g (298.4 mmol) of phenol were mixed and reacted at 150° C. for 12 hours. The resultant was cooled down to 100° C., and a mixed solution of water and ethanol in a ratio of 1:1 was added thereto. A crystal precipitated therein was separated with a filter, washed with water and methanol and dried, obtaining 17.2 g of a yellow solid intermediate product A (a yield: 71%).

Second Step: Synthesis of Intermediate Product (B)

7.7 g (24.1 mmol) of the intermediate product (B), 27.68 g (62.6 mmol) of 2-(9,9'-spirobi[fluoren]-2-yl)-4,4,5,5-tetramethyl-1,3,2-dioxaborolane and 1.9 g (2.4 mmol) of [1,1'-bis(diphenylphosphino)ferrocene]dichloropalladium (II) [Pd(dppf)Cl$_2$] were dissolved in 300 ml of N,N-dimethylformamide (DMF) as a solvent, a solution obtained by dissolving 30.4 g (96.3 mmol) of bariumhydroxide (Ba(OH)2) in 70 ml of water, and the mixture was reacted at 110° C. for 24 hours. After removing the solvent under a reduced pressure, the obtained reactant was washed with water and methanol. The residue was recrystallized with chloroform/methanol, and the precipitated crystal was separated with a filter, washed with methanol and dried, obtaining 14.9 g of a yellow solid intermediate product (B) (a yield: 79%).

Third Step: Synthesis of Intermediate Product (C)

10.0 g (12.6 mmol) of the intermediate product (B) was diluted in 8 ml of phosphorous oxychloride (POCl$_3$) as a solvent, and 1.6 g (13.2 mmol) of N,N-dimethylaniline was added thereto. The reaction mixture was reacted at 140° C. for 7 hours. The obtained reactant was poured into ice water, a solid formed therein was filtered and washed with water and a sodium bicarbonate saturated aqueous solution. The obtained solid mixture was washed with methanol and dried, obtaining 9.0 g of a light yellow solid intermediate product (C) (a yield: 80%).

Fourth Step: Synthesis of Compound A-1

5.0 g (6.0 mmol) of the intermediate product (C), 2.3 g (13.3 mmol) of 3-quinolineboronic acid and 0.4 g (0.3 mmol)

of tetrakis(triphenylphosphine)palladium [Pd(PPh$_3$)$_4$] were dissolved in 300 ml of tetrahydrofuran (THF) as a solvent, a solution obtained by dissolving 3.3 g (24.2 mmol) of potassium carbonate (K$_2$CO$_2$) in 100 ml of water was added thereto, and the mixture was reacted at 90° C. for 12 hours. After removing the solvent under a reduced pressure, the obtained reactant was washed with water and methanol. The residue was recrystallized with monochlorobenzene, and the precipitated crystal was separated with a filter, washed with methanol and dried, obtaining 4.4 g of a white solid compound (a yield: 82%). (calculation value: 1013.19, measurement value: MS[M+1] 1013.54)

Example 6

Synthesis of Compound A-2

The compound A-2 was synthesized through the following Reaction Scheme 6 as specific examples of a compound for an organic optoelectronic device according to the present invention.

[Reaction Scheme 6]

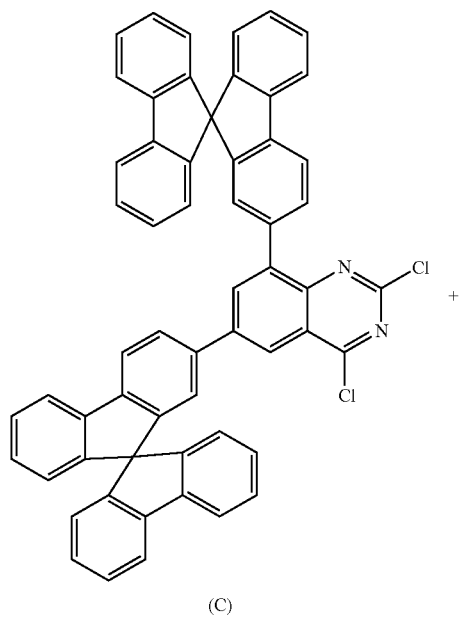

(C)

+

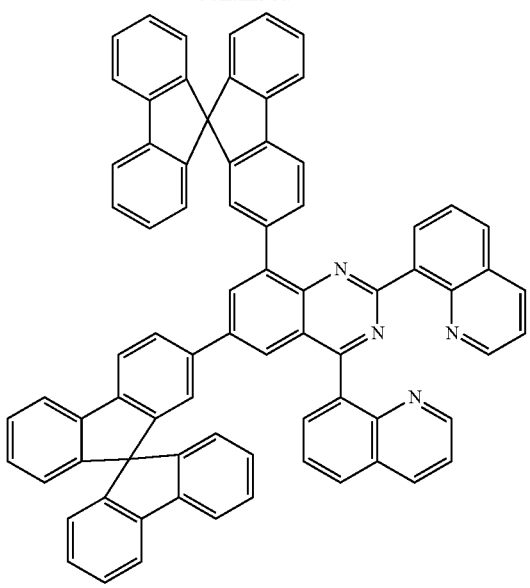

5.0 g (6.0 mmol) of the intermediate product (C), 2.3 g (13.3 mmol) of 8-quinolineboronic acid and 0.4 g (0.3 mmol) of tetrakis(triphenylphosphine)palladium [Pd(PPh$_3$)$_4$] were dissolved in 300 ml of tetrahydrofuran (THF) as a solvent, a solution obtained by dissolving 3.3 g (24.2 mmol) of potassium carbonate (K$_2$CO$_3$) in 100 ml of water was added thereto, and the mixture was reacted at 90° C. for 12 hours. After removing the solvent under a reduced pressure, the obtained reactant was washed with water and methanol. The residue was recrystallized with monochlorobenzene, and the precipitated crystal was separated with a filter, washed with methanol and dried, obtaining 4.0 g of a yellow solid compound (a yield: 76%), (calculation value: 1013.19, measurement value; MS[M+1] 1013.54)

Example 7

Synthesis of Compound A-3

The compound A-3 was synthesized through three steps in the following Reaction Scheme 7 as specific examples of a compound for an organic optoelectronic device according to the present invention.

[Reaction Scheme 7]

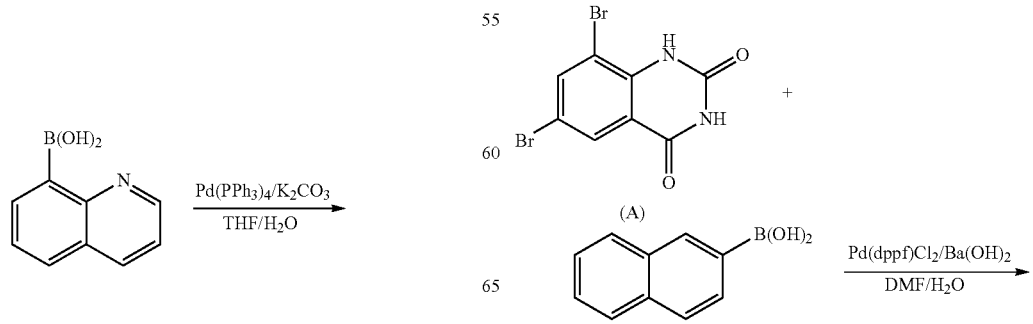

-continued

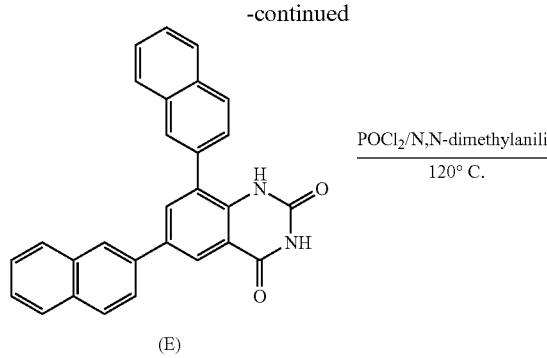

(E)

POCl₂/N,N-dimethylaniline
120° C.

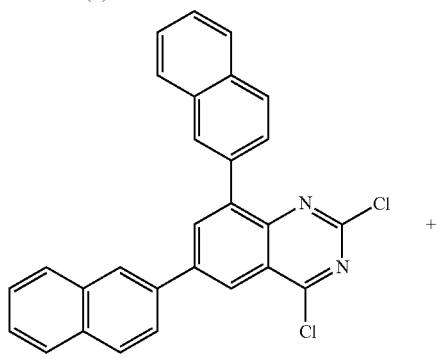

(F)

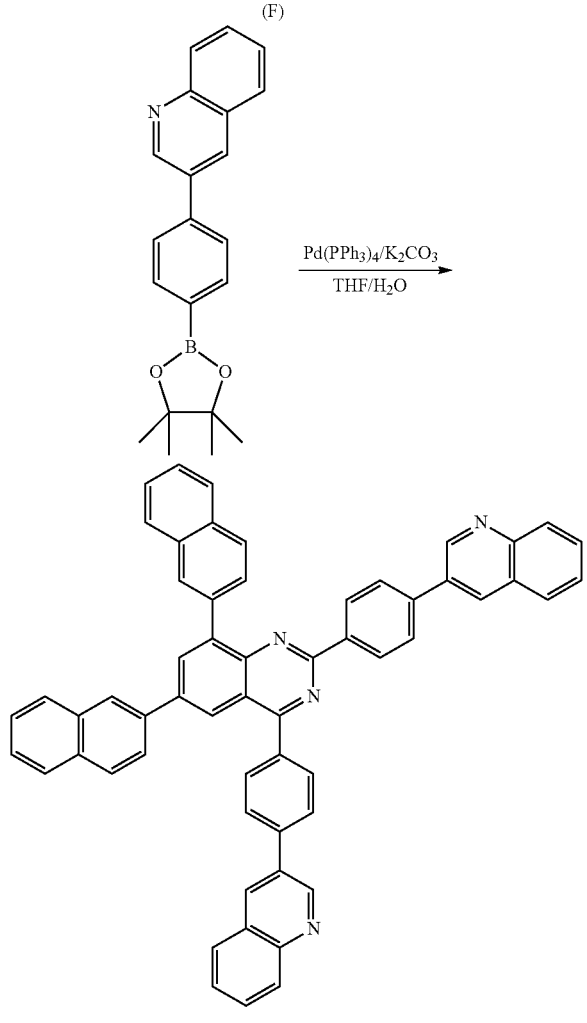

Pd(PPh₃)₄/K₂CO₃
THF/H₂O

First step; Synthesis of Intermediate Product (E)

6.0 g (18.7 mmol) of the intermediate product A, 8.4 g (48.8 mmol) of 2-naphthaleneboronic acid and 1.5 g (1.9 mmol) of [1,1'-bis(diphenylphosphino)ferrocene]dichloropalladium (II) [Pd(dppf)Cl₂] were dissolved in 240 ml of N,N-dimethylformamide (DMF) as a solvent, a solution obtained by dissolving 23.7 g (75.0 mmol) of barium hydroxide (Ba(OH)₂) in 60 ml of water was added thereto, and the mixture was reacted at 110° C. for 24 hours. After removing the solvent under a reduced pressure, the obtained reactant was washed with water and methanol. The residue was recrystallized with chloroform/methanol, and the precipitated crystal was separated with a filter, washed with methanol and dried, obtaining 6.15 g of a yellow solid intermediate product (E) (a yield: 79%).

Second Step; Synthesis of Intermediate Product (F)

6.0 g (14.5 mmol) of the intermediate product (E) was diluted in 8 ml of phosphorousoxy chloride (POCl₃) as a solvent and 1.8 g (15.1 mmol) of N,N-dimethylaniline was added thereto. The reaction mixture was reacted at 140° C. for 7 hours. The obtained reactant was poured into ice water, and a solid formed therein was filtered and washed with water and a sodium bicarbonate-saturated aqueous solution. The obtained solid mixture was washed with methanol and dried, obtaining 4.9 g of a light yellow intermediate product (F) (a yield: 76%).

Third Step: Synthesis of Compound A-3

4.7 g (10.4 mmol) of the intermediate product (F), 7.6 g (22.9 mmol) of 3-(4-(4,4,5,5-tetramethyl-1,3,2-dioxaborolan-2-yl)phenyl)quinoline and 0.06 g (0.5 mmol) of tetrakis (triphenylphospine)palladium [Pd(PPh₃)₄] were dissolved in 200 ml of tetrahydrofuran (THF) as a solvent, a solution obtained by dissolving 5.8 g (41.7 mmol) of potassium carbonate (K₂CO₃) in 100 ml of water was added thereto, and the mixture was reacted at 90° C. for 12 hours. A crystal formed therein was separated with a filter and washed with water and methanol. The residue was recrystallized with chloroform, and the precipitated crystal was separated with a filter, washed with methanol and dried, obtaining 6.8 g of a yellow solid compound (a yield: 82%). (calculation value: 788.93, measurement value: MS[M+1] 789.28)

Example 8

Synthesis of Compound A-6

The compound A-76 was synthesized through the following Reaction Scheme 8 as specific examples of a compound for an organic optoelectronic device according to the present invention.

[Reaction Scheme 8]

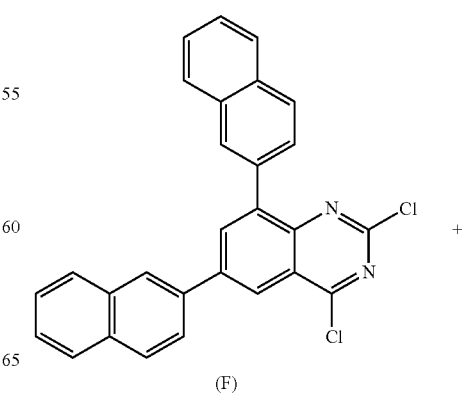

(F)

-continued

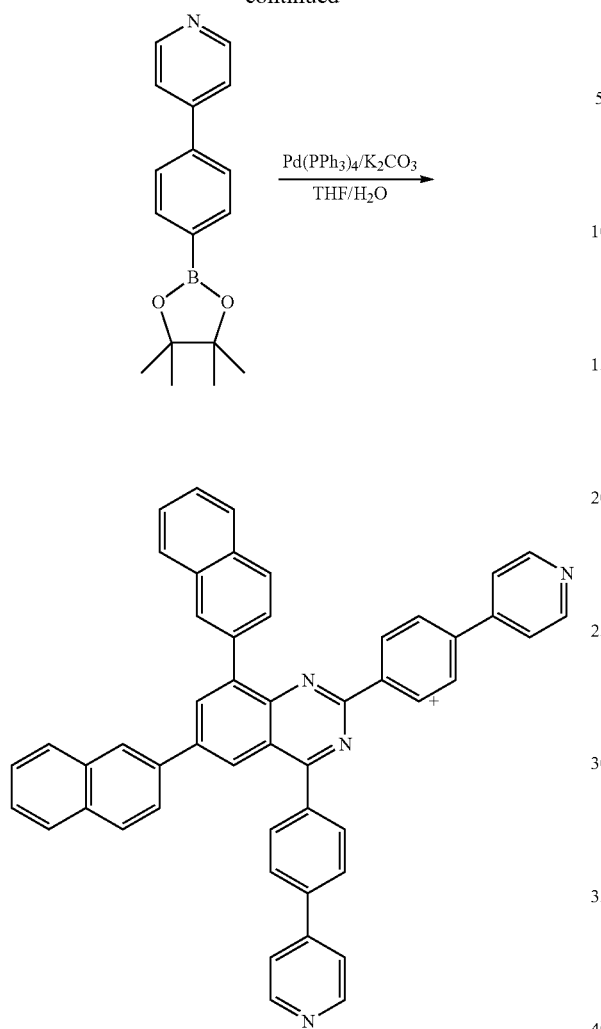

20.0 g (44.3 mmol) of the intermediate product (F), 29.9 g (106.4 mmol) of 4-(4-(4,4,5,5-tetramethyl-1,3,2-dioxaborolan-2-yl)phenyl)pyridine and 2.6 g (2.2 mmol) of tetrakis(triphenylphosphine)palladium [Pd(PPh$_3$)$_4$] were dissolved in 400 ml of tetrahydrofuran (THF) as a solvent, a solution obtained by dissolving 24.5 g (177.3 mmol) of potassium carbonate (K$_2$CO$_3$) in 200 ml of water was added thereto, and the mixture was reacted at 90° C. for 12 hours. A crystal formed therein was separated with a filter and wasted with water and methanol. The residue was recrystallized with chloroform, and the precipitated crystal was separated with a filter, washed with methanol and dried, obtaining 20.0 g of a yellow solid compound (a yield: 66%). (calculation value: 688.82, measurement value: MS[M+1] 689.12)

Example 9

Synthesis of Compound A-78

The compound A-78 was synthesized through the following Reaction Scheme 9 as specific examples of a compound for an organic optoelectronic device according to the present invention.

[Reaction Scheme 9]

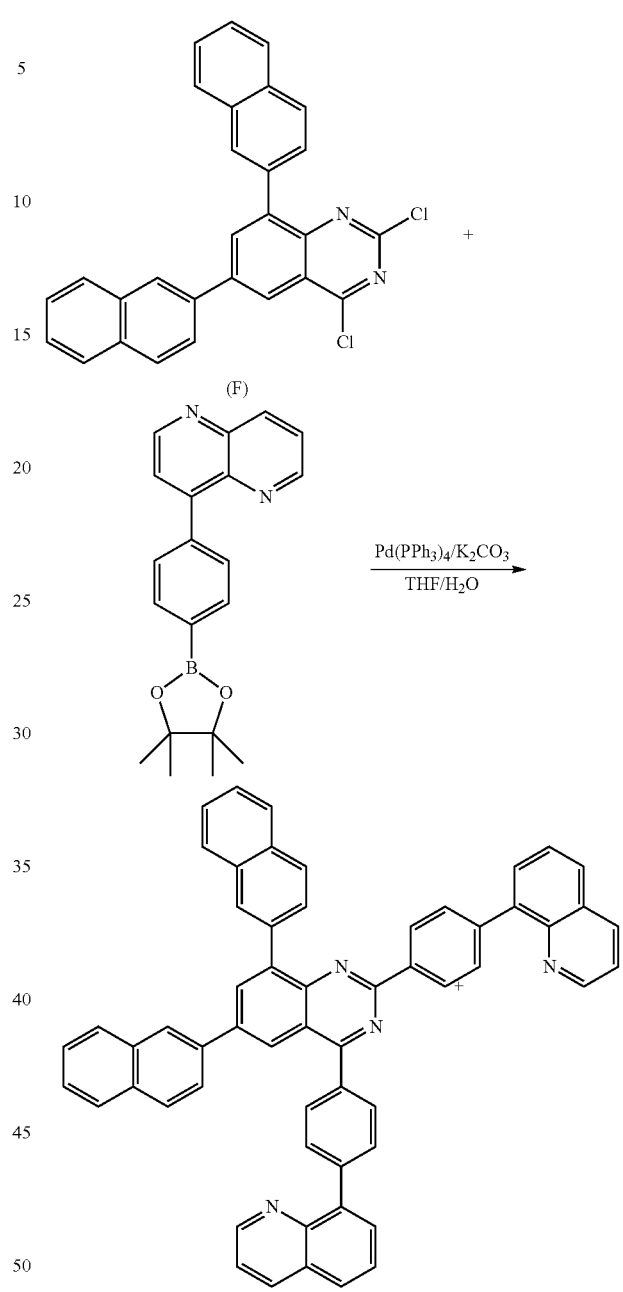

20.0 g (44.3 mmol) of the intermediate product (P), 35.2 g (106.4 mmol) of 8-(4-(4,4,5,5-tetramethyl-1,3,2-dioxaborolan-2-yl)phenyl)quinoline and 2.6 g (2.2 mmol) of tetrakis(triphenylphosphine)palladium [Pd(PPh$_3$)$_4$] were dissolved in 400 ml of tetrahydrofuran (THF) as a solvent, a solution obtained by dissolving 24.3 g (177.3 mmol) of potassium carbonate (K$_2$CO$_3$) in 200 ml of water was added thereto, and the mixture was reacted at 90° C. for 12 hours. A crystal formed therein was separated with a filter and washed with water and methanol. The residue was recrystallized with chloroform, and the precipitated crystal was separated with a filter, washed with methanol and dried, obtaining 25.4 g of a yellow solid compound (a yield: 73%). (calculation value: 788.93, measurement value: MS[M+1] 789.23)

(Manufacture of Organic Light Emitting Diode)

Example 10

Organic Light Emitting Diode

As for an anode, a 1000 Å-thick ITO was used, and as for a cathode, a 1000 Å-thick aluminum (Al) was used.

Specifically, illustrating a method of manufacturing an organic light emitting diode, the anode was manufactured by cutting an ITO glass substrate having 15 Ω/cm² of sheet resistance into a size of 50 mm×50 mm×0.7 mm and washing the cut ITO glass substrate with an ultrasonic wave in acetone, isopropyl alcohol, and pure water respectively for 5 minutes and with a UV ozone for 30 minutes.

On the glass substrate, a hole injection layer (HIL) was formed by depositing N1,N1'-(biphenyl-4,4'-diyl)bis(N1-(naphthalen-2-yl)-N4,N4-diphenylbenzene-1,4-diamine) to be 65 nm thick, and subsequently, a hole transport layer (HTL) was formed by depositing N,N'-di(1-naphthyl)-N,N'-diphenylbenzidine to be 40 nm thick.

Subsequently, an emission layer was formed by depositing 4% N,N,N',N'-tetrakis(3,4-dimethylphenyl)chrysens-6,12-diamine and 96% of 9-(3-(naphthalene-1-yl)phenyl)-10-(naphthalene-2-yl)anthracene to be 25 nm thick.

Then, an electron transport layer (ETL) was formed by depositing the compound of Example 1 to be 30 nm thick.

On the electron transport layer (ETL), a Liq/Al electrode was formed by vacuum-depositing Liq to be 0.5 nm thick as an electron injection layer (EIL) and Al to be 100 nm thick.

Example 11

An organic light emitting diode was manufactured according to the same method as Example 10 except for using the compound of Example 2 instead of the compound of Example 1 to form the electron transport layer (ETL).

Example 12

An organic light emitting diode was manufactured according to the same method as Example 10 except for using the compound of Example 3 instead of the compound of Example 1 to form the electron transport layer (ETL).

Example 13

An organic Light emitting diode was manufactured according to the same method as Example 10 except tor using the compound of Example 4 instead of the compound of Example 1 to form the electron transport layer (ETL).

Example 14

An organic light emitting diode was manufactured according to the same method as Example 10 except for using the compound of Example 8 instead of the compound of Example 1 to form the electron transport layer (ETL).

Example 15

An organic light emitting diode was manufactured according to the same method as Example 10 except for using the compound of Example 9 instead of the compound of Example 1 to form the electron transport layer (ETL).

Example 16

An organic light emitting diode was manufactured according to the same method as Example 10 except for depositing the compound of Example 1 and Liq in a ratio of 1:1 to form the electron transport layer (ETL).

Example 17

An organic light emitting diode was manufactured according to the same method as Example 10 except for depositing the compound of Example 2 and Liq in a ratio of 1:1 to form the electron transport layer (ETL).

Example 18

An organic light emitting diode was manufactured according to the same method as Example 10 except for depositing the compound of Example 3 and Liq in a ratio of 1:1 to form the electron transport layer (ETL).

Example 19

An organic light emitting diode was manufactured according to the same method as Example 11 except for depositing the compound of Example 4 and Liq in a ratio of 1:1 to form the electron transport layer (ETL).

Example 20

An organic light emitting diode was manufactured according to the same method as Example 11 except for depositing the compound of Example 8 and Liq in a ratio of 1:1 to form the electron transport layer (ETL).

Example 21

An organic light emitting diode was manufactured according to the same method as Example 11 except for depositing the compound of Example 9 and Liq in a ratio of 1:1 to form the electron transport layer (ETL).

Comparative Example 1

An organic light emitting diode was manufactured according to the same method as Example 10 except for using a compound represented by the following Formula R1 instead of the compound of Example 1 to form the electron transport layer (ETL).

[Chemical Formula R1]

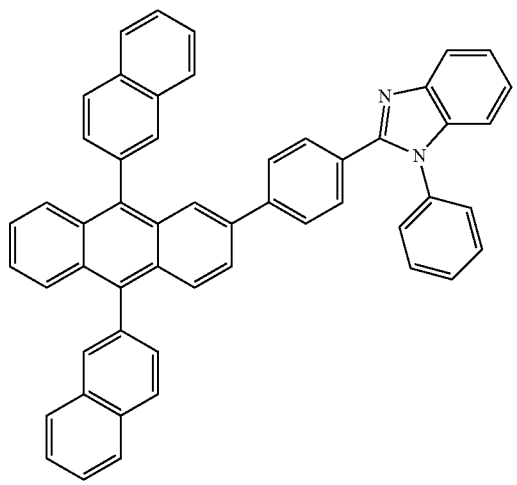

Comparative Example 2

An organic light emitting diode was manufactured according to the same method as Example 16 except for using the above compound represented by Chemical Formula R1 instead of the compound of Example 1 to form the electron transport layer (ETL).

(Performance Measurement of Organic Light Emitting Diode)

Experimental Examples

Current density change, luminance change, and luminous efficiency of each organic light emitting diode according to the Examples 11, 12, 15, 17, 18, and Comparative Examples 1 and 2 depending on a voltage were measured. Specific measurement methods are as follows, and the results are shown in the following Table 1.

(1) Measurement of Current Density Change Depending on Voltage Change

The obtained organic light emitting diodes were measured for current value flowing in the unit device while increasing the voltage from 0 V to 10 V using a current-voltage meter (Keithley 2400), and the measured current value was divided by area to provide the result.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Efficiency

The luminance, current density, and voltage obtained from the (1) and (2) were used to calculate current efficiency (cd/A) and power efficiency (lm/W) at the same luminance (500 cd/m$^2$).

TABLE 1

| | Luminance 500 cd/m$^2$ | | | | |
|---|---|---|---|---|---|
| | Driving voltage (V) | Luminous efficiency (cd/A) | Power efficiency (lm/W) | CIE Chromaticity x | y |
| Example 11 | 4.4 | 4.8 | 3.5 | 0.14 | 0.05 |
| Example 12 | 3.4 | 9.0 | 8.2 | 0.13 | 0.11 |
| Example 15 | 4.0 | 5.4 | 4.2 | 0.14 | 0.05 |
| Comparative Example 1 | 5.1 | 3.7 | 2.3 | 0.14 | 0.05 |
| Example 17 | 3.5 | 5.5 | 4.9 | 0.14 | 0.05 |
| Example 18 | 3.5 | 9.4 | 8.5 | 0.14 | 0.11 |
| Comparative Example 2 | 4.2 | 5.4 | 4.1 | 0.14 | 0.05 |

As shown in Table 1, the organic light emitting diodes according to Examples 11, 12 and 15 showed a low driving voltage and excellent luminous efficiency and power efficiency compared with the organic light emitting diode according to Comparative Example 1.

In addition, the organic light emitting diodes according to Examples 17 and 18 showed a low driving voltage and excellent luminous efficiency and power efficiency compared with the organic light emitting diode according to Comparative Example 2.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

DESCRIPTION OF SYMBOLS

100: organic light emitting diode
110: cathode
120: anode
105: organic thin layer
130: emission layer
140: hole transport layer (HTL)
150: electron transport layer (ETL)
160: electron injection layer (EIL)
170: hole injection layer (HIL)
230: emission layer+electron transport layer (ETL)

What is claimed is:

1. A compound for an organic optoelectronic device represented by the following Chemical Formula 1:

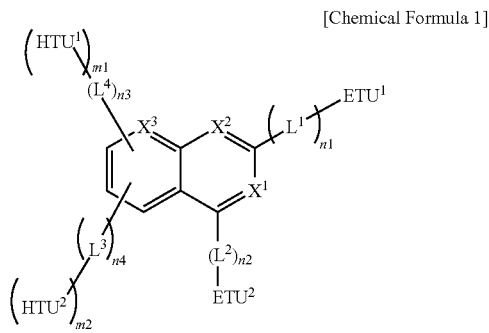

[Chemical Formula 1]

wherein, in the above Chemical Formula 1, at least one of $X^1$ to $X^3$ is N, $X^3$ is N or —CR'—, wherein the R' is hydrogen, a substituted or unsubstituted C1 to C1-alkyl group or is linked to $L^4$, $L^1$ to $L^4$ are independently a single bond, a substituted or unsubstituted C6 to C30 arylene group or a substituted or unsubstituted C2 to C30 heteroarylene group, n1 to n4 are independently integers of 0 to 3, $ETU^1$ and $ETU^2$ are independently a substituted or unsubstituted C2 to C30 heteroaryl group having electron characteristics, HTU$^1$ and HTU$^2$ are independently a substituted or unsubstituted C6 to C30 aryl group having hole characteristics, and m1 and m2 are 0 or 1.

2. The compound for an organic optoelectronic device as claimed in claim 1, wherein the compound for an organic optoelectronic device is represented by the following Chemical Formula 2:

[Chemical Formula 2]

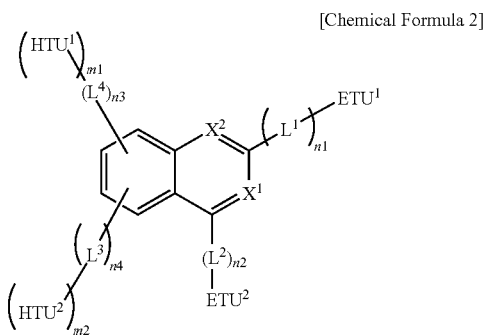

wherein, in the above Chemical Formula 2, at least one of X$^1$ and X$^2$ is N,

L$^1$ to L$^4$ are independently a single bond, a substituted or unsubstituted C6 to C30 arylene group or a substituted or unsubstituted C2 to C30 heteroarylene group, n1 to n4 are independently integers of 0 to 3, ETU$^1$ and ETU$^2$ are independently a substituted or unsubstituted C2 to C30 heteroaryl group having electron characteristics, HTU$^1$ and HTU$^2$ are independently a substituted or unsubstituted C6 to C30 aryl group having hole characteristics, and m1 and m2 are 0 or 1.

3. The compound for an organic optoelectronic device as claimed in claim 1, wherein the compound for an organic optoelectronic device is represented by the following Chemical Formula 3:

[Chemical Formula 3]

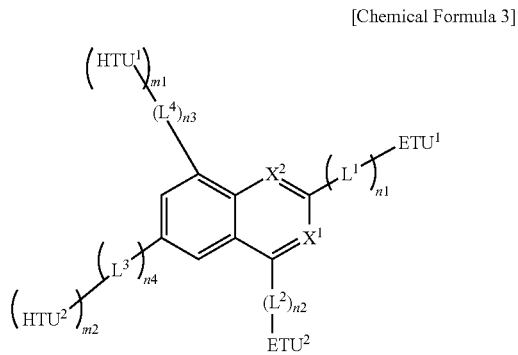

wherein, in the above Chemical Formula 3, at least one of X$^1$ and X$^2$ is N,

L$^1$ to L$^4$ are independently a single bond, a substituted or unsubstituted C6 to C30 arylene group or a substituted or unsubstituted C2 to C30 heteroarylene group, n1 to n4 are independently integers of 0 to 3, ETU$^1$ and ETU$^2$ are independently a substituted or unsubstituted C2 to C30 heteroaryl group having electron characteristics, HTU$^1$ and HTU$^2$ are independently a substituted or unsubstituted C6 to C30 aryl group having hole characteristics, and m1 and m2 are 0 or 1.

4. The compound for an organic optoelectronic device as claimed in claim 2, wherein the X$^2$ is —CH—, and X$^1$ is N.

5. The compound for an organic optoelectronic device as claimed in claim 2, wherein the X$^1$ is —CH—, and X$^2$ is N.

6. The compound for an organic optoelectronic device as claimed in claim 2, wherein the X$^1$ and X$^2$ are N.

7. The compound for an organic optoelectronic device as claimed in claim 2, wherein the n3 and m1 are 0.

8. The compound for an organic optoelectronic device as claimed in claim 2, wherein the m1 and m2 are not 0.

9. The compound for an organic optoelectronic device as claimed in claim 1, wherein the substituted or unsubstituted C2 to C30 heteroaryl group having electron characteristics is a substituted or unsubstituted imidazolyl group, a substituted or unsubstituted triazolyl group, a substituted or unsubstituted tetrazolyl group, a substituted or unsubstituted oxadiazolyl group, a substituted or unsubstituted oxatriazolyl group, a substituted or unsubstituted thiatriazolyl group, a substituted or unsubstituted benzimidazolyl group, a substituted or unsubstituted benzotriazolyl group, a substituted or unsubstituted pyridinyl group, a substituted or unsubstituted pyrimidinyl group, a substituted or unsubstituted triazinyl group, a substituted or unsubstituted pyrazinyl group, a substituted or unsubstituted pyridazinyl group, a substituted or unsubstituted purinyl group, a substituted or unsubstituted quinolinyl group, a substituted or unsubstituted isoquinolinyl group, a substituted or unsubstituted phthalazinyl group, a substituted or unsubstituted naphpyridinyl group, a substituted or unsubstituted quinoxalinyl group, a substituted or unsubstituted quinazolinyl group, a substituted or unsubstituted acridinyl group, a substituted or unsubstituted phenanthrolinyl group, a substituted or unsubstituted phenazinyl group, or a combination thereof.

10. The compound for an organic optoelectronic device as claimed in claim 1, wherein the substituted or unsubstituted C6 to C30 aryl group having hole characteristics is a substituted or unsubstituted phenyl group, a substituted or unsubstituted naphthyl group, a substituted or unsubstituted phenanthrenyl group, a substituted or unsubstituted anthracenyl group, a substituted or unsubstituted fluorenyl group, a substituted or unsubstituted triphenylenyl group, a substituted or unsubstituted spiro-fluorenyl group, a substituted or unsubstituted terphenyl group, a substituted or unsubstituted pyrenyl group, a substituted or unsubstituted perylenyl group, or a combination thereof.

11. The compound for an organic optoelectronic device as claimed in claim 1, wherein the compound for an organic optoelectronic device is one of compounds represented by the following Chemical Formulae A-1 to A-393:

[Chemical Formula A-1]
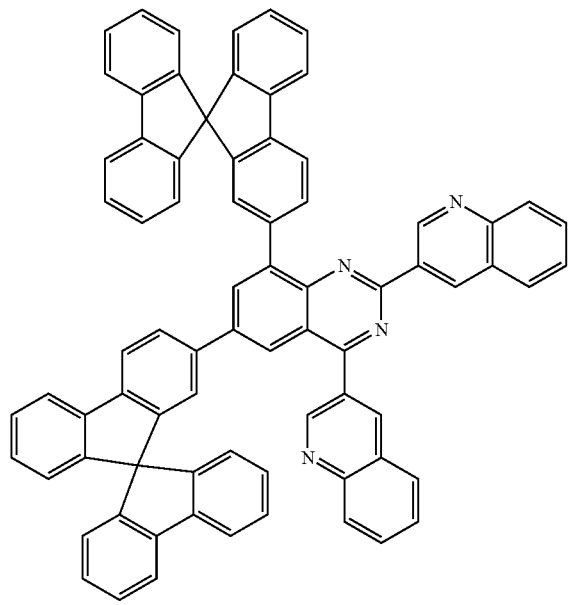
[Chemical Formula A-2]
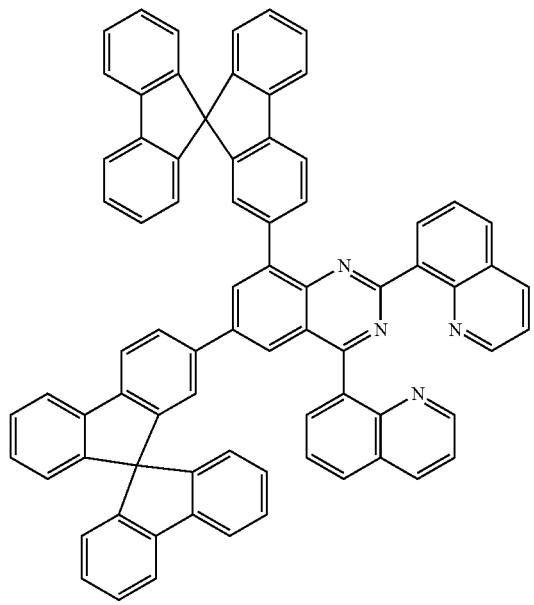
[Chemical Formula A-3]
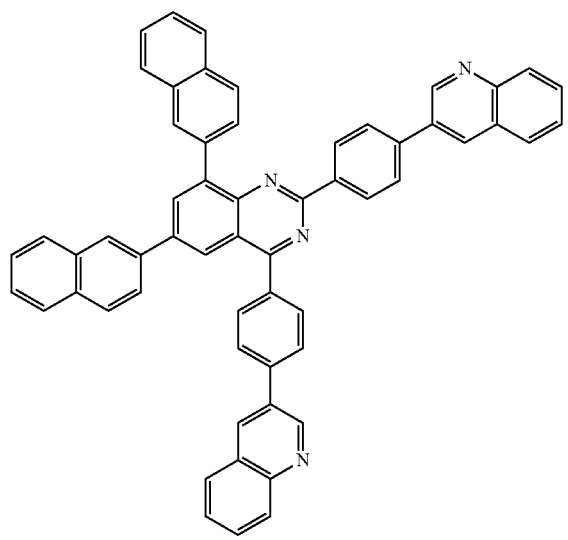
[Chemical Formula A-4]
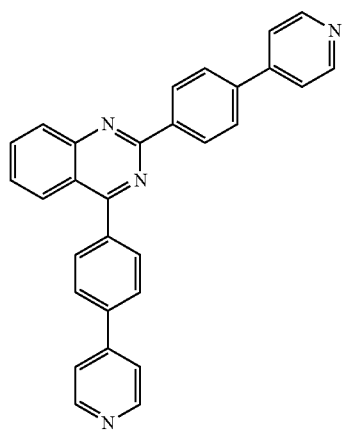

[Chemical Formula A-5]
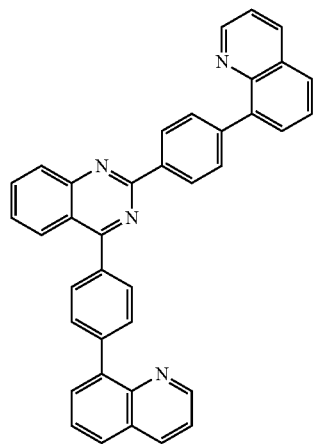
[Chemical Formula A-6]
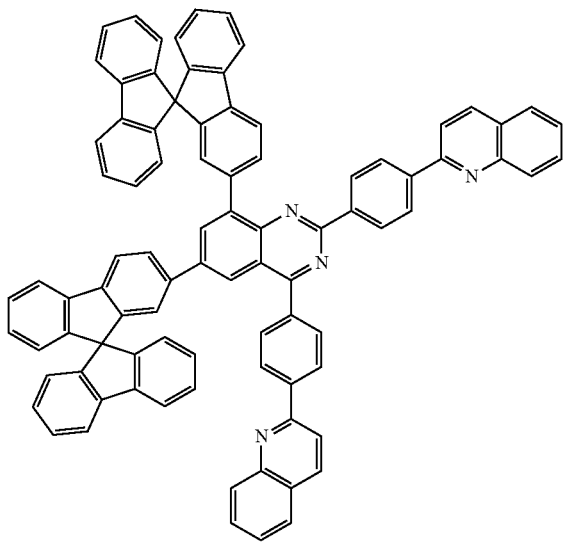
[Chemcial Formula A-7]
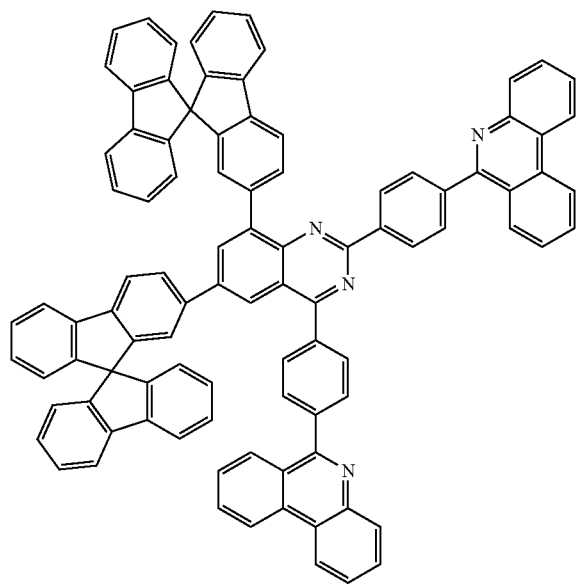
[Chemical Formula A-8]
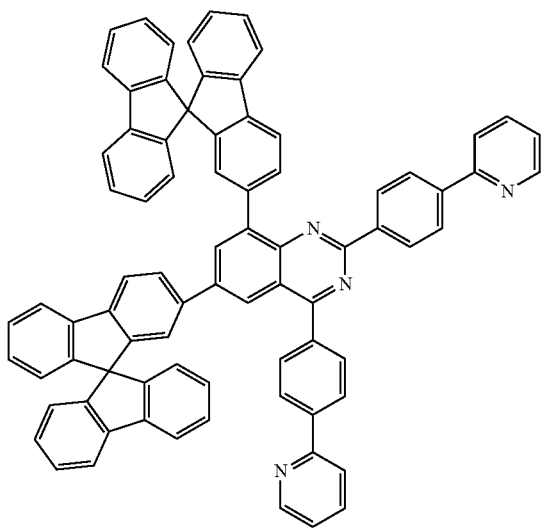

[Chemical Formula A-9]
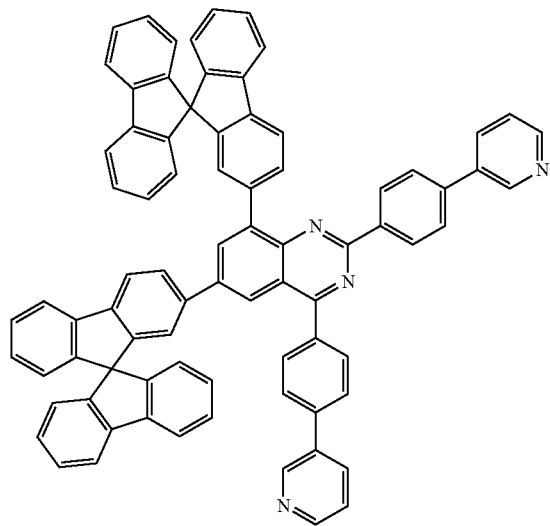
[Chemical Formula A-10]
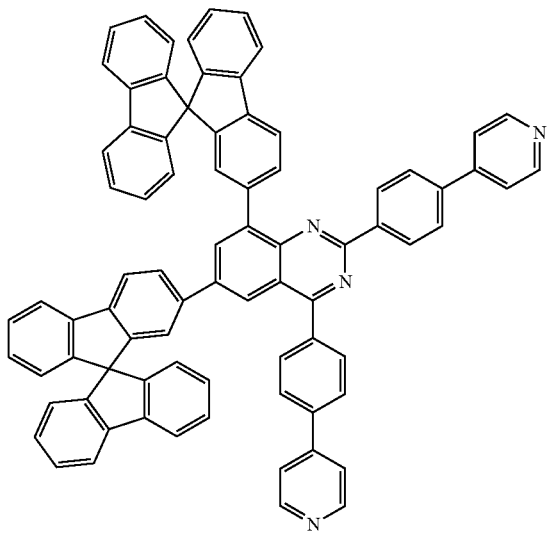
[Chemical Formula A-11]
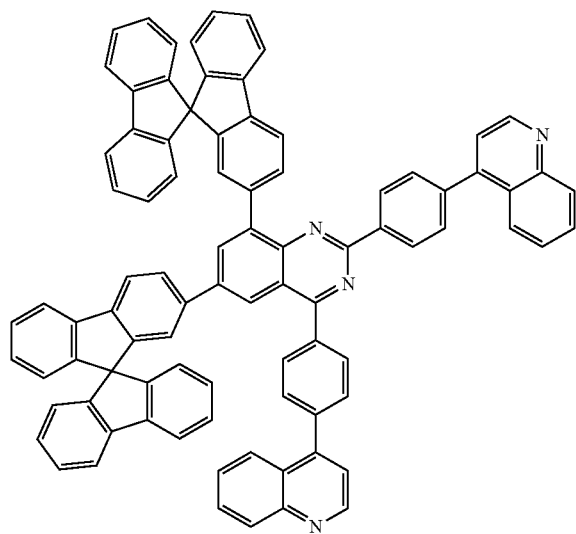
[Chemical Formula A-12]
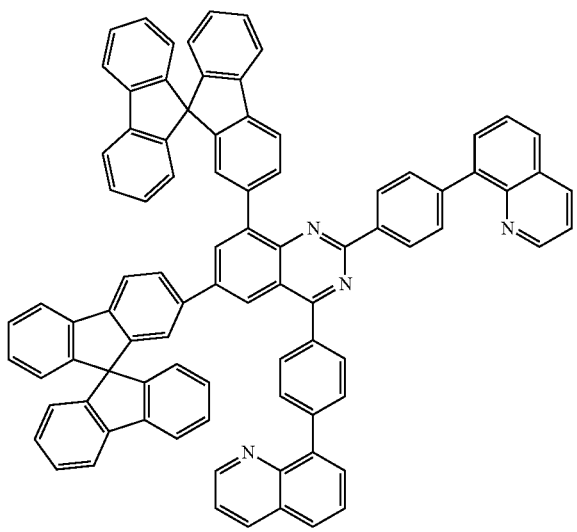

-continued
[Chemical Formula A-13]
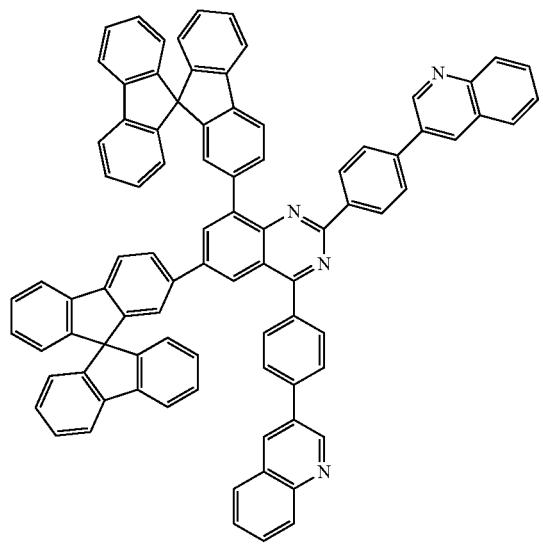
[Chemical Formula A-14]
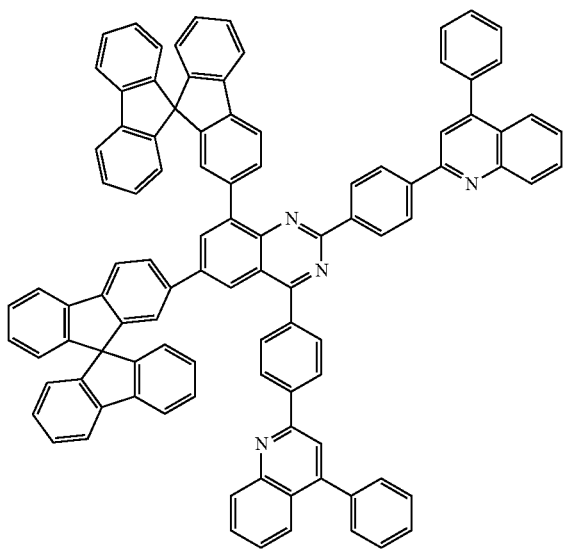
[Chemical Formula A-15]
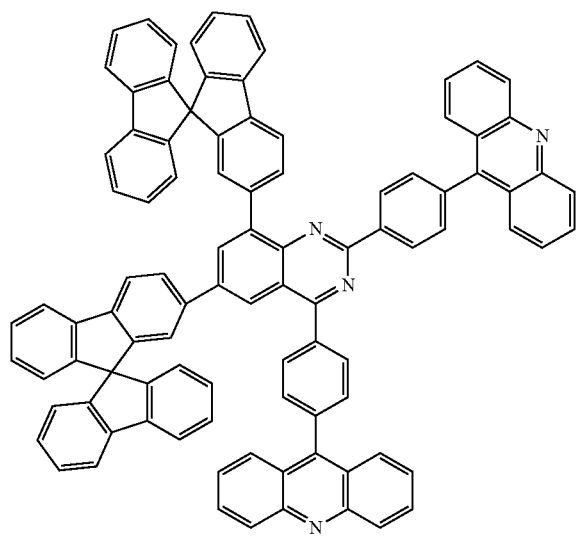
[Chemical Formula A-16]
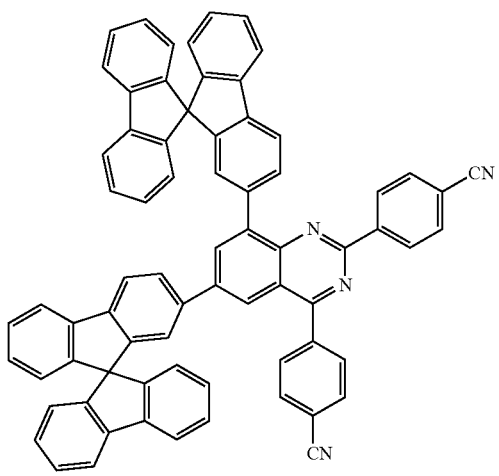

-continued
[Chemical Formula A-17]
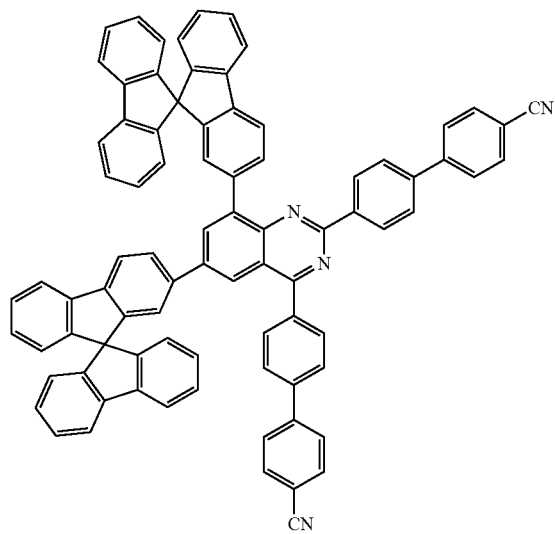
[Chemical Formula A-18]
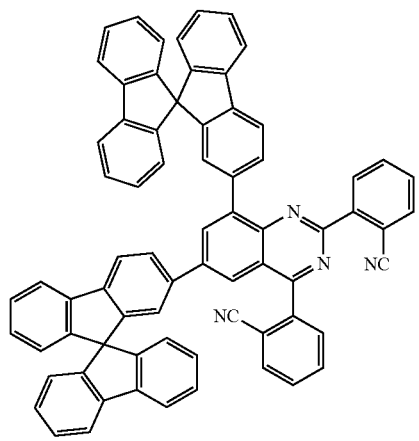
[Chemical Formula A-19]
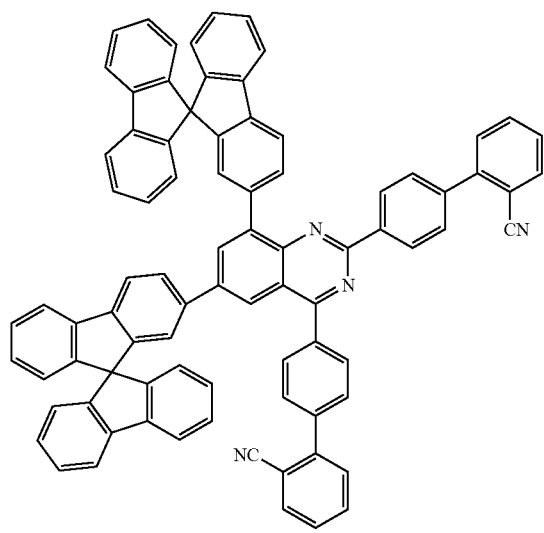
[Chemical Formula A-20]
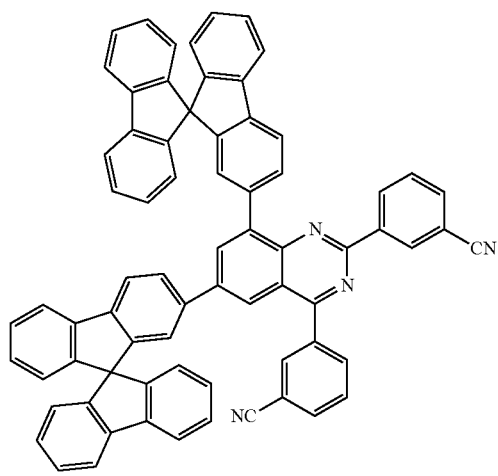
[Chemical Formula A-21]
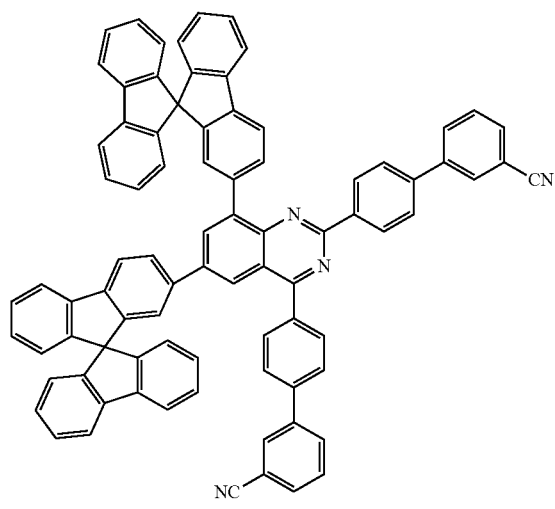
[Chemical Formula A-22]
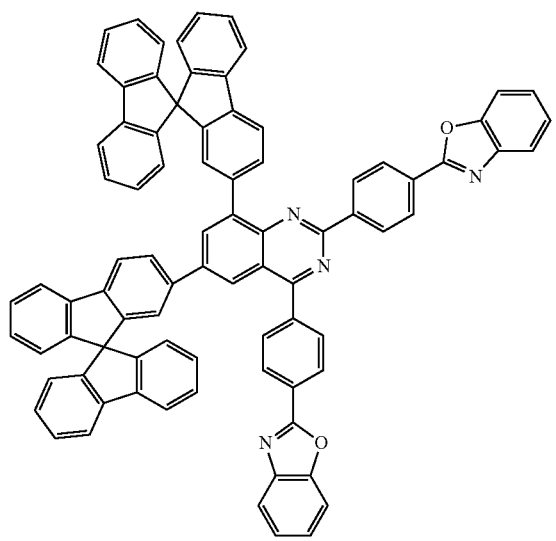

-continued
[Chemical Formula A-23]
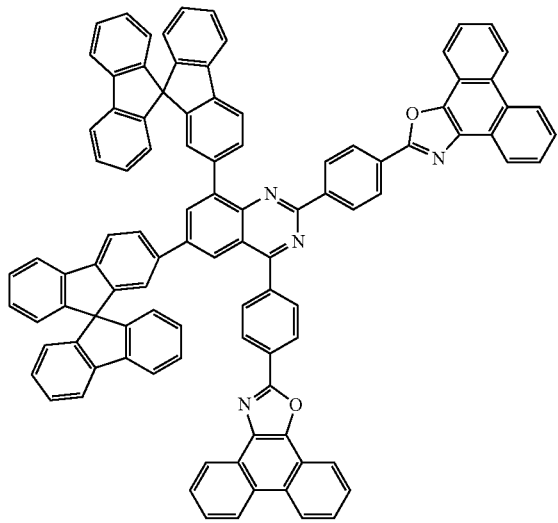
[Chemical Formula A-24]
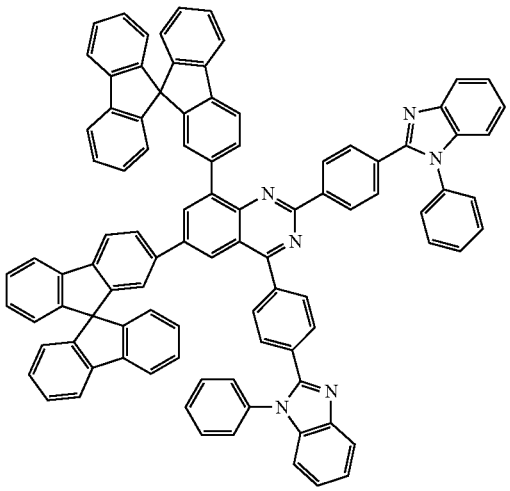
[Chemical Formula A-25]
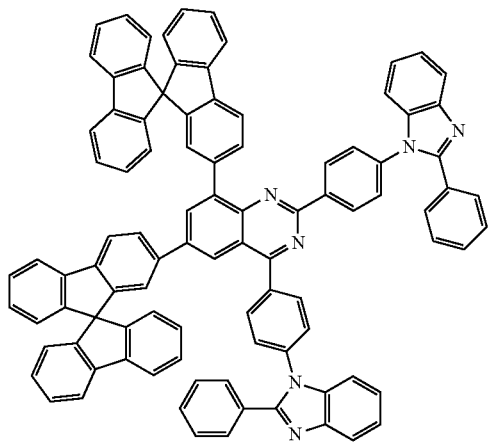
[Chemical Formula A-26]
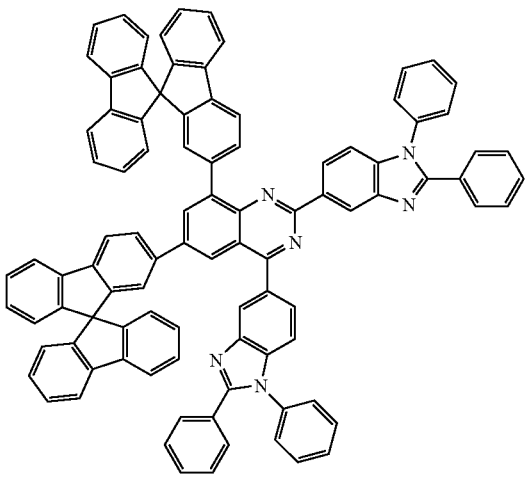
[Chemical Formula A-27]
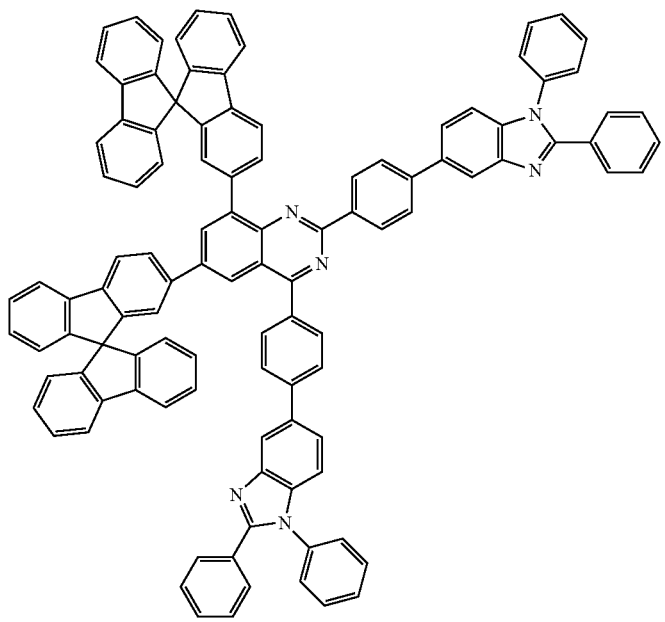

-continued
[Chemical Formula A-28]
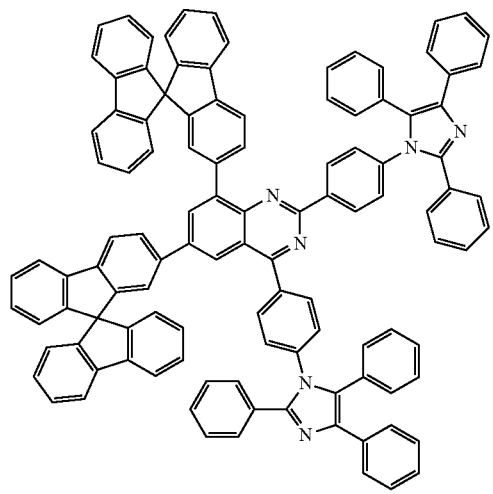
[Chemical Formula A-29]
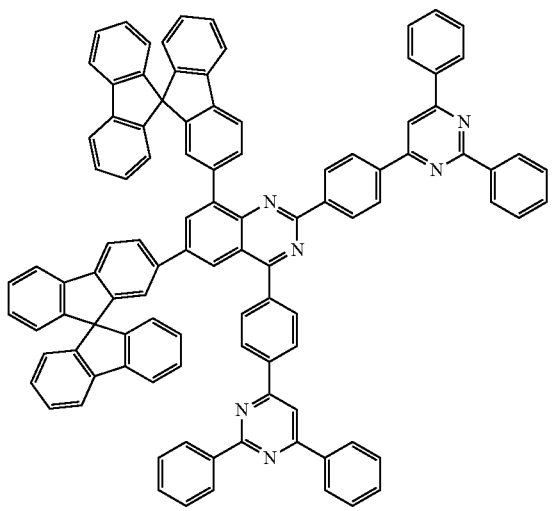
[Chemical Formula A-30]
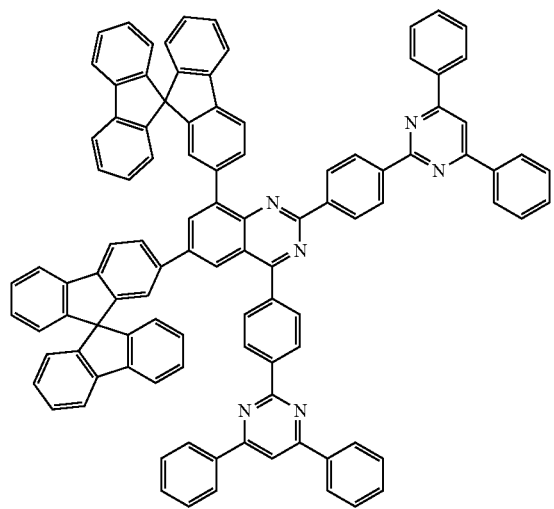
[Chemical Formula A-31]
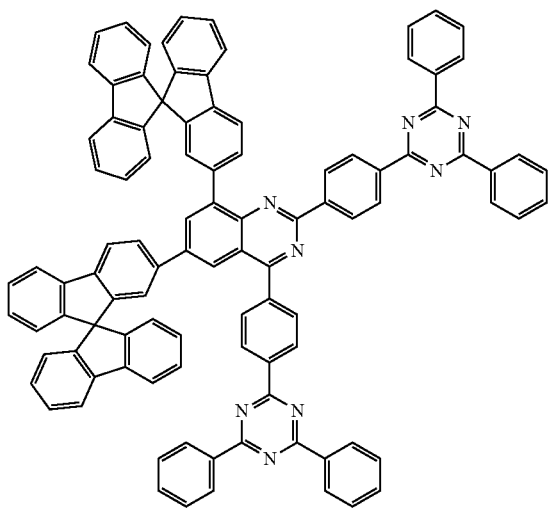
[Chemical Formula A-32]
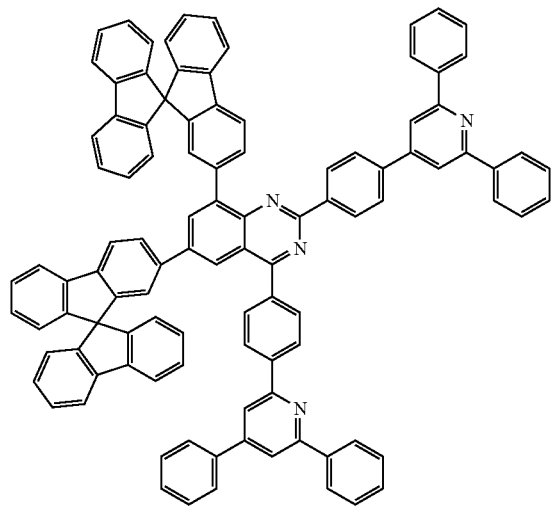
[Chemical Formula A-33]
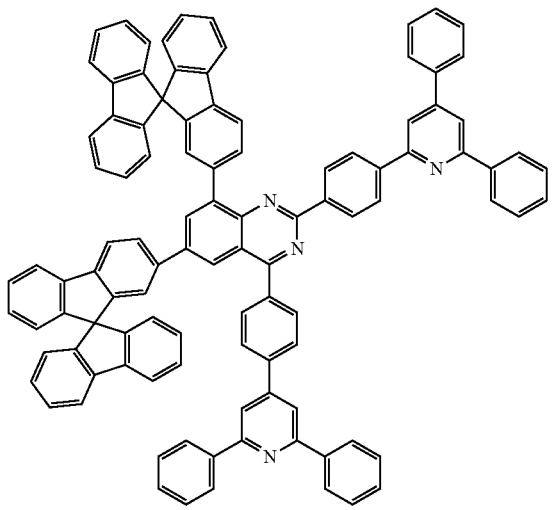

-continued
[Chemical Formula A-34]
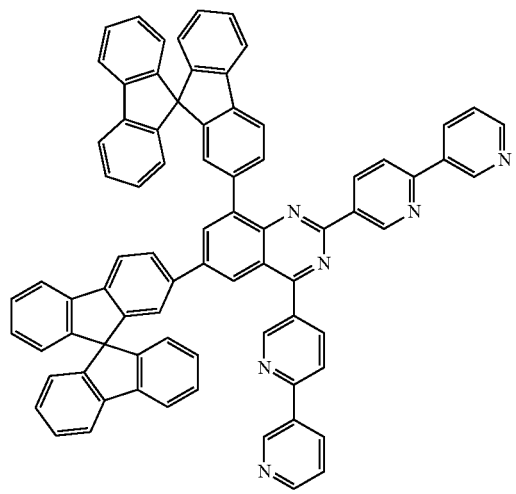
[Chemical Formula A-35]
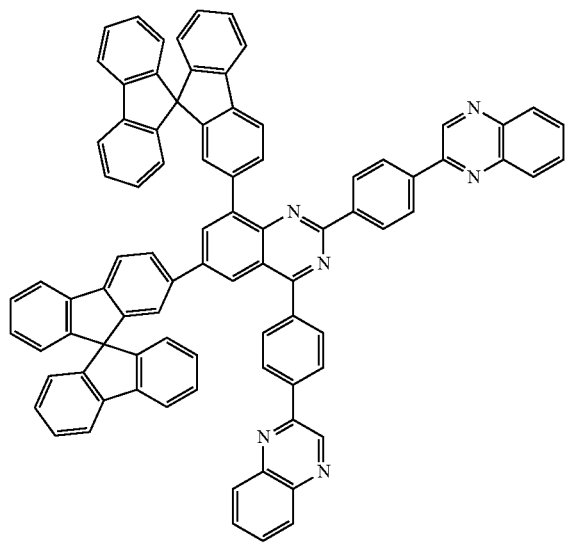
[Chemical Formula A-36]
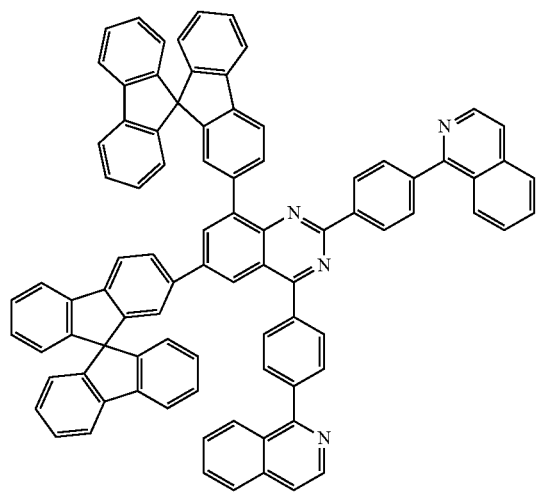
[Chemical Formula A-37]
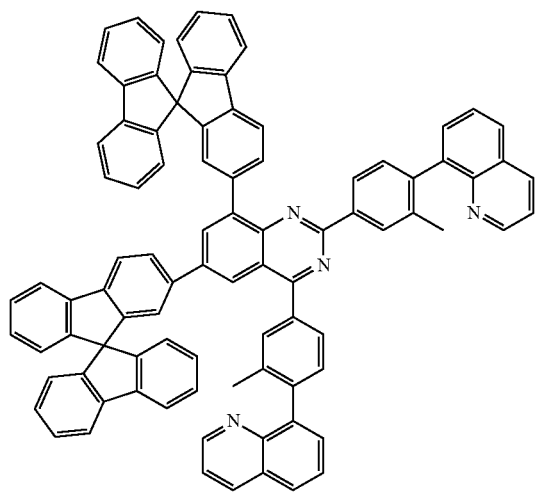
[Chemical Formula A-38]
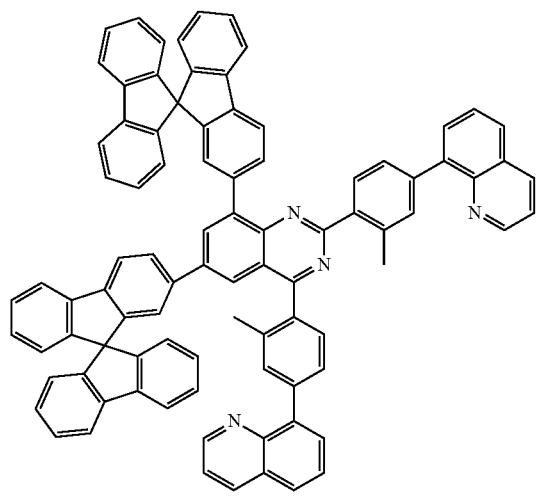
[Chemical Formula A-39]
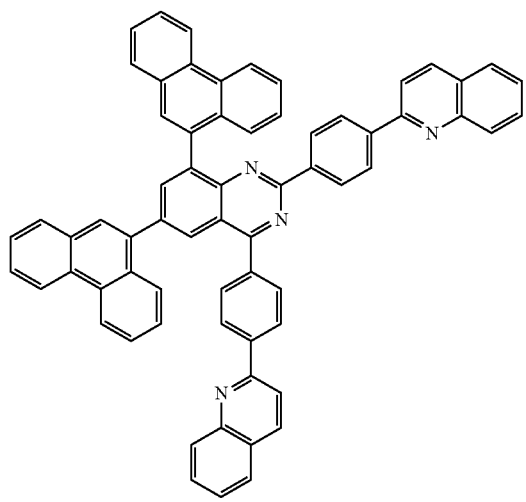

-continued
[Chemical Formula A-40]
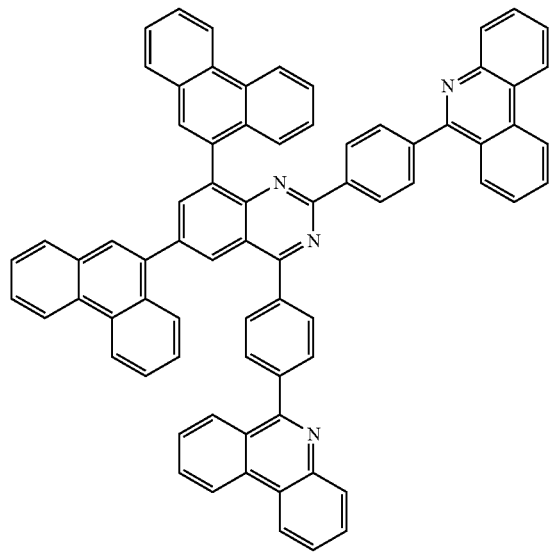
[Chemical Formula A-41]
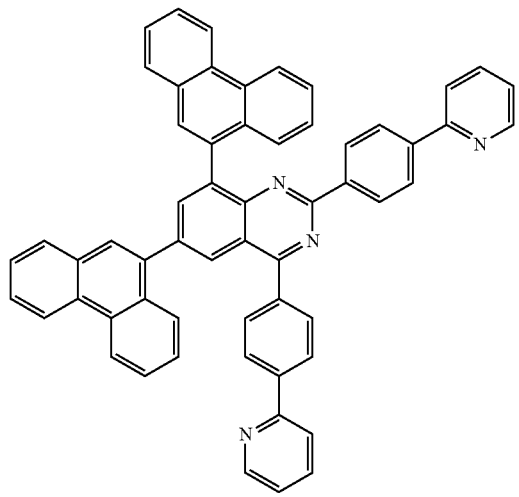
[Chemical Formula A-42]
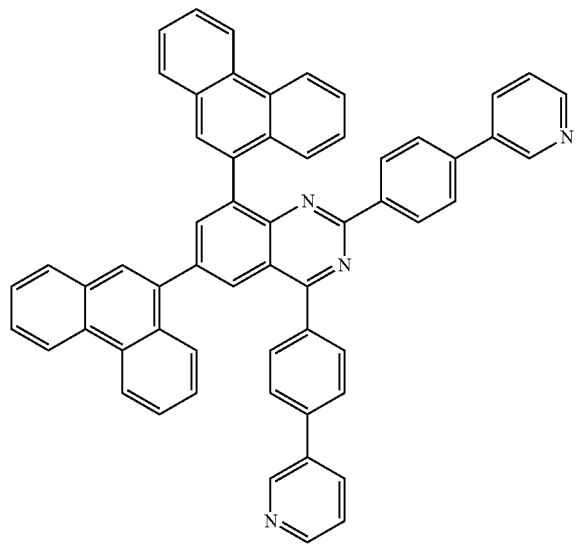
[Chemical Formula A-43]
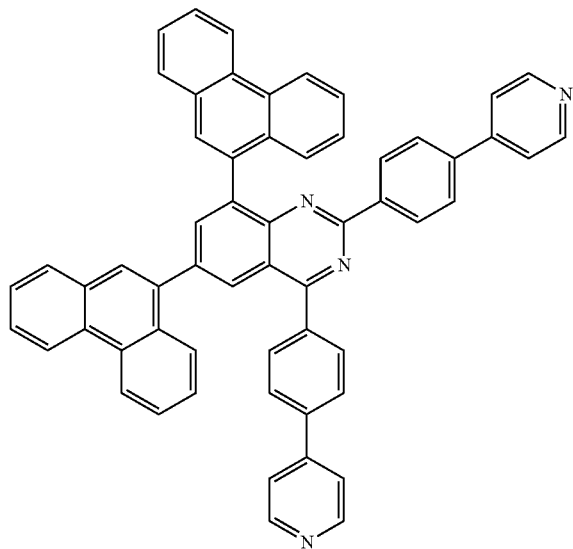
[Chemical Formula A-44]
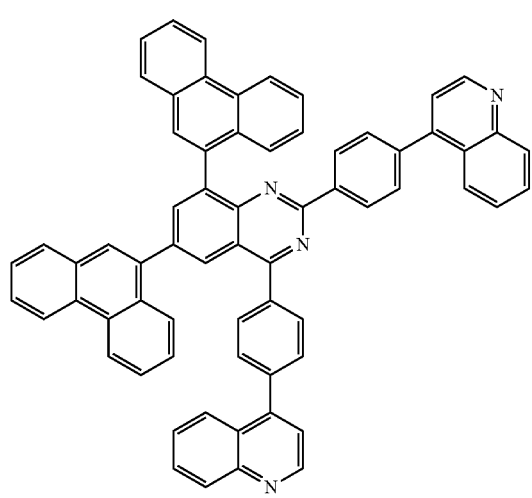
[Chemical Formula A-45]
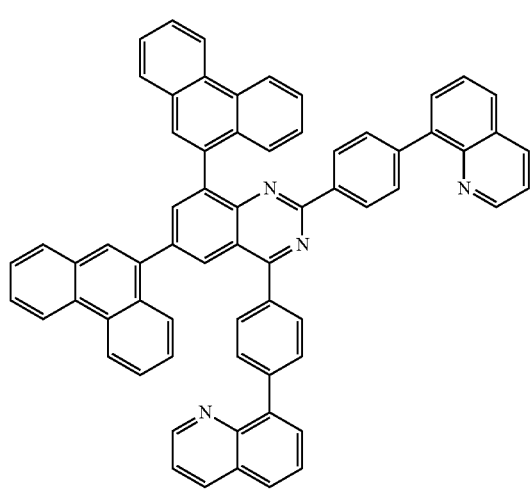

-continued
[Chemical Formula A-46]
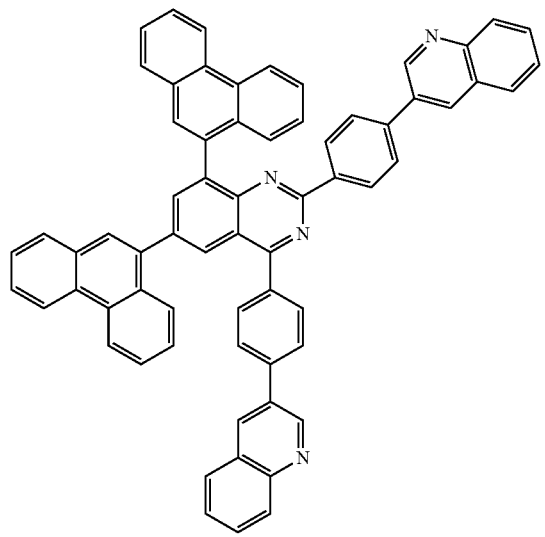
[Chemical Formula A-47]
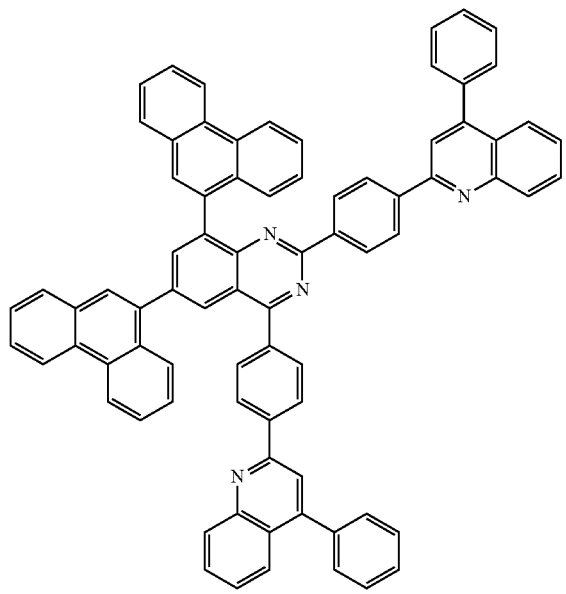
[Chemical Formula A-48]
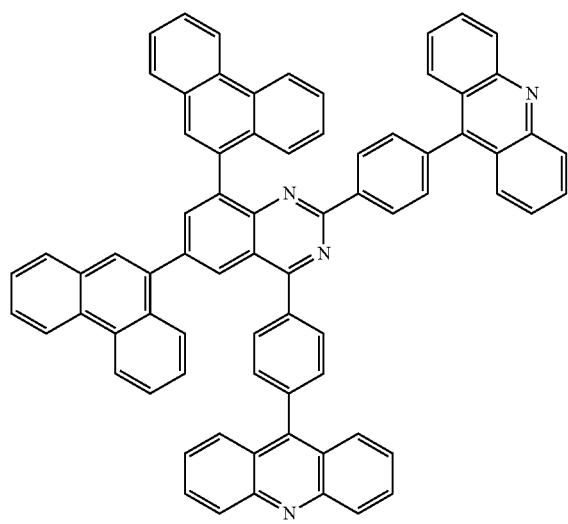
[Chemical Formula A-49]
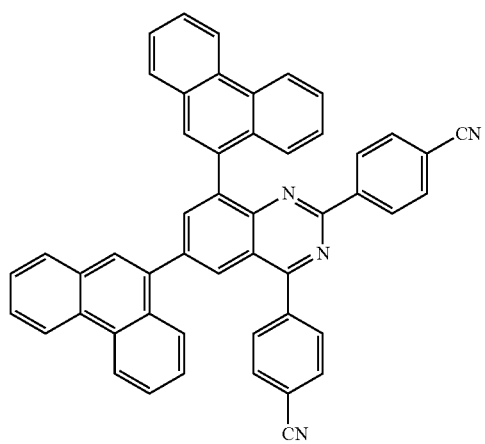

[Chemical Formula A-50]
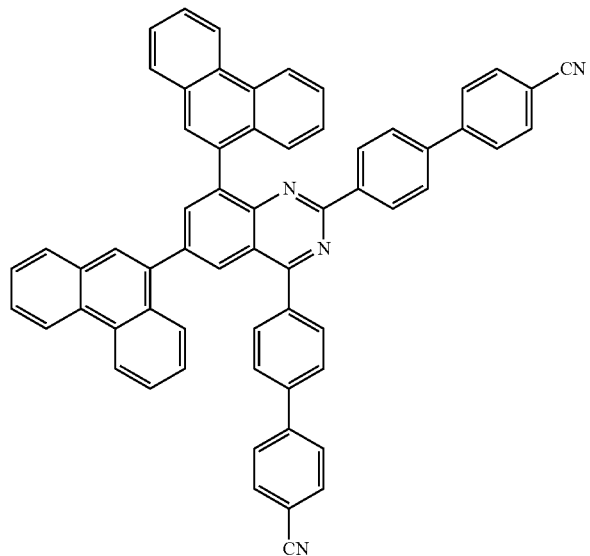
[Chemical Formula A-51]
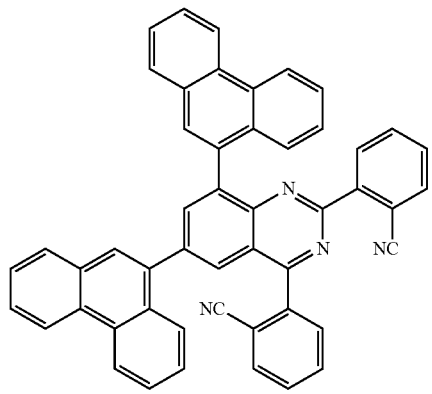
[Chemical Formula A-52]
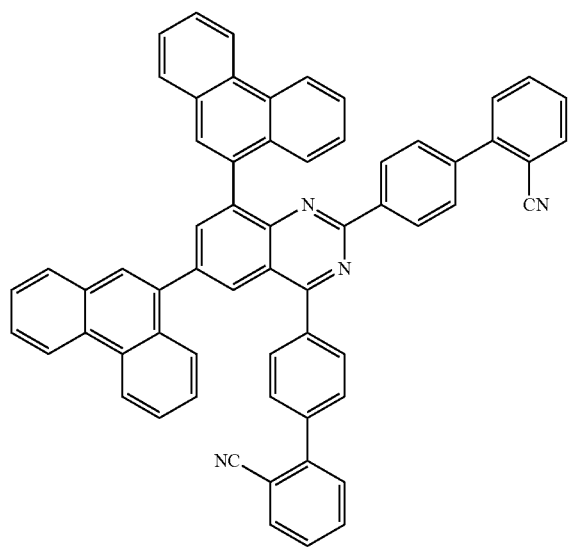
[Chemical Formula A-53]
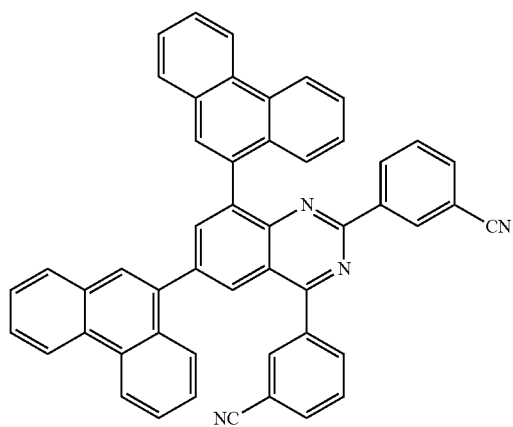

[Chemical Formula A-54]
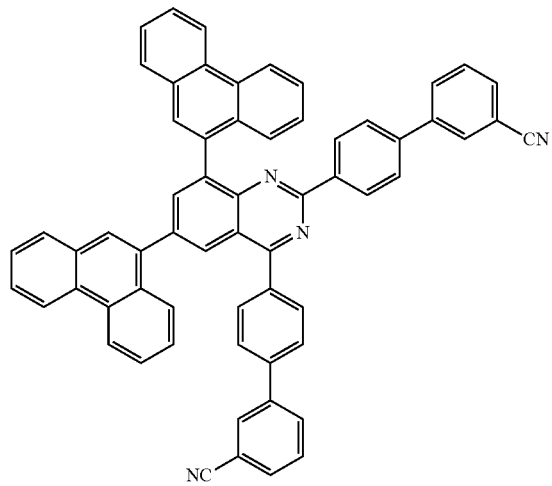
[Chemical Formula A-55]
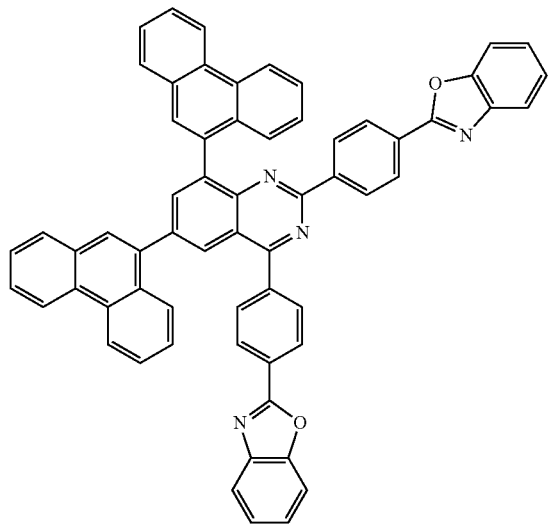
[Chemical Formula A-56]
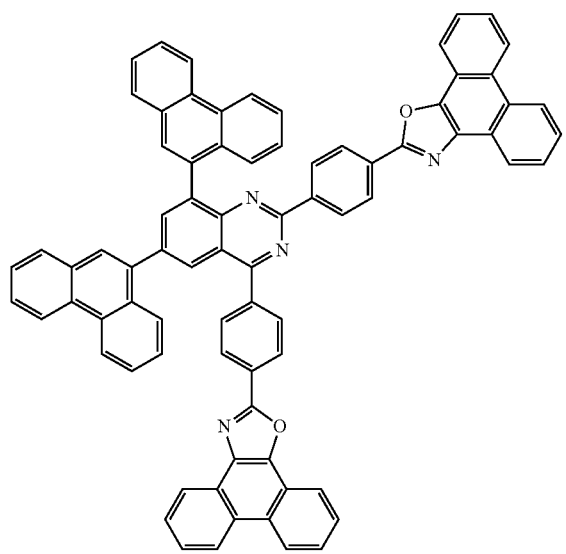
[Chemical Formula A-57]
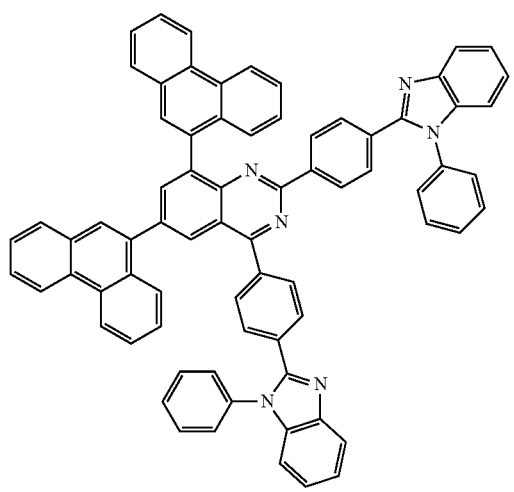
[Chemical Formula A-58]
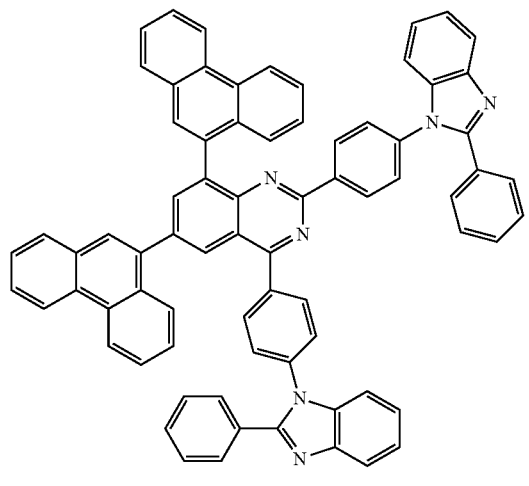
[Chemical Formula A-59]
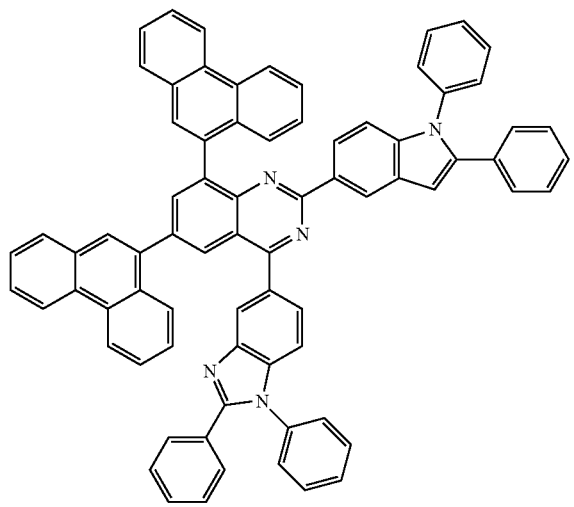

[Chemical Formula A-60]
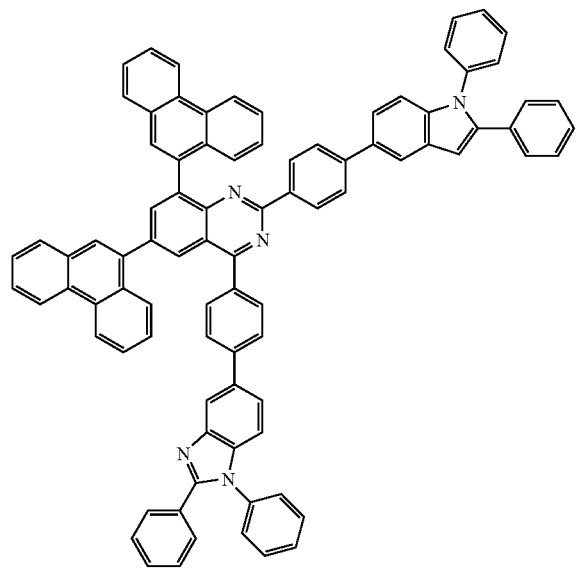
[Chemical Formula A-61]
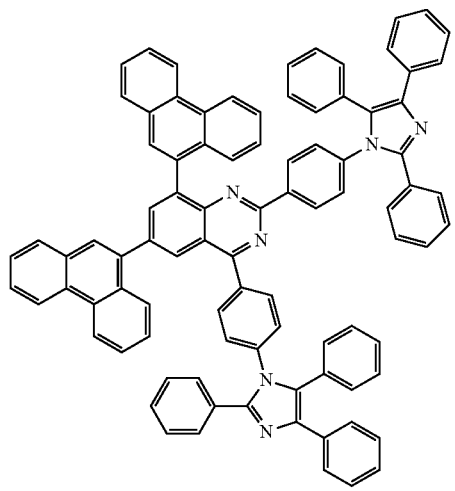
[Chemical Formula A-62]
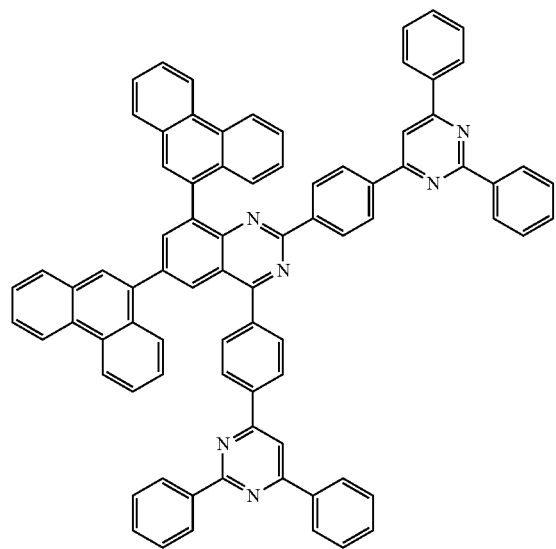
[Chemical Formula A-63]
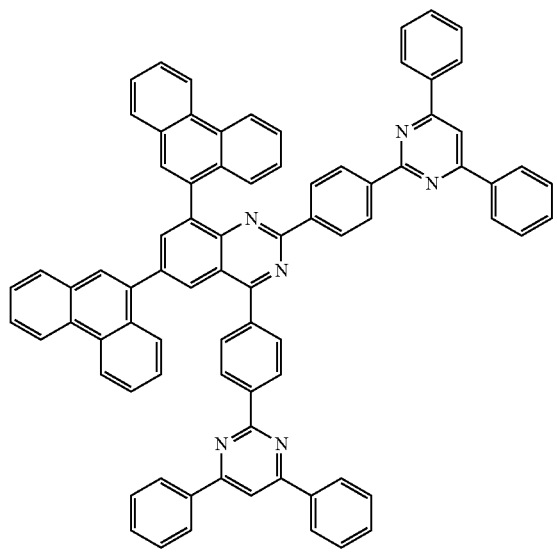

-continued
[Chemical Formula A-64]
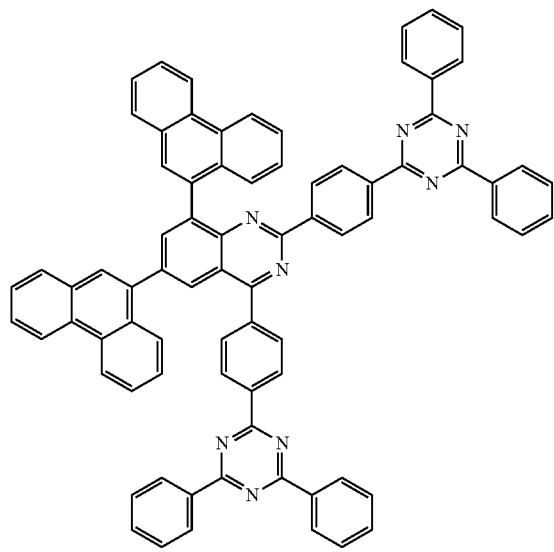
[Chemical Formula A-65]
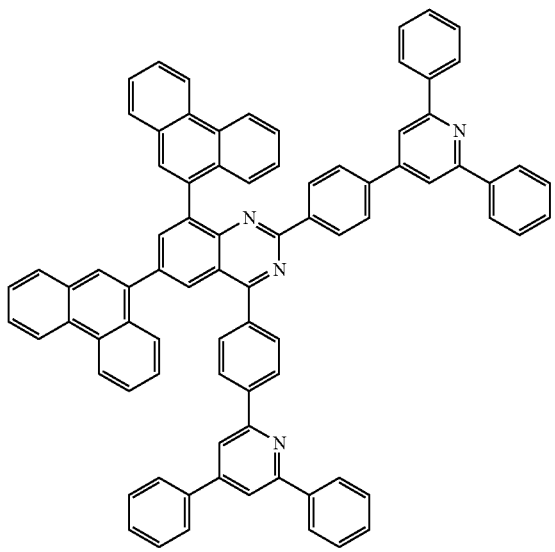
[Chemical Formula A-66]
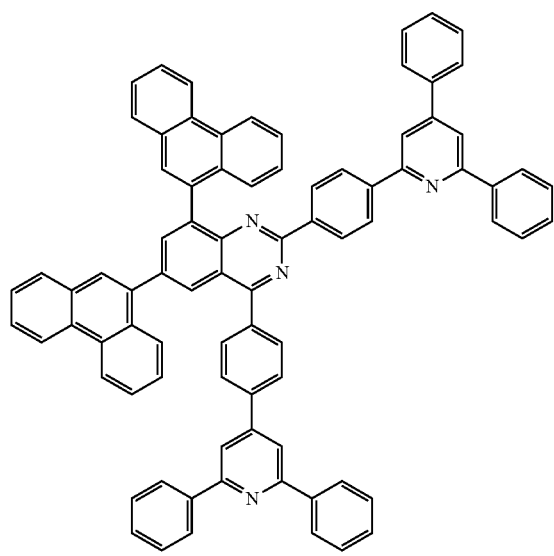
[Chemical Formula A-67]
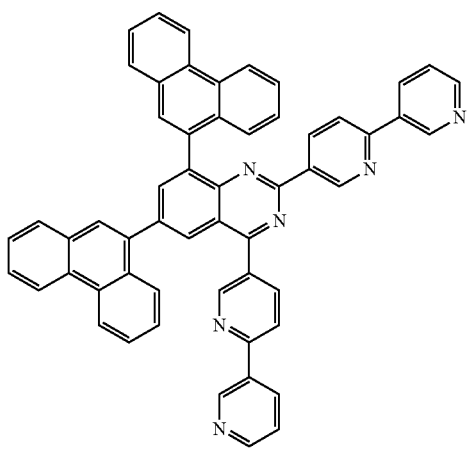

-continued
[Chemical Formula A-68]
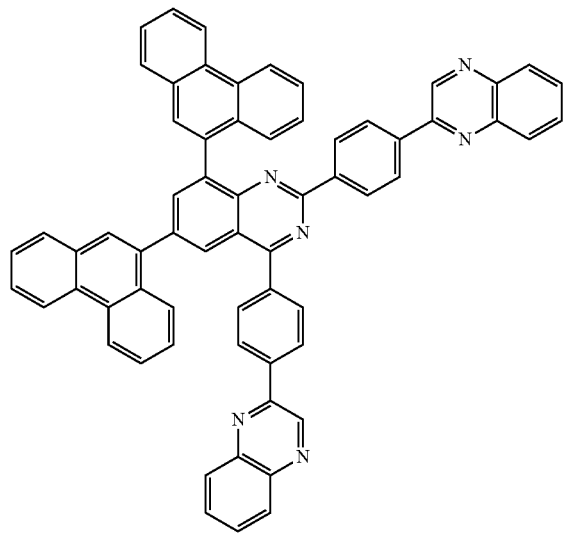
[Chemical Formula A-69]
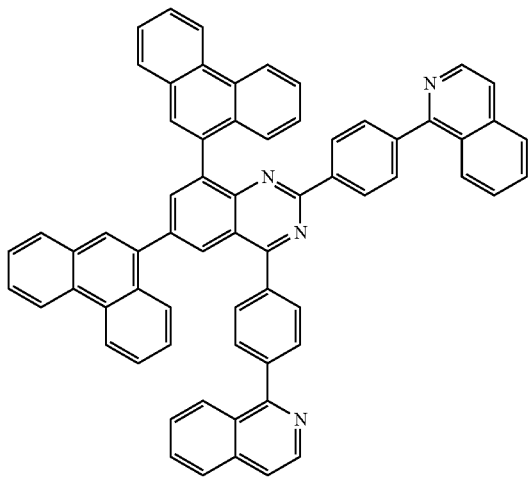
[Chemical Formula A-70]
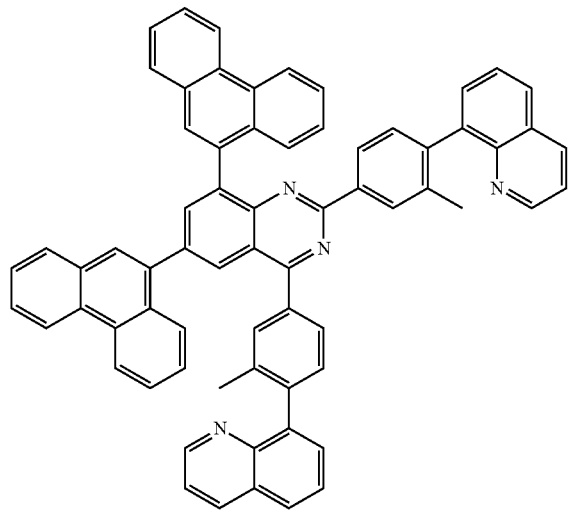
[Chemical Formula A-71]
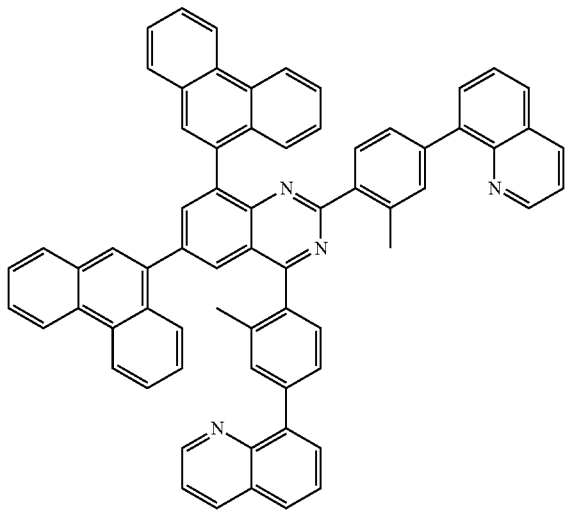
[Chemical Formula A-72]
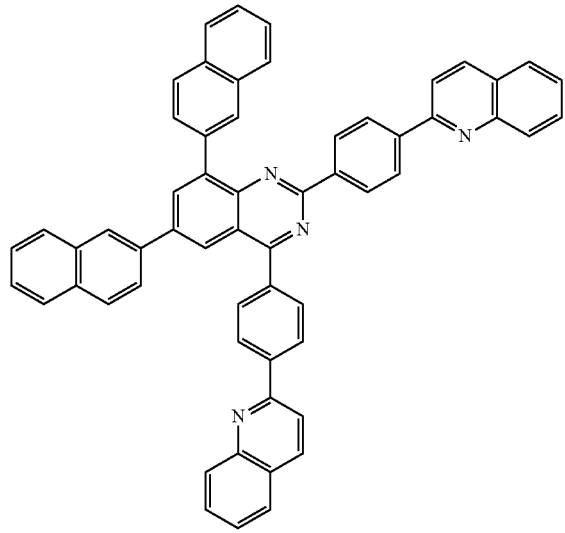
[Chemical Formula A-73]
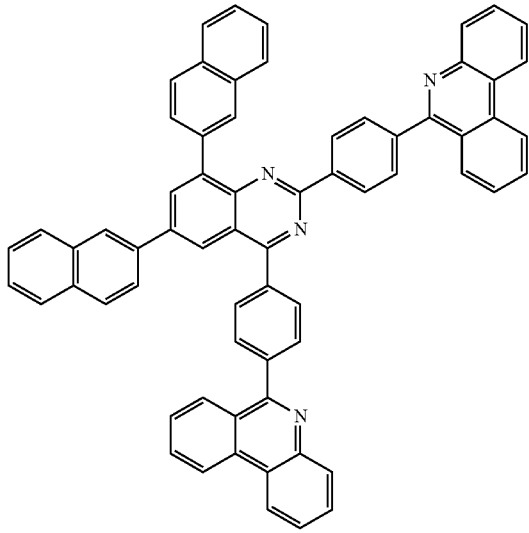

-continued
[Chemical Formula A-74]
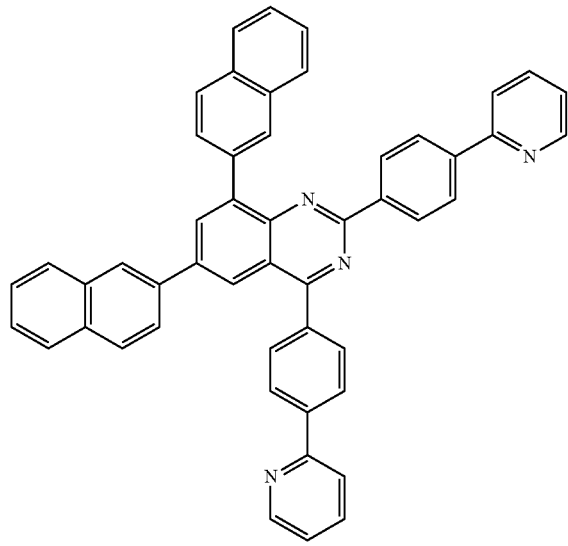
[Chemical Formula A-75]
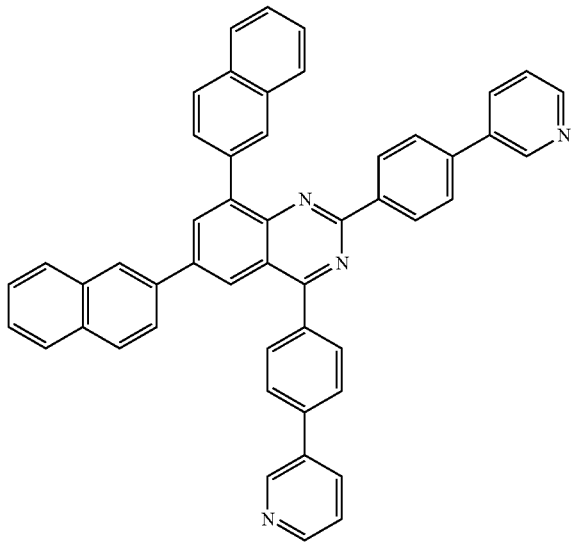
[Chemical Formula A-76]
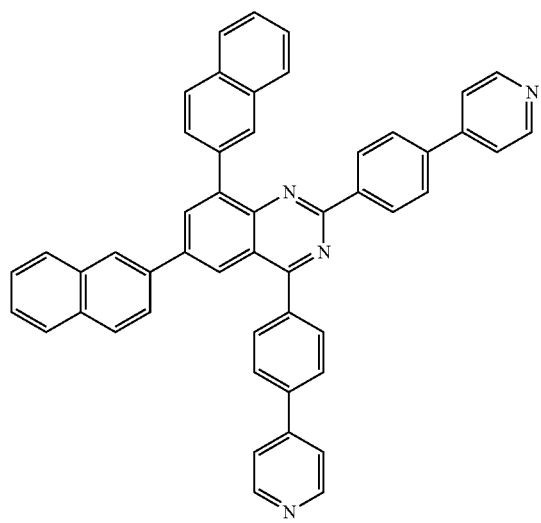
[Chemical Formula A-77]
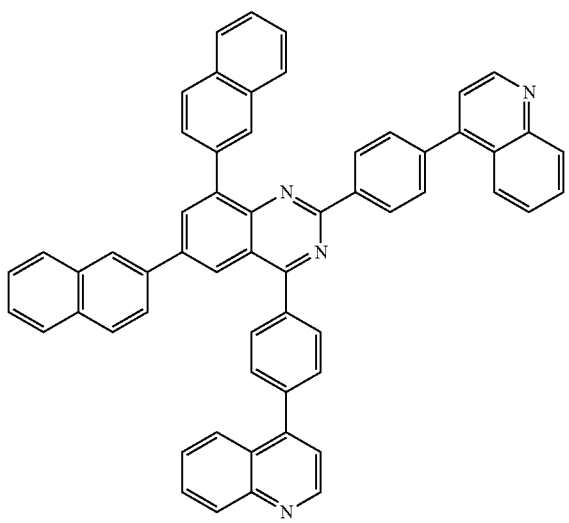

[Chemical Formula A-78]
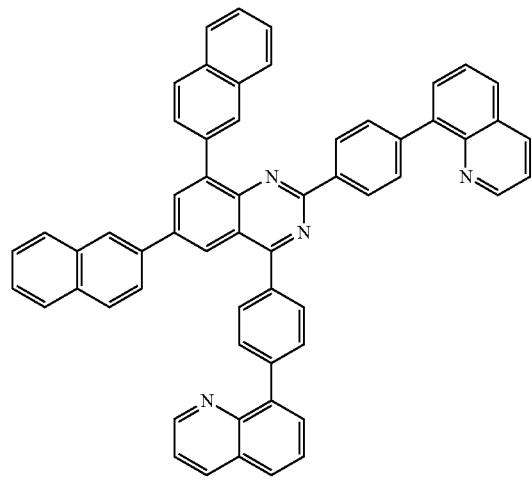
[Chemical Formula A-79]
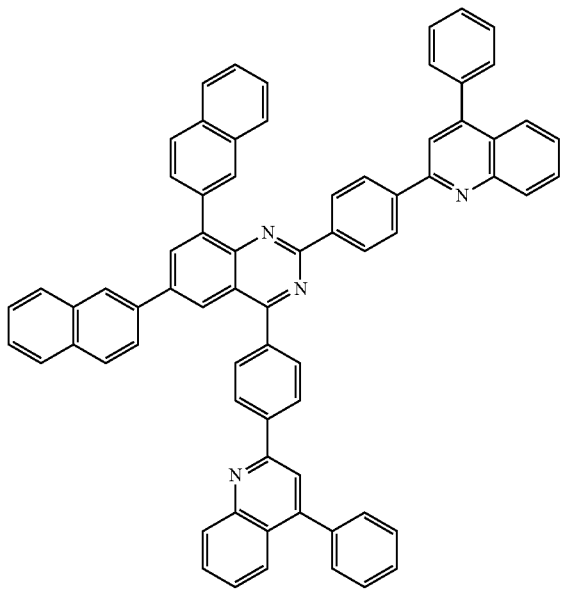
[Chemical Formula A-80]
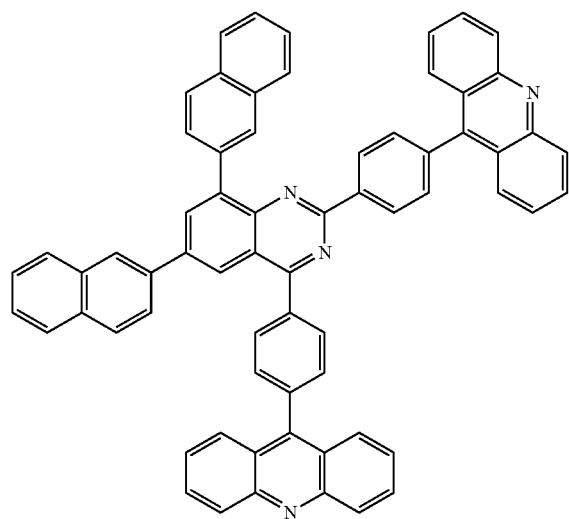
[Chemical Formula A-81]
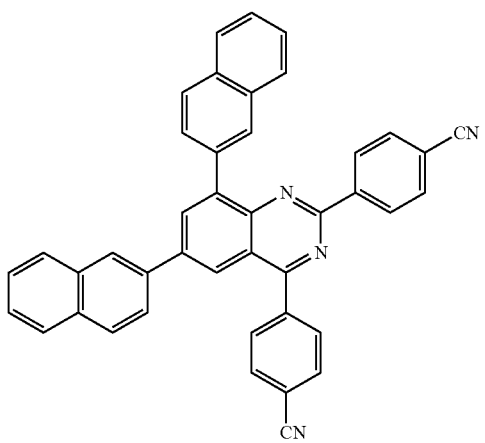

[Chemical Formula A-82]
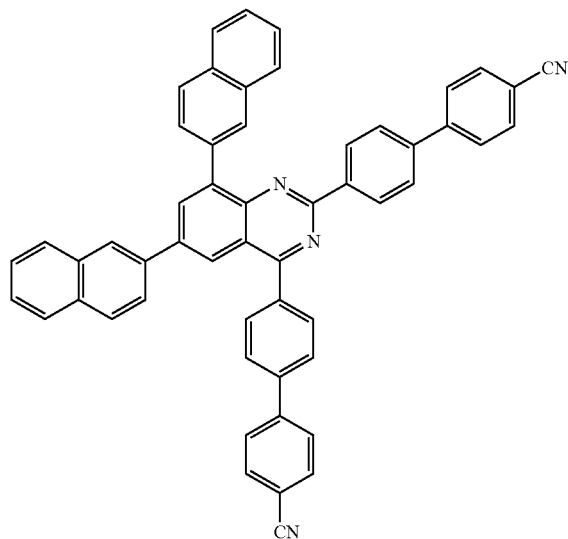
[Chemical Formula A-83]
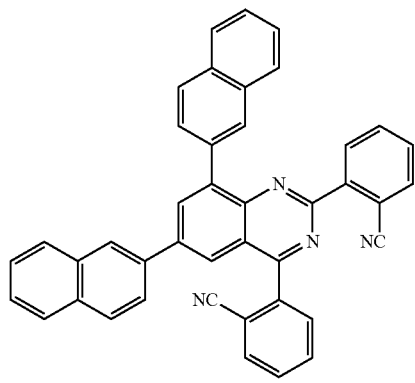
[Chemical Formula A-84]
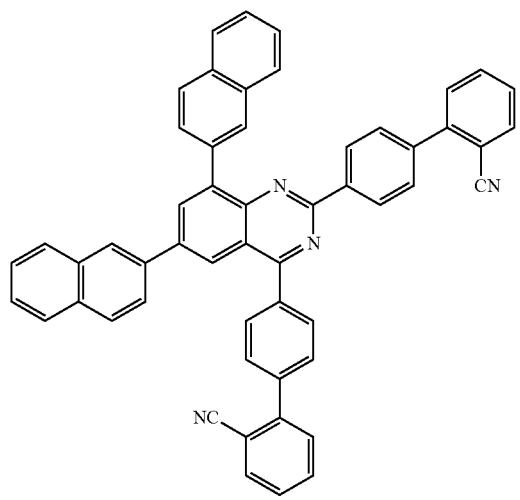
[Chemical Formula A-85]
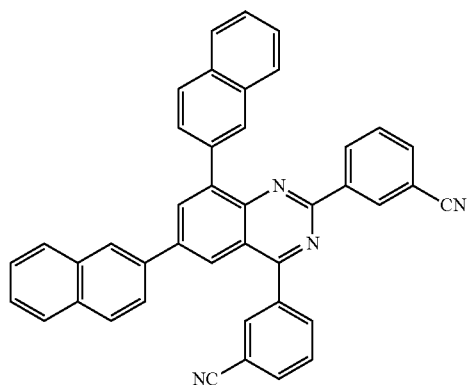
[Chemical Formula A-86]
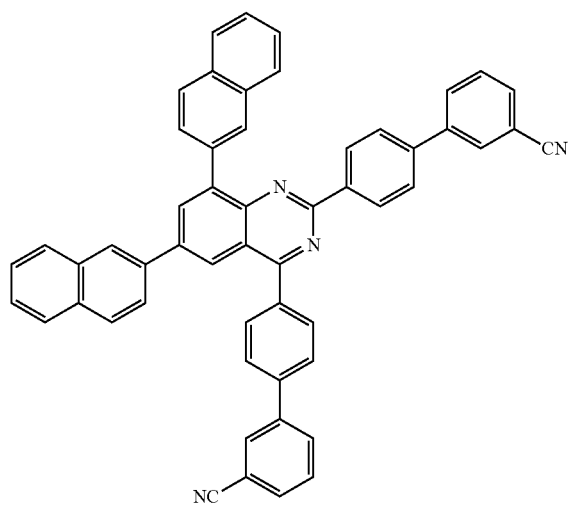
[Chemical Formula A-87]
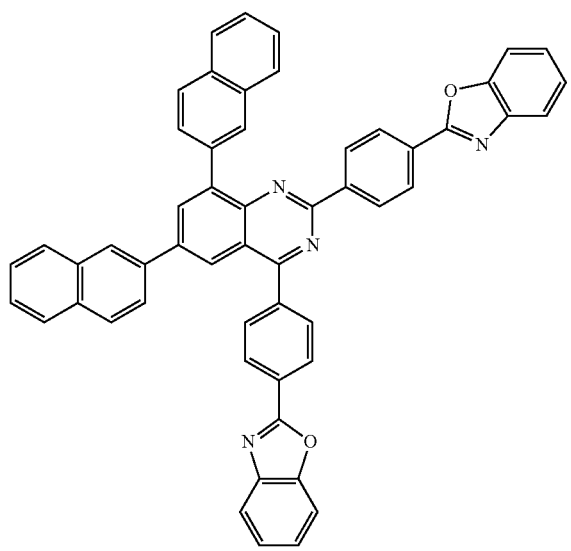

-continued
[Chemical Formula A-88]
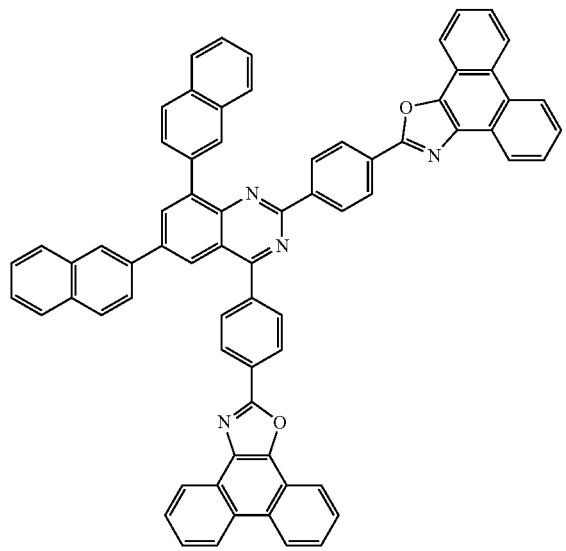
[Chemical Formula A-89]
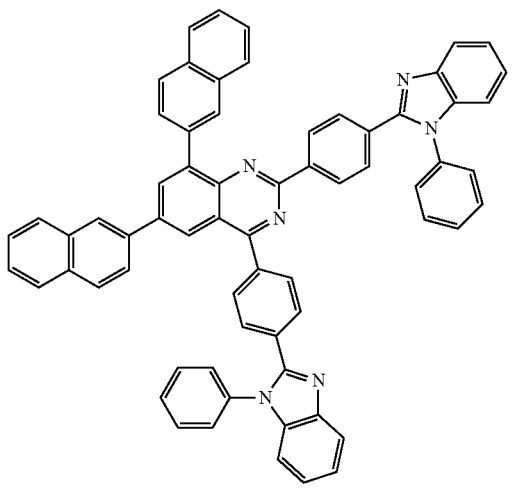
[Chemical Formula A-90]
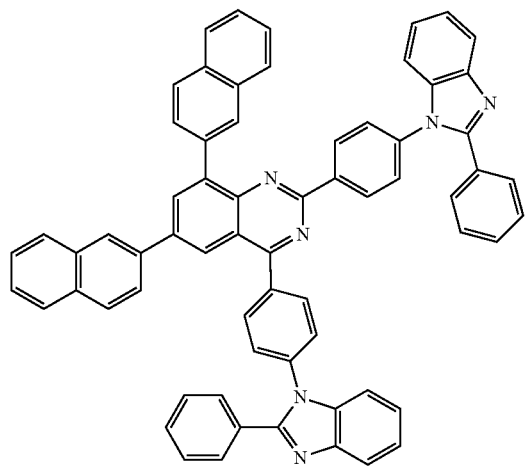
[Chemical Formula A-91]
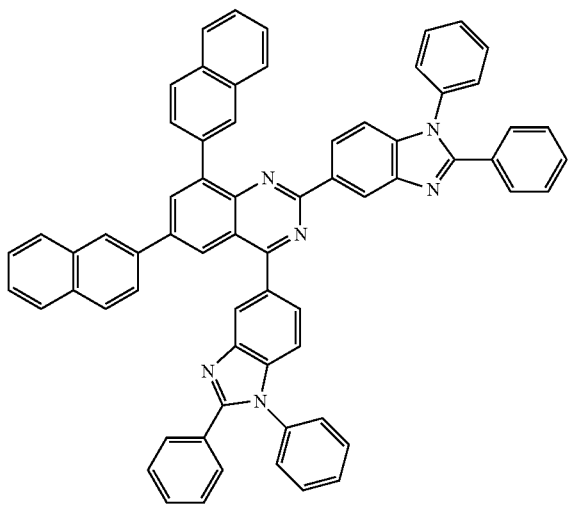
[Chemical Formula A-92]
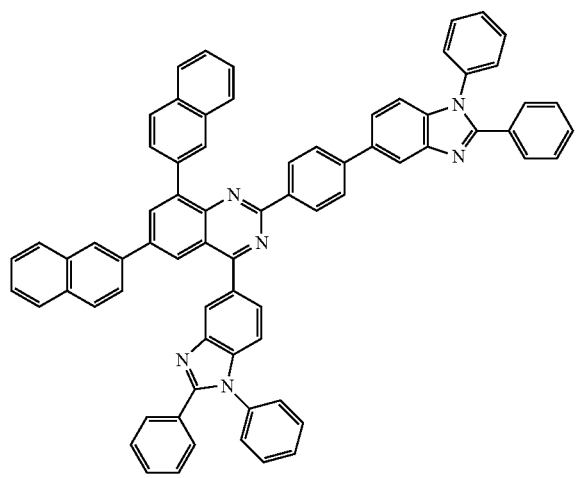
[Chemical Formula A-93]
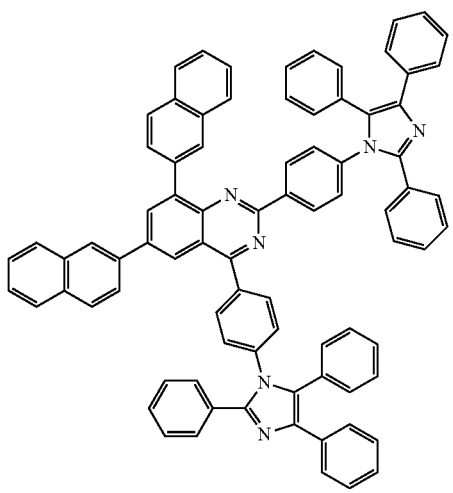

-continued
[Chemical Formula A-94]
[Chemical Formula A-95]
[Chemical Formula A-96]
[Chemical Formula A-97]
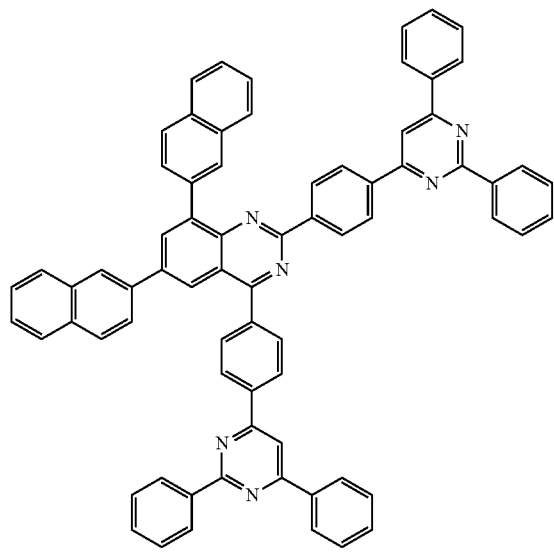

[Chemical Formula A-98]
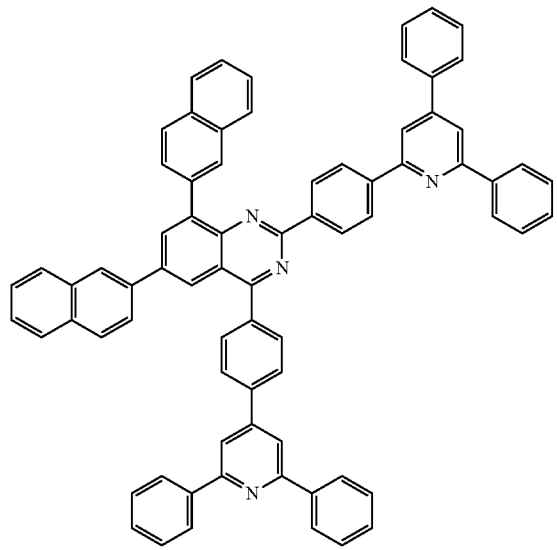
[Chemical Formula A-99]
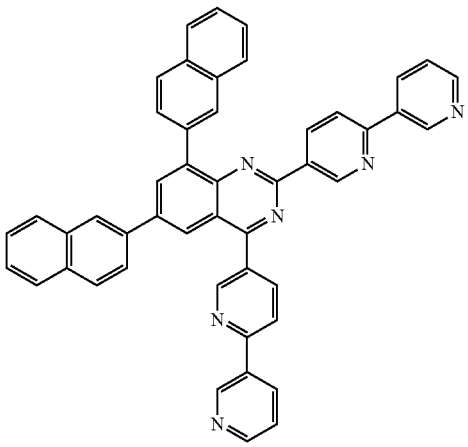
[Chemical Formula A-100]
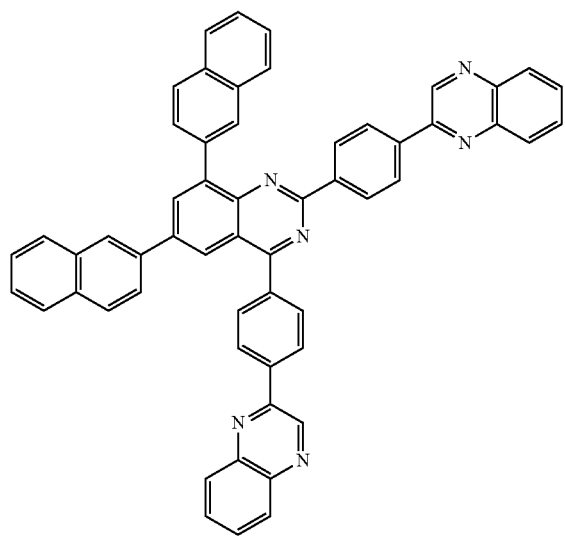
[Chemical Formula A-101]
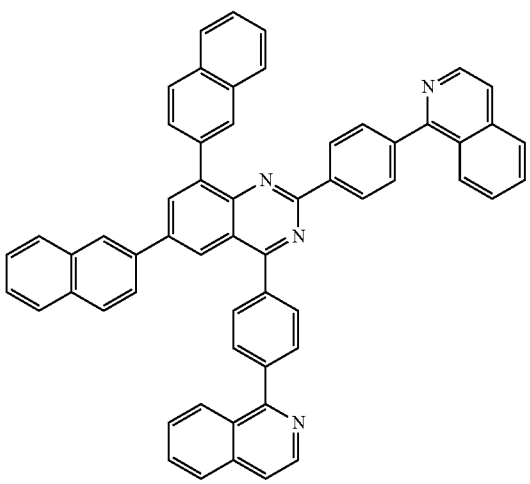
[Chemical Formula A-102]
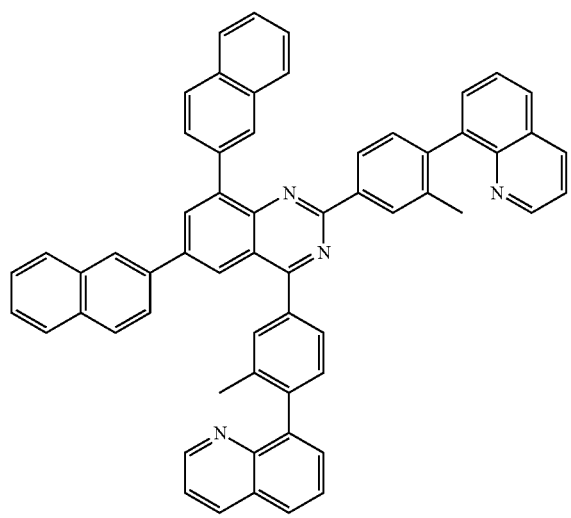
[Chemical Formula A-103]
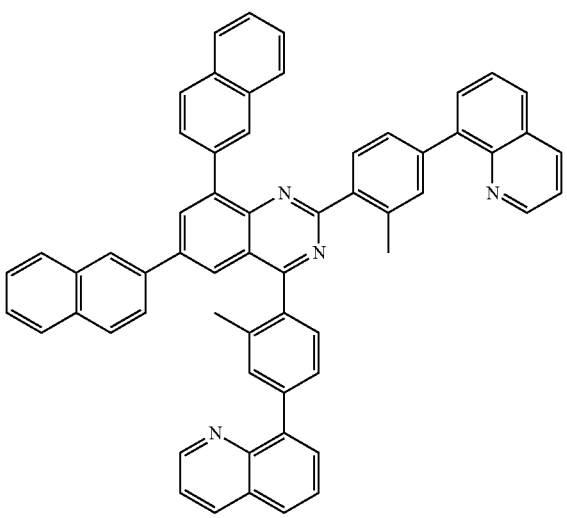

-continued
[Chemical Formula A-104]
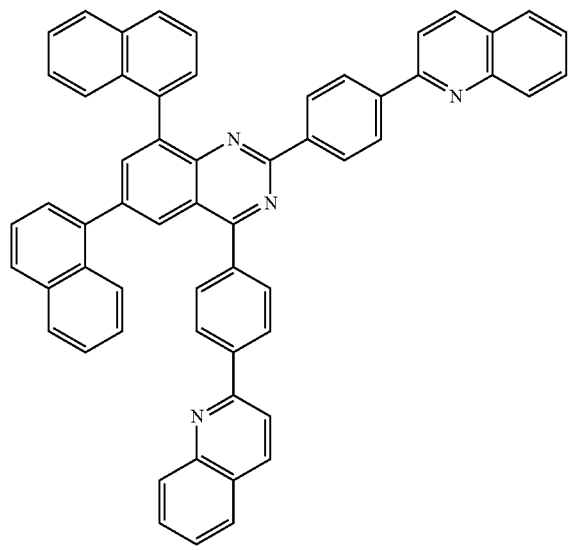
[Chemical Formula A-105]
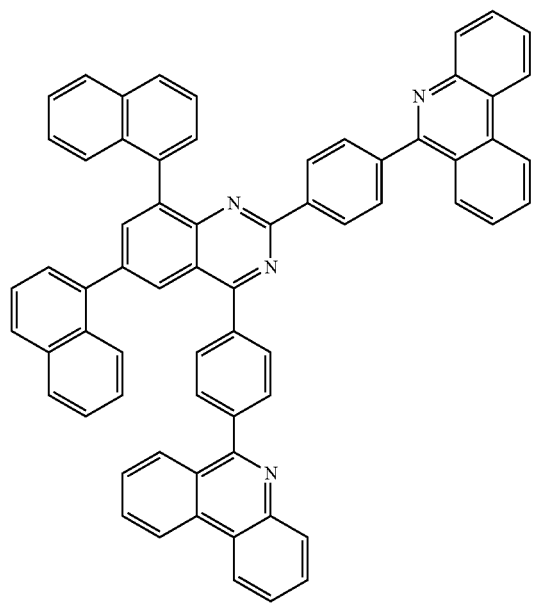
[Chemical Formula A-106]
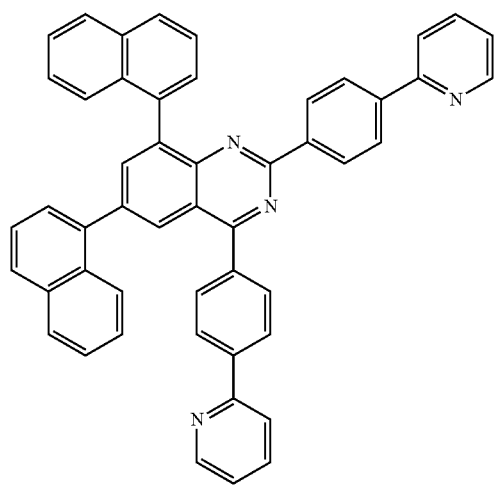
[Chemical Formula A-107]
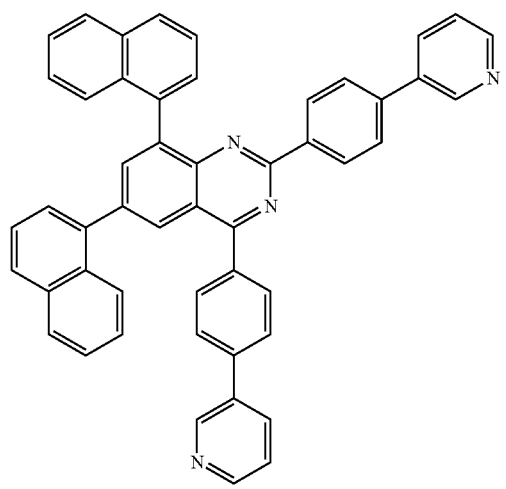
[Chemical Formula A-108]
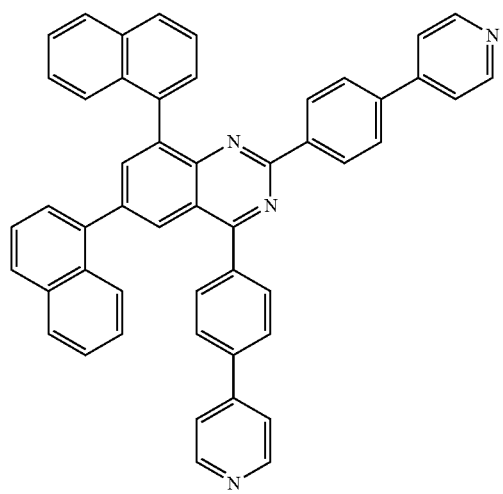
[Chemical Formula A-109]
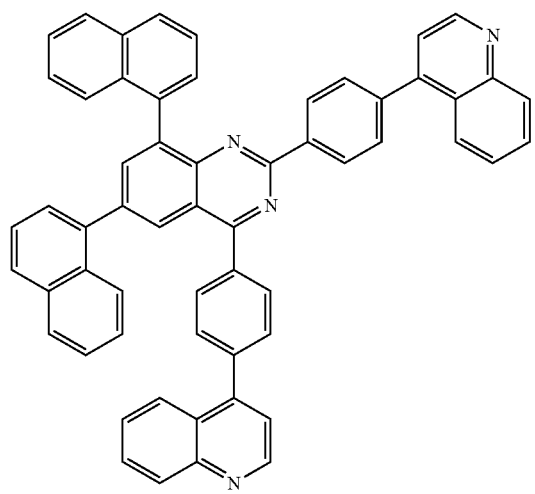

-continued
[Chemical Formula A-110]
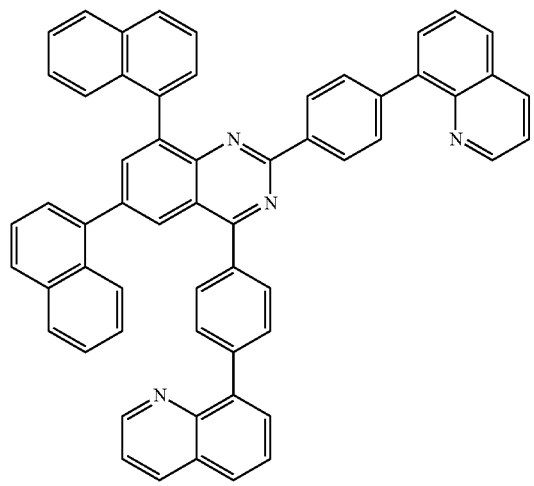
[Chemical Formula A-111]
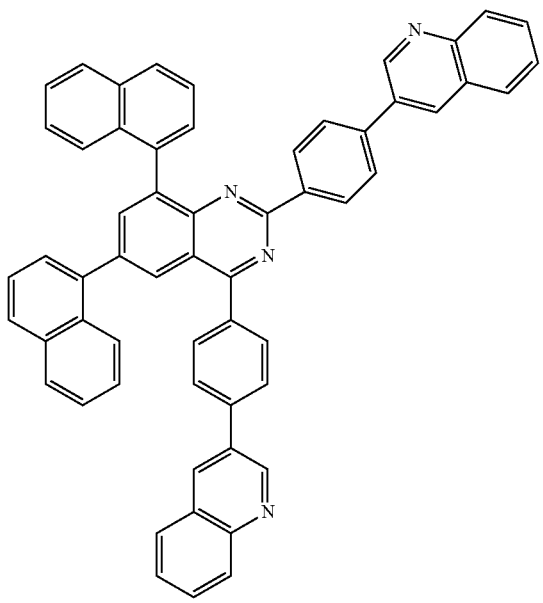
[Chemical Formula A-112]
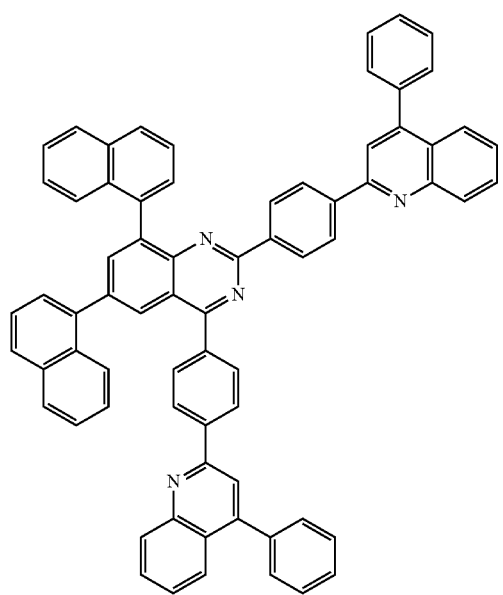
[Chemical Formula A-113]
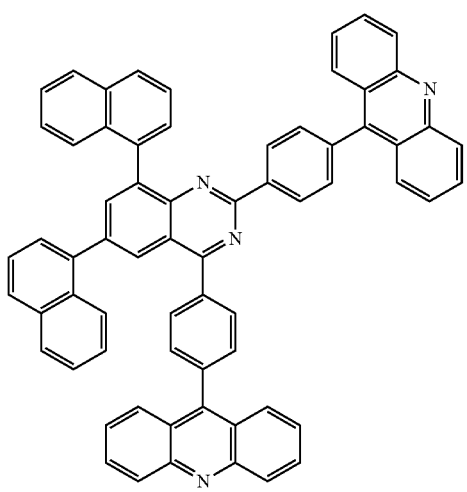

-continued
[Chemical Formula A-114]
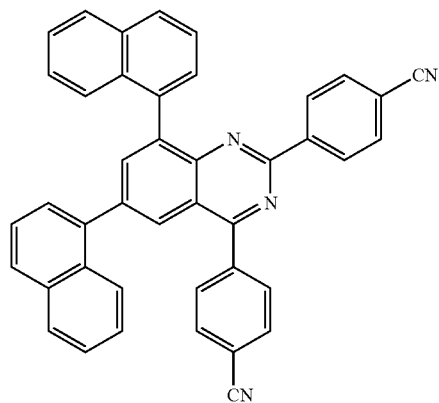
[Chemical Formula A-115]
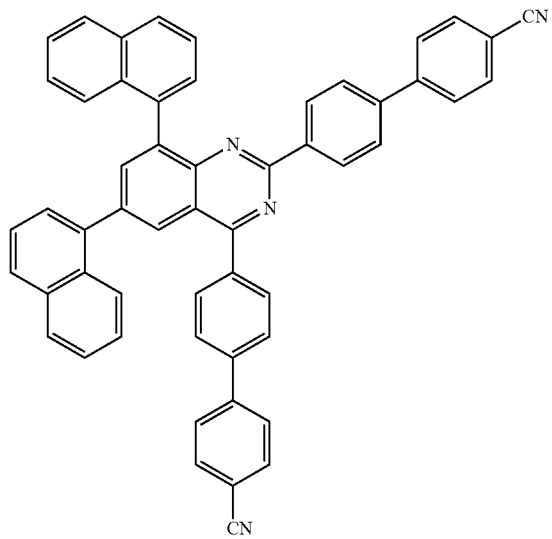
[Chemical Formula A-116]
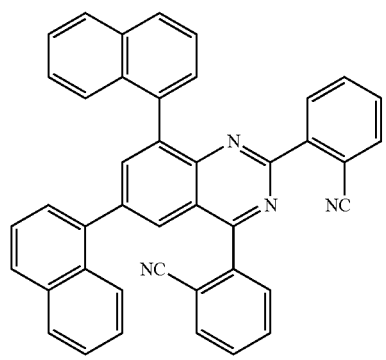
[Chemical Formula A-117]
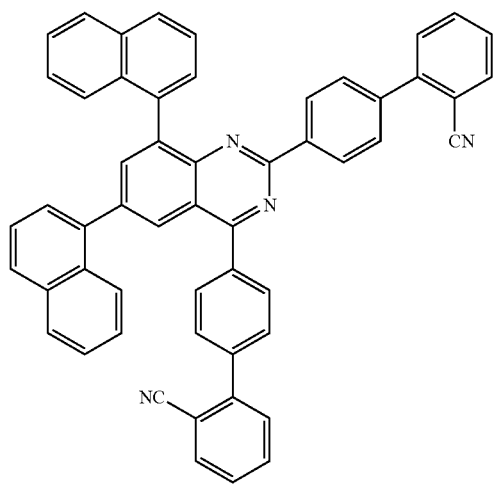
[Chemical Formula A-118]
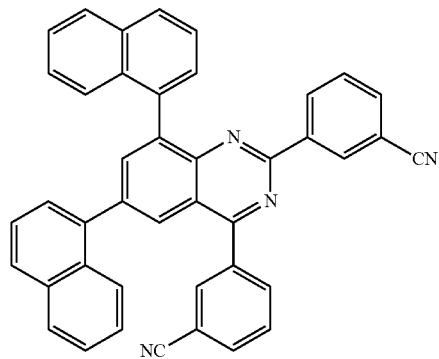
[Chemical Formula A-119]
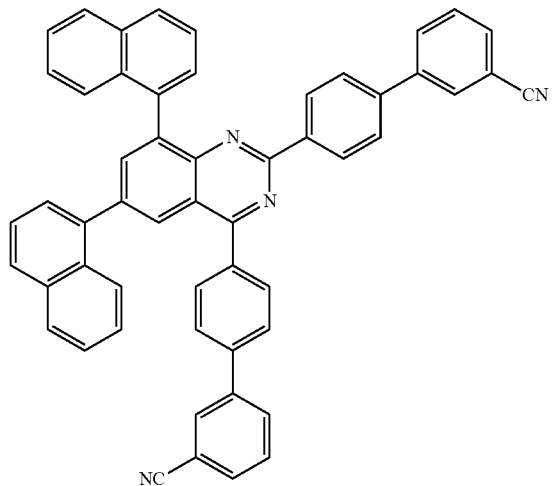

[Chemical Formula A-120]
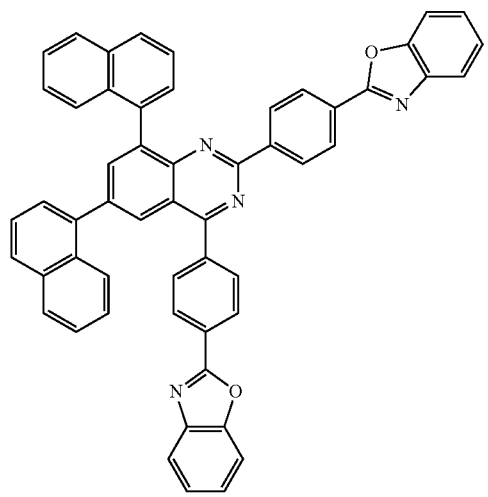
[Chemical Formula A-121]
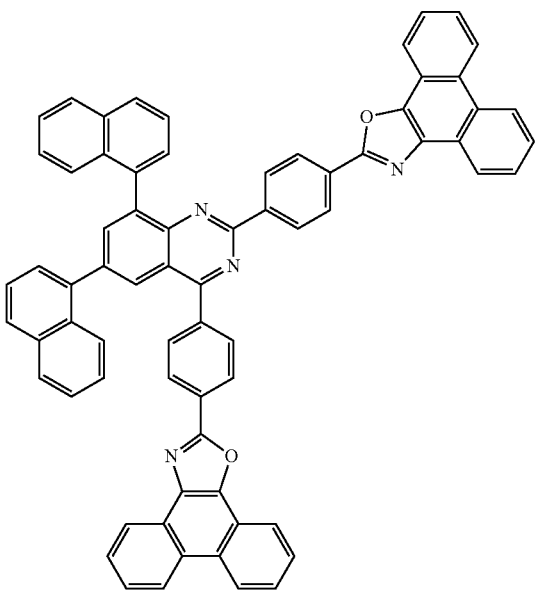
[Chemical Formula A-122]
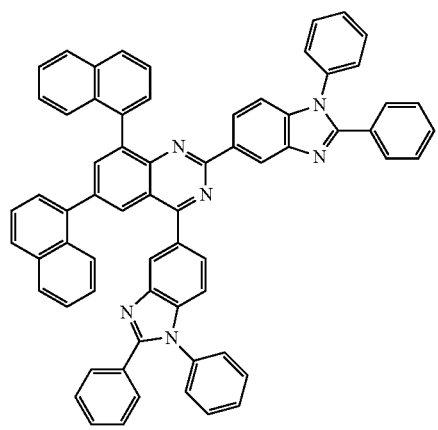
[Chemical Formula A-123]
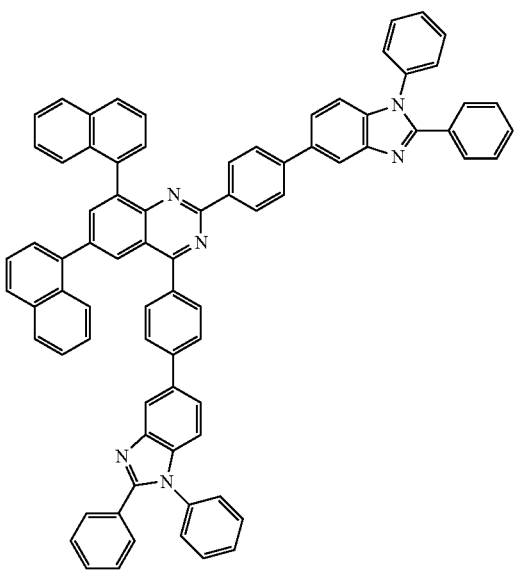

[Chemical Formula A-124]
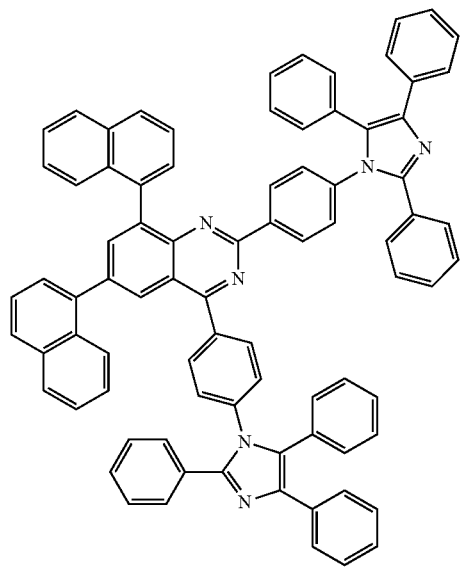
[Chemical Formula A-125]
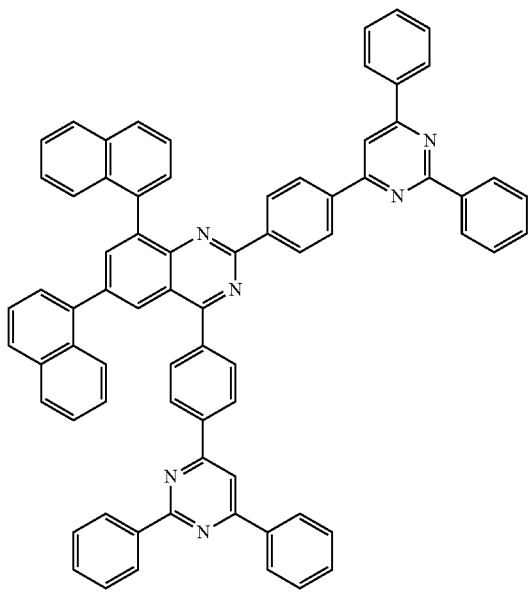
[Chemical Formula A-126]
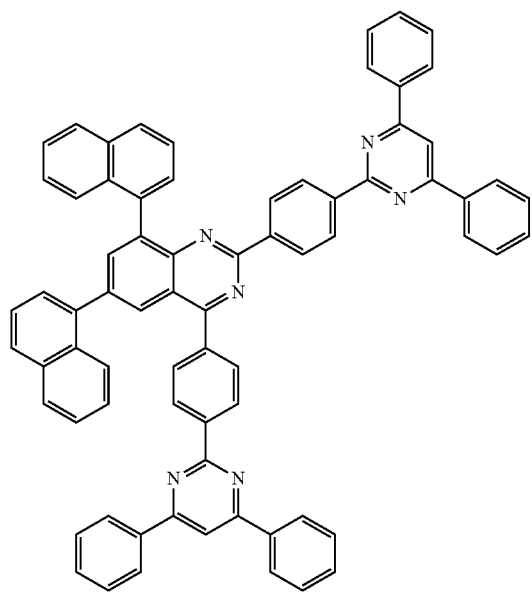
[Chemical Formula A-127]
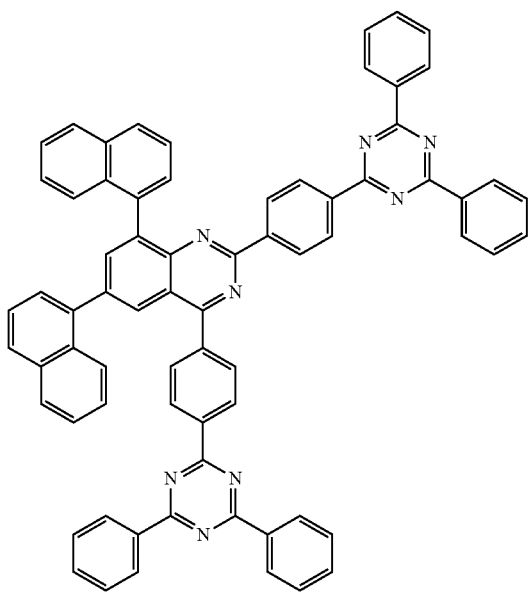

-continued
[Chemical Formula A-128]
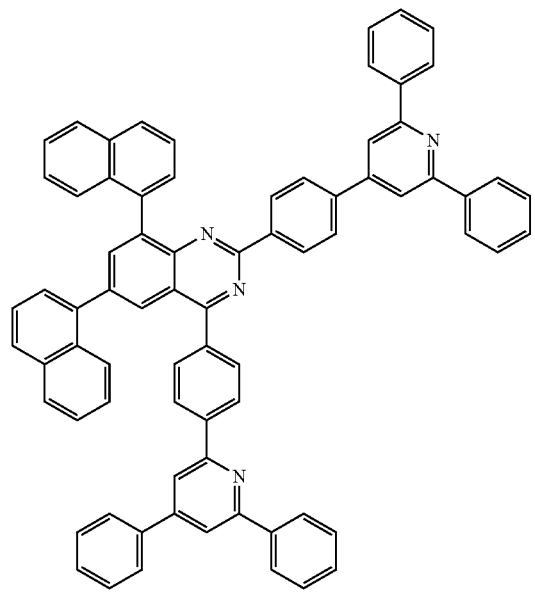
[Chemical Formula A-129]
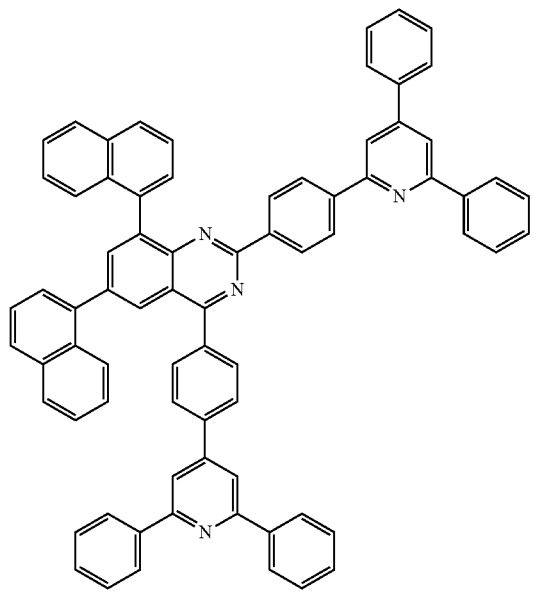
[Chemical Formula A-130]
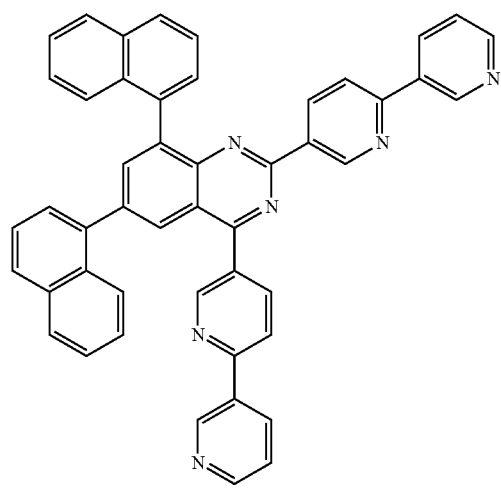
[Chemical Formula A-131]
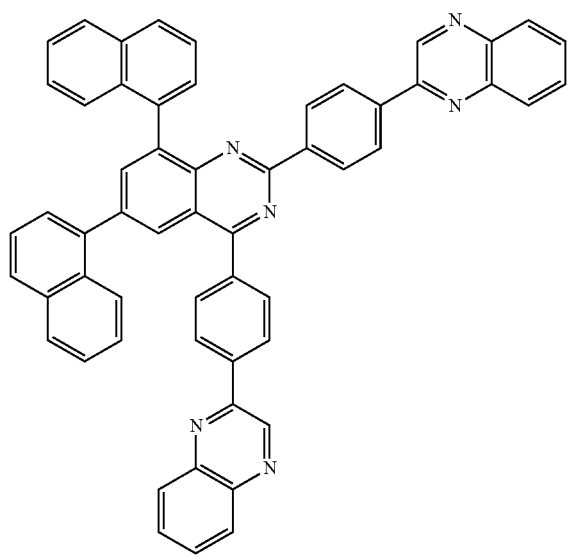

[Chemical Formula A-132]
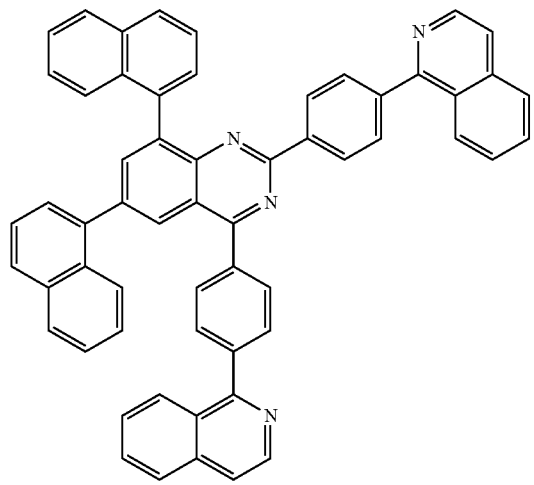
[Chemical Formula A-133]
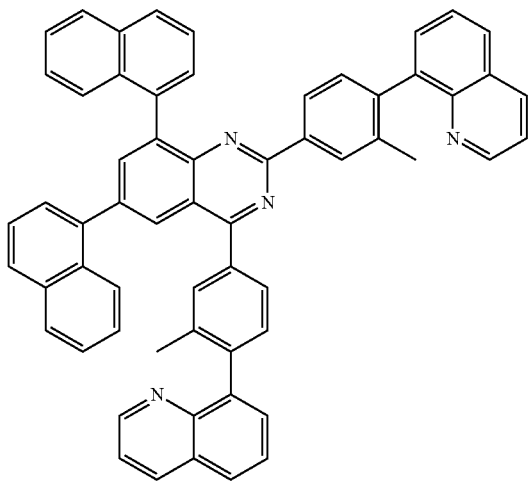
[Chemical Formula A-134]
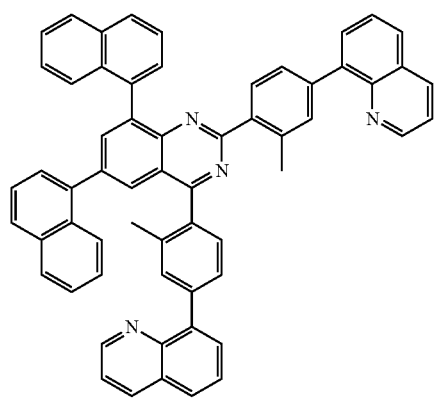
[Chemical Formula A-135]
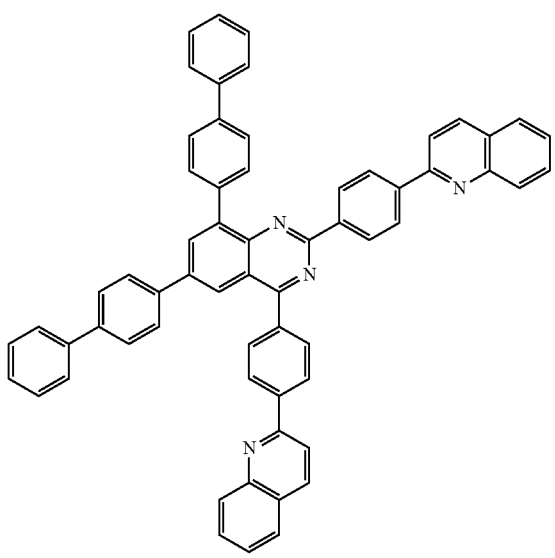

[Chemical Formula A-136]
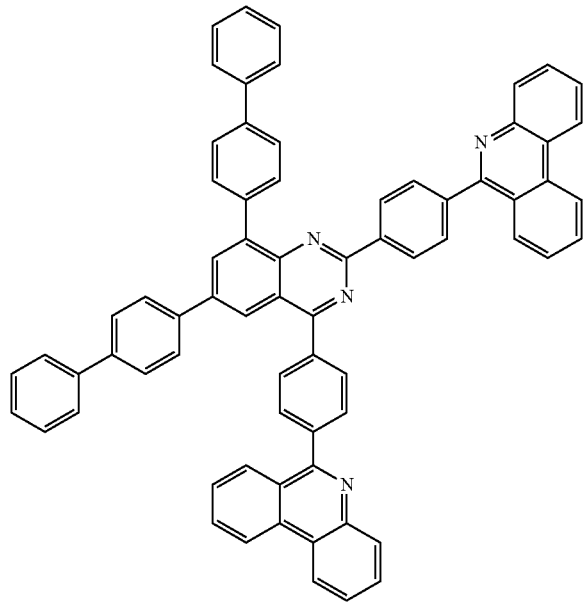
[Chemical Formula A-137]
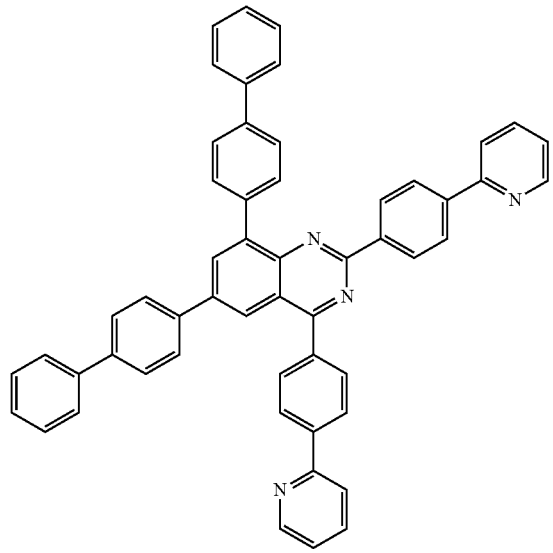
[Chemical Formula A-138]
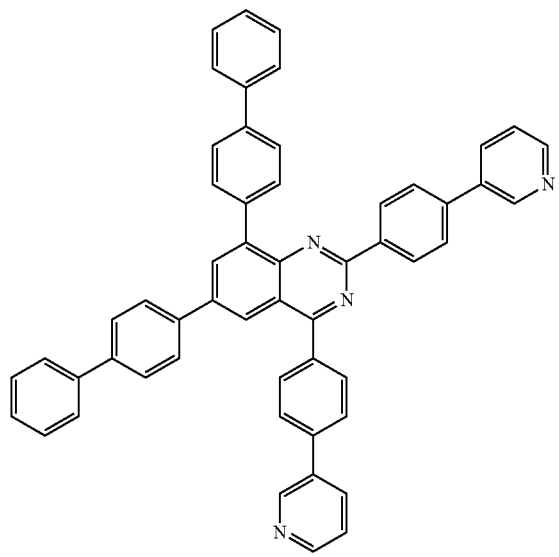
[Chemical Formula A-139]
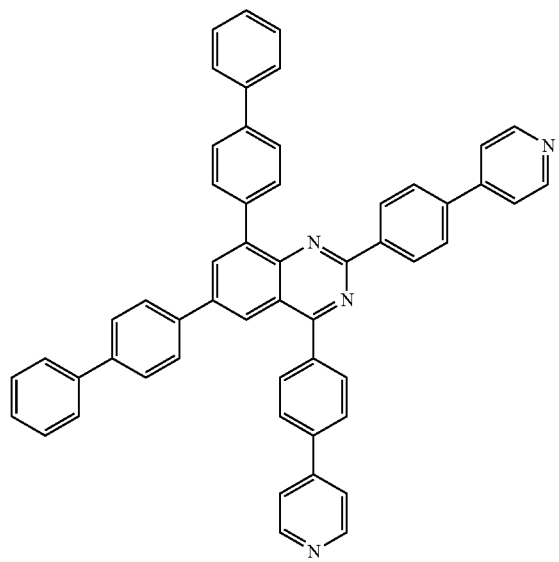

[Chemical Formula A-140]
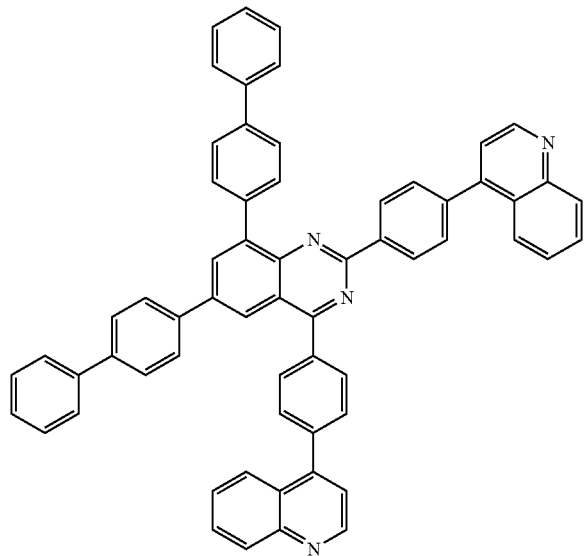
[Chemical Formula A-141]
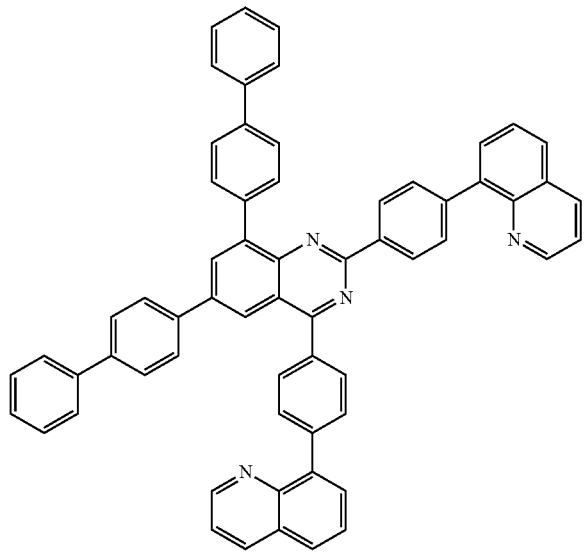
[Chemical Formula A-142]
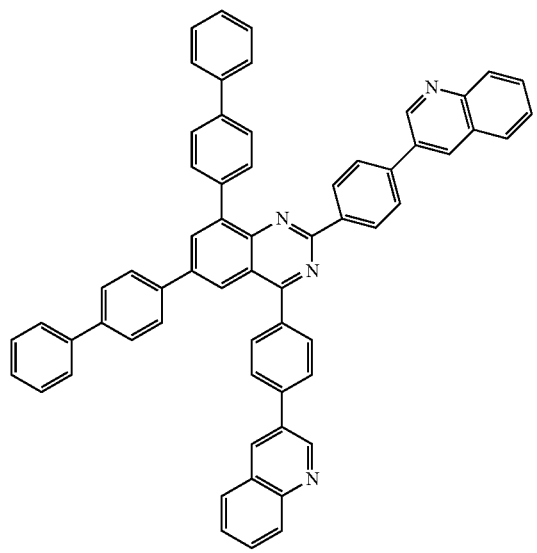
[Chemical Formula A-143]
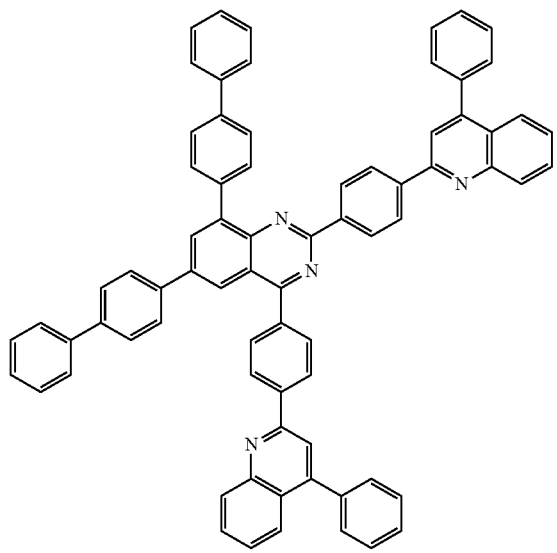

[Chemical Formula A-144]
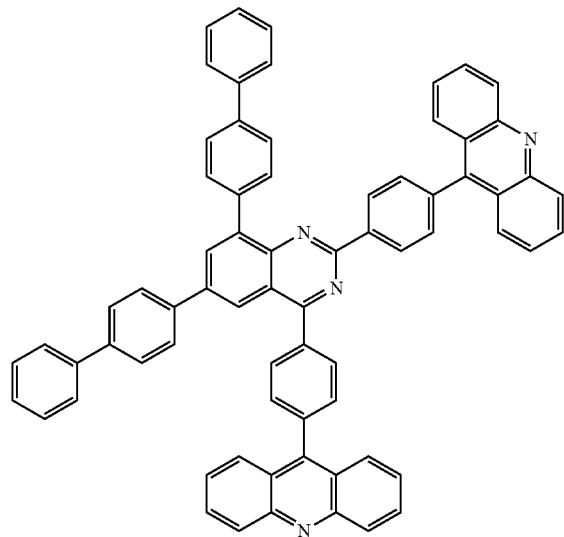
[Chemical Formula A-145]
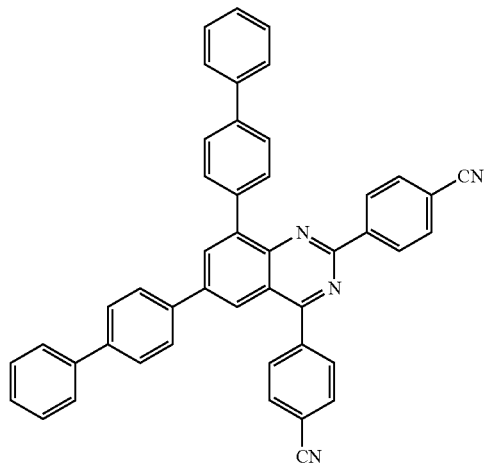
[Chemical Formula A-146]
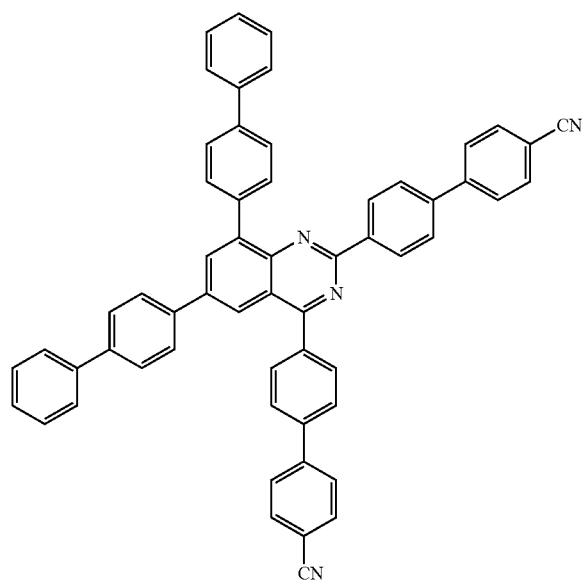
[Chemical Formula A-147]
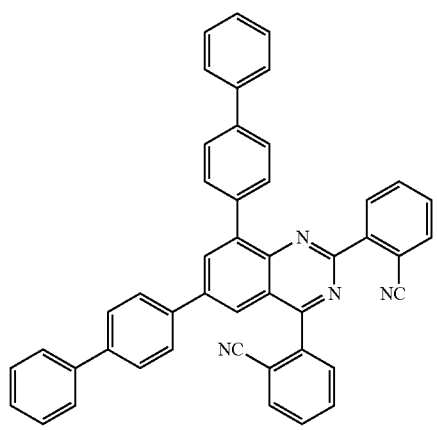

[Chemical Formula A-148]
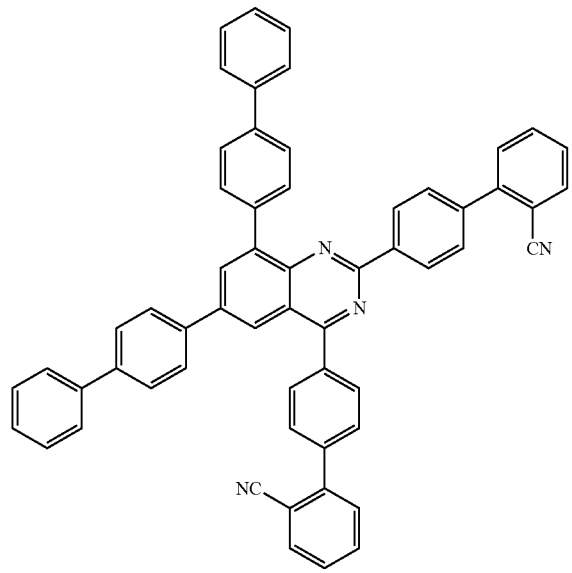
[Chemical Formula A-149]
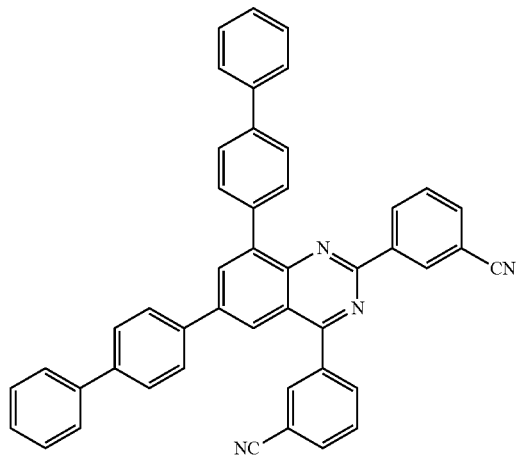
[Chemical Formula A-150]
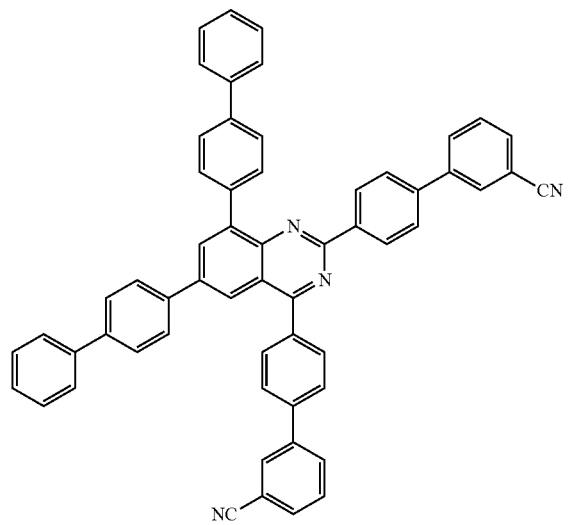
[Chemical Formula A-151]
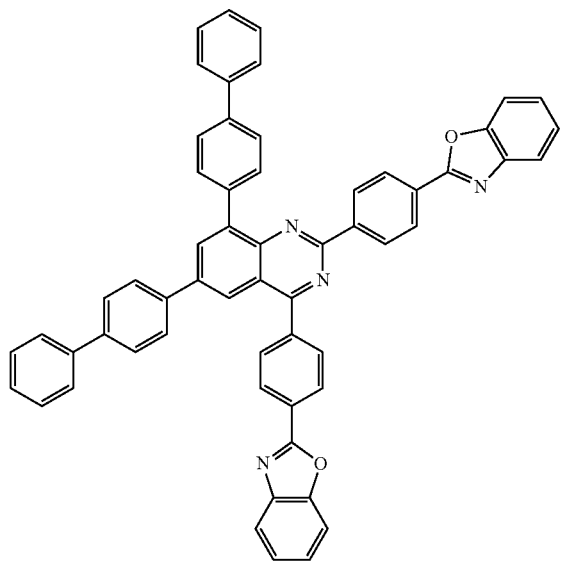

[Chemical Formula A-152]
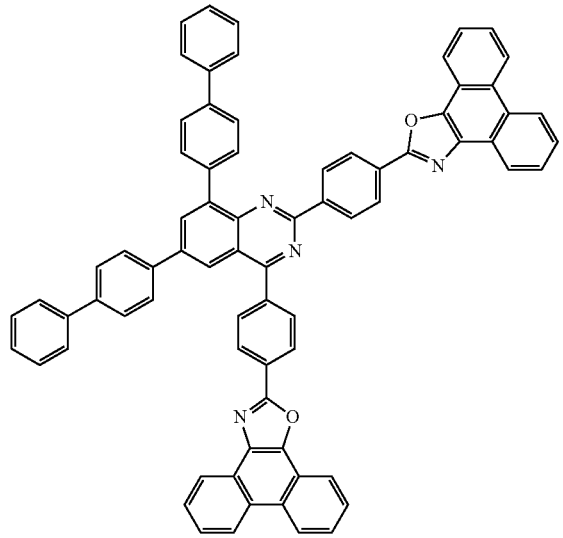
[Chemical Formula A-153]
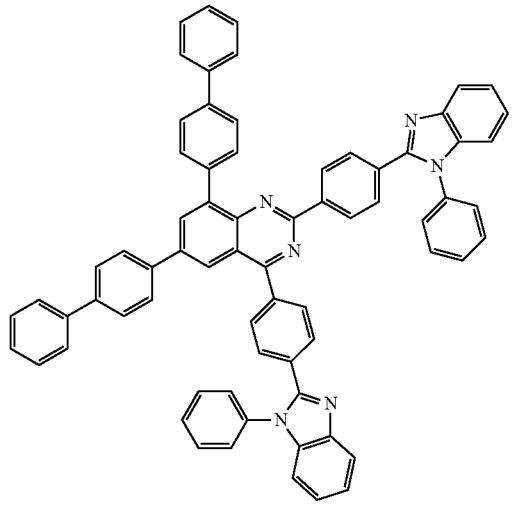
[Chemical Formula A-154]
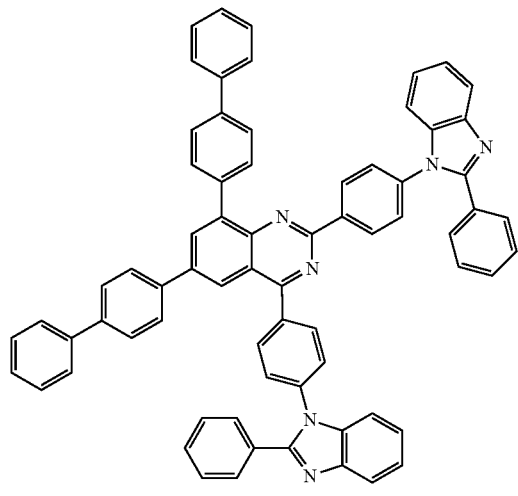
[Chemical Formula A-155]
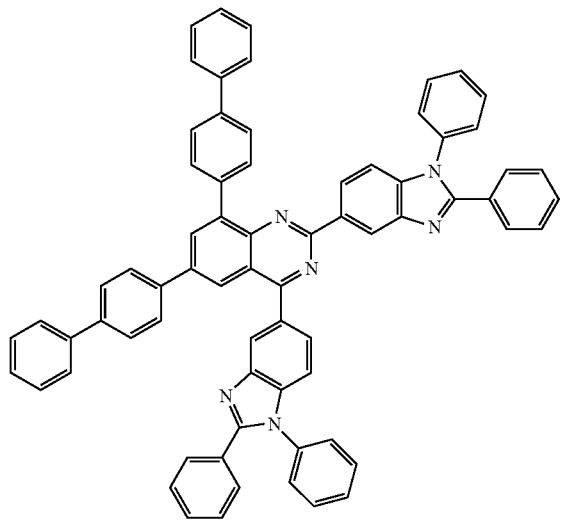

[Chemical Formula A-156]
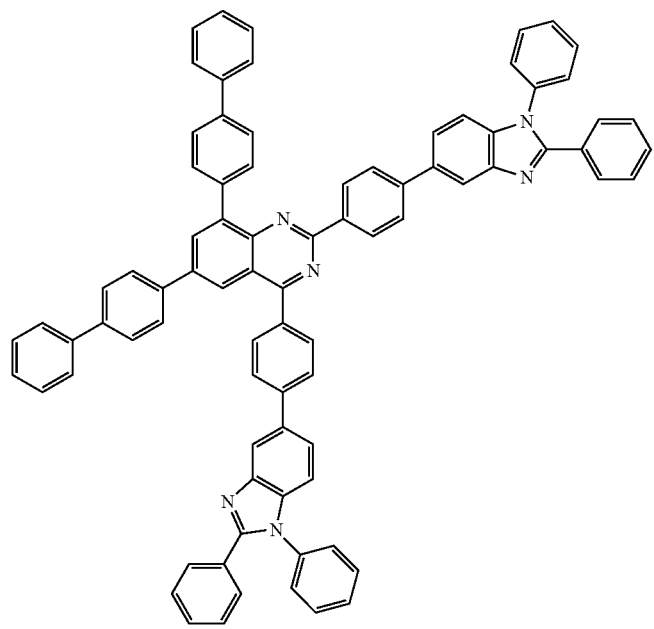
[Chemical Formula A-157]
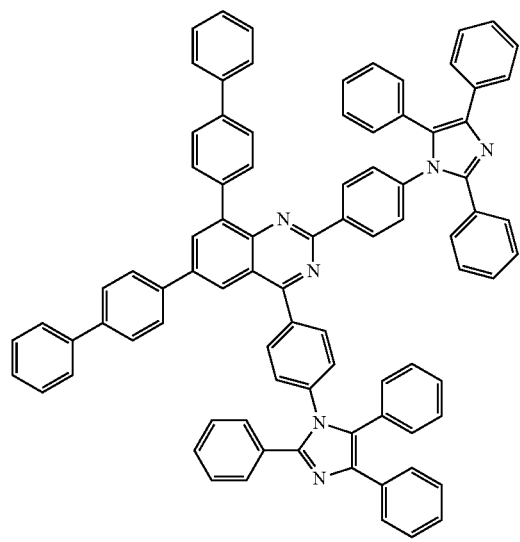
[Chemical Formula A-158]
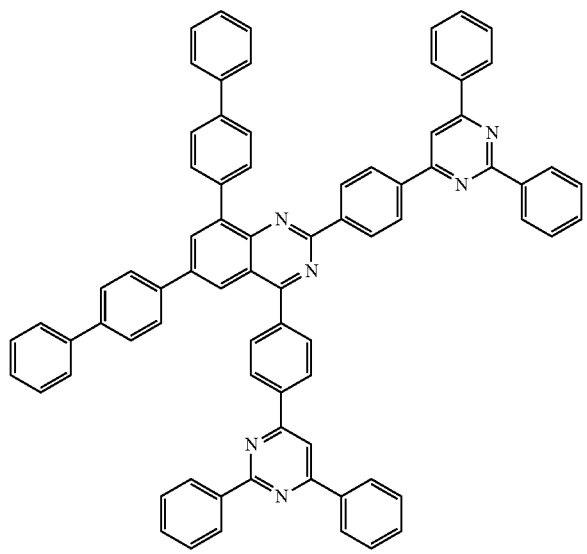

[Chemical Formula A-159]
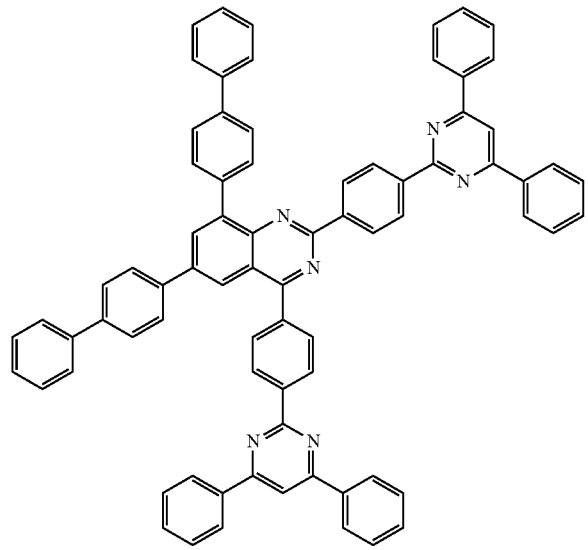
[Chemical Formula A-160]
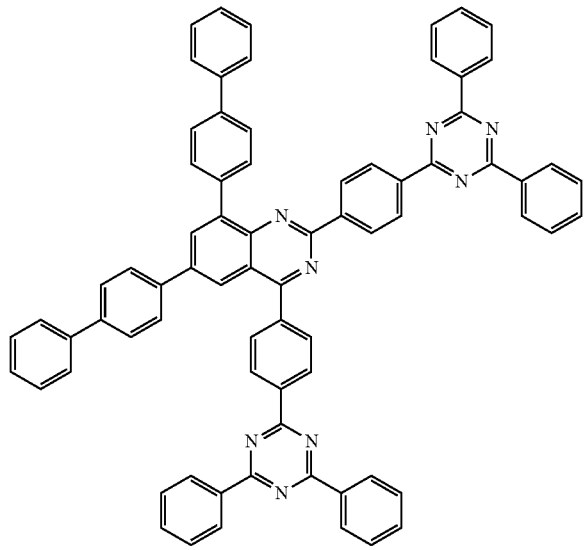
[Chemical Formula A-161]
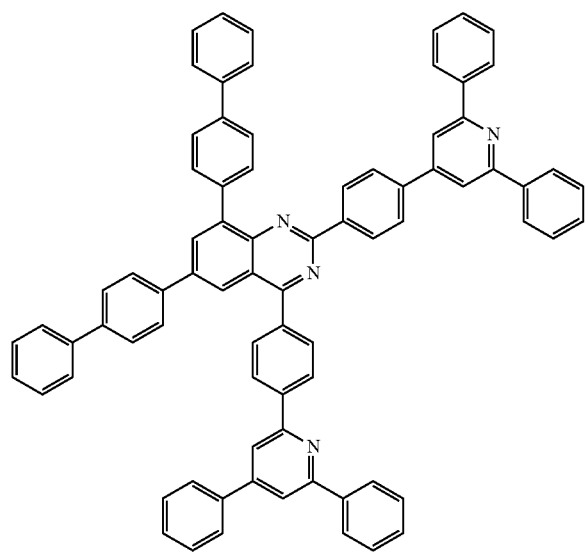
[Chemical Formula A-162]
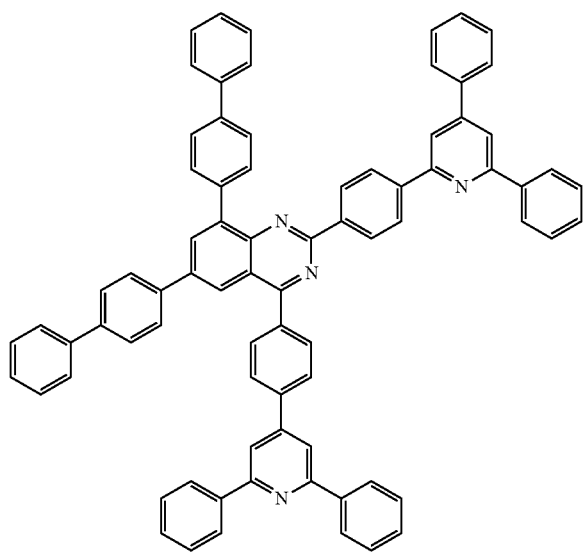

[Chemical Formula A-163]
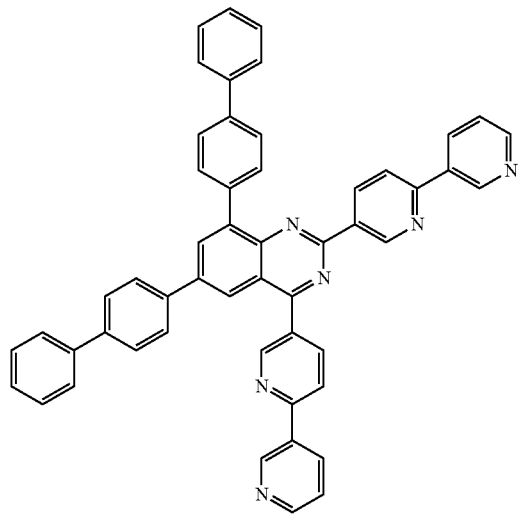
[Chemical Formula A-164]
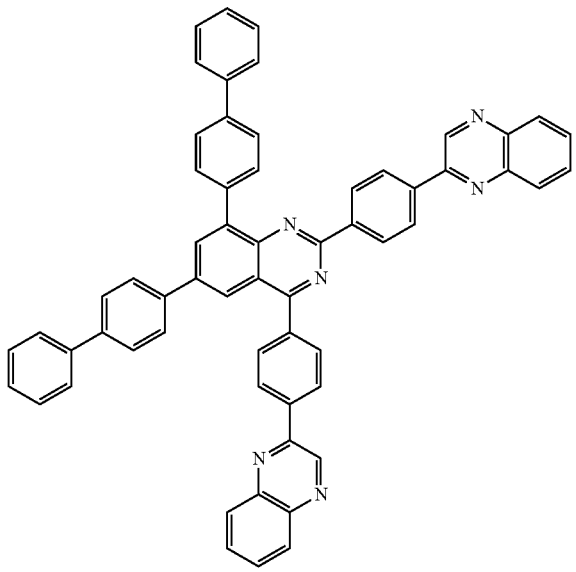
[Chemical Formula A-165]
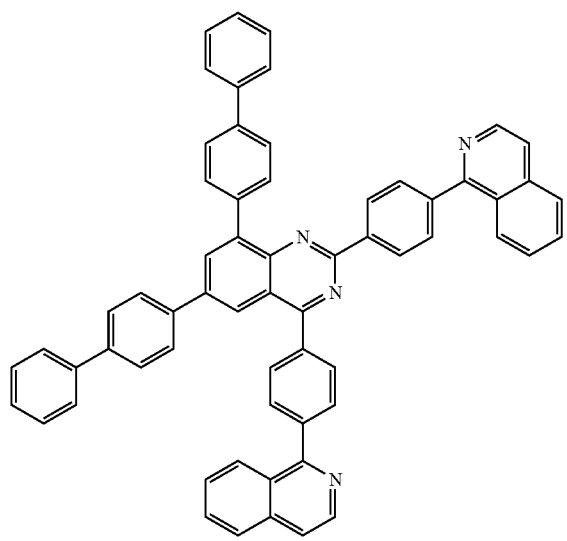
[Chemical Formula A-166]
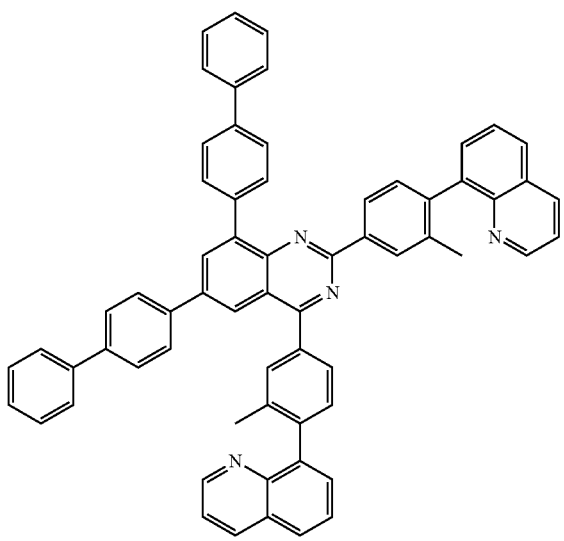

-continued
[Chemical Formula A-167]
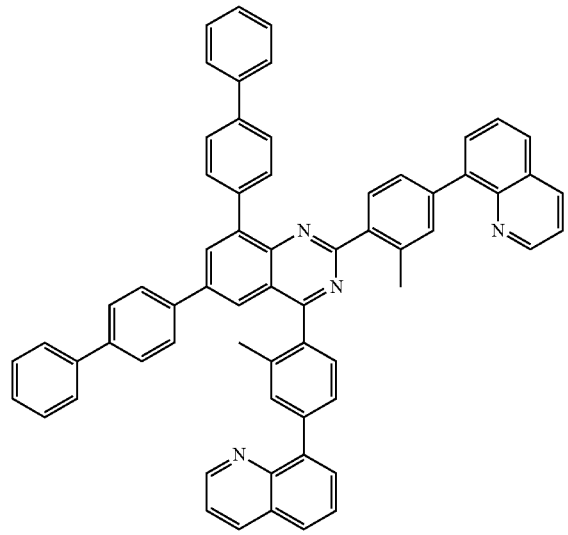
[Chemical Formula A-168]
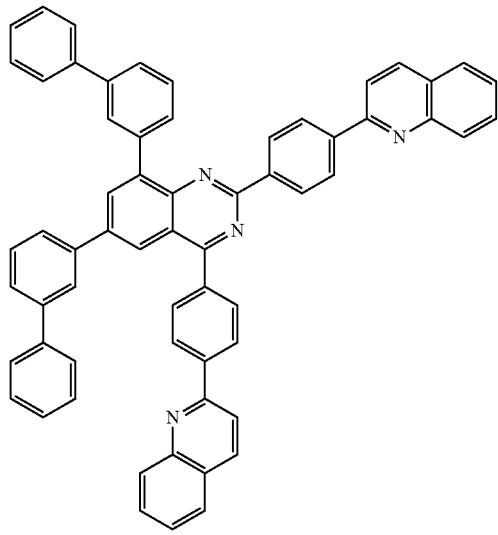
[Chemical Formula A-169]
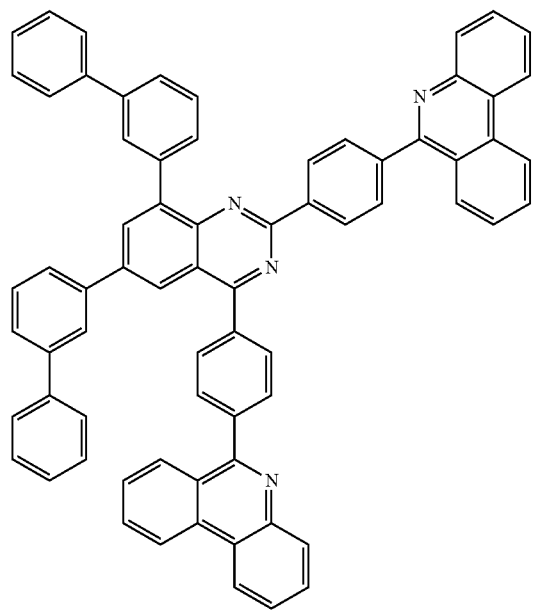
[Chemical Formula A-170]
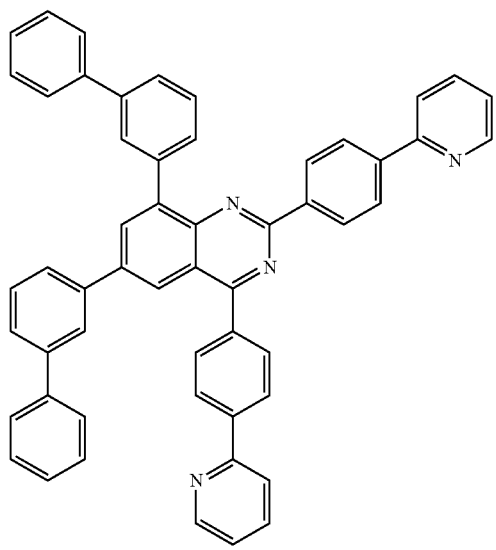

-continued
[Chemical Formula A-171]
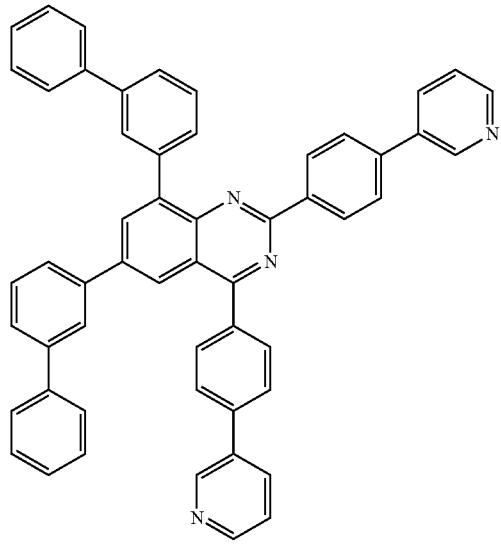
[Chemical Formula A-172]
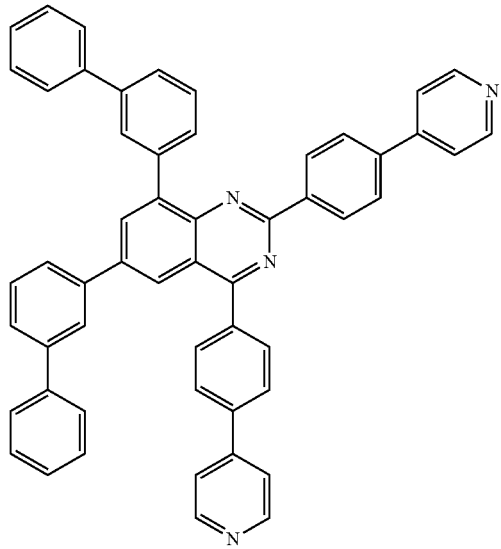
[Chemical Formula A-173]
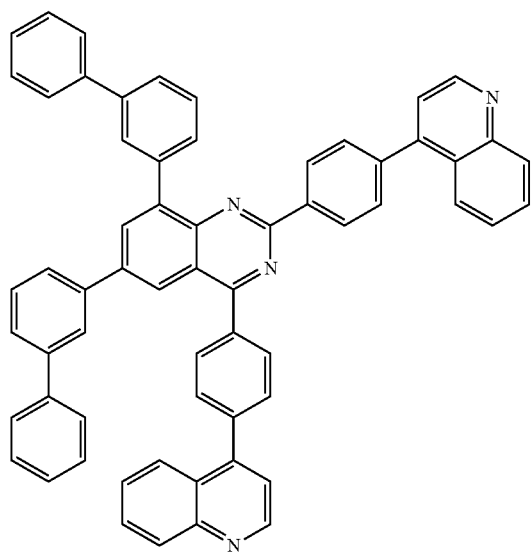
[Chemical Formula A-174]
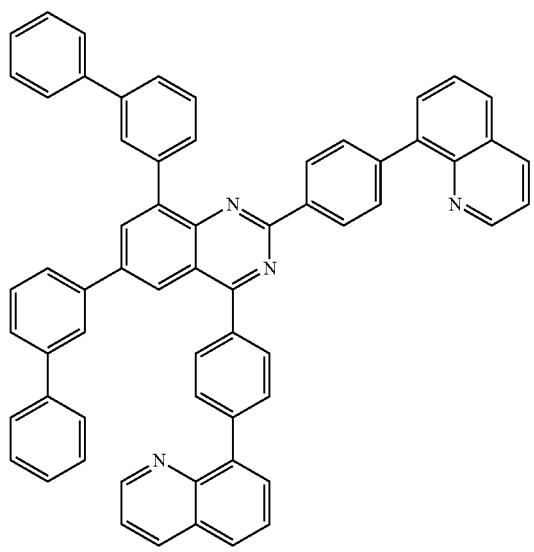

[Chemical Formula A-175]
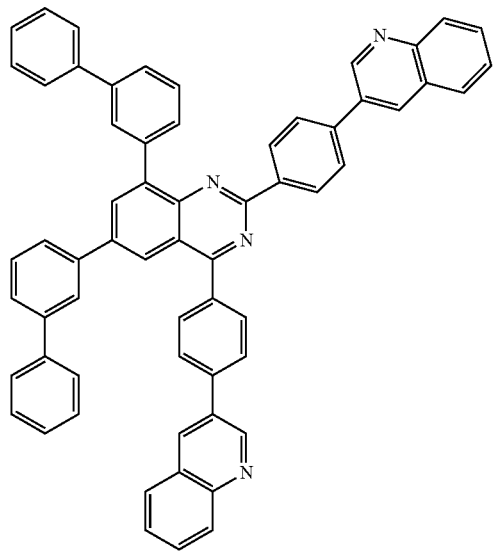
[Chemical Formula A-176]
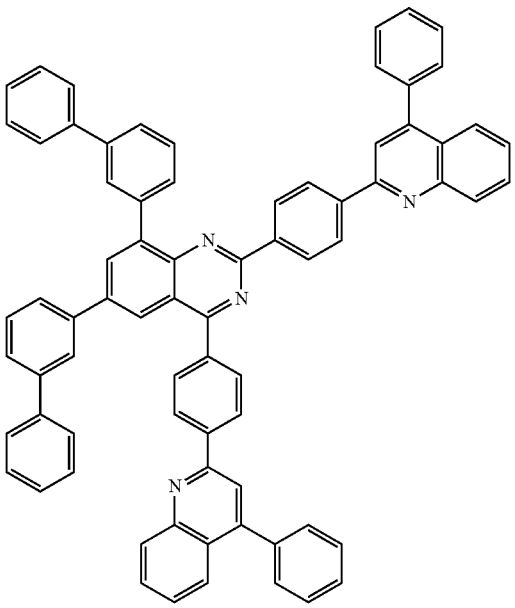
[Chemical Formula A-177]
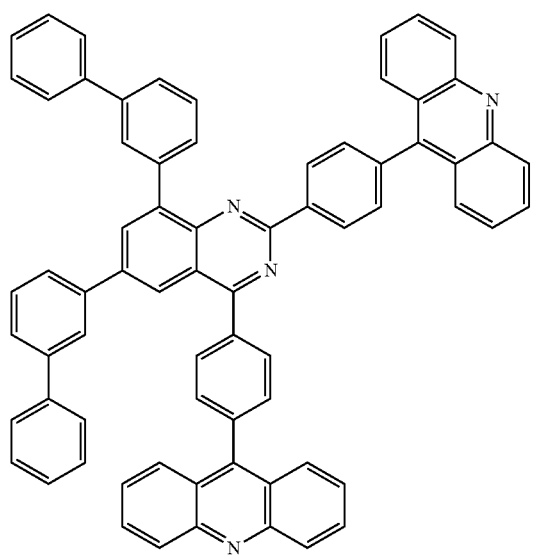
[Chemical Formula A-178]
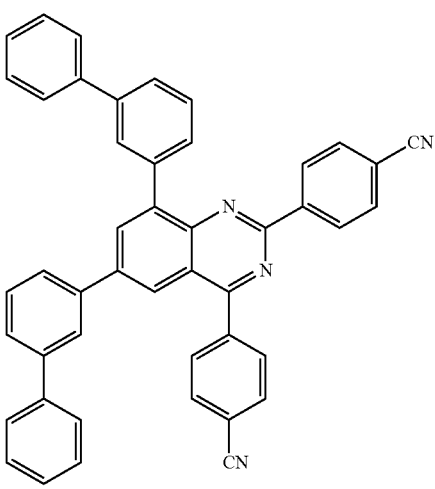

[Chemical Formula A-179]
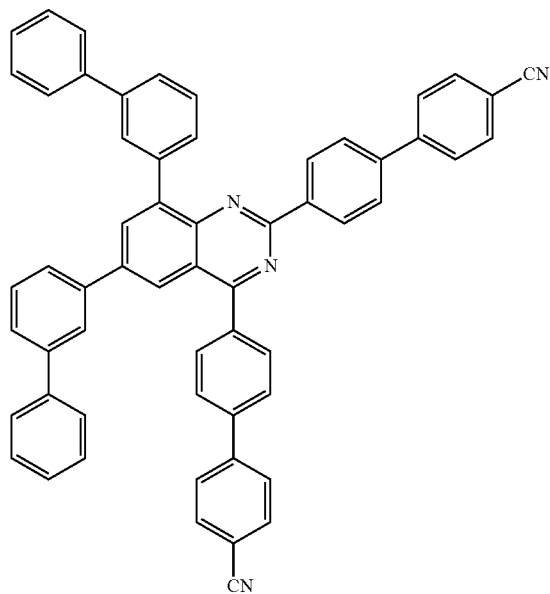
[Chemical Formula A-180]
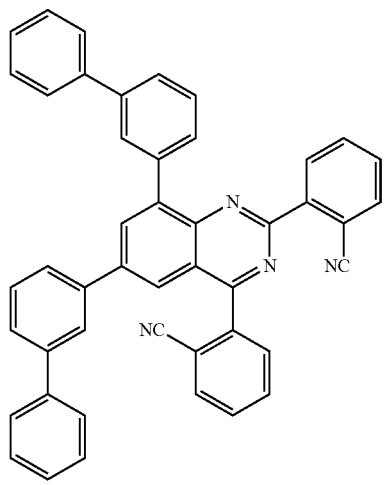
[Chemical Formula A-181]
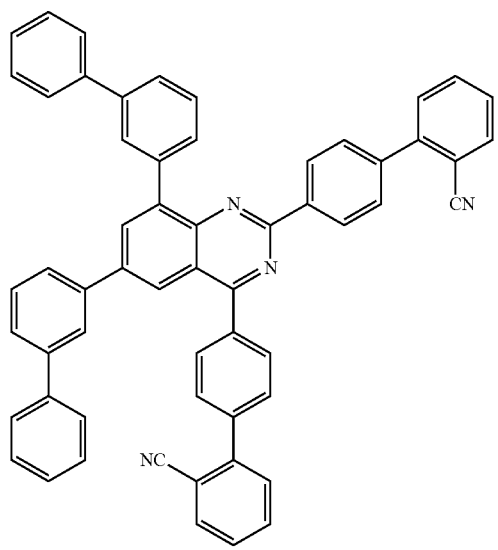
[Chemical Formula A-182]
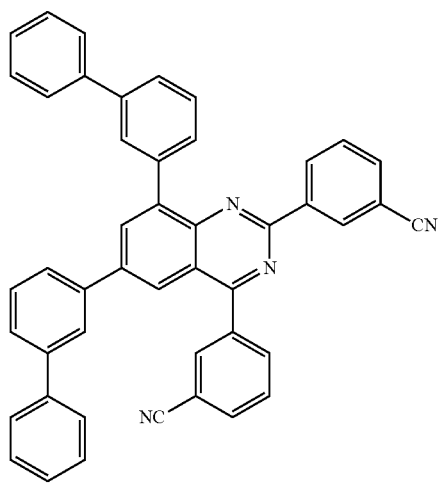

[Chemical Formula A-183]
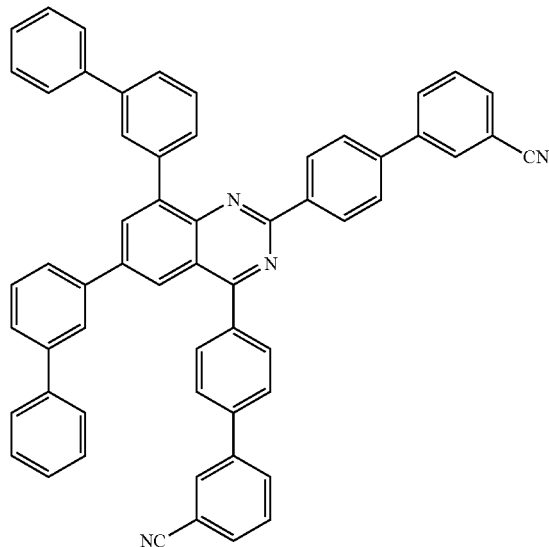
[Chemical Formula A-184]
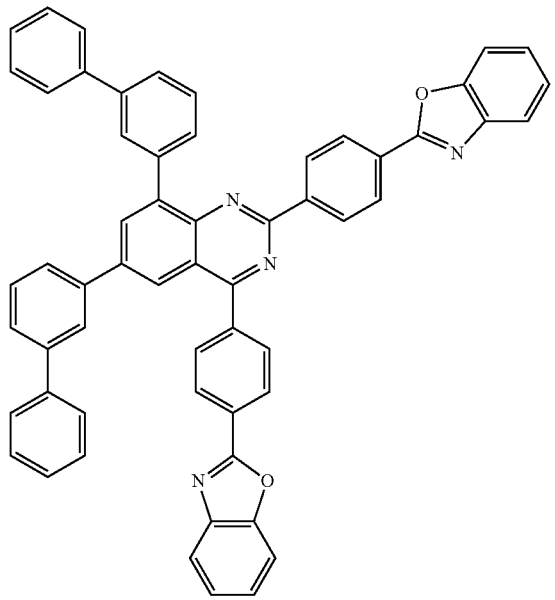
[Chemical Formula A-185]
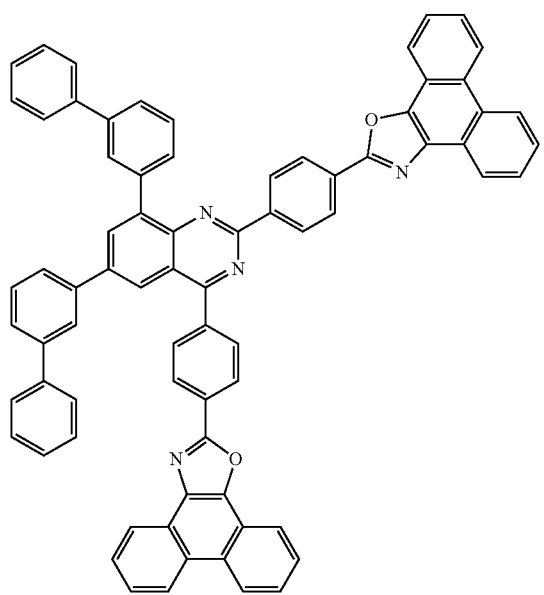
[Chemical Formula A-186]
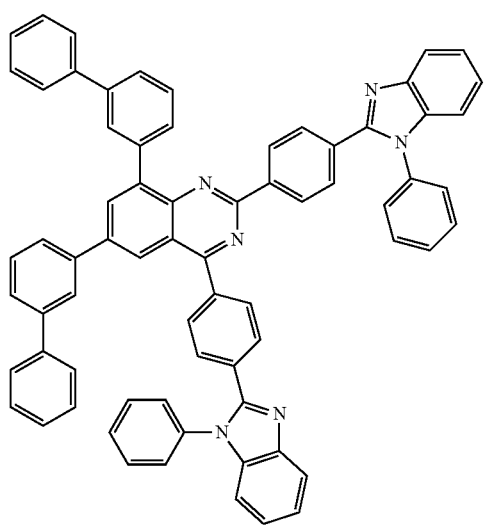

[Chemical Formula A-187]
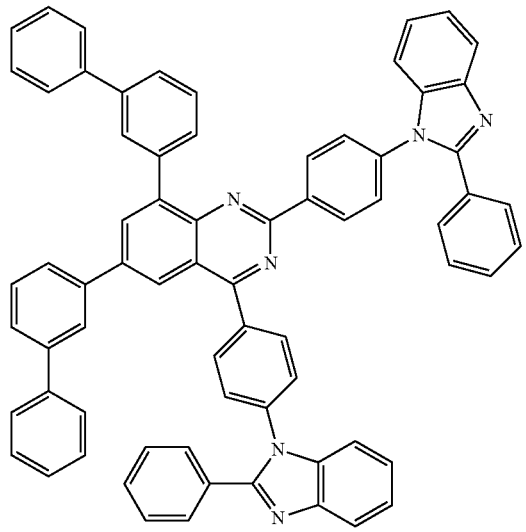
[Chemical Formula A-188]
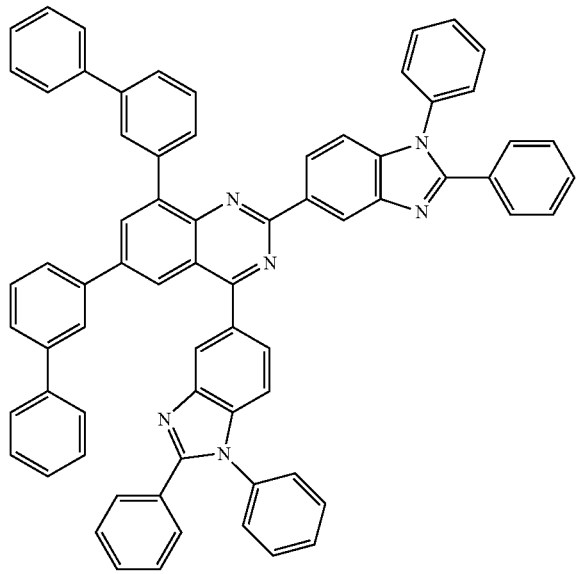
[Chemical Formula A-189]
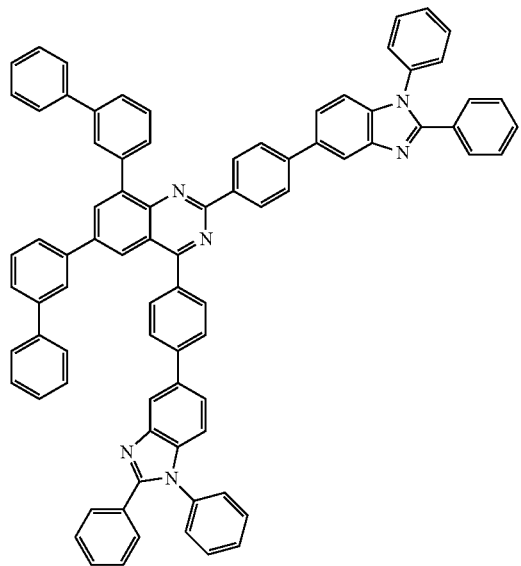
[Chemical Formula A-190]
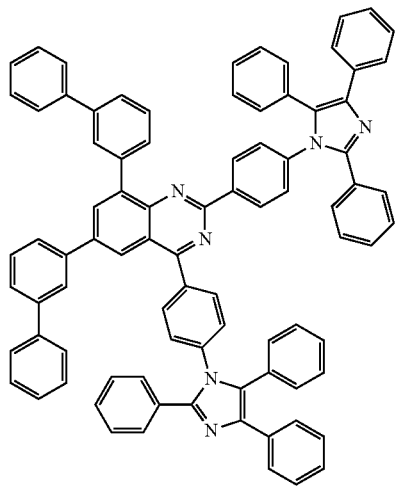

[Chemical Formula A-191]
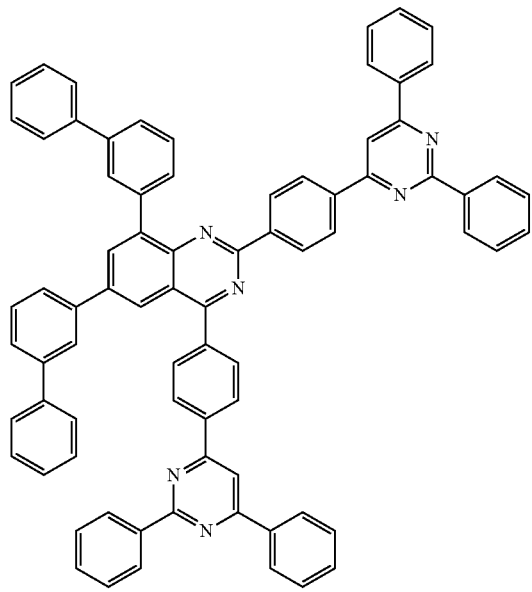
[Chemical Formula A-192]
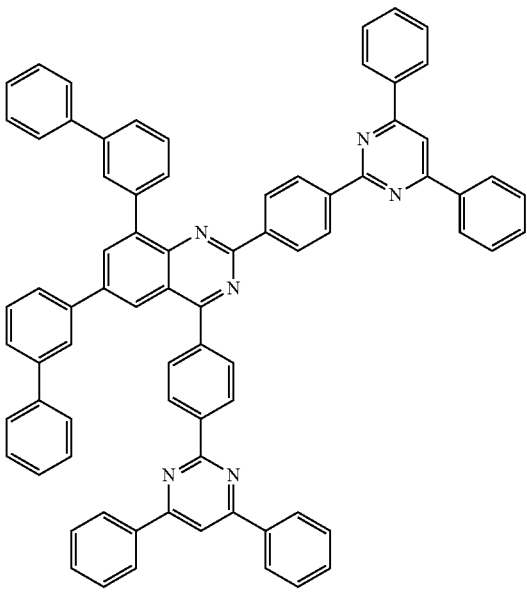
[Chemical Formula A-193]
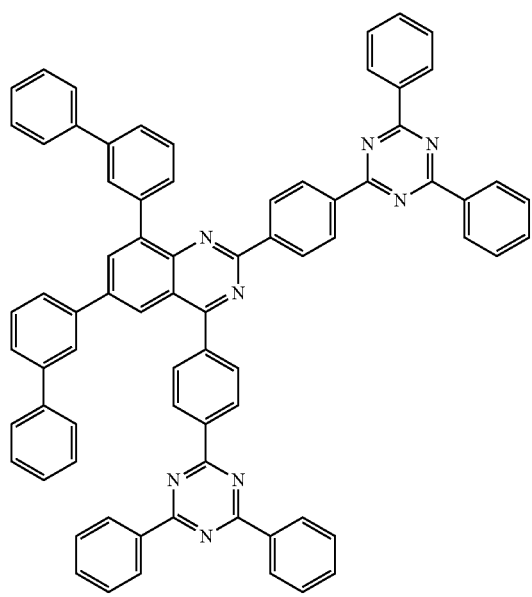
[Chemical Formula A-194]
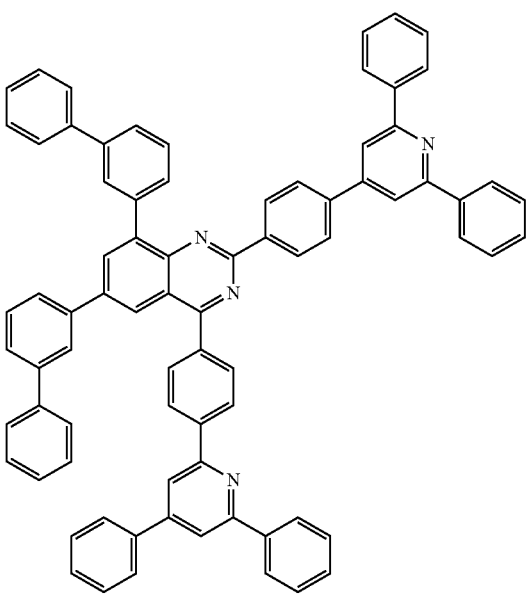

-continued
[Chemical Formula A-195]
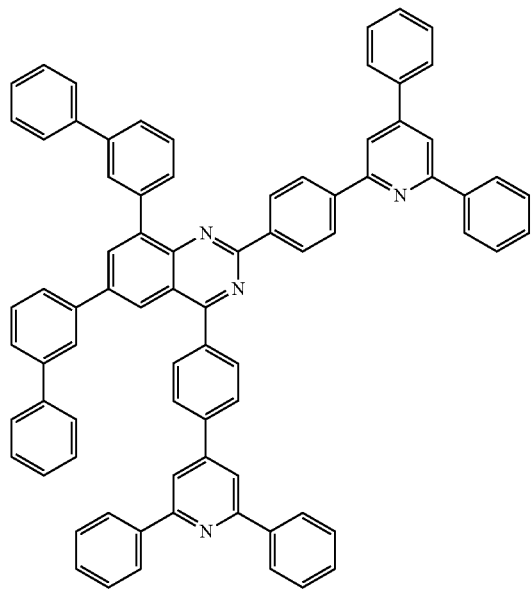
[Chemical Formula A-196]
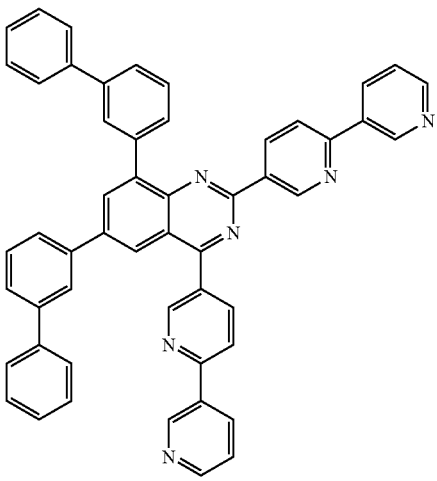
[Chemical Formula A-197]
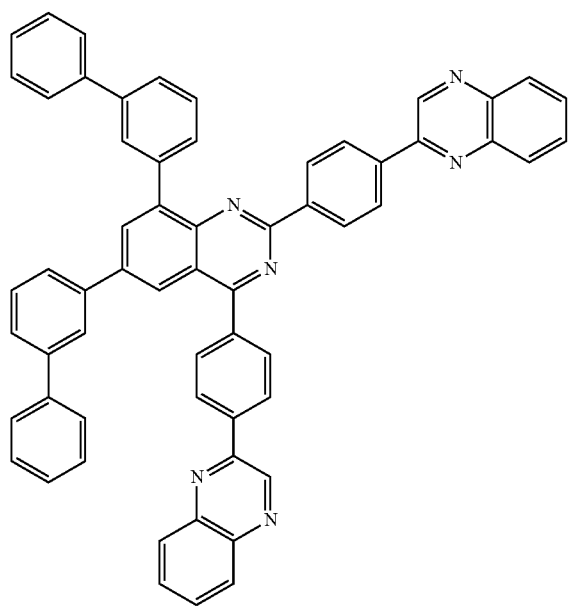
[Chemical Formula A-198]
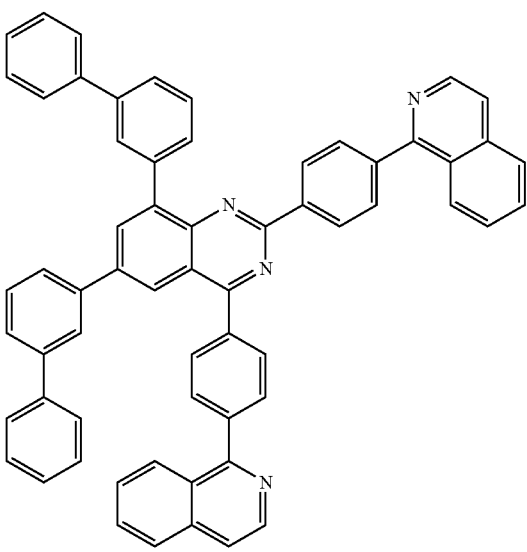

[Chemical Formula A-199]
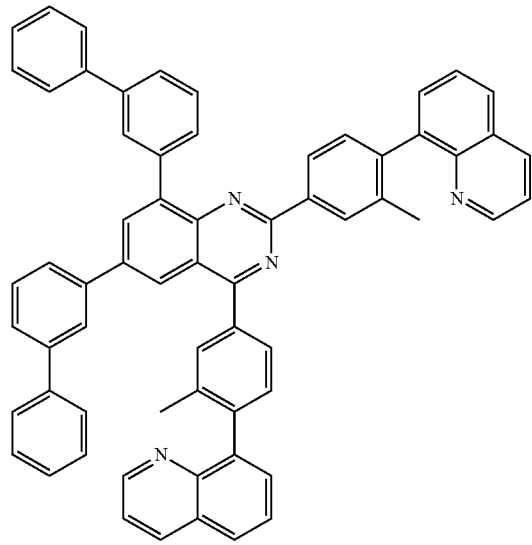
[Chemical Formula A-200]
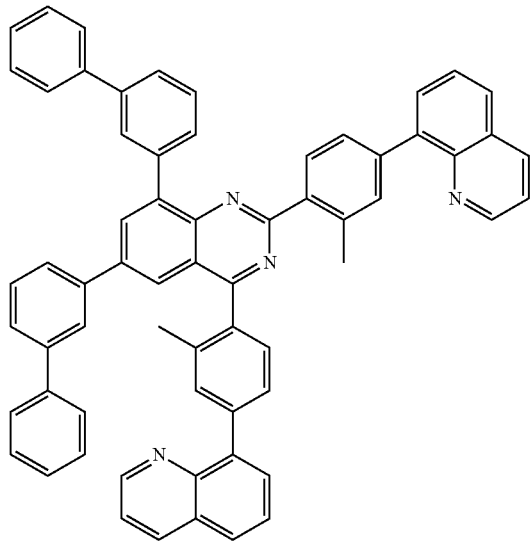
[Chemical Formula A-201]
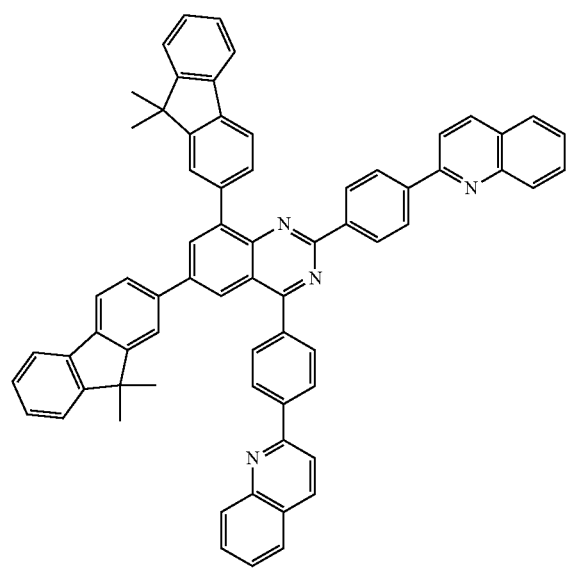
[Chemical Formula A-202]
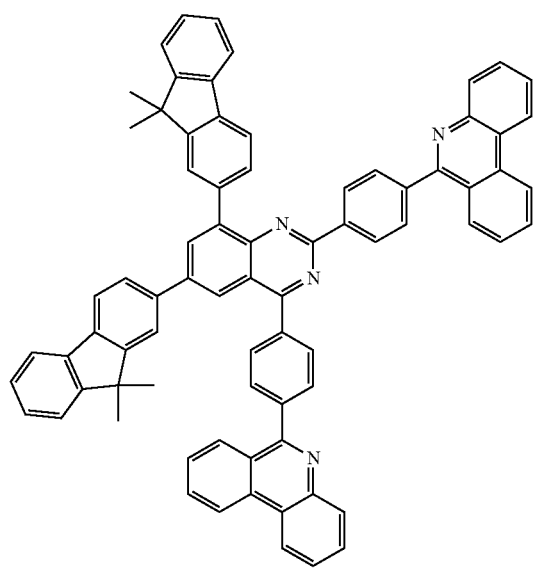

[Chemical Formula A-203]
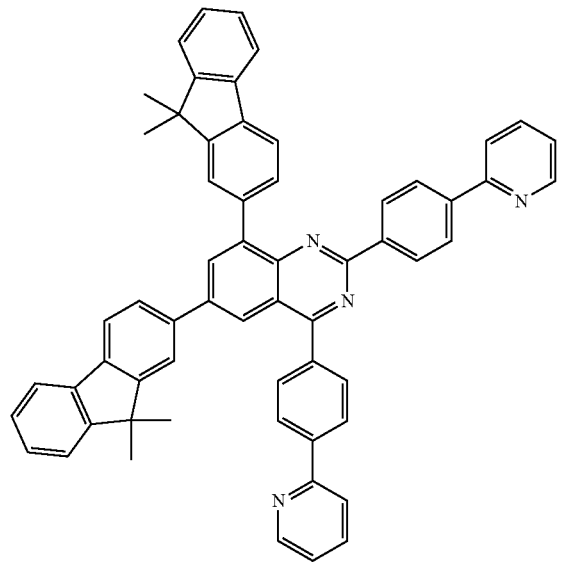
[Chemical Formula A-204]
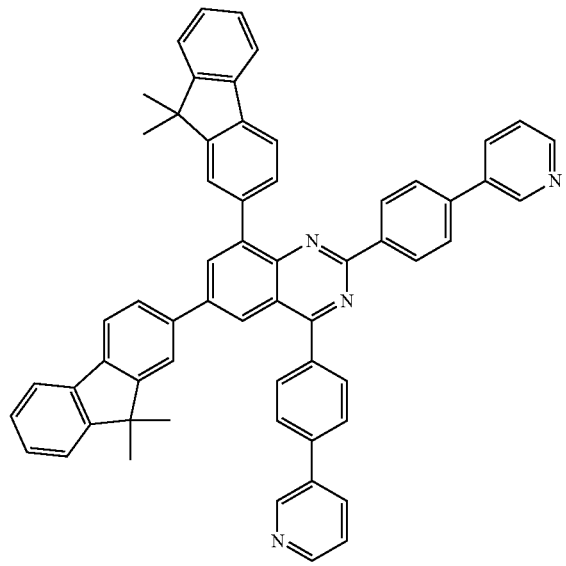
[Chemical Formula A-205]
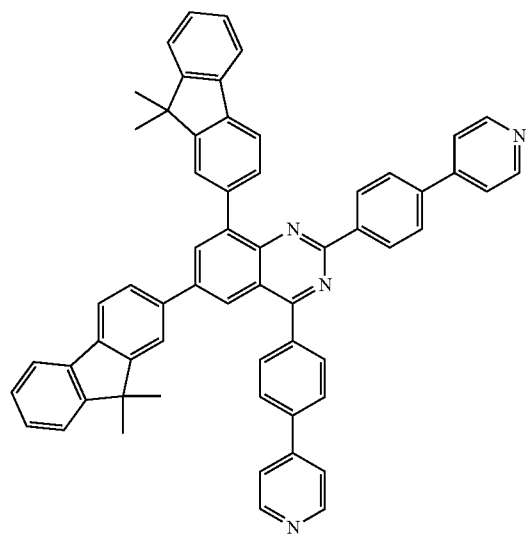
[Chemical Formula A-206]
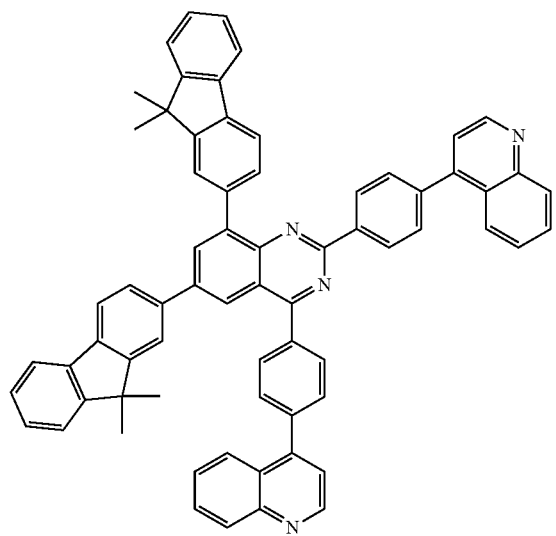

[Chemical Formula A-207]
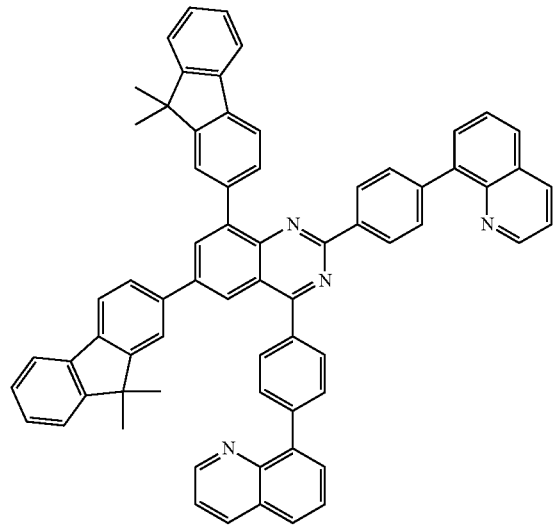
[Chemical Formula A-208]
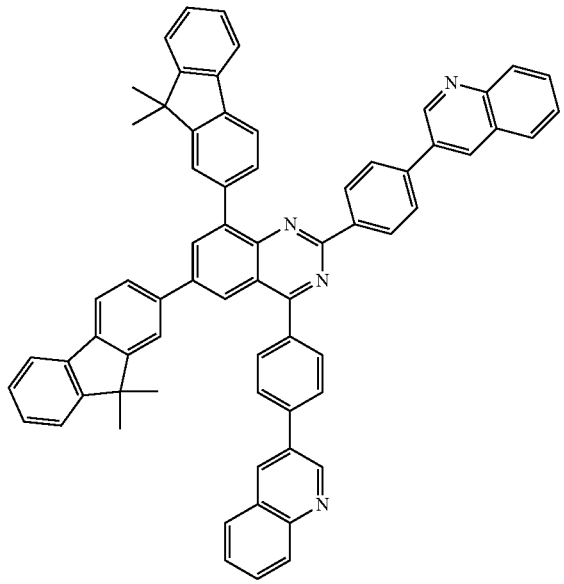
[Chemical Formula A-209]
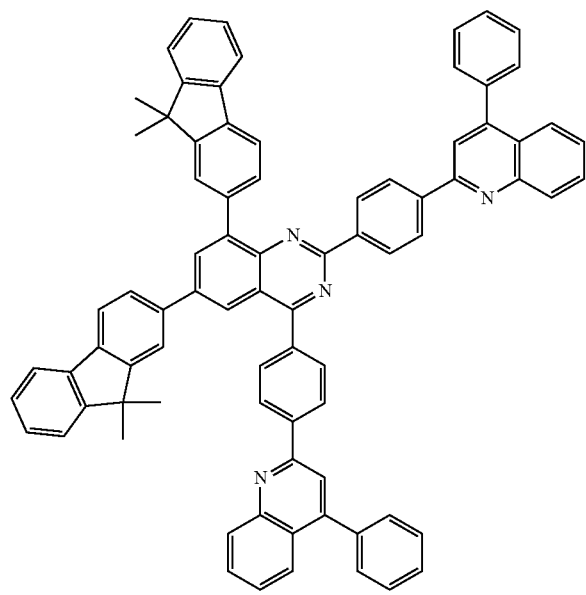
[Chemical Formula A-210]
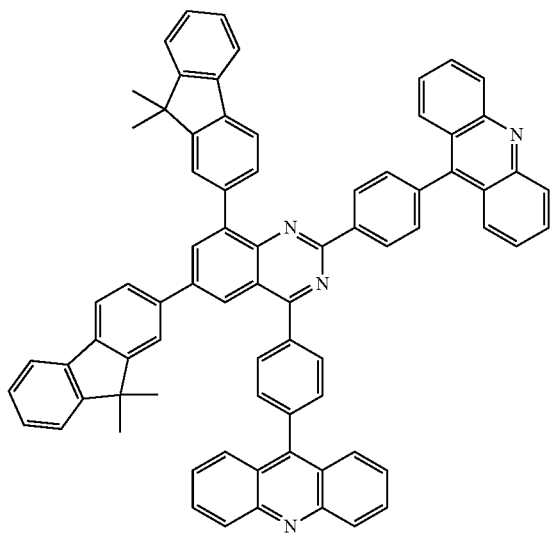

[Chemical Formula A-211]
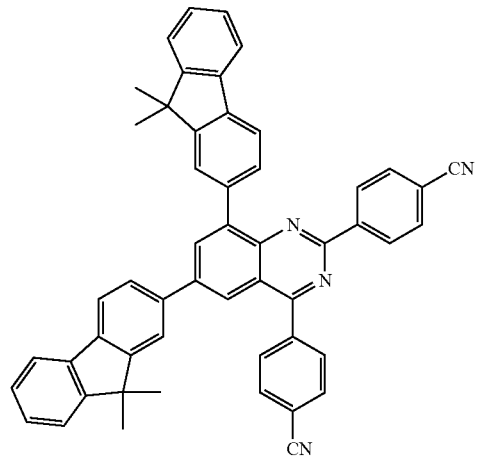
[Chemical Formula A-212]
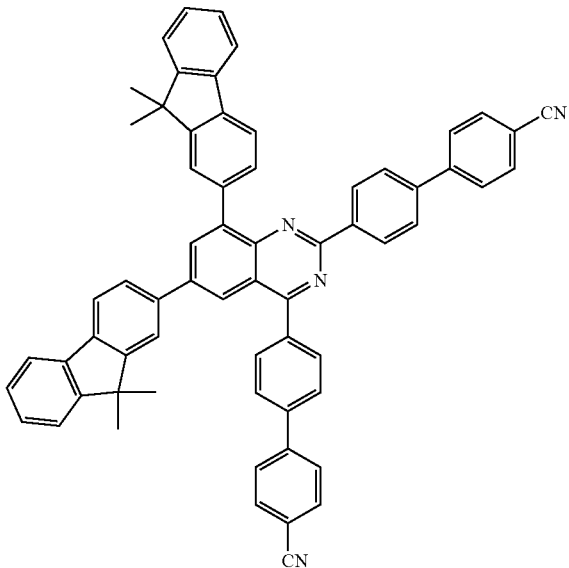
[Chemical Formula A-213]
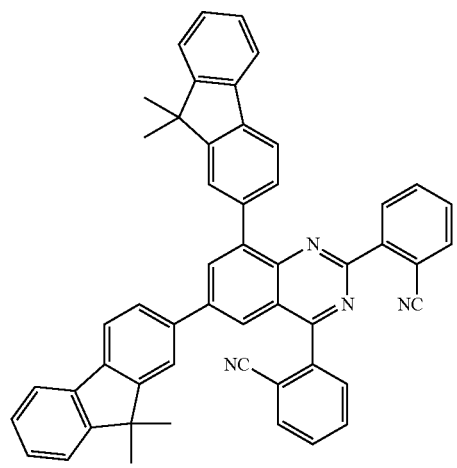
[Chemical Formula A-214]
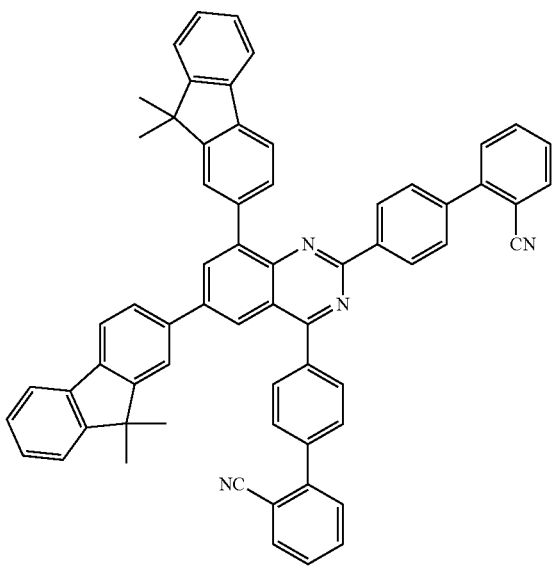

[Chemical Formula A-215]
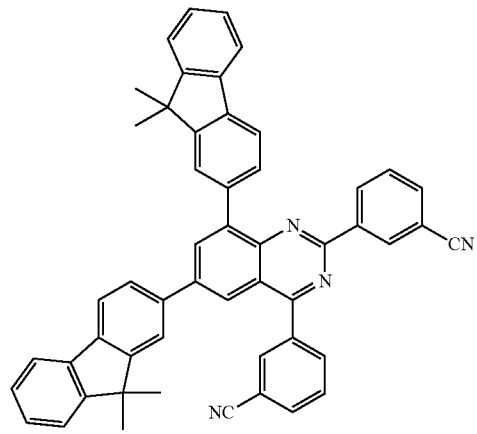
[Chemical Formula A-216]
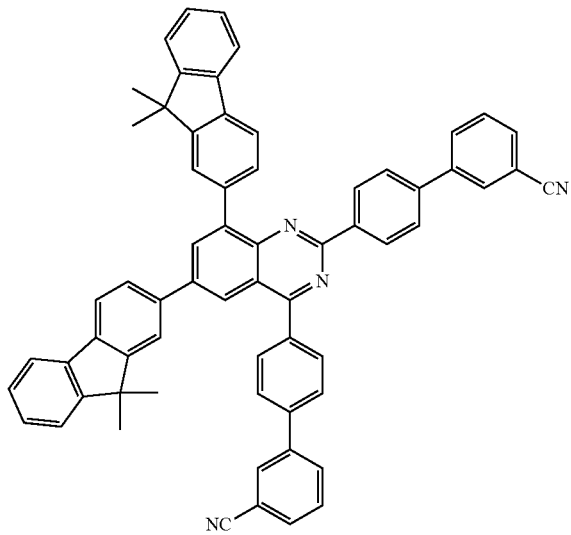
[Chemical Formula A-217]
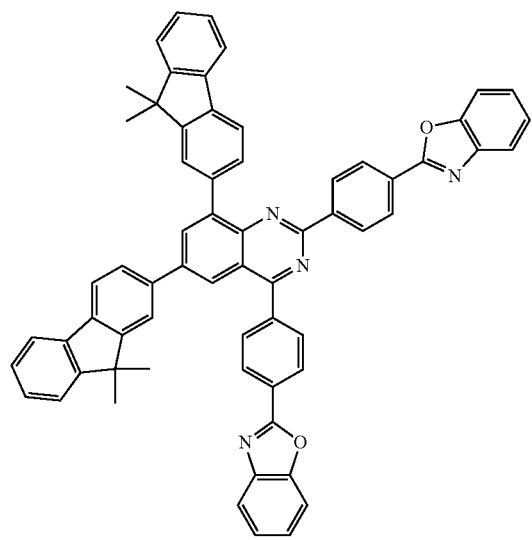
[Chemical Formula A-218]
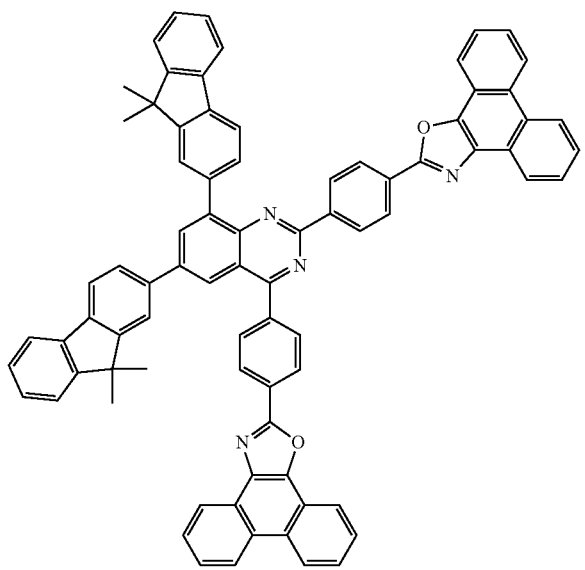

-continued
[Chemical Formula A-219]
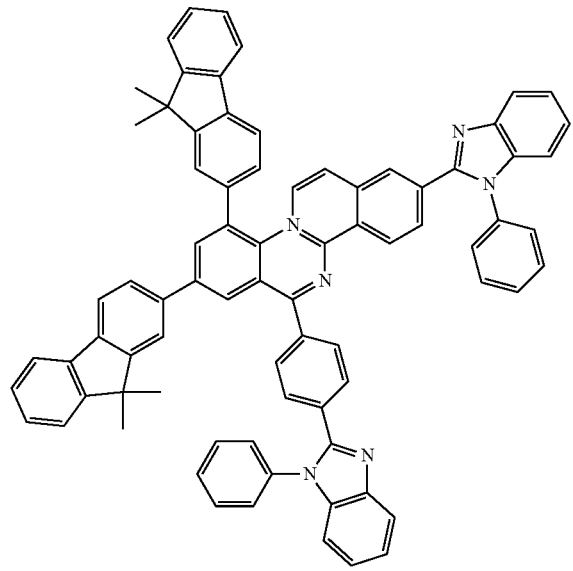
[Chemical Formula A-220]
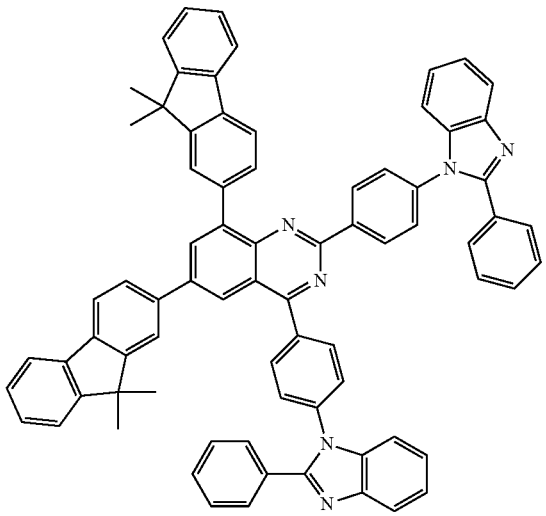
[Chemical Formula A-221]
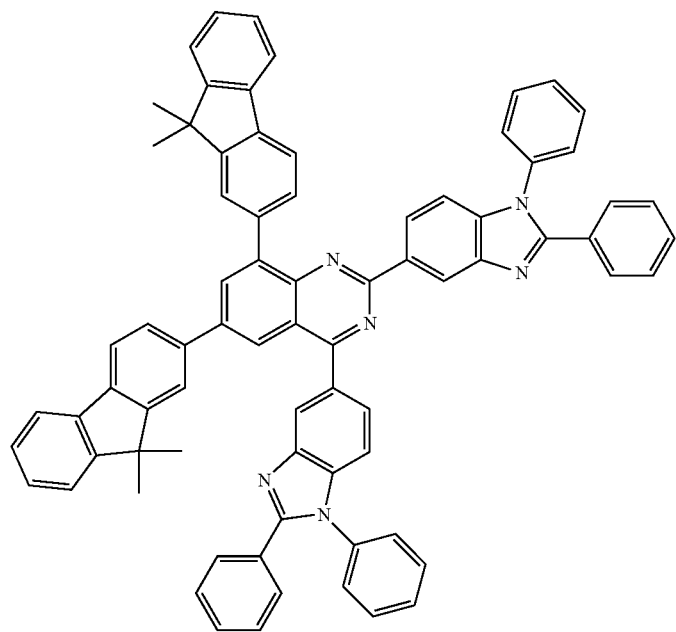

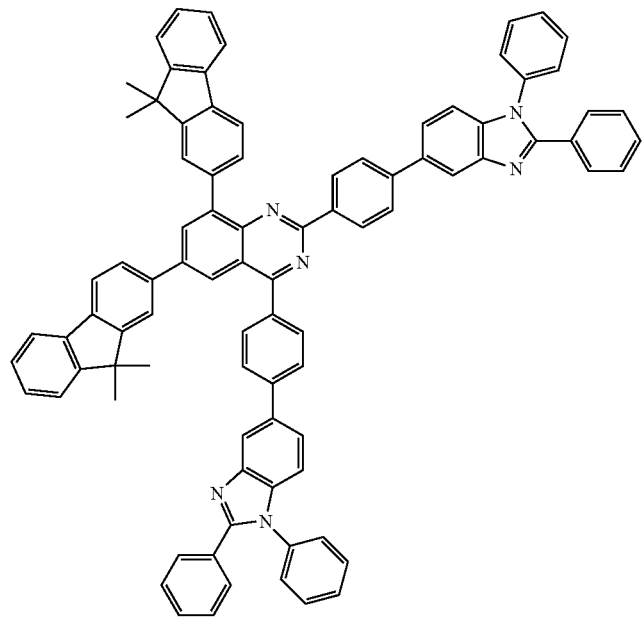
[Chemical Formula A-222]
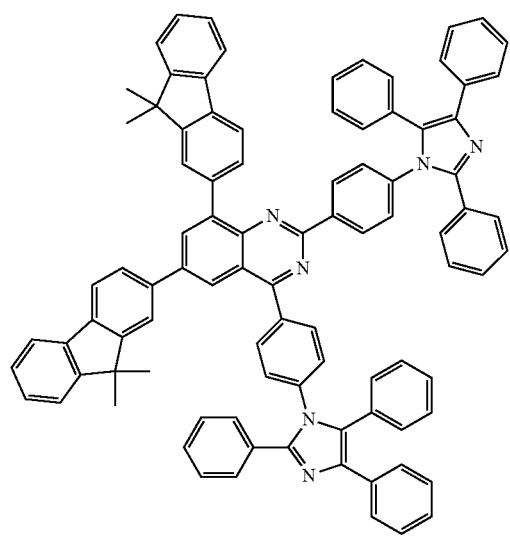
[Chemical Formula A-223]
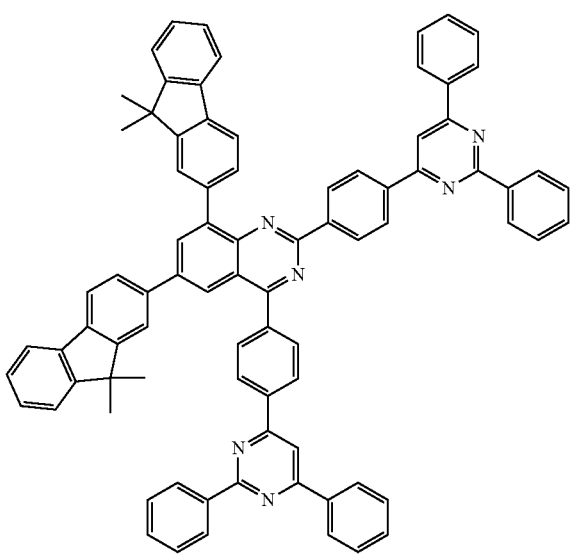
[Chemical Formula A-224]

-continued
[Chemical Formula A-225]
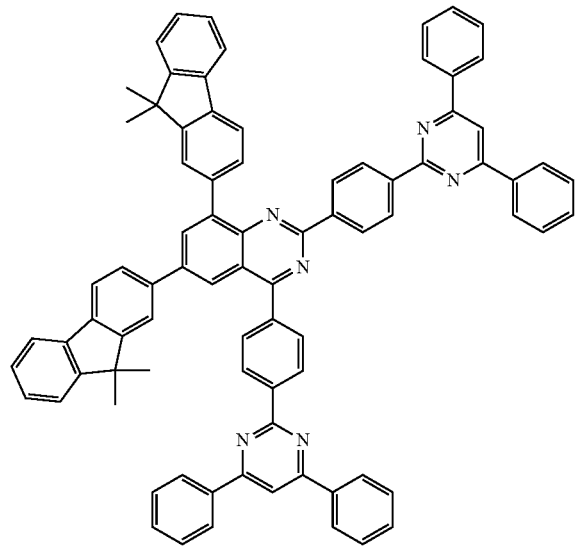
[Chemical Formula A-226]
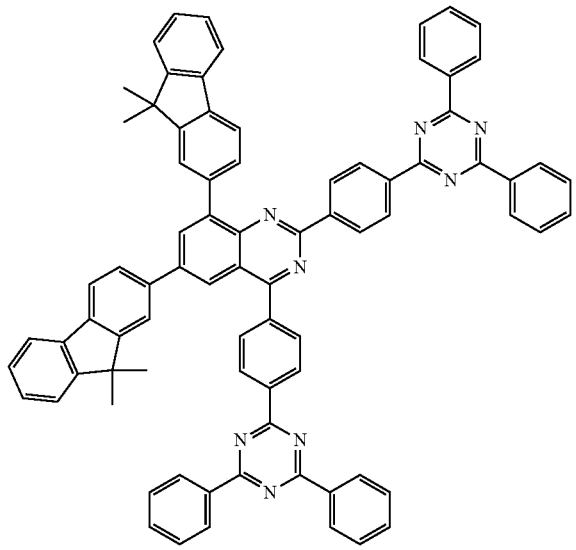
[Chemical Formula A-227]
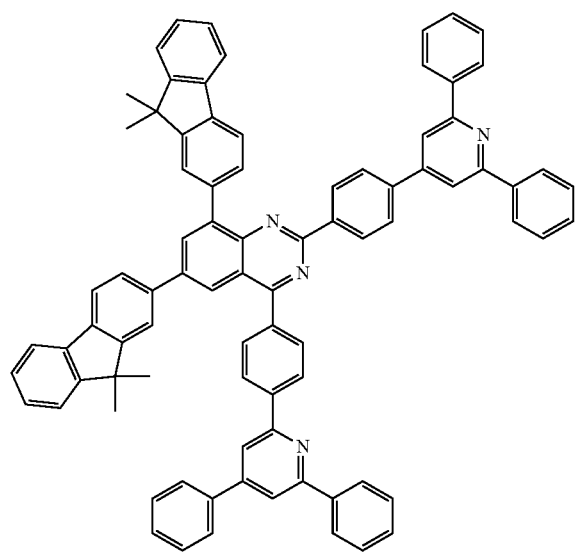
[Chemical Formula A-228]
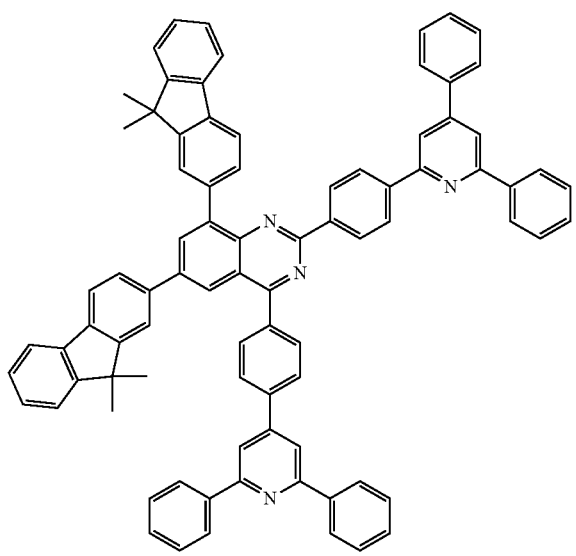

[Chemical Formula A-229]
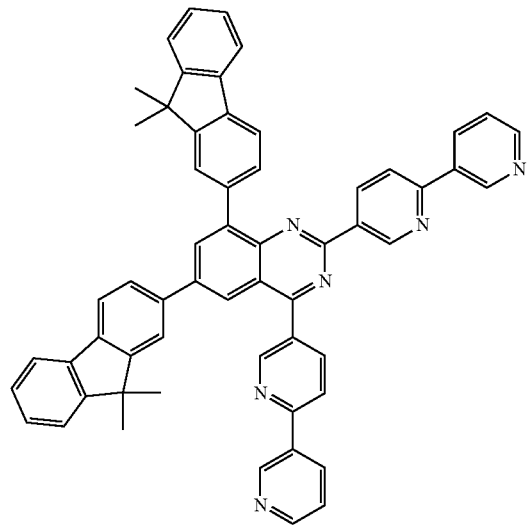
[Chemical Formula A-230]
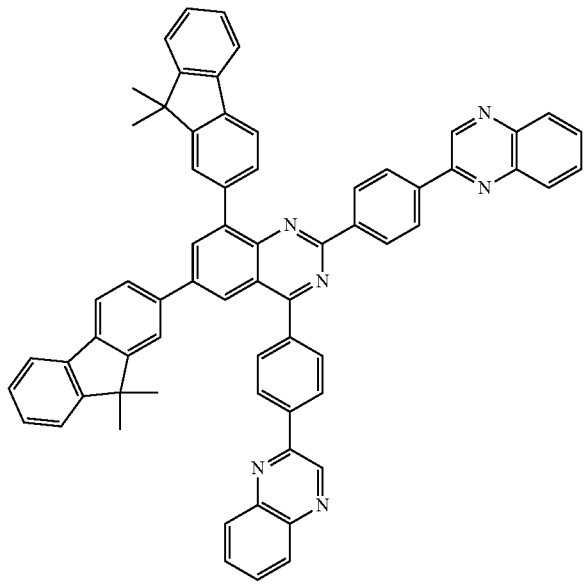
[Chemical Formula A-231]
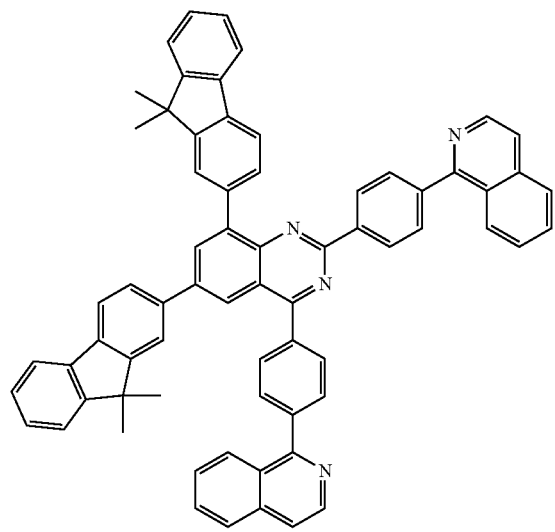
[Chemical Formula A-232]
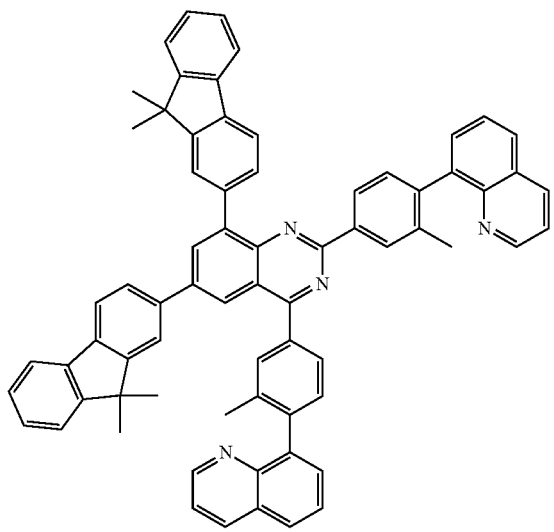

[Chemical Formula A-233]
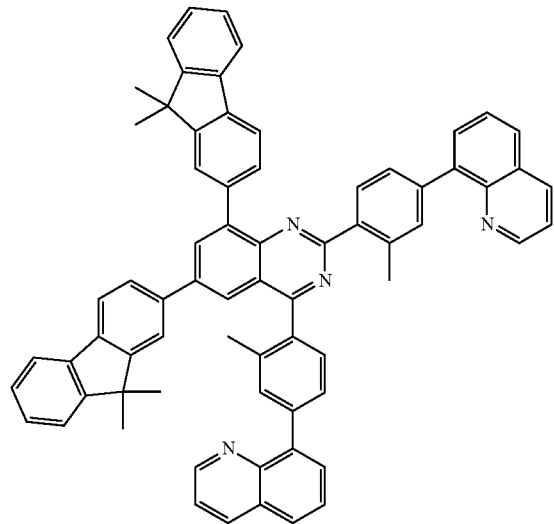
[Chemical Formula A-234]
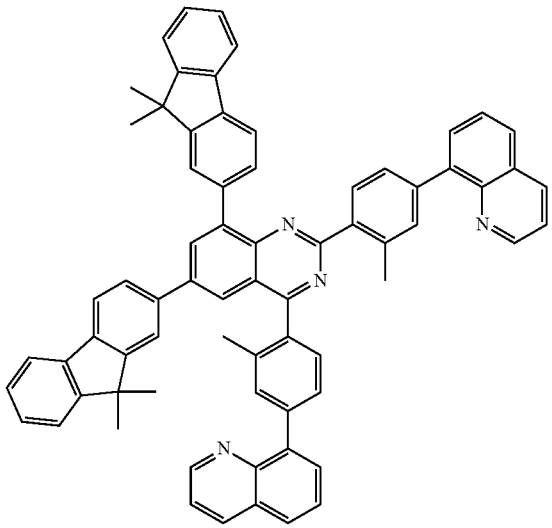
[Chemical Formula A-235]
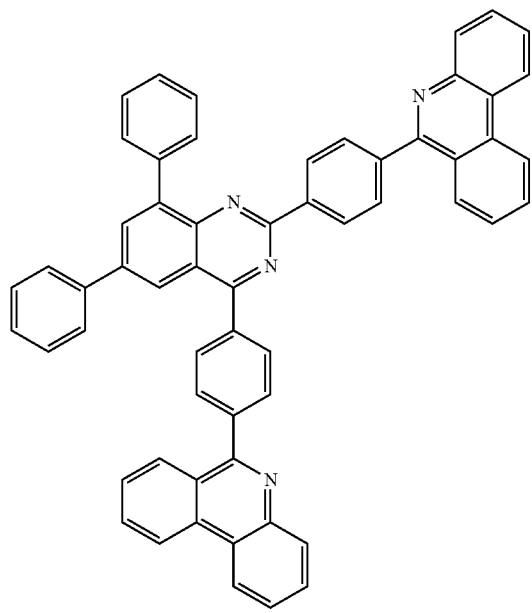
[Chemical Formula A-236]
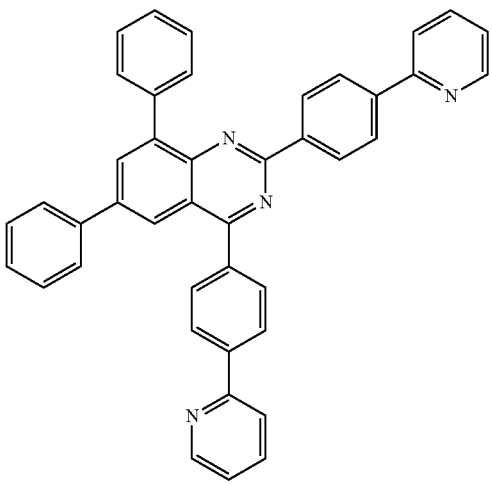

-continued
[Chemical Formula A-237]
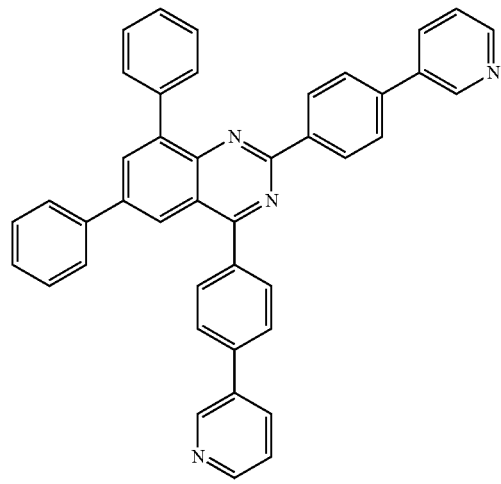
[Chemical Formula A-238]
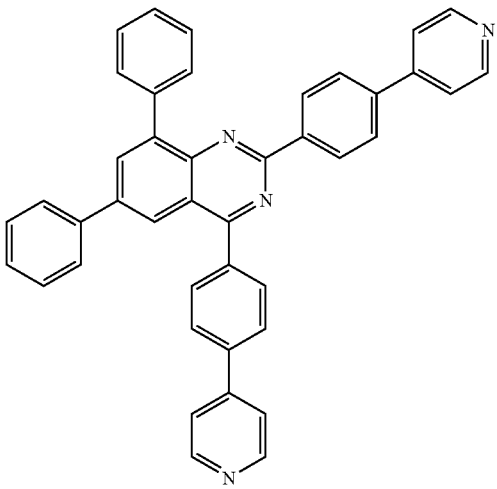
[Chemical Formula A-239]
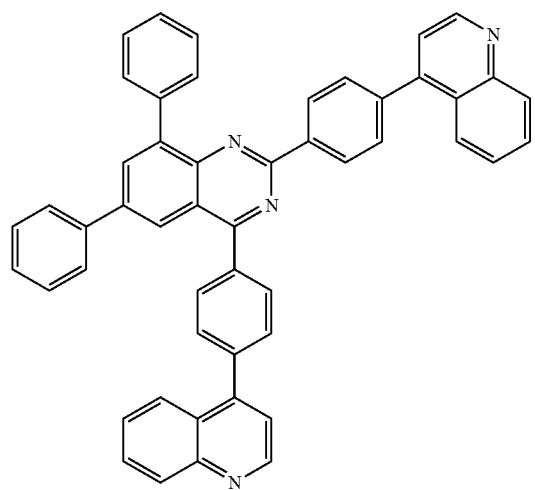
[Chemical Formula A-240]
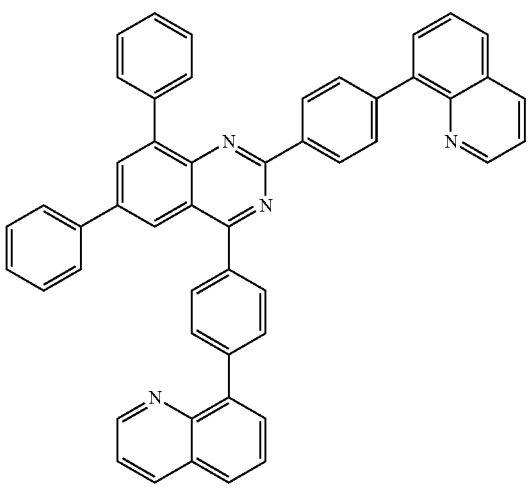

[Chemical Formula A-241]
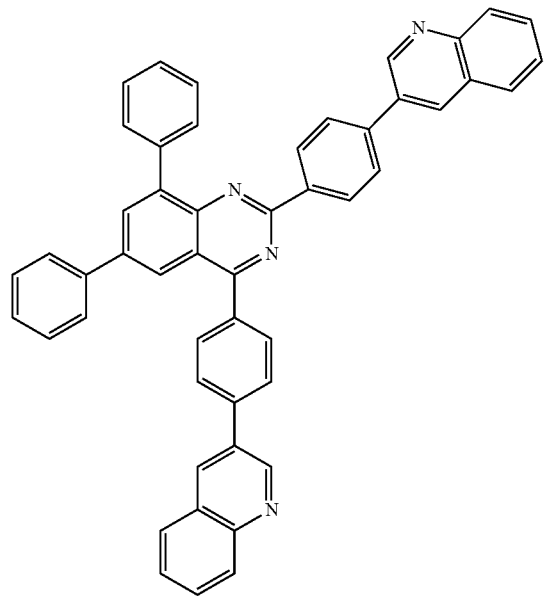
[Chemical Formula A-242]
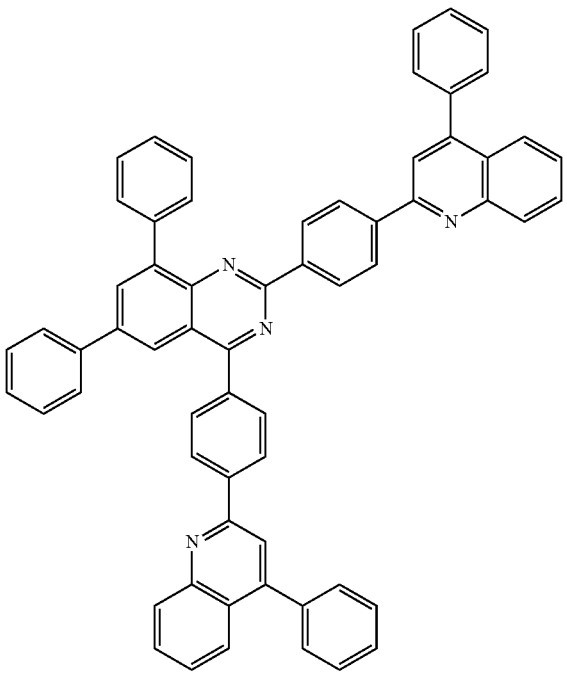
[Chemical Formula A-243]
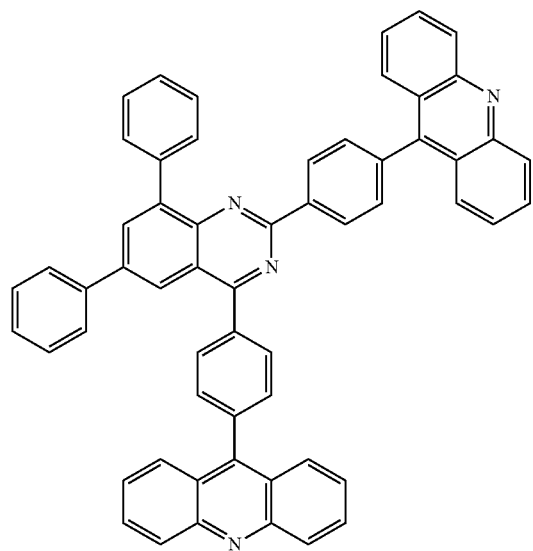
[Chemical Formula A-244]
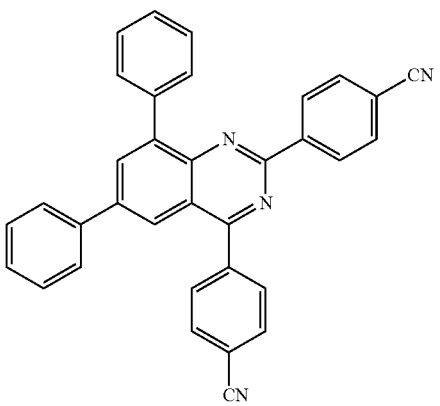

-continued
[Chemical Formula A-245]
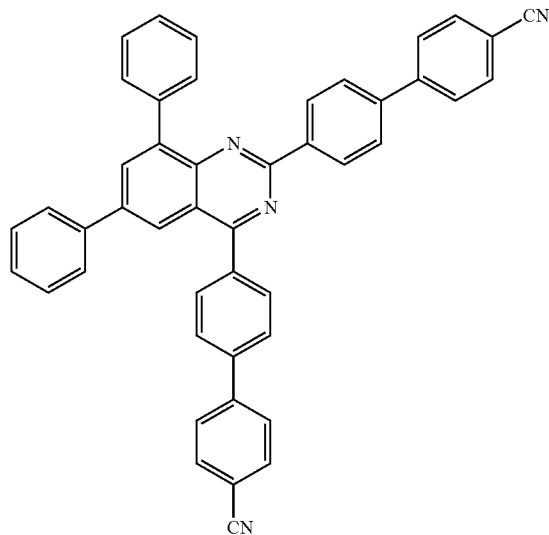
[Chemical Formula A-246]
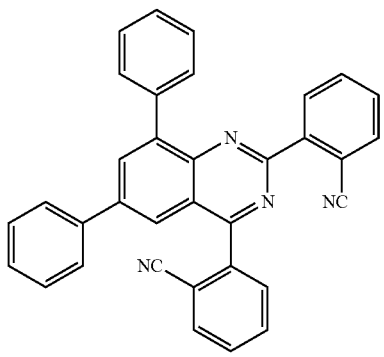
[Chemical Formula A-247]
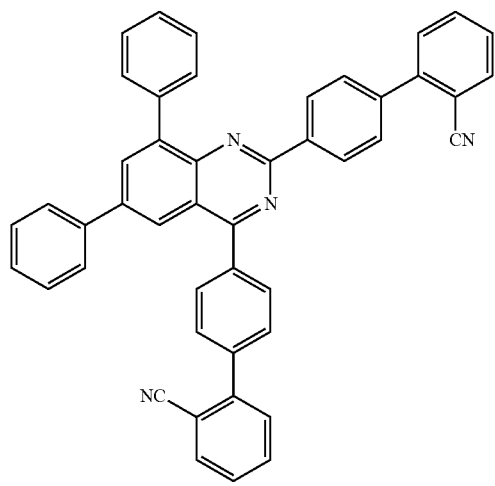
[Chemical Formula A-248]
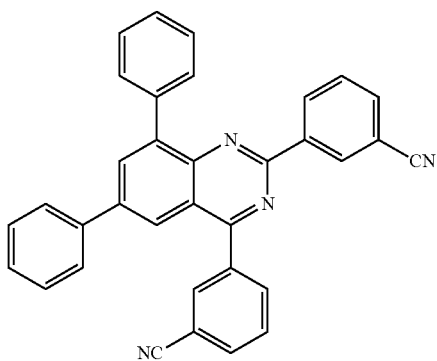
[Chemical Formula A-249]
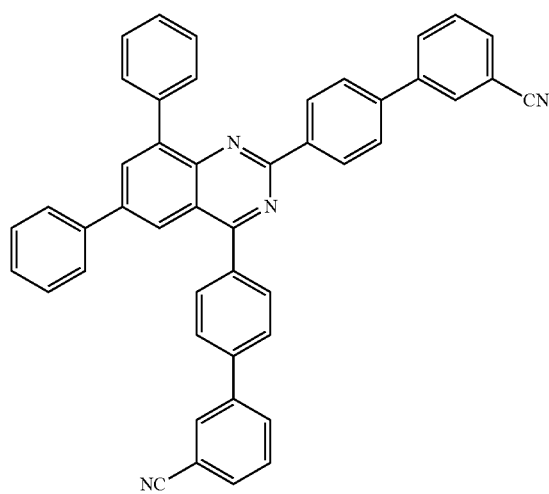
[Chemical Formula A-250]
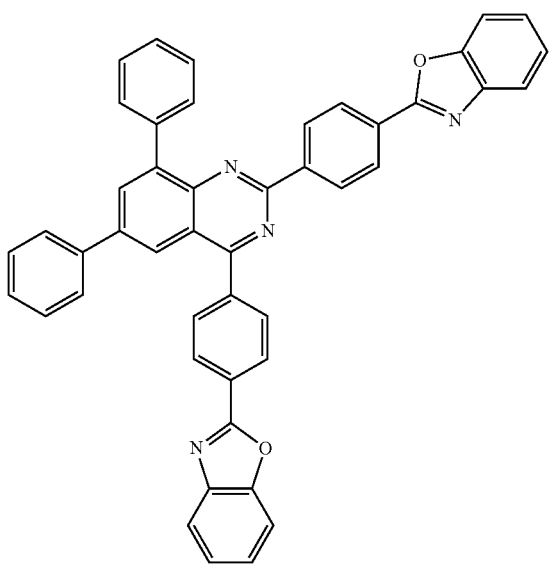

-continued
[Chemical Formula A-251]
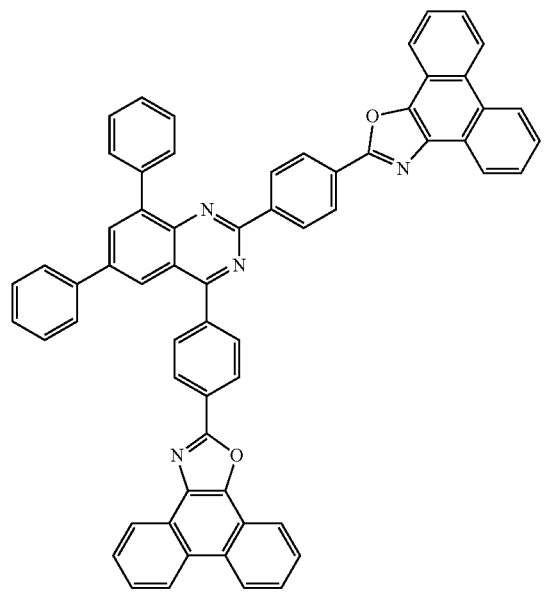
[Chemical Formula A-252]
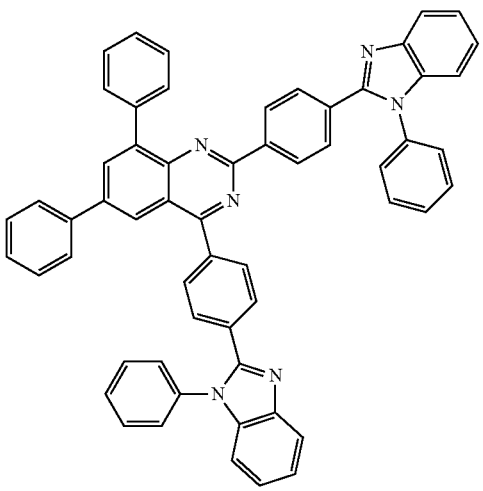
[Chemical Formula A-253]
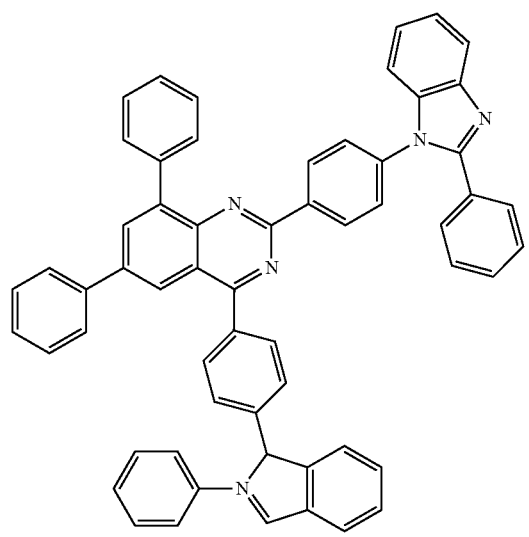
[Chemical Formula A-254]
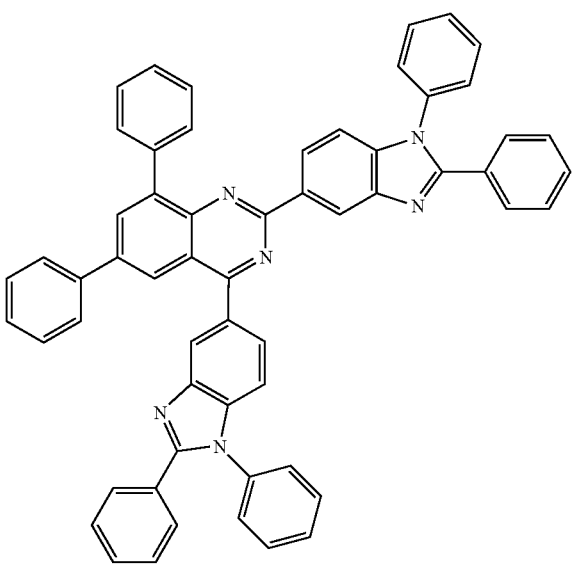

[Chemical Formula A-255]
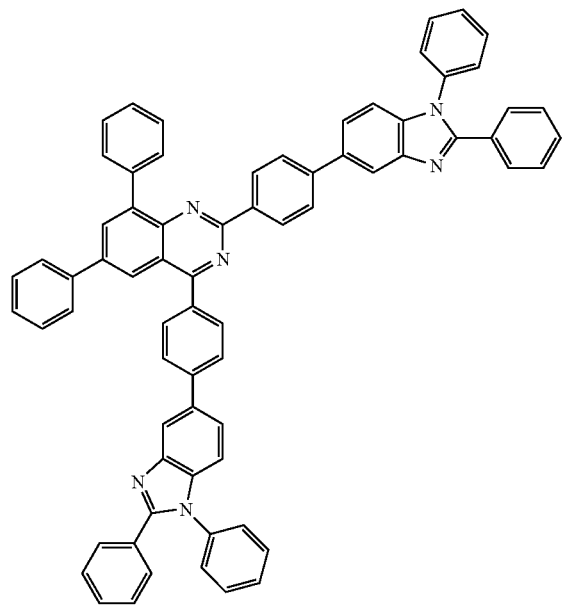
[Chemical Formula A-256]
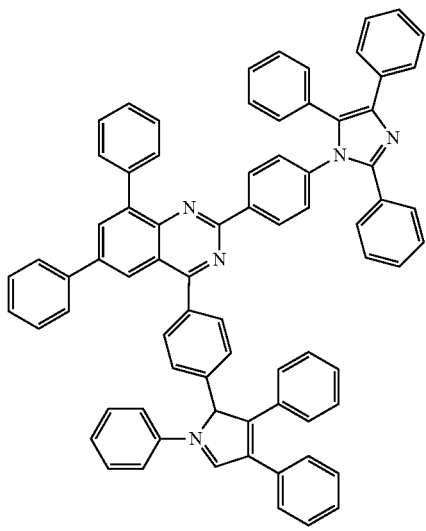
[Chemical Formula A-257]
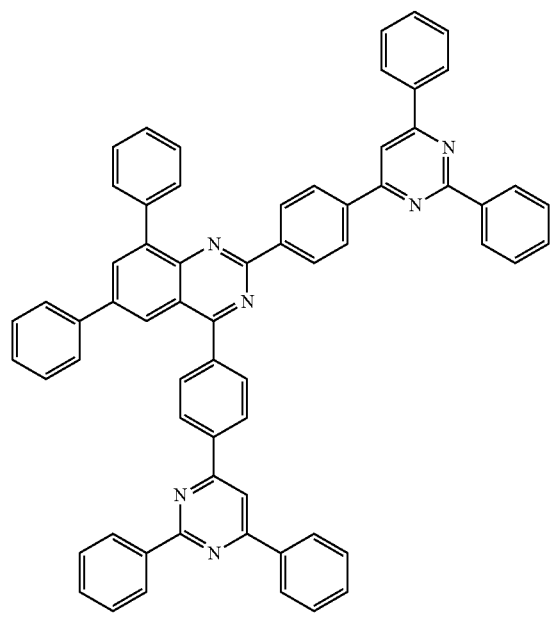
[Chemical Formula A-258]
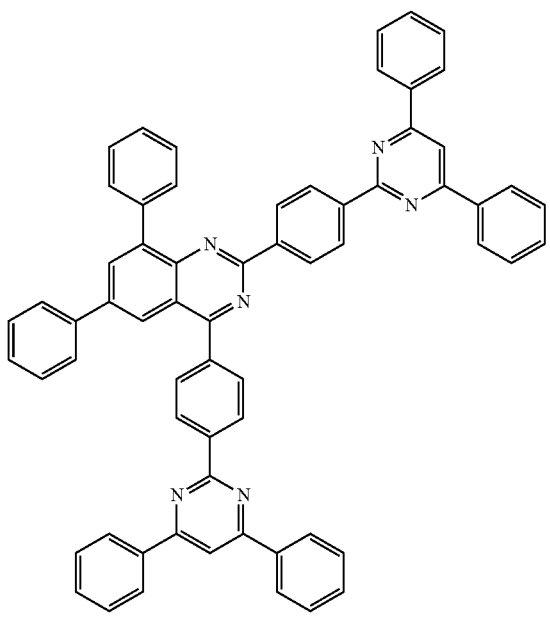

[Chemical Formula A-259]
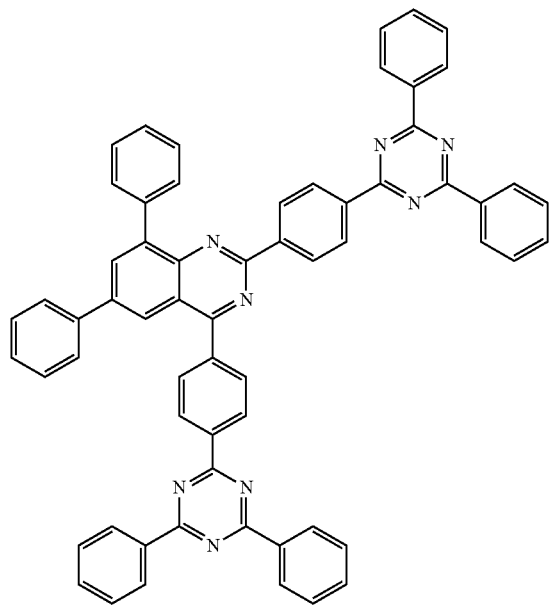
[Chemical Formula A-260]
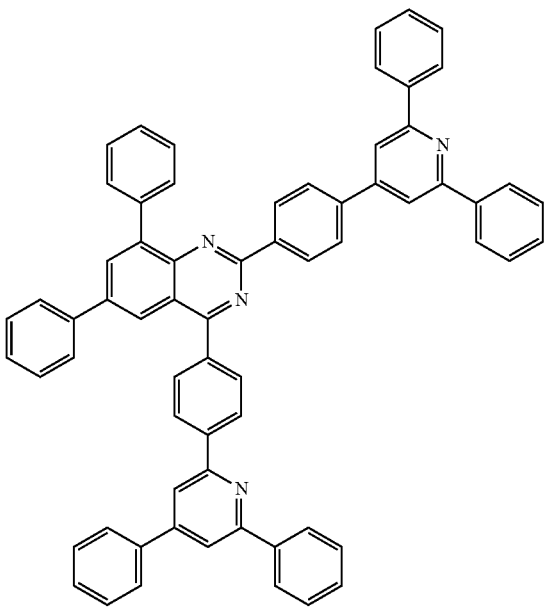
[Chemical Formula A-261]
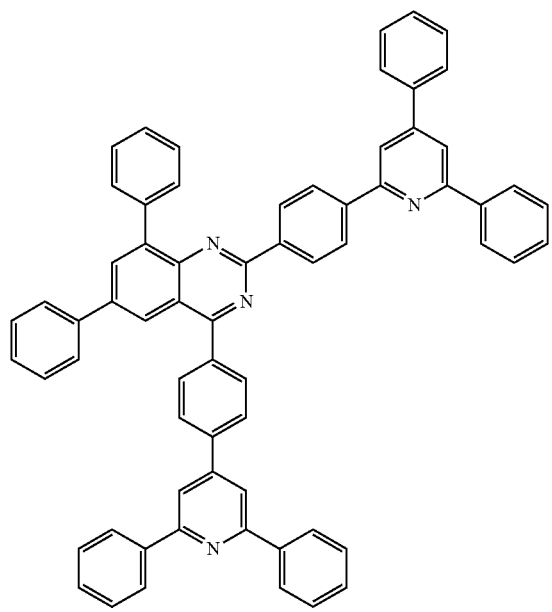
[Chemical Formula A-262]
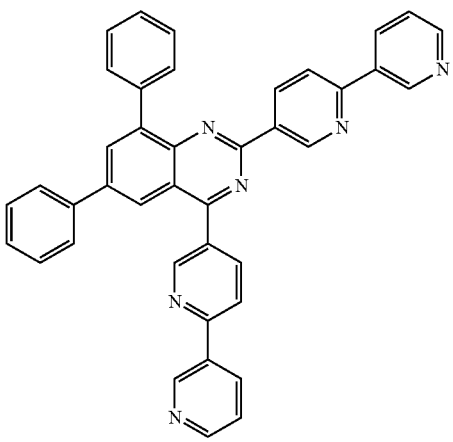

[Chemical Formula A-263]
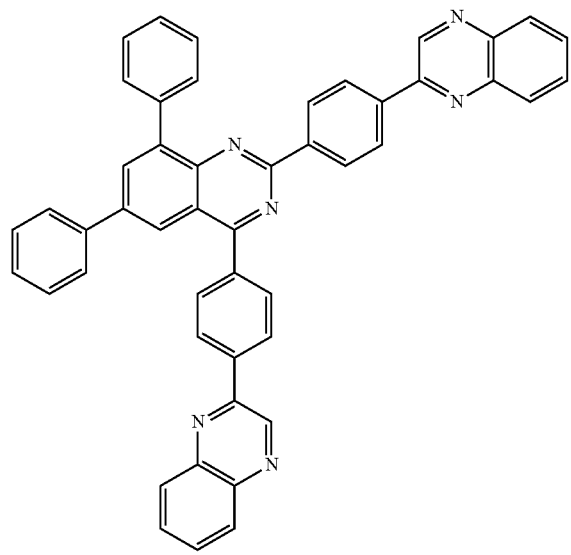
[Chemical Formula A-264]
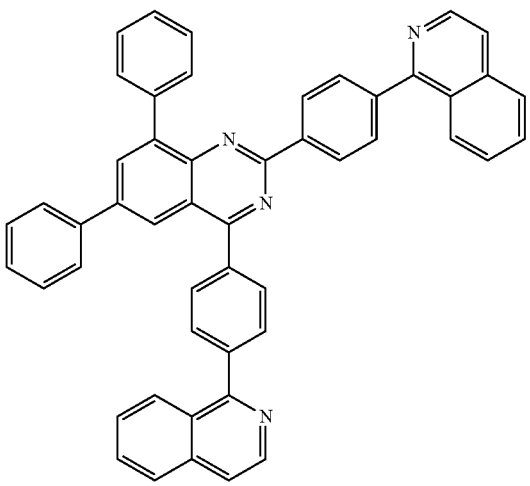
[Chemical Formula A-265]
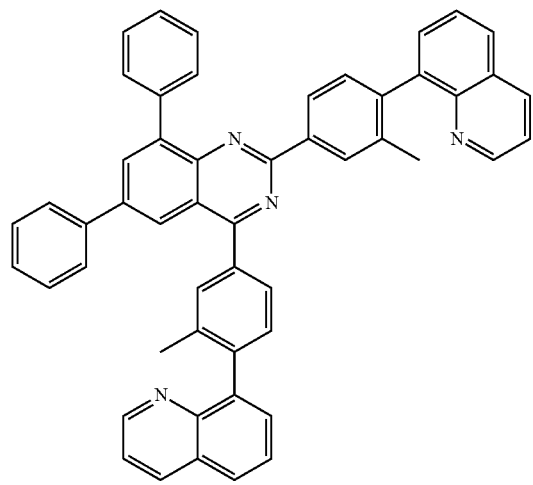
[Chemical Formula A-266]
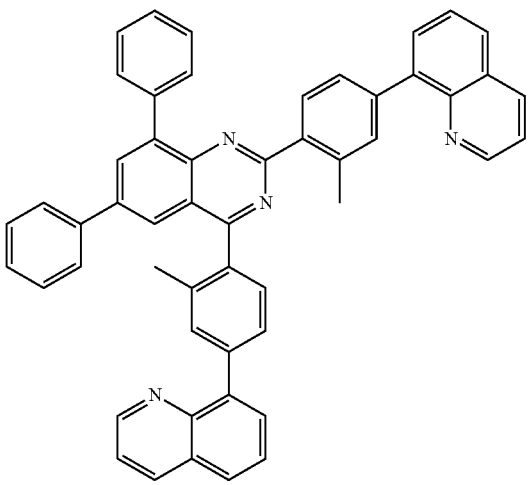
[Chemical Formula A-267]
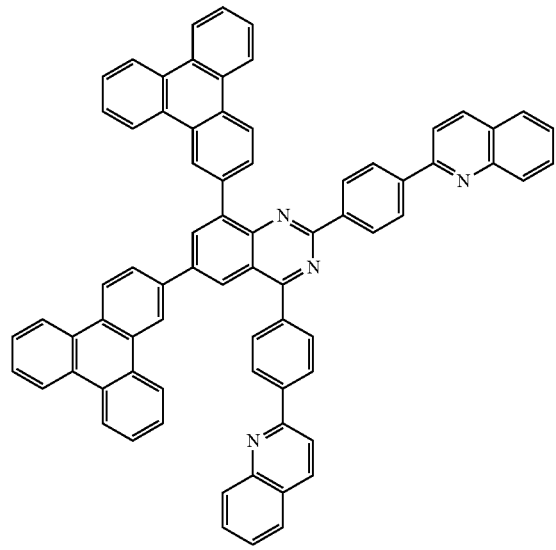
[Chemical Formula A-268]
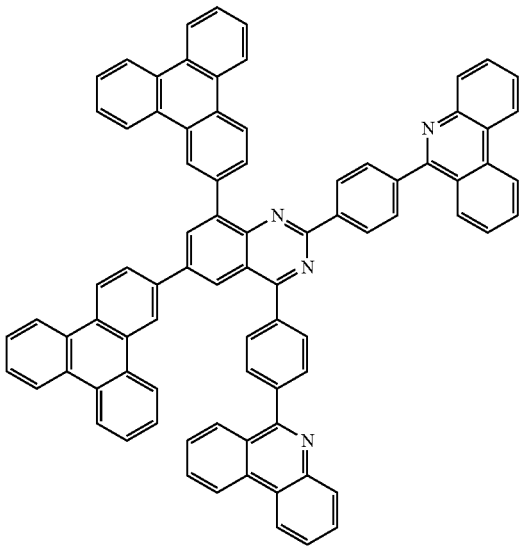

-continued
[Chemical Formula A-269]
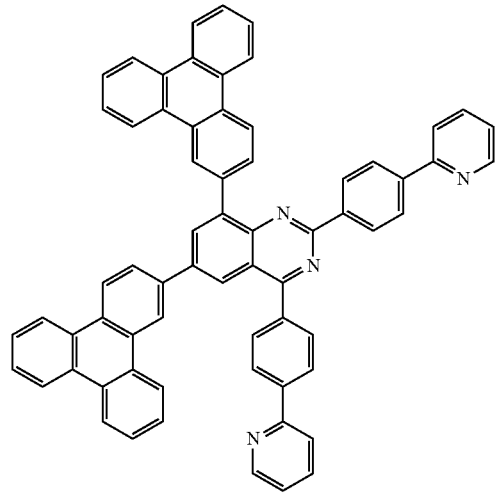
[Chemical Formula A-270]
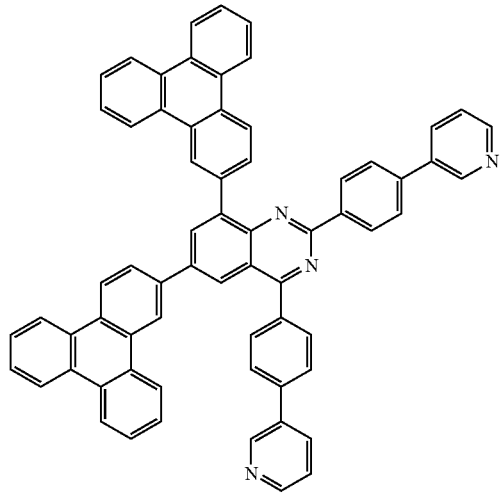
[Chemical Formula A-271]
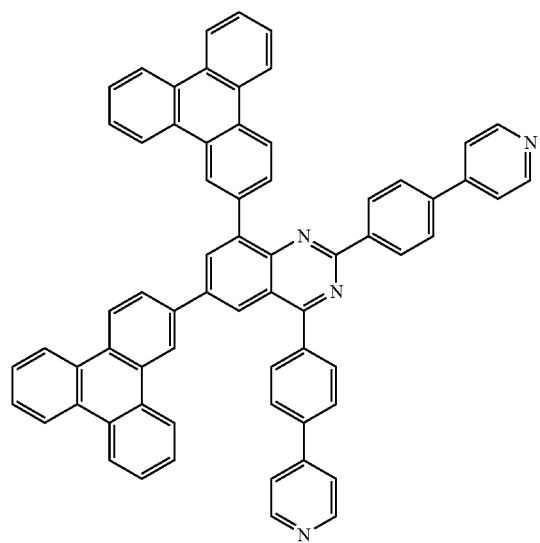
[Chemical Formula A-272]
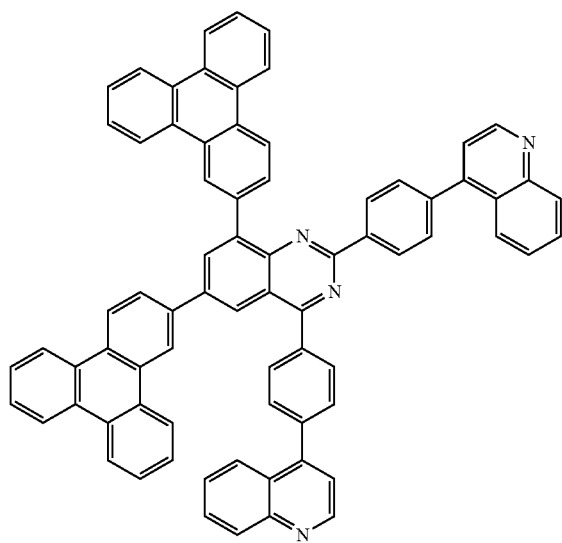

[Chemical Formula A-273]
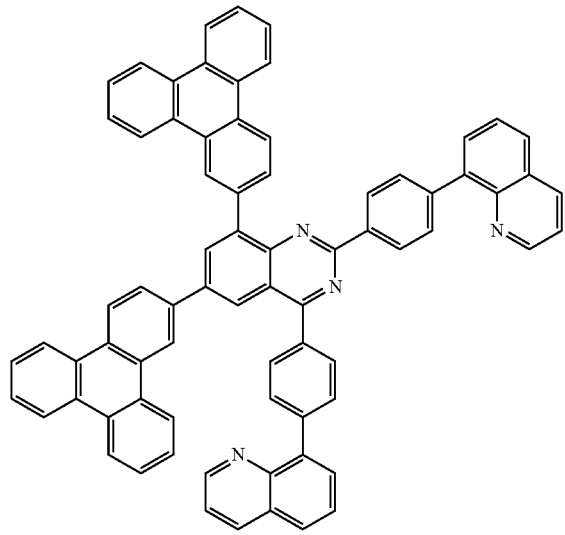
[Chemical Formula A-274]
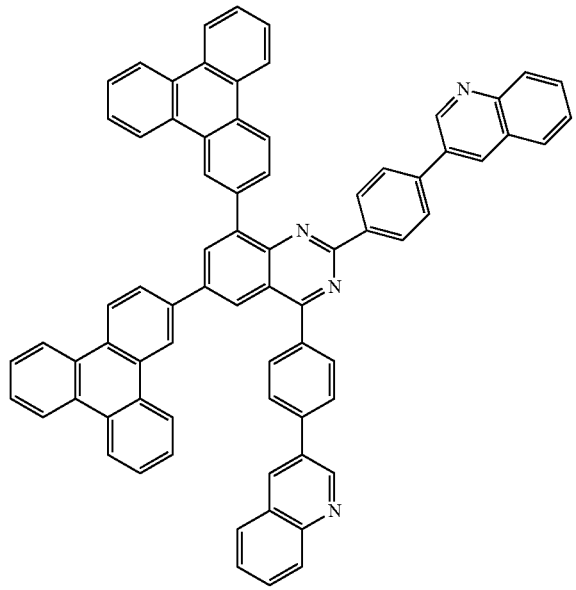
[Chemical Formula A-275]
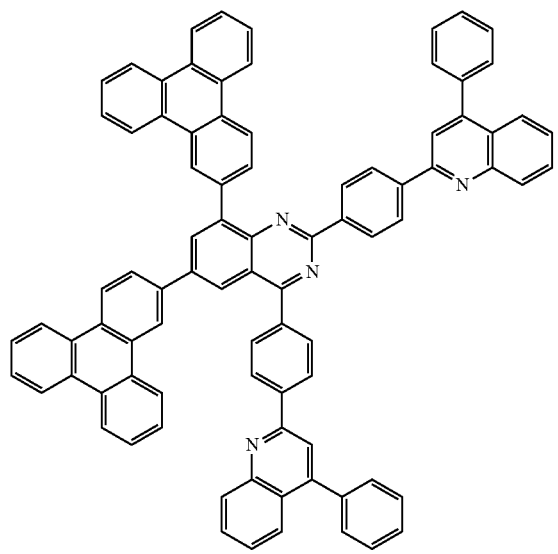
[Chemical Formula A-276]
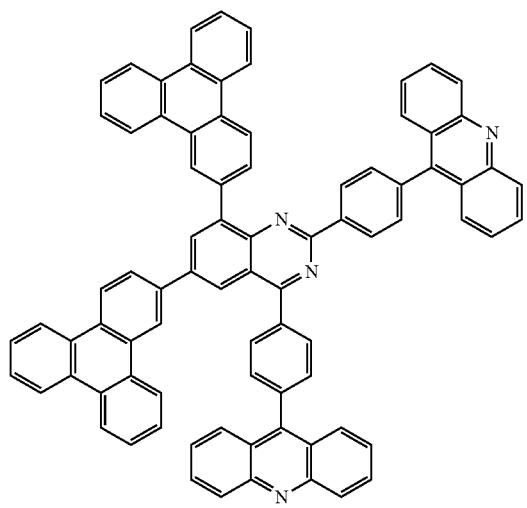

[Chemical Formula A-277]
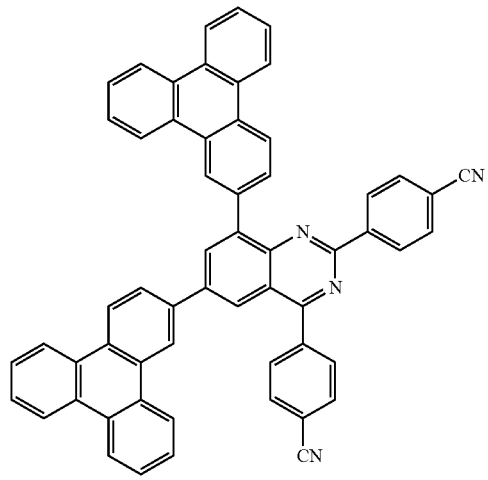
[Chemical Formula A-278]
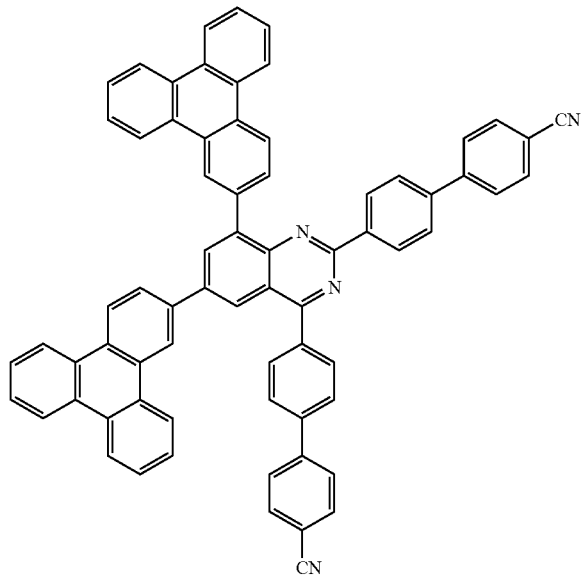
[Chemical Formula A-279]
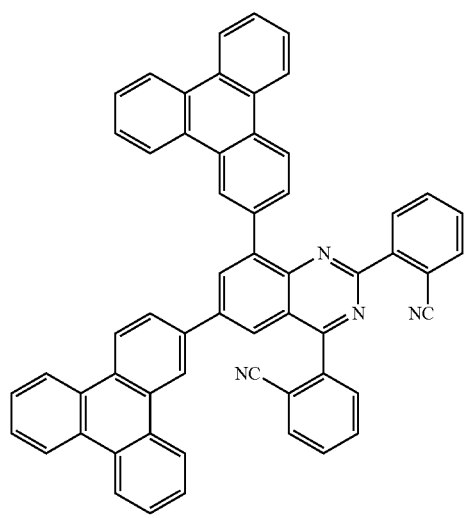
[Chemical Formula A-280]
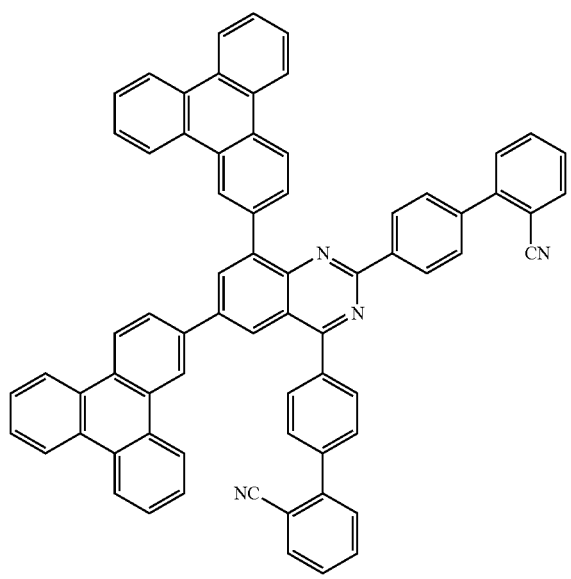

-continued
[Chemical Formula A-281]
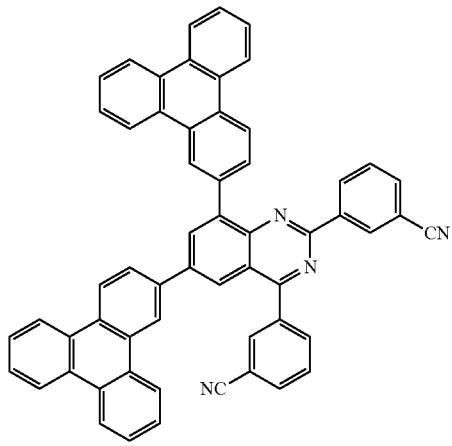
[Chemical Formula A-282]
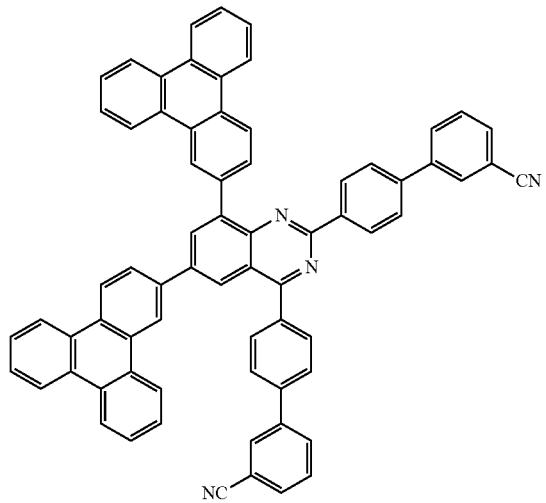
[Chemical Formula A-283]
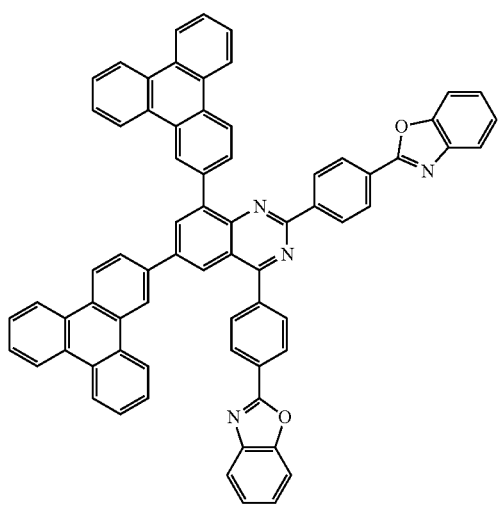
[Chemical Formula A-284]
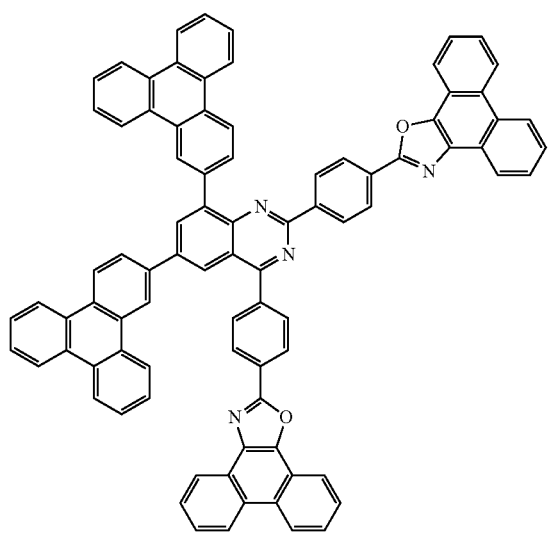
[Chemical Formula A-285]
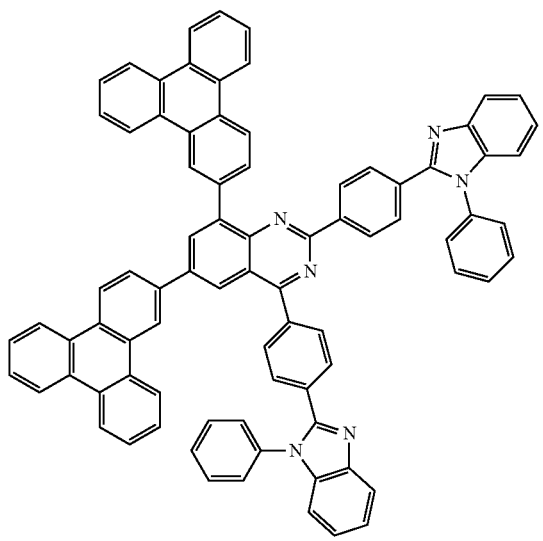
[Chemical Formula A-286]
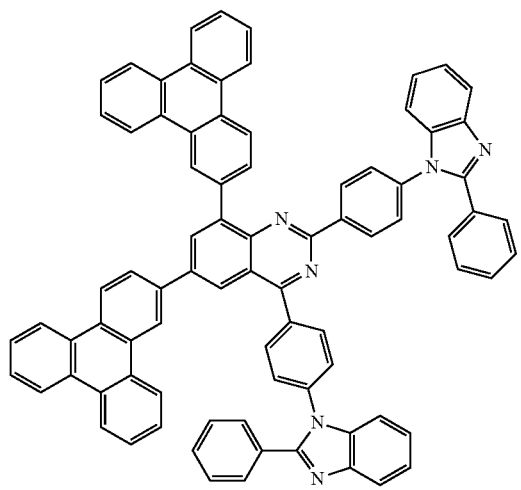

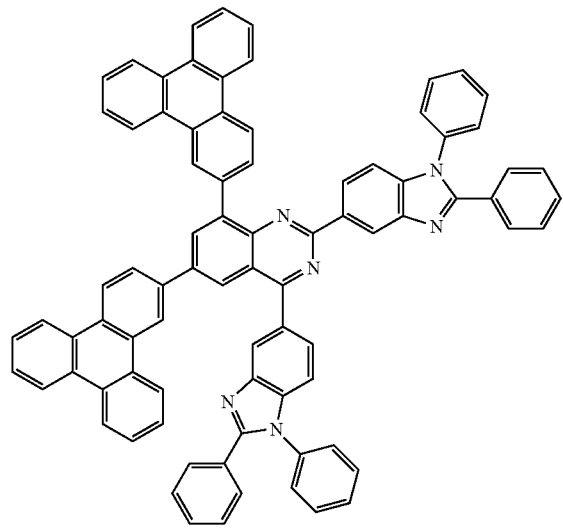
[Chemical Formula A-287]
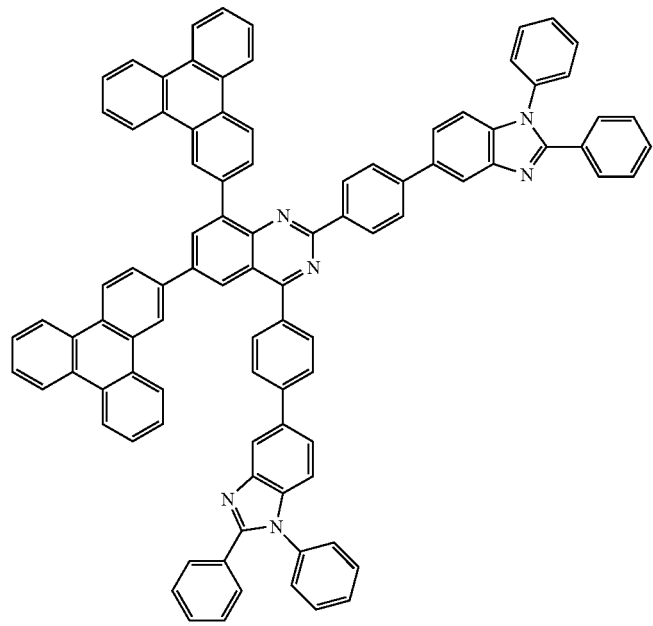
[Chemical Formula A-288]

[Chemical Formula A-289]
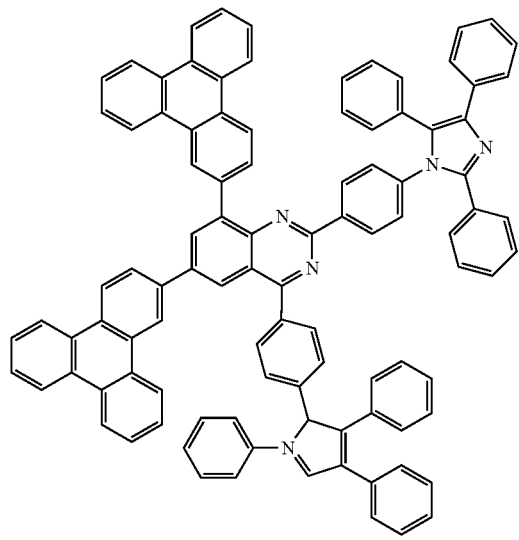
[Chemical Formula A-290]
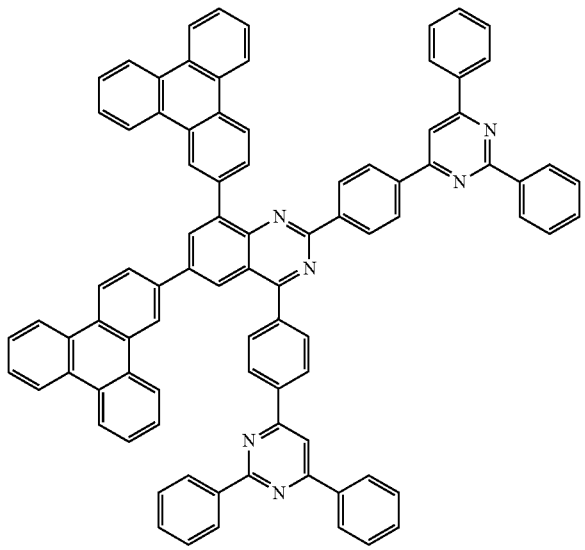
[Chemical Formula A-291]
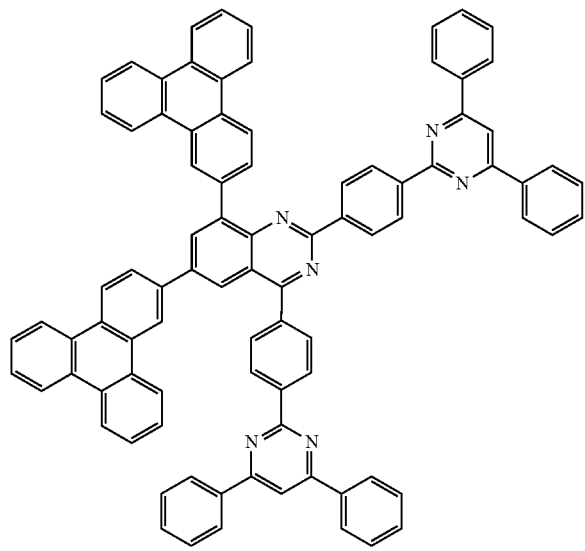
[Chemical Formula A-292]
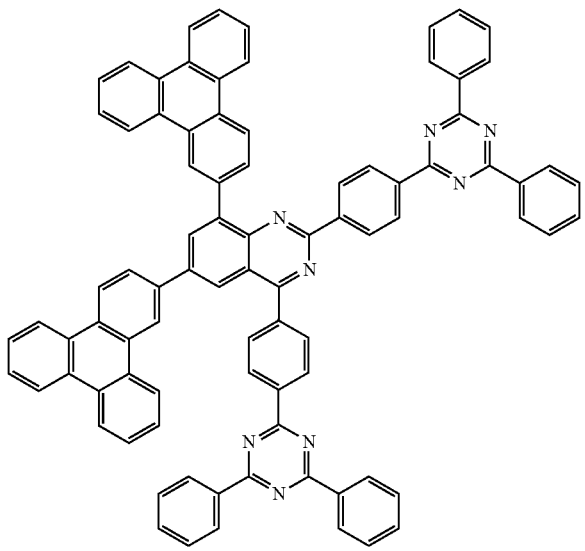

[Chemical Formula A-293]
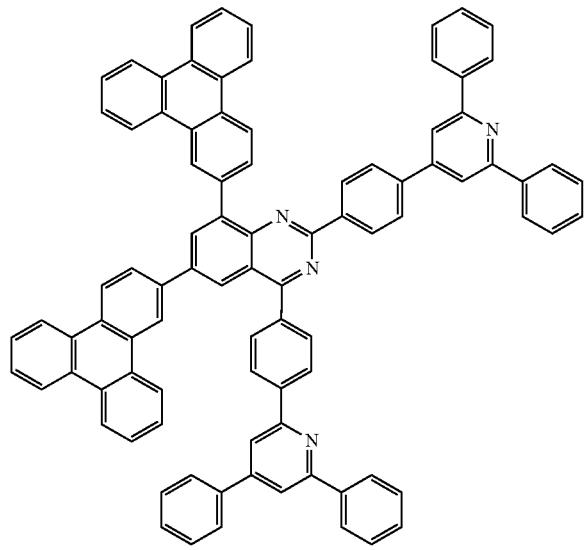
[Chemical Formula A-294]
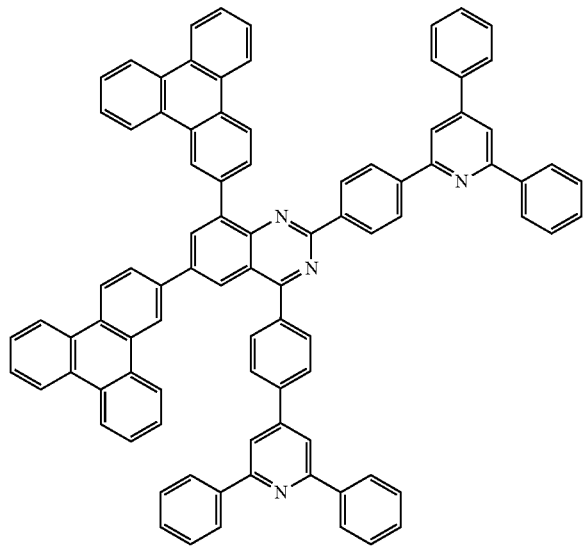
[Chemical Formula A-295]
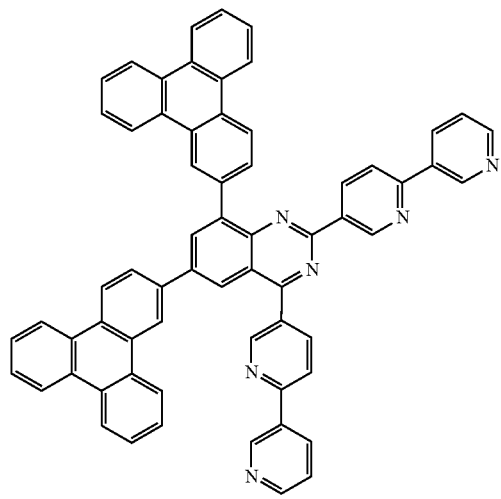
[Chemical Formula A-296]
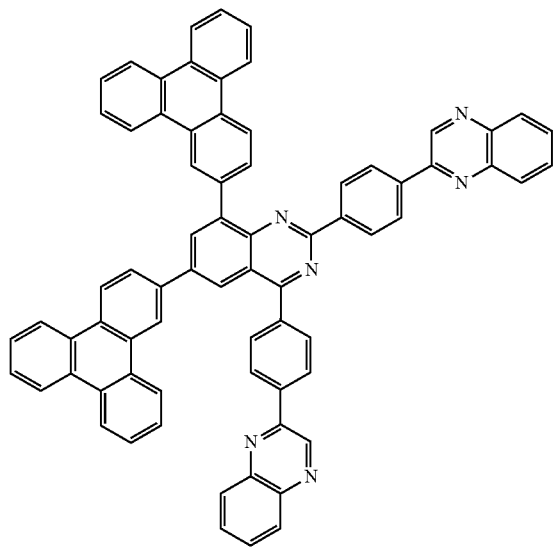

563
-continued
[Chemical Formula A-297]
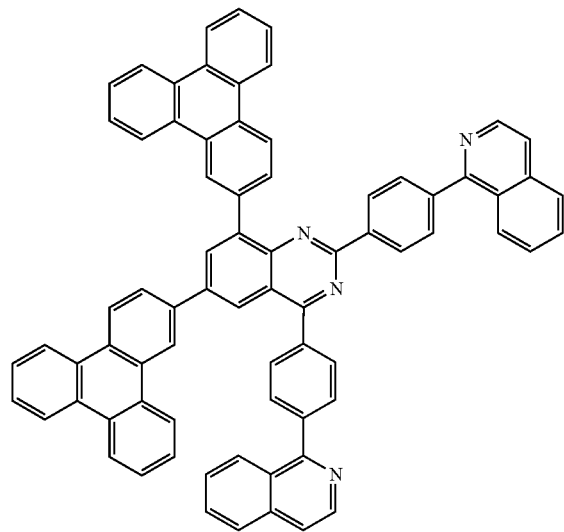
[Chemical Formula A-298]
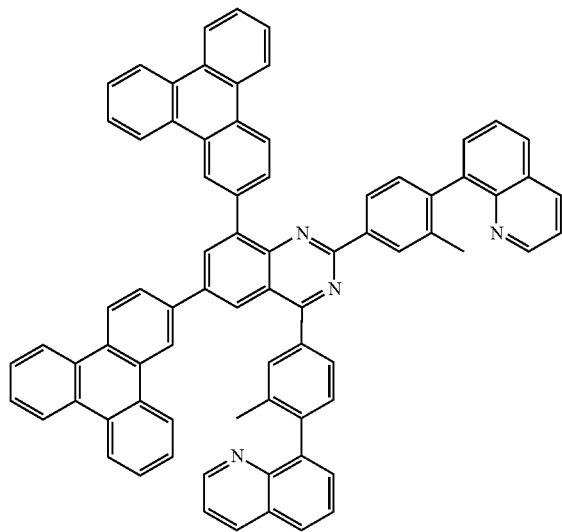
[Chemical Formula A-299]
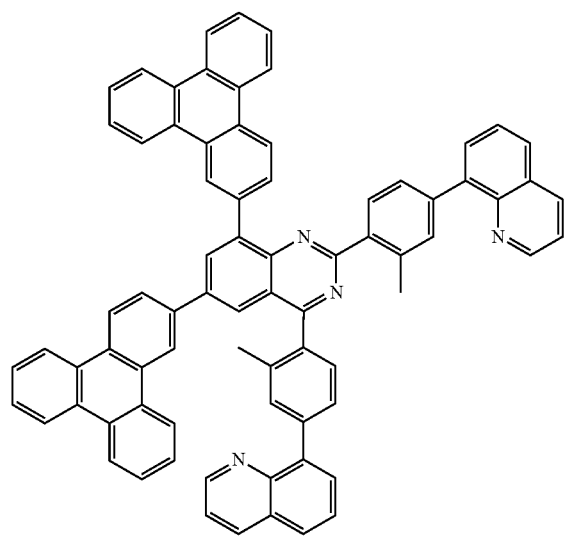
[Chemical Formula A-300]
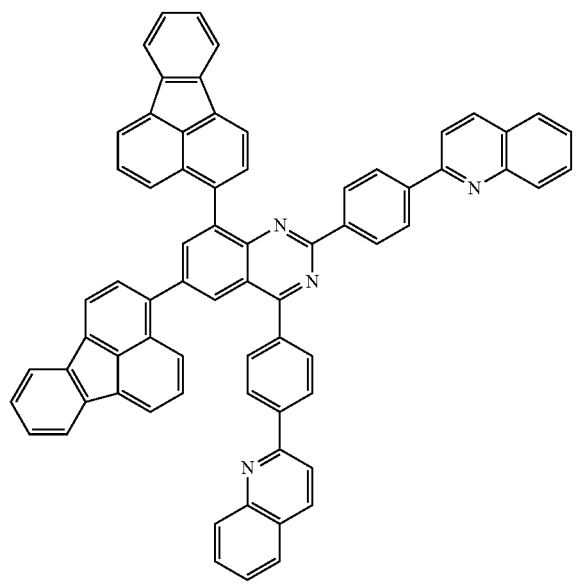

-continued
[Chemical Formula A-301]
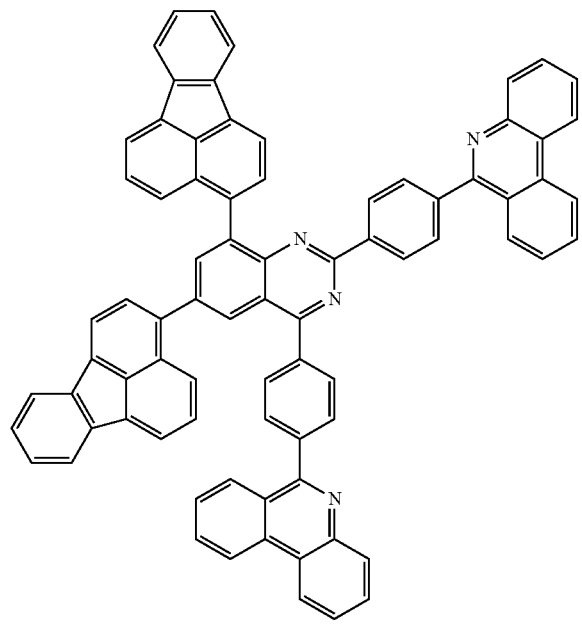
[Chemical Formula A-302]
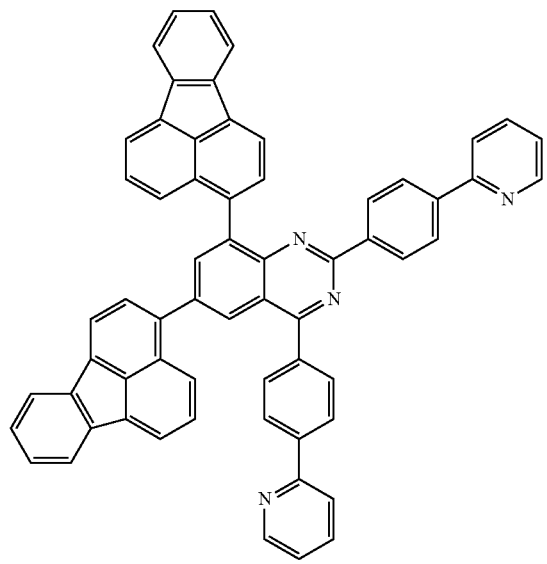
[Chemical Formula A-303]
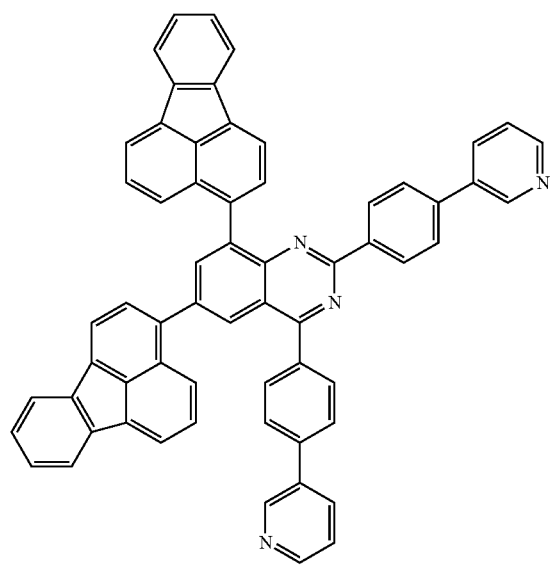
[Chemical Formula A-304]
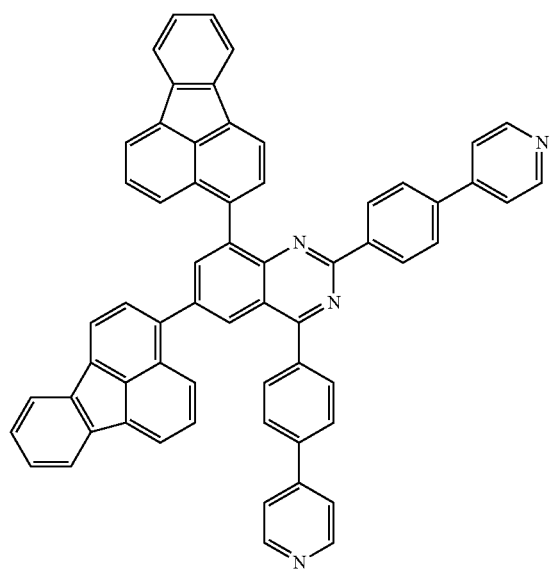

567 568
-continued
[Chemical Formula A-305]
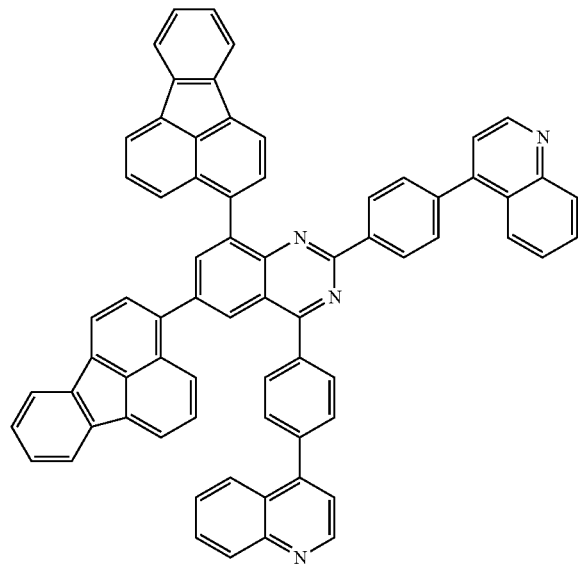
[Chemical Formula A-306]
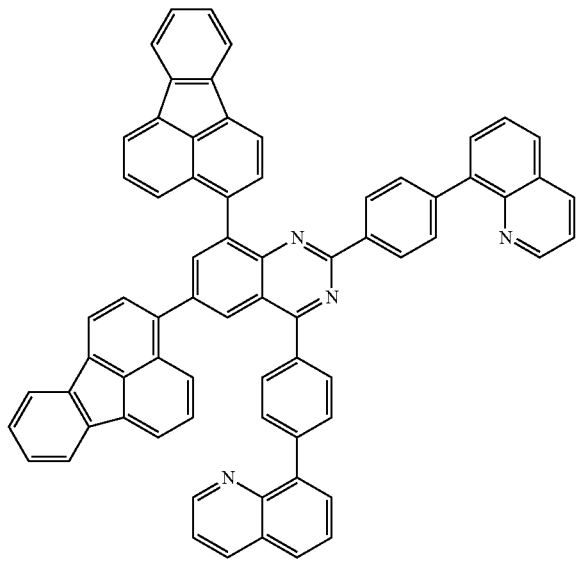
[Chemical Formula A-307]
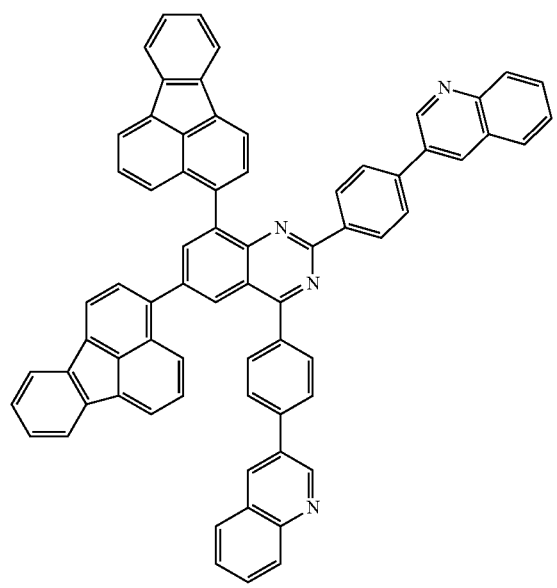
[Chemical Formula A-308]
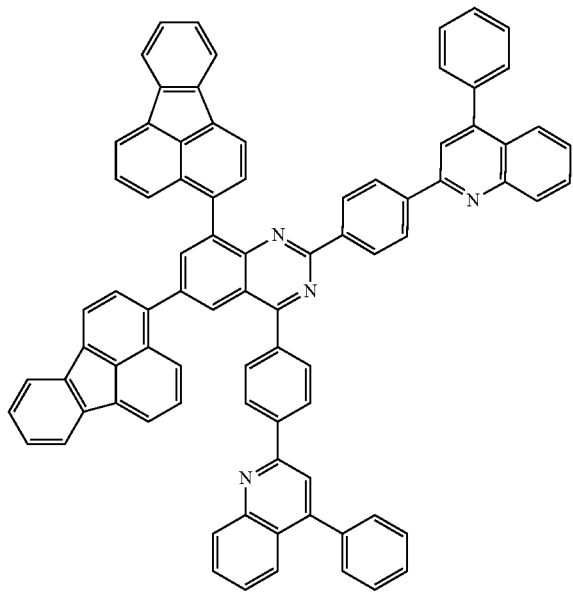

-continued
[Chemical Formula A-309]
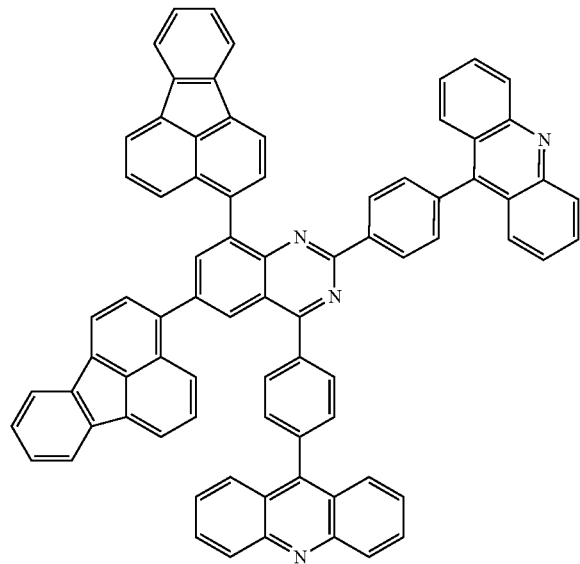
[Chemical Formula A-310]
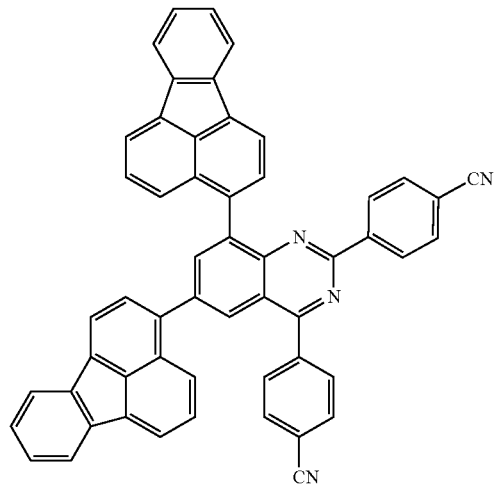
[Chemical Formula A-311]
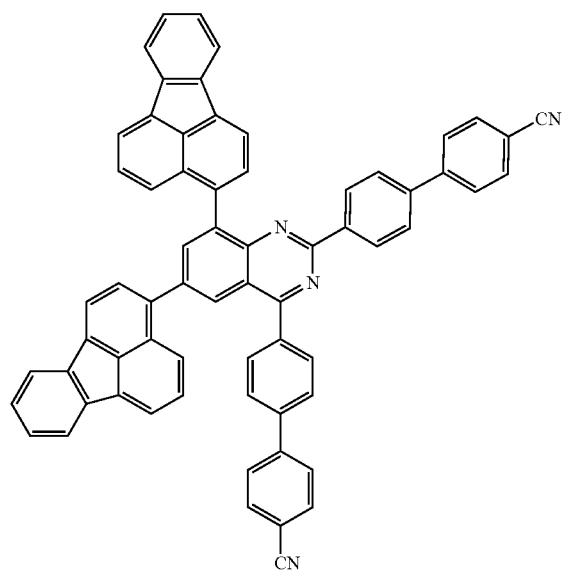
[Chemical Formula A-312]
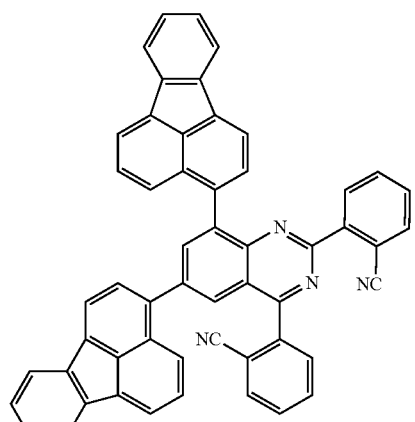

[Chemical Formula A-313]
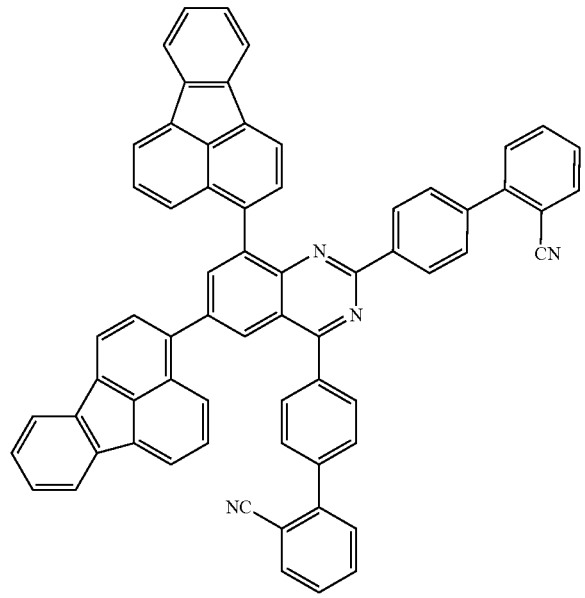
[Chemical Formula A-314]
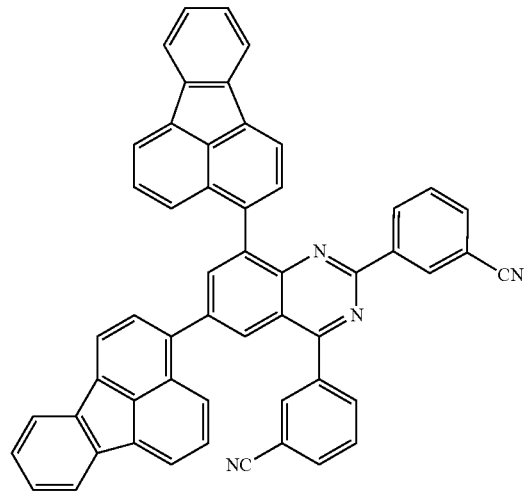
[Chemical Formula A-315]
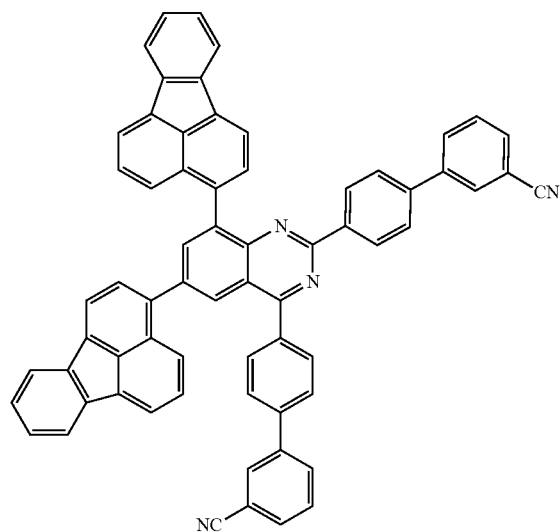
[Chemical Formula A-316]
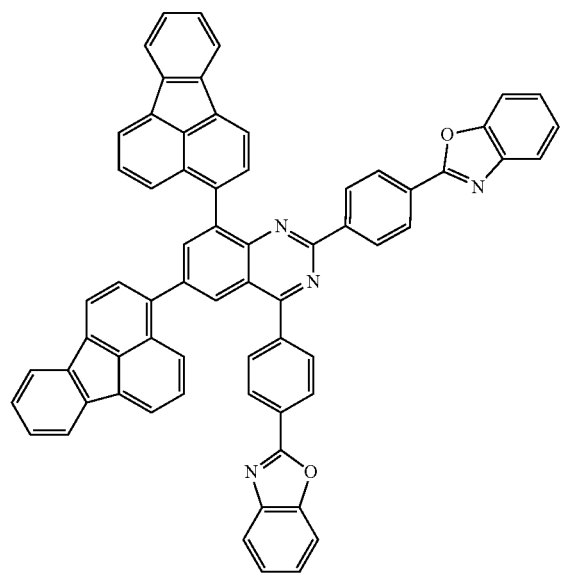

[Chemical Formula A-317]
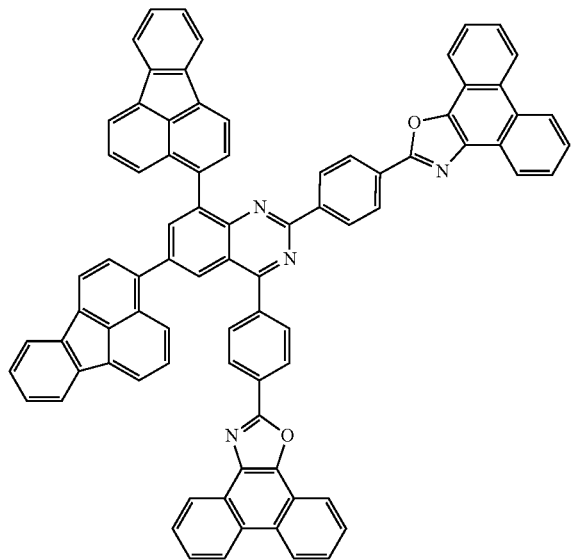
[Chemical Formula A-318]
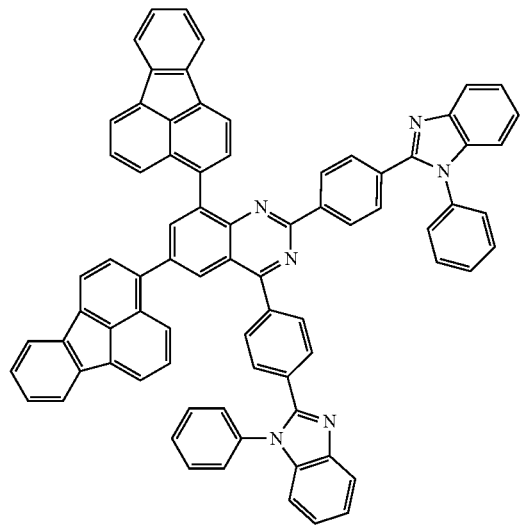
[Chemical Formula A-319]
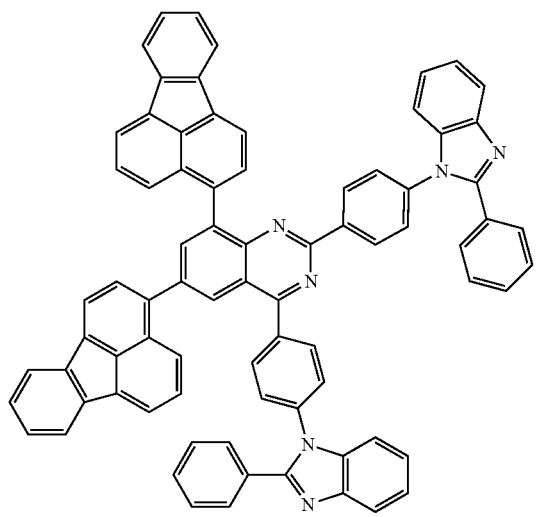
[Chemical Formula A-320]
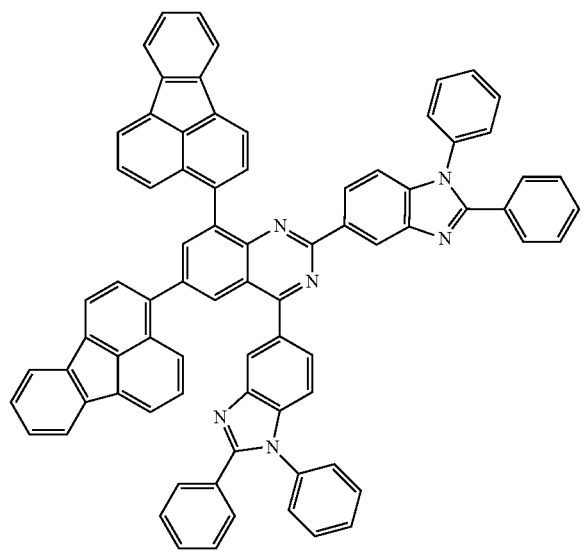

[Chemical Formula A-321]
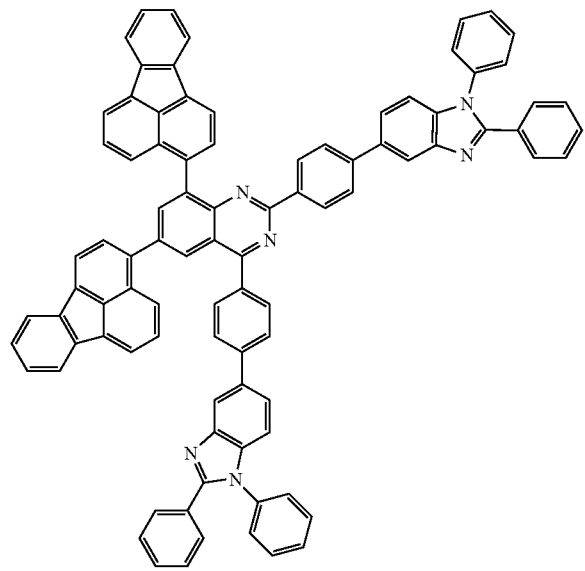
[Chemical Formula A-322]
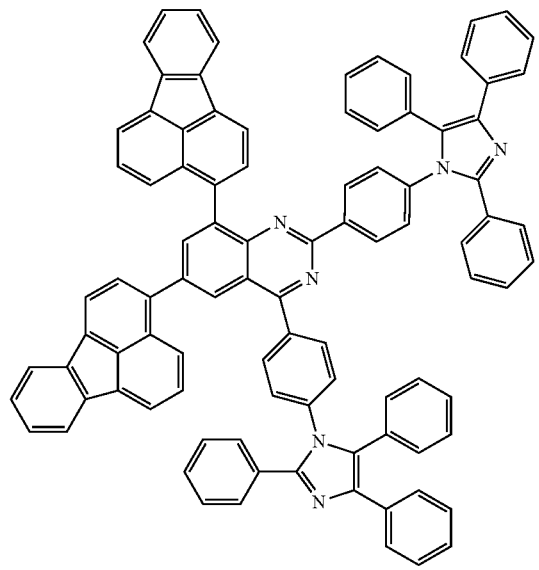
[Chemical Formula A-323]
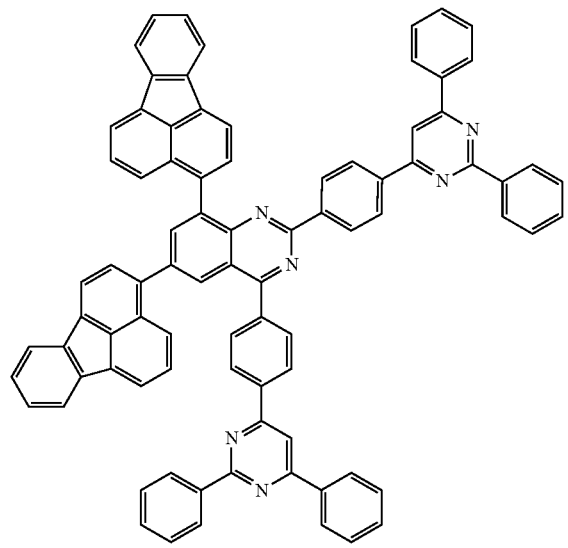
[Chemical Formula A-324]
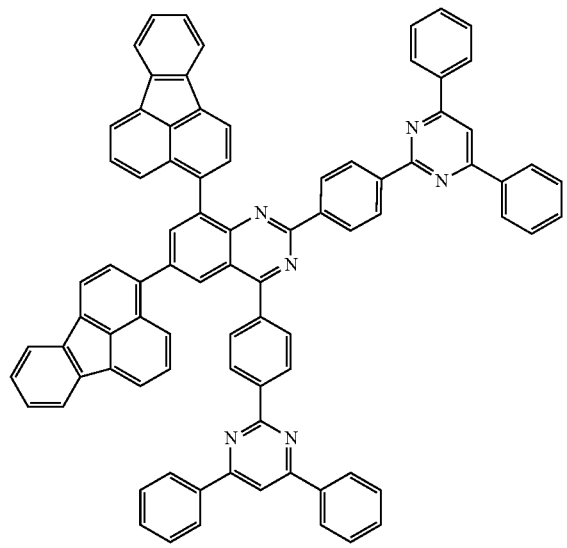

-continued
[Chemical Formula A-325]
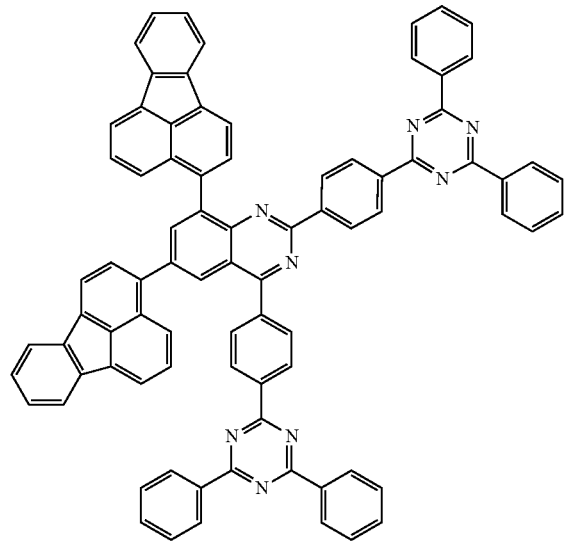
[Chemical Formula A-326]
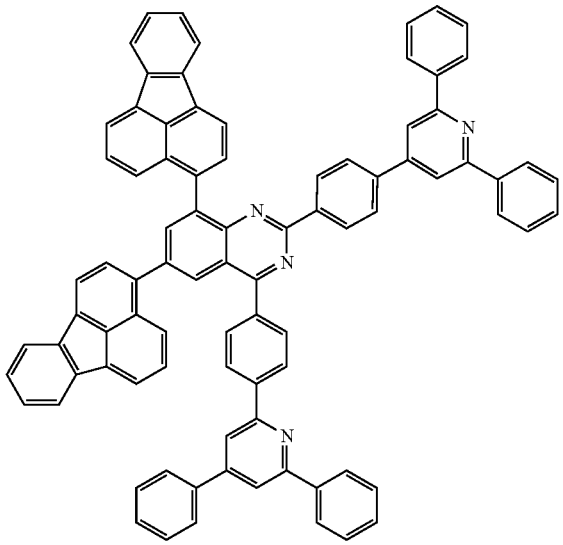
[Chemical Formula A-327]
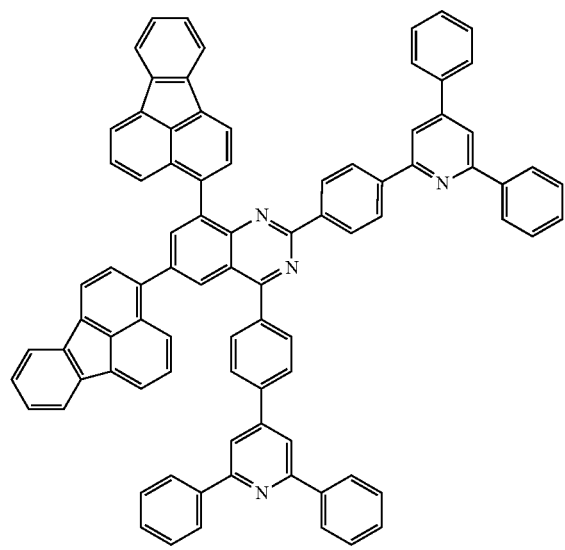
Chemical Formula A-328
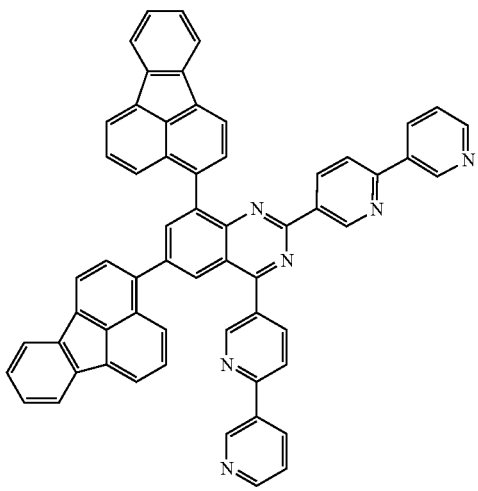

[Chemical Formula A-329]
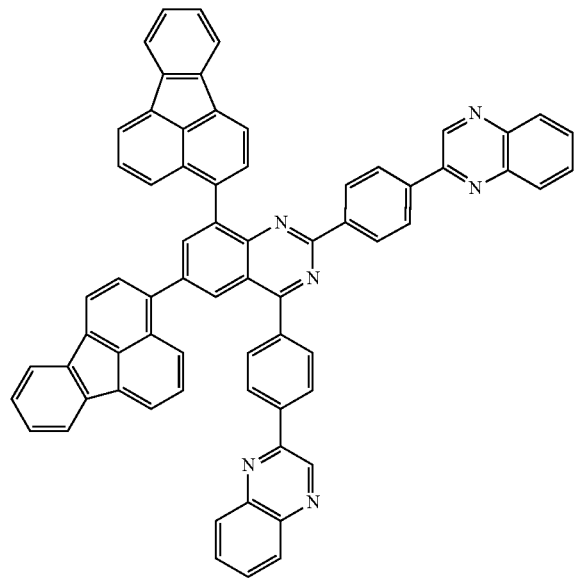
[Chemical Formula A-330]
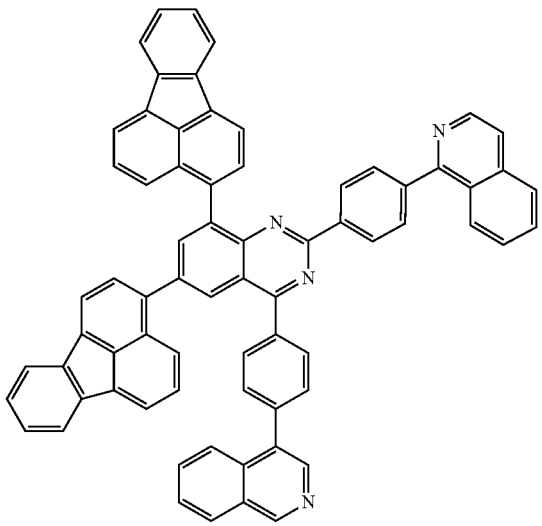
[Chemical Formula A-331]
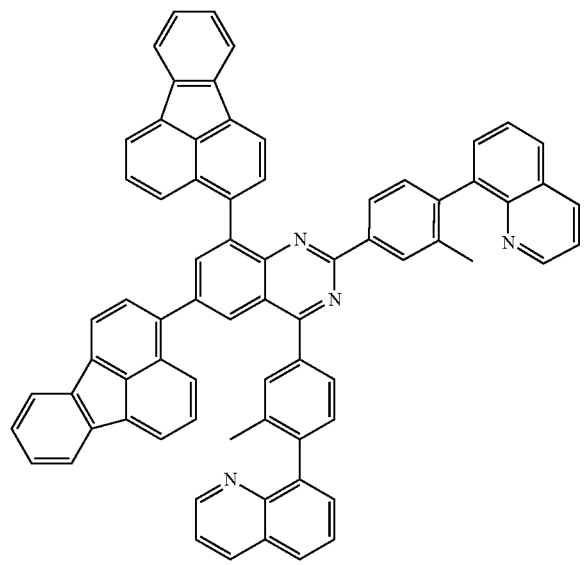
[Chemical Formula A-332]
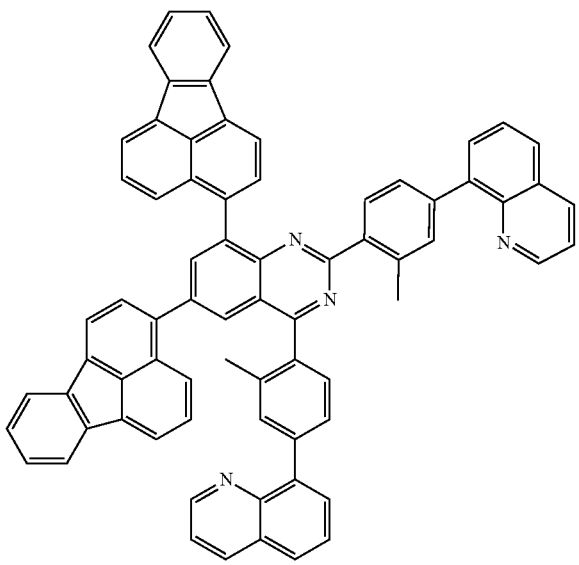

[Chemical Formula A-333]
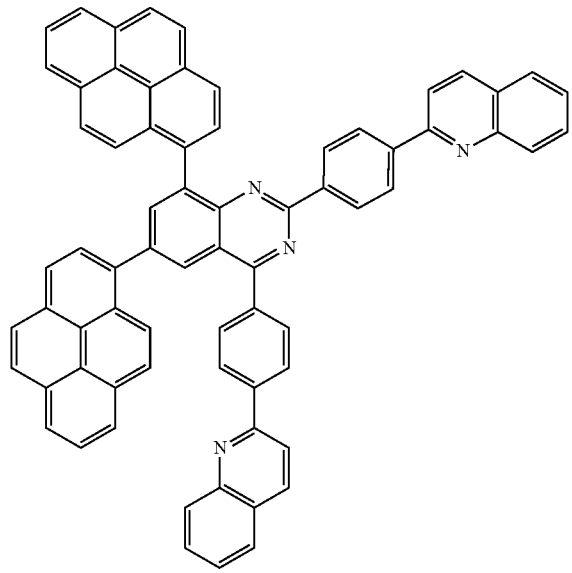
[Chemical Formula A-334]
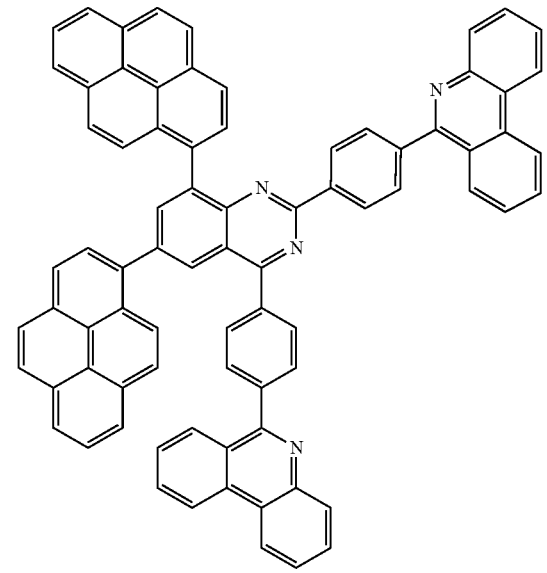
[Chemical Formula A-335]
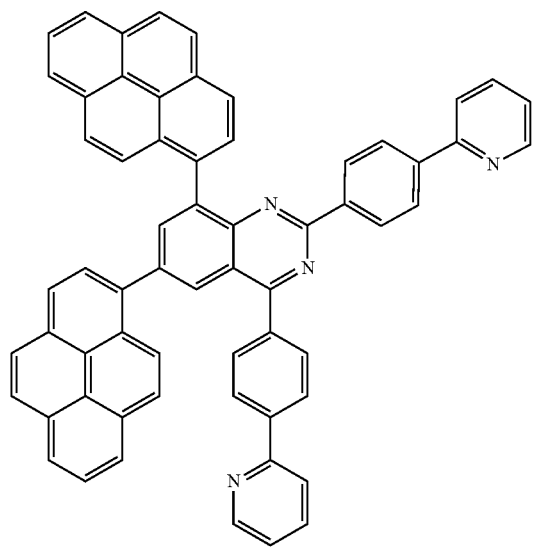
[Chemical Formula A-336]
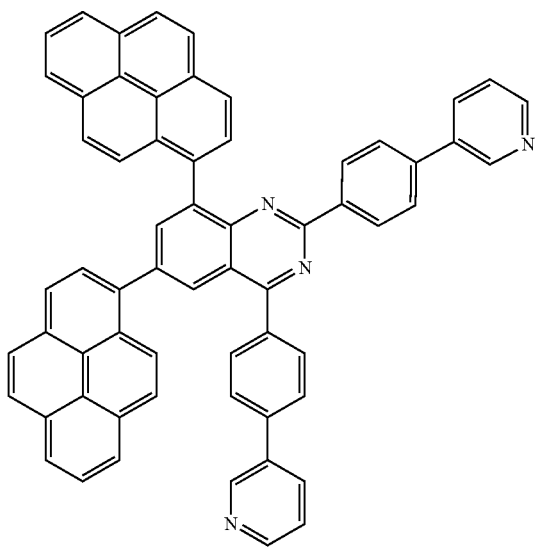

-continued
[Chemical Formula A-337]
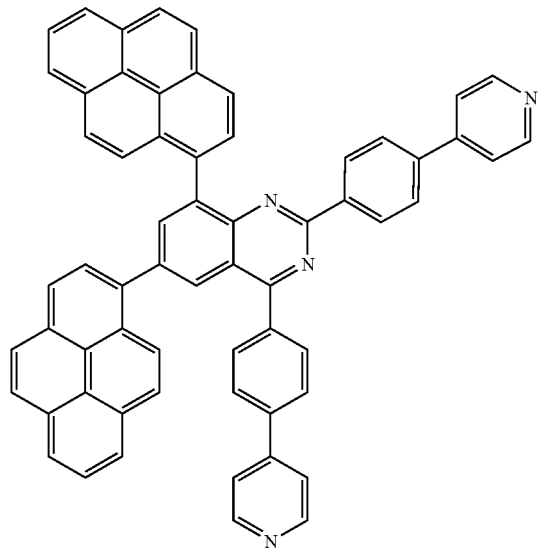
[Chemical Formula A-338]
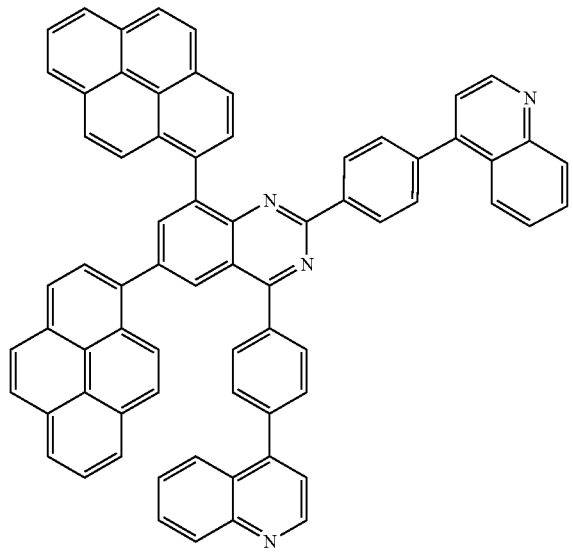
[Chemical Formula A-339]
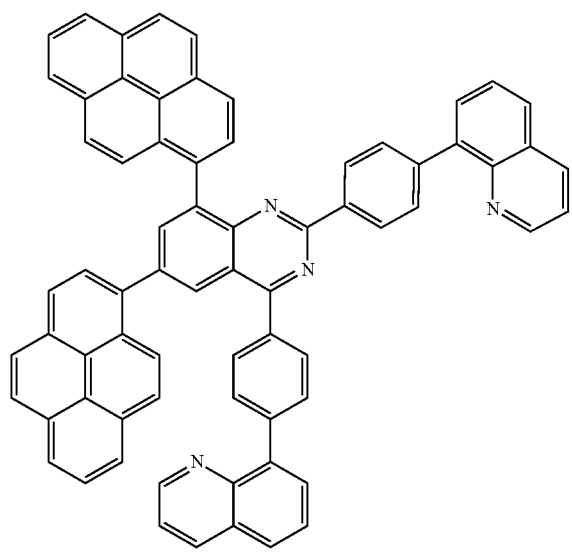
[Chemical Formula A-340]
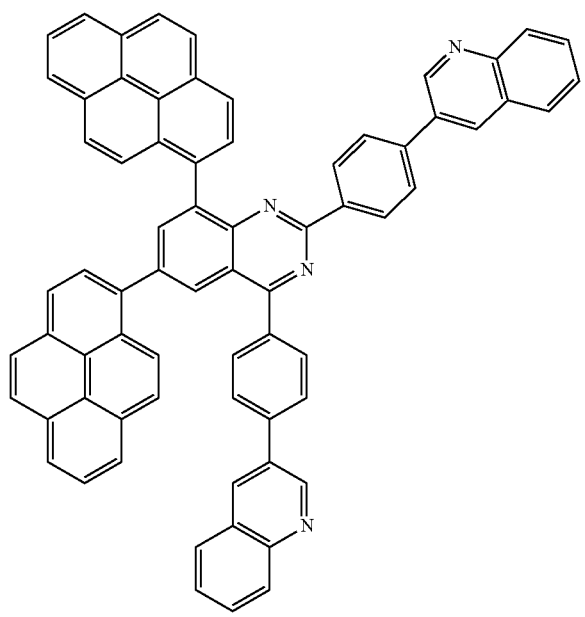

[Chemical Formula A-341]
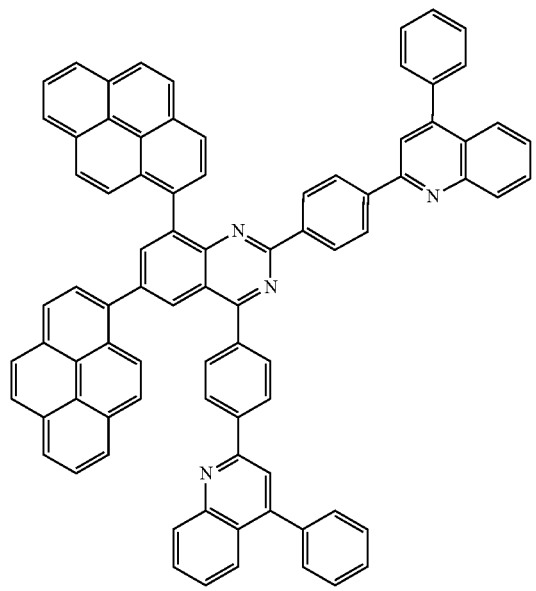
[Chemical Formula A-342]
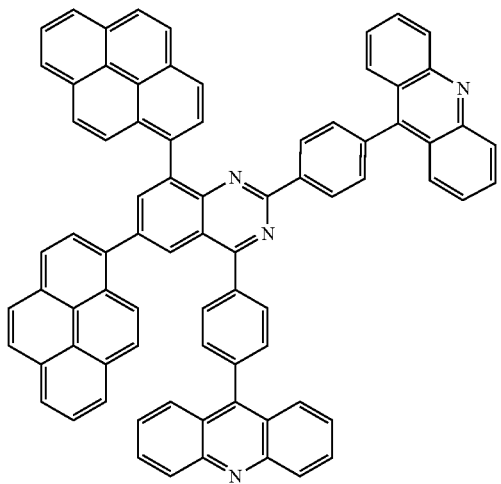
[Chemical Formula A-343]
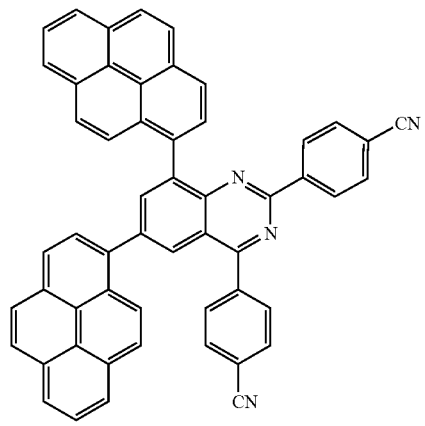
[Chemical Formula A-344]
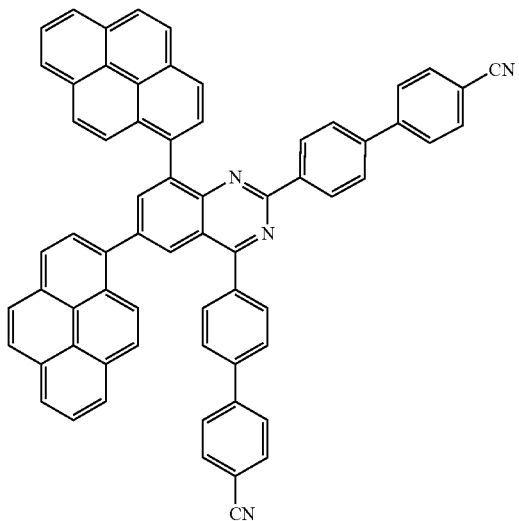

[Chemical Formula A-345]
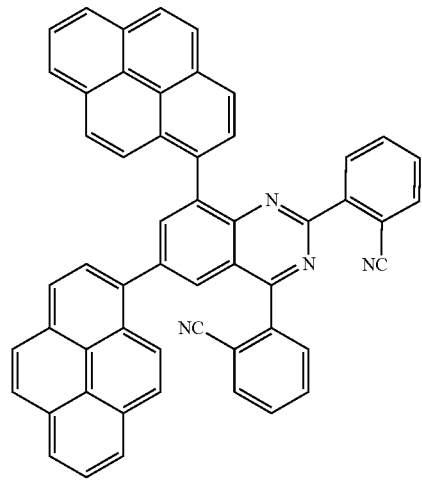
[Chemical Formula A-346]
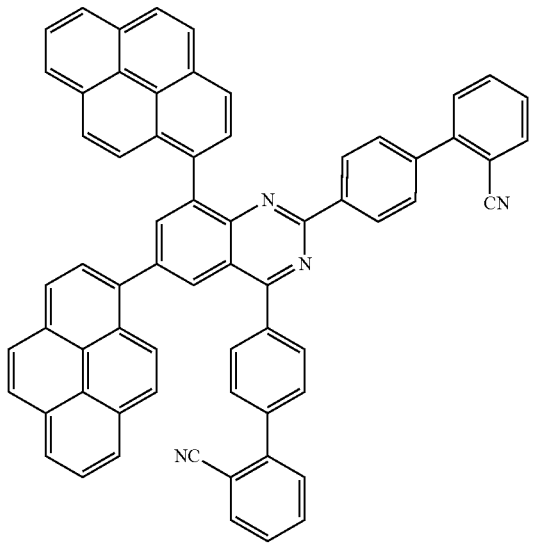
[Chemical Formula A-347]
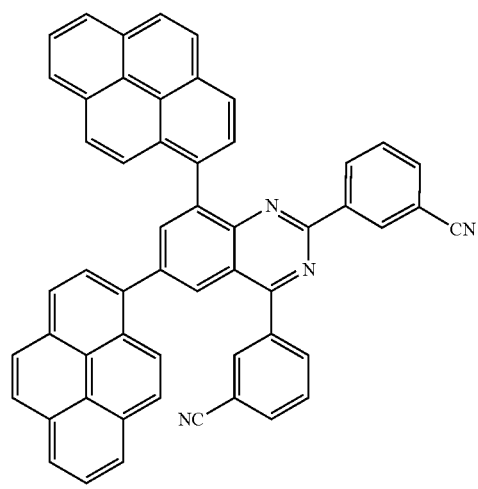
[Chemical Formula A-348]
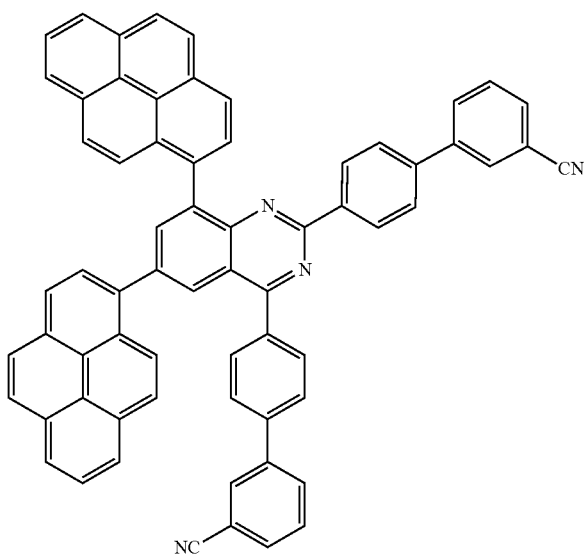

-continued
[Chemical Formula A-349]
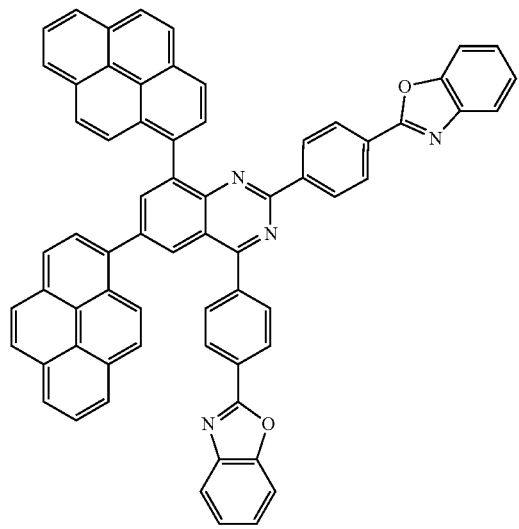
[Chemical Formula A-350]
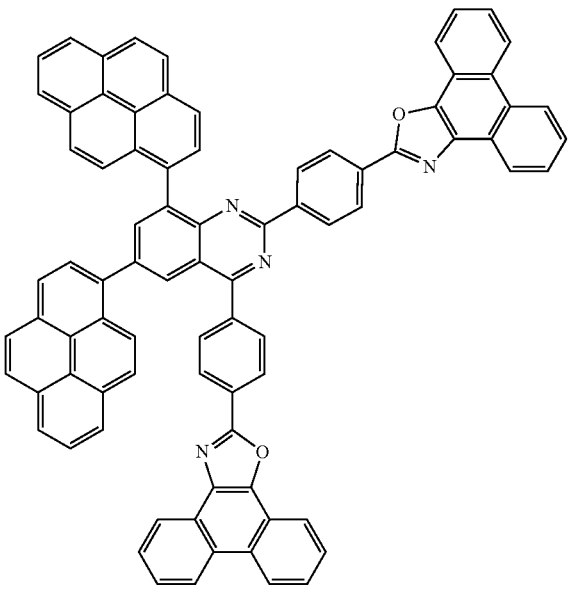
[Chemical Formula A-351]
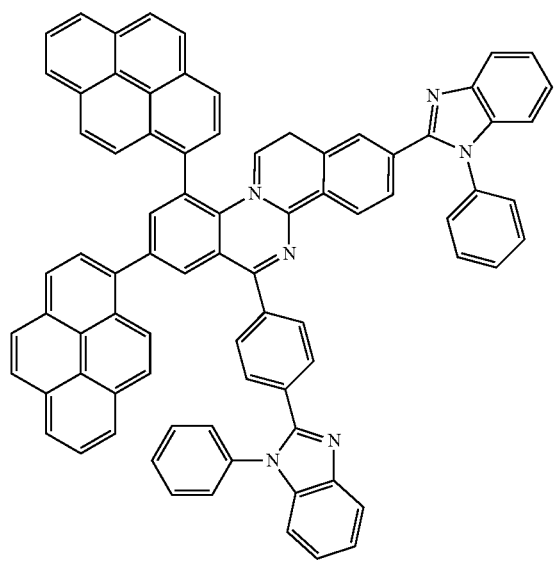
[Chemical Formula A-352]
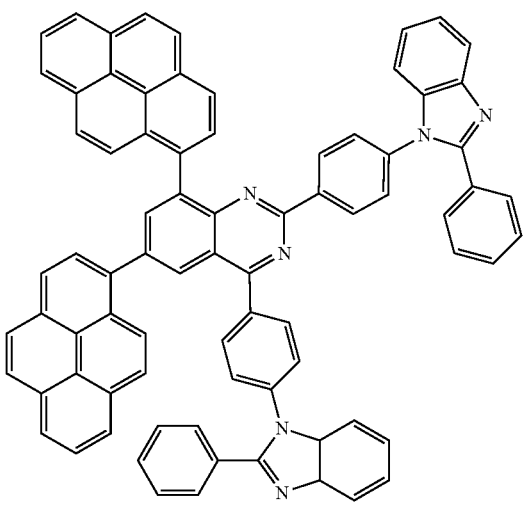

-continued
[Chemical Formula A-353]
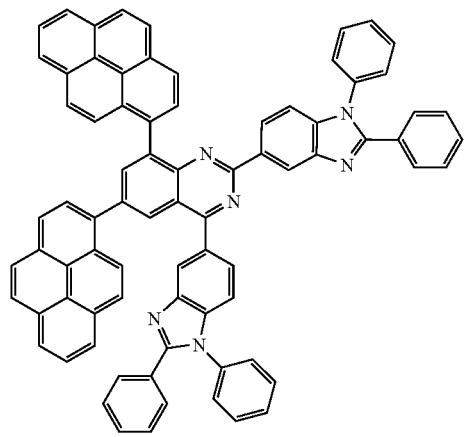
[Chemical Formula A-354]
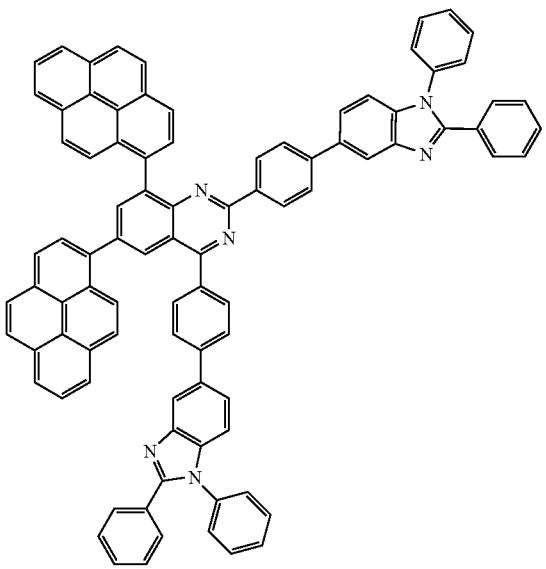
[Chemical Formula A-355]
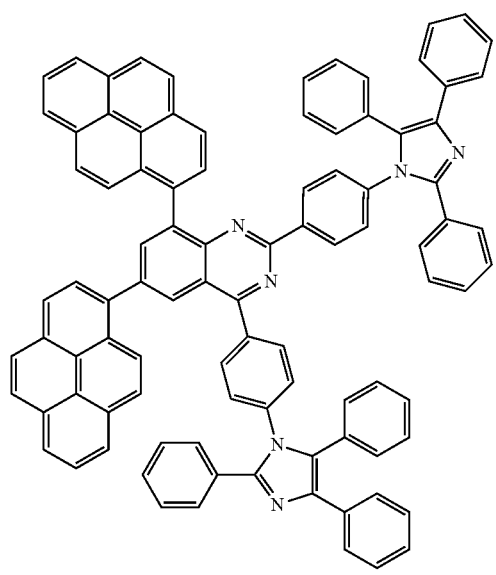
[Chemical Formula A-356]
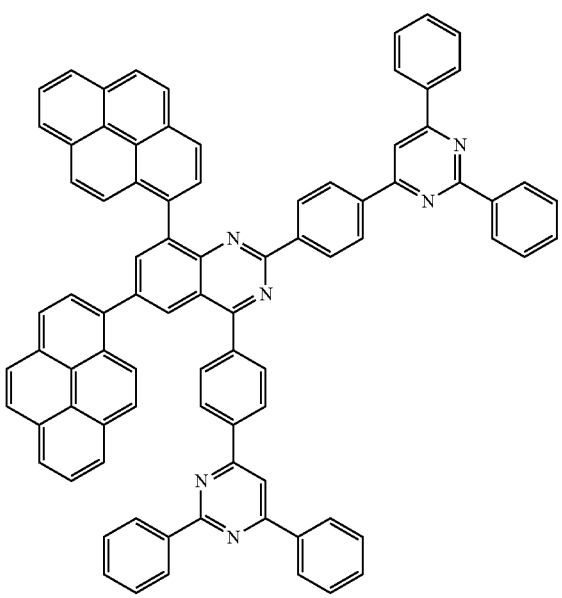

-continued
[Chemical Formula A-357]
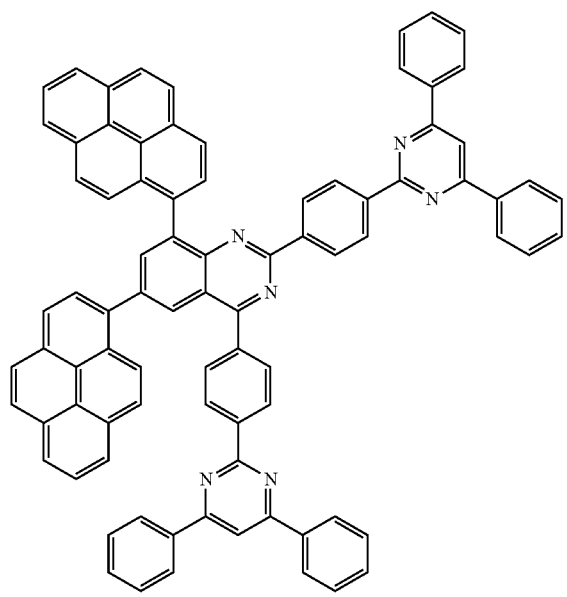
[Chemical Formula A-358]
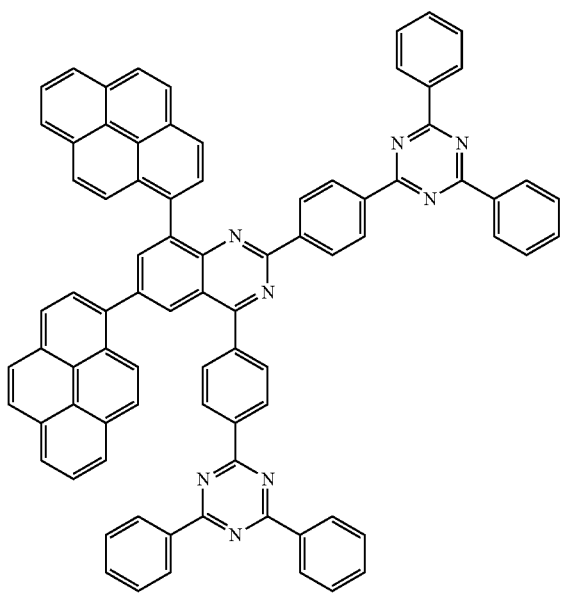
[Chemical Formula A-359]
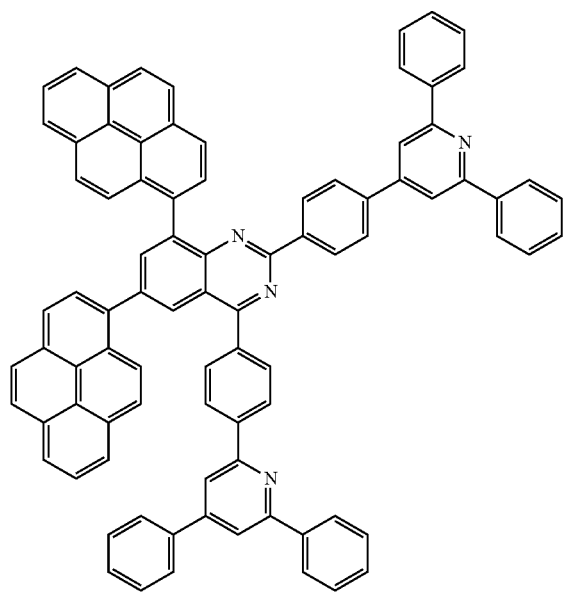
[Chemical Formula A-360]
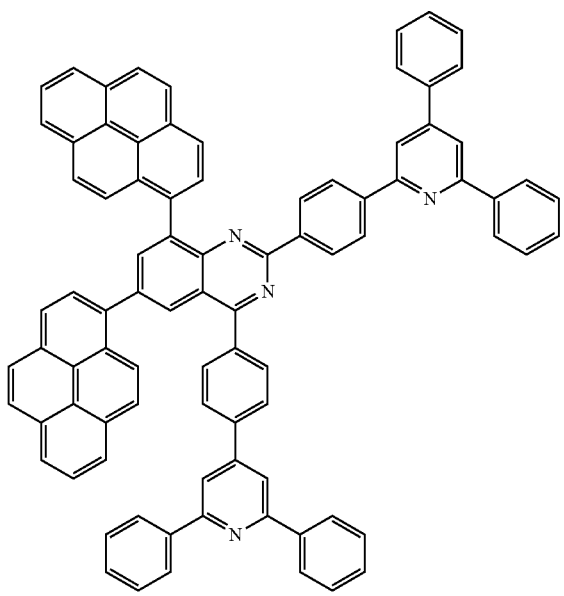

[Chemical Formula A-361]
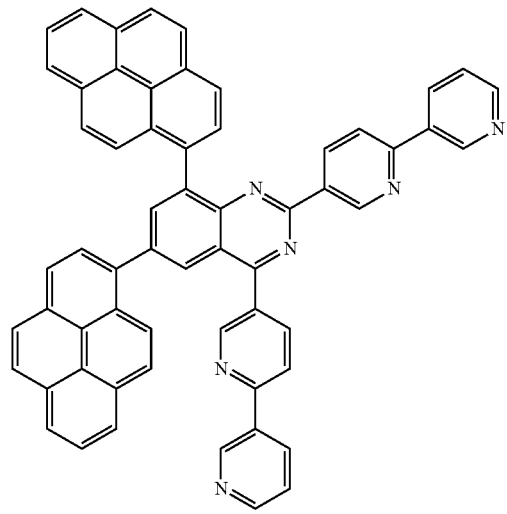
[Chemical Formula A-362]
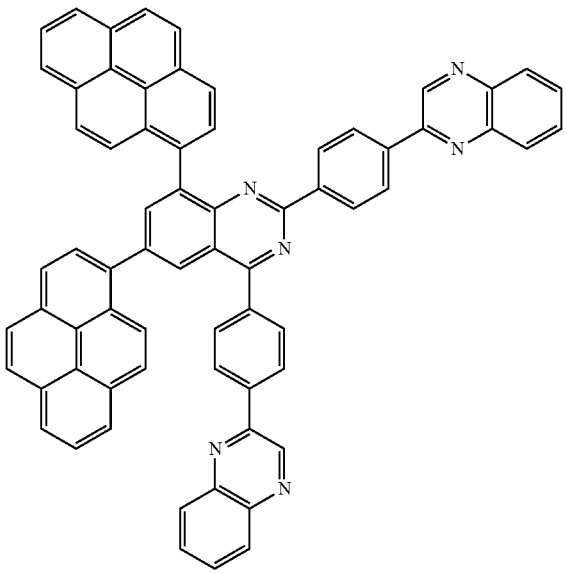
[Chemical Formula A-363]
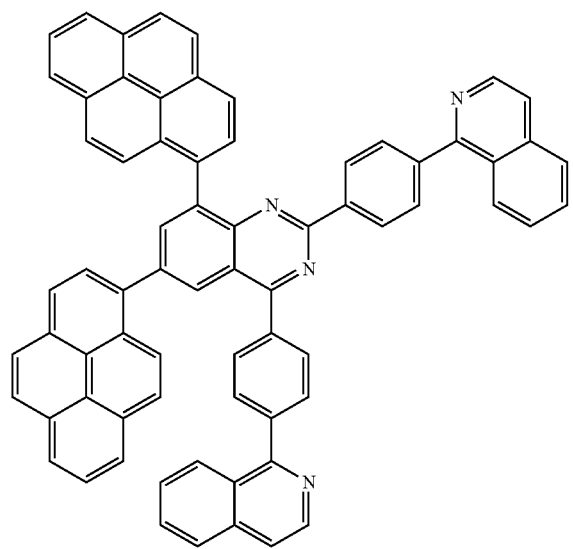
[Chemical Formula A-364]
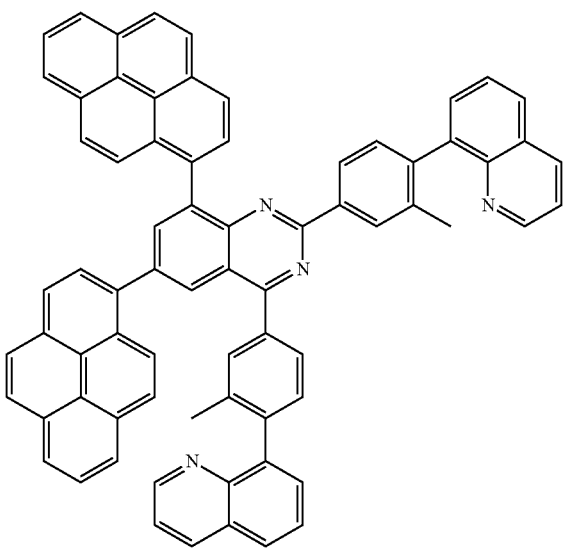

[Chemical Formula A-365]
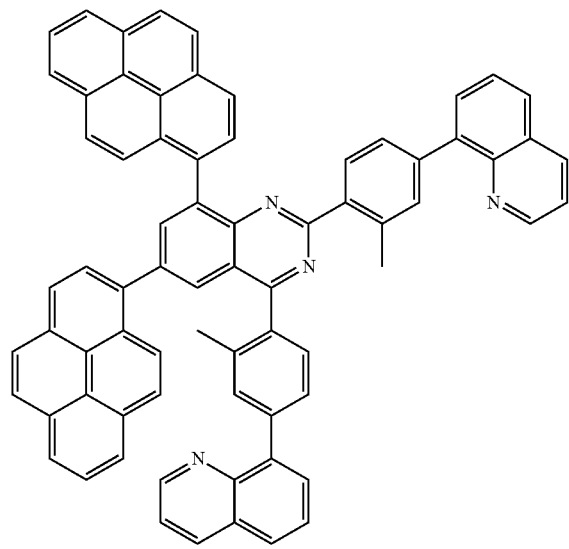
[Chemical Formula A-366]
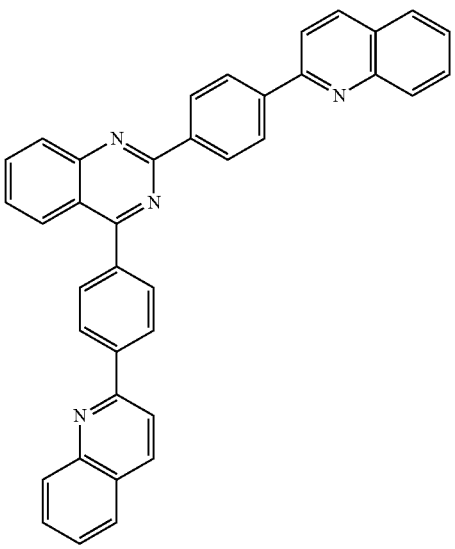
[Chemical Formula A-367]
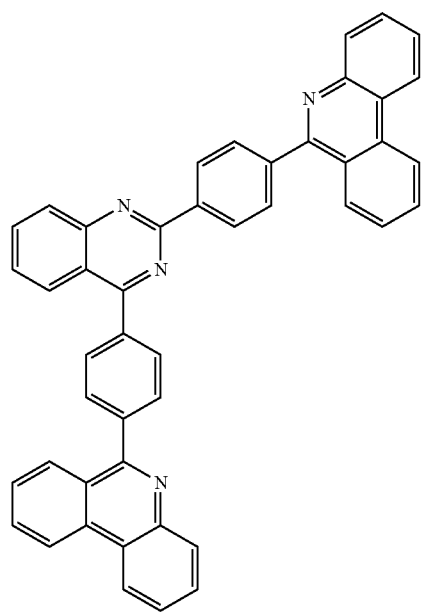
[Chemical Formula A-368]
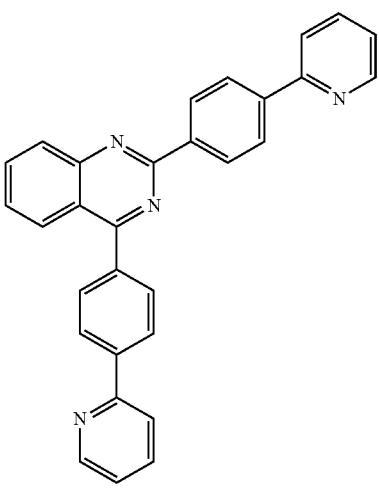

[Chemical Formula A-369]
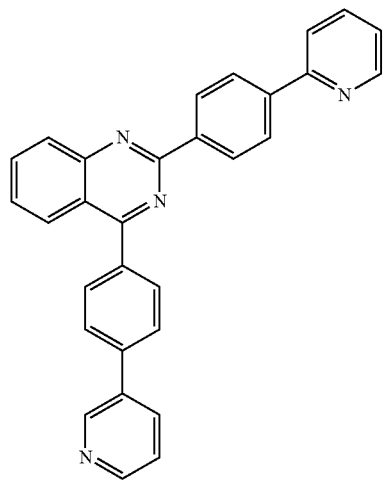
[Chemical Formula A-370]
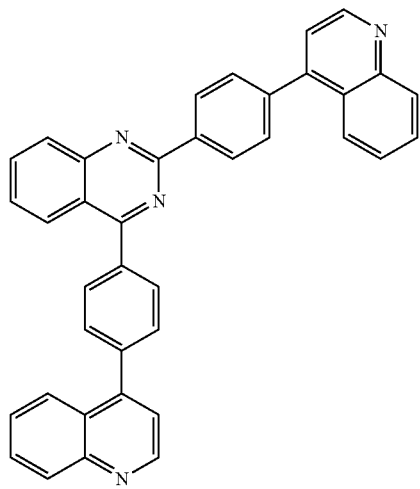
[Chemical Formula A-371]
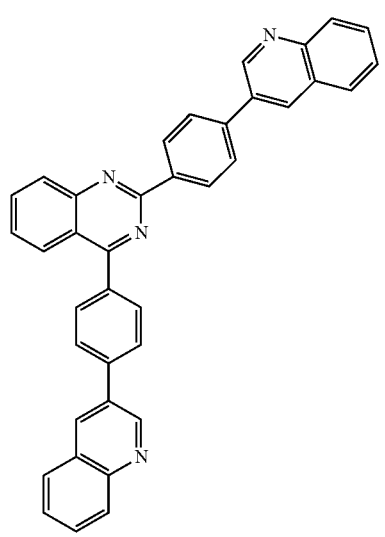
[Chemical Formula A-372]
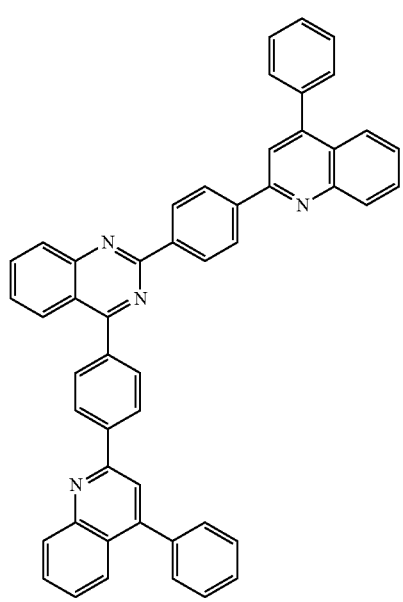

-continued
[Chemical Formula A-373]
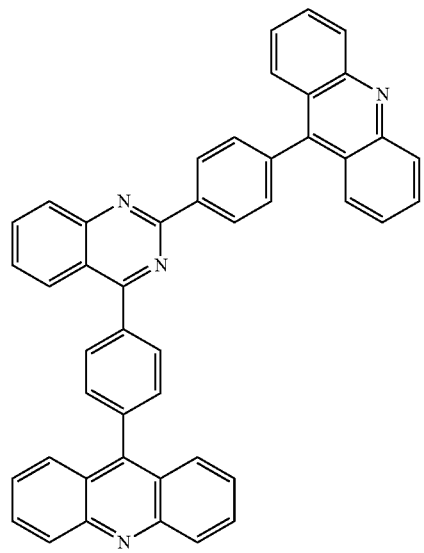
[Chemical Formula A-374]
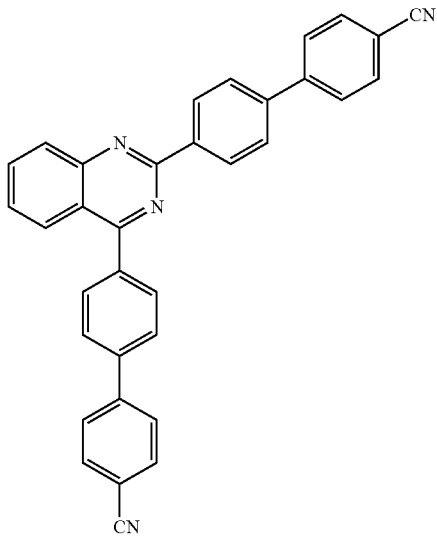
[Chemical Formula A-375]
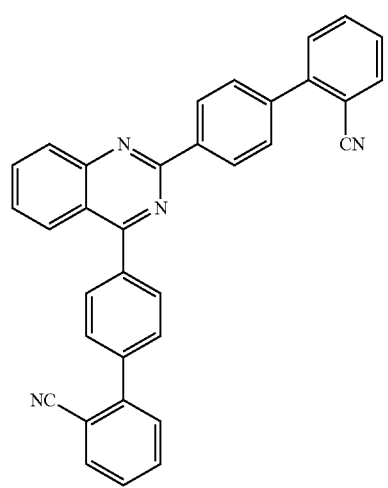
[Chemical Formula A-376]
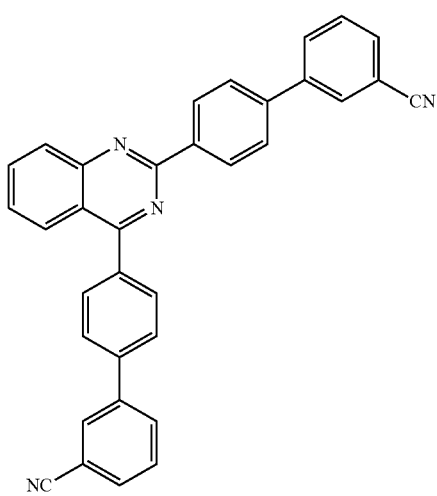

-continued
[Chemical Formula A-377]
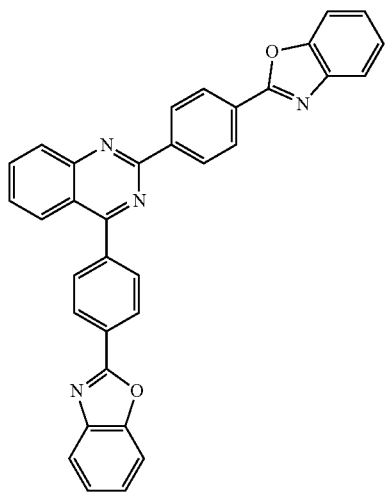
[Chemical Formula A-378]
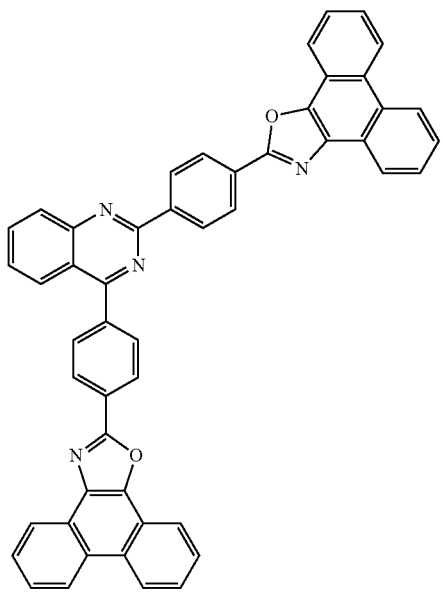
[Chemical Formula A-379]
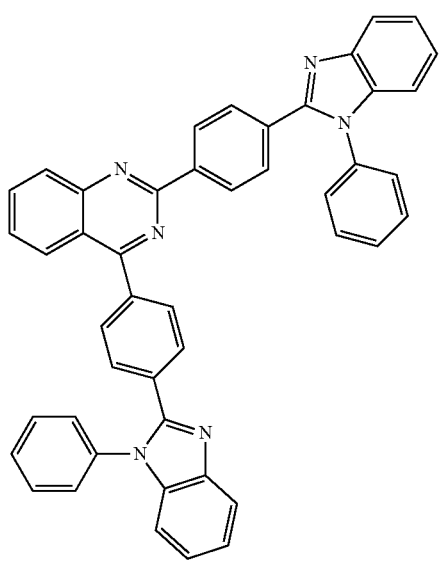
[Chemical Formula A-380]
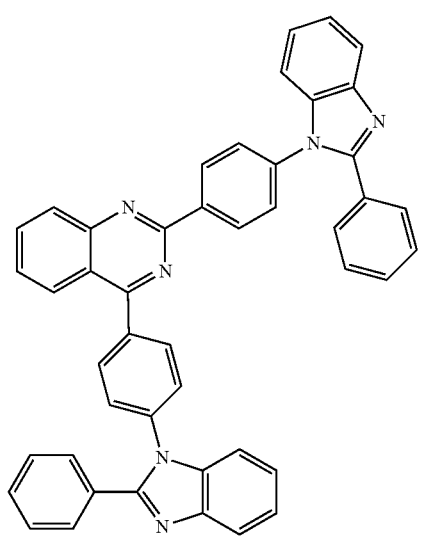

605
-continued
[Chemical Formula A-381]
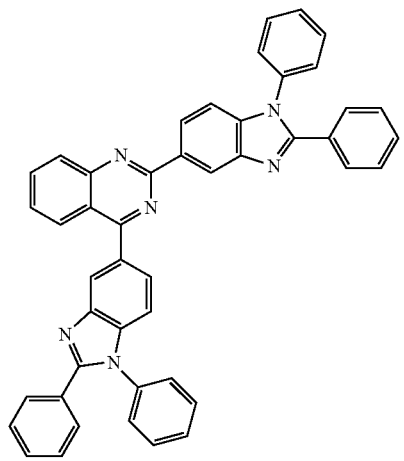
606
[Chemical Formula A-382]
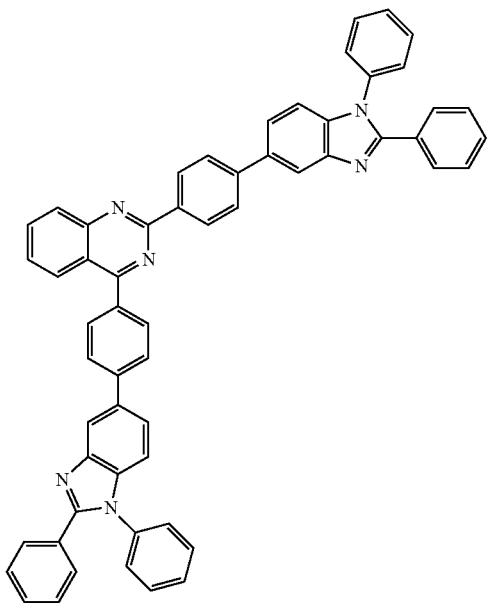
[Chemical Formula A-383]
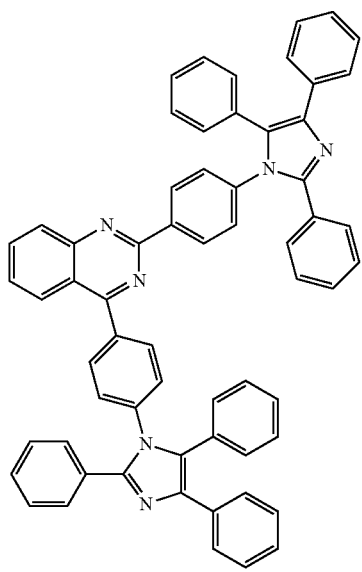
[Chemical Formula A-384]
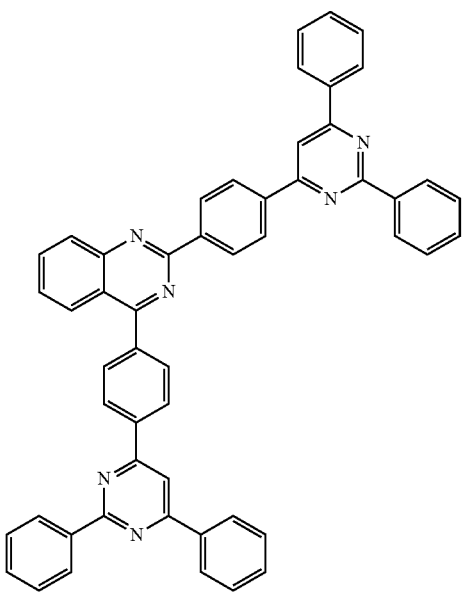

607
-continued
[Chemical Formula A-385]
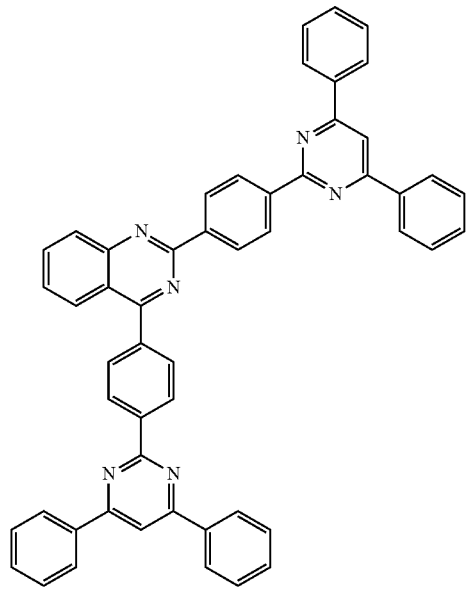
608
[Chemical Formula A-386]
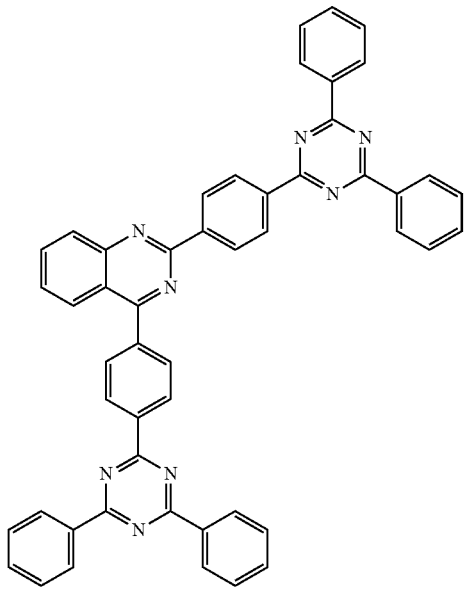
[Chemical Formula A-387]
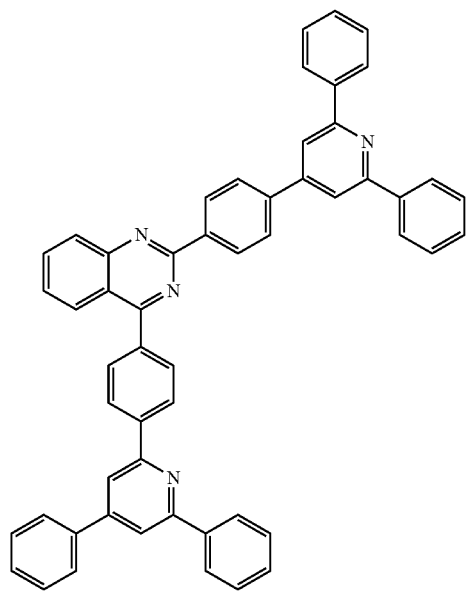
[Chemical Formula A-388]
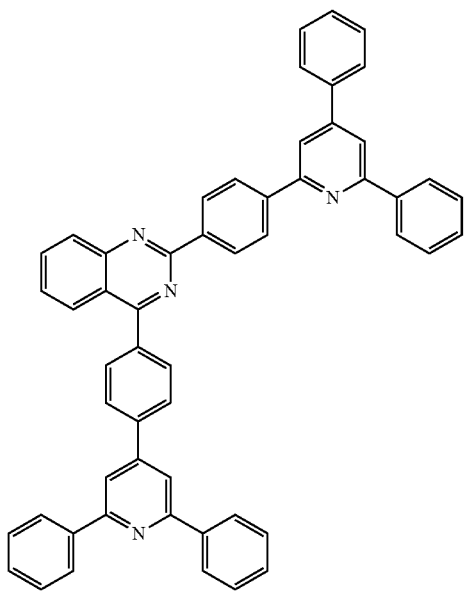

-continued
[Chemical Formula A-389]
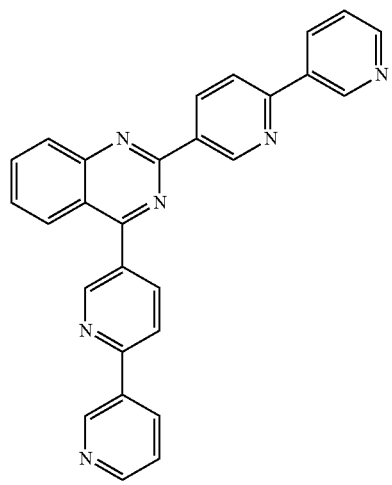
[Chemical Formula A-390]
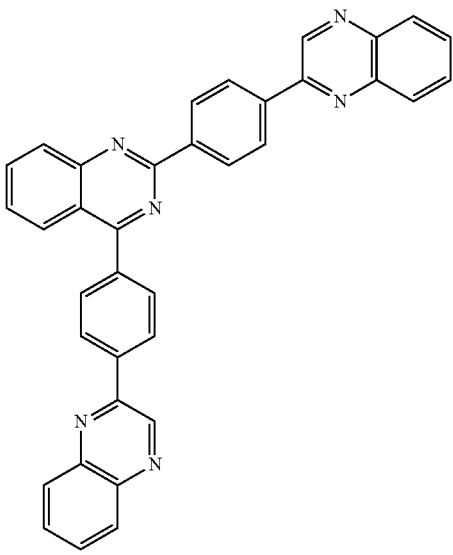
[Chemical Formula A-391]
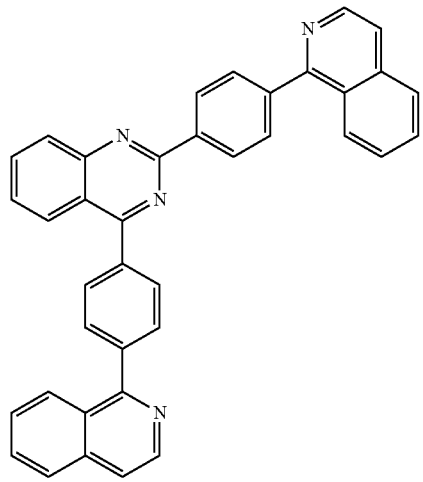
[Chemical Formula A-392]
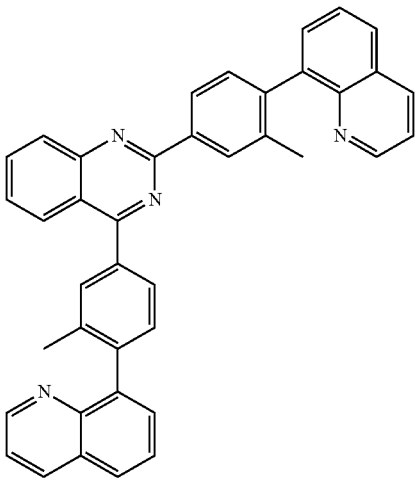
[Chemical Formula A-393]
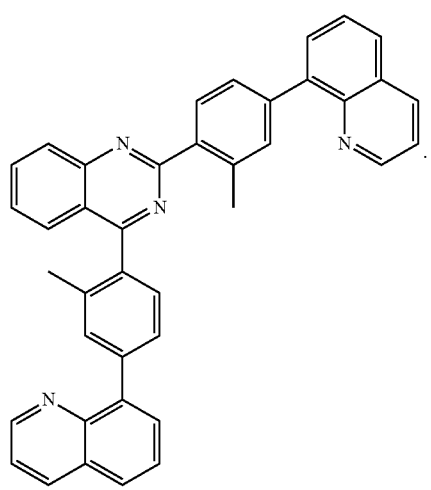

12. The compound for an organic optoelectronic device as claimed to claim 1, wherein the compound for an organic optoelectronic device is one of compounds represented by the following Chemical Formulae B-1 to B-30:
[Chemical Formula B-1]
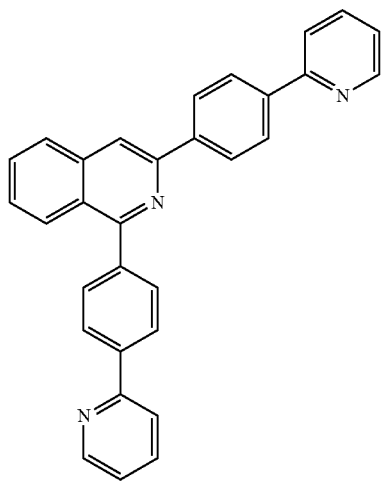
[Chemical Formula B-2]
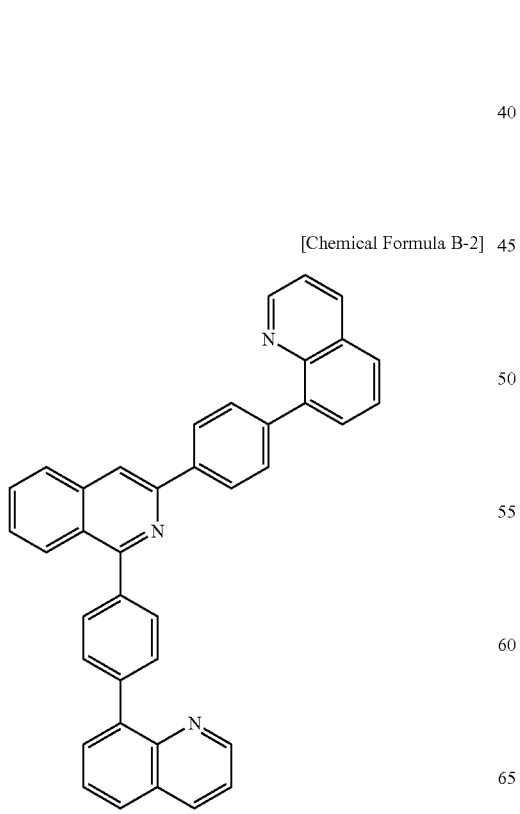
[Chemical Formula B-3]
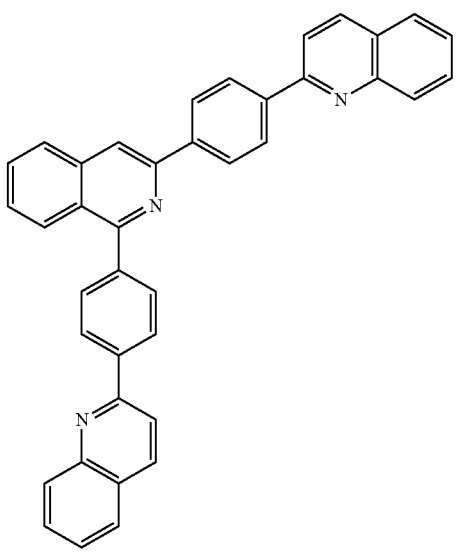
[Chemical Formula B-4]
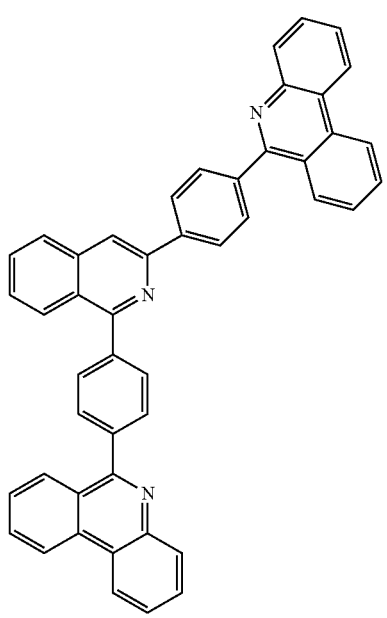

[Chemical Formula B-5]
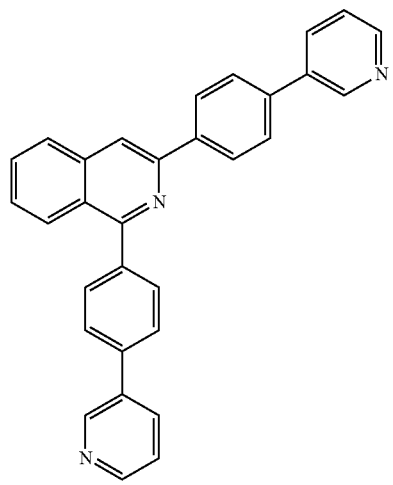
[Chemical Formula B-6]
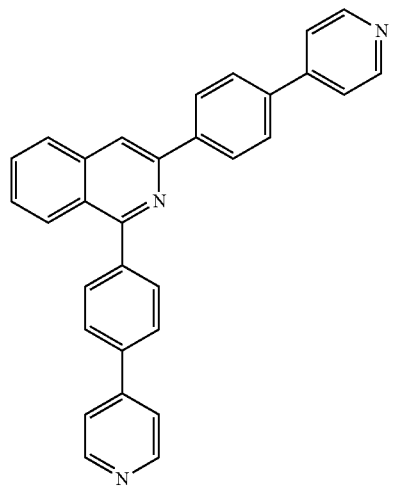
[Chemical Formula B-7]
[Chemical Formula B-8]
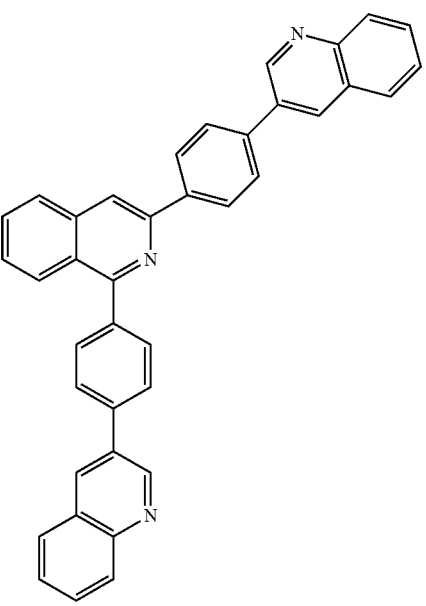
[Chemical Formula B-9]
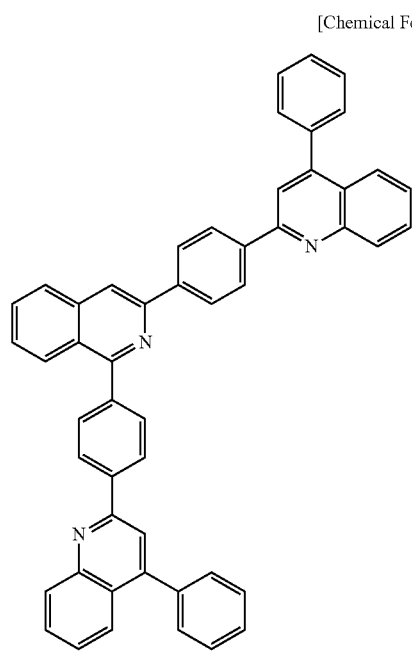

[Chemical Formula B-10]
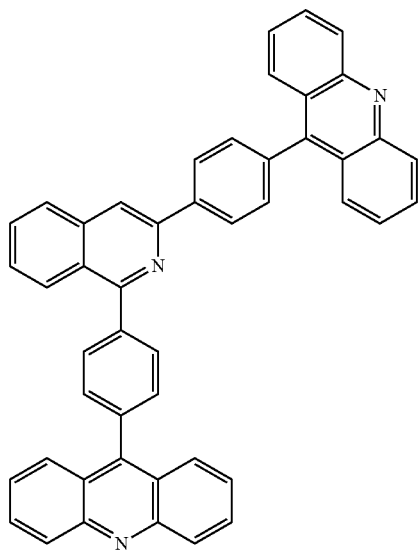
[Chemical Formula B-11]
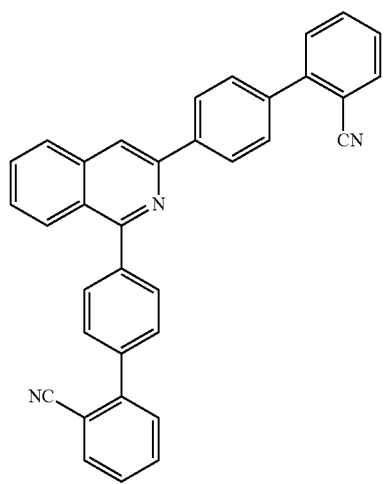
[Chemical Formula B-12]
[Chemical Formula B-13]
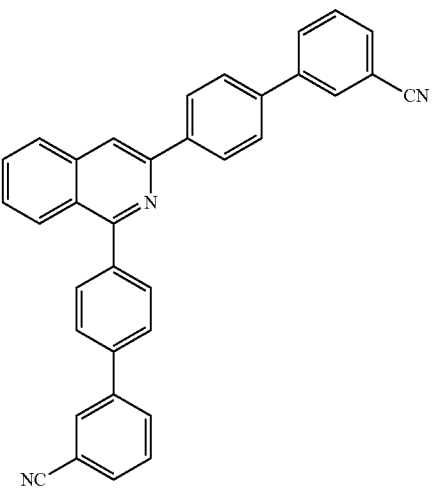
[Chemical Formula B-14]
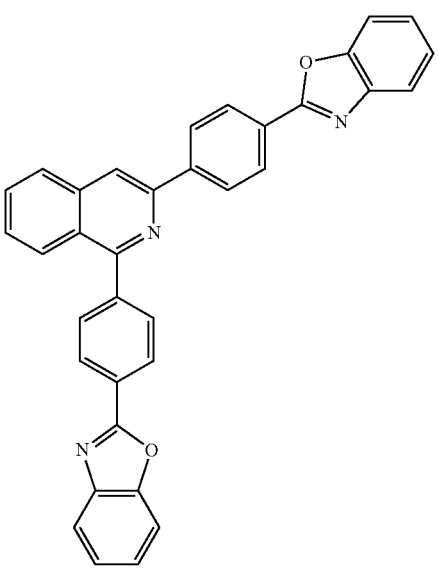

-continued
[Chemical Formula B-15]
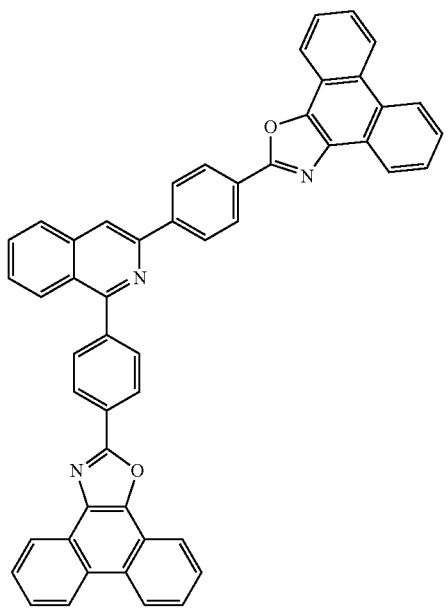
[Chemical Formula B-16]
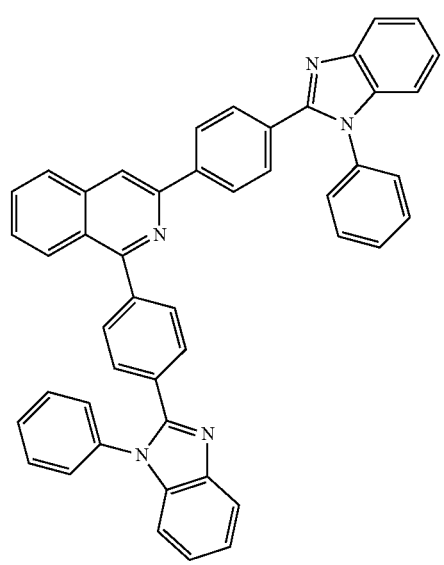
-continued
[Chemcial Formula B-17]
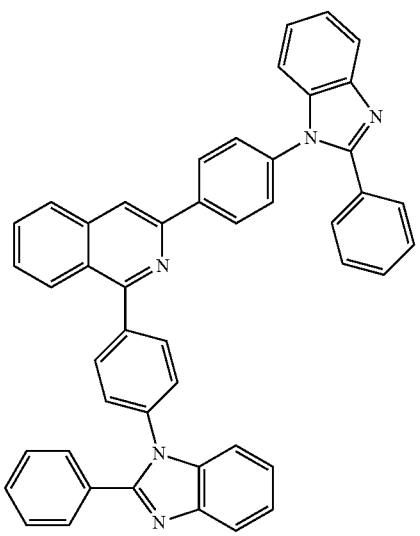
[Chemical Formula B-18]
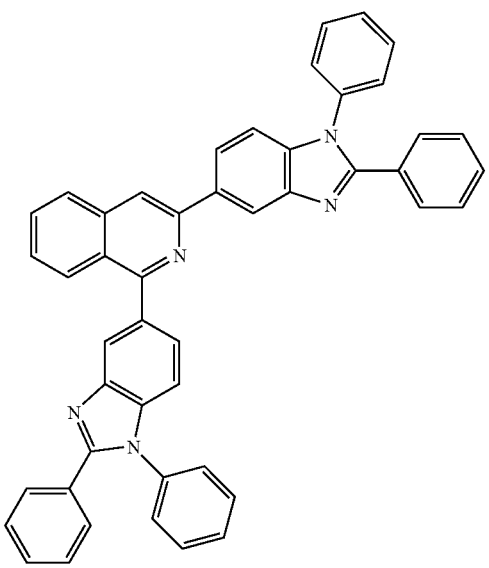

[Chemical Formula B-19]
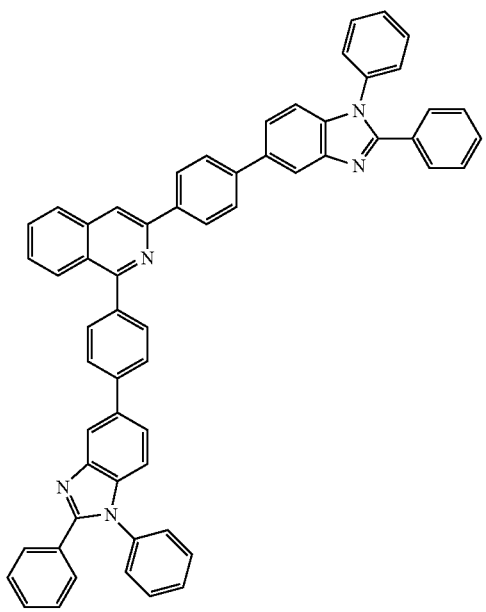
[Chemical Formula B-20]
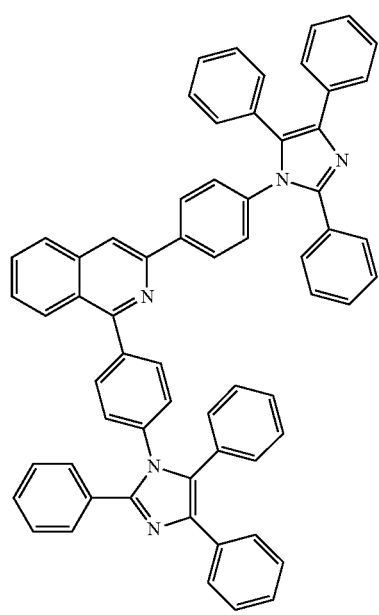
[Chemical Formula B-21]
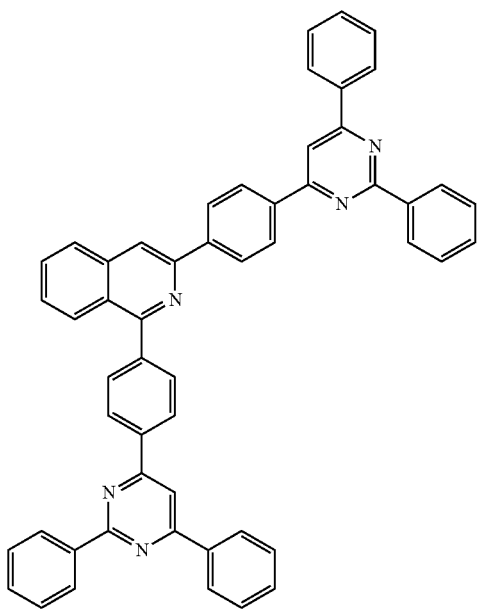
[Chemical Formula B-22]
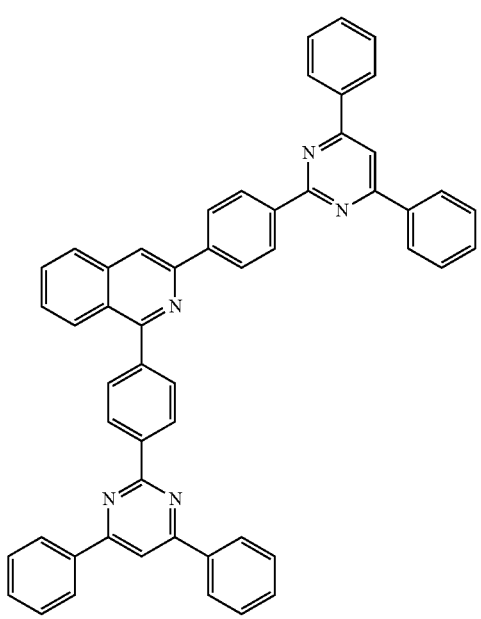

-continued
[Chemical Formula B-23]
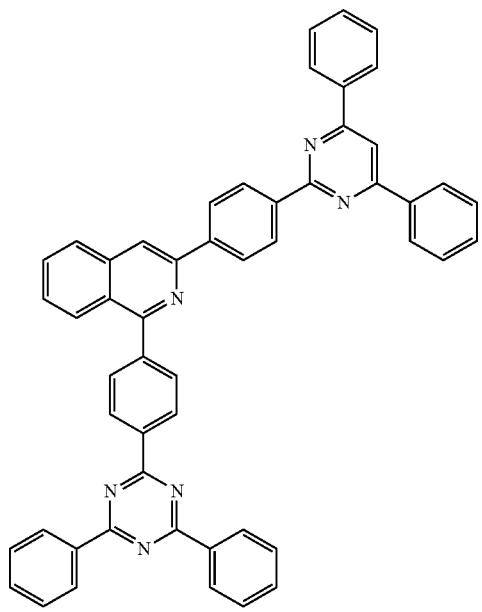
[Chemical Formula B-24]
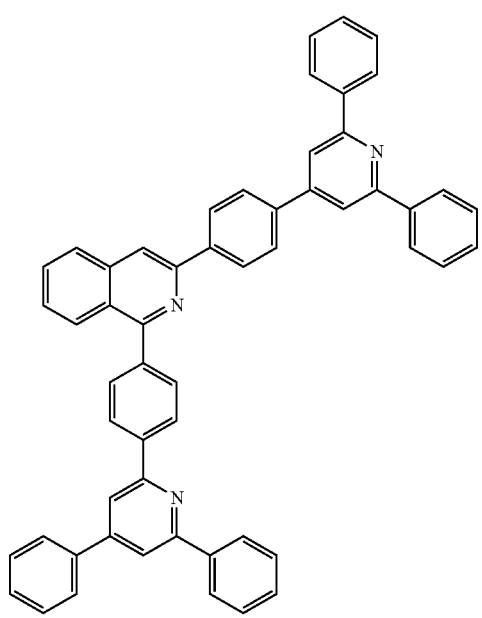
-continued
[Chemical Formula B-25]
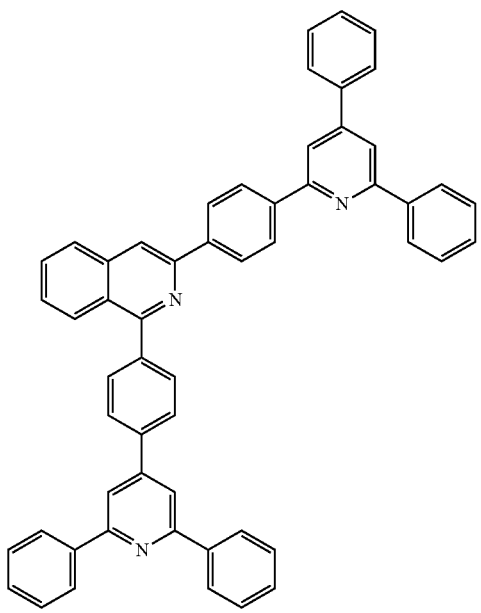
[Chemical Formula B-26]
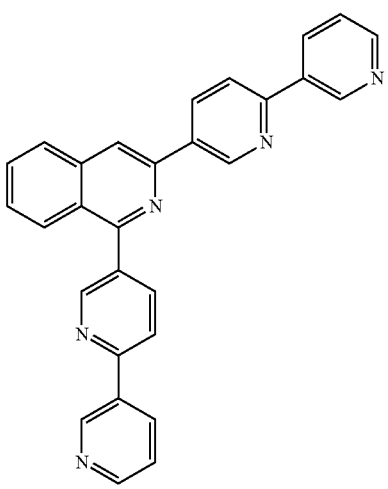

[Chemical Formula B-27]

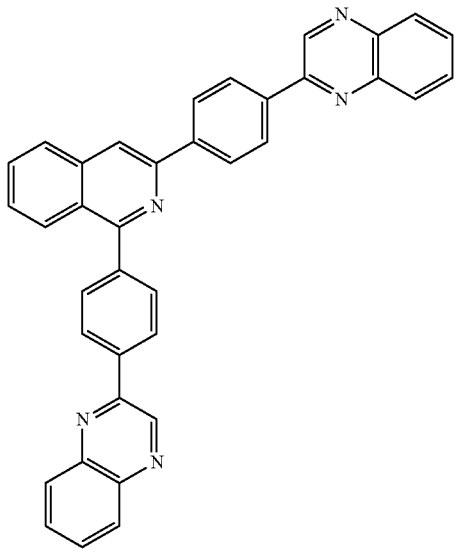

[Chemical Formula B-28]

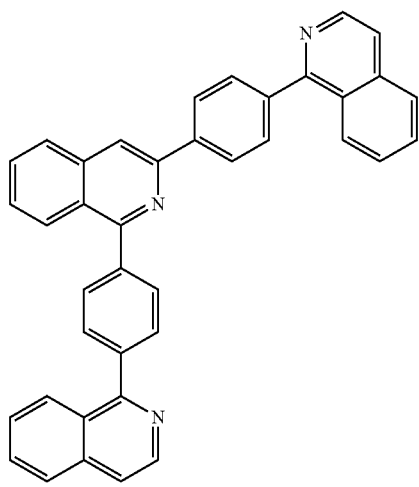

[Chemical Formula B-29]

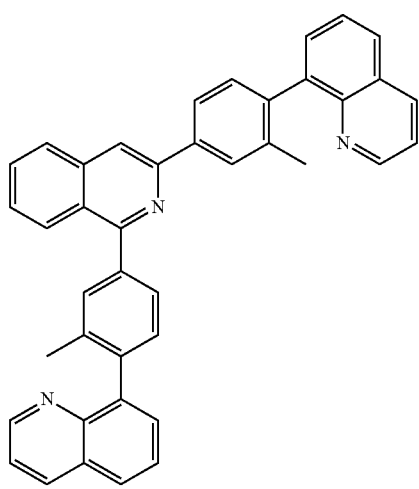

[Chemical Formula B-30]

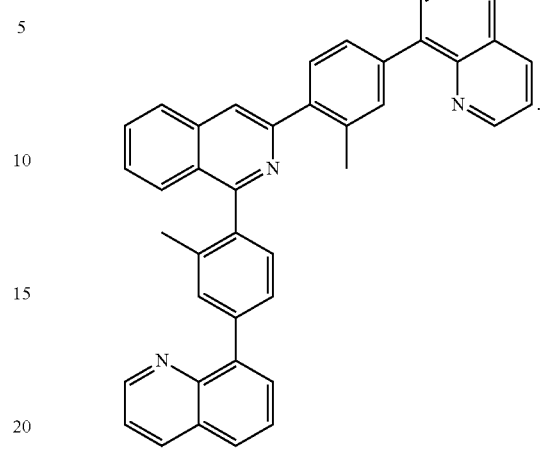

13. The compound for an organic optoelectronic device as claimed in claim 1, wherein the compound for an organic optoelectronic device has triplet exciton energy (T1) of greater than or equal to 2.0 eV.

14. The compound for an organic optoelectronic device as claimed in claim 1, wherein the organic optoelectronic device is selected from the group consisting of an organic photoelectric device, an organic light emitting diode, an organic solar cell, an organic transistor, an organic photo-conductor drum, and an organic memory device.

15. An organic light emitting diode comprising
an anode, a cathode, and at least one organic thin layer interposed between the anode and cathode,
wherein at least one of the organic thin layers comprises the above compound for an organic optoelectronic device as claimed in claim 1.

16. The organic light emitting diode as claimed in claim 15, wherein the organic thin layer is selected from the group consisting of an emission layer, a hole transport layer, a hole injection layer, an electron transport layer, an electron injection layer, a hole blocking layer, and a combination thereof.

17. The organic light emitting diode as claimed in claim 16, wherein the compound for an organic optoelectronic device is included in a hole transport layer or a hole injection layer.

18. The organic light emitting diode as claimed in claim 16, wherein the compound for an organic optoelectronic device is included in an emission layer.

19. The organic light emitting diode as claimed in claim 18, wherein the compound for an organic optoelectronic device is used as a phosphorescent or fluorescent host material in an emission layer.

20. A display device including the above organic light emitting diode as claimed in claim 15.

* * * * *